US012746222B2

(12) United States Patent
Kim et al.

(10) Patent No.: US 12,746,222 B2
(45) Date of Patent: Sep. 29, 2026

(54) IMPLANTABLE DEPOTS FOR LOCALIZED, SUSTAINED, CONTROLLED RELEASE OF THERAPEUTIC AGENTS TO TREAT CANCER AND RELATED CONDITIONS

(71) Applicant: Foundry Therapeutics, Inc., Menlo Park, CA (US)

(72) Inventors: Steven Kim, Los Altos, CA (US); Karun D. Naga, Los Altos, CA (US); Hanson S. Gifford, III, Woodside, CA (US); James Su, Newark, CA (US); Nassireddin Mokarram-Dorri, Campbell, CA (US); Mark Deem, Portola Valley, CA (US); Stephen W. Boyd, San Francisco, CA (US); Koon Kiat Teu, Singapore (SG); Wei Li Lee, Singapore (SG); Darryl Lim Wi Chung, Singapore (SG); Edward D. Gifford, Glastonbury, CT (US)

(73) Assignee: Foundry Therapeutics, Inc., Menlo Park, CA (US)

(*) Notice: Subject to any disclaimer, the term of this patent is extended or adjusted under 35 U.S.C. 154(b) by 453 days.

(21) Appl. No.: 18/249,022

(22) PCT Filed: Oct. 14, 2021

(86) PCT No.: PCT/US2021/071861
§ 371 (c)(1),
(2) Date: Apr. 13, 2023

(87) PCT Pub. No.: WO2022/082196
PCT Pub. Date: Apr. 21, 2022

(65) Prior Publication Data

US 2024/0016774 A1 Jan. 18, 2024

Related U.S. Application Data

(60) Provisional application No. 63/198,381, filed on Oct. 14, 2020.

(51) Int. Cl.

*A61K 9/00* (2006.01)
*A61K 9/70* (2006.01)
*A61K 31/015* (2006.01)
*A61K 31/337* (2006.01)
*A61P 35/00* (2006.01)
*A61K 45/06* (2006.01)

(52) U.S. Cl.

CPC .......... *A61K 31/337* (2013.01); *A61K 9/0024* (2013.01); *A61K 31/015* (2013.01); *A61P 35/00* (2018.01)

(58) Field of Classification Search

CPC ...... A61K 9/0024; A61K 9/7007; A61P 35/00
See application file for complete search history.

(56) References Cited

U.S. PATENT DOCUMENTS

| | | | |
|---|---|---|---|
| 4,601,893 | A | 7/1986 | Cardinal |
| 4,666,704 | A | 5/1987 | Shalati et al. |
| 4,919,939 | A | 4/1990 | Baker |
| 5,227,165 | A | 7/1993 | Domb et al. |
| 5,451,408 | A | 9/1995 | Mezei et al. |
| 5,458,582 | A | 10/1995 | Nakao |
| 5,540,912 | A | 7/1996 | Roorda et al. |
| 5,618,563 | A | 4/1997 | Berde et al. |
| 5,667,523 | A | 9/1997 | Bynon et al. |
| 5,700,485 | A | 12/1997 | Berde et al. |
| 5,747,060 | A | 5/1998 | Sackler et al. |
| 5,807,306 | A | 9/1998 | Shapland et al. |
| 5,919,473 | A | 7/1999 | Elkhoury |
| 5,931,809 | A | 8/1999 | Gruber et al. |
| 5,942,241 | A | 8/1999 | Chasin et al. |
| 6,046,187 | A | 4/2000 | Berde et al. |
| 6,149,937 | A | 11/2000 | Camu et al. |
| 6,214,387 | B1 | 4/2001 | Berde et al. |
| 6,248,345 | B1 | 6/2001 | Goldenheim et al. |
| 6,326,020 | B1 | 12/2001 | Kohane et al. |
| 6,451,335 | B1 | 9/2002 | Goldenheim et al. |
| 6,699,908 | B2 | 3/2004 | Sackler et al. |
| 6,913,760 | B2 | 7/2005 | Carr et al. |
| 7,074,426 | B2 | 7/2006 | Kochinke |

(Continued)

FOREIGN PATENT DOCUMENTS

| | | | |
|---|---|---|---|
| AU | 2012201226 | B2 | 8/2014 |
| AU | 2013200515 | B2 | 1/2016 |

(Continued)

OTHER PUBLICATIONS

Cavazzoni E, Bugiantella W, Graziosi L, Franceschini MS, Donini A. Malignant ascites: pathophysiology and treatment. Int J Clin Oncol. Feb. 2013; 18(1):1-9. doi: 10.1007/s10147-012-0396-6. Epub Mar. 31, 2012. PMID: 22460778. (Year: 2013).*
International Search Report and Written Opinion dated Feb. 17, 2022; International Application No. PCT/US2021/071861; 10 pages.
Ball , et al., "Electrospun Solid Dispersions of Maraviroc for Rapid Intravaginal Preexposure Prophylaxis of HIV", Antimicrobial Agents and Chemotherapy, vol. 58, No. 8, Aug. 2014, pp. 4855-4865.
Bassi , et al., "Polymeric films as a promising carrier for bioadhesive drug delivery: Development, characterization and optimization", Saudi Pharmaceutical Journal, vol. 25, 2017, pp. 32-43.
Chun , et al., "Gastrointestinal and Biliary Stents", Journal of Gastroenterology and Hepatology Foundation and Blackwell Publishing Asia Pty Ltd, vol. 25, 2010, pp. 234-243.

(Continued)

*Primary Examiner* — Bruck Kifle
*Assistant Examiner* — Kevin S Martin
(74) *Attorney, Agent, or Firm* — Fortem IP LLP

(57) ABSTRACT

The present technology relates to implantable depots for the local, sustained, controlled release of a therapeutic agent to treat cancer. An implantable depot may comprise a biodegradable polymer mixed with a locally acting chemotherapeutic agent. The depot may be configured to be implanted within a patient proximate cancerous tissue and, while implanted, provide sustained exposure of the chemotherapeutic agent at the treatment site.

11 Claims, 125 Drawing Sheets

(56) References Cited

U.S. PATENT DOCUMENTS

| | | | |
|---|---|---|---|
| 7,220,433 | B2 | 5/2007 | Cui et al. |
| 7,723,291 | B2 | 5/2010 | Beals et al. |
| 7,727,954 | B2 | 6/2010 | Mckay |
| 7,741,273 | B2 | 6/2010 | Mckay |
| 7,824,703 | B2 | 11/2010 | Scifert et al. |
| 7,947,301 | B2 | 5/2011 | Bischoff et al. |
| 7,993,390 | B2 | 8/2011 | Miller et al. |
| 8,067,026 | B2 | 11/2011 | Ranade et al. |
| 8,080,059 | B2 | 12/2011 | Fell |
| 8,153,149 | B2 | 4/2012 | Verity |
| 8,202,531 | B2 | 6/2012 | Mckay |
| 8,221,358 | B2 | 7/2012 | Mckay |
| 8,231,891 | B2 | 7/2012 | King |
| 8,246,571 | B2 | 8/2012 | Simonton et al. |
| 8,257,393 | B2 | 9/2012 | Cichocki |
| 8,357,388 | B2 | 1/2013 | Mckay |
| 8,420,600 | B2 | 4/2013 | Burch et al. |
| 8,430,852 | B2 | 4/2013 | Bischoff et al. |
| 8,470,360 | B2 | 6/2013 | Mckay |
| 8,523,569 | B2 | 9/2013 | Neshat |
| 8,524,267 | B2 | 9/2013 | Zanella et al. |
| 8,575,092 | B2 | 11/2013 | Domb |
| 8,591,531 | B2 | 11/2013 | Buevich et al. |
| 8,603,528 | B2 | 12/2013 | Kronenthal |
| 8,623,396 | B2 | 1/2014 | Gray et al. |
| 8,629,172 | B2 | 1/2014 | Mckay et al. |
| 8,632,839 | B2 | 1/2014 | Stopek et al. |
| 8,652,504 | B2 | 2/2014 | Li et al. |
| 8,652,525 | B2 | 2/2014 | Moses et al. |
| 8,663,192 | B2 | 3/2014 | Hester et al. |
| 8,697,117 | B2 | 4/2014 | Zilberman |
| 8,703,119 | B2 | 4/2014 | Yankelson et al. |
| 8,708,966 | B2 | 4/2014 | Allen et al. |
| 8,715,223 | B2 | 5/2014 | Mckay |
| 8,728,493 | B2 | 5/2014 | Burton et al. |
| 8,728,509 | B2 | 5/2014 | Mckay |
| 8,750,983 | B2 | 6/2014 | Bonutti |
| 8,758,798 | B2 | 6/2014 | Stopek et al. |
| 8,795,713 | B2 | 8/2014 | Makower et al. |
| 8,809,530 | B1 | 8/2014 | Wu et al. |
| 8,822,492 | B2 | 9/2014 | Schachter |
| 8,846,068 | B2 | 9/2014 | Wohabrebbi et al. |
| 8,865,205 | B2 | 10/2014 | Shalaby |
| 8,877,226 | B2 | 11/2014 | Zanella et al. |
| 8,889,173 | B2 | 11/2014 | Zanella et al. |
| 8,900,620 | B2 | 12/2014 | Fulmer et al. |
| 8,911,765 | B2 | 12/2014 | Moses et al. |
| 8,920,867 | B2 | 12/2014 | Stopek et al. |
| 8,951,552 | B2 | 2/2015 | Shalaby et al. |
| 8,956,642 | B2 | 2/2015 | Hobot et al. |
| 8,968,767 | B2 | 3/2015 | Mckay |
| 8,969,397 | B2 | 3/2015 | Burright et al. |
| 8,980,317 | B2 | 3/2015 | King |
| 8,999,368 | B2 | 4/2015 | Mcdonald et al. |
| 9,005,634 | B2 | 4/2015 | Mcdonald et al. |
| 9,011,965 | B2 | 4/2015 | Gan et al. |
| 9,023,114 | B2 | 5/2015 | Buevich et al. |
| 9,125,814 | B2 | 9/2015 | He et al. |
| 9,125,917 | B2 | 9/2015 | Mckay et al. |
| 9,132,087 | B2 | 9/2015 | Lichter et al. |
| 9,132,194 | B2 | 9/2015 | Mckay |
| 9,155,707 | B2 | 10/2015 | Ying et al. |
| 9,161,903 | B2 | 10/2015 | Drapeau et al. |
| 9,173,732 | B2 | 11/2015 | Langer et al. |
| 9,198,758 | B2 | 12/2015 | Mckay |
| 9,205,052 | B2 | 12/2015 | Kim et al. |
| 9,211,285 | B2 | 12/2015 | Mckay et al. |
| 9,265,733 | B2 | 2/2016 | Mckay |
| 9,283,283 | B2 | 3/2016 | Giammona et al. |
| 9,289,409 | B2 | 3/2016 | Zanella et al. |
| 9,295,462 | B2 | 3/2016 | Choy et al. |
| 9,302,903 | B2 | 4/2016 | Park et al. |
| 9,320,708 | B2 | 4/2016 | Scifert et al. |
| 9,351,924 | B2 | 5/2016 | Cho et al. |
| 9,352,137 | B2 | 5/2016 | Simonton et al. |
| 9,358,223 | B2 | 6/2016 | King |
| 9,375,420 | B2 | 6/2016 | King |
| 9,402,918 | B2 | 8/2016 | Koyakutty et al. |
| 9,402,973 | B2 | 8/2016 | Phillips et al. |
| 9,457,176 | B2 | 10/2016 | Lee et al. |
| 9,504,749 | B2 | 11/2016 | Mckay |
| 9,522,113 | B2 | 12/2016 | Spada et al. |
| 9,549,920 | B2 | 1/2017 | Wohabrebbi et al. |
| 9,566,241 | B2 | 2/2017 | Ravis et al. |
| 9,597,132 | B2 | 3/2017 | Houff |
| 9,610,194 | B2 | 4/2017 | De Juan et al. |
| 9,610,243 | B2 | 4/2017 | Clay et al. |
| 9,623,222 | B2 | 4/2017 | Mckay |
| 9,629,818 | B2 | 4/2017 | Nadkarni et al. |
| 9,655,994 | B2 | 5/2017 | Mckay |
| 9,668,974 | B2 | 6/2017 | Amselem et al. |
| 9,669,117 | B2 | 6/2017 | Campbell et al. |
| 9,694,079 | B2 | 7/2017 | Ottoboni et al. |
| 9,700,567 | B2 | 7/2017 | Zanella et al. |
| 9,724,300 | B2 | 8/2017 | Yamashita et al. |
| 9,764,066 | B2 | 9/2017 | Sim et al. |
| 9,821,091 | B2 | 11/2017 | Hossainy et al. |
| 9,833,548 | B2 | 12/2017 | Mckay et al. |
| 9,861,590 | B2 | 1/2018 | Stopek et al. |
| 9,987,233 | B2 | 6/2018 | Helliwell et al. |
| 11,202,754 | B2 | 12/2021 | Naga et al. |
| 11,224,570 | B2 | 1/2022 | Naga et al. |
| 12,303,619 | B2 | 5/2025 | Ruane et al. |
| 12,364,792 | B2 | 7/2025 | Naga et al. |
| 12,458,589 | B2 | 11/2025 | Naga et al. |
| 2001/0044651 | A1 | 11/2001 | Steinke et al. |
| 2001/0055607 | A1 | 12/2001 | Levin |
| 2002/0106410 | A1 | 8/2002 | Masters |
| 2003/0022876 | A1 | 1/2003 | Ashton et al. |
| 2003/0036803 | A1 | 2/2003 | Mcghan |
| 2003/0074055 | A1 | 4/2003 | Haverkost |
| 2003/0118649 | A1 | 6/2003 | Gao et al. |
| 2003/0152637 | A1 | 8/2003 | Chasin et al. |
| 2003/0157162 | A1 | 8/2003 | Krugner-Higby et al. |
| 2003/0190341 | A1 | 10/2003 | Shalaby et al. |
| 2003/0215496 | A1 | 11/2003 | Patel et al. |
| 2004/0109893 | A1 | 6/2004 | Chen et al. |
| 2004/0249441 | A1 | 12/2004 | Miller et al. |
| 2005/0019404 | A1 | 1/2005 | Sung et al. |
| 2005/0043786 | A1 | 2/2005 | Chu et al. |
| 2005/0048115 | A1 | 3/2005 | Mangena et al. |
| 2005/0152957 | A1 | 7/2005 | Cleary et al. |
| 2005/0158382 | A1 | 7/2005 | Cruz et al. |
| 2005/0206048 | A1 | 9/2005 | Ryu et al. |
| 2005/0266077 | A1 | 12/2005 | Royer |
| 2006/0034887 | A1 | 2/2006 | Pelissier |
| 2006/0052823 | A1 | 3/2006 | Mirizzi et al. |
| 2006/0079558 | A1 | 4/2006 | Aberg et al. |
| 2006/0079559 | A1 | 4/2006 | Aberg et al. |
| 2006/0269475 | A1 | 11/2006 | Ryu et al. |
| 2007/0071790 | A1 | 3/2007 | Ameer et al. |
| 2007/0134292 | A1 | 6/2007 | Suokas et al. |
| 2007/0173787 | A1 | 7/2007 | Huang et al. |
| 2007/0178138 | A1 | 8/2007 | Pal et al. |
| 2007/0258939 | A1 | 11/2007 | Lewis et al. |
| 2008/0089923 | A1 | 4/2008 | Burkstrand et al. |
| 2008/0095849 | A1 | 4/2008 | Wu et al. |
| 2008/0132922 | A1 | 6/2008 | Buevich et al. |
| 2008/0154241 | A1 | 6/2008 | Burkstrand et al. |
| 2008/0228193 | A1 | 9/2008 | Matityahu |
| 2008/0241212 | A1 | 10/2008 | Moses et al. |
| 2008/0311191 | A1 | 12/2008 | Nangia et al. |
| 2009/0076595 | A1 | 3/2009 | Lindquist et al. |
| 2009/0087380 | A1 | 4/2009 | Fasching et al. |
| 2009/0123508 | A1 | 5/2009 | Cheng et al. |
| 2009/0142400 | A1 | 6/2009 | Hiles et al. |
| 2009/0155326 | A1 | 6/2009 | Mack et al. |
| 2009/0177229 | A1 | 7/2009 | Gulotta et al. |
| 2009/0182425 | A1 | 7/2009 | Duda et al. |
| 2009/0198197 | A1 | 8/2009 | Bischoff et al. |
| 2009/0263321 | A1 | 10/2009 | Mcdonald et al. |
| 2009/0263441 | A1 | 10/2009 | Mckay |
| 2009/0263443 | A1 | 10/2009 | King |
| 2009/0263451 | A1 | 10/2009 | King |

(56) References Cited

U.S. PATENT DOCUMENTS

| | | | |
|---|---|---|---|
| 2009/0264472 | A1 | 10/2009 | Wohabrebbi et al. |
| 2009/0264477 | A1 | 10/2009 | Zanella et al. |
| 2009/0264489 | A1 | 10/2009 | Hildebrand et al. |
| 2009/0325879 | A1 | 12/2009 | Norton et al. |
| 2010/0055437 | A1 | 3/2010 | Fink et al. |
| 2010/0158970 | A1 | 6/2010 | Tipton et al. |
| 2010/0168808 | A1 | 7/2010 | Citron |
| 2010/0198278 | A1 | 8/2010 | Cobian et al. |
| 2010/0203100 | A1 | 8/2010 | Cobian et al. |
| 2010/0203102 | A1 | 8/2010 | Wohabrebbi |
| 2010/0222873 | A1 | 9/2010 | Atanasoska et al. |
| 2010/0249783 | A1 | 9/2010 | Trieu |
| 2011/0027331 | A1 | 2/2011 | Hobot |
| 2011/0060309 | A1 | 3/2011 | Lee et al. |
| 2011/0081422 | A1 | 4/2011 | Masinde et al. |
| 2011/0082545 | A1 | 4/2011 | Freund |
| 2011/0129801 | A1 | 6/2011 | Barman |
| 2011/0137243 | A1 | 6/2011 | Hossainy et al. |
| 2011/0152839 | A1 | 6/2011 | Cima et al. |
| 2011/0184037 | A1 | 7/2011 | Haddock et al. |
| 2011/0206752 | A1 | 8/2011 | Carreno et al. |
| 2011/0224245 | A1 | 9/2011 | Schachter |
| 2011/0281882 | A1 | 11/2011 | Zhang et al. |
| 2012/0009240 | A1 | 1/2012 | Stopek et al. |
| 2012/0097194 | A1 | 4/2012 | Mcdaniel et al. |
| 2012/0100192 | A1 | 4/2012 | Penhasi et al. |
| 2012/0114740 | A1 | 5/2012 | Garcia et al. |
| 2012/0165795 | A1 | 6/2012 | Seiler et al. |
| 2012/0239001 | A1 | 9/2012 | Barry et al. |
| 2012/0263761 | A1 | 10/2012 | Mcdonald et al. |
| 2012/0316199 | A1 | 12/2012 | Ward et al. |
| 2013/0018321 | A1 | 1/2013 | Mckay |
| 2013/0071463 | A1 | 3/2013 | Palasis et al. |
| 2013/0136811 | A1 | 5/2013 | Schachter |
| 2013/0158652 | A1 | 6/2013 | Palasis et al. |
| 2013/0164347 | A1 | 6/2013 | Gensini et al. |
| 2013/0261594 | A1 | 10/2013 | Stopek et al. |
| 2013/0280272 | A1 | 10/2013 | Trogden et al. |
| 2014/0052183 | A1 | 2/2014 | Freese |
| 2014/0065202 | A1 | 3/2014 | Ito |
| 2014/0072608 | A1 | 3/2014 | Logothetidis et al. |
| 2014/0086971 | A1 | 3/2014 | Hall et al. |
| 2014/0088347 | A1 | 3/2014 | Frigstad et al. |
| 2014/0105956 | A1 | 4/2014 | Banerjee et al. |
| 2014/0107159 | A1 | 4/2014 | Ebersole et al. |
| 2014/0170204 | A1 | 6/2014 | Desai et al. |
| 2014/0193466 | A1 | 7/2014 | Lawrence et al. |
| 2014/0193504 | A1 | 7/2014 | Wooley et al. |
| 2014/0214175 | A1 | 7/2014 | Barron et al. |
| 2014/0255464 | A1 | 9/2014 | Hakimimehr et al. |
| 2014/0271770 | A1 | 9/2014 | Clay et al. |
| 2014/0287053 | A1 | 9/2014 | Helliwell et al. |
| 2015/0018969 | A1 | 1/2015 | Fulmer et al. |
| 2015/0024031 | A1 | 1/2015 | Rabinow et al. |
| 2015/0024116 | A1 | 1/2015 | Matson et al. |
| 2015/0038415 | A1 | 2/2015 | Zupancich |
| 2015/0039097 | A1 | 2/2015 | Biris |
| 2015/0150988 | A1 | 6/2015 | Shalaby et al. |
| 2015/0246001 | A1 | 9/2015 | Zupancich et al. |
| 2015/0272877 | A1 | 10/2015 | Shi et al. |
| 2015/0290170 | A1 | 10/2015 | Liu et al. |
| 2015/0342964 | A1 | 12/2015 | Gray et al. |
| 2016/0038632 | A1 | 2/2016 | Shah et al. |
| 2016/0089335 | A1 | 3/2016 | Ohri et al. |
| 2016/0136094 | A1 | 5/2016 | Criscione et al. |
| 2016/0144040 | A1 | 5/2016 | Cheng |
| 2016/0144067 | A1 | 5/2016 | Armbruster et al. |
| 2016/0151257 | A1 | 6/2016 | Klingman |
| 2016/0184340 | A1 | 6/2016 | Kritikou |
| 2016/0287367 | A1 | 10/2016 | Rontal |
| 2016/0331853 | A1 | 11/2016 | Taub |
| 2016/0339152 | A1 | 11/2016 | Bonutti et al. |
| 2016/0354309 | A1 | 12/2016 | Heitzmann et al. |
| 2017/0014337 | A1 | 1/2017 | Walsh |
| 2017/0079929 | A1 | 3/2017 | Davey |
| 2017/0112935 | A1 | 4/2017 | Holzer et al. |
| 2017/0128632 | A1 | 5/2017 | Mcjames |
| 2017/0182168 | A1 | 6/2017 | Ottoboni et al. |
| 2017/0196499 | A1 | 7/2017 | Hunter |
| 2017/0196508 | A1 | 7/2017 | Hunter |
| 2017/0216597 | A1 | 8/2017 | Hou et al. |
| 2017/0239183 | A1 | 8/2017 | Reynolds et al. |
| 2017/0246117 | A1 | 8/2017 | Helliwell et al. |
| 2017/0281778 | A1 | 10/2017 | Ottoboni et al. |
| 2018/0092855 | A1 | 4/2018 | Kim et al. |
| 2018/0193537 | A1 | 7/2018 | Honglei et al. |
| 2019/0351108 | A1 | 11/2019 | Wang et al. |
| 2020/0009293 | A1 | 1/2020 | Teu et al. |
| 2020/0246255 | A1 | 8/2020 | Naga et al. |
| 2020/0368398 | A1 | 11/2020 | Naga et al. |
| 2021/0186868 | A1 | 6/2021 | Naga et al. |
| 2021/0308338 | A1 | 10/2021 | Ruane et al. |
| 2021/0361827 | A1 | 11/2021 | Teu et al. |
| 2022/0072207 | A1 | 3/2022 | Wang et al. |
| 2022/0117885 | A1 | 4/2022 | Naga et al. |
| 2022/0183963 | A1 | 6/2022 | Kim et al. |
| 2022/0183964 | A1 | 6/2022 | Naga et al. |
| 2025/0319236 | A1 | 10/2025 | Ruane et al. |

FOREIGN PATENT DOCUMENTS

| | | | | |
|---|---|---|---|---|
| CN | 1344156 | A | 4/2002 | |
| CN | 1655738 | A | 8/2005 | |
| CN | 1762331 | A | 4/2006 | |
| CN | 102000366 | A | 4/2011 | |
| CN | 102341133 | A | 2/2012 | |
| CN | 103405748 | A | 11/2013 | |
| CN | 103703079 | A | 4/2014 | |
| CN | 104474595 | A | 4/2015 | |
| CN | 104474595 | B | 1/2017 | |
| CN | 106344521 | A | 1/2017 | |
| EP | 0311065 | B1 | 2/1994 | |
| EP | 1868662 | B1 | 5/2010 | |
| EP | 2197419 | A2 | 6/2010 | |
| EP | 2209469 | A2 | 7/2010 | |
| EP | 2229171 | A2 | 9/2010 | |
| EP | 2262481 | A2 | 12/2010 | |
| EP | 2285363 | A2 | 2/2011 | |
| EP | 2288352 | A2 | 3/2011 | |
| EP | 2288353 | A2 | 3/2011 | |
| EP | 2368522 | A1 | 9/2011 | |
| EP | 2444074 | A2 | 4/2012 | |
| EP | 2444075 | A2 | 4/2012 | |
| EP | 2696851 | A1 | 2/2014 | |
| EP | 2719717 | A1 | 4/2014 | |
| EP | 3000463 | A1 | 3/2016 | |
| EP | 3085359 | A1 | 10/2016 | |
| EP | 2195073 | B1 | 3/2017 | |
| EP | 2444073 | B1 | 5/2017 | |
| EP | 2911647 | B1 | 3/2018 | |
| EP | 3518999 | A1 | 8/2019 | |
| GB | 201505527 | | 5/2015 | |
| JP | H02119866 | A | 5/1990 | |
| JP | 2006512312 | A | 4/2006 | |
| JP | 2009511196 | A | 3/2009 | |
| JP | 2012017329 | A | 1/2012 | |
| JP | 2015522649 | A | 8/2015 | |
| JP | 2016528949 | A | 9/2016 | |
| JP | 6824188 | B2 | 1/2021 | |
| WO | 9509613 | A1 | 4/1995 | |
| WO | 9858653 | A1 | 12/1998 | |
| WO | 9936071 | A1 | 7/1999 | |
| WO | WO-2004089291 | A2 * | 10/2004 | ............. A61P 35/00 |
| WO | 2006099409 | A3 | 3/2007 | |
| WO | 2007047420 | A2 | 4/2007 | |
| WO | 2008061355 | A1 | 5/2008 | |
| WO | 2008127411 | A1 | 10/2008 | |
| WO | 2008131089 | A2 | 10/2008 | |
| WO | 2008136856 | A2 | 11/2008 | |
| WO | 2009069151 | A2 | 6/2009 | |
| WO | 2009113972 | A2 | 9/2009 | |
| WO | 2009129432 | A2 | 10/2009 | |
| WO | 2009129433 | A2 | 10/2009 | |
| WO | 2009129439 | A2 | 10/2009 | |

(56) References Cited

FOREIGN PATENT DOCUMENTS

| | | | |
|---|---|---|---|
| WO | 2009129453 | A2 | 10/2009 |
| WO | 2009129456 | A2 | 10/2009 |
| WO | 2009129460 | A2 | 10/2009 |
| WO | 2009129464 | A2 | 10/2009 |
| WO | 2009129491 | A2 | 10/2009 |
| WO | 2009129494 | A2 | 10/2009 |
| WO | 2009129509 | A2 | 10/2009 |
| WO | 2009129519 | A2 | 10/2009 |
| WO | 2009129527 | A2 | 10/2009 |
| WO | 2009129531 | A2 | 10/2009 |
| WO | 2010016832 | A1 | 2/2010 |
| WO | 2010075298 | A2 | 7/2010 |
| WO | 2010088697 | A2 | 8/2010 |
| WO | 2011098578 | A2 | 8/2011 |
| WO | 2011139594 | A2 | 11/2011 |
| WO | 2012064963 | A1 | 5/2012 |
| WO | 2012142318 | A1 | 10/2012 |
| WO | 2013013123 | A1 | 1/2013 |
| WO | 2013040325 | A1 | 3/2013 |
| WO | 2014059558 | A1 | 4/2014 |
| WO | 2014064140 | A1 | 5/2014 |
| WO | 2014066653 | A1 | 5/2014 |
| WO | 2014137454 | A1 | 9/2014 |
| WO | 2014172572 | A1 | 10/2014 |
| WO | 2014204708 | A1 | 12/2014 |
| WO | 2015015278 | A1 | 2/2015 |
| WO | 2015135907 | A1 | 9/2015 |
| WO | 2016123352 | A1 | 8/2016 |
| WO | 2016159885 | A1 | 10/2016 |
| WO | 2017019829 | A1 | 2/2017 |
| WO | 2017034363 | A1 | 3/2017 |
| WO | 2017075232 | A1 | 5/2017 |
| WO | 2017146819 | A1 | 8/2017 |
| WO | 2018009637 | A1 | 1/2018 |
| WO | 2018063096 | A1 | 4/2018 |
| WO | 2018067882 | A1 | 4/2018 |
| WO | 2018172494 | A1 | 9/2018 |
| WO | 2018227293 | A1 | 12/2018 |
| WO | 2019071243 | A1 | 4/2019 |
| WO | 2019136490 | A1 | 7/2019 |
| WO | 2019221853 | A8 | 11/2019 |
| WO | 2020046973 | A1 | 3/2020 |
| WO | 2020047013 | A1 | 3/2020 |
| WO | 2020210764 | A1 | 10/2020 |
| WO | 2020210770 | A2 | 10/2020 |
| WO | 2021178930 | A1 | 9/2021 |
| WO | 2022082196 | A1 | 4/2022 |
| WO | 2023056422 | A1 | 4/2023 |

OTHER PUBLICATIONS

De Clercq , et al., "Preclinical evaluation of local prolonged release of paclitaxel from gelatin microspheres for the prevention of recurrence of peritoneal carcinomatosis in advanced ovarian cancer", Science Reports, vol. 9, No. 14881, Oct. 16, 2019, pp. 1-19.

Drager , et al., "Prolonged Intercostal Nerve Blockade in Sheep Using Controlled-release of Bupivacaine and Dexamethasome from Polymer Microspheres", Anesthesiology, vol. 89, No. 4, Oct. 1998, pp. 969-979.

Epstein-Barash , et al., "Prolonged duration local anesthesia with minimal toxicity", PNAS, vol. 106, No. 17, Apr. 28, 2009, pp. 7125-7130.

Farid , et al., "Promote Recurrent Aphthous Ulcer Healing with Low Dose Predisolone Bilayer Mucoadhesive Buccal Film", Current Drug Delivery, vol. 14, No. 1, Jan. 9, 2017, pp. 123-125.

Fites , "Controlled Drug Release through Polymeric Films", Journal of Pharmaceutical Sciences, vol. 59, No. 5, May 1970, pp. 610-613.

Friess, Wolfgang , "Review Article: Collagen—biomaterial for drug delivery", European Journal of Pharmaceutics and Biopharmaceutics, vol. 45, 1998, pp. 113-136.

Goindi , et al., "Development of Novel Ionic Liquid-Based Microemulsion Formulation for Dermal Delivery of 5-Fluorouracil", AAPS PharmSciTech 2014 15(4):810-821 (Year: 2014).

Guo , et al., "A type of esophageal stent coating composed of one 5-fluorouracil-containing EVA layer and one drug-free protective layer: In vitro release, permeation and mechanical properties", Journal of Controlled Release 2007 118:318-324 (Year: 2007).

Hong, Y. , et al., "Generating Elastic, Biodegradable Polyurethane/Poly(lactide-co-glycolide) Fibrous Sheets with Controlled Antibiotic Release via Two-Stream Electrospinning", Biomacromolecules, 2008, 1200-1207.

Irfan , et al., "Orally disintegrating films: A modern expansion in drug delivery system", Saudi Pharmaceutical Journal, vol. 24, 2016, pp. 537-546.

Ito , et al., "Three-Layered Microcapsules as a Long-Term Sustained Release Injection Preparation", International Journal of Pharmaceuticals, vol. 384, No. 1-2, Jan. 1, 2010, pp. 53-59.

Jain , et al., "Injectable formulations of poly(lactic acid) and its copolymers in clinical use", Advanced Drug Delivery Reviews, Elsevier, Amsterdam, NL, vol. 107, Jul. 14, 2016 (Jul. 14, 2016), pp. 213-227, XP029839856, ISSN: 0169-409X, DOI: 10.1016/J.ADDR.2016.07.002, Jul. 14. 2016, pp. 213-227.

Jethara , et al., "Sustained Release Drug Delivery Systems: a Patent Overview", Aperito Journal of Drug Designing and Pharmacology, 2014: 1:1, 15 Pages.

Jin , et al., "A PTX/nitinol stent combination with temperature-responsive phase-change 1-hexadecanol for magnetocaloric drug delivery: Magnetocaloric drug release and esophagus tissue penetration", Biomaterials, 153; Oct. 27, 2017, pp. 49-58.

Kanagale , et al., "Formulation and Optimization of Porous Osmotic Pump-based Controlled Release System and Oxybutynin", AAPA PharmSciTech 2007, vol. 8, No. 3, Article 53, 7 Pages.

Karki , et al., "Thin films as an emerging platform for drug delivery", Asian Journal of Pharmaceutical Sciences, vol. 11, No. 5, 2016, pp. 559-574.

Kau , et al., "Sustained Release of Lidocaine from Solvent-Free Biodegradable Poly [(d,l)-Lactide-co-Glycolide] (PLGA): In Vitro and In Vivo Study", Materials, vol. 7, 2014, pp. 6660-6676.

Knecht , et al., "Mechanical testing of fixation techniques for scaffold-based tissue-engineered grafts", Journal of Biomedical Materials Research Part B: Applied Biomaterials; vol. 83, No., 1, Feb. 22, 2007, pp. 50-57.

Kolek, Matthew J., et al., "Use of an Antibacterial Envelope is Associated with Reduced Cardiac Implantable Electronic Device Infections in High-Risk Patients", Pacing and Clinical Electrophysiology, vol. 36, Mar. 2013, 354-361.

Lee , et al., "Gemcitabine-releasing polymeric films for covered self-expandable metallic stent in treatment of gastrointestinal cancer", International Journal of Pharmaceutics, vol. 427, 2012, pp. 276-283.

Lee , et al., "Results of a model analysis of the cost-effectiveness of liraglutide versus exenatide added to metformin, glimepiride, or both for the treatment of type 2 diabetes in the United States", Clinical Therapeutics, vol. 32, No. 10, 2010, 12 Pages.

Lei , et al., "5-Fluorouracil-loaded multilayered films for drug controlled releasing stent application: Drug release, microstructure, and ex vivo permeation behaviors", Journal of Controlled Release, vol. 146; 2010-05-23; pp. 45-53.

Liu , et al., "Evaluation of two polymeric blends (EVA/PLA and EVA/PEG) as coating film materials for paclitaxel-eluting stent application", Journal of Materials Science: Materials in Medicine, vol. 22, No. 2, Feb. 1, 2011 (Feb. 1, 2011), pp. 327-337.

Liu , et al., "Less harmful acidic degradation of poly(lactic-co-glycolic acid) bone tissue engineering scaffolds through titania nanoparticle addition", International Journal of Nanomedicine; vol. 1, No. 4, Jan. 1, 2006, pp. 541-545.

Liu , et al., "Paclitaxel or 5-fluorouracil/esophageal stent combinations as a novel approach for the treatment of esophageal cancer", Biomaterials, vol. 53, Jun. 1, 2015, pp. 592-599.

Mcalvin , et al., "Local Toxicity from Local Anesthetic Polymeric Microparticles", Anesth Analg., vol. 116, No. 4, Apr. 2013, pp. 794-803.

NIHR HSC , et al., "AIGISRx@ Antibacterial Envelope for Preventing Infection in Implanted Cardiac Devices", Birmingham: NIHR Horizon Scanning Centre (NIHR HSC), Horizon Scanning Review 2012, 1 Page.

(56) References Cited

OTHER PUBLICATIONS

Ohri , "Inhibition by Local Bupivacaine-Releasing Microspheres of Acute Postoperative Pain from Hairy Skin Incision", URL: www.anesthesia-analgesia.org, vol. 117, No. 3, Sep. 2013, 14 Pages.
Padera , et al., "Local myotoxicity from sustained release of bupivacaine from microparticles", Anesthesiology 2008, vol. 108, No. 5, May 2008, pp. 921-928.
Pek , et al., "Sustained Release of Bupivacaine for Post-Surgical Pain Relief Using Core-Shell Microspheres", Journal of Materials Chemistry B, 2014, 9 Pages.
Rong , et al., "PLC films incorporated with paclitaxel/5-flourouracil: Effects of formulation and special architecture on drug release", International Journal of Pharmaceutics, vol. 427, No. 2; The abstract, p. 243 the Section 2.2, Table 3, p. 247 the Section 3.3.3, and p. 250 the Section 4, 2012, pp. 242-251.
Roy , et al., "Effects of plasticizers and surfactants on the film forming properties of hydroxypropyl methylcellulose for the coating of diclofenac sodium tablets", Saudi Pharmaceutical Journal, vol. 17, 2009, pp. 233-241.
Santamaria , "Drug Delivery Systems for Prolonged Duration Local Anesthesia", Materials Today, vol. 20, No. 1, Jan./Feb. 2017., 22 Pages.
Seo , et al., "Polyurethane membrane with porous surface for controlled drug release in drug eluting stent", Biomaterials Research, vol. 18:15, 2014, 5 Pages.
Shaikh , "Engineering Stent Based Delivery System for Esophageal Cancer Using Docetaxel", Molecular Pharmaceutics, vol. 12, No. 7, Jul. 6, 2015, pp. 2305-2317.
Shipton, Edward A., "New Formulations of Local Anaesthetics—Part I", Anesthesiology Research and Practice, 2012, 12 Pages.
Sokolsky-Papkov , et al., "Long-Acting Poly (DL: Lactic Acid-Castor Oil) 3:7-Bupivacaine Formulation: Effect of Hydrophobic Additives", Pharmaceutical Research, Jun. 2011, 10 Pages.
Tallury , et al., "Effects of solubilizing surfactants and loading of antiviral, antimicrobial, and antifungal drugs on their release rates from ethylene vinyl acetate copolymer", Dental Materials 2007 23:977-982 (Year: 2007).
Tanabe , et al., "Controlled Indomethacin Release from Mucoadhesive Film: In Vitro and Clinical Evaluations", Yakugaku Zasshi Journal of the Pharmaceutical Society of Japan, vol. 128, No. 11, Nov. 1, 2008, pp. 1673-1679.
Tarakji , et al., "Cardiac implantable electronic device infections: Presentation, management, and patient outcomes", Heart Rhythm, vol. 7, No. 8, Aug. 2010, 6 Pages.
Voigt , et al., "Continued rise in rates of cardiovascular implantable electronic device infections in the United States; temporal trends and causative insights", PACE, vol. 33, Apr. 2010, 6 Pages.
Weiniger, C. F. , "Extended release formulations for local anaesthetic agents", Anaesthesia 2012, vol. 67, No. 8, pp. 906-916.
Yamamura , et al., "Pain Relief of Oral Ulcer by Dibucaine-film", Elsevier Science Publishers, Amsterdam, NL, vol. 33, 1999, pp. 625-626.
Yan , et al., "Towards nanoporous polymer thin film-based drug delivery systems", Thin Solid Films, vol. 517, 2009, pp. 1794-1798.
Yuan , et al., "Fabrication of a Delaying Biodegradable Magnesium Alloy-Based Esophageal Stent via Coating Elastic Polymer", Materials, vol. 9, No. 384, 2016, pp. 1-11.
Zorzetto, et al., "From micro-to nanostructured implantable device for local anesthetic delivery", International Journal of Nanomedicine, Jun. 8, 2016, pp. 2695-2709.

* cited by examiner

Fig. 2 Scanning electron microscope picture of a $_{DL}$-PLGA (50:50) tablet after 20 days of incubation in phosphate buffer. pH 7.4 at 37°C. (From Ref.[17].)

*taken from Avgoustakis, *K., Synthesis and Evaluation of Some Poly(Lactide-co-Glycolides) for Use in Sustained Release Tablets*, Ph.D. thesis, University of London, 1992.

| Condition/Disease | Therapeutic Agent | Duration of Release | Placement |
|---|---|---|---|
| • **Pneumonitis** | • Glucocorticoids such as Prednisone = 5-1000 mg/kg | • 2 weeks | • Adjacent to lung or respiratory system |
| • **Xerostomia** | • Pilocarpine (10-1000 mg)<br>• Cevimeline (50-2000 mg) | • 2 weeks<br>• 2 weeks | • Adjacent to salivary glands<br>• Adjacent to salivary glands |
| • **Mucositis** | • Palifermin (10-3000 ug/kg) | • 2 weeks | • The oral cavity |
| • **Esophagitis** | • Omeprazole (10-5000 mg) | • 2 weeks | • Esophagus |
| • **Proctitis** | • Sucralfate (14-28 gr per 10-20 ml)<br>• Mesalamine (5-50 gr)<br>• Mesalazine (5-50 gr)<br>• Sulfasalazine (5-50 gr)<br>• Metronidazole (1-10 gr)<br>• Betamethasone (50-300 mg)<br>• Hydrocortisone (1-10 gr) | • 2 weeks<br>• 1 week<br>• 1 week<br>• 1 week<br>• 1 week<br>• 1 week<br>• 1 weeks | • Rectum |

*FIG. 71*

Frontal section of bulbous portion of spongy urethra schematically extended

THE FOUNDRY®

FIGS. 103-1 to 103-10
Mouse Xenograft
Tumor Studies

THE FOUNDRY®

Formulation Selection Study

FIG. 103-1

- Objective
  - Evaluate efficacy potential of all FT2 drug depot formulations
- Subcutaneous xenograft tumor mouse model
  - LNCaP androgen-dependent prostate cancer cell line implanted ($5x10^6$ cells/100 μL) into flank of adult NSG male mice (n=91 mice total)
  - Tumor volumes were measured twice a week post-treatment using a digital caliper and calculated by the formula Width x Width x Length / 2.
  - Initial tumor volume = $133 \pm 50$ $mm^3$ (mean $\pm$ SD tumor volume at depot implantation)
  - All mice received 1 cm of drug or polymer depot (1 cm of each drug for combo therapy), or no treatment
  - Drug depots & delivery system manufactured by Orchid Medical (Singapore)

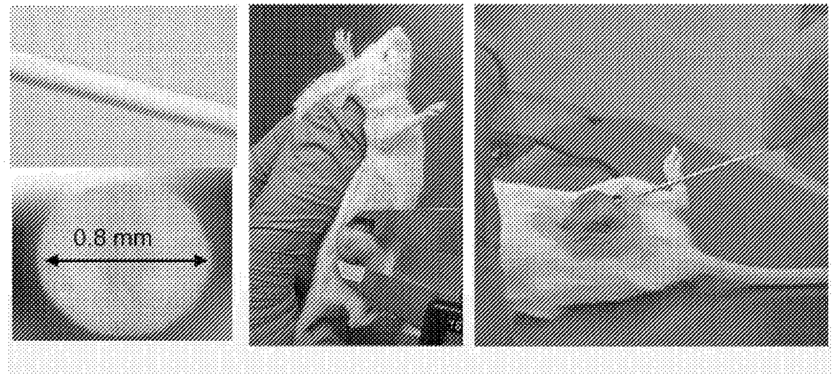

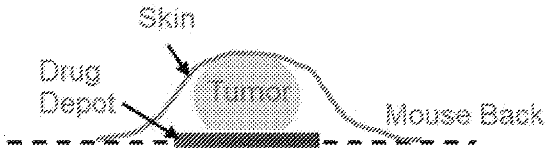

Drug depots were centrally placed underneath the tumor by pulling back on the loader tool while holding the plunger fixed in place (no force exerted on the depot).

Confidential and Proprietary |

THE FOUNDRY®

Study Design

FIG. 103-2

| # | Study Arm[a] | # of Mice | Tumor Measurement Timepoints | Terminal Timepoint | Data Output |
|---|---|---|---|---|---|
| 1 | Docetaxel A 1X | 5 | Pre/Post-treatment: 2x/week (3-4d intervals) | 45 days after treatment or Tumor burden limit (≤3000 $mm^3$)[b] | Tumor Dimensions Drug Remaining |
| 2 | Docetaxel B 1X | 5 | | | |
| 3 | Docetaxel C 1X | 5 | | | |
| 4 | Docetaxel A 2X | 5 | | | |
| 5 | Docetaxel B 2X | 5 | | | |
| 6 | Docetaxel C 2X | 5 | | | |
| 7 | Doce A-Bicalutamide | 5 | | | |
| 8 | Doce C 2X – Bicalutamide | 5 | | | |
| 9 | Doce A-Enzalutamide | 6 | | | |
| 10 | Doce C 2X – Enzalutamide | 5 | | | |
| 11 | Bicalutamide | 10 | | | |
| 12 | Enzalutamide | 10 | | | |
| 13 | Polymer Only | 10 | | | |
| 14 | No Implant | 10 | | | |
| Total # of Mice | | 91 | | | |

a. 1X, 2X and 4X indicates 1-cm, 2-cm and 4-cm total length of depot implanted, respectively.

b. Tumor volumes and tumor burden limits are calculated by Width x Width x Length/2

Confidential and Proprietary

THE FOUNDRY®

Drug Depot Formulations & Delivery System

FIG. 103-3

| Formulation Attributes | Docetaxel A* | Docetaxel B* | Docetaxel C* | Bicalutamide | Enzalutamide | Polymer Only |
|---|---|---|---|---|---|---|
| Lot Number | RD-FT2-041<br>RD-FT2-042 | RD-FT2-043 | RD-FT2-044 | RD-FT2-045 | RD-FT2-046 | RD-FT2-047 |
| Depot Dimensions (OD x L, mm) | 0.8 x 5** | 0.8 x 5** | 0.8 x 5** | 0.8 x 10 | 0.8 x 10 | 0.8 x 10 |
| PLG Lactide to Glycolide Ratio | 50:50 | 50:50 | 75:25 | 50:50 | 50:50 | 50:50 |
| PLG Inherent Viscosity (dL/g) | 0.6 | 1 | 0.2 | 0.6 | 0.6 | 0.6 |
| PEG10K:PLG:API | 5:5:40 | 3:7:40 | 1:9:40 | 5:5:40 | 5:5:40 | 1:1 |
| Total Drug Content (mg/cm) | 3.20±0.12 | 3.28±0.20 | 3.10±0.12 | 4.84±0.24 | 4.20±0.09 | NA |

* Docetaxel A, B, and C formulations were designed to have modest differences in drug release rate, which was shown in vitro. A was the fastest, B was in the middle, and C was the slowest.

** All Docetaxel depots were 5mm in length. Shorter depots used to minimize the potential for skin ulcerations when used on small tumors

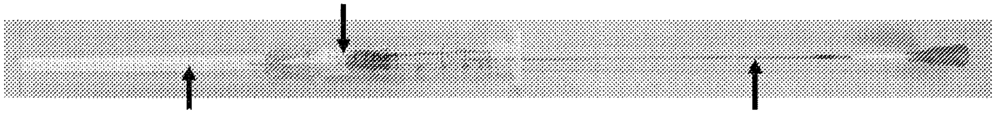

All delivery systems with pre-loaded depots were packaged in individually sealed foil pouches and E-beam sterilized at 30 kGy by contract sterilizer Confidential and Proprietary

THE FOUNDRY®

Docetaxel In Vitro Release Confirms Relative Release Rate Order

FIG. 103-4

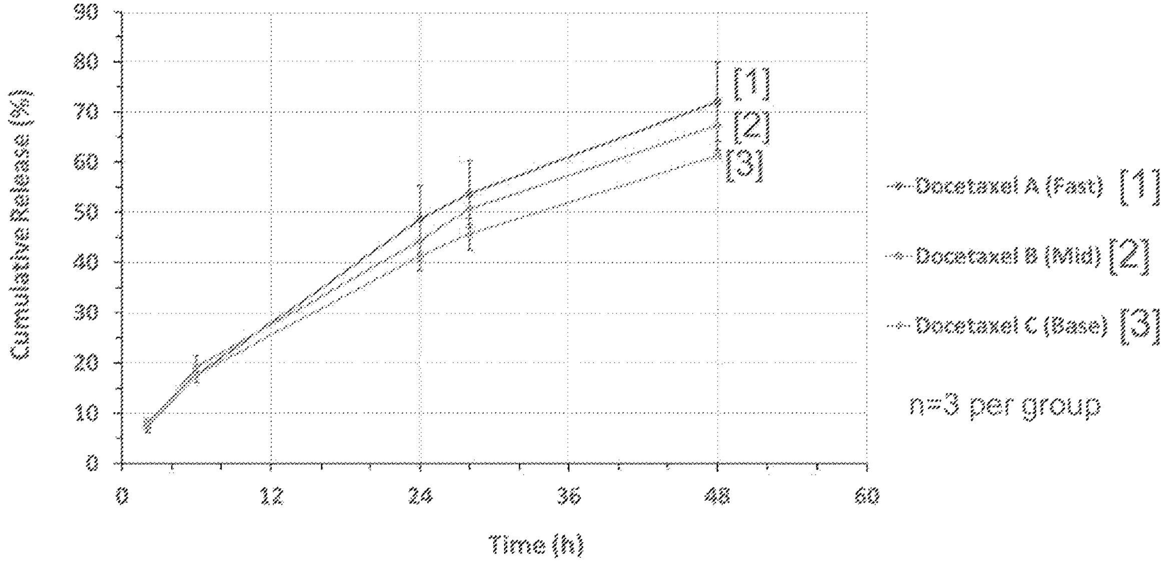

- Accelerated release medium (PBS/EtOH 37.5% @ 37°C)
  - Main purpose is for quick evaluation of prototype formulations, not predictive of in vivo drug release (separately evaluated from tissue drug concentrations)
  - Demonstrates near zero-order release
  - In vitro release rates of Fast, Mid, and Base, although comparable, were observed in expected order up to 48h Confidential and Proprietary

THE FOUNDRY®

Bicalutamide and Enzalutamide Similarly Demonstrate Near Zero Order Release Profiles In Vitro

- Accelerated release medium (PBS/EtOH 37.5% @ 37°C)
  - Main purpose is for quick evaluation of prototype formulations, not predictive of in vivo drug release (separately evaluated from tissue drug concentrations)
  - Demonstrates near zero-order release

THE FOUNDRY®

Mice Study Data Summary

- All study arms containing docetaxel demonstrate significant tumor response
- Tumors treated with anti-androgen monotherapy behave similarly to controls Final study timepoint is 45±3 days. Plotted data points represent at least n=3 mice per group.

THE FOUNDRY®

Bicalutamide and Enzalutamide In Vivo Drug Release

In vivo drug release using antiandrogens demonstrate:

- Zero-order release kinetics out to 45 days
- Sustained doses of 32.8 mcg/day (bicalutamide) and 23.7 mcg/day (enzalutamide) were delivered to the xenograft tumors

THE FOUNDRY®

Docetaxel A Formulation is the Lead Candidate for FIM in Prostate Cancer Opportunity

FIG. 103-10

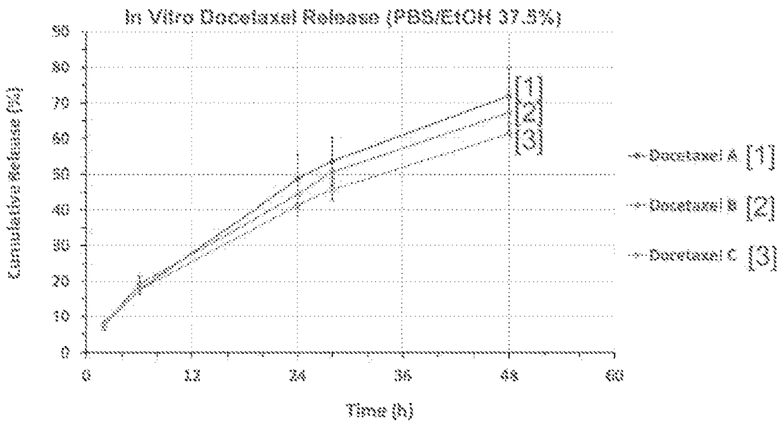

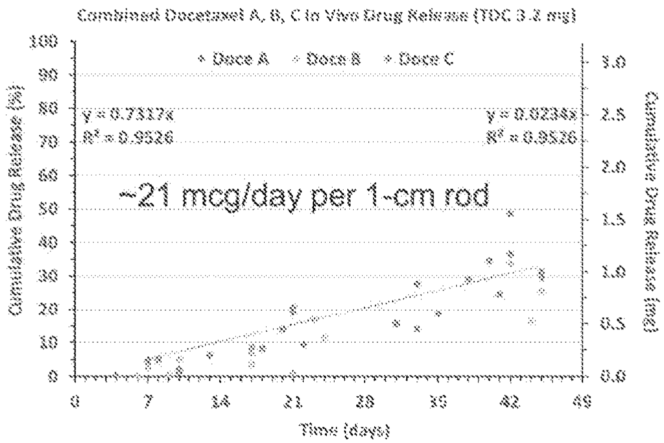

- Both in vitro (accelerated medium) and in vivo drug release data for Doce A, B, C demonstrated similar release profiles between the 3 formulations
- In vivo zero-order release profile shows ~30% (~1mg) drug released by 1.5 months
- Doce A formulation is selected to move forward based on study results
  - Doce A,B, or C could be chosen since they exhibited similar in vitro/ in vivo release kinetics
  - Doce A was the formulation used in the canine prostate study (pilot safety)
  - Drug dosage to the tumor/prostate will be adjustable with the number of depots used

THE FOUNDRY®

FIGS. 104-1 to 104-9
Canine Prostate Study

THE FOUNDRY®

Pilot Safety Study

FIG. 104-1

- Main objectives for this first attempt were to evaluate surgical approach, depot implantation and necropsy procedures in the canine model.
- Objectives for preliminary safety evaluation
  - Dose range (6, 8, 10 cm of docetaxel depot) safety study
    - Systemic toxicities (plasma drug concentration)
    - Local drug concentrations and toxicities (tissue drug concentration and histology)
    - Control = 5 needle punctures (R half prostate) + 5 polymer only depots (L half prostate)
- Intraprostatic canine model
  - Adult healthy male beagles (age 3-4 years; n=4 dogs total)
  - Sacrifice Timepoints = 7 and 28 days
  - PK Timepoints = 0, 1, 2, 3, 6h, 1, 3, 7, 14, 21, 28d
  - Depot implantation performed via open abdominal surgery under general anesthesia
  - Drug depots & delivery system manufactured by Orchid Medical (Singapore)

THE FOUNDRY®

Study Design

FIG. 104-2

| Group | Device | Depot Length/ Animal (cm) | Dosage (mg) | Evaluations | # of Animals | |
|---|---|---|---|---|---|---|
| | | | | | Day 8±1 | Day 28±1 |
| 1 | Drug Depots | 6 | 19.2 | Bioanalytical (plasma + tissue PK)/ Histopathology | 0 | 1 |
| 2 | Drug Depots | 8 | 25.6 | Bioanalytical (plasma + tissue PK)/ Histopathology | 1 | 0 |
| 3 | Drug Depots | 10 | 32.0 | Bioanalytical (plasma + tissue PK)/ Histopathology | 0 | 1 |
| 4* | Controls (Polymer Depots and Needle Punctures) | 5 | 0 | Bioanalytical (plasma only)/ Histopathology | 1 | 1 |
| 5 | Drug Depot | 1 | 3.2 | Bioanalytical (plasma + tissue PK) | 1 | 1 |

*Implantation of n=5 polymer depots and n=5 needle punctures per each half prostate, respectively.

THE FOUNDRY®

TP-0004 Drug Depot Formulations & Delivery System

FIG. 104-3

| Formulation Attributes | Docetaxel A | Polymer Only |
|---|---|---|
| Lot Number | RD-FT2-041 | RD-FT2-047 |
| Depot Dimensions (OD x L, mm) | 0.8 x 5* | 0.8 x 10 |
| PLG Lactide to Glycolide Ratio | 50:50 | 50:50 |
| PLG Inherent Viscosity (dL/g) | 0.6 | 0.6 |
| PEG10K:PLG:API | 5:5:40 | 1:1 |
| Total Drug Content (mg/cm) | 3.20±0.12 | NA |

* All Docetaxel depots were 5mm in length as used in mouse tumor model. Docetaxel A depots were implanted end-to-end in the canine prostate for each cm.

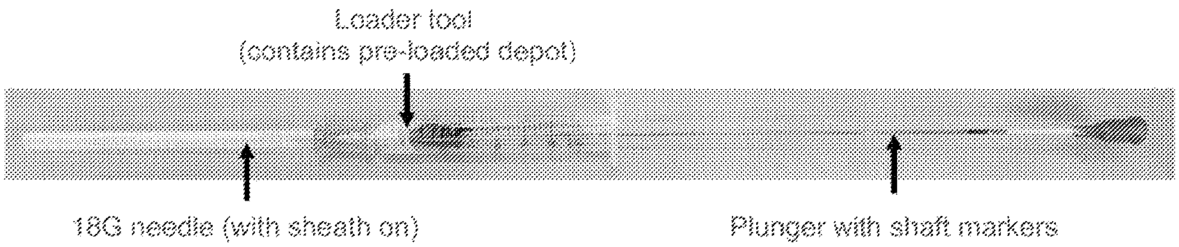

All delivery systems with pre-loaded depots were packaged in individually sealed foil pouches and E-beam sterilized at 30 kGy by contract sterilizer.

THE FOUNDRY®

Minimal Transient Systemic Drug Exposure

FIG. 104-4

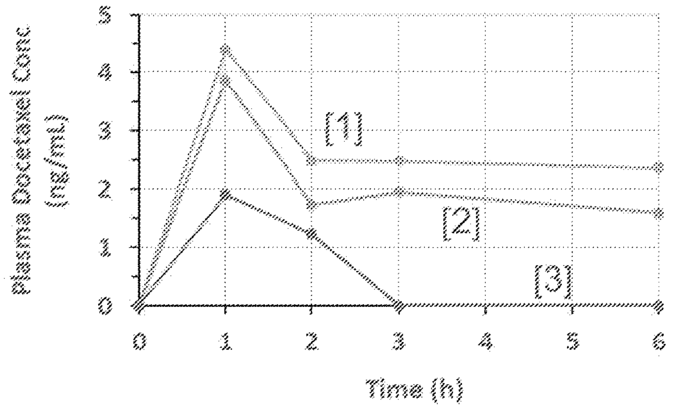

- All 3 animals show $C_{max}$ (1.9 - 4.4 ng/ml) occurring at 1 hour post-implantation (top plot) and BLQ (1 ng/mL) on or after 7 days (bottom plot).
- As a comparison, $C_{max}$ for standard regimen of IV docetaxel in humans is 1300 – 4000 ng/mL.[1]
- BLQ (below limit of quantitation) = 1 ng/mL

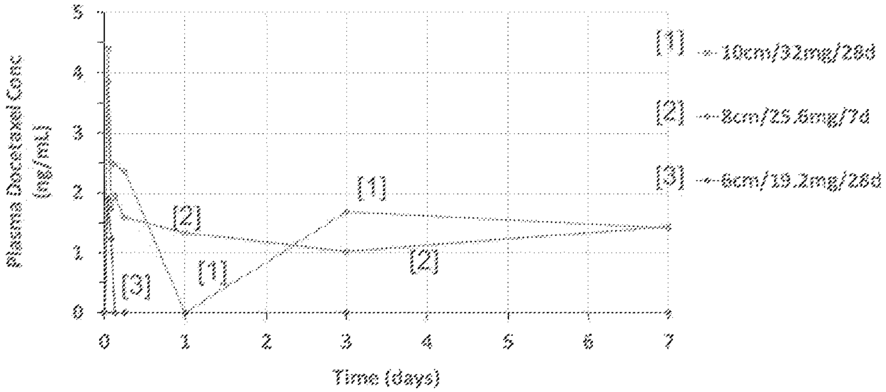

Note: Dog prostate volume is ~25% of human prostate (avg size of prostate cancer patients), therefore 6-cm (19.2 mg), 8-cm (25.6 mg), and 10-cm (32 mg) dosages in dog prostate are approximately equivalent to 24 (76.8 mg), 32 (102.4 mg), and 40-cm (128 mg) dosages in human prostate, which are much higher than expected to be used in humans.

1. Kenmotsu H and Tanigawara Y. Pharmacokinetics, dynamics, and toxicity of docetaxel: why the Japanese dose differs from the western dose. *Cancer Sci*, 2015.

THE FOUNDRY®

High Local Drug Exposure Maintained thru 28 Days

FIG. 104-5

Left Half Prostate (R half prostate was processed for histology)

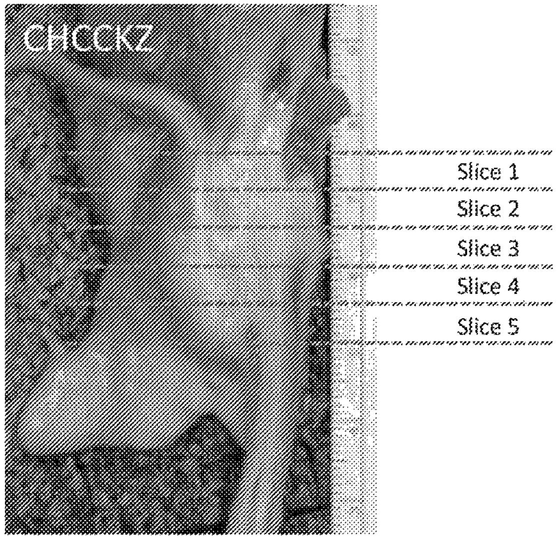

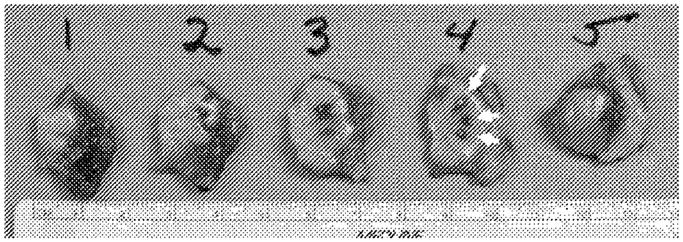

White arrows point to depot locations on prostate slice #4. Depots traverse multiple slices and there may be different number of depots traversing each prostate slice.

| Local Tissue Docetaxel Concentration* (ng/g) | | | |
|---|---|---|---|
| Total Depot Length (Dosage) | 6-cm (19.2 mg) | 8-cm (25.6 mg) | 10-cm (32 mg) |
| Animal # | CHCCHB | CHCCKZ | 3100074 |
| Timepoint (d) | 28 | 7 | 28 |
| Prostate Volume* ($cm^3$) | 11.98 | 7.37 | 6.54 |
| Prostate Slice 1 | 213 | 1270 | 523 |
| Prostate Slice 2 | 205 | 4800 | 422 |
| Prostate Slice 3 | 2910 | 30400 | 3850 |
| Prostate Slice 4 | 30800 | 41600 | 31800 |
| Prostate Slice 5 | 4360 | 39800 | 3330 |
| Prostate Slice 6 | 2180 | NA | NA |
| Prostate Slice 7 | 439 | NA | NA |

NA = Not applicable. There were fewer number of slices from smaller prostates.

THE FOUNDRY®

Systemic Safety with High Local Drug Concentrations

FIG. 104-6

| Docetaxel Administration | Human Intravenous | FTx Localized |
|---|---|---|
| Systemic $C_{max}$ (ng/mL) | 1300 – 4000[a] | 1.9 – 4.4 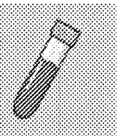 |
| Intraprostatic Concentration (ng/g) | 1829[b] | 30,800 – 41,600[c] 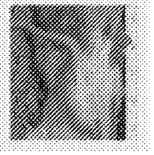 |

FTx localized sustained drug delivery technology dramatically reduces systemic toxicity and maximizes local efficacy potential.

a) Kenmotsu H and Tanigawara Y. Pharmacokinetics, dynamics, and toxicity of docetaxel: why the Japanese dose differs from the western dose. *Cancer Sci*, 2015.
b) Estimated human intraprostatic drug concentration calculated by multiplying standard IV dosage (75 mg/m²) by average body surface area (2 m²), then multiply by ratio of average prostate mass (45g) to average 65 yr old male body weight (82kg), and lastly divide by the average prostate mass (45g).
c) Sustained through 28 days study period.

THE FOUNDRY®

Prostatic Drug Diffusion Study

FIG. 104-7

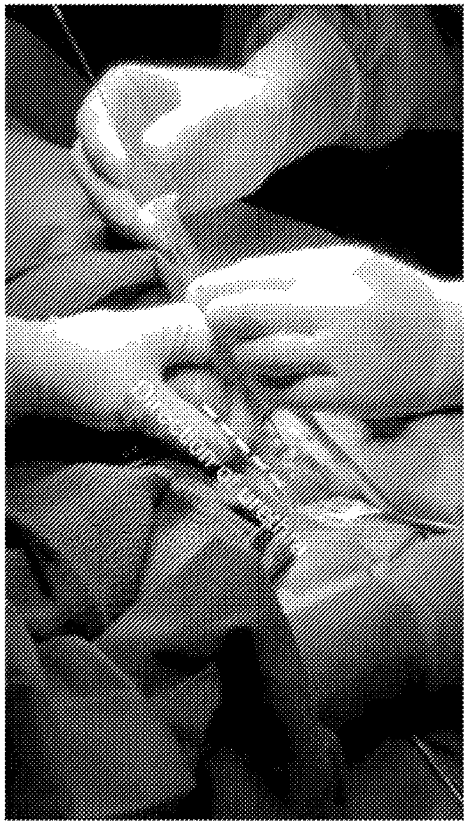

- This single dog study was intended to characterize drug transport in prostate after implantation of a single 1-cm docetaxel depot.
- Drug depot was delivered into the prostate nearly parallel to the urethra.
- The dog was sacrificed at 8 days, then the prostate was taken out, sliced, and biopsied at various locations for tissue drug concentration analysis.

THE FOUNDRY®

Steep Drug Conc Drop Across Implanted Lobule

FIG. 104-8

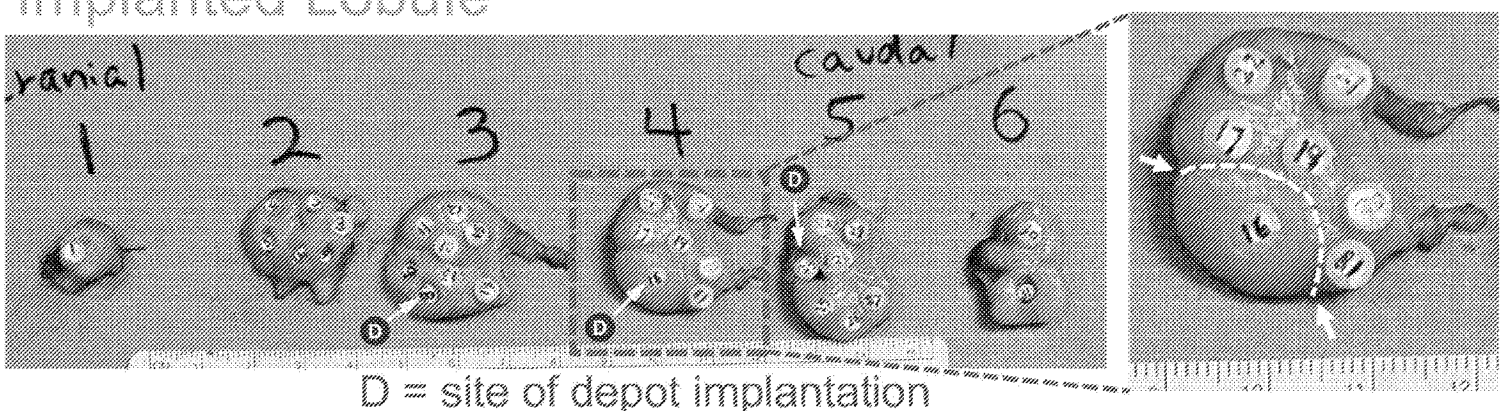

D = site of depot implantation

Animal # CHECJP

| Slice # | 1 | | | 2 | | | 3 | | | 4 | | | 5 | | | 6 | | |
|---|---|---|---|---|---|---|---|---|---|---|---|---|---|---|---|---|---|---|
| # of Plugs | 1 | | | 6 | | | 8 | | | 7 | | | 7 | | | 2 | | |
| | Biopsy # | Tissue Conc (ng/g) | D to rod (mm) | Biopsy # | Tissue Conc (ng/g) | D to rod (mm) | Biopsy # | Tissue Conc (ng/g) | D to rod (mm) | Biopsy # | Tissue Conc (ng/g) | D to rod (mm) | Biopsy # | Tissue Conc (ng/g) | D to rod (mm) | Biopsy # | Tissue Conc (ng/g) | D to rod (mm) |
| | 1 | 493 | 12.0 | 2-U | 424 | 9.8 | 8-D | 111000 | 0 | 16-D | 105000 | 0 | 23-D | 263000 | 0 | 30 | 1060 | 11.2 |
| | | | | 3 | 16100 | 5.0 | 9 | 4240 | 5.8 | 17 | 5310 | 9.1 | 24-U | 1400 | 6.4 | 31 | 7040 | 9.8 |
| | | | | 4 | 309 | 15.5 | 10-U | 378 | 9 | 18 | 15900 | 9.5 | 25 | 3730 | 8.2 | | | |
| | | | | 5 | 775 | 14.9 | 11 | 1870 | 12.9 | 19-U | 3960 | 6.5 | 26 | 1870 | 13.6 | | | |
| | | | | 6 | 143 | 8.1 | 12 | 719 | 16.8 | 20 | 36200 | 10.5 | 27 | 958 | 14.8 | | | |
| | | | | 7 | 4450 | 9.6 | 13 | 913 | 4.9 | 21 | 2100 | 15.1 | 28 | 956 | 9 | | | |
| | | | | | | | 14 | 1070 | 11.4 | 22 | 994 | 14.9 | 29 | 616 | 11.6 | | | |
| | | | | | | | 15 | 349 | 14.5 | | | | | | | | | |

- 1 to 2 orders of magnitude lower tissue drug concentrations are observed across the prostate lobular structure (16-D versus 17, 18, and 19-U).
- Prostate lobules (white dash line and arrows) are fibromuscular structures continuous with the prostatic capsule.

THE FOUNDRY®

Surrounding Tissue Drug Conc Similar to Intraprostatic Tissue Drug Conc Across Implanted Lobule

FIG. 104-9

- Like concentrations across the implanted lobule, peri-prostatic tissue drug concentrations are orders of magnitude lower than concentrations inside the implanted lobule
- Gross pathology at necropsy looked very clean with no adhesions or other visible abnormalities Peri-prostatic Tissue Drug Concentrations
(1-cm, 3.2 mg dose)

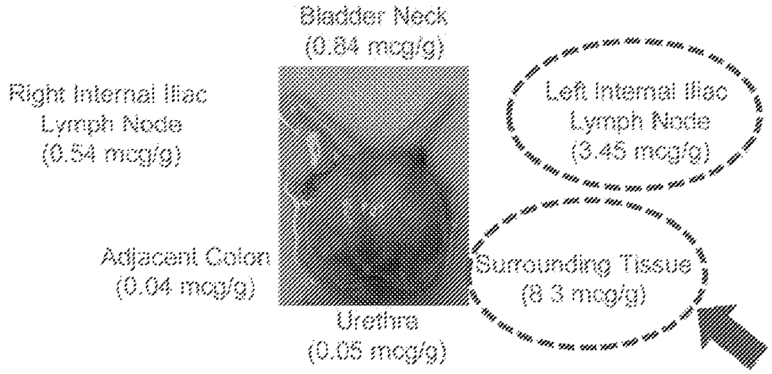

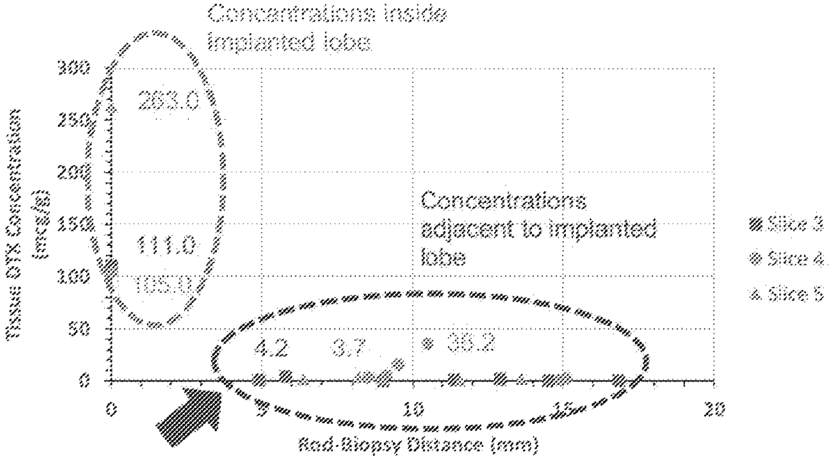

1-2 orders of magnitude lower than concentrations inside treated lobe

| Chemotherapeutics | | |
|---|---|---|
| arsenic trioxide | doxorubicin | Paclitaxel |
| asparaginase | Epirubicin | Paclitaxel Albumin-stabilized Nanoparticle Formulation |
| Azacitidine | Eribulin Mesylate | Panobinostat |
| Belinostat | Etoposide | Pegaspargase |
| Bendamustine Hydrochloride | 5-FU | Pemetrexed Disodium |
| Bexarotene | Fludarabine Phosphate | Pralatrexate |
| Bleomycin Sulfate | gemcitabine | Procarbazine Hydrochloride |
| Busulfan | Hydroxyurea | Romidepsin |
| Cabazitaxel | Idarubicin Hydrochloride | Tagraxofusp-erzs |
| capecitabine | Ifosfamide | Temozolomide |
| carboplatin | irinotecan | Thioguanine |
| carmustine | Ixabepilone | Thiotepa |
| Chlorambucil | Lomustine | Topotecan Hydrochloride |
| cisplatin | Mechlorethamine Hydrochloride | Trabectedin |
| Cladribine | Melphalan | Trifluridine and Tipiracil Hydrochloride |
| Clofarabine | Melphalan Hydrochloride | Valrubicin |
| Cyclophosphamide | Mercaptopurine | Vinblastine Sulfate |
| Cytarabine | Methotrexate | Vincristine Sulfate |
| Dacarbazine | Mitomycin | Vincristine Sulfate Liposome |
| Dactinomycin | Mitoxantrone Hydrochloride | Vinorelbine Tartrate |
| Daunorubicin Hydrochloride | Nelarabine | Vorinostat |
| Decitabine | Omacetaxine Mepesuccinate | |
| docetaxel | Oxaliplatin | |

FIG. 105

| Hormone Therapeutics |
| --- |
| aberaterone acetate |
| Anastrozole |
| apalutamide |
| bicalutamide |
| Darolutamide |
| Degarelix |
| enzalutamide |
| Exemestane |
| flutamide |
| Fulvestrant |
| Goserelin Acetate |
| Lanreotide Acetate |
| Letrozole |
| Leuprolide Acetate |
| Megestrol Acetate |
| Nilutamide |
| Raloxifene Hydrochloride |
| Tamoxifen Citrate |
| Toremifene |

FIG. 106

| Immunotherapeutics | |
|---|---|
| aldesleukin | ipilimumab |
| alemtuzumab | Isatuximab |
| Atezolizumab | Lenalidomide |
| Avelumab | Peginterferon Alfa-2b |
| Axicabtagene Ciloleucel | Pomalidomide |
| Bevacizumab | Recombinant Interferon Alfa-2b |
| Blinatumomab | Sipuleucel-T |
| Caplacizumab | Talimogene Laherparepvec |
| Cemiplimab | Thalidomide |
| Cetuximab | Tisagenlecleucel |
| Daratumumab | Zanubrutinib |
| Dinutuximab | |
| Durvalumab | |
| Elotuzumab | |
| Emapalumab | |
| Enfortumab Vedotin | |
| Gemtuzumab Ozogamicin | |
| Ibritumomab Tiuxetan | |
| Inotuzumab Ozogamicin | |

FIG. 107

| Targeted therapeutics | | |
|---|---|---|
| Abemaciclib | Gilteritinib Fumarate | Propranolol Hydrochloride |
| acalabrutinib | Glasdegib Maleate | Ramucirumab |
| ado-trastuzumab emtansine | Ibrutinib | Ravulizumab-cwvz |
| afatinib | Idelalisib | Regorafenib |
| alectinib | Imatinib Mesylate | Ribociclib |
| alpelisib | Ivosidenib | Ripretinib |
| Avapritinib | Ixazomib Citrate | Rituximab |
| Axitinib | Lapatinib Ditosylate | Rituximab and Hyaluronidase Human |
| Binimetinib | Larotrectinib Sulfate | Rucaparib Camsylate |
| Bortezomib | Lenvatinib Mesylate | Ruxolitinib Phosphate |
| Bosutinib | Lorlatinib | Sacituzumab Govitecan-hziy |
| Brentuximab Vedotin | Midostaurin | Selinexor |
| Brexucabtagene Autoleucel | Mogamulizumab-kpkc | Selpercatinib |
| Brigatinib | Moxetumomab Pasudotox-tdfk | Selumetinib Sulfate |
| Cabozantinib-S-Malate | Necitumumab | Siltuximab |
| Capmatinib Hydrochloride | Neratinib Maleate | Sonidegib |
| Carfilzomib | Nilotinib | Sorafenib Tosylate |
| Ceritinib | Niraparib Tosylate Monohydrate | Sunitinib Malate |
| Cobimetinib Fumarate | Nivolumab | Tafasitamab-cxix |
| Crizotinib | Obinutuzumab | Talazoparib Tosylate |
| Dabrafenib Mesylate | Ofatumumab | Tazemetostat Hydrobromide |
| Dacomitinib | Olaparib | Temsirolimus |
| Dasatinib | Osimertinib Mesylate | Trametinib |
| Denileukin Diftitox | Palbociclib | Trastuzumab |
| Enasidenib Mesylate | Panitumumab | Trastuzumab and Hyaluronidase-oysk |
| Encorafenib | Pazopanib Hydrochloride | Tucatinib |
| Entrectinib | Pembrolizumab | Vandetanib |
| Erdafitinib | Pemigatinib | Vemurafenib |
| Erlotinib Hydrochloride | Pertuzumab | Venetoclax |
| Everolimus | Pexidartinib Hydrochloride | Vismodegib |
| Fam-Trastuzumab Deruxtecan | Plerixafor | Ziv-Aflibercept |
| Gefitinib | Polatuzumab Vedotin-piiq | |

FIG. 108

| Supportive Therapeutics |
| --- |
| amifostine |
| aprepitant |
| Darbepoetin Alfa |
| Denosumab |
| Dexamethasone |
| Dexrazoxane Hydrochloride |
| Filgrastim |
| Glucarpidase |
| Leucovorin Calcium |
| Palifermin |
| Pamidronate Disodium |
| Prednisone |
| Talc |
| Zoledronic Acid |

*FIG. 109*

Adrucil (Pro)
Generic name: fluorouracil

Leustatin (Pro)
Generic name: cladribine

Otrexup (Pro)
Generic name: methotrexate

Purinethol (Pro)
Generic name: mercaptopurine

Alimta (Pro)
Generic name: pemetrexed

Gemzar (Pro)
Generic name: gemcitabine

Xeloda (Pro)
Generic name: capecitabine

Hydrea (Pro)
Generic name: hydroxyurea

Fludara (Pro)
Generic name: fludarabine

Trexall (Pro)
Generic name: methotrexate

Rheumatrex Dose Pack (Pro)
Generic name: methotrexate

Folotyn (Pro)
Generic name: pralatrexate

Arranon (Pro)
Generic name: nelarabine

Clolar (Pro)
Generic name: clofarabine

Dacogen (Pro)
Generic name: decitabine

DepoCyt
Generic name: cytarabine liposomal

Droxia (Pro)
Generic name: hydroxyurea

FUDR (Pro)
Generic name: floxuridine

Infugem (Pro)
Generic name: gemcitabine

Mavenclad (Pro)
Generic name: cladribine

Mylocel
Generic name: hydroxyurea

Oforta (Pro)
Generic name: fludarabine

Rasuvo (Pro)
Generic name: methotrexate

Siklos (Pro)
Generic name: hydroxyurea

Tabloid (Pro)
Generic name: thioguanine

Xatmep (Pro)
Generic name: methotrexate

*FIG. 110*

| Alkaloids | Plant Source | Type of Cancer | Cell Lines ($IC_{50}$) |
|---|---|---|---|
| Liriodenine | *Enicosanthellum pulchrum* (King) Heusden | Ovarian | CAOV-3 (37.3 μM) |
| | | | SKOV-3 (68.0 μM) |
| | | laryngocarcinoma | HEp-2 (2.332 μM) |
| Noscapine | *Papaver somniferum* L. | glioma cell cancer | LN229 (70 μM) |
| | | | A172 (20 μM) |
| | | | U251 (40 μM) |
| | | neuroblastoma | SK-SY5Y, SH-EP1, SK-N-MC, SK-N-AS, LA1-55N, NB1643, NB1691, SK-N-SH, and IMR32 ($IC_{50}$ range for all cell lines: from 21 to 100 μM) |
| | | cervical | HeL |
| | | | Ca Ski |
| | | colon | Caco-2 |
| | | | T84 |
| | | ovarian | SK-OV-3 |
| | | | and SigC |
| | | prostate | DU145 |
| | | human lymphoblast | CEM (14.5 μM) |
| | | human cervix | HeLa (24.0 μM) |
| | | lung adenocarcinoma | A549 (72.9 μM) |
| | | breast epithelial | MCF-7 (42.3 μM) |
| | | breast | MDA-MB-231 (20.15 μM) |
| | | | MCF-7 (15.47 μM) |

FIG. 111A

| Alkaloids | Plant Source | Type of Cancer | Cell Lines ($IC_{50}$) |
|---|---|---|---|
| Cryptolepine | *Cryptolepis sanguinolenta* *Sida acuta* Brum.f. *Sida cordifolia* L. | lung adenocarcinoma | A549 |
| | | Osteosarcoma | MG63 |
| | | T-cell leukemia | CCRF-CEM |
| | | | CEM/VM-1 |
| | | multiple myeloma | RPMI 8226-S |
| | | | 8226/Dox |
| | | | 8226/LR5 |
| | | histiocytic lymphoma | U-937-GTB |
| | | | U-937/Vcr |
| | | small cell lung cancer | NCI-H69 |
| | | | H69/AR |
| | | renal adenocarcinoma | ACHN |
| | | cervical adenocarcinoma | HeLa |
| | | immortalized normal retinal epithelial cells | hTERT-RPE (mean $IC_{50}$ of all cell lines: 0.9 μM) |
| Clausenidin | *Clausena excavata* Burum f. | colon | HT-29 (13.8 μg/mL) |
| Isogravacridone chlorine | *Ruta graveolens* L. | breasts | MDA-MB-231 (2.27 μM) |
| Cycleanine | *Triclisia subcordata* Oliv. | ovarian | Ovcar-8 (10 μM) |
| | | | A2780 (7.6 μM) |
| | | | Ovcar-4 (7.2 μM) |
| | | | Igrov-1 (14 μM) |

FIG. 111B

| Alkaloids | Plant Source | Type of Cancer | Cell Lines ($IC_{50}$) |
|---|---|---|---|
| Cathachunine | *Catharanthus roseus* (L.) G Don. | leukemia | HL60 (9.1 μM) |
| | | | K562 (9.3) μM |
| Brucine | *Strychnos nux-vomica* L. | lung | PC-9 |
| | | hepatocellular carcinoma | HepG2 |
| | | | SMMC-7721 |
| | | colon | LoVo (15.1 μM) |
| | | lung | PC-9 |
| Subditine | *Nauclea subdita* (Korth.) Steud. | prostate | LNCaP (12.24 μM) |
| | | | PC-3 (13.97 μM) |
| Scutebarbatine-A (SBT-A) | *Scutellaria barbata* D Don. | lung | A549 (39.21 μg/mL) |
| Rohitukine | *Dysoxylum binectariferum* Hook.f. | breast | T47D (50 μM), and |
| | | | MIDAMB273 (3 μM) |
| | | | MCF7 (15 μM) |
| | | ovarian | SKOV3 (20 μM) |
| | | lung | A549 (40 μM) |
| Tabernaelegantine C | *Tabernaemontana elegans* Stapf | colon | HCT116 (20 μM) |
| | *Muntafara sessilifolia* Baker | | |
| Tabernaelegantinine B | *Tabernaemontana elegans* Stapf | colon | HCT116 (20 μM) |
| | *Muntafara sessilifolia* Baker | | MRC-5 (0.47 μM) |

FIG. 111C

| Alkaloids | Plant Source | Type of Cancer | Cell Lines ($IC_{50}$) |
|---|---|---|---|
| Hirsutine | Plants of genus *Uncaria* | human breast | MDA-MB-453 |
| | | mouse mammary carcinoma | BT474 |
| | | | 4T1 |
| β-carboline | *Peganum harmala* L. | human promyelocytic leukemia | HL-60 (3.48 μg/mL) |
| | | prostate | PC-3 (10.59 μg/mL) |
| | | gastric | SGC-7901 (11.53 μg/mL) |
| Pretazettine | *Amaryllidaceae* (genus *Amaryllis* L.) | breast | MCF7 (7.869 μM) |
| | | cervical | HeLa (8.853 μM) |
| | | skin epidermoid carcinoma | A431 (5.373 μM) |
| α-tomatine | *Lycopersicon esculentum* Mill. | human lung adenocarcinoma | A549 cells |
| | | human prostatic adenocarcinoma | PC-3 Cells (1.67 μM) |

FIG. 111D

| | |
|---|---|
| Anthracyclines | Doxorubicin, Daunorubicin, Epirubicin, Mitoxantrone, Idarubicin |
| Chromomycins | Dactinomycin and Plicamycin |
| Miscellaneous | Mitomycin and Bleomycin |

FIG. 112

Alkylating agents
- Busulfan
- Carmustine
- Cyclophosphamide
- Lomustine
- Mechlorethamine
- Melphalan
- Thiotepa

Anthracyclines
- Daunorubicin
- Doxorubicin
- Epirubicin
- Idarubicin
- Mitoxantrone

Antitumor antibiotics
- Dactinomycin
- Mitomycin

Camptothecins
- Irinotecan
- Topotecan

Platinum analogs
- Carboplatin
- Cisplatin
- Oxaliplatin

*FIG. 113*

IMPLANTABLE DEPOTS FOR LOCALIZED, SUSTAINED, CONTROLLED RELEASE OF THERAPEUTIC AGENTS TO TREAT CANCER AND RELATED CONDITIONS

CROSS-REFERENCE TO RELATED APPLICATIONS

This application is a 371 national phase application of International Application No. PCT/US2021/071861, filed Oct. 14, 2021, which claims the benefit of U.S. Patent Application No. 63/198,381, filed Oct. 14, 2020, which is incorporated herein by reference in its entirety.

The present application also incorporates by reference each of the following applications in its entirety: International Application No. PCT/US20/27861, filed Apr. 11, 2020, U.S. Provisional Application No. 62/832,876, filed Apr. 11, 2019, U.S. Provisional Application No. 62/907,415, filed Sep. 27, 2019, International Application No. PCT/US2019/012795, filed Jan. 8, 2019; International Application No. PCT/US2018/054777, filed Oct. 6, 2018; U.S. Application No. 62/723,478, filed Aug. 28, 2018; U.S. Application No. 62/670,721, filed May 12, 2018; U.S. Application No. 62/640,571, filed Mar. 8, 2018; U.S. Application No. 62/614,884, filed Jan. 8, 2018; U.S. Patent Application No. 62/742,357, filed Oct. 6, 2018; and U.S. Application No. 62/569,349, filed Oct. 6, 2017.

TECHNICAL FIELD

The present technology relates to implants for the localized, controlled, sustained release of therapeutic agents in vivo to treat cancer and related symptoms and conditions.

BACKGROUND OF THE INVENTION

Most chemotherapeutic drugs act on both normal as well as cancerous tissues. As such, one of the challenges in treating cancerous tumors with chemotherapy is maximizing the killing of cancer cells while minimizing the harming of healthy tissue. Polymer-based drug delivery systems have been investigated over the last few decades as a means of achieving high therapeutic concentrations of chemotherapy to the site of malignant disease in cancer patients. The development of these technologies is guided by the desire to improve overall survival and quality of life by increasing the bioavailability of drug to the site of disease, containing delivery to the cancerous tissues, and minimizing systemic side effects.

Existing chemotherapy delivery systems are either systemic or local. Systemic delivery vehicles find their target by passive diffusion (via leaky tumor vasculature) and/or active targeting of unique tumor cell markers. These nanomaterials are predominantly intended for intravenous administration and, while they promise the ability to target tumor tissues with accumulation of therapeutic concentrations of drug, localization is challenging due to removal and sequestration of these nanomaterials by the reticuloendothelial system. Depending on the administration route (e.g., intravenous) and nature of the drug (e.g., its physical and pharmacokinetic properties), oftentimes only a small fraction of the dose reaches the target cells; the remaining amount of drug acts on other tissues or is rapidly eliminated.

To improve delivery efficiency and reduce toxicity to non-target cells, various strategies have been used to deliver drugs to specific sites in the human body. For example, the use of a monoclonal antibody conjugated to a toxin has been reported in cancer treatment. The antibody provides selectivity for the target, but there still remains the problem of interaction with non-target cells during passage to the intended site of action.

The alternative approach of encapsulating toxins in liposomes has also been actively researched. Liposomes are structures consisting essentially of a membrane bilayer composed of lipids of biological or synthetic origin such as phospholipids, sphingolipids, glycosphingolipids, ceramides or cholesterol. Liposomes can encapsulate large quantities of drug molecules either within their aqueous interiors or dissolved into the hydrocarbon regions of their bilayers. Liposomes can also protect their contents from rapid filtration by the kidneys and from degradation by metabolism, thus enhancing the drug's residence time in the body. Once taken up by a target cell (e.g. by ligand-mediated endocytosis), liposomes may also facilitate the cytoplasmic delivery of encapsulated drug molecules by fusing with the endosomal membrane. However, the clinical utility of liposomes in targeting drug delivery has been severely limited by: (1) the rapid clearance by phagocytic cells of the reticuloendothelial system (RES), (2) the lack of specific tumor targeting, and (3) the premature or inappropriate release of the drug.

The second group of polymer delivery vehicles includes controlled release drug delivery depot systems for implantation intratumorally or adjacent to the cancerous tissue. The potential benefits of localized chemotherapy at the tumor site are numerous and are intended to both enhance the efficacy of treatment and reduce patient morbidity. Drug-loaded implants are administered directly at the site of disease, offering the following advantages over traditional systemic delivery: 1) stabilization of embedded drug molecules and preservation of anticancer activity, 2) controlled and prolonged drug release to ensure adequate diffusion and uptake into cancer cells over many cycles of tumor cell division, 3) loading and release of water-insoluble chemotherapeutics, 4) direct delivery to the site of disease, resulting in less waste of drug, 5) one-time administration of the drug, and 6) diminished side effects due to the avoidance of systemic circulation of chemotherapeutic drugs.

Thus, a need exists for biocompatible implantable systems capable of providing a localized, controlled, sustained release of therapeutic agents to treat cancer.

SUMMARY

The present technology relates to implantable polymer depots for the localized, controlled, sustained release of therapeutic agents to treat cancer and associated symptoms and conditions. The subject technology is illustrated, for example, according to various aspects described below, including with reference to FIGS. 1-127, and as shown in Appendix A. Various examples of aspects of the subject technology are described as numbered Clauses (1, 2, 3, etc.) for convenience. These are provided as examples and do not limit the subject technology.

1. A depot for treating bladder cancer via sustained, controlled release of a therapeutic agent to a patient, the depot comprising:

a therapeutic region comprising a therapeutic agent, the therapeutic agent comprising at least a chemotherapeutic agent;

a control region comprising a polymer and a releasing agent mixed with the polymer, wherein the releasing agent is configured to dissolve when the depot is placed in vivo to form diffusion openings in the control region; and wherein the depot is configured to be implanted at a treatment site proximate a bladder of the patient and, while implanted, release the chemotherapeutic agent at the treatment site for a period of time that is no less than 7 days.

2. A depot for treating bladder cancer via sustained, controlled release of a therapeutic agent to a patient, the depot comprising:

a therapeutic region comprising a therapeutic agent, the therapeutic agent comprising at least a chemotherapeutic agent;

a control region comprising a polymer and a releasing agent mixed with the polymer, wherein the releasing agent is configured to dissolve when the depot is placed in vivo to form diffusion openings in the control region; and wherein the depot is configured to be implanted at a treatment site proximate a bladder of the patient and, while implanted, release the chemotherapeutic agent at the treatment site for a period of time that is no less than 7 days.

3. The depot of any one of the preceding clauses, wherein the depot is configured to self-expand into apposition with an inner surface of the bladder wall when released from a delivery device.

4. The depot of any one of the preceding clauses, wherein the depot is configured to self-expand into apposition with a tumor at an inner surface of the bladder wall when released from a delivery device.

5. The depot of any one of the preceding clauses, wherein the depot contains at least one opening extending therethrough such that, if positioned over the opening to the urethra within the bladder, the depot will not substantially block flow from an interior region of the bladder into the urethra.

6. The depot of any one of the preceding clauses, wherein the depot has a preset shape such that, when released from a delivery device, the depot assumes the preset shape.

7. The depot of any one of the preceding clauses, wherein the depot has a preset shape that is curved.

8. The depot of any one of the preceding clauses, wherein the depot has a first region and a second region, each extending longitudinally and coextensive with one another over all or a portion of their respective lengths, the first region having a first elasticity and the second region having a second elasticity less than the first elasticity.

9. The depot of the preceding clause, wherein the depot has been stretched beyond the elastic hysteresis point of the second region such that, when released from a delivery device, the depot transitions from a straightened state to a curved state in which the second region pulls the depot into the curved shape.

10. The depot of any one of the preceding clauses, wherein the depot has a first region and a second region, each extending longitudinally and coextensive with one another over all or a portion of their respective lengths, the first region being more hydrophilic than the second region.

11. The depot of the preceding clause, wherein, when released from a delivery device, the depot transitions from a straightened state to a curved state in which the second region pulls the depot into the curved shape.

12. The depot of any one of the preceding clauses, wherein the depot includes an axial centerline, a first region sharing the axial centerline, and a second region surrounded by the first region and having an axial centerline offset from the axial centerline of the depot, each of the first and second regions extending longitudinally and coextensive with one another over all or a portion of their respective lengths, and wherein the first region is more elastic or more hydrophilic than the second region such that the depot is biased towards a curved shape.

13. The depot of any one of the preceding clauses, further comprising an impermeable base region surrounding all or a portion of one or both of the control region and the therapeutic region such that, when the depot is positioned at the treatment site, the chemotherapeutic agent is selectively released in a direction away from the base region.

14. The depot of any one of the preceding clauses, wherein the depot comprises an elongated polymer strip having a length between its longitudinal ends and a width between lateral edges, the length greater than the width, and wherein the depot has a preset shape in an expanded configuration in which the strip is curled about an axis with the width of the strip facing the axis, thereby forming a ring-like shape.

15. The depot of any one of the preceding clauses, wherein the chemotherapeutic agent is at least one of epirubicin, doxorubicin, mitomycin C, gemcitabine, and docetaxel.

16. The depot of any one of the preceding clauses, wherein the polymer includes a bioresorbable polymer.

17. The depot of any one of the preceding clauses, wherein the polymer includes a non-bioresorbable polymer.

18. The depot of any one of the preceding clauses, wherein the polymer is a first polymer, and wherein the therapeutic region comprises a second polymer.

19. The depot of any one of the preceding clauses, wherein the first and/or second polymer includes a bioresorbable polymer.

20. The depot of any one of the preceding clauses, wherein the first and/or second polymer includes a non-bioresorbable polymer.

21. The depot of any one of the preceding clauses, wherein the first and/or second polymer includes thermoplastic polyurethane.

22. The depot of any one of the preceding clauses, wherein the first and/or second polymer includes ethyl vinyl acetate.

23. The depot of any one of the preceding clauses, wherein the first polymer is non-bioresorbable and the second polymer is bioresorbable.

24. The depot of any one of the preceding clauses, wherein the first and second polymers are the same.

25. The depot of any one of the preceding clauses, wherein the therapeutic region is configured to release the chemotherapeutic agent continuously at a constant rate for the period of time.

26. The depot of any one of the preceding clauses, wherein the therapeutic region is configured to release the chemotherapeutic agent continuously at a rate that increases over time.

27. The depot of any one of the preceding clauses, wherein the period of time is no less than 2 weeks, no less than 3 weeks, no less than 4 weeks, no less than 5 weeks, no less than 6 weeks, no less than 7 weeks, no less than 8 weeks, no less than 2 months, no less than 3 months, no less than 4 months, no less than 6 months, no less than 7 months, no less than 8 months, no less than 9 months, no less than 10 months, no less than 12 months, no less than 1 year.

28. The depot of any one of the preceding clauses, wherein the chemotherapeutic agent includes mitomycin C, and the depot is configured to release mitomycin at a continuous rate for at least 3 weeks, for at least 4 weeks, for at least 5 weeks, for at least 6 weeks, for at least 7 weeks, or for at least 8 weeks.
29. The depot of any one of the preceding clauses, wherein the chemotherapeutic agent includes mitomycin, and the therapeutic region contains no less than 120 mg, 150 mg, 180 mg, 210 mg, 240 mg, 270 mg, 300 mg, 330 mg, 360 mg, 390 mg, 420 mg, 450 mg, 480 mg, or 510 mg of mitomycin.
30. The depot of any one of the preceding clauses, wherein the chemotherapeutic agent includes gemcitabine, and the depot is configured to release gemcitabine at a continuous rate for at least 3 weeks, for at least 4 weeks, for at least 5 weeks, for at least 6 weeks, for at least 7 weeks, or for at least 8 weeks.
31. The depot of any one of the preceding clauses, wherein the chemotherapeutic agent includes gemcitabine, and the therapeutic region contains no less than 200 mg, 300 mg, 400 mg, 500 mg, 600 mg, 700 mg, 800 mg, 900 mg, 1000 mg, 1100 mg, 1200 mg, 1300 mg, 1400 mg, 1500 mg, 1600 mg, 1700 mg, 1800 mg, 1900 mg, 2000 mg, 2100 mg, 2200 mg, 2300 mg, 2400 mg, 2500 mg, 2600 mg, 2700 mg, 2800 mg, 2900 mg, or 3000 mg of gemcitabine.
32. The depot of any one of the preceding clauses, wherein the period of time is a first period of time, and wherein the therapeutic agent further comprises an immunotherapeutic agent and the depot is configured to release the immunotherapeutic agent for a second period of time.
33. The depot of any one of the preceding clauses, wherein the first period of time is longer than the second period of time.
34. The depot of any one of the preceding clauses, wherein the second period of time is shorter than the first period of time.
35. The depot of any one of the preceding clauses, wherein the first and second periods of time are different.
36. The depot of any one of the preceding clauses, wherein the first and second periods of time are the same.
37. The depot of any one of the preceding clauses, wherein the depot is configured to begin releasing a therapeutic dosage of the chemotherapeutic agent and a therapeutic dosage of the immunotherapeutic agent at substantially the same time.
38. The depot of any one of the preceding clauses, wherein the depot is configured to begin releasing a therapeutic dosage of the chemotherapeutic agent at a first time after implantation, and wherein the depot is configured to begin releasing a therapeutic dosage of the immunotherapeutic agent at a second time after implantation, the second time different than the first time.
39. The depot of any one of the preceding clauses, wherein the second time is 1 day, 2, days, 3 days, 4 days, 5 days, 6 days, one week, two weeks, three weeks, four weeks, five weeks, six weeks, seven weeks, or eight weeks before the first time.
40. The depot of any one of the preceding clauses, wherein the second time is 1 day, 2, days, 3 days, 4 days, 5 days, 6 days, one week, two weeks, three weeks, four weeks, five weeks, six weeks, seven weeks, or eight weeks after the first time.
41. The depot of any one of the preceding clauses, wherein the immunotherapeutic agent includes *bacillus* Calmette-Guerin ("BCG").
42. The depot of any one of the preceding clauses, wherein the therapeutic region includes a first portion and a second portion, wherein the first portion comprises the chemotherapeutic agent and the second portion comprises the immunotherapeutic agent.
43. The depot of any one of the preceding clauses, wherein the first portion is closer to an exterior surface of the depot than the second portion.
44. The depot of any one of the preceding clauses, wherein the first portion is farther from an exterior surface of the depot than the second portion.
45. The depot of any one of the preceding clauses, wherein the depot is configured to release the immunotherapeutic agent continuously over the period of time.
46. The depot of any one of the preceding clauses, wherein the therapeutic region is configured to release the immunotherapeutic agent intermittently over the period of time.
47. The depot of any one of the preceding clauses, wherein the depot is configured to release the chemotherapeutic agent at a first rate and the immunotherapeutic agent at a second rate.
48. The depot of any one of the preceding clauses, wherein the first rate is the same as the second rate.
49. The depot of any one of the preceding clauses, wherein the first rate is different than the second rate.
50. The depot of any one of the preceding clauses, wherein the first rate is greater than the second rate.
51. The depot of any one of the preceding clauses, wherein the first rate is less than the second rate.
52. The depot of any one of the preceding clauses, wherein the depot is configured to be positioned adjacent a wall of the bladder.
53. The depot of any one of the preceding clauses, wherein the depot is configured to be positioned adjacent a wall of the bladder and release the chemotherapeutic agent to treat a tumor at a thickness of the bladder wall corresponding to one or more of the urothelium, lamina propria, muscle, fat, and peritoneum.
54. The depot of any one of the preceding clauses, wherein the depot includes a securing portion configured to adhere to an inner surface of the bladder wall.
55. The depot of any one of the preceding clauses, wherein a surface of the depot comprises a positively-charged polymer configured to secure the depot to the bladder wall.
56. The depot of any one of the preceding clauses, wherein the depot comprises a thermosensitive gel and/or a hydrogel with reverse thermal gelation.
57. The depot of any one of the preceding clauses, wherein the depot includes a fixation portion configured to penetrate at least a portion of the thickness of the bladder wall, thereby securing the depot at the bladder wall.

58. The depot of any one of the preceding clauses, wherein the depot includes an anchor member coupled to the therapeutic region, control region, and/or base region, and wherein the anchor member is configured to self-expand into apposition with at least a portion of the inner surface of the bladder wall, thereby securing the depot at or within the bladder.
59. A system for treating bladder cancer via the controlled, sustained release of a therapeutic agent, the system comprising:
the depot of any one of the preceding clauses; and
a delivery device configured to position the depot in the bladder.
60. The system of any of the preceding clauses, wherein the delivery device is configured to position the depot at a bladder wall.
61. The system of any of the preceding clauses, wherein the delivery device is a catheter configured to be positioned through the urethra.
62. A system for treating bladder cancer via the controlled, sustained release of a therapeutic agent, the system comprising:
the depot of any one of the preceding clauses; and
an anchor member coupled to the depot and configured to secure the depot at an interior region of the bladder.
63. The system of any one of the preceding clauses, wherein the anchor member forms an expanded member in a deployed state, and wherein the depot is coupled to an exterior surface of the expanded member such that, when the anchor member is deployed in the bladder cavity, the anchor member pushes the depot outwardly and secures the depot in contact with the bladder wall and/or tumor at the bladder wall.
64. The system of any one of the preceding clauses, wherein the expanded member comprises a shape of any one of the following: pretzel, donut, infinity, spring, swirl, paperclip.
65. A system for treating bladder cancer, comprising:
a plurality of depots, each comprising a depot of any one of the preceding clauses; and
a delivery device configured to position the depots in the bladder.
66. A method for treating bladder cancer via the controlled, sustained release of a therapeutic agent, the method comprising:
providing a depot of any one of the preceding clauses.
67. A method for treating bladder cancer or overactive bladder disease via the controlled, sustained release of a therapeutic agent, the method comprising:
positioning a depot of any one of the preceding clauses at a treatment site proximate a bladder of a patient;
delivering the therapeutic agent to the treatment site for a period of time that is no less than 7 days.
68. A method for treating at least one of overactive bladder, interstitial cystitis, painful bladder syndrome, urinary tract infection, via the controlled, sustained release of a therapeutic agent, the method comprising:
positioning a depot of any one of the preceding clauses at a treatment site proximate a bladder of a patient;
delivering the therapeutic agent to the treatment site for a period of time that is no less than 7 days.
69. The method of any one of the preceding clauses, further comprising securing the depot within the bladder.
70. The method of any one of the preceding clauses, further comprising securing the depot to a portion of the bladder wall.
71. The method of any one of the preceding clauses, further comprising securing the depot to a portion of the bladder wall such that a first surface of the depot is in contact with a tumor at the bladder wall, and releasing the chemotherapeutic agent towards the first surface and the tumor.
72. The method of any one of the preceding clauses, wherein the period of time is no less than two weeks, no less than three weeks, no less than four weeks, no less than five weeks, no less than 8 weeks, no less than 2 months, no less than 3 months, no less than 4 months, no less than 6 months, no less than 7 months, no less than 8 months, no less than 9 months, no less than 10 months, no less than 12 months, no less than 1 year, no less than 2 years, or no less than 3 years.
73. The method of any one of the preceding clauses, wherein the chemotherapeutic agent is released one or more times in substantially discrete doses after implantation over the period of time.
74. The method of any one of the preceding clauses, wherein the chemotherapeutic agent is released continuously after implantation for the period of time.
75. The method of any one of the preceding clauses, further comprising slowing the growth of a tumor at the bladder wall.
76. The method of any one of the preceding clauses, further comprising shrinking a tumor at the bladder wall.
77. The method of any one of the preceding clauses, further comprising reducing the likelihood of a tumor growing back at the bladder wall.
78. A depot for treating malignant pleural effusion ("MPE") via sustained, controlled release of a therapeutic agent to a patient, the depot comprising:
a therapeutic region comprising a therapeutic agent, the therapeutic agent comprising at least a chemotherapeutic agent;
a control region comprising a polymer and a releasing agent mixed with the polymer, wherein the releasing agent is configured to dissolve when the depot is placed in vivo to form diffusion openings in the control region; and
wherein the depot is configured to be implanted at a treatment site proximate a pleural membrane of the patient and, while implanted, release the chemotherapeutic agent at the treatment site for a period of time that is no less than 7 days.
79. The depot of any one of the preceding clauses, wherein the depot is a flexible, thin film.
80. The depot of any one of the preceding clauses, wherein the depot has a low-profile state for delivery through a delivery device to the treatment site and a deployed state for positioning proximate the pleural membrane.
81. The depot of the preceding clause, wherein the depot is rolled upon itself in the low-profile state and unrolls when released from a delivery device at the treatment site.
82. The depot of any one of the preceding clauses, wherein the depot has a preset shape that is curved.
83. The depot of any one of the preceding clauses, wherein the chemotherapeutic agent is at least one of cisplatin, pemetrexed sodium, carboplatin, irinotecan, and/or liposomal irinotecan.

84. The depot of any one of the preceding clauses, wherein the therapeutic region is configured to release the chemotherapeutic agent intermittently over the period of time.
85. The depot of any one of the preceding clauses, wherein the therapeutic region is configured to release the chemotherapeutic agent continuously over the period of time.
86. The depot of any one of the preceding clauses, wherein the period of time is at least 4 weeks, and wherein the therapeutic region is configured to release a dose of the chemotherapeutic agent once a week or once every 2 weeks over the period of time.
87. The depot of any one of the preceding clauses, wherein the period of time is at least 8 weeks, and wherein the therapeutic region is configured to release a dose of the chemotherapeutic agent once every week or once every 2 weeks over the period of time.
88. The depot of any one of the preceding clauses, wherein the period of time is at least 12 weeks, and wherein the therapeutic region is configured to release a dose of the chemotherapeutic agent once every week, every 2 weeks, or every 3 weeks over the period of time.
89. The depot of any one of the preceding clauses, wherein the period of time is at least 16 weeks, and wherein the therapeutic region is configured to release a dose of the chemotherapeutic agent once every week, every 2 weeks, or every 4 weeks over the period of time.
90. The depot of any one of the preceding clauses, wherein the chemotherapeutic agent includes cisplatin, and wherein each dose of cisplatin is less than or equal to 100 μg/ml.
91. The depot of any one of the preceding clauses, wherein the chemotherapeutic agent includes pemetrexed sodium, and wherein each dose of the pemetrexed sodium is less than or equal to 500 mg/m2.
92. The depot of any one of the preceding clauses, wherein the chemotherapeutic agent includes irinotecan or liposomal irinotecan, and wherein each dose of the irinotecan or liposomal irinotecan is less than or equal to 200 mg/m2.
93. The depot of any one of the preceding clauses, wherein the chemotherapeutic agent includes irinotecan or liposomal irinotecan, and wherein each dose of the irinotecan or liposomal irinotecan is less than or equal to 120 mg/m2.
94. The depot of any one of the preceding clauses, wherein the period of time is no less than 2 weeks, no less than 3 weeks, no less than 4 weeks, no less than 5 weeks, no less than 6 weeks, no less than 7 weeks, no less than 8 weeks, no less than 2 months, no less than 3 months, no less than 4 months, no less than 6 months, no less than 7 months, no less than 8 months, no less than 9 months, no less than 10 months, no less than 12 months, no less than 1 year.
95. The depot of any one of the preceding clauses, wherein the depot has a preset shape such that, when released from a delivery device, the depot assumes the preset shape.
96. The depot of any one of the preceding clauses, wherein the therapeutic agent further comprises a sclerosant.
97. The depot of any one of the preceding clauses, wherein the sclerosant comprises at least one of talc and/or doxycycline.
98. The depot of any one of the preceding clauses, wherein, at least prior to implantation, the portion of the therapeutic region containing the sclerosant is closer to an exterior surface of the depot than the portion of the therapeutic region containing the chemotherapeutic agent.
99. The depot of any one of the preceding clauses, wherein the depot is configured to release all of the sclerosant within less than a day.
100. The depot of any one of the preceding clauses, wherein the depot is configured to release all of the sclerosant within less than 1 hour, 2 hours, 3 hours, 4 hours, 5 hours, 6 hours, 12 hours, 16 hours, or 18 hours.
101. The depot of any one of the preceding clauses, wherein the sclerosant is talc or a talc slurry, and wherein the therapeutic region contains 3-10 g, 4-8 g, about 2 g, 2-3 g, 3-4 g, 4-5 g, 5-6 g, 6-7 g, 7-8 g, 8-9 g, 9-10 g, about 3 g, about 4 g, about 5 g, about 6 g, about 7 g, about 8 g, about 9 g, or about 10 g of talc or a talc slurry.
102. The depot of any one of the preceding clauses, wherein the sclerosant is doxycycline, and wherein the therapeutic region contains at 200-800 mg, 300-700 mg, 400-600 mg, about 300 mg, about 400 mg, about 500 mg, about 600 mg, about 700 mg, or about 800 mg of doxycycline.
103. The depot of any one of the preceding clauses, wherein the therapeutic agent further comprises an analgesic.
104. The depot of any one of the preceding clauses, wherein, at least prior to implantation, the portion of the therapeutic region containing the analgesic is closer to an exterior surface of the depot than the portion of the therapeutic region containing the chemotherapeutic agent.
105. The depot of any one of the preceding clauses, wherein, at least prior to implantation, the portion of the therapeutic region containing the sclerosant is closer to an exterior surface of the depot than the portion of the therapeutic region containing the chemotherapeutic agent and the portion containing the analgesic, and wherein the portion containing the analgesic is closer to the exterior surface of the portion of the therapeutic region containing the chemotherapeutic agent.
106. The depot of any one of the preceding clauses, wherein the therapeutic agent further comprises an immunotherapeutic agent.
107. The depot of any one of the preceding clauses, wherein the therapeutic agent further comprises a targeted therapy.
108. The depot of any one of the preceding clauses, wherein the therapeutic region includes a first portion and a second portion, wherein the first portion comprises the chemotherapeutic agent and the second portion comprises the sclerosant.
109. The depot of any one of the preceding clauses, wherein the first portion is closer to an exterior surface of the depot than the second portion.
110. The depot of any one of the preceding clauses, wherein the first portion is farther from an exterior surface of the depot than the second portion.
111. The depot of any one of the preceding clauses, wherein the depot is configured to release the chemotherapeutic agent at a first rate and the sclerosant at a second rate.

112. The depot of any one of the preceding clauses, wherein the first rate is the same as the second rate.

113. The depot of any one of the preceding clauses, wherein the first rate is different than the second rate.

114. The depot of any one of the preceding clauses, wherein the first rate is greater than the second rate.

115. The depot of any one of the preceding clauses, wherein the first rate is less than the second rate.

116. The depot of any one of the preceding clauses, wherein the depot is configured to be positioned adjacent a chest wall of the patient.

117. The depot of any one of the preceding clauses, wherein the depot is configured to be positioned between a chest wall and a pleural membrane.

118. The depot of any one of the preceding clauses, wherein the depot is configured to be positioned between a visceral pleura and a parietal pleura.

119. The depot of any one of the preceding clauses, wherein the depot is configured to be positioned between at least partially within the pleural space.

120. The depot of any one of the preceding clauses, wherein the depot is configured to be delivered through a tube having an external diameter of from about 3 mm to about 7 mm or of from about 4 mm to about 6 mm.

121. The depot of any of the preceding clauses, wherein the depot comprises a tubular member having an external diameter of from about 6 Fr to about 40 Fr.

122. A system for treating MPE via the controlled, sustained release of a therapeutic agent, the system comprising:

the depot of any one of the preceding clauses; and a delivery device configured to position the depot proximate a pleural membrane of a patient.

123. A system for treating MPE via the controlled, sustained release of a therapeutic agent, the system comprising:

the depot of any one of the preceding clauses; and a delivery device configured to position the depot within a pleural space of a patient.

124. A system for treating MPE, comprising:

a plurality of depots, each comprising a depot of any one of the preceding clauses; and a delivery device configured to position the depots proximate a pleural membrane of a patient.

125. A system for treating MPE, comprising:

a plurality of depots, each comprising a depot of any one of the preceding clauses; and a delivery device configured to position the depots within a pleural space of a patient.

126. The system of any of the preceding clauses, wherein the delivery device comprises a chest tube.

127. The system of any one of the preceding clauses, wherein the delivery device comprises a trocar.

128. The system of any of the preceding clauses, wherein the delivery device comprises a tubular member having an external diameter of from about 6 Fr to about 40 Fr.

129. The system of any one of the preceding clauses, wherein the delivery device comprises a tube having an external diameter of from about 3 mm to about 7 mm or of from about 4 mm to about 6 mm.

130. The system of any one of the preceding clauses, wherein at least two of the plurality of depots have a different size, a different shape, and/or a different therapeutic agent.

131. A method for treating MPE via the controlled, sustained release of a chemotherapeutic agent, the method comprising:

providing a depot of any one of the preceding clauses.

132. A method for treating MPE via the controlled, sustained release of a chemotherapeutic agent, the method comprising:

positioning a depot of any one of the preceding clauses at a treatment site proximate a pleural membrane of a patient; and releasing the chemotherapeutic agent at the treatment site for a period of time that is no less than 7 days.

133. A method for treating MPE via the controlled, sustained release of a chemotherapeutic agent, the method comprising:

positioning a plurality of depots, each being any one of the preceding clauses at a treatment site proximate a pleural membrane of a patient; and releasing the chemotherapeutic agent at the treatment site for a period of time that is no less than 7 days.

134. The method of any one of the preceding clauses, further comprising reducing the distance between the visceral pleura and the parietal pleura.

135. The method of any one of the preceding clauses, further comprising reducing the volume between the visceral pleura and the parietal pleura.

136. The method of any one of the preceding clauses, further comprising slowing the growth of lung cancer.

137. The method of any one of the preceding clauses, further comprising reducing the likelihood of a lung cancer recurring.

138. The method of any one of the preceding clauses, further comprising removing fluid from a pleural space.

139. The method of any one of the preceding clauses, further comprising reducing pain.

140. The method of any one of the preceding clauses, further comprising causing inflammation of one or both pleural membranes.

141. The method of any one of the preceding clauses, wherein positioning the depot(s) at the treatment site comprises delivering the depot(s) through or within a tubular member having an external diameter of from about 6 Fr to about 40 Fr.

142. The method of any one of the preceding clauses, wherein positioning the depot(s) at the treatment site comprises delivering the depot(s) through or within a tubular member having an external diameter of from about 3 mm to about 7 mm or of from about 4 mm to about 6 mm.

143. The method of any one of the preceding clauses, wherein the period of time is no less than two weeks, no less than three weeks, no less than four weeks, no less than five weeks, no less than 8 weeks, no less than 2 months, no less than 3 months, no less than 4 months, no less than 6 months, no less than 7 months, no less than 8 months, no less than 9 months, no less than 10 months, no less than 12 months, no less than 1 year.

144. The method of any one of the preceding clauses, wherein releasing the chemotherapeutic agent includes releasing the chemotherapeutic agent once a week, once every 2 weeks, once every 3 weeks, or once every 4 weeks over the period of time.

145. The method of any one of the preceding clauses, wherein positioning the depot includes positioning the depot at a superior, lateral, posterior, or inferior aspect of a lung of the patient.

146. The method of any one of the preceding clauses, wherein the depots include a first depot and a second depot, and wherein positioning the depots includes positioning the first depot at a first location comprising a superior, lateral, posterior, or inferior aspect of a lung of the patient, and positioning the second depot at a second location comprising at a superior, lateral, posterior, or inferior aspect of the lung, and wherein the second location is different than the first location.

147. The method of any one of the preceding clauses, wherein the depots include a first depot, a second depot, and a third depot, and wherein positioning the depots includes positioning the first depot at a first location comprising a superior, lateral, posterior, or inferior aspect of a lung of the patient, positioning the second depot at a second location comprising at a superior, lateral, posterior, or inferior aspect of the lung, and positioning the third depot at a third location comprising at a superior, lateral, posterior, or inferior aspect of the lung, and wherein the first, second, and third locations are different.

148. The method of any one of the preceding clauses, wherein the depots include a first depot, a second depot, and a third depot, and wherein positioning the depots includes positioning the first depot at a first location comprising a superior, lateral, posterior, or inferior aspect of a lung of the patient, positioning the second depot at a second location comprising at a superior, lateral, posterior, or inferior aspect of the lung, positioning the third depot at a third location comprising at a superior, lateral, posterior, or inferior aspect of the lung, and positioning the fourth depot at a fourth location comprising at a superior, lateral, posterior, or inferior aspect of the lung, and wherein the first, second, third, and fourth locations are different.

149. The method of any one of the preceding clauses, wherein at least two of the plurality of depots have a different size, a different shape, and/or a different therapeutic agent.

150. The method of any one of the preceding clauses, wherein the chemotherapeutic agent is released one or more times in substantially discrete doses after implantation.

151. The method of any one of the preceding clauses, wherein releasing the therapeutic agent includes releasing a sclerosant.

152. The method of any one of the preceding clauses, wherein releasing the therapeutic agent includes releasing all of the sclerosant before releasing half of the chemotherapeutic agent.

153. The method of any one of the preceding clauses, wherein releasing the therapeutic agent includes releasing all of the sclerosant within the first 1 hour, 2 hours, 3 hours, 6 hours, 12 hours, or 24 hours after implantation of the depot.

154. The method of any one of the preceding clauses, wherein releasing the therapeutic agent includes releasing 3-10 g, 4-8 g, 2-3 g, 3-4 g, 4-5 g, 5-6 g, 6-7 g, 7-8 g, 8-9 g, 9-10 g, about 2 g, about 3 g, about 4 g, about 5 g, about 6 g, about 7 g, about 8 g, about 9 g, or about 10 g of talc or a talc slurry.

155. The method of any one of the preceding clauses, wherein releasing the therapeutic agent includes releasing 3-10 g, 4-8 g, 2-3 g, 3-4 g, 4-5 g, 5-6 g, 6-7 g, 7-8 g, 8-9 g, 9-10 g, about 2 g, about 3 g, about 4 g, about 5 g, about 6 g, about 7 g, about 8 g, about 9 g, or about 10 g of talc or a talc slurry within the first 1 hour, 2 hours, 3 hours, 6 hours, 12 hours, or 24 hours after implantation of the depot.

156. The method of any one of the preceding clauses, wherein releasing the therapeutic agent includes releasing 200-800 mg, 300-700 mg, 400-600 mg, about 300 mg, about 400 mg, about 500 mg, about 600 mg, about 700 mg, or about 800 mg of doxycycline.

157. The method of any one of the preceding clauses, wherein releasing the therapeutic agent includes releasing 200-800 mg, 300-700 mg, 400-600 mg, about 300 mg, about 400 mg, about 500 mg, about 600 mg, about 700 mg, or about 800 mg of doxycycline within the first 1 hour, 2 hours, 3 hours, 6 hours, 12 hours, or 24 hours after implantation of the depot.

158. The method of any one of the preceding clauses, wherein releasing the therapeutic agent includes releasing an analgesic.

159. A depot for treating soft tissue sarcoma ("STS") via sustained, controlled release of a therapeutic agent to a patient, the depot comprising:

a therapeutic region comprising a chemotherapeutic agent;

a control region comprising a bioresorbable polymer and a releasing agent mixed with the polymer, wherein the releasing agent is configured to dissolve when the depot is placed in vivo to form diffusion openings in the control region; and wherein the depot is configured to be implanted at a treatment site proximate an STS of the patient and, while implanted, release the chemotherapeutic agent at the treatment site at a first time and a second time, the second time being a period of time after the first time of no less than 7 days.

160. The depot of any one of the preceding clauses, wherein the chemotherapeutic agent comprises a first chemotherapeutic agent and a second chemotherapeutic agent, wherein the depot is configured to release the first chemotherapeutic agent at the first time and the second chemotherapeutic agent at the second time.

161. The depot of any one of the preceding clauses, wherein the depot is configured to release the first chemotherapeutic agent at a consistent, continuous rate that extends from the first time to after the second time.

162. The depot of any one of the preceding clauses, wherein the depot is a flexible, thin film.

163. The depot of any one of the preceding clauses, wherein the chemotherapeutic agent is at least one of doxorubicin, imatinib, sirolimus, sunitinib, sorafenib, rapamycin, trabectedin, eribulin, gemcitabine, cediranib, rapamycin, olaratumab, ifosfamide, paclitaxel, regoraferib, and/or pazopanib.

164. The depot of any one of the preceding clauses, wherein the chemotherapeutic agent includes pazopanib, and wherein the depot is configured to release the pazopanib continuously over the period of time.

165. The depot of any one of the preceding clauses, wherein the chemotherapeutic agent includes doxorubicin, and wherein the depot is configured to release the doxorubicin continuously over the period of time.

166. The depot of any one of the preceding clauses, wherein the chemotherapeutic agent includes trabectedin, and wherein the depot is configured to release the trabectedin intermittently over the period of time.

167. The depot of any one of the preceding clauses, wherein the chemotherapeutic agent includes eribulin, and wherein the depot is configured to release the eribulin intermittently over the period of time.

168. The depot of any one of the preceding clauses, wherein the chemotherapeutic agent includes doxorubicin and olaratumab.

169. The depot of any one of the preceding clauses, wherein the period of time is 2, 3, 4, 5, 6, 7, or 8 weeks, and wherein the chemotherapeutic agent is delivered once a week throughout the period of time.

170. The depot of any one of the preceding clauses, wherein the period of time is 2, 3, 4, 5, 6, 7, or 8 weeks and the chemotherapeutic agent is paclitaxel and/or liposomal doxorubicin, and wherein the depot is configured to deliver the chemotherapeutic agent once a week throughout the period of time.

171. The depot of any one of the preceding clauses, wherein the treatment site is a gastrointestinal stromal sarcoma of the patient and the period of time is 2, 3, 4, 5, 6, 7, or 8 weeks and the chemotherapeutic agent is imatinib and/or sunitinib, and wherein the depot is configured to deliver the chemotherapeutic agent once a week throughout the period of time.

172. The depot of any one of the preceding clauses, wherein the treatment site is a dermatofibrosarcoma of the patient and the period of time is 2, 3, 4, 5, 6, 7, or 8 weeks and the chemotherapeutic agent is imatinib, and wherein the depot is configured to deliver the chemotherapeutic agent to the treatment site once a week throughout the period of time.

173. The depot of any one of the preceding clauses, wherein the treatment site is a perivascular epithelioid cell tumor of the patient and the period of time is 2, 3, 4, 5, 6, 7, or 8 weeks and the chemotherapeutic agent is rapamycin, and wherein depot is configured to deliver the chemotherapeutic agent to the treatment site once a week throughout the period of time.

174. The depot of any one of the preceding clauses, wherein the treatment site is an alveolar soft part sarcoma of the patient and the period of time is 2, 3, 4, 5, 6, 7, or 8 weeks and the chemotherapeutic agent is sunitinib, and wherein the depot is configured to deliver the chemotherapeutic agent to the treatment site once a week throughout the period of time.

175. The depot of any one of the preceding clauses, wherein the treatment site is a leiomyosarcoma of the patient and the period of time is 2, 3, 4, 5, 6, 7, or 8 weeks and the chemotherapeutic agent is rapamycin, and wherein the depot is configured to deliver the chemotherapeutic agent to the treatment site once a week throughout the period of time.

176. The depot of any one of the preceding clauses, wherein the treatment site is a leiomyosarcoma or a liposarcoma of the patient and the period of time is 2, 3, 4, 5, 6, 7, or 8 weeks, and the chemotherapeutic agent is trabectedin, and wherein the depot is configured to deliver the chemotherapeutic agent to the treatment site once a week throughout the period of time.

177. The depot of any one of the preceding clauses, wherein the therapeutic region is configured to release the chemotherapeutic agent intermittently over the period of time.

178. The depot of any one of the preceding clauses, wherein the therapeutic region is configured to release the chemotherapeutic agent continuously over the period of time.

179. The depot of any one of the preceding clauses, wherein the period of time is at least 4 weeks, and wherein the therapeutic region is configured to release a dose of the chemotherapeutic agent once a week or once every 2 weeks over the period of time.

180. The depot of any one of the preceding clauses, wherein the period of time is at least 8 weeks, and wherein the therapeutic region is configured to release a dose of the chemotherapeutic agent once every week or once every 2 weeks over the period of time.

181. The depot of any one of the preceding clauses, wherein the period of time is at least 12 weeks, and wherein the therapeutic region is configured to release a dose of the chemotherapeutic agent once every week, every 2 weeks, or every 3 weeks over the period of time.

182. The depot of any one of the preceding clauses, wherein the period of time is at least 16 weeks, and wherein the therapeutic region is configured to release a dose of the chemotherapeutic agent once every week, every 2 weeks, or every 4 weeks over the period of time.

183. The depot of any one of the preceding clauses, wherein the period of time is no less than 2 weeks, no less than 3 weeks, no less than 4 weeks, no less than 5 weeks, no less than 6 weeks, no less than 7 weeks, no less than 8 weeks, no less than 2 months, no less than 3 months, no less than 4 months, no less than 6 months, no less than 7 months, no less than 8 months, no less than 9 months, no less than 10 months, no less than 12 months, no less than 1 year.

184. The depot of any one of the preceding clauses, wherein the chemotherapeutic agent comprises a first chemotherapeutic agent and a second chemotherapeutic agent different than the first chemotherapeutic agent.

185. The depot of any one of the preceding clauses, wherein the first chemotherapeutic agent comprises doxorubicin and the second chemotherapeutic agent includes at least one of trabectedin, pazopanib, and/or eribulin.

186. The depot of any one of the preceding clauses, wherein the depot is configured to release the first chemotherapeutic agent continuously and the second chemotherapeutic agent intermittently over the period of time.

187. The depot of any one of the preceding clauses, wherein the depot is configured to release the first chemotherapeutic agent at a first rate and the second chemotherapeutic agent at a second rate.

188. The depot of any one of the preceding clauses, wherein the first rate is the same as the second rate.

189. The depot of any one of the preceding clauses, wherein the first rate is different than the second rate.

190. The depot of any one of the preceding clauses, wherein the first rate is greater than the second rate.

191. The depot of any one of the preceding clauses, wherein the first rate is less than the second rate.

192. The depot of any one of the preceding clauses, wherein the treatment site is at a head, neck, and/or face of the patient.

193. The depot of any one of the preceding clauses, wherein the treatment site is at a gastrointestinal tract of the patient.

194. The depot of any one of the preceding clauses, wherein the treatment site is at a retroperitoneum of the patient.

195. The depot of any one of the preceding clauses, wherein the treatment site is at a limb of the patient.

196. The depot of any one of the preceding clauses, wherein the treatment site is at an arm of the patient.

197. The depot of any one of the preceding clauses, wherein the treatment site is at a leg of the patient.

198. The depot of any one of the preceding clauses, wherein the treatment site is at the skin of the patient.

199. The depot of any one of the preceding clauses, wherein the treatment site is at a gynaecological organ of the patient.
200. The depot of any one of the preceding clauses, wherein the treatment site is at a genital region of the patient.
201. The depot of any one of the preceding clauses, wherein the treatment site is at an organ within a trunk region of the patient.
202. The depot of any one of the preceding clauses, wherein the treatment site is at connective tissue within a trunk region of the patient.
203. The depot of any one of the preceding clauses, wherein the depot is configured to be positioned in direct contact with connective tissue of the patient to deliver the chemotherapeutic agent to the connective tissue.
204. The depot of any one of the preceding clauses, wherein the depot is configured to be positioned in direct contact with soft tissue of the patient to deliver the chemotherapeutic agent to the soft tissue.
205. The depot of any one of the preceding clauses, wherein the depot is configured to be positioned in direct contact with fat of the patient to deliver the chemotherapeutic agent to the fat.
206. The depot of any one of the preceding clauses, wherein the depot is configured to be positioned in direct contact with muscle of the patient to deliver the chemotherapeutic agent to the muscle.
207. The depot of any one of the preceding clauses, wherein the depot is configured to be positioned in direct contact with deep skin tissue of the patient to deliver the chemotherapeutic agent to the deep skin tissue.
208. The depot of any one of the preceding clauses, wherein the depot is configured to be positioned in direct contact with a blood vessel of the patient to deliver the chemotherapeutic agent to the blood vessel.
209. The depot of any one of the preceding clauses, wherein the depot is configured to be positioned in direct contact with a cartilage of the patient at the treatment site to deliver the chemotherapeutic agent to the cartilage.
210. The depot of any one of the preceding clauses, wherein the depot is configured to be positioned in direct contact with a tendon of the patient to deliver the chemotherapeutic agent to the tendon.
211. The depot of any one of the preceding clauses, wherein the depot is configured to be positioned in direct contact with a ligament of the patient to deliver the chemotherapeutic agent to the ligament.
212. The depot of any one of the preceding clauses, wherein the chemotherapeutic agent is configured to treat an angiosarcoma at the treatment site.
213. The depot of any one of the preceding clauses, wherein the chemotherapeutic agent is configured to treat an osteosarcoma at the treatment site.
214. The depot of any one of the preceding clauses, wherein the chemotherapeutic agent is configured to treat an Ewing's sarcoma at the treatment site.
215. The depot of any one of the preceding clauses, wherein the chemotherapeutic agent is configured to treat a chondrosarcoma at the treatment site.
216. The depot of any one of the preceding clauses, wherein the chemotherapeutic agent is configured to treat a gastrointestinal stromal tumor at the treatment site.
217. The depot of any one of the preceding clauses, wherein the chemotherapeutic agent is configured to treat a liposarcoma at the treatment site.
218. The depot of any one of the preceding clauses, wherein the chemotherapeutic agent is configured to treat a fibrosarcoma at the treatment site.
219. The depot of any one of the preceding clauses, wherein the chemotherapeutic agent is configured to treat a hemangioendothelioma at the treatment site.
220. A system for treating an STS via the controlled, sustained release of a therapeutic agent, the system comprising:

the depot of any one of the preceding clauses and a delivery device configured to position the depot proximate a soft tissue sarcoma of a patient.

221. A system for treating STS, comprising:

a plurality of depots, each comprising a depot of any one of the preceding clauses and a delivery device configured to position the depots proximate a soft tissue sarcoma of a patient.

222. The system of any one of the preceding clauses, wherein at least two of the plurality of depots have a different size, a different shape, release profile, and/or a different chemotherapeutic agent.
223. A method for treating a STS via the controlled, sustained release of a chemotherapeutic agent, the method comprising:

providing a depot of any one of the preceding clauses

224. A method for treating a STS via the controlled, sustained release of a chemotherapeutic agent, the method comprising:

positioning a depot of any one of the preceding clauses at a treatment site proximate a soft tissue sarcoma of a patient; and releasing the chemotherapeutic agent at the treatment site for a period of time that is no less than 7 days.

225. A method for treating an STS via the controlled, sustained release of a chemotherapeutic agent, the method comprising:

positioning a plurality of depots, each being any one of the preceding clauses at a treatment site proximate an STS of a patient; and releasing the chemotherapeutic agent at the treatment site for a period of time that is no less than 7 days.

226. The method of any one of the preceding clauses, further comprising slowing the growth of the STS.
227. The method of any one of the preceding clauses, further comprising shrinking the STS.
228. The method of any one of the preceding clauses, further comprising reducing the likelihood of the STS recurring.
229. The method of any one of the preceding clauses, wherein the period of time is no less than two weeks, no less than three weeks, no less than four weeks, no less than five weeks, no less than 8 weeks, no less than 2 months, no less than 3 months, no less than 4 months, no less than 6 months, no less than 7 months, no less than 8 months, no less than 9 months, no less than 10 months, no less than 12 months, no less than 1 year.
230. The method of any one of the preceding clauses, wherein releasing the chemotherapeutic agent includes releasing the chemotherapeutic agent once a week, once every 2 weeks, once every 3 weeks, or once every 4 weeks over the period of time.

231. The method of any one of the preceding clauses, wherein at least two of the plurality of depots have a different size, a different shape, and/or a different chemotherapeutic agent.
232. The method of any one of the preceding clauses, wherein the chemotherapeutic agent is at least one of doxorubicin, imatinib, sirolimus, sunitinib, sorafenib, rapamycin, trabectedin, eribulin, gemcitabine, cediranib, rapamycin, olaratumab, ifosfamide, paclitaxel, regoraferib, and/or pazopanib.
233. The method of any one of the preceding clauses, wherein the chemotherapeutic agent includes pazopanib, and wherein releasing the chemotherapeutic agent includes releasing the pazopanib continuously over the period of time.
234. The method of any one of the preceding clauses, wherein the chemotherapeutic agent includes doxorubicin, and wherein releasing the chemotherapeutic agent includes releasing the doxorubicin continuously over the period of time.
235. The method of any one of the preceding clauses, wherein the chemotherapeutic agent includes trabectedin, and wherein releasing the chemotherapeutic agent includes releasing the trabectedin intermittently over the period of time.
236. The method of any one of the preceding clauses, wherein the chemotherapeutic agent includes eribulin, and wherein releasing the chemotherapeutic agent includes releasing the eribulin intermittently over the period of time.
237. The method of any one of the preceding clauses, wherein the chemotherapeutic agent includes doxorubicin and olaratumab.
238. The method of any one of the preceding clauses, wherein the period of time is 2, 3, 4, 5, 6, 7, or 8 weeks, and wherein releasing the chemotherapeutic agent includes releasing the chemotherapeutic agent once a week throughout the period of time.
239. The method of any one of the preceding clauses, wherein the period of time is 2, 3, 4, 5, 6, 7, or 8 weeks and the chemotherapeutic agent is paclitaxel and/or liposomal doxorubicin, and wherein releasing the chemotherapeutic agent includes releasing the chemotherapeutic agent once a week throughout the period of time.
240. The method of any one of the preceding clauses, wherein the treatment site is a gastrointestinal stromal sarcoma of the patient and the period of time is 2, 3, 4, 5, 6, 7, or 8 weeks and the chemotherapeutic agent is imatinib and/or sunitinib, and wherein the depot is configured to deliver the chemotherapeutic agent once a week throughout the period of time.
241. The method of any one of the preceding clauses, wherein the treatment site is a dermatofibrosarcoma of the patient and the period of time is 2, 3, 4, 5, 6, 7, or 8 weeks and the chemotherapeutic agent is imatinib, and wherein the depot is configured to deliver the chemotherapeutic agent to the treatment site once a week throughout the period of time.
242. The method of any one of the preceding clauses, wherein the treatment site is a perivascular epithelioid cell tumor of the patient and the period of time is 2, 3, 4, 5, 6, 7, or 8 weeks and the chemotherapeutic agent is rapamycin, and wherein depot is configured to deliver the chemotherapeutic agent to the treatment site once a week throughout the period of time.
243. The method of any one of the preceding clauses, wherein the treatment site is an alveolar soft part sarcoma and the chemotherapeutic agent is sunitinib.
244. The method of any one of the preceding clauses, wherein the treatment site is a leiomyosarcoma of the patient and the chemotherapeutic agent is rapamycin.
245. The method of any one of the preceding clauses, wherein the treatment site is a leiomyosarcoma or a liposarcoma of the patient and the chemotherapeutic agent is trabectedin.
246. The method of any one of the preceding clauses, wherein the chemotherapeutic agent is released intermittently over the period of time.
247. The method of any one of the preceding clauses, wherein the chemotherapeutic agent is released continuously over the period of time.
248. The method of any one of the preceding clauses, wherein the chemotherapeutic agent is released once every week, every 2 weeks, every 3 weeks, or every 4 weeks over the period of time.
249. The method of any one of the preceding clauses, wherein the period of time is no less than 2 weeks, no less than 3 weeks, no less than 4 weeks, no less than 5 weeks, no less than 6 weeks, no less than 7 weeks, no less than 8 weeks, no less than 2 months, no less than 3 months, no less than 4 months, no less than 6 months, no less than 7 months, no less than 8 months, no less than 9 months, no less than 10 months, no less than 12 months, no less than 1 year.
250. The method of any one of the preceding clauses, wherein the chemotherapeutic agent comprises a first chemotherapeutic agent and a second chemotherapeutic agent different than the first chemotherapeutic agent.
251. The method of any one of the preceding clauses, wherein the first chemotherapeutic agent comprises doxorubicin and the second chemotherapeutic agent includes at least one of trabectedin, pazopanib, and/or eribulin.
252. The method of any one of the preceding clauses, further comprising releasing the first chemotherapeutic agent continuously and the second chemotherapeutic agent intermittently over the period of time.
253. The method of any one of the preceding clauses, wherein the chemotherapeutic agent is released one or more times in substantially discrete doses after implantation.
254. The method of any one of the preceding clauses, further comprising releasing the first chemotherapeutic agent at a first rate and the second chemotherapeutic agent at a second rate.
255. The method of any one of the preceding clauses, wherein the first rate is the same as the second rate.
256. The method of any one of the preceding clauses, wherein the first rate is different than the second rate.
257. The method of any one of the preceding clauses, wherein the first rate is greater than the second rate.
258. The method of any one of the preceding clauses, wherein the first rate is less than the second rate.
259. The method of any one of the preceding clauses, wherein the treatment site is at a head, neck, and/or face of the patient.
260. The method of any one of the preceding clauses, wherein the treatment site is at a gastrointestinal tract of the patient.
261. The method of any one of the preceding clauses, wherein the treatment site is at a retroperitoneum of the patient.

262. The method of any one of the preceding clauses, wherein the treatment site is at a limb of the patient.
263. The method of any one of the preceding clauses, wherein the treatment site is at an arm of the patient.
264. The method of any one of the preceding clauses, wherein the treatment site is at a leg of the patient.
265. The method of any one of the preceding clauses, wherein the treatment site is at the skin of the patient.
266. The method of any one of the preceding clauses, wherein the treatment site is at a gynaecological organ of the patient.
267. The method of any one of the preceding clauses, wherein the treatment site is at a genital region of the patient.
268. The method of any one of the preceding clauses, wherein the treatment site is at an organ within a trunk region of the patient.
269. The method of any one of the preceding clauses, wherein the treatment site is at connective tissue within a trunk region of the patient.
270. A depot for treating head and neck cancer via sustained, controlled release of a therapeutic agent to a patient, the depot comprising:
a therapeutic region comprising a therapeutic agent, the therapeutic agent comprising at least a chemotherapeutic agent;
a control region comprising a bioresorbable polymer and a releasing agent mixed with the polymer, wherein the releasing agent is configured to dissolve when the depot is placed in vivo to form diffusion openings in the control region; and
wherein the depot is configured to be implanted at a treatment site proximate a mouth or throat of the patient and, while implanted, release the chemotherapeutic agent at the treatment site for a period of time that is no less than 7 days.
271. The depot of any one of the preceding clauses, wherein the depot is coupled to a dental implant.
272. The depot of any one of the preceding clauses, wherein the depot is coupled to a dental prosthesis.
273. The depot of any one of the preceding clauses, wherein the depot is coupled to a dental appliance.
274. The depot of any one of the preceding clauses, wherein the dental appliance comprises a removable tray or retainer.
275. The depot of any one of the preceding clauses, wherein the depot comprises a multilayer film laminated over a portion of a dental implant or dental appliance.
276. The depot of any one of the preceding clauses, wherein the depot is wrapped around a portion of a dental implant or dental appliance.
277. The depot of any one of the preceding clauses, wherein the depot extends over at least a portion of an outer surface of a dental implant or dental appliance.
278. The depot of any one of the preceding clauses, wherein the therapeutic region is configured to release the chemotherapeutic agent continuously over the period of time.
279. The depot of any one of the preceding clauses, wherein the period of time is no less than two weeks, no less than three weeks, no less than four weeks, no less than five weeks, no less than 8 weeks, no less than 2 months, no less than 3 months, no less than 4 months, no less than 6 months, no less than 7 months, no less than 8 months, no less than 9 months, no less than 10 months, no less than 12 months, no less than 1 year.
280. The depot of any one of the preceding clauses, wherein the chemotherapeutic agent contains at least 20 mg, at least 50 mg, at least 100 mg, at least 200 mg, at least 300 mg, at least 400 mg, at least 500 mg, at least 600 mg, at least 700 mg, at least 800 mg, or at least 1 g, of the chemotherapeutic agent.
281. The depot of any one of the preceding clauses, wherein the chemotherapeutic agent comprises at least one of: paclitaxel, vincristine, ifosfamide, dacttinomycin, doxorubicin, or cyclophosphamide, ramucirumab, docetaxel, docetaxel, trastuzumab, fluorouracil or 5-FU, oxaliplatin, epirubicin, capecitabine, oxaliplatin, irinotecan, floxuridine, porfimer, aminolevulinic acid, carboplatin, or cisplatin.
282. The depot of any one of the preceding clauses, wherein the therapeutic agent further comprises an agent for the treatment of oral mucositis.
283. The depot of any one of the preceding clauses, wherein the agent for the treatment or oral mucositis comprises at least one of: benzydamine and an oral mucoadhesive.
284. The depot of any one of the preceding clauses, wherein the therapeutic region includes a first portion and a second portion, wherein the first portion comprises the chemotherapeutic agent and the second portion comprises the agent for treatment of oral mucositis.
285. The depot of any one of the preceding clauses, wherein the therapeutic agent further comprises an immunotherapeutic agent.
286. The depot of any one of the preceding clauses, wherein the immunotherapeutic agent comprises at least one of: nivolumab, pembrolizumab, or ramucirumab.
287. The depot of any one of the preceding clauses, wherein the therapeutic region includes a first portion and a second portion, wherein the first portion comprises the chemotherapeutic agent and the second portion comprises the immunotherapeutic agent.
288. The depot of any one of the preceding clauses, wherein the first portion is closer to an exterior surface of the depot than the second portion.
289. The depot of any one of the preceding clauses, wherein the first portion is farther from an exterior surface of the depot than the second portion.
290. The depot of any one of the preceding clauses, wherein therapeutic region is configured to release the immunotherapeutic agent continuously over the period of time.
291. The depot of any one of the preceding clauses, wherein the depot is configured to release the chemotherapeutic agent at a first rate and the immunotherapeutic agent at a second rate.
292. The depot of any one of the preceding clauses, wherein the depot is configured to release the chemotherapeutic agent at a first rate and the agent for the treatment of oral mucositis at a second rate.
293. The depot of any one of the preceding clauses, wherein the first rate is the same as the second rate.
294. The depot of any one of the preceding clauses, wherein the first rate is different than the second rate.
295. The depot of any one of the preceding clauses, wherein the first rate is greater than the second rate.
296. The depot of any one of the preceding clauses, wherein the first rate is less than the second rate.
297. The depot of any one of the preceding clauses, wherein the depot includes an anchor member coupled to the therapeutic region, control region, and/or base region, and wherein the anchor member is configured to be inserted into tissue at the treatment site, thereby securing the depot at or within the mouth or throat of the patient.

298. The depot of any one of the preceding clauses, wherein the anchor comprises a screw.

299. The depot of any one of the preceding clauses, wherein the anchor comprises a dental implant.

300. The depot of any one of the preceding clauses, wherein the anchor comprises a dental prosthesis.

301. A system for treating head and neck cancer via the controlled, sustained release of a therapeutic agent, the system comprising:

the depot of any one of the preceding clauses; and a delivery device configured to position the depot in the throat or mouth of the patient.

302. The system of any of the preceding clauses, wherein the delivery device is configured to position the depot at the oral mucosa and/or jaw bone of the patient.

303. The system of any of the preceding clauses, wherein the delivery device comprises a driver configured to advance a dental implant coupled to the depot into the oral mucosa and/or jaw bone of the patient.

304. A system for treating head and neck cancer, comprising:

a plurality of depots, each comprising a depot of any one of the preceding clauses; and a delivery device configured to position the depots in the neck.

305. A system for treating a cancer patient having a malignant tumor normally treated by radiation, the system comprising:

the depot of any one of the preceding clauses configured to provide a localized, controlled, sustained release of a therapeutic agent; and a delivery device configured to position the depot proximate to the tumor of the patient, thereby subjecting the tumor to a localized, sustained dose of the therapeutic agent via the depot and sparing the patient a full dose of radiation;

wherein the localized, sustained dose of the therapeutic agent reduces the side effect profile associated with the radiation.

306. A method for treating head and neck cancer via the controlled, sustained release of a therapeutic agent, the method comprising:

providing a depot of any one of the preceding clauses.

307. A method for treating head and neck cancer via the controlled, sustained release of a therapeutic agent, the method comprising:

positioning a depot of any one of the preceding clauses at a treatment site proximate a throat or mouth of a patient;

delivering the therapeutic agent to the treatment site for a period of time that is no less than 7 days.

308. The method of any one of the preceding clauses, further comprising securing the depot over one or more teeth of the patient.

309. The method of any one of the preceding clauses, further comprising securing the depot into the oral mucosa and/or jaw bone of the patient.

310. The method of any one of the preceding clauses, wherein the period of time is no less than two weeks, no less than three weeks, no less than four weeks, no less than five weeks, no less than 8 weeks, no less than 2 months, no less than 3 months, no less than 4 months, no less than 6 months, no less than 7 months, no less than 8 months, no less than 9 months, no less than 10 months, no less than 12 months, no less than 1 year.

311. A depot for treating breast cancer via sustained, controlled release of a therapeutic agent to a patient, the depot comprising:

a therapeutic region comprising a therapeutic agent, the therapeutic agent comprising at least a chemotherapeutic agent;

a control region comprising a bioresorbable polymer and a releasing agent mixed with the polymer, wherein the releasing agent is configured to dissolve when the depot is placed in vivo to form diffusion openings in the control region; and wherein the depot is configured to be implanted at a treatment site proximate a breast of the patient, while implanted, release the therapeutic agent at the treatment site for a period of time that is no less than 7 days.

312. The depot of any one of the preceding clauses, wherein the depot has a preset shape such that, when released from a delivery device, the depot assumes the preset shape.

313. The depot of any one of the preceding clauses, wherein the depot has a preset shape that is curved.

314. The depot of any one of the preceding clauses, wherein the depot has a preset, helical shape.

315. The depot of any one of the preceding clauses, wherein the therapeutic region is configured to release the chemotherapeutic agent continuously over the period of time.

316. The depot of any one of the preceding clauses, wherein the period of time is no less than two weeks, no less than three weeks, no less than four weeks, no less than five weeks, no less than 8 weeks, no less than 2 months, no less than 3 months, no less than 4 months, no less than 6 months, no less than 7 months, no less than 8 months, no less than 9 months, no less than 10 months, no less than 12 months, no less than 1 year.

317. The depot of any one of the preceding clauses, wherein the chemotherapeutic agent contains at least 20 mg, at least 50 mg, at least 100 mg, at least 200 mg, at least 300 mg, at least 400 mg, at least 500 mg, at least 600 mg, at least 700 mg, at least 800 mg, or at least 1 g, of the chemotherapeutic agent.

318. The depot of any one of the preceding clauses, wherein the chemotherapeutic agent comprises at least one of: doxorubicin or paclitaxel.

319. The depot of any one of the preceding clauses, wherein the therapeutic agent further comprises an immunotherapeutic agent.

320. The depot of any one of the preceding clauses, wherein the immunotherapeutic agent comprises at least one of: nivolumab, pembrolizumab, or ramucirumab.

321. The depot of any one of the preceding clauses, wherein the therapeutic region includes a first portion and a second portion, wherein the first portion comprises the chemotherapeutic agent and the second portion comprises the immunotherapeutic agent.

322. The depot of any one of the preceding clauses, wherein the first portion is closer to an exterior surface of the depot than the second portion.

323. The depot of any one of the preceding clauses, wherein the first portion is farther from an exterior surface of the depot than the second portion.

324. The depot of any one of the preceding clauses, wherein therapeutic region is configured to release the immunotherapeutic agent continuously for the period of time.

325. The depot of any one of the preceding clauses, wherein the depot is configured to release the chemotherapeutic agent at a first rate and the immunotherapeutic agent at a second rate.

326. The depot of any one of the preceding clauses, wherein the first rate is the same as the second rate.

327. The depot of any one of the preceding clauses, wherein the first rate is different than the second rate.

328. The depot of any one of the preceding clauses, wherein the first rate is greater than the second rate.

329. The depot of any one of the preceding clauses, wherein the first rate is less than the second rate.

330. The depot of any one of the preceding clauses, wherein the depot is configured to be positioned within a tumor in the breast.

331. The depot of any one of the preceding clauses, wherein the depot is configured to be positioned within a tumor bed after resection of a tumor in the breast.

332. A system for treating breast cancer via the controlled, sustained release of a therapeutic agent, the system comprising:

the depot of any one of the preceding clauses and a delivery device configured to position the depot in the breast.

333. The system of any of the preceding clauses, wherein the delivery device is configured to position the depot within a tumor in the breast.

334. The system of any of the preceding clauses, wherein the delivery device is configured to position the depot within a tumor bed following resection of a tumor in the breast.

335. The system of any of the preceding clauses, wherein the delivery device comprises a needle.

336. A system for treating breast cancer, comprising:

a plurality of depots, each comprising a depot of any one of the preceding clauses and a delivery device configured to position the depots in the breast.

337. A method for treating breast cancer via the controlled, sustained release of a therapeutic agent, the method comprising:

providing a depot of any one of the preceding clauses.

338. A method for treating breast cancer via the controlled, sustained release of a therapeutic agent, the method comprising:

positioning a depot of any one of the preceding clauses at a treatment site proximate a breast of a patient;

delivering the therapeutic agent to the treatment site for a period of time that is no less than 7 days.

339. The method of any one of the preceding clauses, further comprising securing the depot within the breast.

340. The method of any one of the preceding clauses, wherein the period of time is no less than two weeks, no less than three weeks, no less than four weeks, no less than five weeks, no less than 8 weeks, no less than 2 months, no less than 3 months, no less than 4 months, no less than 6 months, no less than 7 months, no less than 8 months, no less than 9 months, no less than 10 months, no less than 12 months, no less than 1 year.

341. A depot for treating pancreatic and/or liver cancer via sustained, controlled release of a therapeutic agent to a patient, the depot comprising:

a therapeutic region comprising a therapeutic agent;

a control region comprising a bioresorbable polymer and a releasing agent mixed with the polymer, wherein the releasing agent is configured to dissolve when the depot is placed in vivo to form diffusion openings in the control region; and wherein the depot is configured to be implanted at a treatment site proximate a pancreas of the patient and, while implanted, release the chemotherapeutic agent at the treatment site for a period of time that is no less than 7 days.

342. The depot of any one of the preceding clauses, wherein the depot is configured to be positioned a superior, lateral, posterior, or inferior aspect of the pancreas.

343. The depot of any one of the preceding clauses, wherein the depot is configured to be positioned adjacent an outer surface of the pancreas.

344. The depot of any one of the preceding clauses, wherein the depot includes a securing portion configured to adhere to a surface of the pancreas.

345. The depot of any one of the preceding clauses, wherein the depot includes a fixation portion configured to penetrate at least a portion of the thickness of the pancreas, thereby securing the depot at the pancreas surface.

346. The depot of any one of the preceding clauses, wherein the depot comprises a sheet or film disposed over a surface of the pancreas.

347. The depot of any one of the preceding clauses, wherein the depot comprises a microbead or pellet configured to be positioned at the treatment site.

348. The depot of any one of the preceding clauses, wherein the pancreatic cancer comprises a tumor, and wherein the depot is configured to be placed at a superior, lateral, posterior, or inferior aspect of the tumor.

349. The depot of any one of the preceding clauses, wherein the pancreatic cancer comprises a tumor, and wherein the depot is configured to be placed proximate an artery supplying the tumor.

350. The depot of any one of the preceding clauses, wherein the depot comprises an intravascular stent.

351. The depot of any one of the preceding clauses, wherein the depot is endovascularly delivered to the pancreas.

352. The depot of any one of the preceding clauses, wherein the depot has a preset shape such that, when released from a delivery device, the depot assumes the preset shape.

353. The depot of any one of the preceding clauses, wherein the depot has a preset shape that is curved.

354. The depot of any one of the preceding clauses, wherein the therapeutic region is configured to release the therapeutic agent continuously at a substantially constant rate over the period of time.

355. The depot of any one of the preceding clauses, wherein the therapeutic region is configured to release the therapeutic agent continuously at a rate that increases over the period of time.

356. The depot of any one of the preceding clauses, wherein the period of time includes a first period of time and a second period of time after the first period of time, and wherein the therapeutic region is configured to release the therapeutic agent at a first rate during the first period of time and a second rate during the second period of time, the second rate being less than the first rate.

357. The depot of any one of the preceding clauses, wherein the period of time is no less than two weeks, no less than three weeks, no less than four weeks, no less than five weeks, no less than 8 weeks, no less than 2 months, no less than 3 months, no less than 4 months, no less than 6 months, no less than 7 months, no less than 8 months, no less than 9 months, no less than 10 months, no less than 12 months, no less than 1 year.

358. The depot of any one of the preceding clauses, wherein the therapeutic agent comprises a chemotherapeutic agent.

359. The depot of any one of the preceding clauses, wherein the chemotherapeutic agent includes paclitaxel.

360. The depot of any one of the preceding clauses, wherein the chemotherapeutic agent includes irinotecan.

361. The depot of any one of the preceding clauses, wherein the chemotherapeutic agent includes at least one of cisplatin, oxaliplatin, capecitabine, albumin-bound, irinotecan, 5-fluorouracil, gemcitabine, vinorelbine, pemetrexed, or combinations thereof.

362. The depot of any one of the preceding clauses, wherein the therapeutic agent comprises a targeting agent.

363. The depot of any one of the preceding clauses, wherein the targeting agent includes at least one of palbociclib, abemaciclib, tipifarnib, tanomastat, marimastat erlotinib or algenpanticel-L, ibilimumab.

364. The depot of any one of the preceding clauses, wherein the therapeutic agent comprises an immunotherapeutic agent.

365. The depot of any one of the preceding clauses, wherein the immunotherapeutic agent comprises at least one of: nivolumab, pembrolizumab or ramucirumab.

366. The depot of any one of the preceding clauses, wherein the immunotherapeutic agent is configured to reduce the growth and/or spread of cancerous tissue by targeting the programmed death-ligand 1 and/or programmed cell death protein 1.

367. The depot of any one of the preceding clauses, wherein the therapeutic region contains at least 20 mg, 50 mg, at least 100 mg, at least 200 mg, at least 300 mg, at least 400 mg, at least 500 mg, at least 600 mg, at least 700 mg, at least 800 mg, or at least 1 g, of the therapeutic agent.

368. The depot of any one of the preceding clauses, wherein the therapeutic region is configured to release the therapeutic agent through the period of time at a rate of from about 0.1 mg/day to about 200 mg/day, about 0.1 mg/day to about 150 mg/day, about 0.1 mg/day to about 100 mg/day, about 0.1 mg/day to about 90 mg/day, about 0.1 mg/day to about 80 mg/day, about 0.1 mg/day to about 70 mg/day, about 0.1 mg/day to about 60 mg/day, about 0.1 mg/day to about 50 mg/day, about 0.1 mg/day to about 40 mg/day, about 0.1 mg/day to about 30 mg/day, about 1 mg/day to about 30 mg/day, about 1 mg/day to about 20 mg/day, about 5 mg/day to about 20 mg/day, about 10 mg/day to about 20 mg/day, or about 15 mg/day to about 20 mg/day.

369. The depot of any one of the preceding clauses, wherein the therapeutic region further comprises an anesthetic.

370. The depot of any one of the preceding clauses, wherein the anesthetic includes at least one of bupivacaine, ropivacaine, mepivacaine, etidocaine, levobupivacaine, trimecaine, carticaine, articaine, lidocaine, prilocaine, benzocaine, procaine, tetracaine or chloroprocaine.

371. The depot of any one of the preceding clauses, wherein the therapeutic region further comprises an anti-inflammatory agent.

372. The depot of any one of the preceding clauses, wherein the anti-inflammatory agent includes at least one of prednisone, betamethasone, cortisone, dexamethasone, hydrocortisone, methylprednisolone, aspirin, Ibuprofen, naproxen sodium, diclofenac, diclofenac-misoprostol, celecoxib, piroxicam, indomethacin, meloxicam, ketoprofen, sulindac, diflunisal, nabumetone, oxaprozin, tolmetin, salsalate, etodolac, fenoprofen, flurbiprofen, ketorolac, meclofenamate, mefenamic acid or COX-2 inhibitors.

373. The depot of any one of the preceding clauses, wherein the therapeutic region further comprises an antibiotic and/or antimicrobial agent.

374. The depot of any one of the preceding clauses, wherein the antibiotic and/or antimicrobial agent includes at least one of amoxicillin, amoxicillin/clavulanate, cephalexin, ciprofloxacin, clindamycin, metronidazole, azithromycin, levofloxacin, sulfamethoxazole/trimethoprim, tetracycline(s), minocycline, tigecycline, doxycycline, rifampin, triclosan, chlorhexidine, penicillin(s), aminoglycides, quinolones, fluoroquinolones, vancomycin, gentamycin, cephalosporin(s), carbapenems, imipenem, ertapenem, antimicrobial peptides, cecropin-mellitin, magainin, dermaseptin, cathelicidin, α-defensins or α-protegrins.

375. The depot of any one of the preceding clauses, wherein the therapeutic region further comprises an antifungal agent.

376. The depot of any one of the preceding clauses, wherein the antifungal region includes a first portion and a second portion, wherein the first portion comprises the therapeutic agent and the second portion comprises the immunotherapeutic agent.

377. The depot of any one of the preceding clauses, wherein the first portion is closer to an exterior surface of the depot than the second portion.

378. The depot of any one of the preceding clauses, wherein the first portion is farther from an exterior surface of the depot than the second portion.

379. The depot of any one of the preceding clauses, wherein therapeutic region is configured to release the therapeutic agent continuously for the period of time.

380. The depot of any one of the preceding clauses, wherein the depot is configured to release the therapeutic agent at a first rate and the immunotherapeutic agent at a second rate.

381. The depot of any one of the preceding clauses, wherein the first rate is the same as the second rate.

382. The depot of any one of the preceding clauses, wherein the first rate is different than the second rate.

383. The depot of any one of the preceding clauses, wherein the first rate is greater than the second rate.

384. The depot of any one of the preceding clauses, wherein the first rate is less than the second rate.

385. A system for treating pancreatic cancer via the controlled, sustained release of a therapeutic agent, the system comprising:

the depot of any one of the preceding clauses and a delivery device configured to position the depot proximate to the pancreas.

386. The system of any of the preceding clauses, wherein the delivery device is configured to position the depot at a surface of the pancreas.

387. The system of any of the preceding clauses, wherein the delivery device is a needle.

388. The system of any one of the preceding clauses, wherein the delivery system comprises a catheter.

389. The system of any one of the preceding clauses, wherein the delivery system is configured to facilitate transarterial access to the pancreas.

390. The system of any one of the preceding clauses, wherein the delivery system is configured to facilitate access to the pancreas through the GI tract.

391. A system for treating pancreatic cancer, comprising:

a plurality of depots, each comprising a depot of any one of the preceding clauses and a delivery device configured to position the depots in the pancreas.

392. A method for treating pancreatic cancer via the controlled, sustained release of a therapeutic agent, the method comprising:

providing a depot of any one of the preceding clauses

393. A method for treating pancreatic cancer via the controlled, sustained release of a therapeutic agent, the method comprising:

positioning a depot of any one of the preceding clauses at a treatment site proximate a pancreas of a patient;

delivering the therapeutic agent to the treatment site for a period of time that is no less than 7 days.

394. The method of any one of the preceding clauses, further comprising securing the depot to the pancreas.

395. The method of any one of the preceding clauses, wherein positioning the depot at the treatment site comprises accessing the pancreas transarterially.

396. The method of any one of the preceding clauses, wherein positioning the depot at the treatment site comprises accessing the pancreas via an incision in the patient's skin.

397. The method of any one of the preceding clauses, wherein positioning the depot at the treatment site comprises accessing the pancreas through the patient's GI tract.

398. The method of any one of the preceding clauses, wherein positioning the depot at the treatment site comprises positioning the depot via the patient's bile duct.

399. The method of any one of the preceding clauses, wherein positioning the depot at the treatment site comprises positioning the depot in the patient's bile duct.

400. The method of any one of the preceding clauses, wherein positioning the depot at the treatment site comprises positioning a stent in the patient's bile duct.

401. The method of any one of the preceding clauses, wherein the pancreatic cancer comprises a tumor, and wherein positioning the depot at the treatment site comprises positioning the depot within an artery supplying the tumor.

402. The method of any one of the preceding clauses, wherein the period of time is no less than two weeks, no less than three weeks, no less than four weeks, no less than five weeks, no less than 8 weeks, no less than 2 months, no less than 3 months, no less than 4 months, no less than 6 months, no less than 7 months, no less than 8 months, no less than 9 months, no less than 10 months, no less than 12 months, no less than 1 year.

403. A depot for treating lung cancer via sustained, controlled release of a therapeutic agent to a patient, the depot comprising:

a therapeutic region comprising a therapeutic agent;

a control region comprising a bioresorbable polymer and a releasing agent mixed with the polymer, wherein the releasing agent is configured to dissolve when the depot is placed in vivo to form diffusion openings in the control region; and wherein the depot is configured to be implanted at a treatment site proximate a lung of the patient and, while implanted, release the chemotherapeutic agent at the treatment site for a period of time that is no less than 7 days.

404. The depot of any one of the preceding clauses, wherein the depot is configured to be positioned at a superior, lateral, posterior, or inferior aspect of the lung.

405. The depot of any one of the preceding clauses, wherein the depot is disposed on a buttress configured to be positioned at an edge portion of the lung.

406. The depot of any one of the preceding clauses, wherein the depot includes a securing portion configured to adhere to a surface of the lung tissue.

407. The depot of any one of the preceding clauses, wherein the depot includes a fixation portion configured to penetrate at least a portion of the thickness of the lung tissue, thereby securing the depot at the lung tissue.

408. The depot of any one of the preceding clauses, wherein the depot includes an anchor member coupled to the therapeutic region, control region, and/or base region, and wherein the anchor member is configured to self-expand into a position with at least a portion of the surface of the lung tissue, thereby securing the depot at or within the lung.

409. The depot of any one of the preceding clauses, wherein the therapeutic region is configured to release the therapeutic agent continuously at a substantially constant rate over the period of time.

410. The depot of any one of the preceding clauses, wherein the therapeutic region is configured to release the therapeutic agent continuously at a rate that increases over the period of time.

411. The depot of any one of the preceding clauses, wherein the period of time includes a first period of time and a second period of time after the first period of time, and wherein the therapeutic region is configured to release the therapeutic agent at a first rate during the first period of time and a second rate during the second period of time, the second rate being less than the first rate.

412. The depot of any one of the preceding clauses, wherein the therapeutic agent comprises a chemotherapeutic agent.

413. The depot of any one of the preceding clauses, wherein the chemotherapeutic agent comprises at least one of paclitaxel, cisplatin, carboplatin, albumin-bound paclitaxel, docetaxel, gemcitabine, vinorelbine or pemetrexed.

414. The depot of any one of the preceding clauses, wherein the therapeutic agent comprises a targeting agent.

415. The depot of any one of the preceding clauses, wherein the targeting agent comprises at least one of bevacizumab, erlotinib, afatinib, gefitinib, crizotinib or ceritinib.

416. The depot of any one of the preceding clauses, wherein the therapeutic agent is configured to target vascular endothelial growth factor.

417. The depot of any one of the preceding clauses, wherein the therapeutic agent is configured to target epidermal growth factor receptor.

418. The depot of any one of the preceding clauses, wherein the therapeutic agent comprises an immunotherapy.

419. The depot of any one of the preceding clauses, wherein the immunotherapy comprises at least one of nivolumab, pembrolizumab or cyramza.

420. The depot of any one of the preceding clauses, wherein the therapeutic agent is configured to target programmed death-ligand I or programmed cell death protein 1.

421. The depot of any one of the preceding clauses, wherein the period of time is no less than two weeks, no less than three weeks, no less than four weeks, no less than five weeks, no less than 8 weeks, no less than 2 months, no less than 3 months, no less than 4 months, no less than 6 months, no less than 7 months, no less than 8 months, no less than 9 months, no less than 10 months, no less than 12 months, no less than 1 year.

422. The depot of any one of the preceding clauses, wherein the therapeutic agent contains at least 1 mg, 10 mg, or 100 mg, of the therapeutic agent.

423. The depot of any one of the preceding clauses, wherein the therapeutic region contains at least 20 mg, 50 mg, at least 100 mg, at least 200 mg, at least 300 mg, at least 400 mg, at least 500 mg, at least 600 mg, at least 700 mg, at least 800 mg, or at least 1 g, of the therapeutic agent.

424. The depot of any one of the preceding clauses, wherein the therapeutic region is configured to release the therapeutic agent through the period of time at a rate of from about 0.1 mg/day to about 200 mg/day, about 0.1 mg/day to about 150 mg/day, about 0.1 mg/day to about 100 mg/day, about 0.1 mg/day to about 90 mg/day, about 0.1 mg/day to about 80 mg/day, about 0.1 mg/day to about 70 mg/day, about 0.1 mg/day to about 60 mg/day, about 0.1 mg/day to about 50 mg/day, about 0.1 mg/day to about 40 mg/day, about 0.1 mg/day to about 30 mg/day, about 1 mg/day to about 30 mg/day, about 1 mg/day to about 20 mg/day, about 5 mg/day to about 20 mg/day, about 10 mg/day to about 20 mg/day, or about 15 mg/day to about 20 mg/day.

425. The depot of any one of the preceding clauses, wherein the therapeutic region contains 100 mg to 600 mg of paclitaxel.

426. The depot of any one of the preceding clauses, wherein the therapeutic region contains 100 mg to 600 mg of cisplatin.

427. The depot of any one of the preceding clauses, wherein the therapeutic region further comprises an immunotherapeutic agent.

428. The depot of any one of the preceding clauses, wherein the immunotherapeutic agent includes at least one of nivolumab, pembrolizumab or cyramza.

429. The depot of any one of the preceding clauses, wherein the therapeutic region further comprises an anesthetic.

430. The depot of any one of the preceding clauses, wherein the anesthetic includes at least one of bupivacaine, ropivacaine, mepivacaine, etidocaine, levobupivacaine, trimecaine, carticaine, articaine, lidocaine, prilocaine, benzocaine, procaine, tetracaine or chloroprocaine.

431. The depot of any one of the preceding clauses, wherein the therapeutic region further comprises an anti-inflammatory agent.

432. The depot of any one of the preceding clauses, wherein the anti-inflammatory agent includes at least one of prednisone, betamethasone, cortisone, dexamethasone, hydrocortisone, methylprednisolone, aspirin, Ibuprofen, naproxen sodium, diclofenac, diclofenac-misoprostol, celecoxib, piroxicam, indomethacin, meloxicam, ketoprofen, sulindac, diflunisal, nabumetone, oxaprozin, tolmetin, salsalate, etodolac, fenoprofen, flurbiprofen, ketorolac, meclofenamate, mefenamic acid or COX-2 inhibitors.

433. The depot of any one of the preceding clauses, wherein the therapeutic region further comprises an antibiotic and/or antimicrobial agent.

434. The depot of any one of the preceding clauses, wherein the antibiotic and/or antimicrobial agent includes at least one of amoxicillin, amoxicillin/clavulanate, cephalexin, ciprofloxacin, clindamycin, metronidazole, azithromycin, levofloxacin, sulfamethoxazole/trimethoprim, tetracycline(s), minocycline, tigecycline, doxycycline, rifampin, triclosan, chlorhexidine, penicillin(s), aminoglycides, quinolones, fluoroquinolones, vancomycin, gentamycin, cephalosporin(s), carbapenems, imipenem, ertapenem, antimicrobial peptides, cecropin-mellitin, magainin, dermaseptin, cathelicidin, α-defensins or α-protegrins.

435. The depot of any one of the preceding clauses, wherein the therapeutic region further comprises an antifungal agent.

436. The depot of any one of the preceding clauses, wherein the antifungal agent includes at least one of ketoconazole, clortrimazole, miconazole, econazole, intraconazole, fluconazole, bifoconazole, terconazole, butaconazole, tioconazole, oxiconazole, sulconazole, saperconazole, voriconazole, terbinafine, amorolfine, naftifine, griseofulvin, haloprogin, butenafine, tolnaftate, nystatin, cyclohexamide, ciclopirox, flucytosine, terbinafine or amphotericin.

437. The depot of any one of the preceding clauses, wherein the therapeutic region includes a first portion and a second portion, wherein the first portion comprises the therapeutic agent and the second portion comprises at least one the immunotherapeutic agent, anesthetic, anti-inflammatory agent, antibiotic agent or antifungal agent.

438. The depot of any one of the preceding clauses, wherein the first portion is closer to an exterior surface of the depot than the second portion.

439. The depot of any one of the preceding clauses, wherein the first portion is farther from an exterior surface of the depot than the second portion.

440. The depot of any one of the preceding clauses, wherein therapeutic region is configured to release the immunotherapeutic agent, anesthetic, anti-inflammatory agent, antibiotic agent and/or antifungal agent continuously for the period of time.

441. The depot of any one of the preceding clauses, wherein the depot is configured to release the therapeutic agent at a first rate and the immunotherapeutic agent, anesthetic, anti-inflammatory agent, antibiotic agent or antifungal agent at a second rate.

442. The depot of any one of the preceding clauses, wherein the first rate is the same as the second rate.

443. The depot of any one of the preceding clauses, wherein the first rate is different than the second rate.

444. The depot of any one of the preceding clauses, wherein the first rate is greater than the second rate.

445. The depot of any one of the preceding clauses, wherein the first rate is less than the second rate.

446. A medical device for sealing an edge portion of a resected lung, comprising:

a staple buttress; and the depot of any one of the preceding clauses.

447. The medical device of any one of the preceding clauses, wherein the depot is attached to an inner surface of the buttress.

448. The system of any one of the preceding clauses, wherein the buttress includes a fixation region configured to receive staples via a stapler, and a drug-releasing region comprising the depot.

449. A system for treating lung cancer via the controlled, sustained release of a therapeutic agent, the system comprising:

the depot of any one of the preceding clauses; and a delivery device configured to position the depot at superior, lateral, posterior, or inferior aspect of the lung.

450. The system of any of the preceding clauses, wherein the delivery device is a syringe.

451. The system of any one of the preceding clauses, wherein the delivery device is a stapler.

452. The system of any one of the preceding clauses, further comprising a buttress configured to be fixed to an edge portion of the lung via the stapler, wherein the buttress includes the depot.

453. The system of any one of the preceding clauses, further comprising a buttress configured to be fixed to an edge portion of the lung via the stapler, wherein the depot is coupled to the buttress.

454. The system of any one of the preceding clauses, further comprising a buttress configured to be fixed to an edge portion of the lung via the stapler, wherein the buttress includes a fixation region configured to receive staples via the stapler, and a drug-releasing region separate from the fixation region that comprises the depot.

455. A system for treating lung cancer, comprising:

a plurality of depots, each comprising a depot of any one of the preceding clauses; and a delivery device configured to position the depots proximate lung tissue.

456. The system of any one of the preceding clauses, wherein the delivery device comprises a navigation modality for endobrochial delivery of the plurality of depots.

457. The system of any one of the preceding clauses, wherein the navigation modality comprises endobroncial ultrasound or electromagnetic navigation brochoscopy.

458. A method for treating lung cancer via the controlled, sustained release of a therapeutic agent, the method comprising:

providing a depot of any one of the preceding clauses.

459. A method for treating lung cancer via the controlled, sustained release of a therapeutic agent, the method comprising:

positioning a depot of any one of the preceding clauses at a treatment site proximate a lung of a patient;

releasing the chemotherapeutic agent to the treatment site for a period of time that is no less than 7 days.

460. The method of any one of the preceding clauses, further comprising securing the depot at a superior, lateral, posterior, or inferior aspect of the lung.

461. The method of any one of the preceding clauses, further comprising securing the depot to a portion of the lung.

462. The method of any one of the preceding clauses, wherein the period of time is no less than two weeks, no less than three weeks, no less than four weeks, no less than five weeks, no less than 8 weeks, no less than 2 months, no less than 3 months, no less than 4 months, no less than 6 months, no less than 7 months, no less than 8 months, no less than 9 months, no less than 10 months, no less than 12 months, no less than 1 year.

463. The depot of any one of the preceding clauses, wherein the control region surrounds only a portion of the therapeutic region such that, upon implantation, the remaining exposed portion of the therapeutic region is in direct contact with bodily fluids at the treatment site.

464. The depot of any one of the preceding clauses, wherein the control region does not include the therapeutic agent at least prior to implantation.

465. The depot of any one of the preceding clauses, wherein the polymer includes a bioresorbable polymer.

466. The depot of any one of the preceding clauses, wherein the polymer includes a non-bioresorbable polymer.

467. The depot of any one of the preceding clauses, wherein the polymer is a first polymer, and wherein the therapeutic region comprises a second polymer.

468. The depot of any one of the preceding clauses, wherein the first and/or second polymer includes a bioresorbable polymer.

469. The depot of any one of the preceding clauses, wherein the first and/or second polymer includes a non-bioresorbable polymer.

470. The depot of any one of the preceding clauses, wherein the first polymer is non-bioresorbable and the second polymer is bioresorbable.

471. The depot of any one of the preceding clauses, wherein the first and second polymers are the same.

472. The depot of any one of the preceding clauses, wherein the first and second polymers are different.

473. The depot of any one of the preceding clauses, wherein the releasing agent is a first releasing agent, and the therapeutic region comprises a second releasing agent.

474. The depot of any one of the preceding clauses, wherein the first and second releasing agents are the same.

475. The depot of any one of the preceding clauses, wherein the first and second releasing agents are different.

476. The depot of any one of the preceding clauses, wherein a weight percentage of the first releasing agent within the control region is different than a weight percentage of the second releasing agent within the therapeutic region.

477. The depot of any one of the preceding clauses, wherein a weight percentage of the first releasing agent within the control region is the same as a weight percentage of the second releasing agent within the therapeutic region.

478. The depot of any one of the preceding clauses, wherein a weight percentage of the first releasing agent within the control region is greater than the weight percentage of the second releasing agent within the therapeutic region.

479. The depot of any one of the preceding clauses, wherein a thickness of the control region is equivalent to or less than 1/10, 1/15, 1/20, 1/25, 1/30, 1/40, 1/50, or 1/100 of the thickness of the therapeutic region.

480. The depot of any one of the preceding clauses, further comprising a base region surrounding all or a portion of one or both of the control region and the therapeutic region, and wherein the base region comprises a polymer and does not include a releasing agent or a therapeutic agent.

481. The depot of any one of the preceding clauses, wherein the base region comprises multiple, discrete subregions.

482. The depot of any one of the preceding clauses, wherein the base subregions are directly adjacent one another within the depot at least prior to implantation.

483. The depot of any one of the preceding clauses, wherein, at least prior to implantation, the base subregions are separated from one another within the depot by all or a portion of the therapeutic region and/or all or a portion of the control region.

484. The depot of any one of the preceding clauses, wherein the base subregions have the same thickness.

485. The depot of any one of the preceding clauses, wherein the base subregions have different thicknesses.

486. The depot of any one of the preceding clauses, wherein the base region comprises multiple, discrete subregions.

487. The depot of any one of the preceding clauses, wherein the therapeutic subregions are directly adjacent one another within the depot at least prior to implantation.

488. The depot of any one of the preceding clauses, wherein, at least prior to implantation, the therapeutic subregions are separated from one another within the depot by all or a portion of the control region and/or all or a portion of the base region.

489. The depot of any one of the preceding clauses, wherein the therapeutic subregions have the same thickness.

490. The depot of any one of the preceding clauses, wherein the therapeutic subregions have different thicknesses.

491. The depot of any one of the preceding clauses, wherein the control region comprises multiple, discrete subregions.

492. The depot of any one of the preceding clauses, wherein the control subregions are directly adjacent one another within the depot at least prior to implantation.

493. The depot of any one of the preceding clauses, wherein, at least prior to implantation, the control subregions are separated from one another within the depot by all or a portion of the therapeutic region and/or all or a portion of the base region.

494. The depot of any one of the preceding clauses, wherein the control subregions have the same thickness.

495. The depot of any one of the preceding clauses, wherein the control subregions have different thicknesses.

496. The depot of any one of the preceding clauses, wherein the control subregions contain the same concentration of releasing agent.

497. The depot of any one of the preceding clauses, wherein the control subregions contain different concentrations of releasing agent.

498. The depot of any one of the preceding clauses, wherein the depot is configured to release the chemotherapeutic agent at the treatment site in vivo for no less than 1 day, no less than 2 days, no less than 3 days, no less than 4 days, no less than 5 days, no less than 6 days, no less than 7 days, no less than 8 days, no less than 9 days, no less than 10 days, no less than 11 days, no less than 12 days, no less than 13 days, no less than 14 days, no less than 15 days, no less than 16 days, no less than 17 days, no less than 18 days, no less than 19 days, no less than 20 days, no less than 21 days, no less than 22 days, no less than 23 days, no less than 24 days, no less than 25 days, no less than 26 days, no less than 27 days, no less than 28 days, no less than 29 days, no less than 30 days, no less than 40 days, no less than 50 days, no less than 60 days, no less than 70 days, no less than 90 days, no less than 100 days, no less than 200 days, no less than 300 days, or no less than 365 days.

499. The depot of any one of the preceding clauses, wherein the therapeutic region comprises a covered portion and an exposed portion, wherein the covered portion is covered by the control region such that, when the depot is initially positioned at the treatment site in vivo, the control region is between the covered portion of the therapeutic region and physiologic fluids at the treatment site and the exposed portion of the therapeutic region is exposed to the physiologic fluids.

500. The depot of any one of the preceding clauses, wherein:

the depot has a total surface area comprising the exposed surface area of the cover region plus the exposed surface area of the therapeutic region, and when the depot is initially positioned at the treatment site in vivo, a ratio of the exposed surface area of the therapeutic region to the exposed surface area of the cover region is from about 5% to about 20%, or from about 5% to about 15%, or from about 5% to about 10%.

501. The depot of any one of the preceding clauses, wherein the exposed surface area of the control region is less than the exposed surface area of the therapeutic region.

502. The depot of any one of the preceding clauses, wherein the exposed surface area of the control region is greater than the exposed surface area of the therapeutic region.

503. The depot of any one of the preceding clauses, wherein the control region is a first control region, and wherein the depot comprises a second control region.

504. The depot of any one of the preceding clauses, wherein the first control region is disposed at a first side of the therapeutic region and the second control region is disposed at a second side of the therapeutic region opposite the first side.

505. The depot of any one of the preceding clauses, wherein the depot comprises a plurality of control regions and a plurality of therapeutic regions, and wherein each of the therapeutic regions is separated from an adjacent one of the therapeutic regions by one or more control regions.

506. The depot of any one of the preceding clauses, wherein each of the therapeutic regions and each of the control regions is a micro-thin layer.

507. The depot of any one of the preceding clauses, wherein the depot comprises from about 2 to about 100 therapeutic regions.
508. The depot of any one of the preceding clauses, wherein the depot comprises from about 2 to about 50 therapeutic regions.
509. The depot of any one of the preceding clauses, wherein the depot comprises from about 2 to about 10 therapeutic regions.
510. The depot of any one of the preceding clauses, wherein the therapeutic region is enclosed by the control region such that, when the depot is positioned at the treatment site in vivo, the control region is between the therapeutic region and physiologic fluids at the treatment site.
511. The depot of any one of the preceding clauses, wherein the control region comprises a first control layer and a second control layer.
512. The depot of any one of the preceding clauses, wherein the second control layer is adjacent to the therapeutic region and the first control layer encapsulates/encloses the therapeutic region and the second control layer.
513. The depot of any one of the preceding clauses, wherein the first control layer and the second control layer together enclose the therapeutic region.
514. The depot of any one of the preceding clauses, wherein the first control layer is disposed at a first side of the therapeutic region and the second control layer is disposed at a second side of the therapeutic region opposite the first side.
515. The depot of any one of the preceding clauses, wherein the first control layer comprises a first plurality of sub-layers and the second control layer comprises a second plurality of sub-layers.
516. The depot of any one of the preceding clauses, wherein the first control layer includes a first amount of the releasing agent and the second control layer includes a second amount of the releasing agent different than the first amount.
517. The depot of any one of the preceding clauses, wherein the second control layer is positioned between the first control layer and the therapeutic region, and wherein the first control layer includes a first concentration of the releasing agent and the second control layer includes a second concentration of the releasing agent greater than the first concentration.
518. The depot of any one of the preceding clauses, wherein the second control layer is positioned between the first control layer and the therapeutic region, and wherein the first control layer includes a first concentration of the releasing agent and the second control layer includes a second concentration of the releasing agent less than the first concentration.
519. The depot of any one of the preceding clauses, wherein the second control layer is positioned between the first control layer and the therapeutic region, and wherein:

the first control layer includes up to 5% by weight of the releasing agent, up to 10% by weight of the releasing agent, up to 15% by weight of the releasing agent, up to 20% by weight of the releasing agent, up to 25% by weight of the releasing agent, up to 30% by weight of the releasing agent, up to 35% by weight of the releasing agent, up to 40% by weight of the releasing agent, up to 45% by weight of the releasing agent, or 50% by weight of the releasing agent.

the second control layer includes up to 5% by weight of the releasing agent, up to 10% by weight of the releasing agent, up to 15% by weight of the releasing agent, up to 20% by weight of the releasing agent, up to 25% by weight of the releasing agent, up to 30% by weight of the releasing agent, up to 35% by weight of the releasing agent, up to 40% by weight of the releasing agent, up to 45% by weight of the releasing agent, or up to 50% by weight of the releasing agent.

520. The depot of any one of the preceding clauses, wherein the second control layer is positioned between the first control layer and the therapeutic region, and wherein the first control layer includes a first amount of the releasing agent and the second control layer includes a second amount of the releasing agent, the second amount being at least 2×, at least 3×, at least 4×, or at least 5× the first amount.
521. The depot of any one of the preceding clauses, wherein a thickness of the control region is less than or equal to 1/10 of a thickness of the therapeutic region.
522. The depot of any one of the preceding clauses, wherein a thickness of the control region is less than or equal to 1/15 of a thickness of the therapeutic region.
523. The depot of any one of the preceding clauses, wherein a thickness of the control region is less than or equal to 1/20 of a thickness of the therapeutic region.
524. The depot of any one of the preceding clauses, wherein a thickness of the control region is less than or equal to 1/25 of a thickness of the therapeutic region.
525. The depot of any one of the preceding clauses, wherein a thickness of the control region is less than or equal to 1/30 of a thickness of the therapeutic region.
526. The depot of any one of the preceding clauses, wherein a thickness of the control region is less than or equal to 1/35 of a thickness of the therapeutic region.
527. The depot of any one of the preceding clauses, wherein a thickness of the control region is less than or equal to 1/40 of a thickness of the therapeutic region.
528. The depot of any one of the preceding clauses, wherein a thickness of the control region is less than or equal to 1/45 of a thickness of the therapeutic region.
529. The depot of any one of the preceding clauses, wherein a thickness of the control region is less than or equal to 1/50 of a thickness of the therapeutic region.
530. The depot of any one of the preceding clauses, wherein a thickness of the control region is less than or equal to 1/75 of a thickness of the therapeutic region.
531. The depot of any one of the preceding clauses, wherein a thickness of the control region is less than or equal to 1/100 of a thickness of the therapeutic region.
532. The depot of any one of the preceding clauses, wherein the depot is a flexible solid that is structurally capable of being handled by a clinician during the normal course of a surgery without breaking into multiple pieces and/or losing its general shape.
533. The depot of any one of the preceding clauses, wherein the depot is configured to be placed at a surgical site and release the chemotherapeutic agent in vivo for up to 7 days without breaking into multiple pieces.
534. The depot of any one of the preceding clauses, wherein the depot has a width and a thickness, and wherein a ratio of the width to the thickness is 21 or greater.
535. The depot of any one of the preceding clauses, wherein the ratio is 30 or greater.

536. The depot of any one of the preceding clauses, wherein the ratio is 40 or greater.

537. The depot of any one of the preceding clauses, wherein the depot has a surface area and a volume, and wherein a ratio of the surface area to volume is at least 1.

538. The depot of any one of the preceding clauses, wherein the diffusion openings include at least one or more pores and/or one or more channels.

539. The depot of any one of the preceding clauses, wherein the two or more micro-thin layers of the bioresorbable polymer are bonded via heat compression to form the therapeutic region.

540. The depot of any one of the preceding clauses, wherein the control region and the therapeutic region are bonded via heat compression.

541. The depot of any one of the preceding clauses, wherein the control region and the therapeutic region are thermally bonded.

542. The depot of any one of the preceding clauses, wherein dissolution of the releasing agent following in vivo placement in the treatment site causes the control region and the therapeutic region to transition from a state of lesser porosity to a state of greater porosity to facilitate the release of the chemotherapeutic agent from the depot.

543. The depot of any one of the preceding clauses, wherein the control region does not include the chemotherapeutic agent at least prior to implantation of the depot at the treatment site.

544. The depot of any one of the preceding clauses, wherein the therapeutic region does not include any releasing agent prior to implantation of the depot at the treatment site.

545. The depot of any one of the preceding clauses, wherein the releasing agent is a first releasing agent and the therapeutic region includes a second releasing agent mixed with the chemotherapeutic agent.

546. The depot of any one of the preceding clauses, wherein the releasing agent is a first releasing agent and the polymer is a first polymer, and the therapeutic region includes a second releasing agent and a second polymer mixed with the chemotherapeutic agent.

547. The depot of any one of the preceding clauses, wherein the first releasing agent is the same as the second releasing agent.

548. The depot of any one of the preceding clauses, wherein the first releasing agent is the different than the second releasing agent.

549. The depot of any one of the preceding clauses, wherein a concentration of the first releasing agent within the control region is the greater than a concentration of the second releasing agent within the therapeutic region.

550. The depot of any one of the preceding clauses, wherein a concentration of the first releasing agent within the control region is the less than a concentration of the second releasing agent within the therapeutic region.

551. The depot of any one of the preceding clauses, wherein a concentration of the first releasing agent within the control region is the same as a concentration of the second releasing agent within the therapeutic region.

552. The depot of any one of the preceding clauses, wherein a concentration of the first releasing agent within the control region is different than a concentration of the second releasing agent within the therapeutic region.

553. The depot of any one of the preceding clauses, wherein the therapeutic region includes a plurality of microlayers.

554. The depot of any one of the preceding clauses, wherein the mass of the chemotherapeutic agent comprises at least 50% of the mass of the depot.

555. The depot of any one of the preceding clauses, wherein the ratio of the mass of the chemotherapeutic agent in the depot to the depot polymer mass is at least 3:1.

556. The depot of any one of the preceding clauses, wherein the ratio of the mass of the chemotherapeutic agent in the depot to the depot polymer mass is at least 4:1.

557. The depot of any one of the preceding clauses, wherein the ratio of the mass of the chemotherapeutic agent in the depot to the depot polymer mass is at least 5:1.

558. The depot of any one of the preceding clauses, wherein a ratio of the mass of the chemotherapeutic agent in the depot to the depot polymer mass is at least 6:1.

559. The depot of any one of the preceding clauses, wherein a ratio of the mass of the chemotherapeutic agent in the depot to the depot polymer mass is at least 7:1.

560. The depot of any one of the preceding clauses, wherein a ratio of the mass of the chemotherapeutic agent in the depot to the depot polymer mass is at least 8:1.

561. The depot of any one of the preceding clauses, wherein a ratio of the mass of the chemotherapeutic agent in the depot to the depot polymer mass is at least 10:1.

562. The depot of any one of the preceding clauses, wherein a ratio of the mass of the chemotherapeutic agent in the depot to the depot polymer mass is at least 16:1.

563. The depot of any one of the preceding clauses, wherein the therapeutic region includes at least 60% by weight of the chemotherapeutic agent, 60% by weight of the chemotherapeutic agent, at least 70% by weight of the chemotherapeutic agent, at least 80% by weight of the chemotherapeutic agent, at least 90% by weight of the chemotherapeutic agent, or 100% by weight of the chemotherapeutic agent.

564. The depot of any one of the preceding clauses, wherein the depot includes at least 15% by weight of the chemotherapeutic agent, at least 20% by weight of the chemotherapeutic agent, at least 30% by weight of the chemotherapeutic agent, at least 40% by weight of the chemotherapeutic agent, at least 50% by weight of the chemotherapeutic agent, at least 60% by weight of the chemotherapeutic agent, at least 70% by weight of the chemotherapeutic agent, at least 80% by weight of the chemotherapeutic agent, at least 90% by weight of the chemotherapeutic agent, or 100% by weight of the chemotherapeutic agent.

565. The depot of any one of the preceding clauses, further comprising an analgesic, and wherein the analgesic comprises at least one of: simple analgesics, local anesthetics, NSAIDs and opioids.

566. The depot of any one of the preceding clauses, further comprising an analgesic, and wherein the analgesic comprises a local anesthetic selected from at least one of bupivacaine, ropivacaine, mepivacaine, and lidocaine.

567. The depot of any one of the preceding clauses, further comprising an antibiotic, an antifungal, and/or an antimicrobial, wherein the antibiotic, the antifungal, and/or the antimicrobial is selected from at least one of amoxicillin, amoxicillin/clavulanate, cephalexin, ciprofloxacin, clindamycin, metronidazole, azithromycin, levofloxacin, sulfamethoxazole/trimethoprim, tetracycline(s), minocycline, tigecycline, doxycycline, rifampin, triclosan, chlorhexidine, penicillin(s), aminoglycides, quinolones, fluoroquinolones, vancomycin, gentamycin, cephalosporin(s), carbapenems, imipenem, ertapenem, antimicrobial peptides, cecropin-mellitin, magainin, dermaseptin, cathelicidin, α-defensins, and α-protegrins, ketoconazole, clortrimazole, miconazole, econazole, intraconazole, fluconazole, bifoconazole, terconazole, butaconazole, tioconazole, oxiconazole, sulconazole, saperconazole, voriconazole, terbinafine, amorolfine, naftifine, griseofulvin, haloprogin, butenafine, tolnaftate, nystatin, cyclohexamide, ciclopirox, flucytosine, terbinafine, and amphotericin B.

568. The depot of any one of the preceding clauses, further comprising an anti-inflammatory agent selected from at least one of steroids, prednisone, betamethasone, cortisone, dexamethasone, hydrocortisone and methylprednisolone, non-steroidal anti-inflammatory drugs (NSAIDs), aspirin, Ibuprofen, naproxen sodium, diclofenac, diclofenac-misoprostol, celecoxib, piroxicam, indomethacin, meloxicam, ketoprofen, sulindac, diflunisal, nabumetone, oxaprozin, tolmetin, salsalate, etodolac, fenoprofen, flurbiprofen, ketorolac, meclofenamate, mefenamic acid, and COX-2 inhibitors.

569. The depot of any one of the preceding clauses, further comprising at least one of: epinephrine, clonidine, transexamic acid.

570. The depot of any one of the preceding clauses, wherein the releasing agent is a non-ionic surfactant.

571. The depot of any one of the preceding clauses, wherein the releasing agent has hydrophilic properties.

572. The depot of any one of the preceding clauses, wherein the releasing agent is a polysorbate.

573. The depot of any one of the preceding clauses, wherein the releasing agent is Tween 20.

574. The depot of any one of the preceding clauses, wherein the releasing agent is Tween 80.

575. The depot of any one of the preceding clauses, wherein the releasing agent is non-polymeric.

576. The depot of any one of the preceding clauses, wherein the releasing agent is not a plasticizer.

577. The depot of any one of the preceding clauses, wherein the polymer is configured to degrade only after substantially all of the chemotherapeutic agent has been released from the depot.

578. The depot of any one of the preceding clauses, wherein the polymer is a copolymer.

579. The depot of any one of the preceding clauses, wherein the polymer is a terpolymer.

580. The depot of any one of the preceding clauses, wherein the polymer includes at least one of polyglycolide (PGA), polycaprolactone (PCL), poly(DL-lactic acid) (PLA), poly(alpha-hydroxy acids), poly(lactide-co-glycolide)(PLGA or DLG), poly(DL-lactide-co-caprolactone) (DL-PLCL), poly(trimethylene carbonate) (PTMC), polydioxanone (PDO), poly(4-hydroxy butyrate) (PHB), polyhydroxyalkanoates (PHA), poly(phosphazene), polyphosphate ester), poly(amino acid), polydepsipeptides, poly(butylene succinate) (PBS), polyethylene oxide, polypropylene fumarate, polyiminocarbonates, poly(lactide-co-caprolactone) (PLCL), poly(glycolide-co-caprolactone) (PGCL) copolymer, poly(D,L-lactic acid), polyglycolic acid, poly(L-lactide-co-D,L-lactide), poly(L-lactide-co-glycolide), poly(D,L-lactide-co-glycolide), poly(gycolide-trimethylene carbonate), poly(ethyl glutamate-co-glutamic acid), poly(tert-butyloxy-carbonylmethyl glutamate), poly(glycerol sebacate), tyrosine-derived polycarbonate, poly 1,3-bis-(p-carboxyphenoxy) hexane-co-sebacic acid, polyphosphazene, ethyl glycinate polyphosphazene, polycaprolactone co-butylacrylate, a copolymer of polyhydroxybutyrate, a copolymer of maleic anhydride, a copolymer of poly(trimethylene carbonate), polyethylene glycol (PEG), hydroxypropylmethylcellulose and cellulose derivatives, polysaccharides (such as hyaluronic acid, chitosan and starch), proteins (such as gelatin and collagen) or PEG derivatives, polyaspirins, polyphosphagenes, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, D-lactide, D,L-lactide, L-lactide, D,L-lactide-caprolactone (DL-CL), D,L-lactide-glycolide-caprolactone (DL-G-CL), dextrans, vinylpyrrolidone, polyvinyl alcohol (PVA), PVA-g-PLGA, PEGT-PBT copolymer (polyactive), methacrylates, poly(N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate) hydroxypropyl cellulose, hydroxypropyl methylcellulose, hydroxyethyl methylcellulose, carboxymethylcellulose or salts thereof, Carbopol®, poly(hydroxyethylmethacrylate), poly(methoxyethylmethacrylate), poly(methoxyethoxy-ethylmethacrylate), polymethylmethacrylate (PMMA), methylmethacrylate (MMA), gelatin, polyvinyl alcohols, propylene glycol, and poly(DL-lactide-co-glycolide-co-caprolactone).

581. The depot of any one of the preceding clauses, wherein the polymer is one of poly(DL-lactide-co-glycolide-co-caprolactone) and poly(DL-lactide-co-glycolide)(PLGA).

582. The depot of any one of the preceding clauses, wherein the polymer is poly(DL-lactide-co-glycolide-co-caprolactone) in a molar ratio of 60:30:10.

583. The depot of any one of the preceding clauses, wherein the polymer is poly(DL-lactide-co-glycolide) (PLGA) in a molar ratio of 50:50.

584. The depot of any one of the preceding clauses, wherein the polymer is ester-terminated.

585. The depot of any one of the preceding clauses, wherein the polymer is a terpolymer that includes three polymers selected from the following: polyglycolide (PGA), polycaprolactone (PCL), poly(L-lactic acid) (PLA), poly(DL-lactic acid) (PLA), poly(trimethylene carbonate) (PTMC), polydioxanone (PDO), poly(4-hydroxy butyrate) (PHB), polyhydroxyalkanoates (PHA), poly(phosphazene), and polyethylene glycol.

586. The depot of any one of the preceding clauses, wherein the polymer is a first polymer, and the therapeutic region includes a second polymer mixed with the chemotherapeutic agent.
587. The depot of any one of the preceding clauses, wherein the first polymer and the second polymer are the same.
588. The depot of any one of the preceding clauses, wherein the first polymer and the second polymer are different.
589. The depot of any one of the preceding clauses, wherein the first polymer and/or the second polymer include at least one of polyglycolide (PGA), polycaprolactone (PCL), poly(DL-lactic acid) (PLA), poly(alpha-hydroxy acids), poly(lactide-co-glycolide)(PLGA or DLG), poly(DL-lactide-co-caprolactone) (DL-PLCL), poly(trimethylene carbonate) (PTMC), polydioxanone (PDO), poly(4-hydroxy butyrate) (PHB), polyhydroxyalkanoates (PHA), poly(phosphazene), polyphosphate ester), poly(amino acid), polydepsipeptides, poly(butylene succinate) (PBS), polyethylene oxide, polypropylene fumarate, polyiminocarbonates, poly(lactide-co-caprolactone) (PLCL), poly(glycolide-co-caprolactone) (PGCL) copolymer, poly(D,L-lactic acid), polyglycolic acid, poly(L-lactide-co-D,L-lactide), poly(L-lactide-co-glycolide), poly(D,L-lactide-co-glycolide), poly(gycolide-trimethylene carbonate), poly(ethyl glutamate-co-glutamic acid), poly(tert-butyloxy-carbonylmethyl glutamate), poly(glycerol sebacate), tyrosine-derived polycarbonate, poly 1,3-bis-(p-carboxyphenoxy) hexane-co-sebacic acid, polyphosphazene, ethyl glycinate polyphosphazene, polycaprolactone co-butylacrylate, a copolymer of polyhydroxybutyrate, a copolymer of maleic anhydride, a copolymer of poly(trimethylene carbonate), polyethylene glycol (PEG), hydroxypropylmethylcellulose and cellulose derivatives, polysaccharides (such as hyaluronic acid, chitosan and starch), proteins (such as gelatin and collagen) or PEG derivatives, polyaspirins, polyphosphagenes, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, D-lactide, D,L-lactide, L-lactide, D,L-lactide-caprolactone (DL-CL), D,L-lactide-glycolide-caprolactone (DL-G-CL), dextrans, vinylpyrrolidone, polyvinyl alcohol (PVA), PVA-g-PLGA, PEGT-PBT copolymer (polyactive), methacrylates, poly(N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate)hydroxypropyl cellulose, hydroxypropyl methylcellulose, hydroxyethyl methylcellulose, carboxymethylcellulose or salts thereof, Carbopol®, poly(hydroxyethylmethacrylate), poly(methoxyethylmethacrylate), poly(methoxyethoxy-ethylmethacrylate), polymethylmethacrylate (PMMA), methylmethacrylate (MMA), gelatin, polyvinyl alcohols, propylene glycol, poly(DL-lactide-co-glycolide-co-caprolactone).
590. The depot of any one of the preceding clauses, wherein the first polymer and/or the second polymer selected from the following: poly(DL-lactide-co-glycolide-co-caprolactone) and poly(DL-lactide-co-glycolide)(PLGA).
591. The depot of any one of the preceding clauses, wherein the first polymer and/or the second polymer is poly(DL-lactide-co-glycolide-co-caprolactone) and has a molar ratio of 60:30:10.
592. The depot of any one of the preceding clauses, wherein the first polymer and/or the second polymer is poly(DL-lactide-co-glycolide) and has a molar ratio of 50:50.
593. The depot of any one of the preceding clauses, wherein the first polymer and/or the second polymer is ester-terminated.
594. The depot of any one of the preceding clauses, wherein the first polymer and/or the second polymer is a terpolymer that includes three polymers selected from the following: polyglycolide (PGA), polycaprolactone (PCL), poly(L-lactic acid) (PLA), poly(trimethylene carbonate) (PTMC), polydioxanone (PDO), poly(4-hydroxy butyrate) (PHB), polyhydroxyalkanoates (PHA), poly(phosphazene), and polyethylene glycol.
595. The depot of any one of the preceding clauses, wherein the ratio of the releasing agent to the polymer in the control region is less than or equal to 1:1.
596. The depot of any one of the preceding clauses, wherein the ratio of the releasing agent to the polymer in the control region is less than or equal to 1:2.
597. The depot of any one of the preceding clauses, wherein the ratio of the releasing agent to the polymer in the control region is less than or equal to 1:3.
598. The depot of any one of the preceding clauses, wherein the ratio of the releasing agent to the polymer in the control region is less than or equal to 1:4.
599. The depot of any one of the preceding clauses, wherein the ratio of the releasing agent to the polymer in the control region is less than or equal to 1:5.
600. The depot of any one of the preceding clauses, wherein the ratio of the releasing agent to the polymer in the control region is less than or equal to 1:6.
601. The depot of any one of the preceding clauses, wherein the ratio of the releasing agent to the polymer in the control region is less than or equal to 1:7.
602. The depot of any one of the preceding clauses, wherein the ratio of the releasing agent to the polymer in the control region is less than or equal to 1:8.
603. The depot of any one of the preceding clauses, wherein the ratio of the releasing agent to the polymer in the control region is less than or equal to 1:9.
604. The depot of any one of the preceding clauses, wherein the ratio of the releasing agent to the polymer in the control region is less than or equal to 1:10.
605. The depot of any one of the preceding clauses, wherein the ratio of the releasing agent to the polymer in the control region is less than or equal to 1:15.
606. The depot of any one of the preceding clauses, wherein:

the polymer is a first polymer and the therapeutic region further includes a second polymer, the depot has a depot polymer mass equivalent to a mass of the first polymer plus a mass of the second polymer, and a ratio of a mass of the chemotherapeutic agent in the depot to the depot polymer mass is approximately 1:1.

607. The depot of any one of the preceding clauses, wherein the first polymer is the same as the second polymer.
608. The depot of any one of the preceding clauses, wherein the first polymer is different than the second polymer.

609. The depot of any one of the preceding clauses, wherein the ratio of the mass of the chemotherapeutic agent in the depot to the depot polymer mass is at least 2:1.

610. The depot of any one of the preceding clauses, wherein the ratio of the mass of the chemotherapeutic agent in the depot to the depot polymer mass is at least 3:1.

611. The depot of any one of the preceding clauses, wherein the ratio of the mass of the chemotherapeutic agent in the depot to the depot polymer mass is at least 4:1.

612. The depot of any one of the preceding clauses, wherein the ratio of the mass of the chemotherapeutic agent in the depot to the depot polymer mass is approximately 5:1.

613. The depot of any one of the preceding clauses, wherein a ratio of the mass of the chemotherapeutic agent in the depot to the depot polymer mass is at least 6:1.

614. The depot of any one of the preceding clauses, wherein a ratio of the mass of the chemotherapeutic agent in the depot to the depot polymer mass is at least 7:1.

615. The depot of any one of the preceding clauses, wherein a ratio of the mass of the chemotherapeutic agent in the depot to the depot polymer mass is at least 8:1.

616. The depot of any one of the preceding clauses, wherein a ratio of the mass of the chemotherapeutic agent in the depot to the depot polymer mass is at least 10:1.

617. The depot of any one of the preceding clauses, wherein a ratio of the mass of the chemotherapeutic agent in the depot to the depot polymer mass is at least 16:1.

618. The depot of any one of the preceding clauses, wherein depot is configured to inhibit the growth of bacteria and fungi such that a number of bacteria on the depot is 10×, 20×, 30×, 40×, or 50× less than a number of bacteria present on a comparable depot containing no chemotherapeutic agent.

619. A depot for sustained, controlled release of a therapeutic agent, comprising: a therapeutic region comprising the therapeutic agent;

a control region comprising a bioresorbable polymer and a releasing agent mixed with the polymer, wherein the releasing agent is configured to dissolve when the depot is placed in contact with a fluid to form diffusion openings in the control region; and wherein, when the depot is placed in contact with a fluid, the depot is configured to release the therapeutic agent into the surrounding fluid for no less than 14 days, and wherein about 20% to about 50% of the therapeutic agent is released in the first about 3 to about 5 days of the 14 days, and wherein at least 80% of the remaining therapeutic agent is released in the last 11 days of the 14 days.

620. The depot of any one of the preceding clauses, wherein at least 85% of the remaining therapeutic agent is released in the last 11 days of the 14 days.

621. The depot of any one of the preceding clauses, wherein the releasing agent is configured to dissolve when the depot is placed in contact with phosphate buffered saline to form diffusion openings.

622. The depot of any one of the preceding clauses, further comprising dissolving the releasing agent in response to contact between the control region and the physiologic fluids at the treatment site.

623. The depot of any one of the preceding clauses, further comprising creating diffusion openings in the control region via the dissolution of the releasing agent in response to physiologic fluids at the treatment site.

624. A depot for the release of a therapeutic agent to treat or manage a particular condition or disease, comprising:

a therapeutic region comprising the therapeutic agent and a bioresorbable polymer carrier;

a control region comprising a bioresorbable polymer layer and a releasing agent mixed with the polymer, wherein the releasing agent is configured to dissolve over a first period of time following in vivo placement to form diffusion openings in the control region; and wherein the depot is configured to be implanted at a treatment site in vivo and, while implanted, release the therapeutic agent at the treatment site for a second period of time;

wherein the second period of time is greater than the first period of time;

wherein following the second period of time the polymer carrier of the therapeutic region and the polymer layer of the control region comprise a highly porous polymer structure configured to degrade in vivo without core acidification.

625. The depot of any one of the preceding clauses, wherein the highly porous polymer structure at the end of the second period of time has a mass that is no greater than 50% of the mass of the depot prior to in vivo placement.

626. The depot of any one of the preceding clauses, wherein the highly porous polymer structure is configured to degrade in vivo via surface erosion.

627. A depot for the controlled, sustained release of a therapeutic agent, comprising:

a therapeutic region comprising the therapeutic agent, the therapeutic region elongated along a first axis; and a control region at least partially surrounding the therapeutic region and elongated along the first axis, the control region comprising a bioresorbable polymer and a releasing agent mixed with the polymer, wherein the releasing agent is configured to dissolve when the depot is placed in vivo to form diffusion openings in the control region;

wherein the depot is configured to be implanted at a treatment site in vivo and, while implanted, release the therapeutic agent at the treatment site for a period of time not less than 3 days.

628. The depot of any one of the preceding clauses, wherein the depot is at least 5 times longer along the first axis than a maximum transverse dimension along a second axis orthogonal to the first.

629. The depot of any one of the preceding clauses, wherein the depot is at least 10 times longer along the first axis than a maximum transverse dimension along a second axis orthogonal to the first.

630. The depot of any one of the preceding clauses, wherein the depot is substantially columnar.

631. The depot of any one of the preceding clauses, wherein the depot is substantially cylindrical.

632. The depot of any one of the preceding clauses, wherein the therapeutic region is substantially cylindrical.

633. The depot of any one of the preceding clauses, further comprising at least one opening extending through the therapeutic region.

634. The depot of any one of the preceding clauses, wherein the opening forms a cylindrical lumen extending parallel to the first axis.

635. The depot of any of the preceding clauses, wherein the opening comprises a lumen extending along a second axis substantially perpendicular to the first axis.

636. The depot of any of the preceding clauses, further comprising a plurality of elongated openings extending parallel to the second axis.

637. The depot of any one of the preceding clauses, wherein the therapeutic region comprises a plurality of separate elongated sub-regions extending substantially parallel to the first axis.

638. The depot of any one of the preceding clauses, wherein each of the elongated sub-regions is substantially cylindrical.

639. The depot of any one of the preceding clauses, wherein each of the elongated sub-regions are radially separated from one another by the control region.

640. The depot of any one of the preceding clauses, wherein a radially outermost dimension of the depot varies along the first axis.

641. The depot of any one of the preceding clauses, wherein a radially outermost dimension of the therapeutic region varies along the first axis.

642. The depot of any one of the preceding clauses, wherein the therapeutic region is a series of separate regions, covered by and connected by a continuous control region.

643. The depot of the preceding clauses, wherein the control region is narrower in the regions without an internal therapeutic region.

644. The depot of the preceding clauses, wherein the control region is designed to bend or break during or after delivery.

645. The depot of any one of the preceding clauses, wherein the control region has a variable thickness along a length of the depot along the first axis.

646. The depot of any one of the preceding clauses, wherein the control region has a thickness that varies radially around the first axis.

647. The depot of any one of the preceding clauses, wherein the variable thickness of the control region causes the depot to curve or bend when deployed in vivo.

648. The depot of any one of the preceding clauses, wherein the depot is configured to curve or bend preferentially when placed in contact with physiological fluids in vivo.

649. The depot of any one of the preceding clauses, wherein the depot comprises an elongated polymer strip having a length between its longitudinal ends and a width between lateral edges, the length greater than the width, and wherein the depot has a preset shape in an expanded configuration in which the strip is curled about an axis with the width of the strip facing the axis, thereby forming a ring-like shape.

650. The depot of any one of the preceding clauses, wherein the depot forms an annular or semi-annular shape.

651. The depot of any one of the preceding clauses, wherein the depot has a first region and a second region, each extending longitudinally and coextensive with one another over all or a portion of their respective lengths, the first region having a first elasticity and the second region having a second elasticity less than the first elasticity.

652. The depot of the preceding clause, wherein the depot has been stretched beyond the elastic hysteresis point of the second region such that, when released from a delivery device, the depot transitions from a straightened state to a curved state in which the second region pulls the depot into the curved shape.

653. The depot of any one of the preceding clauses, wherein the depot has a first region and a second region, each extending longitudinally and coextensive with one another over all or a portion of their respective lengths, the first region being more hydrophilic than the second region.

654. The depot of the preceding clause, wherein, when released from a delivery device, the depot transitions from a straightened state to a curved state in which the second region pulls the depot into the curved shape.

655. The depot of any one of the preceding clauses, wherein the control region has first and second portions having a first thickness, the first and second portions separated along the first axis by a third portion having a second thickness different from the first.

656. The depot of any one of the preceding clauses, wherein the depot extends along the first axis from a first end to a second end, and wherein the control region has a thickness that increases from the first end to the second end.

657. The depot of any one of the preceding clauses, wherein the depot extends along the first axis from a first end to a second end, and wherein the control region does not cover the therapeutic region at the first end of the depot.

658. The depot of any one of the preceding clauses, wherein the depot extends along the first axis from a first end to a second end, and wherein the control region does not cover the therapeutic region at the first end or the second end.

659. The depot of any one of the preceding clauses, wherein the control region has a plurality of discrete openings formed therein.

660. The depot of any one of the preceding clauses, wherein the control region has an opening elongated along the first axis.

661. The depot of any one of the preceding clauses, wherein the elongated opening in the control region extends along the entire length of the depot.

662. The depot of any one of the preceding clauses, wherein the control region comprises a plurality of circular apertures formed therein.

663. The depot of any one of the preceding clauses, wherein the therapeutic region is a first therapeutic region, the depot further comprising a second therapeutic region, each of the first and second therapeutic regions being elongated along the first axis, wherein the first and second therapeutic regions are configured to release the therapeutic agent at different rates.

664. The depot of any one of the preceding clauses, wherein the therapeutic region is a first therapeutic region, the depot further comprising a second therapeutic region, each of the first and second therapeutic regions being elongated along the first axis, wherein the first and second therapeutic regions comprise different therapeutic agents.

665. The depot of any one of the preceding clauses, wherein the first and second therapeutic regions are coaxially aligned.

666. The depot of any one of the preceding clauses, wherein the first and second therapeutic regions extend parallel to one another along a length of the depot.

667. The depot of any one of the preceding clauses, further comprising a delay region configured to dissolve in vivo more slowly than the control region or the therapeutic region.

668. The depot of any one of the preceding clauses, further comprising a delay region configured to slow the passage of physiological fluids in vivo therethrough to the control region or the therapeutic region.

669. The depot of any one of the preceding clauses, wherein the delay region is disposed coaxially with the therapeutic region, such that the control region at least partially surrounds both the therapeutic region and the delay region.

670. The depot of any one of the preceding clauses, wherein the delay region is a first delay region, the depot further comprising a second delay region, the first and second delay regions separated axially from one another by the therapeutic region.

671. The depot of any one of the preceding clauses, wherein the first and second delay regions have different dimensions.

672. The depot of any one of the preceding clauses, wherein the delay region is disposed coaxially with the control region, such that the control region and delay region together at least partially surround the therapeutic region.

673. The depot of any one of the preceding clauses, wherein the first and second delay regions are separated axially from one another by the control region.

674. The depot of any one of the preceding clauses, wherein the depot extends along the first axis from a first end to a second end, and wherein the delay region is disposed over the first end of the depot.

675. The depot of any one of the preceding clauses, wherein the depot extends along the first axis from a first end to a second end, and wherein the delay region comprises a first end cap disposed over the first end of the depot and a second end cap disposed over the second end of the depot.

676. The depot of any one of the preceding clauses, wherein the therapeutic region comprises a covered portion and an exposed portion, wherein the covered portion is covered by the control region such that, when the depot is initially positioned at the treatment site in vivo, the control region is between the covered portion of the therapeutic region and physiologic fluids at the treatment site and the exposed portion of the therapeutic region is exposed to the physiologic fluids.

677. The depot of any one of the preceding clauses, wherein the therapeutic agent in the therapeutic region comprises at least 50% of the total weight of the depot.

678. The depot of any one of the preceding clauses, wherein the period of time is not less not less than 7 days, than 15 days, not less than 30 days, not less than 45 days, not less than 60 days, or not less than 90 days.

679. The depot of any one of the preceding clauses, wherein about 40% to about 60% of the therapeutic agent in the therapeutic region is released in the first half of the period of time.

680. The depot of any one of the preceding clauses, wherein at least 90% of the therapeutic agent in the therapeutic region is released within the period of time.

681. The depot of any one of the preceding clauses, wherein the depot is configured to release about 2 μg to about 5 mg of the therapeutic agent to the treatment site per day.

682. The depot of any one of the preceding clauses, wherein the depot is configured to release the therapeutic agent at the treatment site in vivo for no less than 8 days, no less than 9 days, no less than 10 days, no less than 11 days, no less than 12 days, no less than 13 days, no less than 14 days, no less than 15 days, no less than 16 days, no less than 17 days, no less than 18 days, no less than 19 days, no less than 20 days, no less than 21 days, no less than 22 days, no less than 23 days, no less than 24 days, no less than 25 days, no less than 26 days, no less than 27 days, no less than 28 days, no less than 29 days, no less than 30 days, no less than 40 days, no less than 50 days, no less than 60 days, no less than 70 days, no less than 90 days, no less than 100 days, no less than 200 days, no less than 300 days, or no less than 365 days.

683. The depot of any one of the preceding clauses, wherein the therapeutic agent is released at a substantially steady state rate throughout the period of time.

684. The depot of any one of the preceding clauses, wherein, the depot has a total surface area comprising the exposed surface area of the control region plus the exposed surface area of the therapeutic region, and when the depot is initially positioned at the treatment site in vivo, a ratio of the exposed surface area of the therapeutic region to the exposed surface area of the control region is from about 5% to about 20%, or from about 5% to about 15%, or from about 5% to about 10%.

685. The depot of any one of the preceding clauses, wherein the exposed surface area of the control region is less than the exposed surface area of the therapeutic region.

686. The depot of any one of the preceding clauses, wherein the exposed surface area of the control region is greater than the exposed surface area of the therapeutic region.

687. The depot of any one of the preceding clauses, wherein the control region is a first control region, and wherein the depot comprises a second control region.

688. The depot of any one of the preceding clauses, wherein the first control region is disposed at a first side of the therapeutic region and the second control region is disposed at a second side of the therapeutic region opposite the first side.

689. The depot of any one of the preceding clauses, wherein the depot comprises a plurality of control regions and a plurality of therapeutic regions, and wherein each of the therapeutic regions is separated from an adjacent one of the therapeutic regions by one or more control regions.

690. The depot of any one of the preceding clauses, wherein the depot comprises from about 2 to about 10 therapeutic regions.

691. The depot of any one of the preceding clauses, wherein the control region comprises a first control layer and a second control layer.

692. The depot of any one of the preceding clauses, wherein the second control layer is adjacent to the therapeutic region and the first control layer encapsulates/encloses the therapeutic region and the second control layer.

693. The depot of any one of the preceding clauses, wherein the first control layer and the second control layer together enclose the therapeutic region.

694. The depot of any one of the preceding clauses, wherein the first control layer comprises a first plurality of sub-layers and the second control layer comprises a second plurality of sub-layers.

695. The depot of any one of the preceding clauses, wherein the first control layer includes a first amount of the releasing agent and the second control layer includes a second amount of the releasing agent different than the first amount.

696. The depot of any one of the preceding clauses, wherein the second control layer is positioned between the first control layer and the therapeutic region, and wherein the first control layer includes a first concentration of the releasing agent and the second control layer includes a second concentration of the releasing agent greater than the first concentration.

697. The depot of any one of the preceding clauses, wherein the second control layer is positioned between the first control layer and the therapeutic region, and wherein the first control layer includes a first concentration of the releasing agent and the second control layer includes a second concentration of the releasing agent less than the first concentration.

698. The depot of any one of the preceding clauses, wherein the second control layer is positioned between the first control layer and the therapeutic region, and wherein the first control layer includes up to 5% by weight of the releasing agent, up to 10% by weight of the releasing agent, up to 15% by weight of the releasing agent, up to 20% by weight of the releasing agent, up to 25% by weight of the releasing agent, up to 30% by weight of the releasing agent, up to 35% by weight of the releasing agent, up to 40% by weight of the releasing agent, up to 45% by weight of the releasing agent, or 50% by weight of the releasing agent; and the second control layer includes up to 5% by weight of the releasing agent, up to 10% by weight of the releasing agent, up to 15% by weight of the releasing agent, up to 20% by weight of the releasing agent, up to 25% by weight of the releasing agent, up to 30% by weight of the releasing agent, up to 35% by weight of the releasing agent, up to 40% by weight of the releasing agent, up to 45% by weight of the releasing agent, or up to 50% by weight of the releasing agent.

699. The depot of any one of the preceding clauses, wherein the second control layer is positioned between the first control layer and the therapeutic region, and wherein the first control layer includes a first amount of the releasing agent and the second control layer includes a second amount of the releasing agent, the second amount being at least 2×, at least 3×, at least 4×, or at least 5× the first amount.

700. The depot of any one of the preceding clauses, wherein a thickness of the control region is less than or equal to 1/10, 1/15, 1/20, 1/25, 1/30, 1/35, 1/40, 1/45, 1/50, 1/75, or 1/100 of a thickness of the therapeutic region.

701. The depot of any one of the preceding clauses, wherein the depot comprises an elongate columnar structure configured to be implanted in a patient.

702. The depot of any one of the preceding clauses, wherein the depot comprises one of a plurality of beads or microspheres.

703. The depot of any one of the preceding clauses, wherein the beads or microspheres have varying release profiles.

704. The depot of any one of the preceding clauses, wherein the beads or microspheres comprise varying amounts of therapeutic agent.

705. The depot of any one of the preceding clauses, wherein the beads or microspheres comprise varying thicknesses of their respective control regions.

706. The depot of any one of the preceding clauses, wherein the beads of microspheres have varying dimensions.

707. The depot of any one of the preceding clauses, wherein the depot comprises one of a plurality of pellets.

708. The depot of any one of the preceding clauses, wherein the pellets have varying release profiles.

709. The depot of any one of the preceding clauses, wherein the pellets comprise varying amounts of therapeutic agent.

710. The depot of any one of the preceding clauses, wherein the pellets comprise varying thicknesses of their respective control regions.

711. The depot of any one of the preceding clauses, wherein the pellets have varying dimensions.

712. The depot of any one of the preceding clauses, wherein the pellets are substantially cylindrical.

713. The depot of any one of the preceding clauses, wherein the depot comprises a plurality of substantially cylindrical beads, each comprising a therapeutic region and control region and wherein the plurality of beads are substantially aligned along a common longitudinal axis.

714. The depot of any one of the preceding clauses, wherein the depot is biodegradable and/or bioerodible.

715. The depot of any one of the preceding clauses, wherein the depot is a flexible solid that is structurally capable of being handled by a clinician during the normal course of a surgery without breaking into multiple pieces and/or losing its general shape.

716. The depot of any one of the preceding clauses, wherein the depot is configured to be subcutaneously placed within a patient and release the therapeutic agent in vivo for up to 7 days without breaking into multiple pieces.

717. The depot of any one of the preceding clauses, wherein the depot has a surface area and a volume, and wherein a ratio of the surface area to volume is at least 1.

718. The depot of any one of the preceding clauses, wherein the diffusion openings include at least one or more pores and/or one or more channels.

719. The depot of any one of the preceding clauses, wherein dissolution of the releasing agent following in vivo placement in the treatment site causes the control region and the therapeutic region to transition from a state of lesser porosity to a state of greater porosity to facilitate the release of the therapeutic agent from the depot.

720. The depot of any one of the preceding clauses, wherein the releasing agent is a first releasing agent and the therapeutic region includes a second releasing agent mixed with the therapeutic agent.

721. The depot of any one of the preceding clauses, wherein the releasing agent is a first releasing agent and the polymer is a first polymer, and the therapeutic region includes a second releasing agent and a second polymer mixed with the therapeutic agent.
722. The depot of any one of the preceding clauses, wherein the first releasing agent is the same as the second releasing agent.
723. The depot of any one of the preceding clauses, wherein the first releasing agent is the different than the second releasing agent.
724. The depot of any one of the preceding clauses, wherein a concentration of the first releasing agent within the control region is the greater than a concentration of the second releasing agent within the therapeutic region.
725. The depot of any one of the preceding clauses, wherein a concentration of the first releasing agent within the control region is the less than a concentration of the second releasing agent within the therapeutic region.
726. The depot of any one of the preceding clauses, wherein a concentration of the first releasing agent within the control region is the same as a concentration of the second releasing agent within the therapeutic region.
727. The depot of any one of the preceding clauses, wherein a concentration of the first releasing agent within the control region is different than a concentration of the second releasing agent within the therapeutic region.
728. The depot of any one of the preceding clauses, wherein the therapeutic region includes a plurality of microlayers.
729. The depot of any one of the preceding clauses, wherein the mass of the therapeutic agent comprises at least 50% of the mass of the depot.
730. The depot of any one of the preceding clauses, wherein the ratio of the mass of the therapeutic agent in the depot to the depot polymer mass is at least at least 1:1, at least 2:1, 3:1, at least 4:1, at least 5:1, at least 6:1, at least 7:1, at least 8:1, at least 9:1, at least 10:1, or at least 16:1.
731. The depot of any one of the preceding clauses, wherein the therapeutic region comprises a bioresorbable polymer and the therapeutic agent.
732. The depot of any one of the preceding clauses, wherein the therapeutic region includes at least 40% by weight of the therapeutic agent, at least 50% by weight of the therapeutic agent, at least 60% by weight of the therapeutic agent, 60% by weight of therapeutic agent, at least 70% by weight of the therapeutic agent, at least 80% by weight of the therapeutic agent, at least 90% by weight of the therapeutic agent, or 100% by weight of the therapeutic agent.
733. The depot of any one of the preceding clauses, wherein the depot includes at least 15% by weight of the therapeutic agent, at least 20% by weight of the therapeutic agent, at least 30% by weight of the therapeutic agent, at least 40% by weight of the therapeutic agent, at least 50% by weight of the therapeutic agent, at least 60% by weight of the therapeutic agent, at least 70% by weight of the therapeutic agent, at least 80% by weight of the therapeutic agent, at least 90% by weight of the therapeutic agent, 99% by weight of the therapeutic agent, or 99.99% by weight of the therapeutic agent.
734. The depot of any one of the preceding clauses, wherein the releasing agent is a non-ionic surfactant.
735. The depot of any one of the preceding clauses, wherein the releasing agent has hydrophilic properties.
736. The depot of any one of the preceding clauses, wherein the releasing agent is a polysorbate.
737. The depot of any one of the preceding clauses, wherein the releasing agent is Tween 20.
738. The depot of any one of the preceding clauses, wherein the releasing agent is Tween 80.
739. The depot of any one of the preceding clauses, wherein the releasing agent is non-polymeric.
740. The depot of any one of the preceding clauses, wherein the releasing agent is not a plasticizer.
741. The depot of any one of the preceding clauses, wherein the polymer is configured to degrade only after substantially all of the therapeutic agent has been released from the depot.
742. The depot of any one of the preceding clauses, wherein the polymer is a copolymer.
743. The depot of any one of the preceding clauses, wherein the polymer is a terpolymer.
744. The depot of any one of the preceding clauses, wherein the polymer includes at least one of polyglycolide (PGA), polycaprolactone (PCL), poly(DL-lactic acid) (PLA), poly(alpha-hydroxy acids), poly(lactide-co-glycolide)(PLGA or DLG), poly(DL-lactide-co-caprolactone) (DL-PLCL), poly(trimethylene carbonate) (PTMC), polydioxanone (PDO), poly(4-hydroxy butyrate) (PHB), polyhydroxyalkanoates (PHA), poly (phosphazene), polyphosphate ester), poly(amino acid), polydepsipeptides, poly(butylene succinate) (PBS), polyethylene oxide, polypropylene fumarate, polyiminocarbonates, poly(lactide-co-caprolactone) (PLCL), poly(glycolide-co-caprolactone) (PGCL) copolymer, poly(D,L-lactic acid), polyglycolic acid, poly(L-lactide-co-D,L-lactide), poly(L-lactide-co-glycolide), poly(D,L-lactide-co-glycolide), poly(gycolide-trimethylene carbonate), poly(ethyl glutamate-co-glutamic acid), poly(tert-butyloxy-carbonylmethyl glutamate), poly(glycerol sebacate), tyrosine-derived polycarbonate, poly 1,3-bis-(p-carboxyphenoxy) hexane-co-sebacic acid, polyphosphazene, ethyl glycinate polyphosphazene, polycaprolactone co-butylacrylate, a copolymer of polyhydroxybutyrate, a copolymer of maleic anhydride, a copolymer of poly(trimethylene carbonate), polyethylene glycol (PEG), hydroxypropylmethylcellulose and cellulose derivatives, polysaccharides (such as hyaluronic acid, chitosan and starch), proteins (such as gelatin and collagen) or PEG derivatives, polyaspirins, polyphosphagenes, pre-gelatinized starch, hyaluronic acid, chitosans, gelatin, alginates, albumin, fibrin, vitamin E analogs, such as alpha tocopheryl acetate, d-alpha tocopheryl succinate, D-lactide, D,L-lactide, L-lactide, D,L-lactide-caprolactone (DL-CL), D,L-lactide-glycolide-caprolactone (DL-G-CL), dextrans, vinylpyrrolidone, polyvinyl alcohol (PVA), PVA-g-PLGA, PEGT-PBT copolymer (polyactive), methacrylates, poly(N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate)hydroxypropyl cellulose, hydroxypropyl methylcellulose, hydroxyethyl methylcellulose, carboxymethylcellulose or salts thereof, Carbopol®, poly(hydroxyethylmethacrylate), poly(methoxyethylmethacrylate), poly(methoxyethoxy-ethylmethacrylate), polymethylmethacrylate (PMMA), polyvinyl alcohols, propylene glycol, and poly(DL-lactide-co-glycolide-co-caprolactone).

745. The depot of any one of the preceding clauses, wherein the polymer is one of poly(DL-lactide-co-glycolide-co-caprolactone) and poly(DL-lactide-co-glycolide)(PLGA).

746. The depot of any one of the preceding clauses, wherein the polymer is poly(DL-lactide-co-glycolide-co-caprolactone) in a molar ratio of about 60:30:10.

747. The depot of any one of the preceding clauses, wherein the polymer is poly(DL-lactide-co-glycolide) (PLGA) in a molar ratio of between about 10:90 and about 90:10.

748. The depot of any one of the preceding clauses, wherein the polymer is poly(DL-lactide-co-glycolide) (PLGA) in a molar ratio of about 50:50.

749. The depot of any one of the preceding clauses, wherein the polymer is ester-terminated.

750. The depot of any one of the preceding clauses, wherein the polymer is a terpolymer that includes three polymers selected from the following: polyglycolide (PGA), polycaprolactone (PCL), poly(L-lactic acid) (PLA), poly(DL-lactic acid) (PLA), poly(trimethylene carbonate) (PTMC), polydioxanone (PDO), poly(4-hydroxy butyrate) (PHB), polyhydroxyalkanoates (PHA), poly(phosphazene), and polyethylene glycol.

751. The depot of any one of the preceding clauses, wherein the polymer is a first polymer, and the therapeutic region includes a second polymer mixed with the therapeutic agent.

752. The depot of any one of the preceding clauses, wherein the first polymer and/or the second polymer include at least one of polyglycolide (PGA), polycaprolactone (PCL), poly(DL-lactic acid) (PLA), poly(alpha-hydroxy acids), poly(lactide-co-glycolide)(PLGA or DLG), poly(DL-lactide-co-caprolactone) (DL-PLCL), poly(trimethylene carbonate) (PTMC), polydioxanone (PDO), poly(4-hydroxy butyrate) (PHB), polyhydroxyalkanoates (PHA), poly(phosphazene), polyphosphate ester), poly(amino acid), polydepsipeptides, poly(butylene succinate) (PBS), polyethylene oxide, polypropylene fumarate, polyiminocarbonates, poly(lactide-co-caprolactone) (PLCL), poly(glycolide-co-caprolactone) (PGCL) copolymer, poly(D,L-lactic acid), polyglycolic acid, poly(L-lactide-co-D,L-lactide), poly(L-lactide-co-glycolide), poly(D,L-lactide-co-glycolide), poly(gycolide-trimethylene carbonate), poly(ethyl glutamate-co-glutamic acid), poly(tert-butyloxy-carbonylmethyl glutamate), poly(glycerol sebacate), tyrosine-derived polycarbonate, poly 1,3-bis-(p-carboxyphenoxy) hexane-co-sebacic acid, polyphosphazene, ethyl glycinate polyphosphazene, polycaprolactone co-butylacrylate, a copolymer of polyhydroxybutyrate, a copolymer of maleic anhydride, a copolymer of poly(trimethylene carbonate), polyethylene glycol (PEG), hydroxypropylmethylcellulose and cellulose derivatives, polysaccharides (such as hyaluronic acid, chitosan and starch), proteins (such as gelatin and collagen) or PEG derivatives, polyaspirins, polyphosphagenes, pre-gelatinized starch, hyaluronic acid, chitosans, gelatin, alginates, albumin, fibrin, vitamin E analogs, such as alpha tocopheryl acetate, d-alpha tocopheryl succinate, D-lactide, D,L-lactide, L-lactide, D,L-lactide-caprolactone (DL-CL), D,L-lactide-glycolide-caprolactone (DL-G-CL), dextrans, vinylpyrrolidone, polyvinyl alcohol (PVA), PVA-g-PLGA, PEGT-PBT copolymer (polyactive), methacrylates, poly(N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate)hydroxypropyl cellulose, hydroxypropyl methylcellulose, hydroxyethyl methylcellulose, carboxymethylcellulose or salts thereof, Carbopol®, poly(hydroxyethylmethacrylate), poly(methoxyethylmethacrylate), poly(methoxyethoxy-ethylmethacrylate), polymethylmethacrylate (PMMA), polyvinyl alcohols, propylene glycol, poly(DL-lactide-co-glycolide-co-caprolactone).

753. The depot of any one of the preceding clauses, wherein the first polymer and/or the second polymer selected from the following: poly(DL-lactide-co-glycolide-co-caprolactone) and poly(DL-lactide-co-glycolide)(PLGA).

754. The depot of any one of the preceding clauses, wherein the first polymer and/or the second polymer is poly(DL-lactide-co-glycolide-co-caprolactone) and has a molar ratio of about 60:30:10.

755. The depot of any one of the preceding clauses, wherein the first polymer and/or the second polymer is poly(DL-lactide-co-glycolide) and has a molar ratio of about 50:50.

756. The depot of any one of the preceding clauses, wherein the first polymer and/or the second polymer is ester-terminated.

757. The depot of any one of the preceding clauses, wherein the first polymer and/or the second polymer is a terpolymer that includes three polymers selected from the following: polyglycolide (PGA), polycaprolactone (PCL), poly(L-lactic acid) (PLA), poly(trimethylene carbonate) (PTMC), polydioxanone (PDO), poly(4-hydroxy butyrate) (PHB), polyhydroxyalkanoates (PHA), poly(phosphazene), and polyethylene glycol.

758. The depot of any one of the preceding clauses, wherein the ratio of the polymer to the releasing agent in the control region is at least 1:1, at least 2:1, at least 3:1, at least 4:1, at least 5:1, at least 6:1, at least 7:1, at least 8:1, at least 9:1, at least 10:1, or at least 15:1 759. The depot of any one of the preceding clauses, wherein the releasing agent is configured to dissolve when the depot is placed in contact with phosphate buffered saline to form diffusion openings.

760. A system for delivering a therapeutic agent to a treatment site, the system comprising:

a shaft having a lumen;

a pusher operatively coupled to the lumen; and a depot disposed within the lumen and configured to be displaced from the shaft via activation of the pusher, the depot comprising:

a therapeutic region comprising the therapeutic agent, the therapeutic region elongated along a first axis;

a control region at least partially surrounding the therapeutic region and elongated along the first axis, the control region comprising a bioresorbable polymer and a releasing agent mixed with the polymer, wherein the releasing agent is configured to dissolve when the depot is placed in vivo to form diffusion openings in the control region; and wherein the depot is configured to be implanted at a treatment site in vivo and, while implanted, release the therapeutic agent at the treatment site for a period of time not less than 3 days.

761. The system of clause 760, wherein the depot comprises the depot of any one of the preceding clauses.

762. The system of clause 760, wherein the shaft comprises a needle, and wherein the pusher comprises a plunger.

763. A system for delivering a therapeutic agent to a treatment site, the system comprising:

an expandable member configured to be expanded from a reduced-volume configuration for delivery to an expanded-volume configuration for deployment at the treatment site; and a depot carried by the expandable member, the depot comprising:

a therapeutic region comprising the therapeutic agent, the therapeutic region elongated along a first axis;

a control region at least partially surrounding the therapeutic region and elongated along the first axis, the control region comprising a bioresorbable polymer and a releasing agent mixed with the polymer, wherein the releasing agent is configured to dissolve when the depot is placed in vivo to form diffusion openings in the control region; and wherein the depot is configured to be implanted at a treatment site in vivo and, while implanted, release the therapeutic agent at the treatment site for a period of time not less than 3 days.

764. The system of clause 763, wherein the depot comprises the depot of any one of the preceding clauses.

765. The system of any one of the preceding clauses, wherein the expandable member comprises a stent.

766. The system of any one of the preceding clauses, wherein the expandable member comprises a spherical, semi-spherical, ellipsoid, or semi-ellipsoid structure.

767. The system of any one of the preceding clauses, wherein the expandable member comprises a curved outer surface, and wherein the depot is disposed over the curved outer surface.

768. The system of any one of the preceding clauses, wherein the depot substantially covers at least one surface of the expandable member.

769. The system of any one of the preceding clauses, wherein the expandable member comprises a shape-memory material.

770. The system of any one of the preceding clauses, wherein the depot is disposed in a lubricious coating and wherein the lubricious coating comprises a hydrogel.

771. A method for delivering a therapeutic agent to a treatment site within a body, the method comprising:

positioning a depot at a treatment site in vivo having physiologic fluids, the depot comprising:

a therapeutic region comprising the therapeutic agent, the therapeutic region elongated along a first axis;

a control region at least partially surrounding the therapeutic region and elongated along the first axis, the control region comprising a bioresorbable polymer and a releasing agent mixed with the polymer; and allowing the releasing agent to dissolve at the treatment site to form diffusion openings in the control region, thereby releasing the therapeutic agent from the depot to the treatment site for a period of time not less than 3 days.

772. The method of clause 771, wherein the depot comprises the depot of any one of the preceding clauses.

773. The method of any one of the preceding clauses, wherein positioning the depot comprises inserting the depot subcutaneously at the treatment site via a needle.

774. The method of any one of the preceding clauses, wherein positioning the depot comprises positioning the depot proximate to a nerve bundle at the treatment site.

775. The method of any one of the preceding clauses, further comprising dissolving the releasing agent at a first rate and degrading the polymer at a second rate, wherein the first rate is greater than the second rate.

776. The method of any one of the preceding clauses, further comprising dissolving the releasing agent in response to contact between the control region and the physiologic fluids at the treatment site.

777. The method of any one of the preceding clauses, further comprising creating diffusion openings in the control region via the dissolution of the releasing agent in response to physiologic fluids at the treatment site.

778. The method of any one of the preceding clauses, wherein the releasing agent is a first releasing agent and the therapeutic region includes a second releasing agent, and wherein the method further comprises creating microchannels in the therapeutic region and the control region via dissolution of the first and/or second releasing agents.

779. The method of any one of the preceding clauses, wherein at least some of the microchannels penetrate both the therapeutic region and the control region.

780. The method of any one of the preceding clauses, further including increasing a porosity of the depot via dissolution of the releasing agent.

781. The method of any one of the preceding clauses, wherein the therapeutic agent is released one or more times in substantially discrete doses after implantation.

782. The method of any one of the preceding clauses, wherein the therapeutic agent is released at a substantially steady state rate for the period of time.

783. The method of any one of the preceding clauses, wherein the period of time is not less than 8 days, no less than 9 days, no less than 10 days, no less than 11 days, no less than 12 days, no less than 13 days, no less than 14 days, no less than 15 days, no less than 16 days, no less than 17 days, no less than 18 days, no less than 19 days, no less than 20 days, no less than 21 days, no less than 22 days, no less than 23 days, no less than 24 days, no less than 25 days, no less than 26 days, no less than 27 days, no less than 28 days, no less than 29 days, no less than 30 days, no less than 40 days, no less than 50 days, no less than 60 days, no less than 70 days, no less than 90 days, no less than 100 days, no less than 200 days, no less than 300 days, or no less than 365 days.

784. The method of any one of the preceding clauses, wherein the depot is a first depot and the method further comprises positioning a second depot at the treatment site.

785. A system for treating a patient with a tumor, the system comprising:

a depot for localized, sustained release of a therapeutic agent, the depot comprising:

a therapeutic region comprising the therapeutic agent; and a control region comprising a polymer and a releasing agent mixed with the polymer, wherein the releasing agent is configured to dissolve when the depot is placed in vivo to form diffusion openings in the control region;

a radiation source configured to administer a dose of radiation to the tumor that is therapeutically effective, whereby exposing the patient to the dose of radiation subjects the patient to complications associated with the radiation; and wherein the depot is configured to be implanted at a treatment site proximate to the tumor and, while implanted, release the therapeutic agent at the treatment site for a period of time sufficient to reduce the therapeutically effective dose of radiation to the patient, thereby reducing the complications associated with the radiation.

786. A method for treating a patient with a tumor, the method comprising:

administering a localized, sustained dose of therapeutic agent to the tumor of the patient, wherein administering the dose of therapeutic agent comprises:

positioning a depot proximate to the tumor of the patient, the depot comprising:

a therapeutic region comprising a therapeutic agent; and a control region comprising a polymer and a releasing agent mixed with the polymer, wherein the releasing agent is configured to dissolve when the depot is placed in vivo to form diffusion openings in the control region;

administering a therapeutically effective dose of radiation to the patient, wherein both the tumor and a non-target tissue is exposed to the dose of radiation, the non-target tissue being subject to a side effect profile associated with the radiation;

wherein the therapeutically effective dose of radiation to the patient in combination with the localized, sustained dose of therapeutic agent is less than the therapeutically effective dose of radiation to the patient in the absence of the localized, sustained dose of therapeutic agent, and wherein the non-target tissue is subjected to a reduced side effect profile associated with the lesser therapeutically effective dose of radiation.

787. A depot for treating prostate cancer via sustained, controlled release of a therapeutic agent to a patient, the depot comprising:

a therapeutic region comprising a biodegradable polymer mixed with a therapeutic agent configured to treat prostate cancer, wherein the depot is configured to be implanted at a treatment site at a prostate gland of the patient and, while implanted, release the therapeutic agent at the treatment site for a period of time that is no less than 7 days.

788. The depot of Clause 787, further comprising a releasing agent mixed with the polymer, wherein the releasing agent is configured to dissolve when the depot is placed in vivo to form diffusion openings in the therapeutic region.

789. A depot for treating prostate cancer via sustained, controlled release of a therapeutic agent to a patient, the depot comprising:

a therapeutic region comprising a therapeutic agent configured to treat prostate cancer;

a control region comprising a biodegradable polymer and a releasing agent mixed with the polymer, wherein the releasing agent is configured to dissolve when the depot is placed in vivo to form diffusion openings in the control region; and wherein the depot is configured to be implanted at a treatment site at a prostate gland of the patient and, while implanted, release the therapeutic agent at the treatment site for a period of time that is no less than 7 days.

790. The depot of Clause 789, wherein the therapeutic region further comprises a polymer mixed with the therapeutic agent.

791. The depot of any one of the preceding Clauses, wherein the therapeutic region further comprises a releasing agent mixed with the therapeutic agent.

792. The depot of Clause 789, wherein the therapeutic region further comprises a polymer and a releasing agent mixed with the therapeutic agent.

793. The depot of any one of Clauses 789 to 792, wherein the control region does not include any therapeutic agent prior to implantation of the depot.

794. The depot of any one of Clauses 787 to 793, wherein the depot comprises a substantially impermeable base region, and wherein the therapeutic region is configured to release the therapeutic agent in a direction away from the substantially impermeable base region.

795. The depot of any one of Clauses 787 to 794, wherein the depot includes one or more radiopaque elements configured to improve visualization of the depot in vivo.

796. The depot of Clause 795, wherein the radiopaque element comprises a contrast media selected from barium sulfate, iodine, air and carbon dioxide.

797. The depot of any one of the preceding Clauses, wherein the depot is generally cylindrically-shaped.

798. The depot of any one of the preceding Clauses, wherein the depot comprises one or more microbeads configured to be positioned at the treatment site.

799. The depot of any one of the preceding Clauses, wherein the depot comprises one or more pellets configured to be positioned at the treatment site.

800. The depot of any one of the preceding Clauses, wherein the depot comprises one or more discs configured to be positioned at the treatment site.

801. The depot of any one of the preceding Clauses, wherein the depot has an average diameter along its length of about 0.5 mm to about 3 mm, about 0.5 mm to about 2 mm, about 0.5 mm to about 1.5 mm, no greater than 1.5 mm, or no greater than 1.0 mm.

802. The depot of any one of the preceding Clauses, wherein the depot has a first end and a second end opposite the first end with a longitudinal axis extending therebetween, and wherein the depot has a length measured along it longitudinal axis of about 5 mm to about 4 cm, of about 5 mm to about 3 cm, of about 5 mm to about 2.5 cm, of about 1 cm to about 3 cm, of about 1 cm to 2 cm, about 1 cm or less, about 1.1 cm or less, about 1.2 cm or less, about 1.3 cm or less, about 1.4 cm or less, about 1.5 cm or less, about 1.6 cm or less, about 1.7 cm or less, about 1.8 cm or less, about 1.9 cm or less, or about 2 cm or less.

803. The depot of any one of the preceding Clauses, wherein:

the depot has an average diameter along its length of about 0.5 mm to about 3 mm, about 0.5 mm to about 2 mm, about 0.5 mm to about 1.5 mm, no greater than 1.5 mm, or no greater than 1.0 mm, and the depot has a first end and a second end opposite the first end with a longitudinal axis extending therebetween, and the depot has a length measured along it longitudinal axis of about 5 mm to about 4 cm, of about 5 mm to about 3 cm, of about 5 mm to about 2.5 cm, of about 1 cm to about 3 cm, of about 1 cm to 2 cm, about 1 cm or less, about 1.1 cm or less, about 1.2 cm or less, about 1.3 cm or less, about 1.4 cm or less, about 1.5 cm or less, about 1.6 cm or less, about 1.7 cm or less, about 1.8 cm or less, about 1.9 cm or less, or about 2 cm or less.

804. The depot of any one of the preceding Clauses, wherein the depot has a length and wherein a ratio of the length of the depot to an average cross-sectional dimension of the depot along its length is at least 10/1, at least 12.5/1, at least 15/1, at least 17.5/1, at least 20/1, at least 22.5/1, at least 25/1, at least 27.5/1, at least 30/1, at least 32.5/1, at least 35/1, at least 37.5/1, or at least 40/1.

805. The depot of any one of the preceding Clauses, wherein the depot has a volume of no more than 10 $mm^3$, 11 $mm^3$, 12 $mm^3$, 13 $mm^3$, 14 $mm^3$, 15 $mm^3$, 16 $mm^3$, 17 $mm^3$, 18 $mm^3$, 19 $mm^3$, 20 $mm^3$, 21 $mm^3$, or 22 $mm^3$.

806. The depot of any one of the preceding Clauses, wherein the therapeutic agent includes a chemotherapeutic agent.

807. The depot of any one of the preceding Clauses, wherein the depot is configured to release the therapeutic agent at the treatment site for a period of time that is no less than 30 days.

808. The depot of any one of the preceding Clauses, wherein the depot is configured to release the therapeutic agent at the treatment site for a period of time that is no less than 35 days.

809. The depot of any one of the preceding Clauses, wherein the depot is configured to release the therapeutic agent at the treatment site for a period of time that is no less than 40 days.

810. The depot of any one of the preceding Clauses, wherein the depot is configured to release the therapeutic agent at the treatment site for a period of time that is no less than 45 days.

811. The depot of any one of the preceding Clauses, wherein the depot is configured to release the therapeutic agent at the treatment site for a period of time between about 30 days and about 45 days.

812. The depot of any one of the preceding Clauses, wherein the therapeutic agent includes a chemotherapeutic agent that is an antimicrotubule agent.

813. The depot of any one of the preceding Clauses, wherein the therapeutic agent includes docetaxel.

814. The depot of Clause 812, wherein the therapeutic region contains no less than 1 mg, no less than 2 mg, no less than 3 mg, no less than 4 mg, no less than 5 mg, no less than 6 mg, no less than 7 mg, no less than 8 mg, no less than 9 mg, no less than 10 mg, no less than 11 mg, no less than 12 mg, no less than 13 mg, no less than 14 mg, no less than 15 mg, no less than 16 mg, no less than 17 mg, no less than 18 mg, less than 19 mg, no less than 20 mg, no less than 22 mg, no less than 24 mg, no less than 26 mg, no less than 28 mg, no less than 30 mg, no less than 32 mg, no less than 34 mg, no less than 36 mg, no less than 38 mg, or no less than 40 mg of docetaxel.

815. The depot of any one of the preceding Clauses, wherein the therapeutic region contains no less than 1 mg of docetaxel.

816. The depot of any one of the preceding Clauses, wherein the therapeutic region contains between about 1 mg and 2 mg of docetaxel.

817. The depot of any one of the preceding Clauses, wherein the therapeutic region contains no less than 2 mg of docetaxel.

818. The depot of any one of the preceding Clauses, wherein the therapeutic region contains no less than 3 mg of docetaxel.

819. The depot of any one of the preceding Clauses, wherein the therapeutic agent includes paclitaxel.

820. The depot of any one of the preceding Clauses, wherein the therapeutic agent includes cabazitaxel.

821. The depot of Clause 819, wherein the therapeutic region contains no less than 3 mg, no less than 4 mg, no less than 5 mg, no less than 6 mg, no less than 7 mg, no less than 8 mg, no less than 9 mg, no less than 10 mg, no less than 11 mg, no less than 12 mg, no less than 13 mg, no less than 14 mg, no less than 15 mg, no less than 16 mg, no less than 17 mg, no less than 18 mg, less than 19 mg, no less than 20 mg, no less than 22 mg, no less than 24 mg, no less than 26 mg, no less than 28 mg, no less than 30 mg, no less than 32 mg, no less than 34 mg, no less than 36 mg, no less than 38 mg, no less than 40 mg, no less than 42 mg, no less than 44 mg, no less than 46 mg, no less than 48 mg, no less than 50 mg, no less than 52 mg, no less than 54 mg, no less than 56 mg, no less than 58 mg, or no less than 60 mg of paclitaxel.

822. The depot of any one of the preceding Clauses, wherein the period of time is no less than 2 weeks, no less than 3 weeks, no less than 4 weeks, no less than 5 weeks, no less than 6 weeks, no less than 7 weeks, no less than 8 weeks, no less than 2 months, no less than 3 months, no less than 4 months, no less than 6 months, no less than 7 months, no less than 8 months, no less than 9 months, no less than 10 months, no less than 11 months, no less than 12 months, no less than 13 months, no less than 14 months, no less than 15 months, no less than 16 months, no less than 17 months, or no less than 18 months.

823. The depot of any one of the preceding Clauses, wherein the therapeutic region is configured to release the therapeutic agent continuously at a substantially constant rate for the period of time.

824. The depot of any one of the preceding Clauses, wherein the therapeutic agent includes a chemotherapeutic agent, and the depot is configured to release the chemotherapeutic agent continuously over the period of time.

825. The depot of any one of the preceding clauses, wherein the therapeutic agent includes a chemotherapeutic agent, and the depot is configured to release the chemotherapeutic agent intermittently over the period of time.

826. The depot of any one of the preceding Clauses, wherein the therapeutic agent includes an antiandrogen.

827. The depot of any one of the preceding Clauses, wherein the therapeutic agent includes an antiandrogen comprising at least one of abiraterone acetate, apalutimide, darolutimide, enzalutamide, and bicalutamide.

828. The depot of any one of the preceding clauses, wherein the depot is configured to release the antiandrogen continuously over the period of time.

829. The depot of any one of the preceding clauses, wherein the therapeutic region is configured to release the antiandrogen intermittently over the period of time.

830. The depot of any one of the preceding Clauses, wherein the therapeutic agent includes abiraterone acetate, and wherein the therapeutic region contains at least at least 4 mg, at least 6 mg, at least 8 mg, at least 10 mg, at least 20 mg, at least 30 mg, at least 40 mg, at least 50 mg, at least 60 mg, at least 70 mg, or at least 80 mg of abiraterone acetate.

831. The depot of any one of the preceding Clauses, wherein the therapeutic agent includes enzalutamide, and wherein the therapeutic region contains at least 0.5 mg, at least 1 mg, at least 2 mg, at least 3 mg, at least 4 mg, at least 5 mg, at least 6 mg, at least 7 mg, at least 8 mg, at least 9 mg, at least 10 mg, at least 11 mg, at least 12 mg, at least 13 mg, at least 14 mg, or at least 15 mg of enzalutamide.

832. The depot of any one of the preceding Clauses, wherein the therapeutic agent includes enzalutamide, and wherein the therapeutic region contains no less than 3 mg of enzalutamide.

833. The depot of any one of the preceding Clauses, wherein the therapeutic agent includes enzalutamide, and wherein the therapeutic region contains no less than 4 mg of enzalutamide.

834. The depot of any one of the preceding Clauses, wherein the therapeutic agent includes enzalutamide, and wherein the therapeutic region contains no less than 5 mg of enzalutamide.

835. The depot of any one of the preceding Clauses, wherein the therapeutic agent includes enzalutamide, and wherein the therapeutic region contains between about 3 mg and about 4 mg of enzalutamide.

836. The depot of any one of the preceding Clauses, wherein the therapeutic agent includes bicalutamide, and wherein the therapeutic region contains at least 0.5 mg, at least 1 mg, at least 2 mg, at least 3 mg, at least 4 mg, at least 5 mg, at least 6 mg, at least 7 mg, at least 8 mg, at least 9 mg, at least 10 mg, at least 11 mg, at least 12 mg, at least 13 mg, at least 14 mg, or at least 15 mg of bicalutamide.

837. The depot of any one of the preceding Clauses, wherein the therapeutic agent includes bicalutamide, and wherein the therapeutic region contains no less than 3 mg of bicalutamide.

838. The depot of any one of the preceding Clauses, wherein the therapeutic agent includes bicalutamide, and wherein the therapeutic region contains no less than 4 mg of bicalutamide.

839. The depot of any one of the preceding Clauses, wherein the therapeutic agent includes bicalutamide, and wherein the therapeutic region contains no less than 5 mg of bicalutamide.

840. The depot of any one of the preceding Clauses, wherein the therapeutic agent includes bicalutamide, and wherein the therapeutic region contains between about 3 mg and about 4 mg of bicalutamide.

841. The depot of any one of the preceding Clauses, wherein the therapeutic agent includes bicalutamide and enzalutamide, and wherein the therapeutic region contains no less than 3 mg of bicalutamide and no less than 3 mg of enzalutamide.

842. The depot of any one of the preceding Clauses, wherein the therapeutic agent includes bicalutamide and enzalutamide, and wherein the therapeutic region contains between about 3 mg and about 4 mg of bicalutamide and between about 3 mg and about 4 mg of enzalutamide.

843. The depot of any one of the preceding Clauses, wherein the therapeutic agent includes a chemotherapeutic agent and an antiandrogen.

844. The depot of any one of the preceding Clauses, wherein the chemotherapeutic agent comprises at least one of docetaxel and paclitaxel and the antiandrogen comprises at least one of abiraterone acetate, apalutimide, darolutimide enzalutamide, and bicalutamide.

845. The depot of any one of the preceding Clauses, wherein the chemotherapeutic agent comprises at least one of docetaxel, paclitaxel, and cabazitaxel and the antiandrogen comprises at least one of enzalutamide and bicalutamide.

846. The depot of any one of the preceding Clauses, wherein the chemotherapeutic agent comprises docetaxel and the antiandrogen comprises at least one of enzalutamide and bicalutamide.

847. The depot of any one of the preceding Clauses, wherein the polymer includes at least one of polyglycolide (PGA), polycaprolactone (PCL), poly(DL-lactic acid) (PLA), poly(alpha-hydroxy acids), poly(lactide-co-glycolide)(PLGA or DLG), poly(DL-lactide-co-caprolactone) (DL-PLCL), poly(trimethylene carbonate) (PTMC), polydioxanone (PDO), poly(4-hydroxy butyrate) (PHB), polyhydroxyalkanoates (PHA), poly(phosphazene), polyphosphate ester), poly(amino acid), polydepsipeptides, poly(butylene succinate) (PBS), polyethylene oxide, polypropylene fumarate, polyiminocarbonates, poly(lactide-co-caprolactone) (PLCL), poly(glycolide-co-caprolactone) (PGCL) copolymer, poly(D,L-lactic acid), polyglycolic acid, poly(L-lactide-co-D,L-lactide), poly(L-lactide-co-glycolide), poly(D,L-lactide-co-glycolide), poly(gycolide-trimethylene carbonate), poly(ethyl glutamate-co-glutamic acid), poly(tert-butyloxy-carbonylmethyl glutamate), poly(glycerol sebacate), tyrosine-derived polycarbonate, poly 1,3-bis-(p-carboxyphenoxy) hexane-co-sebacic acid, polyphosphazene, ethyl glycinate polyphosphazene, polycaprolactone co-butylacrylate, a copolymer of polyhydroxybutyrate, a copolymer of maleic anhydride, a copolymer of poly(trimethylene carbonate), polyethylene glycol (PEG), PEG 400, PEG 500, PEG 600, PEG 700, PEG 800, PEG 900, PEG 10K, hydroxypropylmethylcellulose and cellulose derivatives, polysaccharides (such as hyaluronic acid, chitosan and starch), proteins (such as gelatin and collagen) or PEG derivatives, polyaspirins, polyphosphagenes, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, D-lactide, D,L-lactide, L-lactide, D,L-lactide-caprolactone (DL-CL), D,L-lactide-glycolide-caprolactone (DL-G-CL), dextrans, polyvinylpyrrolidone, polyvinyl alcohol (PVA), PVA-g-PLGA, PEGT-PBT copolymer (polyactive), methacrylates, poly(N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate)hydroxypropyl cellulose, hydroxypropyl methylcellulose, hydroxyethyl methylcellulose, carboxymethylcellulose or salts thereof, Carbopol®, poly(hydroxyethylmethacrylate), poly(methoxyethylmethacrylate), poly(methoxyethoxy-ethylmethacrylate), polymethylmethacrylate (PMMA), methylmethacrylate (MMA), gelatin, propylene glycol, and poly(DL-lactide-co-glycolide-co-caprolactone).

848. The depot of any one of the preceding Clauses, wherein the polymer comprises a polyester.

849. The depot of any one of the preceding Clauses, wherein the polymer comprises a synthetic polyether.

850. The depot of any one of the preceding Clauses, wherein the polymer comprises a polyester and a synthetic polyether.

851. The depot of any one of the preceding Clauses, wherein the polymer comprises PEG.

852. The depot of any one of the preceding Clauses, wherein the polymer comprises PEG10K.

853. The depot of any one of the preceding Clauses, wherein the polymer comprises PLGA.

854. The depot of any one of the preceding Clauses, wherein the polymer comprises PLGA having a lactide to glycolide ratio of 50:50.

855. The depot of any one of the preceding Clauses, wherein the polymer comprises PLGA having a lactide to glycolide ratio of 75:25.

856. The depot of any one of the preceding Clauses, wherein the polymer comprises PLGA and PEG.

857. The depot of Clause 856, wherein the polymer comprises no more than 5% PEG.

858. The depot of Clause 856, wherein the polymer comprises no more than 10% PEG.

859. The depot of any one of the preceding Clauses, wherein the polymer comprises PLGA and PEG10K.

860. The depot of Clause 858, wherein the polymer comprises no more than 5% PEG10K.

861. The depot of Clause 858, wherein the polymer comprises no more than 10% PEG10K.

862. The depot of any one of the preceding Clauses, wherein the polymer comprises a first polymer and a second polymer, and the therapeutic region comprises a first polymer to second polymer to therapeutic agent ratio of 5:5:40.

863. The depot of Clause 862, wherein the first polymer is PEG and the second polymer is PLGA.

864. The depot of Clause 862, wherein the first polymer is PEG10K and the second polymer is PLGA.

865. The depot of any one of the preceding Clauses, wherein the polymer comprises a first polymer and a second polymer, and the therapeutic region comprises a first polymer to second polymer to therapeutic agent ratio of 3:7:40.

866. The depot of Clause 865, wherein the first polymer is PEG and the second polymer is PLGA.

867. The depot of Clause, wherein the first polymer is PEG10K and the second polymer is PLGA.

868. The depot of any one of the preceding Clauses, wherein the polymer comprises a first polymer and a second polymer, and the therapeutic region comprises a first polymer to second polymer to therapeutic agent ratio of 1:9:40.

869. The depot of Clause 868, wherein the first polymer is PEG and the second polymer is PLGA.

870. The depot of Clause 868, wherein the first polymer is PEG10K and the second polymer is PLGA.

871. The depot of any one of the preceding Clauses, wherein the period of time is a first period of time and the therapeutic agent comprises a chemotherapeutic agent and an antiandrogen, wherein the depot is configured to release the chemotherapeutic agent for a first period of time and the antiandrogen for a second period of time.

872. The depot of Clause 871, wherein the first period of time is longer than the second period of time.

873. The depot Clause 871, wherein the first period of time is shorter than the second period of time.

874. The depot of any one of Clauses 871 to 873, wherein the first and second periods of time are different.

875. The depot of Clause 871, wherein the first and second periods of time are the same.

876. The depot of any one of Clauses 871 to 875, wherein the depot is configured to begin releasing a therapeutic dosage of the chemotherapeutic agent and a therapeutic dosage of the antiandrogen at substantially the same time.

877. The depot of any one of Clauses 871 to 875, wherein the depot is configured to begin releasing a therapeutic dosage of the chemotherapeutic agent at a first time after implantation, and wherein the depot is configured to begin releasing a therapeutic dosage of the antiandrogen at a second time after implantation, the second time different than the first time.

878. The depot of any one of Clauses 871 to 877, wherein the second time is 1 day, 2, days, 3 days, 4 days, 5 days, 6 days, one week, two weeks, three weeks, four weeks, five weeks, six weeks, seven weeks, or eight weeks before the first time.

879. The depot of any one of Clauses 871 to 877, wherein the second time is 1 day, 2, days, 3 days, 4 days, 5 days, 6 days, one week, two weeks, three weeks, four weeks, five weeks, six weeks, seven weeks, or eight weeks after the first time.

880. The depot of any one of Clauses 871 to 879, wherein the depot is configured to release the chemotherapeutic agent at a first rate and the antiandrogen at a second rate.

881. The depot of any one of Clauses 871 to 880, wherein the first rate is the same as the second rate.

882. The depot of any one of Clauses 871 to 880, wherein the first rate is different than the second rate.

883. The depot of any one of Clauses 871 to 880 and 882, wherein the first rate is greater than the second rate.

884. The depot of any one of Clauses 871 to 880 and 882, wherein the first rate is less than the second rate.

885. The depot of any one of the preceding Clauses, wherein the therapeutic region includes a first portion and a second portion, wherein the first portion includes a chemotherapeutic agent and the second portion includes an antiandrogen.

886. The depot of Clause 885, wherein the first portion completely surrounds the second portion such that the first portion is between the second portion and adjacent tissue when the depot is implanted at the treatment site.

887. The depot of Clause 885, wherein the second portion completely surrounds the first portion such that the second portion is between the first portion and adjacent tissue when the depot is implanted at the treatment site.

888. The depot of Clause 885, wherein the first portion is closer to an exterior surface of the depot than the second portion.

889. The depot of Clause 885, wherein the first portion is farther from an exterior surface of the depot than the second portion.

890. The depot of any one of the preceding Clauses, wherein the depot is generally cylindrical and comprises a first half-cylinder and a second half-cylinder configured to be positioned within a lumen of a delivery device such that a generally flat side of the first half-cylinder faces a generally flat surface of the second half-cylinder to form a full cylinder.

891. The depot of any one of the preceding Clauses, wherein the depot is configured to be positioned at least partially within a tumor of the prostate gland.

892. The depot of any one of the preceding Clauses, wherein the prostate cancer comprises a tumor, and wherein the depot is configured to be positioned completely within a tumor of the prostate gland.

893. The depot of any one of the preceding Clauses, wherein the prostate cancer comprises a tumor, and wherein the depot is configured to be placed at a superior, lateral, posterior, or inferior aspect of the tumor.

894. The depot of any one of the preceding Clauses, wherein the prostate cancer comprises a tumor, and wherein the depot is configured to be placed proximate an artery supplying the tumor.

895. A system for treating prostate cancer via the controlled, sustained release of a therapeutic agent, the system comprising:

a plurality of depots, each being one of the depots of Clauses 787 to 894.

896. The system of Clause 895, wherein the plurality of depots collectively have a diffusion radius which encompasses the entire prostate gland.

897. The system of Clause 895, wherein the plurality of depots together include at least 6 mg of a chemotherapeutic agent.

898. The system of Clause 895, wherein the plurality of depots together include at least 3 mg of an antiandrogen.

899. The system of Clause 895, wherein the plurality of depots together include at least 6 mg of a chemotherapeutic agent and at least 3 mg of an antiandrogen.

900. The system of Clause 895, wherein the plurality of depots comprises a first depot and a second depot, each having a different therapeutic agent.

901. The system of Clause 895, wherein the plurality of depots comprises a first depot including a chemotherapeutic agent and a second depot including an antiandrogen.

902. The system of any one of Clause 899 or Clause 900, wherein the first and second depots are loaded within the delivery device such that the first depot is expelled from the delivery device at a first location within the prostate gland at a first time and the second depot is expelled from the delivery device at a second location within the prostate gland at a second time.

903. A system for treating prostate cancer via the controlled, sustained release of a therapeutic agent, the system comprising:

the depot of any one of Clauses 787 to 894; and a delivery device configured to position the depot at or within a prostate gland.

904. A system for treating prostate cancer via the controlled, sustained release of a therapeutic agent, the system comprising:

a plurality of depots, each being one of the depots of Clauses 787 to 894; and a delivery device configured to position the depot at or within a prostate gland.

905. The system of any one of the preceding Clauses, wherein the delivery device comprises a catheter.

906. The system of any one of the preceding Clauses, wherein the delivery device comprises a hollow needle.

907. The system of any one of the preceding Clauses, wherein the delivery device comprises a needle and an elongated member configured to be slidably received through a lumen of the needle.

908. The system of any one of the preceding Clauses, wherein the delivery device comprises a needle, a tubular braid configured to be positioned within a lumen of the needle, and an elongated member configured to be positioned within a lumen of the braid.

909. The system of any one of the preceding Clauses, wherein the delivery device comprises a delivery shaft and a needle having a distal portion with a curved, preset shape, wherein the needle is configured to be delivered to the prostate gland through the delivery shaft.

910. The system of any of the preceding Clauses, wherein the delivery device is configured to position the depot at or within the prostate gland via a transrectal approach.

911. The system of any one of the preceding Clauses, further comprising an ultrasound probe.

912. The system of any of the preceding Clauses, wherein the delivery device is configured to position the depot at or within the prostate gland via a transperineal approach.

913. The system of any one of the preceding Clauses, further comprising a biopsy grid.

914. The system of any of the preceding Clauses, wherein the delivery device is configured to position the depot at or within the prostate gland via a transurethral approach.

915. The system of any of the preceding Clauses, wherein the delivery device is a catheter configured to be positioned through the urethra.

916. The system of any one of the preceding Clauses, wherein the delivery device includes a resectoscope.

917. The system of any of the preceding Clauses, wherein the delivery device is configured to position the depot at or within the prostate gland via a transarterial approach.

918. The system of any one of the preceding Clauses, wherein the delivery device is disposable.

919. The system of any one of the preceding Clauses, wherein the delivery device includes a needle and a disposable cartridge configured to be positioned within a lumen of the needle, wherein the disposable cartridge includes one or more of the depots of any one of the preceding clauses pre-loaded.

920. The system of any one of the preceding Clauses, wherein the delivery device includes one or more features configured to reduce cytotoxic exposure to a caregiver.

921. The system of any one of the preceding Clauses, wherein the plurality of depots comprises at least one depot configured for placement in at least one lobe/lobule of the prostate gland.

922. A method for treating prostate cancer via the controlled, sustained release of a therapeutic agent, the method comprising:

providing a depot of any one of Clauses 787 to 894.

923. A sustained release formulation of therapeutic agent for use in the treatment of prostate cancer, wherein the formulation is configured to release the therapeutic agent for no less than 7 days and wherein the therapeutic agent is selected from the group consisting of paclitaxel, docetaxel, abiraterone acetate, apalutimide, darolutimide, enzalutamide, and bicalutamide.

924. A method for treating prostate cancer via the controlled, sustained release of a therapeutic agent, the method comprising:

positioning a depot of any one of Clauses 787 to 894 at a treatment site at or within a prostate gland of a patient; and delivering the therapeutic agent to the treatment site for a period of time that is no less than 7 days.

925. The method of Clause 924, wherein the plurality of depots deliver a toxic dose to prostate cancer throughout the prostate gland.

926. A method for treating prostate cancer via the controlled, sustained release of a therapeutic agent, the method comprising:

positioning a plurality of depots at a treatment site at or within a prostate gland of a patient, each of the depots being any one of the depots of Clauses 787 to 894; and delivering the therapeutic agent to the treatment site for a period of time that is no less than 7 days.

927. The method of any one of the preceding Clauses, wherein positioning the plurality of depots includes positioning a first depot at a first location within the prostate gland and a second depot at a second location within the prostate gland.

928. The method of Clause 924, wherein the first depot includes a chemotherapeutic agent and the second depot includes an antiandrogen.

929. The method of any one of the preceding Clauses, wherein the prostate cancer comprises a tumor at a first lobe of the prostate gland, and wherein positioning the plurality of depots includes positioning a first depot at the first lobe proximate the tumor and positioning a second depot at a second lobe of the prostate gland different than the first lobe.

930. The method of any one of the preceding Clauses, wherein the prostate cancer comprises a cancerous and/or pre-cancerous tissue within the prostate gland.

931. The method of Clause 927, wherein positioning the plurality of depots includes positioning first and second depots at the prostate gland proximate to the cancerous and/or pre-cancerous tissue.

932. The method of Clause 928, wherein the first depot has a first diffusion radius and the second depot has a second diffusion radius, and wherein the method further comprises positioning the first and second depots such that (a) the first and second diffusion radii overlap, and (b) one or both of the first and second diffusion radii overlap the cancerous and/or pre-cancerous tissue.

933. The method of Clause 928, wherein the first depot has a first diffusion radius and the second depot has a second diffusion radius, and wherein the method further comprises positioning the first and second depots such that (a) the first and second diffusion radii do not overlap, and (b) one or both of the first and second diffusion radii overlap the cancerous and/or pre-cancerous tissue.

934. The method of Clause 928, wherein the first depot has a first diffusion radius and the second depot has a second diffusion radius, and wherein the method further comprises positioning the first and second depots such that (a) the first and second diffusion radii are spaced apart, and (b) one or both of the first and second diffusion radii overlap the cancerous and/or pre-cancerous tissue.

935. The method of Clause 928, wherein the first depot has a first treatment zone and the second depot has a second treatment zone, and wherein the method further comprises positioning the first and second depots such that (a) the first and second treatment zones overlap, and (b) one or both of the first and second treatment zones overlap the cancerous and/or pre-cancerous tissue.

936. The method of Clause 928, wherein the first depot has a first treatment zone and the second depot has a second treatment zone, and wherein the method further comprises positioning the first and second depots such that (a) the first and second treatment zones do not overlap, and (b) one or both of the first and second treatment zones overlap the cancerous and/or pre-cancerous tissue.

937. The method of Clause 928, wherein the first depot has a first treatment zone and the second depot has a second treatment zone, and wherein the method further comprises positioning the first and second depots such that (a) the first and second treatment zones are spaced apart, and (b) one or both of the first and second treatment zones overlap the cancerous and/or pre-cancerous tissue.

938. The method of any one of the preceding Clauses, wherein positioning the depot at the treatment site comprises accessing the prostate gland via a transrectal approach.

939. The method of any one of the preceding Clauses, wherein positioning the depot at the treatment site comprises accessing the prostate gland via a transperineal approach.

940. The method of any one of the preceding Clauses, wherein positioning the depot at the treatment site comprises accessing the prostate gland via a transurethral approach.

941. The method of any one of the preceding Clauses, wherein positioning the depot at the treatment site comprises accessing the prostate gland via a transarterial approach.

942. The method of any one of the preceding Clauses, wherein the prostate cancer comprises a tumor, and wherein positioning the depot at the treatment site comprises positioning the depot within an artery supplying the tumor.

943. The method of any one of the preceding Clauses, wherein the period of time is no less than two weeks, no less than three weeks, no less than four weeks, no less than five weeks, no less than 8 weeks, no less than 2 months, no less than 3 months, no less than 4 months, no less than 6 months, no less than 7 months, no less than 8 months, no less than 9 months, no less than 10 months, no less than 12 months, no less than 13 months, no less than 14 months, no less than 15 months, no less than 16 months, no less than 17 months, or no less than 18 months.

944. The method of any one of the preceding Clauses, further comprising reducing the likelihood of the prostate cancer recurring.

945. The method of any one of the preceding Clauses, further comprising reducing the volume of the prostate cancer.

946. The method of any one of the preceding Clauses, further comprising reducing pain associated with prostate cancer.

947. The method of any one of the preceding Clauses, further comprising reducing an amount of radiation required to treat the prostate cancer.

948. The method of any one of the preceding Clauses, further comprising reducing a radiation side effect profile.

949. The method of any one of the preceding Clauses, further comprising increasing a susceptibility of the prostate cancer to radiation therapy.

950. The method of any one of the preceding Clauses, further comprising shielding non-target tissue from radiation with at least a portion of the depot.

951. The method of any one of the preceding Clauses, releasing a toxic concentration of the therapeutic agent to the prostate tissue without delivering a toxic concentration of the therapeutic agent to tissue immediately adjacent the prostate tissue.

952. The method of any one of the preceding Clauses, wherein the depot is positioned adjacent the capsule, the method comprising releasing a toxic concentration of the therapeutic agent to the prostate tissue without delivering a toxic concentration of the therapeutic agent to tissue immediately adjacent the prostate tissue.

953. The method of any one of the preceding Clauses, wherein the depot is positioned within the prostate adjacent the capsule, the method comprising releasing a toxic concentration of the therapeutic agent to the prostate tissue without delivering a toxic concentration of the therapeutic agent to tissue immediately adjacent the prostate tissue.

954. The method of any one of the preceding Clauses, wherein the depot is positioned less than a centimeter from the capsule, the method comprising releasing a toxic concentration of the therapeutic agent to the prostate tissue without delivering a toxic concentration of the therapeutic agent to tissue immediately adjacent the prostate tissue.

955. The method of any one of the preceding Clauses, wherein the depot is positioned within the prostate less than a centimeter from the capsule, the method comprising releasing a toxic concentration of the therapeutic agent to the prostate tissue without delivering a toxic concentration of the therapeutic agent to tissue immediately adjacent the prostate tissue.

956. The method of any one of the preceding Clauses, further comprising releasing a toxic concentration of the therapeutic to an intra-capsular space without delivering a toxic concentration of the therapeutic agent to an extra-capsular space.

957. A method for treating prostate cancer with any one of the systems of Clauses 895 to 919.

958. A depot for treating prostate cancer via sustained, controlled release of a therapeutic agent to a patient, the depot comprising:

a therapeutic region comprising a biodegradable polymer mixed with a therapeutic agent configured to treat prostate cancer, the therapeutic agent comprising a chemotherapeutic agent, wherein the depot is configured to be implanted at a treatment site at a prostate gland of the patient and, while implanted, release the therapeutic agent at the treatment site for a period of time that is no less than 15 days.

959. The depot of Clause 953, wherein the depot is configured to release the chemotherapeutic agent at the treatment site for no less than 30 days.

960. The depot of Clause 953 or Clause 954, wherein the therapeutic agent further comprises an antiandrogen.

961. The depot of Clause 955, wherein the antiandrogen is at least one of bicalutamide and enzalutamide.

962. The depot of any one of Clauses 953 to 956, wherein the depot is configured to be delivered to the prostate gland through a needle.

963. The depot of any one of Clauses 953 to 957, wherein the depot has a first end, a second end, and a length measured between the first and second ends along a longitudinal axis of the depot, and wherein the depot has a substantially constant cross-sectional dimension along its length.

964. The depot of any one of Clauses 953 to 958, wherein the depot has a cross-sectional dimension that is between about 0.7 mm and about 1.2 mm.

965. The depot of any one of Clauses 953 to 959, wherein the polymer comprises poly(lactide-co-glycolide) (PLGA) and poly(ethylene glycol) (PEG).

966. A depot for treating prostate cancer via sustained, controlled release of a therapeutic agent to a patient, the depot comprising:

a substantially cylindrical member formed of a biodegradable polymer and a therapeutic agent configured to treat prostate cancer, the therapeutic agent comprising a chemotherapeutic agent, wherein the depot is configured to be implanted at a treatment site at a prostate gland of the patient and, while implanted, release the therapeutic agent at the treatment site for a period of time of about 30 days to about 45 days.

967. The depot of Clause 961, wherein the therapeutic agent further comprises an antiandrogen.

968. The depot of Clause 962, wherein the antiandrogen is at least one of bicalutamide and enzalutamide.

969. The depot of Clause 963, wherein the chemotherapeutic agent is docetaxel.

970. The depot of Clause 963 or Clause 964, wherein the substantially cylindrical member has a cross-sectional dimension that is between about 0.7 mm and about 1.2 mm.

971. The depot of any one of Clauses 961 to 965, wherein the substantially cylindrical member is configured to be delivered to the prostate gland through a needle.

972. A system for treating prostate cancer via sustained, controlled release of a therapeutic agent to a patient, the system comprising:

a plurality of depots, each comprising a biodegradable polymer mixed with a therapeutic agent configured to treat prostate cancer, wherein at least some of the depots include a therapeutic agent comprising a chemotherapeutic agent, and wherein each of the depots is configured to be implanted at a treatment site at a prostate gland of the patient and, while implanted, release the chemotherapeutic agent at the treatment site for a period of time that is no less than 15 days.

973. The system of Clause 967, wherein each of the depots is configured to release the chemotherapeutic agent at the treatment site for no less than 30 days.

974. The system of Clause 967 or Clause 968, further comprising a tubular delivery device, wherein each of the depots is loaded within the delivery device such that the depots are configured to be expelled from the delivery device into the prostate gland sequentially.

975. The system of any one of Clauses 967 to 969, wherein at least two of the plurality of depots have a different length.

976. The system of any one of Clauses 967 to 970, wherein the plurality of depots together contain about 1 mg to about 4 mg of the therapeutic agent.

977. The system of any one of Clauses 967 to 971, wherein at least some of the depots include a therapeutic agent comprising an antiandrogen.

978. A drug delivery implant comprising a polymer and hydrophobic drug, wherein the hydrophobicity of the implant is less than the hydrophobicity of the hydrophobic drug.

979. A method of treating a patient with cancer by (a) administering cytoreductive therapy at or around the originating/primary tumor via localized, sustained drug delivery; and (b) administering non-localized therapy.

980. A method of treating a patient with bile duct cancer, the method comprising:

administering a sustained release formulation of a therapeutic agent to the patient's bile duct or liver; and reducing the rate and/or risk of progression of the patient's bile duct cancer in comparison to a bile duct cancer patient who does not receive the sustained release formulation, whereby reducing the rate and/or risk of progression comprises improving a prognosis of the patient following surgical intervention.

981. The method of Clause 980, wherein the surgical intervention is surgical resection of a tumor in a bile duct or a liver of the patient.

982. The method of Clause 980 or Clause 981, wherein improving the prognosis of the patient following surgical intervention comprises increasing a 5-year survival rate following surgical intervention.

983. A method of treating bile duct cancer, the method comprising locally exposing the patient's bile duct or liver to a therapeutic agent, the therapeutic agent comprising a chemotherapeutic agent, whereby locally exposing comprises causing a greater exposure in the bile duct or liver to the therapeutic agent over time as compared to exposure resulting from systemic administration of the therapeutic agent.

984. A method of decreasing mortality caused by cholangiocarcinoma in a patient in need thereof which comprises administering an implantable formulation for localized, sustained release of a chemotherapeutic agent to the patient's bile duct or liver.

985. The method of Clause 984, further comprising administering one or more treatments selected from the group consisting of surgery, radiation, and systemic drug therapy in conjunction with administering the implantable formulation.

986. The method of Clause 985, wherein the surgery comprises open surgery, laparoscopic surgery, or endoscopic surgery.

987. The method of Clause 985 or Clause 986, wherein the radiation comprises external beam radiation, brachytherapy seed radiation, or stereotactic radiotherapy.

988. The method of any one of Clauses 985 to 987, wherein the systemic drug therapy comprises chemotherapy, targeted therapy, or immunotherapy.

989. A method of treating bile duct cancer in a human patient having a tumor in a bile duct or a liver of the patient, the method comprising:

implanting one or more depots within the patient's bile duct or liver, each of the one or more depots comprising a biodegradable sustained release formulation that includes a therapeutic agent, the therapeutic agent comprising a chemotherapeutic agent;

administering the chemotherapeutic agent to the bile duct or liver over a period of time via the sustained release formulation; and reducing a sum of diameters of the tumor by at least 20%.

990. The method of Clause 989, wherein reducing the sum of the diameters of the tumor by at least 20% comprises reducing the sum of the diameters of the tumor by at least 30%.

991. The method of Clause 989 or Clause 990, wherein reducing the sum of the diameters of the by at least 20% comprises reducing the sum of the diameters of the tumor by at least 40%.

992. The method of any one of Clauses 989 to 991, wherein reducing the sum of the diameters of the tumor by at least 20% comprises reducing the sum of the diameters of the tumor by at least 50%.

993. A method of treating a patient with target lesions in a bile duct or liver of the patient, wherein the target lesions have been measured via medical imaging, the method comprising:

administering a sustained release formulation of a therapeutic agent to the patient's bile duct or liver, the therapeutic agent comprising a chemotherapeutic agent; and reducing a size of the target lesions such that the target lesions are not detectable via medical imaging.

994. A method of treating a patient with target lesions in a bile duct or liver of the patient, wherein the target lesions have been measured via medical imaging, the method comprising:

administering a sustained release formulation of a therapeutic agent to the patient's bile duct or liver, the therapeutic agent comprising a chemotherapeutic agent; and reducing a size of at least one target lesion such that the at least one target lesion is not detectable via medical imaging.

995. A method of treating bile duct cancer in a patient, the method comprising:

administering a sustained release formulation of a therapeutic agent to the patient's bile duct or liver, the therapeutic agent comprising a chemotherapeutic agent; and improving a quality of life parameter of the patient, wherein the quality of life parameter is measured by a quality of life measurement instrument.

996. The method of Clause 995, wherein the quality of life parameter is a health-related quality of life parameter.

997. The method of Clause 995 or Clause 996, wherein the quality of life measurement instrument is a EuroQol-5D, a EORTC QLQ-C30, a FACT-Hep, or a FACT-G quality of life measurement instrument.

998. A method of treating a patient with a cancerous bile duct tumor, the method comprising:

administering a sustained release formulation of a therapeutic agent to the patient's bile duct or liver over a period of time, the therapeutic agent comprising a chemotherapeutic agent; and slowing or halting growth of the cancerous bile duct tumor, wherein slowing or halting the growth is indicated by the cancerous bile duct tumor having a sum of diameters after the period of time that is no more than 20% greater than a sum of diameters of the cancerous bile duct tumor prior to administering the sustained release formulation.

999. The method of Clause 998, wherein slowing or halting the growth is indicated by the sum of diameters after the period of time being substantially equivalent to the sum of diameters of prior to administering the sustained release formulation.

1000. The method of Clause 998, wherein slowing or halting the growth is indicated by the sum of diameters after the period of time being less than the sum of diameters prior to administering the sustained release formulation.

1001. A method of treating a patient with bile duct cancer having a tumor in a bile duct or a liver of the patient, the method comprising:

administering a sustained release formulation of a therapeutic agent to the patient's bile duct or liver; and relative to a patient who does not receive the sustained release formulation, increasing a length of a period of progression-free survival of the patient, wherein the period of progression-free survival begins prior to administering the sustained release formulation and ends when a sum of diameters of the tumor is at least 20% greater than a sum of diameters of the tumor prior to administering the sustained release formulation.

1002. A method of treating a cancerous tumor within a bile duct or a liver of a patient, the method comprising:

administering a sustained release formulation of a therapeutic agent to the patient's bile duct or liver; and increasing the likelihood that (i) a sum of diameters of the cancerous tumor will not increase by 20% or more after administering the sustained release formulation, (ii) the sum of diameters of the cancerous tumor will decrease by at least 20% after administering the sustained release formulation, and/or (iii) a size of the tumor will be reduced after administering the sustained release formulation such that the tumor is not detectable via medical imaging.

1003. A method of treating a patient with bile duct cancer, the method comprising:

administering a sustained release formulation of a therapeutic agent to the patient's bile duct or liver; and relative to a patient who does not receive the sustained release formulation, administering one or more further treatments at an earlier time.

1004. The method of Clause 1003, wherein the one or more further treatments comprise surgery, radiation, or systemic drug therapy.

1005. The method of any one of Clauses 980 to 1004, wherein the chemotherapeutic agent is FDA-approved for systemic administration to treat one or more cancers of the human body.

1006. The method of any one of Clauses 980 to 1005, wherein the chemotherapeutic agent is an antimetabolite, genotoxic, or a mitotic or spindle inhibitor, or any combination thereof.

1007. The method of any one of Clauses 980 to 1006, wherein the chemotherapeutic agent is a taxane.

1008. The method of any one of Clauses 980 to 1007, wherein the chemotherapeutic agent is docetaxel.

1009. The method of any one of Clauses 980 to 1008, wherein the period of time is at least 1 month.

1010. The method of any one of Clauses 980 to 1009, wherein the period of time is at least 3 months.

1011. The method of any one of Clauses 980 to 1010, wherein the period of time is at least 6 months.

1012. The method of any one of Clauses 980 to 1011, wherein the period of time is at least 12 months.

1013. A method of treating a patient with liver cancer, the method comprising:

administering a sustained release formulation of a therapeutic agent to the patient's liver;

reducing the rate and/or risk of progression of the patient's liver cancer in comparison to a liver cancer patient who does not receive the sustained release formulation, whereby reducing the rate and/or risk of progression comprises improving a prognosis of the patient following surgical intervention.

1014. The method of Clause 1013, wherein the surgical intervention is surgical resection of a tumor in a liver of the patient.

1015. The method of Clause 1013 or Clause 1014, wherein improving the prognosis of the patient following surgical intervention comprises increasing a 5-year survival rate following surgical intervention.

1016. A method of treating liver cancer, the method comprising locally exposing the patient's liver to a therapeutic agent, the therapeutic agent comprising a chemotherapeutic agent, whereby locally exposing comprises causing a greater exposure in the liver to the therapeutic agent over time as compared to exposure resulting from systemic administration of the therapeutic agent.

1017. A method of decreasing mortality caused by hepatic cancer in a patient in need thereof which comprises administering an implantable formulation for localized, sustained release of a chemotherapeutic agent to the patient's liver.

1018. The method of Clause 1017, further comprising administering one or more treatments selected from the group consisting of surgery, ablation, radiation, and systemic drug therapy in conjunction with administering the implantable formulation.

1019. The method of Clause 1018, wherein the surgery comprises open surgery, laparoscopic surgery, or endoscopic surgery.

1020. The method of Clause 1018 or Clause 1019, wherein the radiation comprises external beam radiation, brachytherapy seed radiation, or stereotactic radiotherapy.

1021. The method of any one of Clauses 1018 to 1020, wherein the systemic drug therapy comprises chemotherapy, targeted therapy, or immunotherapy.

1022. A method of treating liver cancer in a human patient having a tumor in a liver of the patient, the method comprising:

implanting one or more depots within the patient's liver, each of the one or more depots comprising a biodegradable sustained release formulation that includes a therapeutic agent, the therapeutic agent comprising a chemotherapeutic agent;

administering the chemotherapeutic agent to the liver over a period of time via the sustained release formulation; and reducing a sum of diameters of the tumor by at least 20%.

1023. The method of Clause 1022, wherein reducing the sum of the diameters of the tumor by at least 20% comprises reducing the sum of the diameters of the tumor by at least 30%.

1024. The method of Clause 1022 or Clause 1023, wherein reducing the sum of the diameters of the by at least 20% comprises reducing the sum of the diameters of the tumor by at least 40%.

1025. The method of any one of Clauses 1022 to 1024, wherein reducing the sum of the diameters of the tumor by at least 20% comprises reducing the sum of the diameters of the tumor by at least 50%.

1026. A method of treating a patient with target lesions in a liver of the patient, wherein the target lesions have been measured via medical imaging, the method comprising:

administering a sustained release formulation of a therapeutic agent to the patient's liver, the therapeutic agent comprising a chemotherapeutic agent; and reducing a size of the target lesions such that the target lesions are not detectable via medical imaging.

1027. A method of treating a patient with target lesions in a liver of the patient, wherein the target lesions have been measured via medical imaging, the method comprising:

administering a sustained release formulation of a therapeutic agent to the patient's liver, the therapeutic agent comprising a chemotherapeutic agent; and reducing a size of at least one target lesion such that the at least one target lesion is not detectable via medical imaging.

1028. A method of treating liver cancer in a patient, the method comprising:

administering a sustained release formulation of a therapeutic agent to the patient's liver, the therapeutic agent comprising a chemotherapeutic agent; and improving a quality of life parameter of the patient, wherein the quality of life parameter is measured by a quality of life measurement instrument.

1029. The method of Clause 1028, wherein the quality of life parameter is a health-related quality of life parameter.

1030. The method of Clause 1028 or Clause 1029, wherein the quality of life measurement instrument is a EuroQol-5D, a EORTC QLQ-C30, a FACT-Hep, a FHSI-8, or a FACT-G quality of life measurement instrument.

1031. A method of treating a patient with a cancerous liver tumor, the method comprising:

administering a sustained release formulation of a therapeutic agent to the patient's liver over a period of time, the therapeutic agent comprising a chemotherapeutic agent; and slowing or halting growth of the cancerous liver tumor, wherein slowing or halting the growth is indicated by the cancerous liver tumor having a sum of diameters after the period of time that is no more than 20% greater than a sum of diameters of the cancerous liver tumor prior to administering the sustained release formulation.

1032. The method of Clause 1031, wherein slowing or halting the growth is indicated by the sum of diameters after the period of time being substantially equivalent to the sum of diameters of prior to administering the sustained release formulation.

1033. The method of Clause 1031, wherein slowing or halting the growth is indicated by the sum of diameters after the period of time being less than the sum of diameters prior to administering the sustained release formulation.

1034. A method of treating a patient with liver cancer having a tumor in a liver of the patient, the method comprising:

administering a sustained release formulation of a therapeutic agent to the patient's liver; and relative to a patient who does not receive the sustained release formulation, increasing a length of a period of progression-free survival of the patient, wherein the period of progression-free survival begins prior to administering the sustained release formulation and ends when a sum of diameters of the tumor is at least 20% greater than a sum of diameters of the tumor prior to administering the sustained release formulation.

1035. A method of treating a cancerous tumor within a liver of a patient, the method comprising:

administering a sustained release formulation of a therapeutic agent to the patient's liver; and increasing the likelihood that (i) a sum of diameters of the cancerous tumor will not increase by 20% or more after administering the sustained release formulation, (ii) the sum of diameters of the cancerous tumor will decrease by at least 20% after administering the sustained release formulation, and/or (iii) a size of the tumor will be reduced after administering the sustained release formulation such that the tumor is not detectable via medical imaging.

1036. A method of treating a patient with a liver cancer, the method comprising:

administering a sustained release formulation of a therapeutic agent to the patient's liver, the therapeutic agent comprising a chemotherapeutic agent; and reducing an amount of a tumor marker in the patient's serum.

1037. The method of Clause 1036, wherein the tumor marker comprises an embryonic antigen, a proteantigen, an enzyme, an isozyme, a cytokine, or a genetic biomarker.

1038. The method of Clause 1037, wherein the embryonic antigen comprises alpha-fetoprotein.

1039. The method of Clause 1037, wherein the proteantigen comprises heat shock protein, glypican-3, squamous cell carcinoma antigen, golgi protein 73, fucosylated GP73, tumor-associated glycoprotein 72, or zinc-α2-glycoprotein.

1040. The method of Clause 1037, wherein the enzyme comprises des-gamma-carboxyprothrombin, gamma-glutamyl transferase, or alpha-L-fucosidase.

1041. The method of Clause 1037, wherein the cytokine comprises transforming growth factor-β1 or vascular endothelial growth factor.

1042. The method of Clause 1037, wherein the genetic biomarker comprises alpha-fetoprotein mRNA, microRNAs, A-like 1 homolog, hepatoma-associated gene, or villin1.

1043. A method of treating a patient with liver cancer, the method comprising:

administering a sustained release formulation of a therapeutic agent to the patient's liver; and relative to a patient who does not receive the sustained release formulation, administering one or more further treatments at an earlier time.

1044. The method of Clause 1043, wherein the one or more further treatments comprise surgery, radiation, or systemic drug therapy.

1045. The method of any one of Clauses 1013 to 1044, wherein the chemotherapeutic agent is FDA-approved for systemic administration to treat one or more cancers of the human body.

1046. The method of any one of Clauses 1013 to 1045, wherein the chemotherapeutic agent is an alkylating agent, an antimetabolite, an anthracycline antibiotic, an antitumor antibiotic, or any combination thereof.

1047. The method of any one of Clauses 1013 to 1046, wherein the period of time is at least 1 month.

1048. The method of any one of Clauses 1013 to 1047, wherein the period of time is at least 3 months.

1049. The method of any one of Clauses 1013 to 1048, wherein the period of time is at least 6 months.

1050. The method of any one of Clauses 1013 to 1049, wherein the period of time is at least 12 months.

1051. A method of treating a patient with colorectal cancer, the method comprising:
administering a sustained release formulation of a therapeutic agent to the patient's colon or rectum;
reducing the rate and/or risk of progression of the patient's colorectal cancer in comparison to a colorectal cancer patient who does not receive the sustained release formulation, whereby reducing the rate and/or risk of progression comprises improving a prognosis of the patient following surgical intervention.
1052. The method of Clause 1051, wherein the surgical intervention is surgical resection of a tumor in a colon or a rectum of the patient.
1053. The method of Clause 1051 or Clause 1052, wherein improving the prognosis of the patient following surgical intervention comprises increasing a 5-year survival rate following surgical intervention.
1054. A method of treating colorectal cancer, the method comprising locally exposing the patient's colon or rectum to a therapeutic agent, the therapeutic agent comprising a chemotherapeutic agent, whereby locally exposing comprises causing a greater exposure in the colon or rectum to the therapeutic agent over time as compared to exposure resulting from systemic administration of the therapeutic agent.
1055. A method of decreasing mortality caused by colorectal cancer in a patient in need thereof which comprises administering an implantable formulation for localized, sustained release of a chemotherapeutic agent to the patient's colon or rectum.
1056. The method of Clause 1055, further comprising administering one or more treatments selected from the group consisting of surgery, radiation, and systemic drug therapy in conjunction with administering the implantable formulation.
1057. The method of Clause 1056, wherein the surgery comprises open surgery, laparoscopic surgery, or endoscopic surgery.
1058. The method of Clause 1056 or Clause 1057, wherein the radiation comprises external beam radiation, brachytherapy seed radiation, or stereotactic radiotherapy.
1059. The method of any one of Clauses 1056 to 1058, wherein the systemic drug therapy comprises chemotherapy, targeted therapy, or immunotherapy.
1060. A method of treating colorectal cancer in a human patient having a tumor in a colon or a rectum of the patient, the method comprising:
implanting one or more depots within the patient's colon or rectum, each of the one or more depots comprising a biodegradable sustained release formulation that includes a therapeutic agent, the therapeutic agent comprising a chemotherapeutic agent;
administering the chemotherapeutic agent to the colon or rectum over a period of time via the sustained release formulation; and
reducing a sum of diameters of the tumor by at least 20%.
1061. The method of Clause 1060, wherein reducing the sum of the diameters of the tumor by at least 20% comprises reducing the sum of the diameters of the tumor by at least 30%.
1062. The method of Clause 1060 or Clause 1061, wherein reducing the sum of the diameters of the by at least 20% comprises reducing the sum of the diameters of the tumor by at least 40%.
1063. The method of any one of Clauses 1060 to 1062, wherein reducing the sum of the diameters of the tumor by at least 20% comprises reducing the sum of the diameters of the tumor by at least 50%.
1064. A method of treating a patient with target lesions in a colon or a rectum of the patient, wherein the target lesions have been measured via medical imaging, the method comprising:
administering a sustained release formulation of a therapeutic agent to the patient's colon or rectum, the therapeutic agent comprising a chemotherapeutic agent; and
reducing a size of the target lesions such that the target lesions are not detectable via medical imaging.
1065. A method of treating a patient with target lesions in a colon or a rectum of the patient, wherein the target lesions have been measured via medical imaging, the method comprising:
administering a sustained release formulation of a therapeutic agent to the patient's colon or rectum, the therapeutic agent comprising a chemotherapeutic agent; and
reducing a size of at least one target lesion such that the at least one target lesion is not detectable via medical imaging.
1066. A method of treating colorectal cancer in a patient, the method comprising:
administering a sustained release formulation of a therapeutic agent to the patient's colon or rectum, the therapeutic agent comprising a chemotherapeutic agent; and
improving a quality of life parameter of the patient, wherein the quality of life parameter is measured by a quality of life measurement instrument.
1067. The method of Clause 1066, wherein the quality of life parameter is a health-related quality of life parameter.
1068. The method of Clause 1066 or Clause 1067, wherein the quality of life measurement instrument is a EuroQol-5D, a EORTC QLQ-C30, a FACT-C, or a mCOH-QOAL quality of life measurement instrument.
1069. A method of treating a patient with a cancerous tumor in a colon or a rectum of the patient, the method comprising:
administering a sustained release formulation of a therapeutic agent to the patient's colon or rectum over a period of time, the therapeutic agent comprising a chemotherapeutic agent; and
slowing or halting growth of the cancerous tumor, wherein slowing or halting the growth is indicated by the cancerous tumor having a sum of diameters after the period of time that is no more than 20% greater than a sum of diameters of the cancerous tumor prior to administering the sustained release formulation.
1070. The method of Clause 1069, wherein slowing or halting the growth is indicated by the sum of diameters after the period of time being substantially equivalent to the sum of diameters of prior to administering the sustained release formulation.
1071. The method of Clause 1069, wherein slowing or halting the growth is indicated by the sum of diameters after the period of time being less than the sum of diameters prior to administering the sustained release formulation.
1072. A method of treating a patient with colorectal cancer having a tumor in a colon or a rectum of the patient, the method comprising:
administering a sustained release formulation of a therapeutic agent to the patient's colon or rectum; and relative to a patient who does not receive the sustained release formulation, increasing a length of a period of progression-free survival of the patient, wherein the period of progression-free survival begins prior to administering the sustained release formulation and ends when a sum of diameters of the tumor is at least 20% greater than a sum of diameters of the tumor prior to administering the sustained release formulation.

1073. A method of treating a patient with colorectal cancer having a tumor in a colon or a rectum of the patient, the method comprising:

administering a sustained release formulation of a therapeutic agent to the patient's colon or rectum; and relative to a patient who does not receive the sustained release formulation, increasing a length of a response period of the patient, wherein:

the response period begins when, after administering the sustained release formulation, a sum of diameters of the tumor decreases by at least 20% and/or a size of the tumor reduces such that the tumor is not detectable via medical imaging; and the response period ends when the sum of diameters of the tumor increases by at least 20% and/or recurrent disease is detected.

1074. A method of treating a cancerous tumor within a colon or a rectum of a patient, the method comprising:

administering a sustained release formulation of a therapeutic agent to the patient's colon or rectum; and increasing the likelihood that (i) a sum of diameters of the cancerous tumor will not increase by 20% or more after administering the sustained release formulation, (ii) the sum of diameters of the cancerous tumor will decrease by at least 20% after administering the sustained release formulation, and/or (iii) a size of the tumor will be reduced after administering the sustained release formulation such that the tumor is not detectable via medical imaging.

1075. A method of treating a patient with colorectal cancer, the method comprising:

administering a sustained release formulation of a therapeutic agent to the patient's colon or rectum; and relative to a patient who does not receive the sustained release formulation, administering one or more further treatments at an earlier time.

1076. The method of Clause 1075 wherein the one or more further treatments comprise surgery, radiation, or systemic drug therapy.

1077. The method of any one of Clauses 1051 to 1076, wherein the chemotherapeutic agent is FDA-approved for systemic administration to treat one or more cancers of the human body.

1078. The method of any one of Clauses 1051 to 1077, wherein the chemotherapeutic agent is a plant alkaloid, a topoisomerase I inhibitor, an antimetabolite, an alkylating agent, a thymidine phosphorylase inhibitor, a nucleoside analog, or any combination thereof.

1079. The method of any one of Clauses 1051 to 1078, wherein the chemotherapeutic agent is a taxane.

1080. The method of any one of Clauses 1051 to 1079, wherein the chemotherapeutic agent is docetaxel.

1081. The method of any one of Clauses 1051 to 1080, wherein the period of time is at least I month.

1082. The method of any one of Clauses 1051 to 1081, wherein the period of time is at least 3 months.

1083. The method of any one of Clauses 1051 to 1082, wherein the period of time is at least 6 months.

1084. The method of any one of Clauses 1051 to 1083, wherein the period of time is at least 12 months.

1085. A method of treating a patient with prostate cancer, comprising:

administering a sustained release formulation of a therapeutic agent to the patient's prostate;

reducing the rate and/or risk of progression of the patient's prostate cancer in comparison to a prostate cancer patient who does not receive the sustained release formulation, whereby reducing the rate and/or risk of progression comprises reducing the likelihood that the patient will require radical therapy within the 2 years from treatment.

1086. A method of treating prostate cancer in a human patient, the method comprising:

implanting one or more depots at or within the patient's prostate gland, each of the one or more depots comprising a biodegradable sustained release formulation that includes a therapeutic agent, the therapeutic agent comprising a chemotherapeutic agent;

administering the chemotherapeutic agent to the prostate gland over a period of time via the sustained release formulation; and reducing the patient's prostate-specific antigen (PSA) levels by at least 10%.

1087. A method of treating prostate cancer, the method comprising locally exposing the patient's prostate gland to a therapeutic agent, the therapeutic agent comprising a chemotherapeutic agent, whereby locally exposing comprises causing a greater exposure in the prostate to the therapeutic agent over time as compared to exposure resulting from systemic administration of the therapeutic agent.

1088. A method of treating prostate cancer in a human patient, the method comprising:

implanting one or more depots at or within the patient's prostate gland, each of the one or more depots comprising a biodegradable sustained release formulation that includes a therapeutic agent, the therapeutic agent comprising a chemotherapeutic agent;

administering the sustained release formulation to the prostate gland over a period of time; and reducing the patient's prostate-specific antigen (PSA) levels by at least 20%.

1089. A method of treating prostate cancer in a human patient, the method comprising:

implanting one or more depots at or within the patient's prostate gland, each of the one or more depots comprising a biodegradable sustained release formulation that includes a therapeutic agent, the therapeutic agent comprising a chemotherapeutic agent;

administering the sustained release formulation to the prostate gland over a period of time; and reducing the patient's prostate-specific antigen (PSA) levels by at least 50%.

1090. A method of treating prostate cancer in a patient, the method comprising:

delivering a therapeutic agent locally to the patient's prostate gland over a period of time, the therapeutic agent comprising a chemotherapeutic agent; and slowing or halting the progression of the prostate cancer, wherein slowing or halting the progression is indicated by the patient having a PSA level at the end of the period of time that is less than double a PSA level of the patient prior to the therapeutic agent being delivered to the prostate.

1091. A method of treating a prostate tumor of a patient, the method comprising:
delivering a therapeutic agent locally to the patient's prostate gland over a period of time, the therapeutic agent comprising a chemotherapeutic agent; and
reducing a volume of the tumor by at least 25%, wherein the reduction is measured via endorectal magnetic resonance imaging.
1092. A method of treating a patient with a cancerous prostate tumor, the method comprising:
delivering a therapeutic agent locally to the patient's prostate gland over a period of time, the therapeutic agent comprising a chemotherapeutic agent; and
slowing or halting progression of the prostate tumor, wherein slowing or halting the progression is indicated by the tumor having a Gleason Grade Group after the period of time that is the same as or lower than the Gleason Grade Group prior to the therapeutic agent being delivered locally to the prostate gland.
1093. The method of Clause 1092, wherein the Gleason Grade Group prior to delivery of the therapeutic agent is a Gleason Grade Group 2, and the Gleason Grade Group after the period of time is a Gleason Grade Group 2 or a Gleason Grade Group 1.
1094. The method of Clause 1092, wherein the Gleason Grade Group prior to delivery of the therapeutic agent is a Gleason Grade Group 3, and the Gleason Grade Group after the period of time is a Gleason Grade Group 3, 2, or 1.
1095. A method of treating a patient with prostate cancer, the method comprising:
delivering a therapeutic agent locally to the patient's prostate gland over a period of time, the therapeutic agent comprising a chemotherapeutic agent; and
slowing or halting progression of the prostate cancer, wherein slowing or halting the progression is indicated by reduced expression of an androgen gene and reduced tumor cell proliferation, as measured by one or both of biomarker assessment and genomic analysis.
1096. The method of any one of Clauses 1085 to 1095, wherein the chemotherapeutic agent is FDA-approved for systemic administration to treat one or more cancers of the human body.
1097. The method of any one of Clauses 1085 to 1096, wherein the chemotherapeutic agent is selected from any of the following classes: antimetabolite, genotoxic, mitotic or spindle inhibitor.
1098. The method of any one of Clauses 1085 to 1096, wherein the chemotherapeutic agent is one or more of gemcitabine, capecitabine, or 5-fluorouracil.
1099. The method of any one of Clauses 1085 to 1096, wherein the chemotherapeutic agent is one or more of cisplatin or oxaliplatin.
1100. The method of any one of Clauses 1085 to 1096, wherein the chemotherapeutic agent is one or more of docetaxel or paclitaxel.
1101. The method of any one of Clauses 1085 to 1096, wherein the chemotherapeutic agent is a taxane.
1102. The method of any one of Clauses 1085 to 1096, wherein the chemotherapeutic agent is docetaxel.
1103. The method of any one of Clauses 1085 to 1096, wherein the period of time is at least 1 month.
1104. The method of any one of Clauses 1085 to 1096, wherein the period of time is at least 3 months.
1105. The method of any one of Clauses 1085 to 1096, wherein the period of time is at least 6 months.
1106. The method of any one of Clauses 1085 to 1096, wherein the period of time is at least 12 months.
1107. A method of reducing/decreasing mortality (or improving/increasing survival) caused by cancer in a patient in need thereof, the method comprising administering an implantable formulation for localized, sustained release of a chemotherapeutic agent in conjunction with administering one or more treatments selected from the group consisting of surgery, radiation and systemic drug therapy.
1108. The method of Clause 1107, wherein surgery is one of open surgery, laparoscopic surgery, or endoscopic surgery.
1109. The method of Clause 1107, wherein radiation is one or more of external beam radiation, brachytherapy seed delivery, or stereotactic radiotherapy.
1110. The method of Clause 1107, wherein systemic drug therapy is one or more of chemotherapy, targeted therapy, or immunotherapy.
1111. A method of treating a patient with cancer having a tumor in tissue of the patient, the method comprising:
administering a sustained release formulation of a therapeutic agent to the patient's tissue; and
relative to a patient who does not receive the sustained release formulation, increasing a length of a period of progression-free survival of the patient, wherein the period of progression-free survival begins prior to administering the sustained release formulation and ends when a sum of diameters of the tumor is at least 20% greater than a sum of diameters of the tumor prior to administering the sustained release formulation.
1112. A method of treating cancer in a human patient having a measurable tumor in tissue of the patient, the method comprising:
implanting one or more depots at or within the patient's tissue, each of the one or more depots comprising a biodegradable sustained release formulation that includes a therapeutic agent, the therapeutic agent comprising a chemotherapeutic agent;
administering the chemotherapeutic agent to the tissue over a period of time via the sustained release formulation; and
reducing a sum of diameters of the tumor by at least 20%.
1113. The method of Clause 1112, wherein reducing the sum of the diameters of the tumor by at least 20% comprises reducing the sum of the diameters of the tumor by at least 30%.
1114. The method of Clause 1112 or Clause 1113, wherein reducing the sum of the diameters of the by at least 20% comprises reducing the sum of the diameters of the tumor by at least 40%.
1115. The method of any one of Clauses 1112 to 1114, wherein reducing the sum of the diameters of the tumor by at least 20% comprises reducing the sum of the diameters of the tumor by at least 50%.
1116. A method of treating a patient with target lesions in tissue of the patient, wherein the target lesions have been measured via medical imaging, the method comprising:
administering a sustained release formulation of a therapeutic agent to the patient's tissue, the therapeutic agent comprising a chemotherapeutic agent; and
reducing a size of the target lesions such that the target lesions are not detectable via medical imaging.

1117. A method of treating a patient with target lesions in tissue of the patient, wherein the target lesions have been measured via medical imaging, the method comprising:

administering a sustained release formulation of a therapeutic agent to the patient's tissue, the therapeutic agent comprising a chemotherapeutic agent; and reducing a size of at least one target lesion such that the at least one target lesion is not detectable via medical imaging.

1118. A method of treating cancer in a human patient having a tumor in tissue of the patient, the method comprising:

implanting one or more depots at or within the patient's tissue, each of the one or more depots comprising a biodegradable sustained release formulation that includes a therapeutic agent, the therapeutic agent comprising a chemotherapeutic agent;

administering the chemotherapeutic agent to the tissue over a period of time via the sustained release formulation; and reducing a sum of diameters of the tumor by at least 20%.

1119. The method of Clause 1118, wherein reducing the sum of the diameters of the tumor by at least 20% comprises reducing the sum of the diameters of the tumor by at least 30%.

1120. The method of Clause 1118 or Clause 1119, wherein reducing the sum of the diameters of the by at least 20% comprises reducing the sum of the diameters of the tumor by at least 40%.

1121. The method of any one of Clauses 1118 to 1120, wherein reducing the sum of the diameters of the tumor by at least 20% comprises reducing the sum of the diameters of the tumor by at least 50%.

1122. A method of treating lung cancer, the method comprising locally exposing at least one of the patient's lungs to a therapeutic agent, the therapeutic agent, whereby locally exposing comprises causing a greater exposure in the at least one lung to the therapeutic agent over time as compared to exposure resulting from systemic administration of the therapeutic agent.

1123. The method of Clause 1122, wherein the therapeutic agent comprises a chemotherapeutic agent, a targeted therapeutic agent, and/or an immunotherapy agent.

1124. A method of decreasing mortality caused by lung cancer in a patient in need thereof which comprises administering an implantable formulation for localized, sustained release of a chemotherapeutic agent to at least one of the patient's lungs.

1125. The method of Clause 1124, wherein decreasing mortality comprises increasing a duration of time from randomization of the patient in a clinical trial to death of the patient in comparison to the duration of time for a patient who does not receive the implantable formulation.

1126. The method of Clause 1124 or Clause 1125, further comprising administering one or more treatments selected from the group consisting of surgery, ablation, radiation, and systemic drug therapy in conjunction with administering the implantable formulation.

1127. The method of Clause 1126, wherein the surgery comprises open surgery, laparoscopic surgery, or endoscopic surgery.

1128. The method of Clause 1126 or Clause 1019, wherein the radiation comprises external beam radiation, brachytherapy seed radiation, or stereotactic radiotherapy.

1129. A method of treating a patient with lung cancer, the method comprising:

administering a sustained release formulation of a therapeutic agent to at least one of the patient's lungs; and reducing the rate and/or risk of progression of the patient's lung cancer in comparison to a lung cancer patient who does not receive the sustained release formulation, whereby reducing the rate and/or risk of progression comprises improving a prognosis of the patient following surgery, radiation, targeted therapy, and/or systemic chemotherapy.

1130. The method of Clause 1129, wherein improving the prognosis comprises increasing a 5-year survival rate following the surgery, radiation, targeted therapy, and/or systemic chemotherapy.

1131. A method of treating lung cancer in a human patient having a tumor in a lung of the patient, the method comprising:

implanting one or more depots within the patient's lung, each of the one or more depots comprising a biodegradable sustained release formulation that includes a therapeutic agent, the therapeutic agent comprising a chemotherapeutic agent;

administering the chemotherapeutic agent to the lung over a period of time via the sustained release formulation; and reducing a sum of diameters of the tumor by at least 20%.

1132. The method of Clause 1131, wherein reducing the sum of the diameters of the tumor by at least 20% comprises reducing the sum of the diameters of the tumor by at least 30%.

1133. The method of Clause 1131 or Clause 1132, wherein reducing the sum of the diameters of the by at least 20% comprises reducing the sum of the diameters of the tumor by at least 40%.

1134. The method of any one of Clauses 1131 to 1133, wherein reducing the sum of the diameters of the tumor by at least 20% comprises reducing the sum of the diameters of the tumor by at least 50%.

1135. A method of treating a patient with target lesions in a lung of the patient, wherein the target lesions have been measured via medical imaging, the method comprising:

administering a sustained release formulation of a therapeutic agent to the patient's lung, the therapeutic agent comprising a chemotherapeutic agent; and reducing a size of the target lesions such that the target lesions are not detectable via medical imaging.

1136. A method of treating a patient with target lesions in a lung of the patient, wherein the target lesions have been measured via medical imaging, the method comprising:

administering a sustained release formulation of a therapeutic agent to the patient's lung, the therapeutic agent comprising a chemotherapeutic agent; and reducing a size of at least one target lesion such that the at least one target lesion is not detectable via medical imaging.

1137. A method of treating a lung cancer patient having a tumor in a lung of the patient, the method comprising:

administering a sustained release formulation of a therapeutic agent to the patient's lung, the therapeutic agent comprising a chemotherapeutic agent; and slowing and/or halting progression of the tumor in comparison to a lung cancer patient who does not receive the sustained release formulation.

1138. The method of Clause 1137, wherein slowing and/or halting the progression comprises increasing a time to progression, a duration of progression free survival, a duration of recurrence free survival, and/or a duration of response.

1139. A method of treating a patient with a lung tumor, the method comprising:

administering a treatment comprising surgery, radiation, targeted therapy, and/or systemic chemotherapy;

administering a sustained release formulation of a therapeutic agent to one or more lungs of the patient; and relative to a patient who receives the treatment but does not receive the sustained release formulation, slowing and/or halting progression of the tumor to a greater extent.

1140. A method of treating lung cancer in a patient, the method comprising:

administering a sustained release formulation of a therapeutic agent to a lung of the patient, the therapeutic agent comprising a chemotherapeutic agent; and improving a quality of life parameter of the patient, wherein the quality of life parameter is measured by a quality of life measurement instrument.

1141. The method of Clause 1140, wherein the quality of life parameter is a health-related quality of life parameter.

1142. The method of Clause 1140 or Clause 1141, wherein the quality of life measurement instrument comprises EORTC QLQ-C30+LC13, LCSS, and/or FACT-G+FACT-L.

1143. The method of any one of Clauses 1122 to 1142, wherein the therapeutic agent comprises a chemotherapeutic agent, a targeted therapeutic agent, and/or an immunotherapy agent.

1144. The method of any one of Clauses 1122 to 1143, wherein the chemotherapeutic agent is FDA-approved for systemic administration to treat one or more cancers of the human body.

1145. The method of any one of Clauses 1122 to 1144, wherein the chemotherapeutic agent is an alkylating agent, an antimetabolite, a taxane, a plant alkaloid, an antimicrotubule agent, or any combination thereof.

1146. The method of any one of Clauses 1122 to 1145, wherein the period of time is at least 1 month.

1147. The method of any one of Clauses 1122 to 1146, wherein the period of time is at least 3 months.

1148. The method of any one of Clauses 1122 to 1147, wherein the period of time is at least 6 months.

1149. The method of any one of Clauses 1122 to 1148, wherein the period of time is at least 12 months.

1150. A method of treating pancreatic cancer, the method comprising locally exposing the patient's pancreas to a therapeutic agent, the therapeutic agent, whereby locally exposing comprises causing a greater exposure in the pancreas to the therapeutic agent over time as compared to exposure resulting from systemic administration of the therapeutic agent.

1151. The method of Clause 1150, wherein the therapeutic agent comprises a chemotherapeutic agent, a targeted therapeutic agent, and/or an immunotherapy agent.

1152. A method of decreasing mortality caused by pancreatic cancer in a patient in need thereof which comprises administering an implantable formulation for localized, sustained release of a chemotherapeutic agent to the patient's pancreas.

1153. The method of Clause 1152, wherein decreasing mortality comprises increasing a duration of time from randomization of the patient in a clinical trial to death of the patient in comparison to the duration of time for a patient who does not receive the implantable formulation.

1154. The method of Clause 1152 or Clause 1153, further comprising administering one or more treatments selected from the group consisting of surgery, ablation, radiation, and systemic drug therapy in conjunction with administering the implantable formulation.

1155. The method of Clause 1154, wherein the surgery comprises open surgery, laparoscopic surgery, or endoscopic surgery.

1156. The method of Clause 1154 or Clause 1155, wherein the radiation comprises external beam radiation, brachytherapy seed radiation, or stereotactic radiotherapy.

1157. A method of treating a patient with pancreatic cancer, the method comprising:

administering a sustained release formulation of a therapeutic agent to the patient's pancreas; and reducing the rate and/or risk of progression of the patient's pancreatic cancer in comparison to a pancreatic cancer patient who does not receive the sustained release formulation, whereby reducing the rate and/or risk of progression comprises improving a prognosis of the patient following surgery, radiation, targeted therapy, and/or systemic chemotherapy.

1158. The method of Clause 1157, wherein improving the prognosis comprises increasing a 5-year survival rate following the surgery, radiation, targeted therapy, and/or systemic chemotherapy.

1159. A method of treating pancreatic cancer in a human patient having a tumor in a pancreas of the patient, the method comprising:

implanting one or more depots within the patient's pancreatic, each of the one or more depots comprising a biodegradable sustained release formulation that includes a therapeutic agent, the therapeutic agent comprising a chemotherapeutic agent;

administering the chemotherapeutic agent to the pancreas over a period of time via the sustained release formulation; and reducing a sum of diameters of the tumor by at least 20%.

1160. The method of Clause 1159, wherein reducing the sum of the diameters of the tumor by at least 20% comprises reducing the sum of the diameters of the tumor by at least 30%.

1161. The method of Clause 1159 or Clause 1160, wherein reducing the sum of the diameters of the by at least 20% comprises reducing the sum of the diameters of the tumor by at least 40%.

1162. The method of any one of Clauses 1159 to 1161, wherein reducing the sum of the diameters of the tumor by at least 20% comprises reducing the sum of the diameters of the tumor by at least 50%.

1163. A method of treating a patient with target lesions in a pancreas of the patient, wherein the target lesions have been measured via medical imaging, the method comprising:

administering a sustained release formulation of a therapeutic agent to the patient's pancreas, the therapeutic agent comprising a chemotherapeutic agent; and reducing a size of the target lesions such that the target lesions are not detectable via medical imaging.

1164. A method of treating a patient with target lesions in a pancreas of the patient, wherein the target lesions have been measured via medical imaging, the method comprising:

administering a sustained release formulation of a therapeutic agent to the patient's pancreas, the therapeutic agent comprising a chemotherapeutic agent; and reducing a size of at least one target lesion such that the at least one target lesion is not detectable via medical imaging.

1165. A method of treating a pancreatic cancer patient having a tumor in a pancreas of the patient, the method comprising:

administering a sustained release formulation of a therapeutic agent to the patient's pancreas, the therapeutic agent comprising a chemotherapeutic agent; and slowing and/or halting progression of the tumor in comparison to a pancreatic cancer patient who does not receive the sustained release formulation.

1166. The method of Clause 1165, wherein slowing and/or halting the progression comprises increasing a time to progression, a duration of progression free survival, a duration of recurrence free survival, and/or a duration of response.

1167. A method of treating a patient with a pancreatic tumor, the method comprising:

administering a treatment comprising surgery, radiation, targeted therapy, and/or systemic chemotherapy;

administering a sustained release formulation of a therapeutic agent to a pancreas of the patient; and relative to a patient who receives the treatment but does not receive the sustained release formulation, slowing and/or halting progression of the tumor to a greater extent.

1168. A method of treating pancreatic cancer in a patient, the method comprising:

administering a sustained release formulation of a therapeutic agent to the patient's pancreas, the therapeutic agent comprising a chemotherapeutic agent; and improving a quality of life parameter of the patient, wherein the quality of life parameter is measured by a quality of life measurement instrument.

1169. The method of Clause 1168, wherein the quality of life parameter is a health-related quality of life parameter.

1170. The method of Clause 1168 or Clause 1169, wherein the quality of life measurement instrument comprises EORTC QLQ-C30.

1171. The method of any one of Clauses 1150 to 1170, wherein the therapeutic agent comprises a chemotherapeutic agent, a targeted therapeutic agent, and/or an immunotherapy agent.

1172. The method of any one of Clauses 1150 to 1171, wherein the chemotherapeutic agent is FDA-approved for systemic administration to treat one or more cancers of the human body.

1173. The method of any one of Clauses 1150 to 1172, wherein the chemotherapeutic agent is an alkylating agent, an antimetabolite, a taxane, a plant alkaloid, an antimicrotubule agent, or any combination thereof.

1174. The method of any one of Clauses 1150 to 1173, wherein the period of time is at least 1 month.

1175. The method of any one of Clauses 1150 to 1174, wherein the period of time is at least 3 months.

1176. The method of any one of Clauses 1150 to 1175, wherein the period of time is at least 6 months.

1177. The method of any one of Clauses 1150 to 1176, wherein the period of time is at least 12 months.

1178. A method of treating malignant ascites, the method comprising locally exposing the patient's peritoneal cavity to a therapeutic agent, the therapeutic agent comprising a chemotherapeutic agent, whereby locally exposing comprises causing a greater exposure in the peritoneal cavity to the therapeutic agent over time as compared to exposure resulting from systemic administration of the therapeutic agent.

1179. A method of decreasing mortality caused by malignant ascites in a patient in need thereof which comprises administering an implantable formulation for localized, sustained release of a therapeutic agent to the patient's peritoneal cavity.

1180. The method of Clause 1179, further comprising administering one or more treatments selected from the group consisting of surgery, ablation, radiation, and systemic drug therapy in conjunction with administering the implantable formulation.

1181. The method of Clause 1180, wherein the surgery comprises open surgery, laparoscopic surgery, or endoscopic surgery.

1182. The method of Clause 1180 or Clause 1181, wherein the radiation comprises external beam radiation, brachytherapy seed radiation, or stereotactic radiotherapy.

1183. A method of treating malignant ascites in a patient, the method comprising:

administering a sustained release formulation of a therapeutic agent to the patient's peritoneal cavity, the therapeutic agent comprising a chemotherapeutic agent, a VEGF inhibitor, a matrix metalloproteinase inhibitor, an interferon, a tumor necrosis factor-α, a monoclonal antibody, and/or a trifunctional antibody; and relieving one or more symptoms experienced by the patient as a result of the malignant ascites.

1184. The method of Clause 1183, wherein the one or more symptoms comprise anorexia, nausea, vomiting, abdominal pain, abdominal swelling, abdominal distension, or dyspnea.

1185. The method of Clause 1183 or Clause 1184, wherein relieving the one or more symptoms comprises completely relieving the one or more symptoms.

1186. The method of any one of Clauses 1183 to 1185, wherein relieving the one or more symptoms comprises reducing a severity and/or a frequency of the one or more symptoms.

1187. The method of any one of Clauses 1183 to 1186, wherein the one or more symptoms is relieved to a greater extent in comparison to a patient with malignant ascites who does not receive the sustained release formulation.

1188. A method of treating a patient with malignant ascites, the method comprising:

administering a sustained release formulation of a therapeutic agent to the patient's peritoneal cavity; and slowing and/or halting fluid accumulation in the peritoneal cavity of the patient to a greater extent in comparison to a patient with malignant ascites who does not receive the sustained release formulation.

1189. The method of Clause 1188, wherein fluid accumulation is evaluated via radiographic imaging.

1190. A method of treating a patient with malignant ascites within a peritoneal cavity of the patient, wherein the patient is experiencing one or more symptoms as a result of the malignant ascites, the method comprising:

removing fluid from the peritoneal cavity of the patient;

administering a sustained release formulation of a therapeutic agent to the patient's peritoneal cavity; and relative to a patient who undergoes peritoneal cavity fluid removal but does not receive the sustained release formulation, relieving the one or more symptoms to a greater extent and/or slowing and/or halting fluid accumulation in the peritoneal cavity to a greater extent.

1191. A method of treating a patient with malignant ascites within a peritoneal cavity of the patient, the method comprising:

removing fluid from the peritoneal cavity of the patient;

administering a sustained release formulation of a therapeutic agent to the patient's peritoneal cavity; and relative to a patient who undergoes peritoneal cavity fluid removal but does not receive the sustained release formulation, increasing a duration of a period of puncture-free survival of the patient, wherein the period of puncture-free survival begins when fluid is removed from the peritoneal cavity of the patient and ends upon the first of when fluid is removed from the peritoneal cavity of the patient for a second time or the death of the patient.

1192. A method of treating a patient with malignant ascites within a peritoneal cavity of the patient, the method comprising:

performing a first paracentesis on the patient to remove fluid from the patient's peritoneal cavity;

administering a sustained release formulation of a therapeutic agent to the patient's peritoneal cavity;

measuring a duration of time from the first paracentesis to the first to occur of a second paracentesis or the death of the patient; and increasing puncture-free survival of the patient, wherein increasing puncture-free survival of the patient comprises achieving a greater duration of time relative to that of a patient who does not receive the sustained release formulation.

1193. A method of treating a patient with malignant ascites, the method comprising:

administering a sustained release formulation of a therapeutic agent to the patient's peritoneal cavity; and reducing an amount of a biomarker in the patient.

1194. The method of Clause 1193, wherein the biomarker comprises vascular endothelial growth factor, epithelial cell adhesion molecule, cancer antigen 125, pteroyl-D-glutamic acid, or human epidermal growth factor receptor 2.

1195. The method of Clause 1193 or 1194, further comprising administering one or more treatments to the patient, wherein the one or more treatments comprise local or non-local treatment.

1196. The method of any one of Clauses 1193 to 1195, further comprising reducing the amount of the biomarker in the patient to a greater extent in comparison to a patient who does not receive the sustained release formulation.

1197. A method of treating malignant ascites in a patient, the method comprising:

administering a sustained release formulation of a therapeutic agent to the patient's peritoneal cavity; and improving a quality of life parameter of the patient, wherein the quality of life parameter is measured by a quality of life measurement instrument.

1198. The method of Clause 1197, wherein the quality of life parameter is a health-related quality of life parameter.

1199. The method of Clause 1197 or Clause 1198, wherein the quality of life measurement instrument is a EuroQol-5D, a FACIT-AI, or a EORTC QLQ-C30 quality of life measurement instrument.

1200. A method of treating a cancer patient with malignant ascites associated with a primary cancer, the method comprising:

administering a sustained release formulation of a therapeutic agent to the patient's peritoneal cavity;

reducing the rate and/or risk of progression of the patient's malignant ascites in comparison to a cancer patient who does not receive the sustained release formulation, whereby reducing the rate and/or risk of progression comprises improving a prognosis of the patient following paracentesis.

1201. The method of Clause 1200, further comprising treating the primary cancer, wherein a type of the primary cancer is ovarian, colorectal, pancreatic, uterine, lung, breast, stomach, esophageal, and/or liver.

1202. A method of treating a patient with malignant ascites in a peritoneal cavity of the patient, wherein the patient is experiencing a symptom associated with the malignant ascites, the method comprising:

administering a sustained release formulation of a therapeutic agent to the patient's peritoneal cavity;

administering one or more treatments to the patient; and relative to a patient who receives the one or more treatments but does not receive the sustained release formulation, relieving the symptom, slowing fluid accumulation in the peritoneal cavity, and/or reducing fluid accumulation in the peritoneal cavity to a greater extent.

1203. The method of Clause 1202, wherein the symptom comprises anorexia, nausea, vomiting, abdominal pain, abdominal swelling, abdominal distension, or dyspnea.

1204. The method of Clause 1202 or Clause 1203, wherein the one or more treatments comprises surgery, radiation, intraperitoneal chemotherapy, and/or systemic drug therapy.

1205. The method of any one of Clauses 1178 to 1204, wherein the therapeutic agent comprises a chemotherapeutic agent, a VEGF inhibitor, a matrix metalloproteinase inhibitor, an interferon, a tumor necrosis factor-α, a monoclonal antibody, and/or a trifunctional antibody.

1206. The method of any one of Clauses 1178 to 1205, wherein the chemotherapeutic agent is FDA-approved for systemic administration to treat one or more cancers of the human body.

1207. The method of any one of Clauses 1178 to 1206, wherein the chemotherapeutic agent is an alkylating agent, an antimetabolite, an anthracycline antibiotic, an antitumor antibiotic, a taxane, a plant alkaloid, an antimicrotubule agent, or any combination thereof.

1208. The method of any one of Clauses 1178 to 1207, wherein the period of time is at least 1 month.

1209. The method of any one of Clauses 1178 to 1208, wherein the period of time is at least 3 months.

1210. The method of any one of Clauses 1178 to 1209, wherein the period of time is at least 6 months.

1211. The method of any one of Clauses 1178 to 1210, wherein the period of time is at least 12 months.

1212. A method of treating a patient with stomach cancer, the method comprising:
administering a sustained release formulation of a therapeutic agent to the patient's stomach; and
reducing the rate and/or risk of progression of the patient's stomach cancer in comparison to a stomach cancer patient who does not receive the sustained release formulation, whereby reducing the rate and/or risk of progression comprises improving a prognosis of the patient following surgical intervention.

1213. The method of Clause 1212, wherein the surgical intervention is total or partial excision of the stomach.

1214. The method of Clause 1212 or Clause 1213, wherein improving the prognosis of the patient following surgical intervention comprises increasing a 5-year survival rate following surgical intervention.

1215. A method of treating stomach cancer, the method comprising locally exposing the patient's stomach to a therapeutic agent, the therapeutic agent comprising a chemotherapeutic agent, whereby locally exposing comprises causing a greater exposure in the stomach to the therapeutic agent over time as compared to exposure resulting from systemic administration of the therapeutic agent.

1216. A method of decreasing mortality caused by stomach cancer in a patient in need thereof which comprises administering an implantable formulation for localized, sustained release of a chemotherapeutic agent to the patient's stomach.

1217. The method of Clause 1216, further comprising administering one or more treatments selected from the group consisting of surgery, radiation, and systemic drug therapy in conjunction with administering the implantable formulation.

1218. The method of Clause 1217, wherein the surgery comprises open surgery, laparoscopic surgery, or endoscopic surgery.

1219. The method of Clause 1217 or Clause 1218, wherein the radiation comprises external beam radiation, brachytherapy seed radiation, or stereotactic radiotherapy.

1220. The method of any one of Clauses 1217 to 1219, wherein the systemic drug therapy comprises chemotherapy, targeted therapy, or immunotherapy.

1221. A method of treating stomach cancer in a human patient having a tumor in a stomach of the patient, the method comprising:
implanting one or more depots within the patient's stomach, each of the one or more depots comprising a biodegradable sustained release formulation that includes a therapeutic agent, the therapeutic agent comprising a chemotherapeutic agent;
administering the chemotherapeutic agent to the stomach over a period of time via the sustained release formulation; and
reducing a sum of diameters of the tumor by at least 20%.

1222. The method of Clause 1221, wherein reducing the sum of the diameters of the tumor by at least 20% comprises reducing the sum of the diameters of the tumor by at least 30%.

1223. The method of Clause 1221 or Clause 1222, wherein reducing the sum of the diameters of the by at least 20% comprises reducing the sum of the diameters of the tumor by at least 40%.

1224. The method of any one of Clauses 1221 to 1223, wherein reducing the sum of the diameters of the tumor by at least 20% comprises reducing the sum of the diameters of the tumor by at least 50%.

1225. A method of treating a patient with target lesions in a stomach of the patient, wherein the target lesions have been measured via medical imaging, the method comprising:
administering a sustained release formulation of a therapeutic agent to the patient's stomach, the therapeutic agent comprising a chemotherapeutic agent; and
reducing a size of the target lesions such that the target lesions are not detectable via medical imaging.

1226. A method of treating a patient with target lesions in a stomach of the patient, wherein the target lesions have been measured via medical imaging, the method comprising:
administering a sustained release formulation of a therapeutic agent to the patient's stomach, the therapeutic agent comprising a chemotherapeutic agent; and
reducing a size of at least one target lesion such that the at least one target lesion is not detectable via medical imaging.

1227. A method of treating stomach cancer in a patient, the method comprising:
administering a sustained release formulation of a therapeutic agent to the patient's stomach, the therapeutic agent comprising a chemotherapeutic agent; and
improving a quality of life parameter of the patient, wherein the quality of life parameter is measured by a quality of life measurement instrument.

1228. The method of Clause 1227, wherein the quality of life parameter is a health-related quality of life parameter.

1229. A method of treating a patient with a cancerous stomach tumor, the method comprising:
administering a sustained release formulation of a therapeutic agent to the patient's stomach over a period of time, the therapeutic agent comprising a chemotherapeutic agent; and
slowing or halting growth of the cancerous stomach tumor, wherein slowing or halting the growth is indicated by the cancerous stomach tumor having a sum of diameters after the period of time that is no more than 20% greater than a sum of diameters of the cancerous stomach tumor prior to administering the sustained release formulation.

1230. The method of Clause 1229, wherein slowing or halting the growth is indicated by the sum of diameters after the period of time being substantially equivalent to the sum of diameters of prior to administering the sustained release formulation.

1231. The method of Clause 1230, wherein slowing or halting the growth is indicated by the sum of diameters after the period of time being less than the sum of diameters prior to administering the sustained release formulation.

1232. A method of treating a patient with gastric cancer having a tumor in a stomach of the patient, the method comprising:
administering a sustained release formulation of a therapeutic agent to the patient's stomach; and
relative to a patient who does not receive the sustained release formulation, increasing a length of a period of progression-free survival of the patient, wherein the period of progression-free survival begins prior to administering the sustained release formulation and ends when a sum of diameters of the tumor is at least 20% greater than a sum of diameters of the tumor prior to administering the sustained release formulation.

1233. A method of treating a cancerous tumor within a stomach of a patient, the method comprising:

administering a sustained release formulation of a therapeutic agent to the patient's stomach; and increasing the likelihood that (i) a sum of diameters of the cancerous tumor will not increase by 20% or more after administering the sustained release formulation, (ii) the sum of diameters of the cancerous tumor will decrease by at least 20% after administering the sustained release formulation, and/or (iii) a size of the tumor will be reduced after administering the sustained release formulation such that the tumor is not detectable via medical imaging.

1234. A method of treating a patient with stomach cancer, the method comprising:

administering a sustained release formulation of a therapeutic agent to the patient's stomach; and relative to a patient who does not receive the sustained release formulation, administering one or more further treatments at an earlier time.

1235. The method of Clause 1234, wherein the one or more further treatments comprise surgery, radiation, or systemic drug therapy.

1236. The method of any one of Clauses 1212 to 1235, wherein the chemotherapeutic agent is FDA-approved for systemic administration to treat one or more cancers of the human body.

1237. The method of any one of Clauses 1212 to 1236, wherein the chemotherapeutic agent is an alkylating agent, an antimetabolite, an anthracycline antitumor antibiotic, a plant alkaloid, genotoxic, or a mitotic or spindle inhibitor, or any combination thereof.

1238. The method of any one of Clauses 1212 to 1237, wherein the chemotherapeutic agent is a taxane.

1239. The method of any one of Clauses 1212 to 1238, wherein the chemotherapeutic agent is docetaxel.

1240. The method of any one of Clauses 1212 to 1239, wherein the period of time is at least 1 month.

1241. The method of any one of Clauses 1212 to 1240, wherein the period of time is at least 3 months.

1242. The method of any one of Clauses 1212 to 1241, wherein the period of time is at least 6 months.

1243. The method of any one of Clauses 1212 to 1242, wherein the period of time is at least 12 months.

1244. A method of treating malignant pleural effusion, the method comprising locally exposing the patient's pleural cavity to a therapeutic agent, the therapeutic agent comprising a chemotherapeutic agent, whereby locally exposing comprises causing a greater exposure in the pleural cavity to the therapeutic agent over time as compared to exposure resulting from systemic administration of the therapeutic agent.

1245. A method of decreasing mortality caused by malignant pleural effusion in a patient in need thereof which comprises administering an implantable formulation for localized, sustained release of a therapeutic agent to the patient's pleural cavity.

1246. The method of Clause 1245, further comprising administering one or more treatments selected from the group consisting of surgery, ablation, radiation, and systemic drug therapy in conjunction with administering the implantable formulation.

1247. The method of Clause 1246, wherein the surgery comprises open surgery, laparoscopic surgery, or endoscopic surgery.

1248. The method of Clause 1246 or Clause 1247, wherein the radiation comprises external beam radiation, brachytherapy seed radiation, or stereotactic radiotherapy.

1249. A method of treating malignant pleural effusion in a patient, the method comprising:

administering a sustained release formulation of a therapeutic agent to the patient's pleural cavity, the therapeutic agent comprising a chemotherapeutic agent, an interferon, a tumor infiltrating lymphocyte, a monoclonal antibody, and/or a trifunctional antibody; and relieving one or more symptoms experienced by the patient as a result of the malignant pleural effusion.

1250. The method of Clause 1249, wherein the one or more symptoms comprise dyspnea, pleuritic pain, cough, fever, hypotension, recurrent respiratory infection, and/or weight loss.

1251. The method of Clause 1249 or Clause 1250, wherein relieving the one or more symptoms comprises completely relieving the one or more symptoms.

1252. The method of any one of Clauses 1249 to 1251, wherein relieving the one or more symptoms comprises reducing a severity and/or a frequency of the one or more symptoms.

1253. The method of any one of Clauses 1249 to 1252, wherein the one or more symptoms is relieved to a greater extent in comparison to a patient with malignant pleural effusion who does not receive the sustained release formulation.

1254. A method of treating a patient with malignant pleural effusion, the method comprising:

administering a sustained release formulation of a therapeutic agent to the patient's pleural cavity, the therapeutic agent; and slowing and/or halting fluid accumulation in the pleural cavity of the patient to a greater extent in comparison to a patient with malignant pleural effusion who does not receive the sustained release formulation.

1255. The method of Clause 1254, wherein fluid accumulation is evaluated via radiographic imaging.

1256. A method of treating a patient with malignant pleural effusion within a pleural cavity of the patient, wherein the patient is experiencing one or more symptoms as a result of the malignant pleural effusion, the method comprising:

removing fluid from the pleural cavity of the patient;

administering a sustained release formulation of a therapeutic agent to the patient's pleural cavity; and relative to a patient who undergoes pleural cavity fluid removal but does not receive the sustained release formulation, relieving the one or more symptoms to a greater extent and/or slowing and/or halting fluid accumulation in the pleural cavity to a greater extent.

1257. A method of treating a patient with malignant pleural effusion within a pleural cavity of the patient, the method comprising:

removing fluid from the pleural cavity of the patient;

administering a sustained release formulation of a therapeutic agent to the patient's pleural cavity; and relative to a patient who undergoes pleural cavity fluid removal but does not receive the sustained release formulation, increasing a duration of a period of puncture-free survival of the patient, wherein the period of puncture-free survival begins when fluid is removed from the pleural cavity of the patient and ends upon the first of when fluid is removed from the pleural cavity of the patient for a second time or the death of the patient.

1258. A method of treating a patient with malignant pleural effusion within a pleural cavity of the patient, the method comprising:

performing a first thoracentesis on the patient to remove fluid from the patient's pleural cavity;

administering a sustained release formulation of a therapeutic agent to the patient's pleural cavity;

measuring a duration of time from the first thoracentesis to the first to occur of a second thoracentesis or the death of the patient; and increasing puncture-free survival of the patient, wherein increasing puncture-free survival of the patient comprises achieving a greater duration of time relative to that of a patient who does not receive the sustained release formulation.

1259. A method of treating a patient with malignant pleural effusion, the method comprising:

administering a sustained release formulation of a therapeutic agent to the patient's pleural cavity; and reducing an amount of a biomarker in the patient.

1260. The method of Clause 1259, wherein the biomarker comprises CEA, CA15-3, CA125, CYFRA 21-1, CD163+, OPN, fibulin-3, EGFR, EML4-ALK, and/or KRAS.

1261. A method of treating malignant pleural effusion in a patient, the method comprising:

administering a sustained release formulation of a therapeutic agent to the patient's pleural cavity, the therapeutic agent; and improving a quality of life parameter of the patient, wherein the quality of life parameter is measured by a quality of life measurement instrument.

1262. The method of Clause 1261, wherein the quality of life parameter is a health-related quality of life parameter.

1263. The method of Clause 1261 or Clause 1262, wherein the quality of life measurement instrument is a FACIT-TS, FACIT-PAL, or a EORTC QLQ-C30 quality of life measurement instrument.

1264. A method of treating a cancer patient with malignant pleural effusion associated with a primary cancer, the method comprising:

administering a sustained release formulation of a therapeutic agent to the patient's pleural cavity;

reducing the rate and/or risk of progression of the patient's malignant pleural effusion in comparison to a cancer patient who does not receive the sustained release formulation, whereby reducing the rate and/or risk of progression comprises improving a prognosis of the patient following thoracentesis.

1265. The method of Clause 1264, further comprising treating the primary cancer, wherein a type of the primary cancer is lung, breast, ovarian, prostate, and/or lymphoma.

1266. A method of treating a patient with malignant pleural effusion in a pleural cavity of the patient, wherein the patient is experiencing a symptom associated with the malignant pleural effusion, the method comprising:

administering a sustained release formulation of a therapeutic agent to the patient's pleural cavity;

administering one or more treatments to the patient; and relative to a patient who receives the one or more treatments but does not receive the sustained release formulation, relieving the symptom, slowing fluid accumulation in the pleural cavity, and/or reducing fluid accumulation in the pleural cavity to a greater extent.

1267. The method of Clause 1266, wherein the symptom comprises anorexia, nausea, vomiting, abdominal pain, abdominal swelling, abdominal distension, or dyspnea.

1268. The method of Clause 1266 or Clause 1267, wherein the one or more treatments comprises surgery, radiation, local drug therapy, and/or systemic drug therapy.

1269. A method of treating a patient with malignant pleural effusion in a pleural cavity of the patient, the method comprising:

administering a sustained release formulation of a therapeutic agent to the patient's pleural cavity; and reducing hospitalization of the patient, wherein reducing hospitalization comprises reducing a duration of time during which the patient is hospitalized and/or reducing a frequency of hospitalization of the patient.

1270. The method of Clause 1269, further comprising administering one or more treatments to the patient, wherein the one or more treatments comprise local and/or non-local treatment.

1271. The method of any one of Clauses 1269 to 1270, further comprising reducing hospitalization of the patient to a greater extent in comparison to a patient who does not receive the sustained release formulation.

1272. The method of any one of Clauses 1244 to 1271, wherein the therapeutic agent comprises a chemotherapeutic agent, an interferon, a tumor infiltrating lymphocyte, a monoclonal antibody, and/or a trifunctional antibody.

1273. The method of any one of Clauses 1244 to 1272, wherein the chemotherapeutic agent is FDA-approved for systemic administration to treat one or more cancers of the human body.

1274. The method of any one of Clauses 1244 to 1273, wherein the chemotherapeutic agent is an alkylating agent, an antimetabolite, an anthracycline antibiotic, an antitumor antibiotic, a taxane, a plant alkaloid, an antimicrotubule agent, a genotoxic, a microtubule or spindle inhibitor, or any combination thereof.

1275. The method of any one of Clauses 1244 to 1274, wherein the period of time is at least 1 month.

1276. The method of any one of Clauses 1244 to 1275, wherein the period of time is at least 3 months.

1277. The method of any one of Clauses 1244 to 1276, wherein the period of time is at least 6 months.

1278. The method of any one of Clauses 1244 to 1277, wherein the period of time is at least 12 months.

1279. A method of treating a patient with head and/or neck cancer, the method comprising:

administering a sustained release formulation of a therapeutic agent to the patient's head and/or neck;

administering one or more first treatments to the patient; and relative to a patient who receives the one or more first treatments but does not receive the sustained release formulation, decreasing mortality, increasing a duration of time between the one or more first treatments and one or more second treatments, and/or reducing an extent of the one or more first treatments and/or the one or more second treatments.

1280. The method of Clause 1279, wherein the one or more first treatments comprise surgical intervention, radiation therapy, chemotherapy, targeted therapy, immunotherapy, and/or any combination thereof.

1281. The method of Clause 1279 or Clause 1280, wherein the one or more second treatments comprise surgical intervention, radiation therapy, chemotherapy, targeted therapy, immunotherapy, and/or any combination thereof.

1282. The method of any one of Clauses 1279 to 1281, wherein reducing an extent of the one or more first treatments and/or the one or more second treatments comprises reducing an amount of tissue removed by surgical resection, reducing a dosage and/or frequency of radiation therapy, reducing a dosage and/or frequency.

1283. The method of any one of Clauses 1279 to 1282, wherein reducing an extent of the one or more first treatments and/or the one or more second treatments comprises reducing a dosage and/or frequency of radiation therapy, chemotherapy, targeted therapy, and/or immunotherapy.

1284. A method of treating a patient with head and/or neck cancer, the method comprising:

administering a sustained release formulation of a therapeutic agent to the patient's head and/or neck; and improving a quality of life parameter of the patient, wherein the quality of life parameter is measured by a quality of life measurement instrument.

1285. The method of Clause 1284, wherein the quality of life parameter is a health-related quality of life parameter.

1286. The method of Clause 1284 or Clause 1285, wherein the quality of life measurement instrument is a FACIT-H&N, FACIT-N&P, or a EORTC QLQ-C30-H&N35, or a UWQOL quality of life measurement instrument.

1287. The method of any one of Clauses 1284 to 1286, further comprising administering systemic chemotherapy, radiation therapy, targeted therapy, immunotherapy, and/or surgical intervention in conjunction with administering the sustained release formulation.

1288. A method of treating cancer, the method comprising locally exposing a tissue of a patient to a therapeutic agent, whereby locally exposing comprises causing a greater exposure in the tissue to the therapeutic agent over time as compared to exposure resulting from systemic administration of the therapeutic agent.

1289. The method of Clause 1288, further comprising administering one or more treatments to the patient.

1290. The method of Clause 1289, wherein the one or more treatments comprises surgery, radiation therapy, ablation, local drug therapy, and/or systemic drug therapy.

1291. The method of Clause 1290, wherein the local drug therapy and/or the systemic drug therapy comprise chemotherapy, targeted therapy, and/or immunotherapy.

1292. A method of decreasing mortality caused by cancer in a patient in need thereof which comprises administering an implantable formulation for localized, sustained release of a therapeutic agent to a tissue of the patient.

1293. A method of increasing overall survival of a cancer patient which comprises administering an implantable formulation for localized, sustained release of a therapeutic agent to a tissue of the patient, wherein overall survival comprises a duration of time beginning when the implantable formulation is administered and ending upon death of the cancer patient.

1294. The method of Clause 1293, further comprising administering one or more treatments to the patient.

1295. The method of Clause 1294, wherein the one or more treatments comprises surgery, radiation therapy, ablation, local drug therapy, and/or systemic drug therapy.

1296. The method of Clause 1295, wherein the local drug therapy and/or the systemic drug therapy comprise chemotherapy, targeted therapy, and/or immunotherapy.

1297. A method of treating a cancer patient having a tumor in a tissue of the patient, the method comprising:

administering a sustained release formulation of a therapeutic agent to the patient's tissue; and slowing and/or halting progression of the tumor in comparison to a cancer patient who does not receive the sustained release formulation.

1298. The method of Clause 1297, wherein slowing and/or halting the progression comprises increasing a time to progression, a duration of progression free survival, a duration of recurrence free survival, and/or a response duration.

1299. The method of Clause 1297 or Clause 1298, wherein slowing and/or halting the progression comprises decreasing a time to response.

1300. The method of any one of Clauses 1297 to 1299, further comprising administering a treatment comprising surgery, radiation, ablation, local drug therapy, and/or systemic drug therapy, wherein, slowing and/or halting progression of the tumor comprises slowing and/or halting progression of the tumor to a greater extent in comparison to a patient who receives the treatment but does not receive the sustained release formulation.

1301. A method of treating a patient with cancer, the method comprising:

administering a sustained release formulation of a therapeutic agent to a tissue of the patient; and reducing the rate and/or risk of progression of the patient's cancer in comparison to a cancer patient who does not receive the sustained release formulation, whereby reducing the rate and/or risk of progression comprises improving a prognosis of the patient following surgery, radiation, local drug therapy, and/or systemic drug therapy.

1302. The method of Clause 1301, wherein improving the prognosis comprises increasing a 5-year survival rate following the surgery, radiation, local drug therapy, and/or systemic drug therapy.

1303. A method of treating a patient with cancer having a tumor in tissue of the patient, the method comprising:

administering a sustained release formulation of a therapeutic agent to the patient's tissue; and relative to a patient who does not receive the sustained release formulation, increasing a length of a period of progression-free survival of the patient, wherein the period of progression-free survival begins prior to administering the sustained release formulation and ends when a sum of diameters of the tumor is at least 20% greater than a sum of diameters of the tumor prior to administering the sustained release formulation.

1304. A method of treating a patient with a cancerous tumor, the method comprising:

administering a sustained release formulation of a therapeutic agent to a tissue of the patient over a period of time; and slowing or halting growth of the cancerous tumor, wherein slowing or halting the growth is indicated by the cancerous tumor having a sum of diameters after the period of time that is no more than 20% greater than a sum of diameters of the cancerous tumor prior to administering the sustained release formulation.

1305. The method of Clause 1304, wherein slowing or halting the growth is indicated by the sum of diameters after the period of time being substantially equivalent to the sum of diameters of prior to administering the sustained release formulation.

1306. The method of Clause 1305, wherein slowing or halting the growth is indicated by the sum of diameters after the period of time being less than the sum of diameters prior to administering the sustained release formulation.

1307. A method of treating cancer in a human patient having a measurable tumor in tissue of the patient, the method comprising:

implanting one or more depots at or within the patient's tissue, each of the one or more depots comprising a biodegradable sustained release formulation that includes a therapeutic agent;

administering the therapeutic agent to the tissue over a period of time via the sustained release formulation; and reducing a sum of diameters of the tumor by at least 20%.

1308. The method of Clause 1307, wherein reducing the sum of the diameters of the tumor by at least 20% comprises reducing the sum of the diameters of the tumor by at least 30%.

1309. The method of Clause 1307 or Clause 1308, wherein reducing the sum of the diameters of the by at least 20% comprises reducing the sum of the diameters of the tumor by at least 40%.

1310. The method of any one of Clauses 1307 to 1309, wherein reducing the sum of the diameters of the tumor by at least 20% comprises reducing the sum of the diameters of the tumor by at least 50%.

1311. A method of treating a patient with target lesions in tissue of the patient, wherein the target lesions have been measured via medical imaging, the method comprising:

administering a sustained release formulation of a therapeutic agent to the patient's tissue, the therapeutic agent comprising a chemotherapeutic agent; and reducing a size of the target lesions such that the target lesions are not detectable via medical imaging.

1312. A method of treating a patient with target lesions in tissue of the patient, wherein the target lesions have been measured via medical imaging, the method comprising:

administering a sustained release formulation of a therapeutic agent to the patient's tissue, the therapeutic agent comprising a chemotherapeutic agent; and reducing a size of at least one target lesion such that the at least one target lesion is not detectable via medical imaging.

1313. A method of treating a cancerous tumor within a tissue of a patient, the method comprising:

administering a sustained release formulation of a therapeutic agent to the patient's tissue; and increasing the likelihood that (i) a sum of diameters of the cancerous tumor will not increase by 20% or more after administering the sustained release formulation, (ii) the sum of diameters of the cancerous tumor will decrease by at least 20% after administering the sustained release formulation, and/or (iii) a size of the tumor will be reduced after administering the sustained release formulation such that the tumor is not detectable via medical imaging.

1314. A method of treating a patient with cancer having a tumor in a tissue of the patient, the method comprising:

administering a sustained release formulation of a therapeutic agent to the patient's tissue; and relative to a patient who does not receive the sustained release formulation, increasing a length of a response period of the patient, wherein:

the response period begins when, after administering the sustained release formulation, a sum of diameters of the tumor decreases by at least 20% and/or a size of the tumor reduces such that the tumor is not detectable via medical imaging; and the response period ends when the sum of diameters of the tumor increases by at least 20% and/or recurrent disease is detected.

1315. A method of treating a cancer patient, the method comprising:

administering a sustained release formulation of a therapeutic agent to a tissue of the patient; and reducing an amount of a biomarker in the patient.

1316. A method of treating cancer in a patient, the method comprising:

administering a sustained release formulation of a therapeutic agent to the patient's tissue; and improving a quality of life parameter of the patient, wherein the quality of life parameter is measured by a quality of life measurement instrument.

1317. A method of treating cancer in a patient, the method comprising:

administering a sustained release formulation of a therapeutic agent to a tissue of the patient; and relieving one or more symptoms experienced by the patient as a result of the cancer.

1318. The method of Clause 1317, wherein relieving the one or more symptoms comprises completely relieving the one or more symptoms.

1319. The method of Clause 1317 or Clause 1318, wherein relieving the one or more symptoms comprises reducing a severity and/or a frequency of the one or more symptoms.

1320. The method of any one of Clauses 1317 to 1319, wherein the one or more symptoms is relieved to a greater extent in comparison to a patient with cancer who does not receive the sustained release formulation.

1321. A method of treating a cancer patient a tumor in a tissue of the patient, wherein the patient is experiencing a symptom associated with the cancer, the method comprising:

administering a sustained release formulation of a therapeutic agent to the patient's tissue;

administering one or more treatments to the patient; and relative to a patient who receives the one or more treatments but does not receive the sustained release formulation, relieving the symptom to a greater extent.

1322. The method of Clause 1321, wherein the one or more treatments comprises surgery, radiation, intraperitoneal chemotherapy, and/or systemic drug therapy.

1323. A method of treating a cancer patient with a tumor in a tissue of the patient, the method comprising:

administering a sustained release formulation of a therapeutic agent to the patient's tissue; and reducing hospitalization of the patient, wherein reducing hospitalization comprises reducing a duration of time during which the patient is hospitalized and/or reducing a frequency of hospitalization of the patient.

1324. The method of Clause 1323, further comprising reducing hospitalization of the patient to a greater extent in comparison to hospitalization of a patient who does not receive the sustained release formulation.

1325. A method of treating a patient with cancer, the method comprising:

administering a sustained release formulation of a therapeutic agent to a tissue of the patient;

administering one or more first treatments to the patient; and relative to a patient who receives the one or more first treatments but does not receive the sustained release formulation, decreasing mortality, increasing a duration of time between the one or more first treatments and one or more second treatments, and/or reducing an amount of the one or more first treatments and/or the one or more second treatments.

1326. The method of Clause 1325, wherein the one or more first treatments comprise surgical intervention, radiation therapy, chemotherapy, targeted therapy, immunotherapy, and/or any combination thereof.

1327. The method of Clause 1325 or Clause 1326, wherein the one or more second treatments comprise surgical intervention, radiation therapy, chemotherapy, targeted therapy, immunotherapy, and/or any combination thereof.

1328. The method of any one of Clauses 1325 to 1327, wherein reducing an amount of the one or more first treatments and/or the one or more second treatments comprises reducing an amount of tissue removed by surgical resection, reducing a dosage and/or frequency of radiation therapy, reducing a dosage and/or frequency.

1329. The method of any one of Clauses 1325 to 1328, wherein reducing an amount of the one or more first treatments and/or the one or more second treatments comprises reducing a dosage and/or frequency of radiation therapy, chemotherapy, targeted therapy, and/or immunotherapy.

1330. The method of any one of Clauses 1288 to 1329, wherein the therapeutic agent comprises a chemotherapeutic agent.

1331. The method of Clause 1330, wherein the chemotherapeutic agent is FDA-approved for systemic administration to treat one or more cancers of the human body.

1332. The method of any one of Clauses 1288 to 1329, wherein the therapeutic agent comprises a hormonal therapeutic agent, a targeted therapeutic agent, or an immunotherapeutic agent.

1333. The method of any one of Clauses 1288 to 1332, wherein the period of time over which the sustained release formulation is administered is at least 1 month.

1334. The method of any one of Clauses 1288 to 1333, wherein the period of time over which the sustained release formulation is administered is at least 3 months.

1335. The method of any one of Clauses 1288 to 1334, wherein the period of time over which the sustained release formulation is administered is at least 6 months.

1336. The method of any one of Clauses 1288 to 1335, wherein the period of time over which the sustained release formulation is administered is at least 12 months.

1337. The method of any one of Clauses 1288 to 1336, wherein administering the sustained release formulation comprises administering a surgical intervention, a radiological therapy, an ablation therapy, a local drug therapy, a systemic drug therapy, or any combination thereof in conjunction with the sustained release formulation.

1338. The method of any one of Clauses 1288 to 1337, wherein the cancer is bladder cancer.

1339. The method of any one of Clauses 1288 to 1337, wherein the cancer is ovarian cancer.

1340. The method of any one of Clauses 1288 to 1337, wherein the cancer is uterine and/or cervical cancer.

1341. The method of any one of Clauses 1288 to 1337, wherein the cancer is thyroid cancer.

1342. The method of any one of Clauses 1288 to 1337, wherein the cancer is breast cancer.

1343. The method of any one of Clauses 1288 to 1337, wherein the cancer is prostate cancer.

1344. The method of any one of Clauses 1288 to 1337, wherein the cancer is bile duct cancer.

1345. The method of any one of Clauses 1288 to 1337, wherein the cancer is liver cancer.

1346. The method of any one of Clauses 1288 to 1337, wherein the cancer is colorectal cancer.

1347. The method of any one of Clauses 1288 to 1337, wherein the cancer is lung cancer.

1348. The method of any one of Clauses 1288 to 1337, wherein the cancer is pancreatic cancer.

1349. The method of any one of Clauses 1288 to 1337, wherein the cancer is stomach cancer.

1350. The method of any one of Clauses 1288 to 1337, wherein the cancer is head and/or neck cancer.

1351. The method of any one of Clauses 1288 to 1337, wherein the cancer is malignant ascites.

1352. The method of any one of Clauses 1288 to 1337, wherein the cancer is malignant pleural effusion.

1353. The method of any one of Clauses 1288 to 1337, wherein the cancer is brain cancer.

1354. The method of any one of Clauses 1288 to 1337, wherein the cancer is soft tissue sarcoma.

1355. The method of any one of Clauses 1288 to 1337, wherein the cancer is esophageal cancer.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

FIG. 71 is a table showing different side effects related to cancer and/or cancer treatment and corresponding depots of the present technology configured to treat these side effects.

FIG. 101 depicts a depot implanted in a prostate gland in accordance with some embodiments of the present technology.

FIG. 102 is a graph showing a percentage change in tumor volume versus time for several example depots of the present technology.

Figure 1:
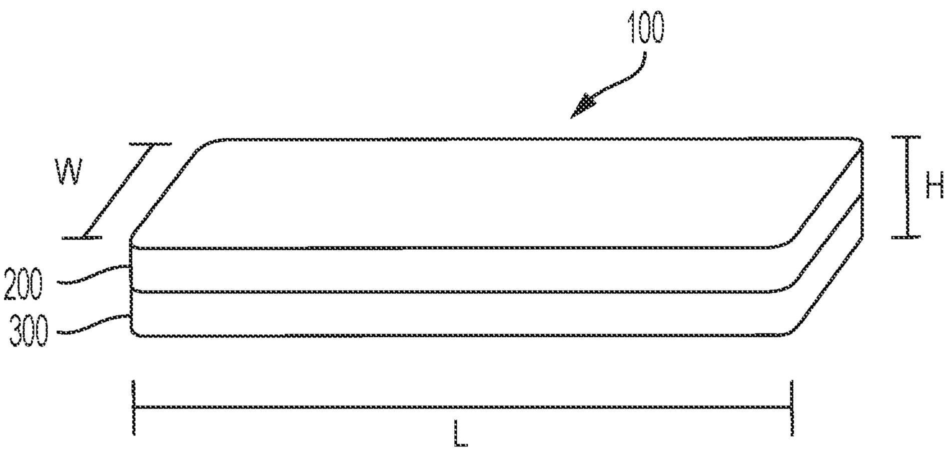
FIG. 1 is an isometric view of a depot configured in accordance with the present technology.
Figure 103:
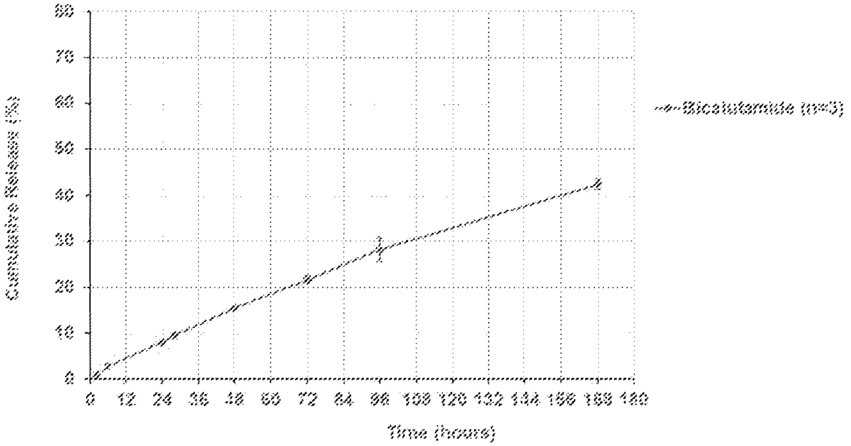
Figure 5:
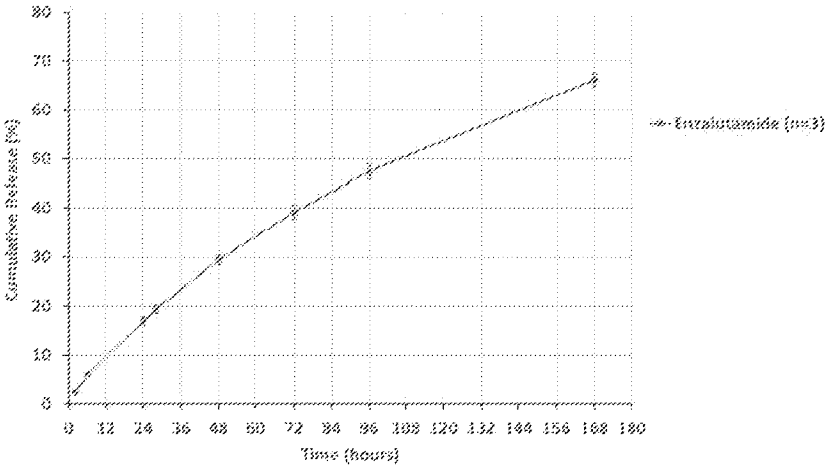
Figures 6, 103:
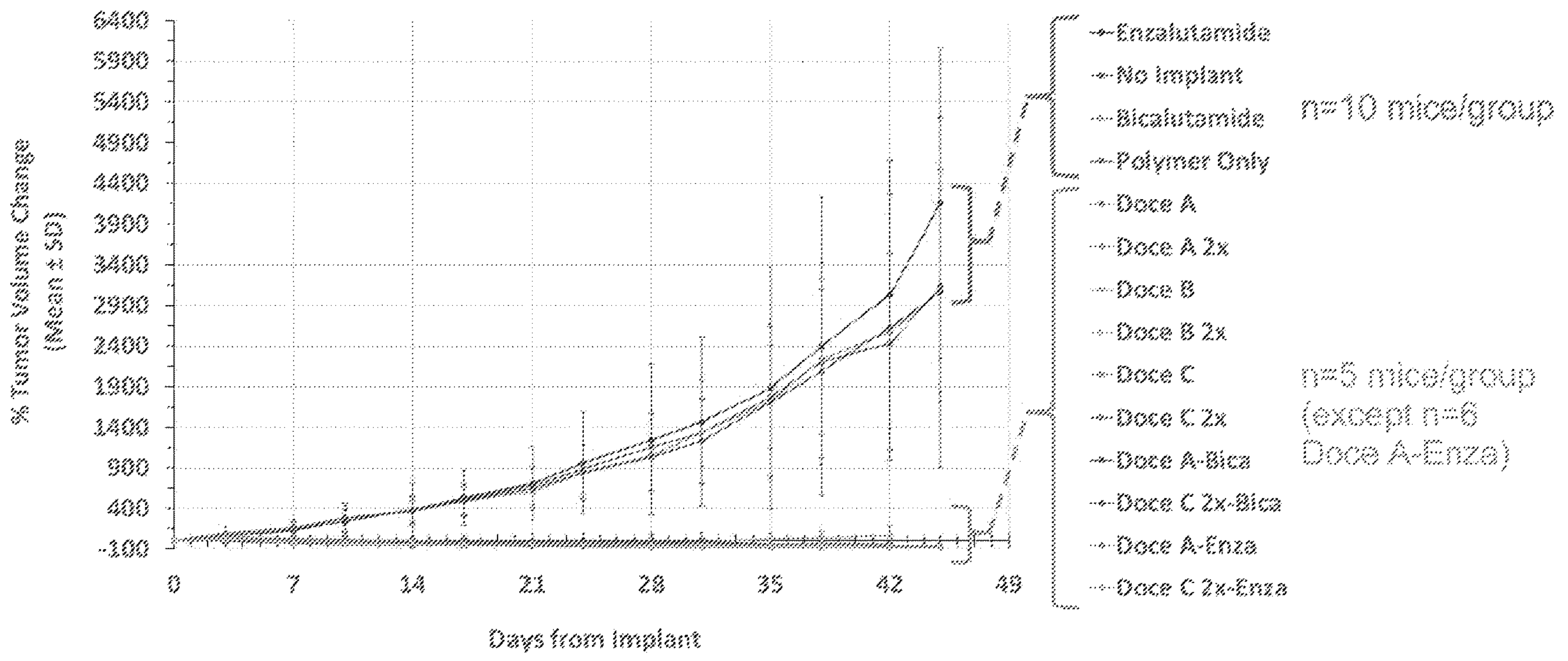
Figures 7, 103:
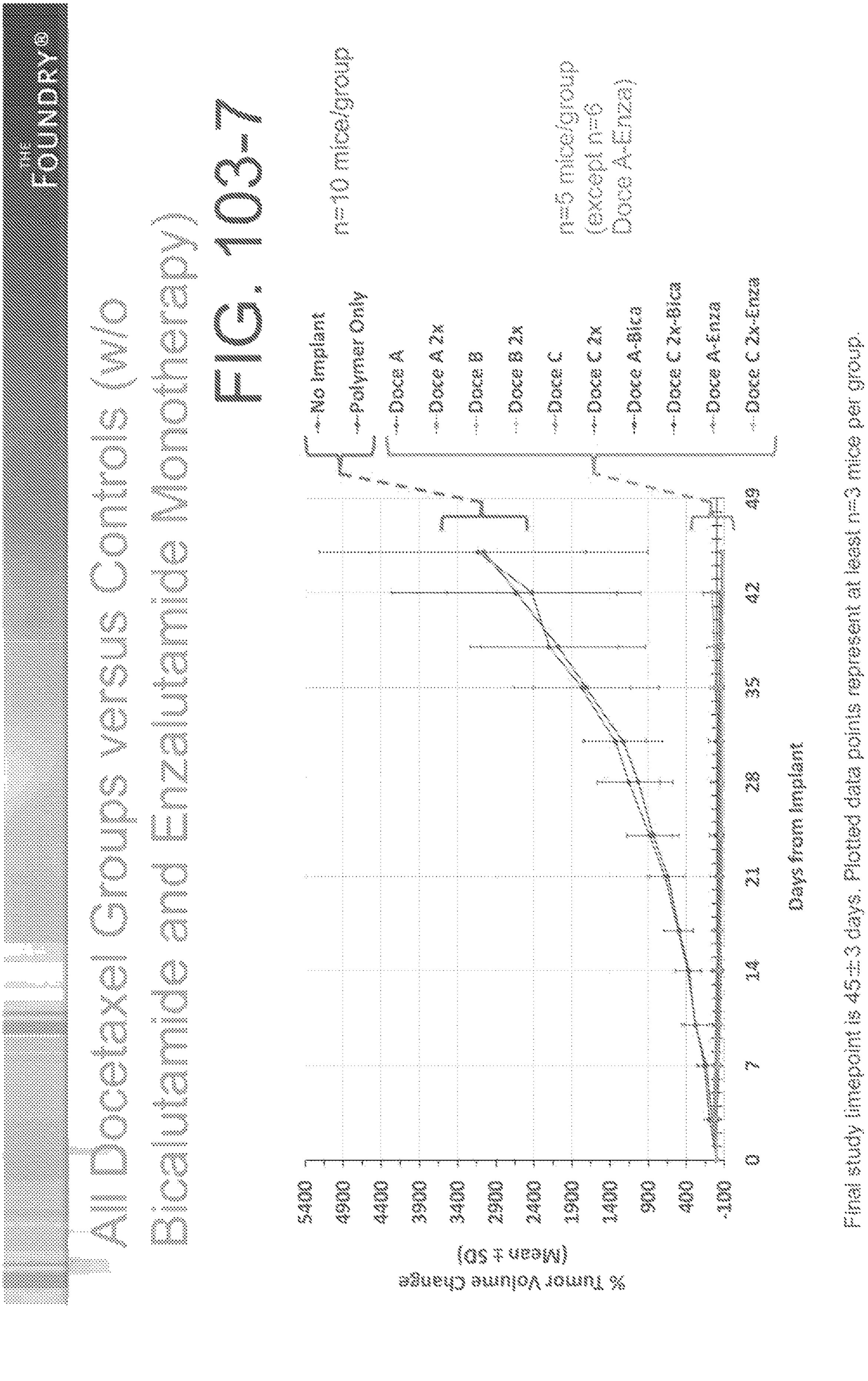
Figures 8, 103:
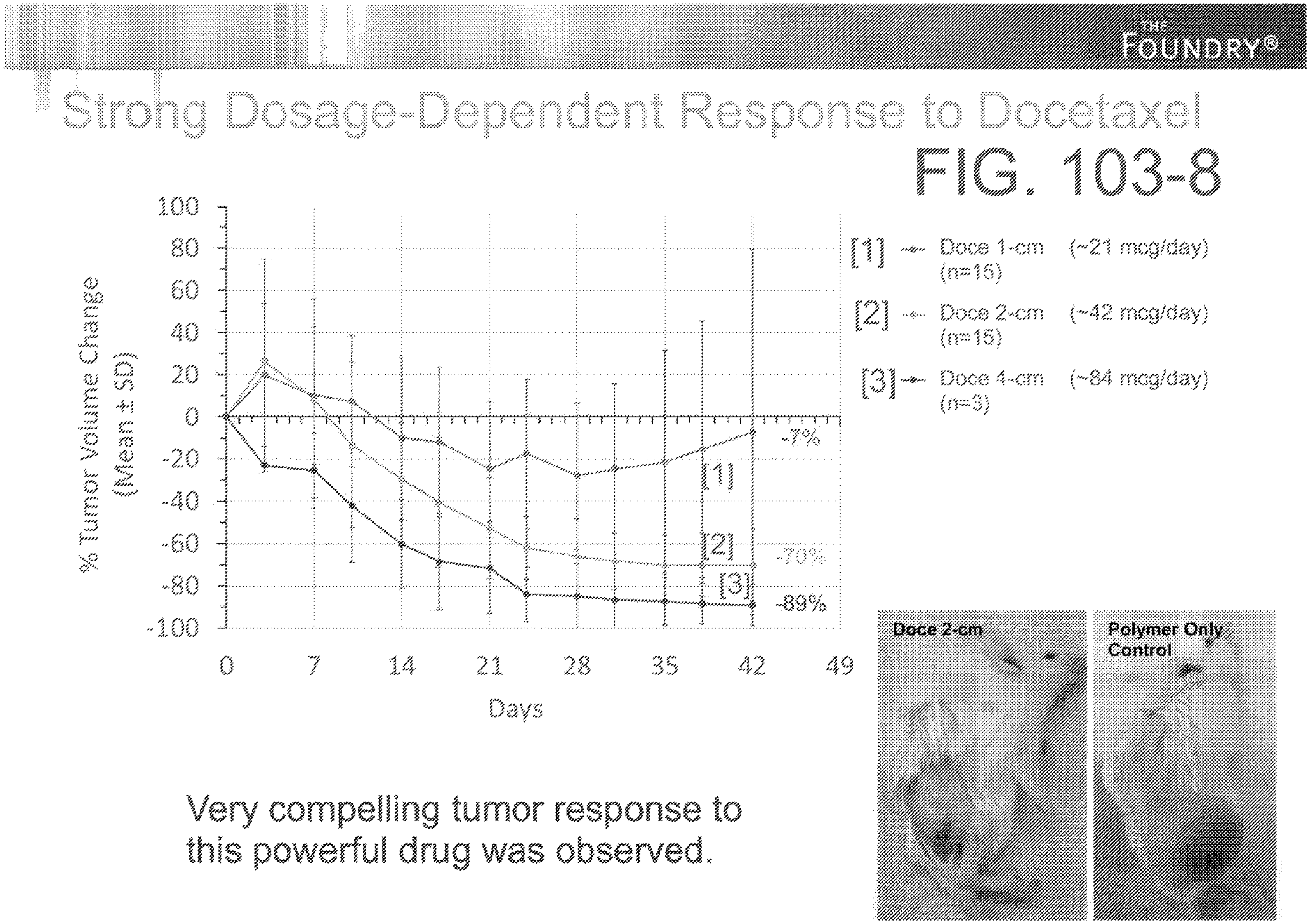
Figure 103:
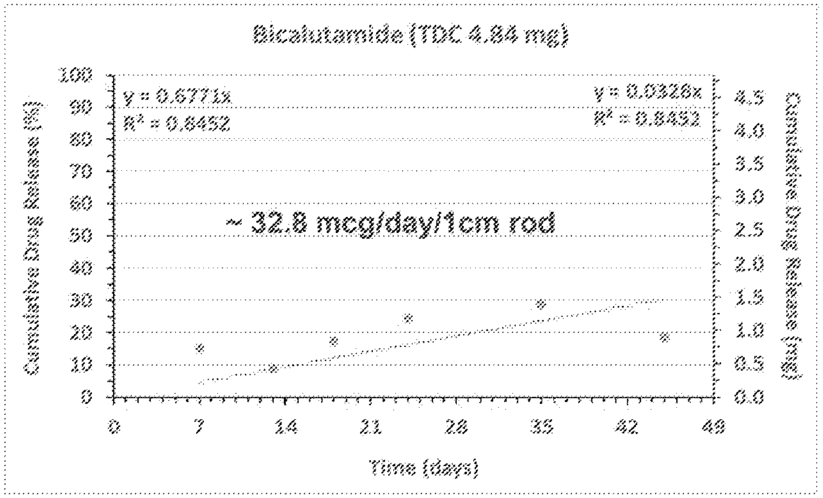
Figure 9:
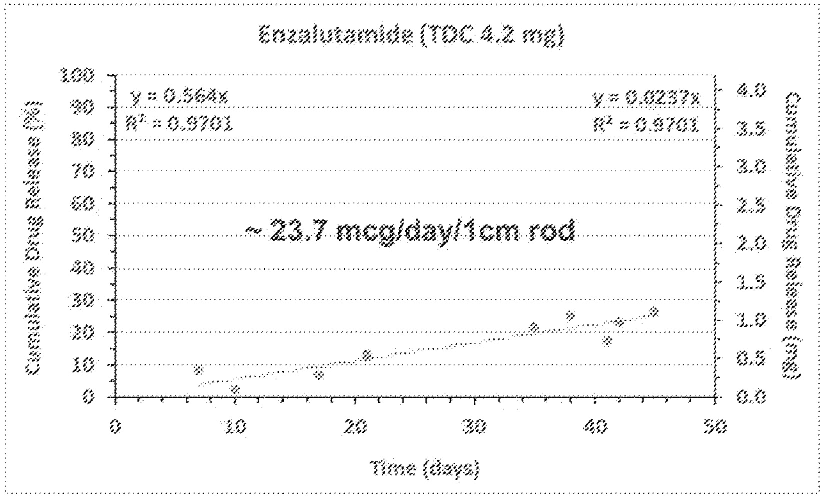

FIG. 103-1 outlines a study to evaluate the efficacy of a depot of the present technology.

Figure 2:
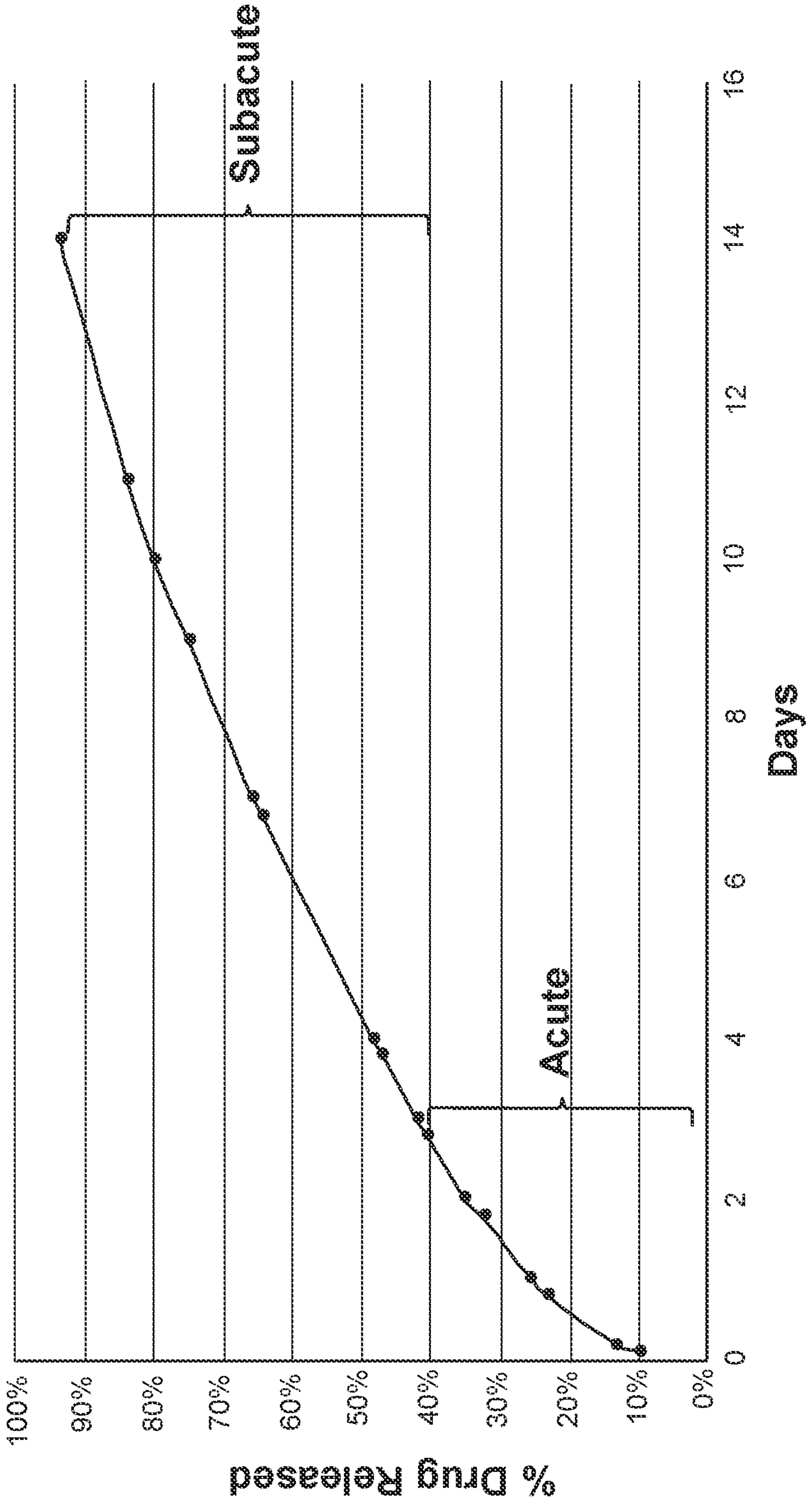
FIG. 2 depicts the release profile over time of one or more depots of the present technology.

FIG. 103-2 is a table of parameters related to a study evaluating a depot of the present technology.

Figure 3:
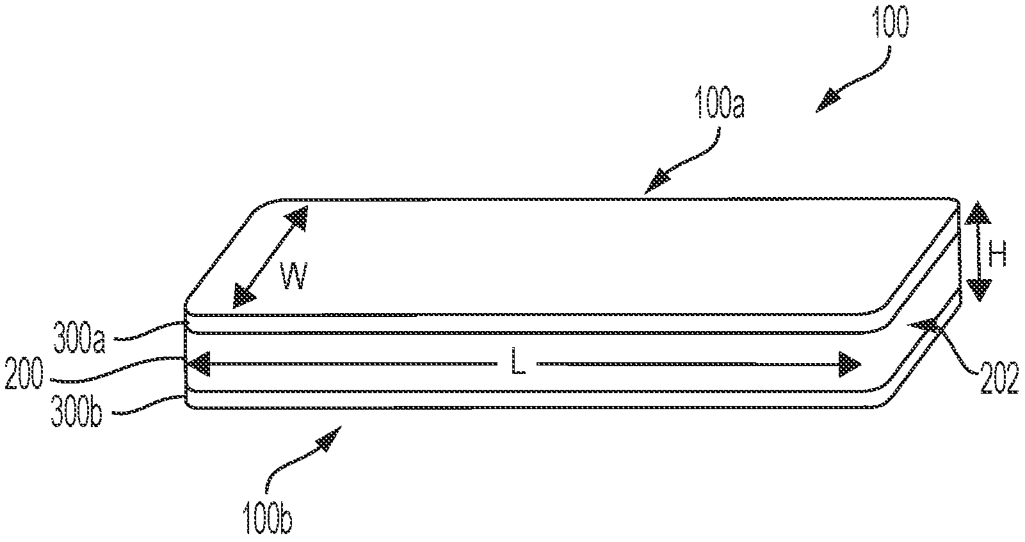
FIG. 3 is an isometric view of a depot in accordance with some embodiments of the present technology.

FIG. 103-3 is a table of drug depot formulations and delivery system parameters for a study of the present technology.

Figure 4:
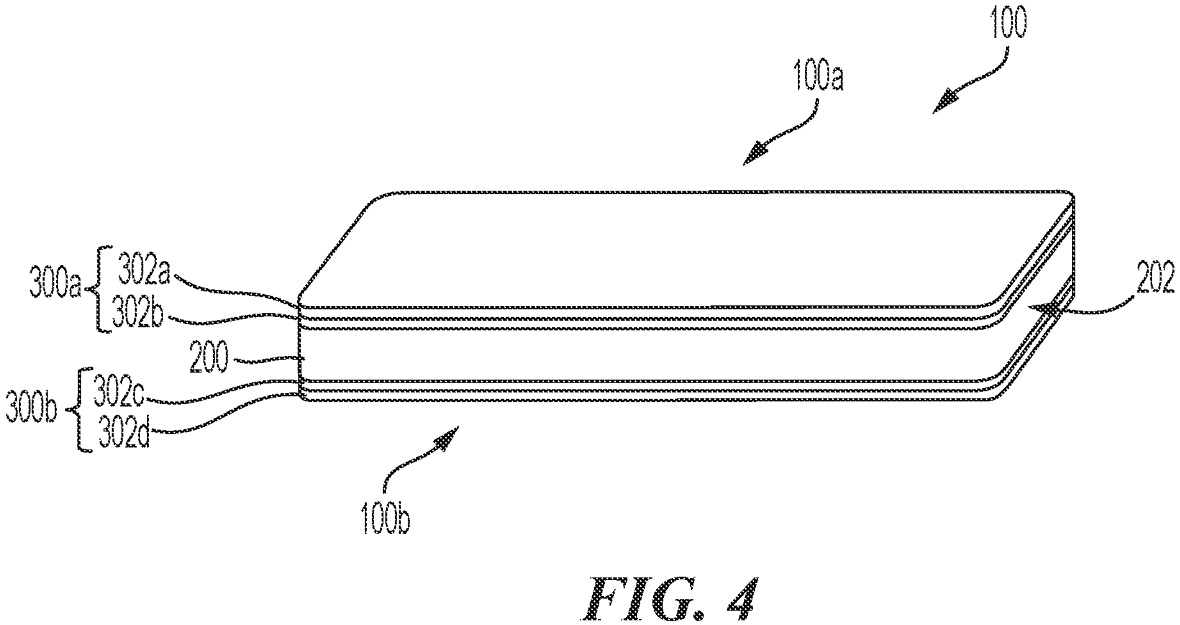
FIG. 4 is an isometric view of a depot in accordance with some embodiments of the present technology.

FIG. 103-4 is a graph showing a cumulative release percentage of a drug versus time for several examples of the present technology.

Figure 5:
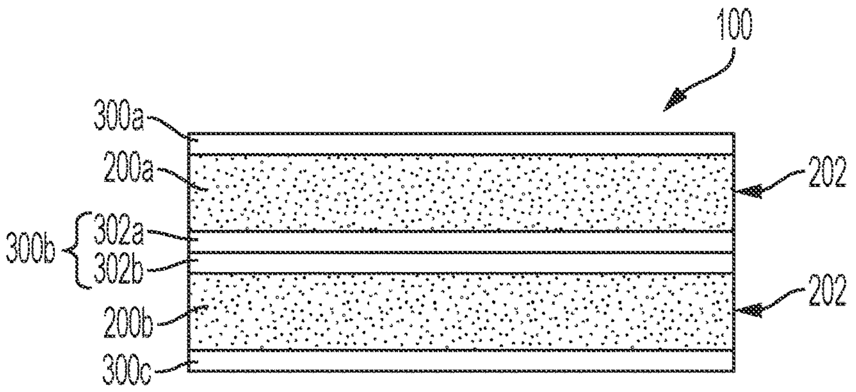
FIG. 5 is a cross-sectional view of a depot in accordance with some embodiments of the present technology.

FIG. 103-5 is two graphs showing a cumulative release percentage of a drug versus time for several examples of the present technology.

Figure 6:
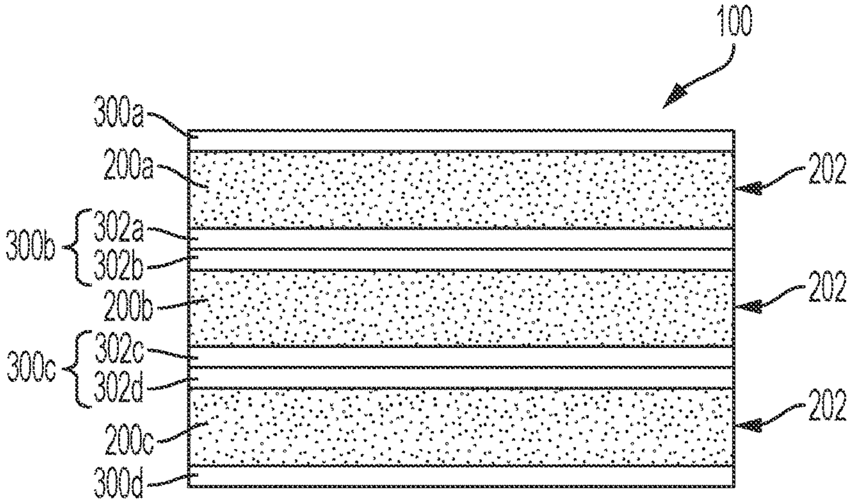
FIG. 6 is a cross-sectional view of a depot in accordance with some embodiments of the present technology.

FIG. 103-6 is a graph showing a percentage change in tumor volume versus time for several example depots of the present technology.

Figure 7:
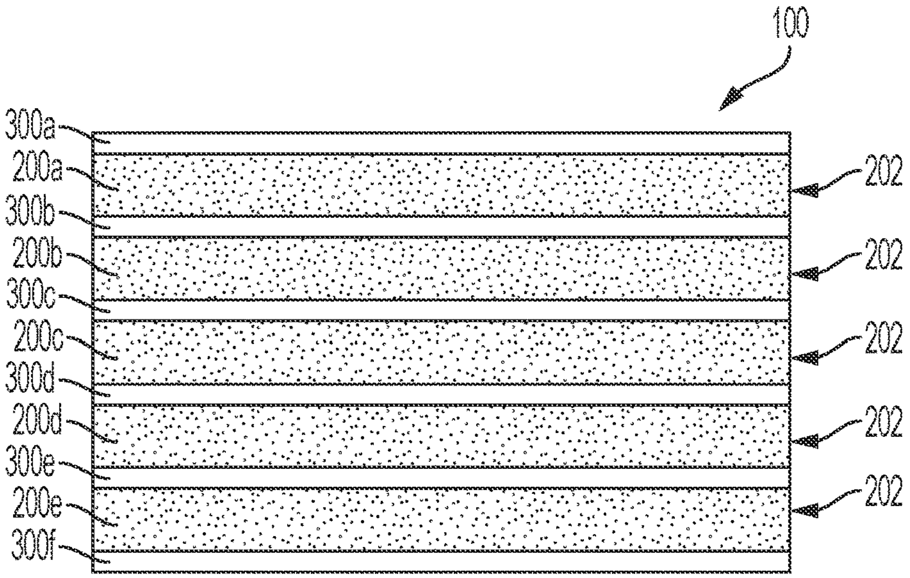
FIG. 7 is a cross-sectional view of a depot in accordance with some embodiments of the present technology.

FIG. 103-7 is a graph showing a percentage change in tumor volume versus time for several example depots of the present technology.

Figure 8:
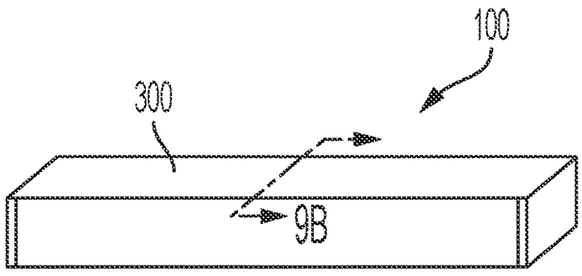
FIG. 8 is an isometric view of a depot in accordance with some embodiments of the present technology.

FIG. 103-8 is a graph showing a percentage change in tumor volume versus time for several example depots of the present technology.

Figure 9:
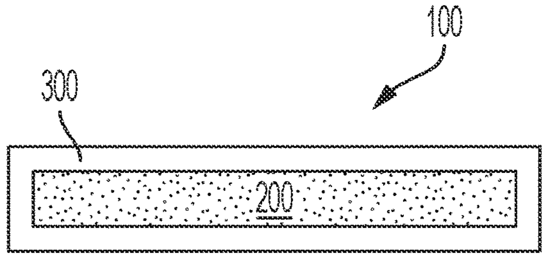
FIG. 9 is a cross-sectional view of the depot shown in FIG. 8.

FIG. 103-9 is two graphs showing a cumulative drug release percentage versus time for several examples of the present technology.

Figure 10:
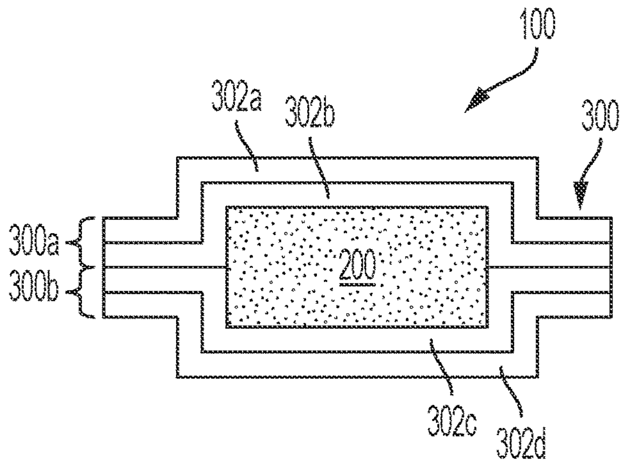
FIG. 10 is a cross-sectional view of a depot in accordance with some embodiments of the present technology.

FIG. 103-10 is two graphs showing a cumulative release percentage versus time for several examples of the present technology.

FIG. 104-1 outlines a study to evaluate the efficacy of several example depots of the present technology.

FIG. 104-2 is a table of parameters related to a study evaluating several example depots of the present technology.

FIG. 104-3 is a table of parameters for a study of several example depots of the present technology.

FIG. 104-4 is two graphs showing plasma drug concentrations versus time for several example depots of the present technology.

FIG. 104-5 depicts study outcomes related to drug exposure for several example depots of the present technology.

FIG. 104-6 depicts study outcomes related to drug exposure for several example depots of the present technology.

FIG. 104-7 outlines a study to evaluate the efficacy of several example depots of the present technology.

FIG. 104-8 depicts study outcomes related to drug exposure for several example depots of the present technology.

FIG. 104-9 depicts study outcomes related to drug exposure for several example depots of the present technology.

FIG. 105 depicts examples of chemotherapeutic drugs for use with the depots of the present technology.

FIG. 106 depicts examples of hormone therapy drugs for use with the depots of the present technology.

FIG. 107 depicts examples of immunotherapy drugs for use with the depots of the present technology.

FIG. 108 depicts examples of targeted therapy drugs for use with the depots of the present technology.

FIG. 109 depicts examples of supportive therapy drugs for use with the depots of the present technology.

FIG. 110 depicts examples of antimetabolites for use with the depots of the present technology.

FIGS. 111A-111D depict examples of plant alkaloids for use with the depots of the present technology. FIGS. 111A-111D are one table split into four parts across four pages.

FIG. 112 depicts examples of antitumor antibiotics for use with the depots of the present technology.

FIG. 113 depicts examples of cell cycle non-specific drugs for use with the depots of the present technology.

Figure 114:
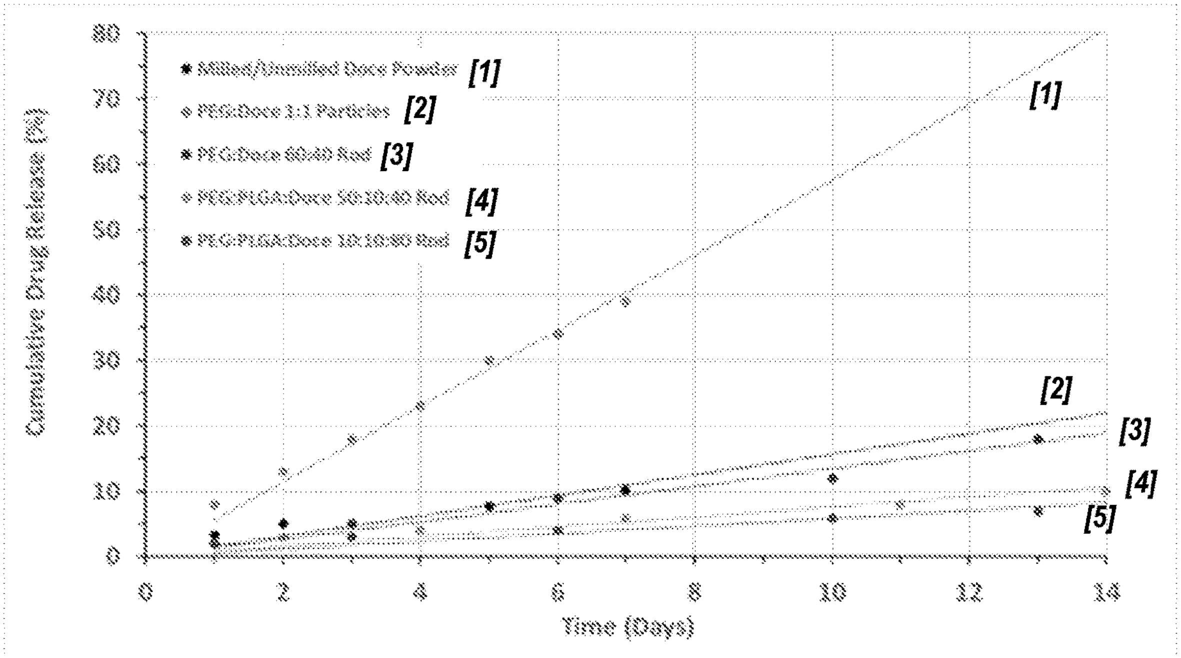

FIG. 114 is a graph showing a cumulative drug release percentage versus time for several example depots of the present technology.

Figure 115:
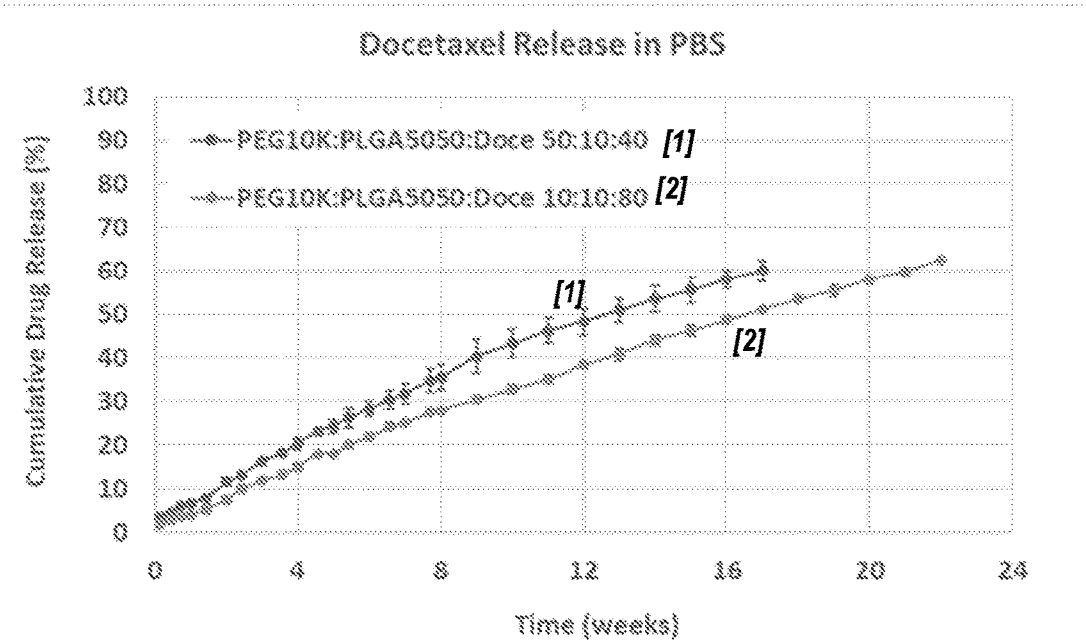

FIG. 115 is a graph showing a cumulative drug release percentage versus time for several example depots of the present technology.

Figure 116:
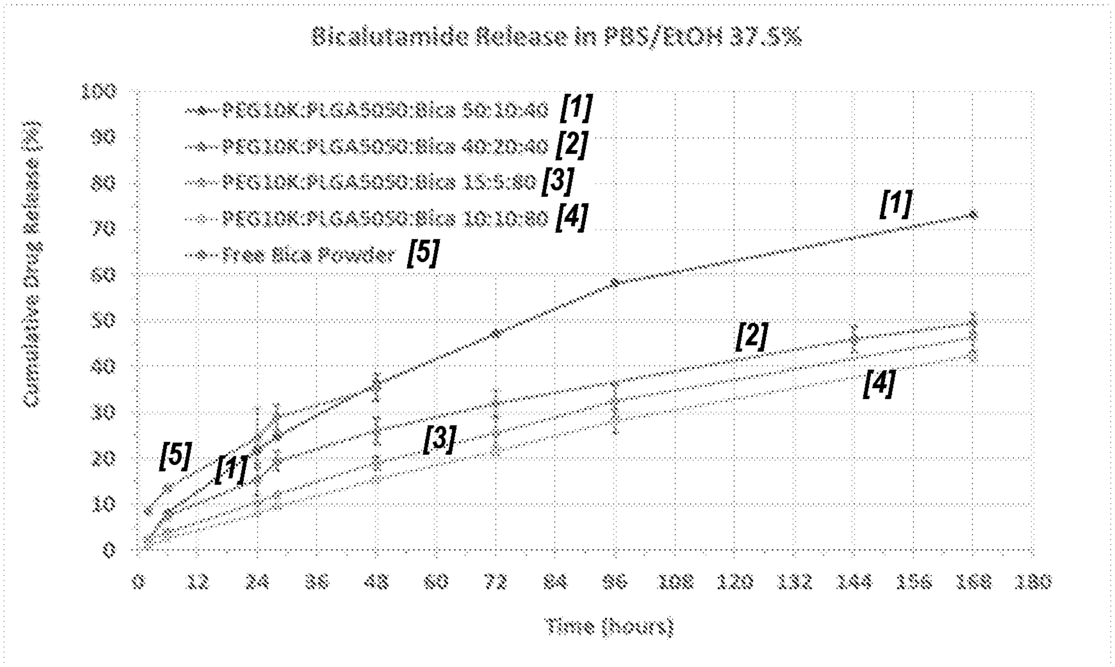

FIG. 116 is a graph showing a cumulative drug release percentage versus time for several example depots of the present technology.

Figure 117:
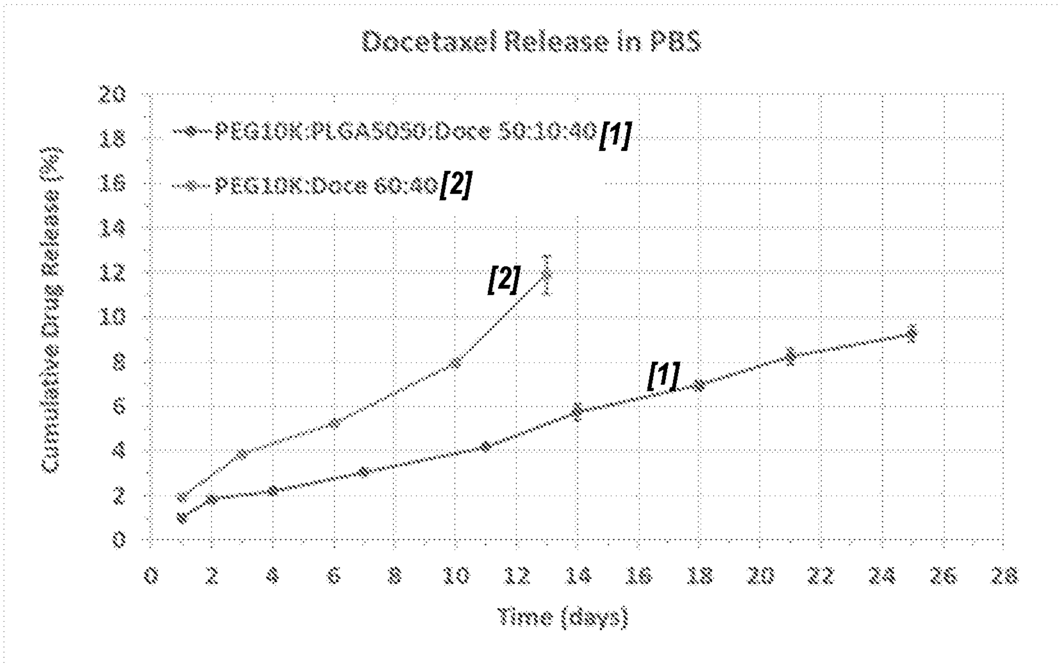

FIG. 117 is a graph showing a cumulative drug release percentage versus time for several example depots of the present technology.

Figure 118:
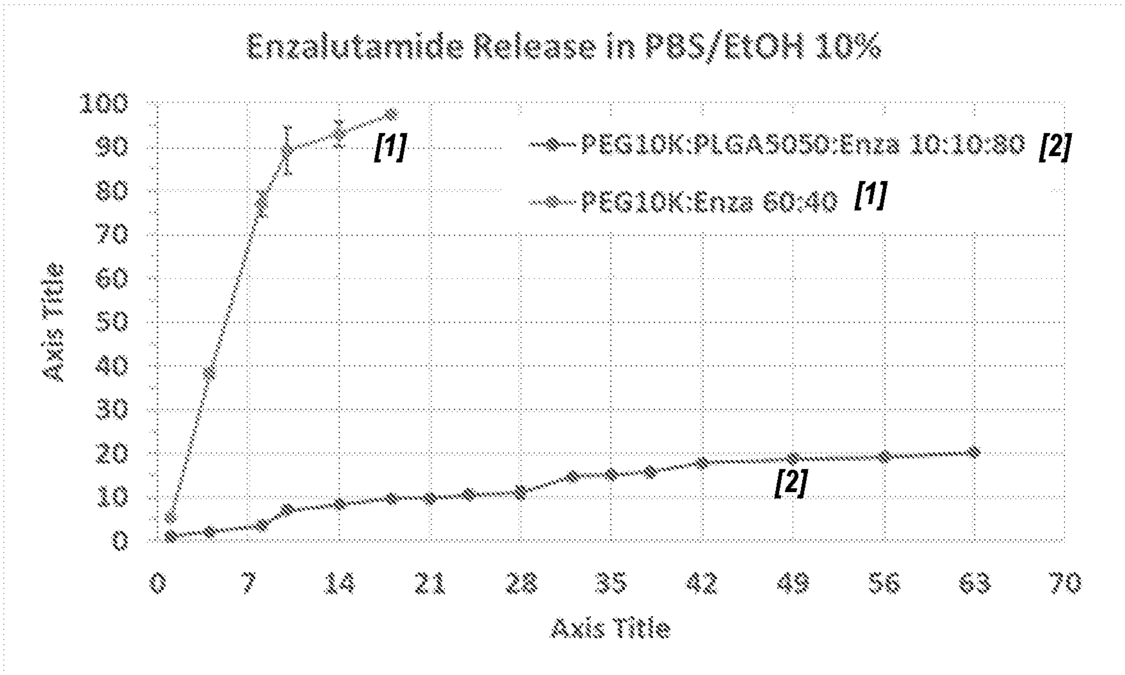

FIG. 118 is a graph showing a cumulative drug release percentage versus time for several example depots of the present technology.

Figure 119:
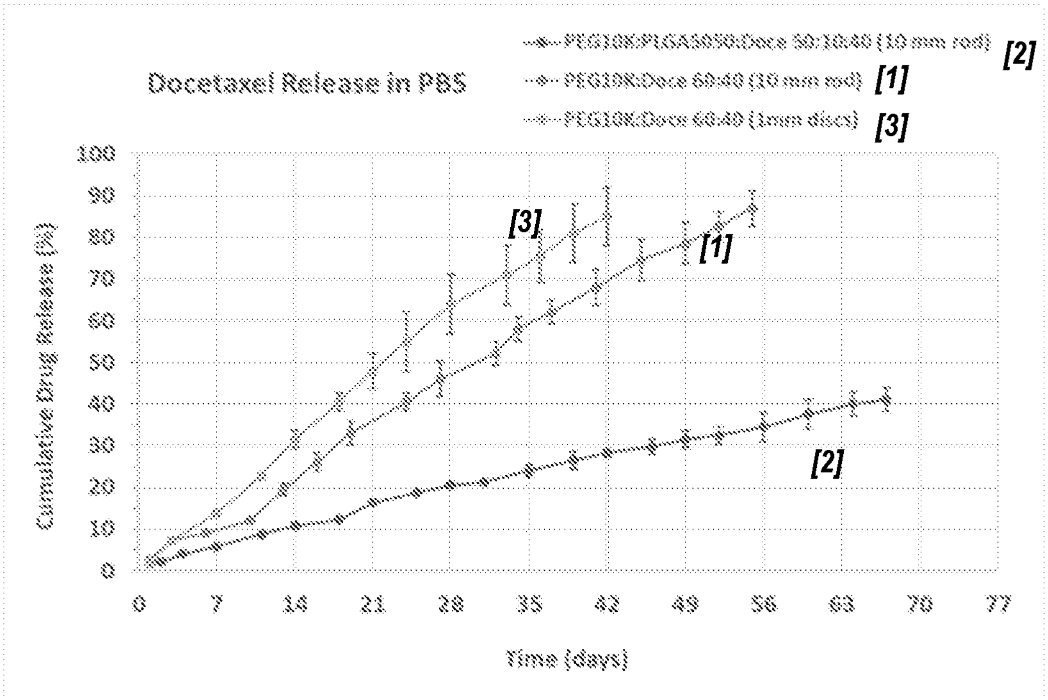

FIG. 119 is a graph showing a cumulative drug release percentage versus time for several example depots of the present technology.

Figure 120:
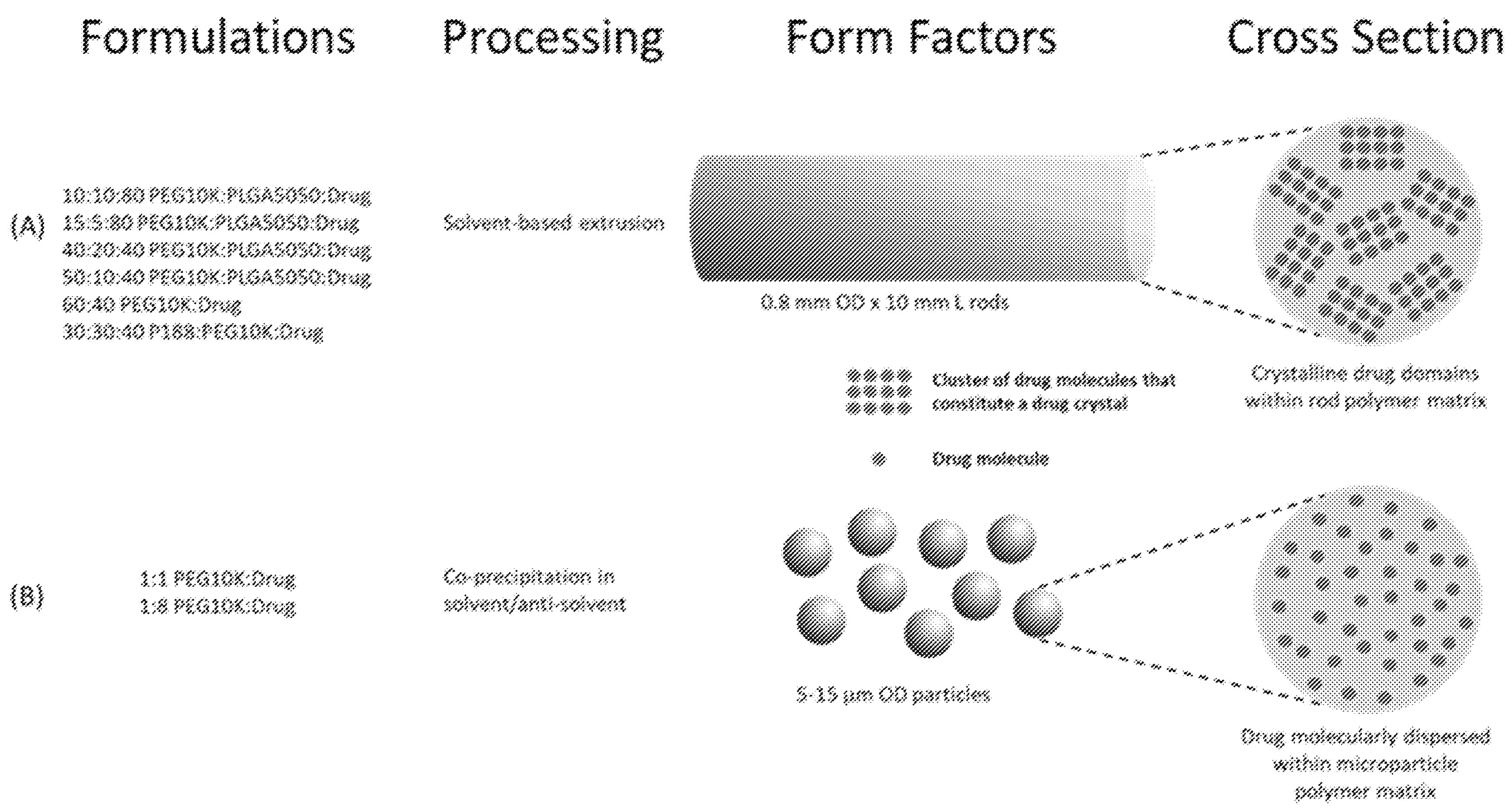

FIG. 120 is a schematic of the structural differences between a rod created via solvent-based extrusion and microparticles created via co-precipitation using solvent/non-solvent mixing.

Figure 121:
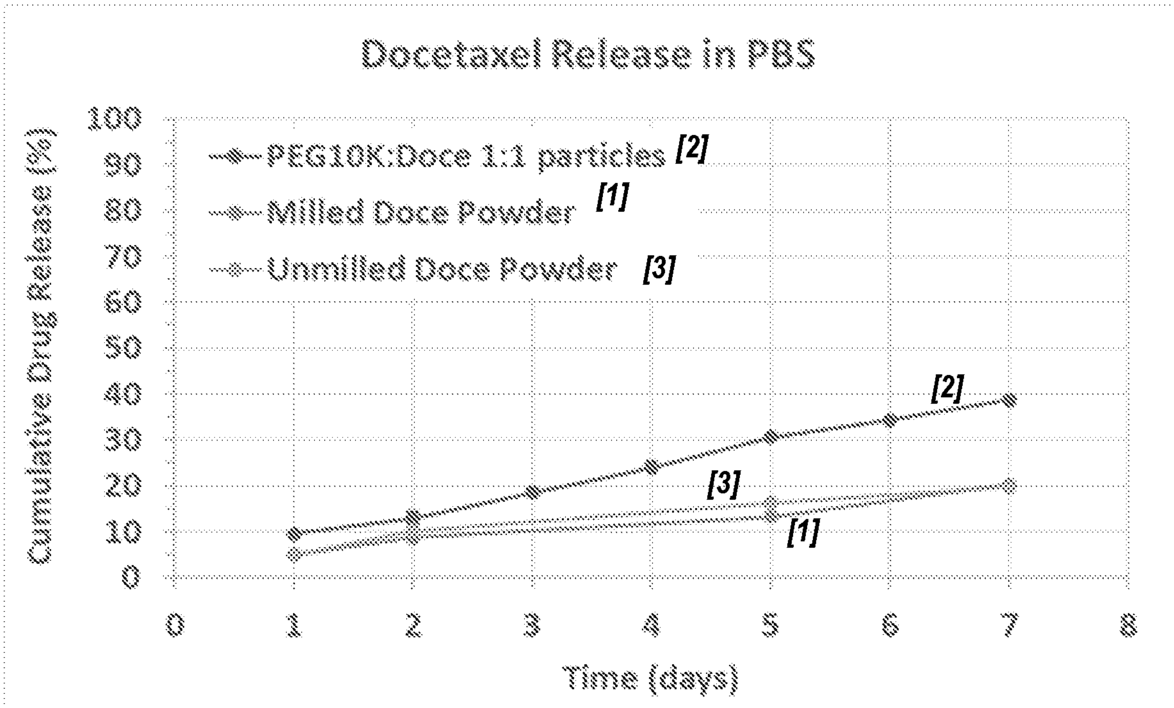

FIG. 121 is a graph showing a cumulative drug release percentage versus time for several example depots of the present technology.

Figure 122:
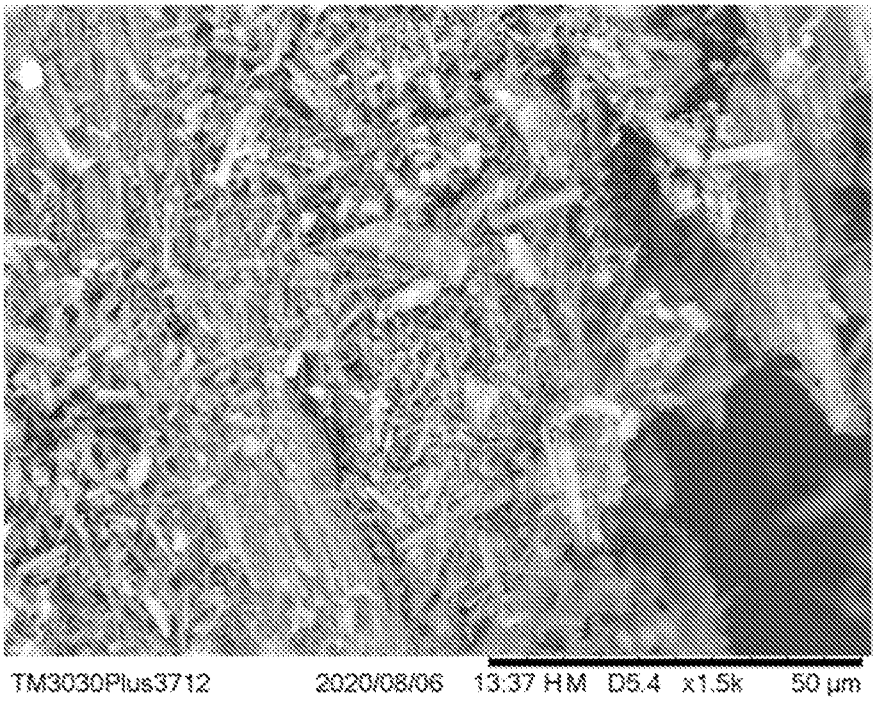

FIG. 122 is an SEM image of raw drug particles.

Figure 123:
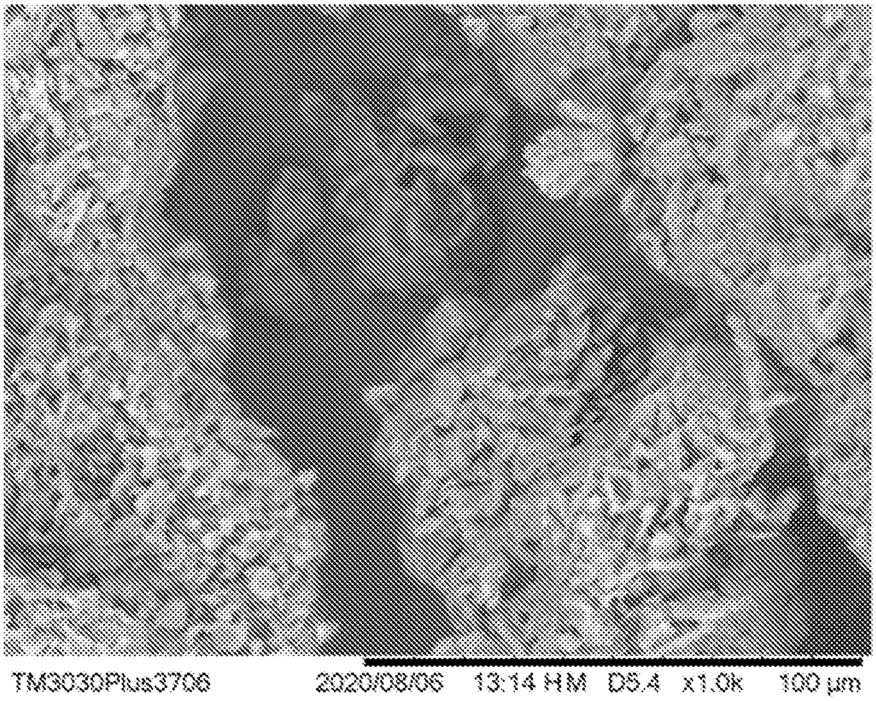

FIG. 123 is an SEM image of microparticles.

Figure 124:
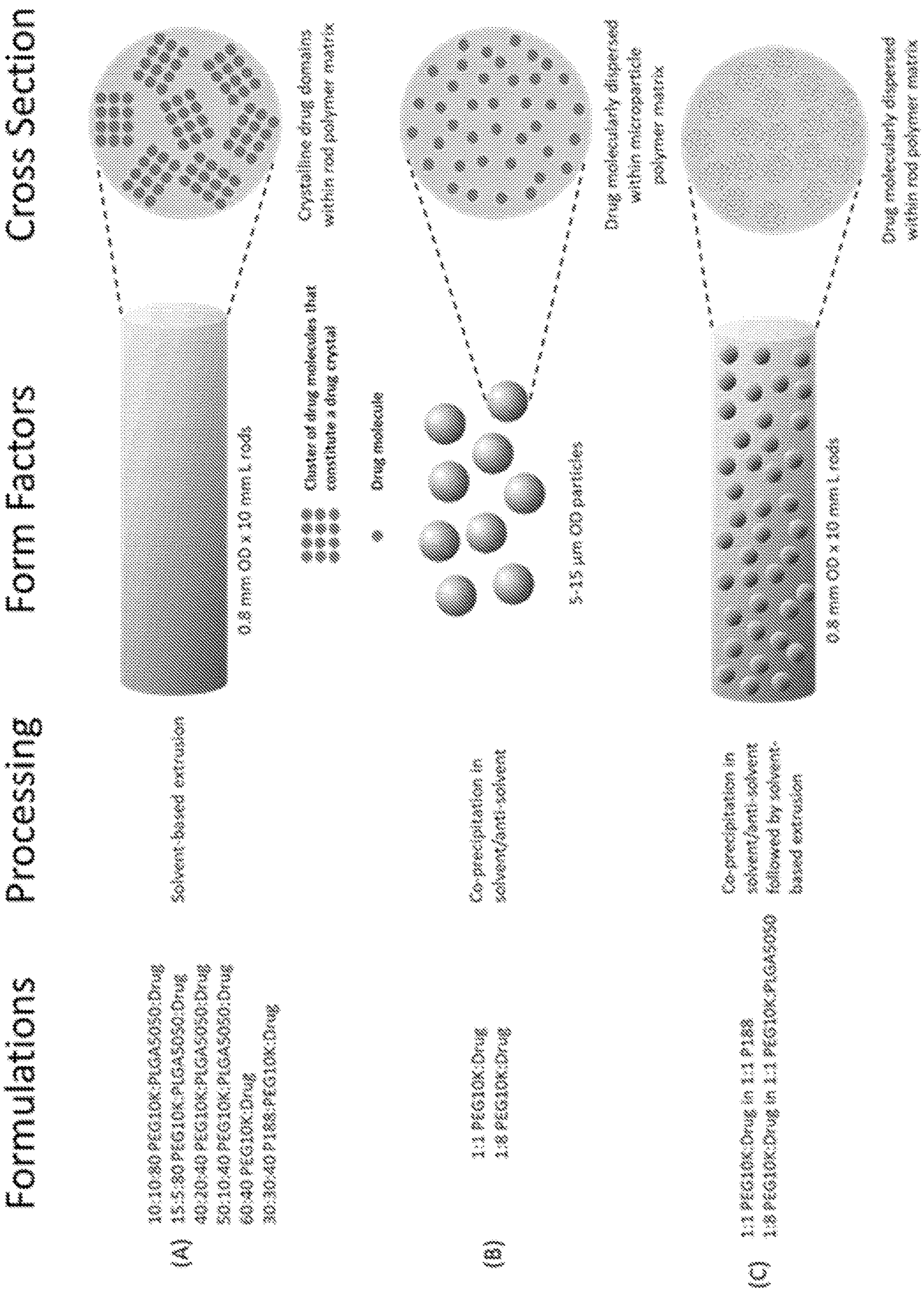

FIG. 124 depicts several examples of the present technology wherein microparticles were embedded into an implantable rod form factor.

Figure 125:
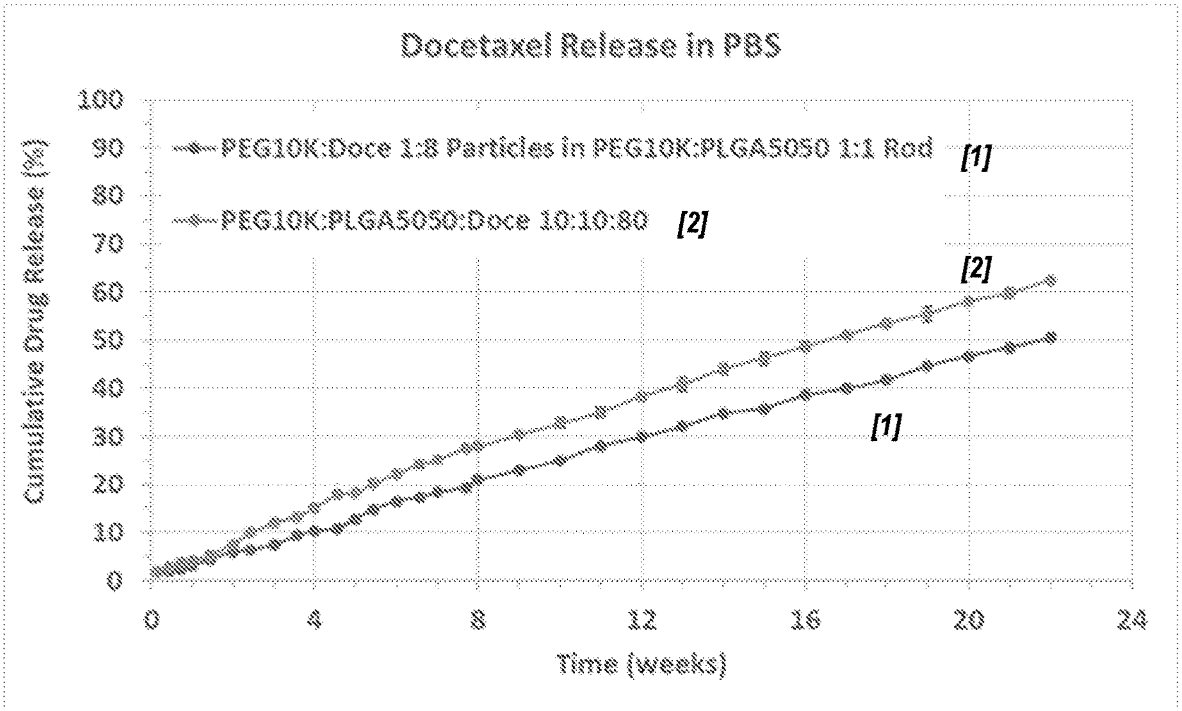

FIG. 125 is a graph showing a cumulative drug release percentage versus time for several example depots of the present technology.

Figure 126:
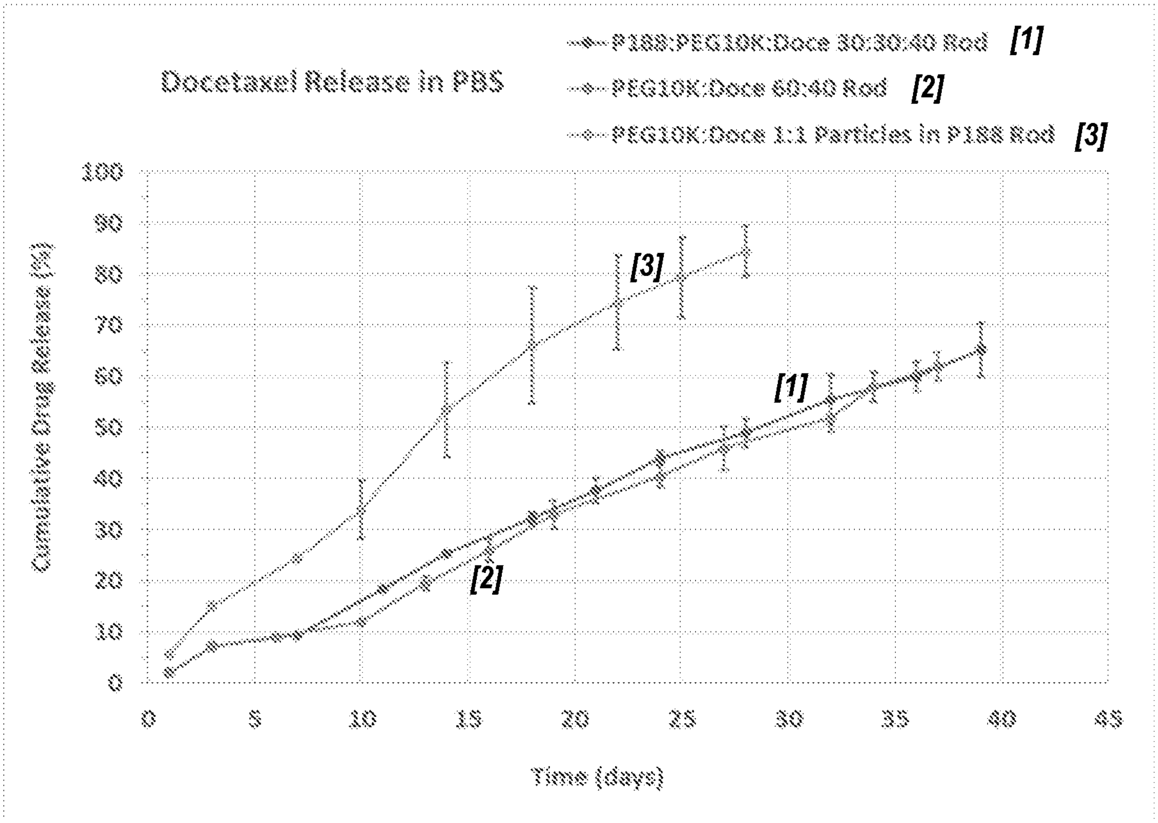

FIG. 126 is a graph showing a cumulative drug release percentage versus time for several example depots of the present technology.

Figure 127:
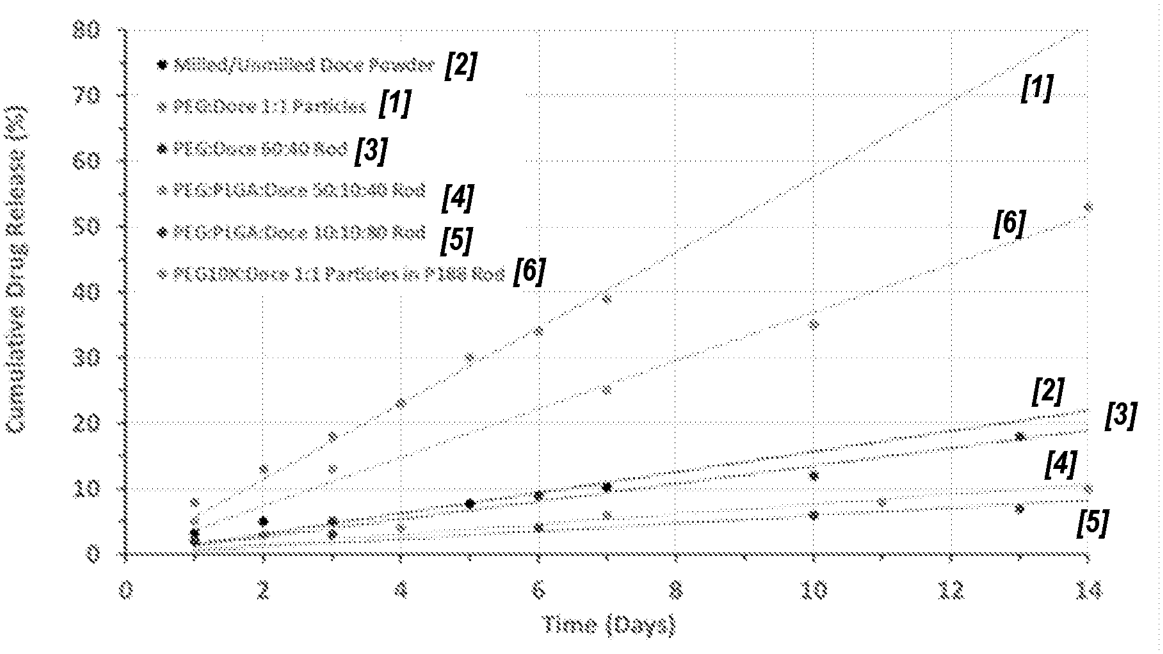

FIG. 127 is a graph showing a cumulative drug release percentage versus time for several example depots of the present technology.

DETAILED DESCRIPTION

The present technology relates to implantable depots for the sustained, controlled release of therapeutic agents, and associated devices, systems, and methods of use. Examples of the depots of the present technology are described below with reference to FIGS. 1-52C and Section I. Selected devices, systems, and methods for using the depots of the present technology for treating bladder cancer are described below with reference to FIGS. 53-57 and Section III. Selected devices, systems, and methods for using the depots of the present technology for treating malignant pleural effusion are described below with reference to FIGS. 58 and 59 and Section IV. Selected devices, systems, and methods for using the depots of the present technology for treating soft tissue sarcoma are described below with reference to FIGS. 60 and Section V. Selected devices, systems, and methods for using the depots of the present technology for treating head and neck tumors are described below with reference to FIGS. 61-63 and Section VI. Selected devices, systems, and methods for using the depots of the present technology for treating breast cancer are described below with reference to FIG. 64 and Section VII. Selected devices, systems, and methods for using the depots of the present technology for treating pancreatic cancer are described below with reference to FIG. 65 and Section VIII. Selected devices, systems, and methods for using the depots of the present technology for treating lung cancer are described below with reference to FIGS. 67-70 and Section IX. Selected devices, systems, and methods for using the depots of the present technology for treating prostate cancer are described below with reference to FIGS. 71-104-9 and Section x. Selected devices, systems, and methods for using the depots of the present technology for treating various other cancers and other conditions are described below with reference to Sections XI-XX.

I. Examples of Depots of the Present Technology

Disclosed herein are implantable depots and associated devices, systems, and methods for treating cancer via sustained, controlled release of a locally acting therapeutic agent while the depot is implanted at a treatment site in vivo. As is understood in the art, "release" of the therapeutic agent includes movement of the therapeutic agent away from the depot, as well as the sustained presence of the therapeutic agent at the treatment site following implantation of the depot, regardless of the relative movement of the therapeutic agent with respect to the confines of the depot. Thus, any therapeutic agent that remains substantially stationary relative to its position when first implanted is still considered "released" so long as it provides a therapeutic benefit at the treatment site.

Many of the depots of the present technology are configured to be implanted proximate cancerous tissue and provide a sustained presence of a locally acting therapeutic agent to a targeted tumor. Because the depots disclosed herein administer a therapeutic agent locally, the present technology can deliver greater amounts of certain therapeutic agents (such as chemotherapeutic agents) to a tumor locally than would be possible through systemic administration without exposing the patient to toxic levels of the agent systemically. For example, locally delivering an acute chemotherapeutic dose to the prostate at 100 times the typical concentration for systemic chemotherapy would still expose the body to only 1% of the drug used in systemic chemotherapy.

The depots of the present technology are configured to deliver a high, sustained local dose to cancer tissue over the course of days, weeks, or months. The depots may provide a high local concentration of therapeutic agent over a sustained period of time sufficient to cause toxicity of cancerous or neoplastic tissue while avoiding toxic exposure outside of the targeted tissue and, particularly, avoiding toxic exposure to the aforementioned critical, non-target structures. This pharmacokinetic profile may optimize treatment of the cancer while minimizing complications.

As used herein, "treat" or "treatment" or "treating" as it relates to cancer includes eradicating cancerous tissue, slowing the progression of cancerous tissue, reducing the mass and/or volume of cancerous tissue, eliminating or reducing the frequency or intensity of the side effects of the cancerous tissue, increasing the susceptibility of the cancerous tissue to more conventional treatments (e.g., systemic pharmacological therapy, radiation, etc.), preventing recurrence of cancerous tissue, and/or reducing the side effects of chemotherapy and/or radiation therapy directed at the cancerous tissue. As used herein, "cancer" or "cancerous tissue" includes cancer tissue as well as non- or pre-cancerous tissue (i.e., tissue with an increased risk of developing into cancer).

As used herein, "cancer" or "cancerous tissue" includes cancer tissue as well as non- or pre-cancerous tissue (i.e., tissue with an increased risk of developing into cancer). For example, "cancer" and "cancerous tissue," as used herein, include prostatic intraepithelial neoplasia ("PIN"). In addition, the devices, systems, and methods may also be utilized to deliver a therapeutic agent configured to treat diseases other than cancer, such as benign prostate hyperplasia ("BPH").

As used herein, a "depot" comprises a composition configured to administer at least one therapeutic agent to a treatment site in the body of a patient in a controlled, sustained manner. The depot also comprises the therapeutic agent itself. A depot may comprise a physical structure or carrier to configured to perform or enhance one or more functions related to treatment, such as facilitating implantation and/or retention in a treatment site (e.g., at or proximate a tumor), modulating the release profile of the therapeutic agent, increasing release towards a treatment site, reducing release away from a treatment site, or combinations thereof. In some embodiments, a "depot" includes but is not limited to rods, discs, films, sheets, strips, ribbons, capsules, coatings, matrices, wafers, pills, pellets, or other pharmaceutical delivery apparatus or a combination thereof. In some embodiments, the depot may be an injectable composition and/or substance. Moreover, as used herein, "depot" may refer to a single depot, or may refer to multiple depots. As an example, the statement "The depot may be configured to release 2 g of therapeutic agent to a treatment site" describes (a) a single depot that is configured to release 2 g of therapeutic agent to a treatment site, and (b) a plurality of depots that collectively are configured to release 2 g of therapeutic agent to a treatment site.

FIG. 1 is an isometric view of an implantable depot 100 in accordance with several embodiments of the present technology. The depot 100 may comprise a polymer matrix configured to be implanted at a treatment site. The polymer matrix may comprise a therapeutic region 200 containing a locally acting therapeutic agent. The therapeutic region 200 may comprise all or a portion of the polymer matrix. The depot 100 may include a high therapeutic payload of the therapeutic agent, especially as compared to other known films of equal thickness or polymer weight percentage, while exhibiting mechanical properties (e.g., flexural strength) sufficient to withstand storage, handling, implantation, and/or retention in the treatment site. For example, in some embodiments, the depot 100 comprises at least 50% by weight of the therapeutic agent.

According to some embodiments, for example as shown in FIG. 1, the depot 100 optionally includes a control region 300 configured to regulate the release of the therapeutic agent from the depot 100 in a controlled and sustained manner. The control region 300 may comprise at least one bioresorbable polymer and at least one releasing agent mixed with the polymer, and the therapeutic region 200 may comprise at least one bioresorbable polymer and at least one releasing agent mixed with the polymer and the therapeutic agent. The control region 300 may optionally include a therapeutic agent, or the control region 300 may include no therapeutic agent at all. The therapeutic region 200 may optionally include no releasing agent at all. The releasing agent in the control region 300 may be the same or may be different from the releasing agent in the therapeutic region 200. The bioresorbable polymer in the control region 300 may be the same or may be different from the bioresorbable polymer in the therapeutic region 200. As detailed below, in some embodiments the therapeutic region 200 and/or the control region 300 may have different constituents and/or formulations.

When exposed to a fluid (e.g., physiologic fluid), the releasing agent can have a dissolution rate that is faster than the degradation rate of the bioresorbable polymer. Accordingly, when a fluid contacts the depot 100 (e.g., after implantation of the depot 100 in a treatment site), the releasing agent dissolves within the surrounding polymer of the control region 300 and/or therapeutic region 200 faster than the polymer degrades. As the releasing agent dissolves, the space vacated by the dissolved releasing agent forms diffusion openings (e.g., channels, voids, pores, etc.) in the surrounding polymer region. The formation of diffusion openings may enhance the release of therapeutic agent from the polymer region and into the surrounding physiologic fluid. In some embodiments, the release rate of the therapeutic agent is higher when there are diffusion openings in the polymer region, compared to when there are no diffusion openings in the polymer region.

The concentration and type of releasing agent, among other parameters, can be selected to regulate the release of the therapeutic agent from the therapeutic region 200 and/or through the control region 300 into the surrounding fluid at a controlled dosage rate over a desired period of time. For example, a higher concentration of releasing agent may increase the release rate of the therapeutic agent, while a lower concentration of releasing agent may decrease the release rate of the therapeutic agent. The therapeutic region 200 may comprise a different concentration and/or type of releasing agent than the control region 300, or may comprise the same concentration and/or type of releasing agent.

The position and/or geometry of the control region 300 can be configured to modulate the release profile of the therapeutic agent from the therapeutic region 200. As shown in FIG. 1, at least a portion of the control region 300 may be disposed on or adjacent the therapeutic region 200 such that, when the depot 100 is initially positioned in vivo, the control region 300 is between at least a portion of the therapeutic region 200 and physiologic fluids at the treatment site. For example, the control region 300 can cover all or a portion of one or more surfaces of the therapeutic region 200. When the depot 100 is exposed to physiologic fluids, the therapeutic agent elutes from the exposed surfaces of the therapeutic region 200 and through the control region 300 by way of the diffusion openings created by dissolution of the releasing agent. In general, the therapeutic agent elutes from the exposed surfaces of the therapeutic region 200 at a faster (e.g., greater) rate than through the control region 300. As a result, the control region 300 prolongs the release of the therapeutic agent from the therapeutic region 200 to provide for longer release times and regulates the dosage rate, e.g., to provide the desired degree of therapeutic benefit and avoid complications related to overdosing.

The depots 100 of the present technology is configured to release a therapeutic agent in a highly controlled, predetermined manner that is specifically tailored to the medical condition being treated and the therapeutic agent used. As described in greater detail below, the release kinetics of the depots may be customized for a particular application by varying one or more aspects of the depot's composition and/or structure, such as the shape and/or size of the depot, therapeutic region 200, and/or control region 300; the exposed surface area of the therapeutic region 200; the type of polymer (in the therapeutic region 200 and/or in the control region 300); the weight percentage of the therapeutic agent, the polymer, and/or the releasing agent (within a particular region or generally throughout the depot 100); and the composition of the therapeutic region 200 and the control region 300.

As shown in FIG. 2, in many embodiments the depot 100 (or a system of depots 100) is configured to release a disproportionately larger volume of a therapeutic agent per day for a first period of time than for a longer second period of time. In some embodiments, the depot 100 (or a system of depots 100) is configured to release the therapeutic agent for at least 14 days post-implantation (or post-immersion in a fluid), where a controlled burst of about 20% to about 50% of the therapeutic agent payload is released in the first 3-5 days, and at least 80% of the remaining therapeutic agent payload is released at a slower rate over the last 10-11 days. In some embodiments, at least 90% of the therapeutic agent payload is released by the end of 14 days. Many other release profiles are possible, as discussed herein.

Depending on the type or cancer being targeted and/or the physiological conditions at the treatment site, the release profile of the depot 100 may be tuned to release a therapeutic agent for a desired duration and release rate by adjusting the structure, composition, and the process by which the depot is manufactured. For example, in some embodiments the depot 100 may be configured to release the therapeutic agent at a constant rate throughout the entire duration of release. In particular embodiments, the depot 100 may be configured to release the therapeutic agent at a constant rate for a first period of time and at a non-constant rate for a second period of time (which may occur before or after the first period of time).

In some embodiments, the depot 100 is configured to release no more than 20%, no more than 25%, no more than 30%, no more than 35%, no more than 40%, no more than 45%, no more than 50%, no more than 55%, no more than 60%, no more than 65%, or no more than 70% of the therapeutic agent in the first day, 2 days, 3 days, 4 days, 5 days, 6 days, 8 days, 9 days, 10 days, 11 days, 12 days, or 13 days of the duration of release, and wherein at least 75%, at least 80%, at least 85%, at least 90%, at least 95%, or 100% of the remaining therapeutic agent is released in the remaining days of the duration of release. The intended duration of release may be at least 1 day, at least 2 days, at least 3 days, at least 4 days, at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, at least 20 days, at least 21 days, at least 22 days, at least 23 days, at least 24 days, at least 25 days, at least 26 days, at least 27 days, at least 28 days, at least 29 days, or at least 30 days.

In some embodiments, the depot 100 is configured to release at least 70%, at least 75%, at least 80%, at least 85%, at least 90%, at least 95%, at least 96%, at least 97%, at least 98%, at least 99%, or 100% of the therapeutic agent in the depot 100 within the intended duration of treatment. The intended duration of treatment may be at least 1 day, at least 2 days, at least 3 days, at least 4 days, at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, at least 20 days, at least 21 days, at least 22 days, at least 23 days, at least 24 days, at least 25 days, at least 26 days, at least 27 days, at least 28 days, at least 29 days, at least 30 days, at least 40 days, at least 50 days, at least 60 days, at least 70 days, at least 90 days, at least 100 days, at least 200 days, at least 300 days, or at least 365 days.

In some embodiments, the depot 100 is configured to release from about 50 mg/day to about 600 mg/day, 100 mg/day to about 500 mg/day, or from about 100 mg/day to about 400 mg/day, or from about 100 mg/day to about 300 mg/day of the therapeutic agent to the treatment site. In general, the release rate can be selected to deliver the desired dosage to provide a therapeutic effect while still controlling toxicity.

In some embodiments, the depot 100 is configured to release from about 50 mg/day to about 600 mg/day, from about 100 mg/day to about 500 mg/day, or from about 100 mg/day to about 400 mg/day, or from about 100 mg/day to about 300 mg/day of the therapeutic agent to the treatment site within a first period of release. The depot 100 can further be configured to release from about 500 mg/day to about 600 mg/day, about 100 mg/day to about 500 mg/day, or from about 100 mg/day to about 400 mg/day, or from about 100 mg/day to about 300 mg/day of the therapeutic agent to the treatment site within a second period of release. The release rate during the first period may be the same as, different than, less than, or greater than the release rate during the second period. Moreover, the first period may be longer or shorter than the second period. The first period may occur before or after the second period.

In some embodiments, the depot 100 is configured to release no more than 50 mg, no more than 100 mg, no more than 150 mg, no more than 200 mg, no more than 250 mg, no more than 300 mg, no more than 350 mg, no more than 400 mg, no more than 450 mg, no more than 500 mg, no more than 600 mg, no more than 700 mg, no more than 800 mg, no more than 900 mg, no more than 1000 mg, at least 10 mg, at least 20 mg, at least 30 mg, at least 40 mg, at least 50 mg, at least 60 mg, at least 70 mg, at least 80 mg, at least 90 mg, at least 100 mg, at least 110 mg, at least 120 mg, at least 130 mg, at least 140 mg, at least 150 mg, at least 160 mg, at least 170 mg, at least 180 mg, at least 190 mg, at least 200 mg, at least 210 mg, at least 220 mg, at least 230 mg, at least 240 mg, at least 250 mg, at least 260 mg, at least 270 mg, at least 280 mg, at least 290 mg, or at least 300 mg of the therapeutic agent within any day of a first period of release. This may be useful for providing different degrees of pain relief at different times after the surgical procedure, and it may also be useful to control toxicity. In such embodiments, the depot 100 may be configured to release no more than 50 mg, no more than 100 mg, no more than 150 mg, no more than 200 mg, no more than 250 mg, no more than 300 mg, no more than 350 mg, no more than 400 mg, no more than 450 mg, no more than 500 mg, no more than 600 mg, no more than 700 mg, no more than 800 mg, no more than 900 mg, no more than 1000 mg, at least 10 mg, at least 20 mg, at least 30 mg, at least 40 mg, at least 50 mg, at least 60 mg, at least 70 mg, at least 80 mg, at least 90 mg, at least 100 mg, at least 110 mg, at least 120 mg, at least 130 mg, at least 140 mg, at least 150 mg, at least 160 mg, at least 170 mg, at least 180 mg, at least 190 mg, at least 200 mg, at least 210 mg, at least 220 mg, at least 230 mg, at least 240 mg, at least 250 mg, at least 260 mg, at least 270 mg, at least 280 mg, at least 290 mg, or at least 300 mg of the therapeutic agent within any day of a second period of release. The first period of release and/or the second period of release may be 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, or 30 days. The depot 100 may be configured to release the therapeutic agent at a first rate during the first period and at a second rate during the second period. The first rate may be the same as, different than, less than, or greater than the second rate. In some embodiments, the first rate is at least 2-fold, 3-fold, 4-old, 5-fold, 6-fold, 7-fold, 8-fold, 9-fold, or 10-fold greater than the second rate, or vice versa. Moreover, the first period may be longer or shorter than the second period. The first period may come before or after the second period.

In some embodiments, the depot 100 is configured to release no more than 50 mg, no more than 100 mg, no more than 150 mg, no more than 200 mg, no more than 250 mg, no more than 300 mg, no more than 350 mg, no more than 400 mg, no more than 450 mg, no more than 500 mg, no more than 600 mg, no more than 700 mg, no more than 800 mg, no more than 900 mg, or no more than 1000 mg of therapeutic agent within any day of the duration of release.

In some embodiments, the depot 100 is configured to release the therapeutic agent at a treatment site in vivo and/or in the presence of one or more fluids for no less than 1 day, no less than 2 days, no less than 3 days, no less than 4 days, no less than 5 days, no less than 6 days, no less than 7 days, no less than 8 days, no less than 9 days, no less than 10 days, no less than 11 days, no less than 12 days, no less than 13 days, no less than 14 days, no less than 15 days, no less than 16 days, no less than 17 days, no less than 18 days, no less than 19 days, no less than 20 days, no less than 21 days, no less than 22 days, no less than 23 days, no less than 24 days, no less than 25 days, no less than 26 days, no less than 27 days, no less than 28 days, no less than 29 days, no less than 30 days, no less than 40 days, no less than 50 days, no less than 60 days, no less than 70 days, no less than 90 days, no less than 100 days, no less than 200 days, no less than 300 days, or no less than 365 days.

The release kinetics of the depots of the present technology may be tuned for a particular application by varying one or more aspects of the depot's structure and/or composition, such as the exposed surface area of the therapeutic region 200, the porosity of the control region 300 during and after dissolution of the releasing agent, the concentration of the therapeutic agent in the therapeutic region, the post-manufacturing properties of the polymer, the structural integrity of the depots to avoid a sudden release of the therapeutic agent, the relative thicknesses of the therapeutic region 200 compared to the control region 300, and other properties of the depots. Several embodiments of depots of the present technology combine one or more of these properties in a manner that produces exceptional two-phase release profiles in animal studies that significantly outperform existing injectable or implantable systems, while also overcoming the shortcomings of disclosed prophetic devices. For example, several embodiments have exhibited two-phase release profiles that deliver an adequate mass of therapeutic agent to treat pain associated with joint replacement surgery or other applications over a 14-day period while maintaining sufficient structural integrity to withstand the forces of a joint to avoid a sudden release of too much therapeutic agent. This surprising result enables depots of the present technology to at least reduce, if not replace, opioids and/or enhance other existing pain relief systems for orthopedic surgical applications, non-orthopedic surgical applications, and for other applications (e.g., oncological).

For example, the release profile can be tuned by, at least in part, controlling the amount of exposed surface area of the therapeutic region 200 because depots having a therapeutic region 200 covered only partially by a control region 300 (see, for example, FIGS. 2, 4-8, and 13) will generally release a higher proportion of the total payload over a shorter period of time as compared to embodiments where the therapeutic region 200 is completely encapsulated by the control region 300 (see, for example, FIGS. 9A-12). More specifically, depot designs having a therapeutic region 200 with exposed surfaces will typically release the therapeutic agent at a high, substantially linear rate for a first period of time and then at a lower, substantially linear rate for a second period of time. Alternatively, depot designs having a therapeutic region 200 with surfaces that are substantially covered by one or more control regions 300 may achieve a zero-order release such that the release of the payload of therapeutic agent is at substantially the same rate.

As shown in FIG. 3, in some embodiments the depot 100 may comprise a multi-layer polymer film having a therapeutic region 200 and first and second control regions 300*a*, 300*b* positioned at opposite surfaces 100*a*, 100*b* of the therapeutic region 200. The depot 100 may be in the form of a flexible, rectangular strip having a length L, a width W, and a height H (or thickness). In some embodiments, the depot 100 has (a) a length L of from about 5-40 mm, about 10-30 mm, about 15-20 mm, about 20-35 mm, about 20-30 mm, about 20-25 mm, about 26-30 mm, about 5 mm, about 10 mm, about 11 mm, about 12 mm, about 13 mm, about 14 mm, about 15 mm, about 16 mm, about 17 mm, about 18 mm, about 19 mm about 20 mm, about 21 mm, about 22 mm, about 23 mm, about 24 mm, about 25 mm, about 26 mm, about 27 mm, about 28 mm, about 29 mm, about 30 mm, about 10-15 mm, about 12-16 mm, about 15-20 mm, about 21-23 mm, about 22-24 mm, about 23-25 mm, about 24-26 mm, about 25-27 mm, about 26-28 mm, about 27-29 mm, or about 28-30 mm, (b) a width W of from about 5-40 mm, about 10-30 mm, about 15-20 mm, about 20-35 mm, about 20-30 mm, about 20-25 mm, about 26-30 mm, about 5 mm, about 10 mm, about 11 mm, about 12 mm, about 13 mm, about 14 mm, about 15 mm, about 16 mm, about 17 mm, about 18 mm, about 19 mm about 20 mm, about 21 mm, about 22 mm, about 23 mm, about 24 mm, about 25 mm, about 26 mm, about 27 mm, about 28 mm, about 29 mm, about 30 mm, about 10-15 mm, about 12-16 mm, about 15-20 mm, about 21-23 mm, about 22-24 mm, about 23-25 mm, about 24-26 mm, about 25-27 mm, about 26-28 mm, about 27-29 mm, or about 28-30 mm (c) a height H of from about 0.4 mm to about 4 mm, about 1 mm to about 3 mm, about 1 mm to about 2 mm, at least 0.4 mm, at least 0.5 mm, at least 0.6 mm, at least 0.7 mm, at least 0.8 mm, at least 0.9 mm, at least 1 mm, at least 1.2 mm, at least 1.4 mm, at least 1.5 mm, at least 1.6 mm, at least 1.7 mm, at least 1.8 mm, at least 2 mm, at least about 3 mm, no more than 0.5 mm, no more than 0.6 mm, no more than 0.7 mm, no more than 0.8 mm, no more than 0.9 mm, etc.). In some embodiments, the depot 100 may have a L×W×H of about 26 mm×about 16 mm×about 1 mm, and in some embodiments, about 27 mm×about 17 mm×about 1 mm. In some embodiments, the depot 100 may have other shapes and/or dimensions, such as those detailed below.

Additionally, some embodiments of the depot shown in FIG. 3 are configured such that a thickness of the control regions 300*a* and 300*b*, either individually or collectively, is less than or equal to 1/10 of a thickness of the therapeutic region 200. The thickness of the control regions 300*a* and 300*b*, either individually or collectively, can further be no more than 1/12.5, 1/15, 1/17.5, 1/20, 1/22.5, 1/25, 1/30, 1/40, 1/50, 1/75, or 1/100 of the thickness of the therapeutic region 200. In those embodiments with multiple sub-control regions, one or more of the sub-control regions may individually be less than or equal to 1/10, 1/12.5, 1/15, 1/17.5, 1/20, 1/22.5, 1/25, 1/27.5, 1/30, 1/32.5, 1/35, 1/37.5, 1/40, 1/42.5, 1/45, 1/47.5, 1/50, 1/55, 1/60, 1/65, 1/70, 1/75, 1/80, 1/85, 1/90, 1/95, or 1/100 of a thickness of the therapeutic region. In those embodiments where the control region comprises a single control region, the control region may have a thickness that is less than or equal to 1/10, 1/12.5, 1/15, 1/17.5, 1/20, 1/22.5, 1/25, 1/27.5, 1/30, 1/32.5, 1/35, 1/37.5, 1/40, 1/42.5, 1/45, 1/47.5, 1/50, 1/55, 1/60, 1/65, 1/70, 1/75, 1/80, 1/85, 1/90, 1/95, or 1/100 of a thickness of the therapeutic region. In those embodiments with multiple sub-control regions, one or more of the sub-control regions may individually be less than or equal to 1/10, 1/12.5, 1/15, 1/17.5, 1/20, 1/22.5, 1/25, 1/27.5, 1/30, 1/32.5, 1/35, 1/37.5, 1/40, 1/42.5, 1/45, 1/47.5, 1/50, 1/55, 1/60, 1/65, 1/70, 1/75, 1/80, 1/85, 1/90, 1/95, or 1/100 of a thickness of the depot. In those embodiments where the control region comprises a single control region, the control region may have a thickness that is less than or equal to 1/10, 1/12.5, 1/15, 1/17.5, 1/20, 1/22.5, 1/25, 1/27.5, 1/30, 1/32.5, 1/35, 1/37.5, 1/40, 1/42.5, 1/45, 1/47.5, 1/50, 1/55, 1/60, 1/65, 1/70, 1/75, 1/80, 1/85, 1/90, 1/95, or 1/100 of a thickness of the depot.

The control regions 300*a*, 300*b* may only cover a portion of the therapeutic region 200 such that a portion of each of the lateral surfaces (e.g., sidewall) of the therapeutic region 200 is exposed to physiologic fluids immediately upon implantation of the depot 100 in vivo. For example, at least prior to implantation, the exposed surfaces of the therapeutic region 200 may account for about 2% to about 15%, about 3% to about 12%, about 5% to about 10%, about 6% to about 8%, about 2%, about 3%, about 4%, about 5%, about 6%, about 7%, about 8%, about 9%, about 10% of the surface area of the depot 100. In some embodiments, at least prior to implantation, the ratio of the exposed surfaces of the therapeutic region 200 to the exposed surfaces of the control region 300 may be about 2% to about 15%, about 3% to about 12%, about 5% to about 10%, about 6% to about 8%, about 2%, about 3%, about 4%, about 5%, about 6%, about 7%, about 8%, about 9%, about 10% of the surface area of the depot 100.

When the depot 100 is exposed to physiologic fluids (or any similar fluid in an in vitro setting), the therapeutic agent will elute from the exposed surfaces 202 (in addition to through the control regions 300*a*, 300*b*), such that the therapeutic agent is released faster than if the therapeutic region 200 had no exposed regions. As such, the surface area of the exposed surfaces 202 may be tailored to provide an initial, controlled burst, followed by a tapering release (for example, similar to that shown at FIG. 3). The initial, more aggressive release of the therapeutic agent is slowed in part by the control regions 300*a*, 300*b* that initially reduce the surface area of the therapeutic region 200 exposed to the fluids. Unlike the depots 100 of the present technology, many conventional drug-eluting technologies provide an initial, uncontrolled burst release of drug when exposed to physiologic fluids. Several embodiments of depots of the present technology not only enable enough therapeutic agent to be implanted for several days' or weeks' worth of dosage to achieve a sustained, durable, in vivo pharmacological treatment, but they also release the therapeutic agent as prescribed and thereby prevent a substantial portion of the entire payload being released in an uncontrolled manner that could potentially result in complications to the patient and/or reduce the remaining payload such that there is not enough therapeutic agent remaining in the depot to deliver a therapeutic amount for the remaining duration of release.

In some embodiments, the depot 100 shown in FIG. 3 is configured such that about 20% to about 50% of the analgesic is released in the first about 3 days to about 5 days of the 14 days, and wherein at least 80% of the remaining analgesic is released in the last about 9 days to about 11 days of the 14 days. This release profile provides higher dosages of the therapeutic agent during the acute period after surgery compared to the subacute period. In some embodiments, the depot 100 shown in FIG. 3 is configured to release about 100 mg to about 500 mg of analgesic to the treatment site per day, and in some cases no more than 400 mg or no more than 300 mg of analgesic per day within the first 3 days of implantation and no more than 200 mg per day in the remaining days.

Several embodiments of the depot 100 shown in FIG. 3 are also configured to maintain their structural integrity even after a substantial portion of the releasing agent has eluted from the depot 100. As the releasing agent(s) dissolves and therapeutic agent(s) elutes, the functional mechanical aspects of the depot 100 may change over time. Such mechanical aspects include structural integrity, flexural strength, tensile strength, or other mechanical characteristics of the depot. If a depot 100 experiences too much degradation too fast, it may fail mechanically and release an undesirable burst of therapeutic agent into the body. Several embodiments of depots 100 shown in FIG. 3 are loaded with enough therapeutic agent to deliver 100 mg to 500 mg of the therapeutic agent per day while still being able to maintain its structural integrity such that depot remains largely intact up to at least 14 days after implantation. A depot can be sufficiently intact, for example, if it does not fracture into multiple component pieces with two or more of the resulting pieces being at least 5% of the previous size of the depot. Alternatively, or additionally, a depot can be considered to be sufficiently intact if the release rate of the therapeutic agent does not increase by more than a factor of three as compared to the release rate of therapeutic agent in a control depot submerged in a buffered solution.

The therapeutic agent can be at least 50%-95% by weight of the total weight of the depot 100 before implantation, or 55%-85% by weight of the total weight of the depot 100 before implantation, or 60%-75% by weight of the total weight of the depot 100 before implantation. Likewise, the polymer may be no more than 5%-50% by weight of the total weight of the depot 100 before implantation, or 10%-50% by weight of the total weight of the depot 100 before implantation, or 15%-45% by weight of the total weight of the depot 100 before implantation, or 20%-40% by weight of the total weight of the depot 100 before implantation, or no more than 25%, no more than 30%, no more than 35%, or no more than 40%. The ratio of the mass of the therapeutic agent in the depot 100 to the mass of the polymer in the depot 100 can be at least 16:1, 15:1, 14:1, 13:1, 12:1, 11:1, 10:1, 9:1, 8:1, 7:1, 6:1, 5:1, 4:1, 3:1, or 2:1.

Several embodiments of the depot 100 shown in FIG. 3 having one or more combinations of the parameters described in the preceding paragraphs have provided exceptional results in animal studies as described herein. For example, a depot 100 was configured such that (a) the thickness of the control regions 300*a-b* were each or collectively less than or equal to 1/50 of the thickness of the therapeutic region 200, (b) the mass of therapeutic agent payload was sufficient to release about 100 mg to about 500 mg of analgesic to the treatment site per day, and (c) the structural integrity was such that the depot remained largely intact for at least 14 days after implantation. These embodiments were able to release about 20% to about 50% of the analgesic payload in the first about 3 days to about 5 days of the 14 days, and then release at least 80% of the remaining analgesic payload in the last about 9 days to about 11 days of the 14 days. This was unexpected because, at least in part, (a) providing such a large payload of therapeutic agent in the therapeutic region was expected to cause the depot 100 fail mechanically on or before 14 days post-implant, and (b) no disclosed devices had achieved a release profile wherein about 20% to about 50% of the analgesic was released in the first about 3 days to about 5 days of the 14 days, and then at least 80% of the remaining analgesic was released in the last about 9 days to about 11 days of the 14 days.

In some embodiments, one or more control regions 300 of the depot 100 may comprise two or more sub-control regions. For example, as shown in FIG. 4, the depot 100 may have a first control region 300*a* and a second control region 300*b*, each of which comprises first and second sub-control regions 302*a*, 302*b* and 302*c*, 302*d*, respectively. The first and second control regions 300*a*, 300*b* and/or one, some or all of the sub-control regions 302*a*-302*d* may have the same or different amounts of releasing agent, the same or different concentrations of releasing agent, the same or different releasing agents, the same or different amounts of polymer, the same or different polymers, the same or different polymer to releasing agent ratios, and/or the same or different thicknesses. In some embodiments, the concentration of the releasing agent in the individual outer control sub-regions 302*a*, 302*d* is less than the concentration of the releasing agent in the individual inner control sub-regions 302*b*, 302*c* such that the outer portion of the collective control region will elute the therapeutic agent more slowly than the inner portion of the collective control region. In some embodiments, the concentration of the releasing agent in the individual outer control sub-regions 302*a*, 302*d* is greater than the concentration of the releasing agent in the individual inner control sub-regions 302*b*, 302*c*. In those embodiments where the control region includes more than two sub-regions, the concentration of releasing agent per sub-region or layer may increase, decrease, or remain constant as the sub-control regions are farther away from the therapeutic region 200.

In certain embodiments, the outer control sub-regions include at least 5% by weight of the releasing agent, at least 10% by weight of the releasing agent, at least 15% by weight of the releasing agent, at least 20% by weight of the releasing agent, at least 25% by weight of the releasing agent, at least 30% by weight of the releasing agent, at least 35% by weight of the releasing agent, at least 40% by weight of the releasing agent, at least 45% by weight of the releasing agent, or at least 50% by weight of the releasing agent. In some embodiments, the inner control sub-regions include at least 5% by weight of the releasing agent, at least 10% by weight of the releasing agent, at least 15% by weight of the releasing agent, at least 20% by weight of the releasing agent, at least 25% by weight of the releasing agent, at least 30% by weight of the releasing agent, at least 35% by weight of the releasing agent, at least 40% by weight of the releasing agent, at least 45% by weight of the releasing agent, or at least 50% by weight of the releasing agent. In some embodiments, the outer control sub-regions may include a first amount of the releasing agent and the inner control sub-regions may include a second amount of the releasing agent, where the second amount is at least 200%, at least 300%, at least 400%, or at least 500% greater than the first amount.

FIGS. 5-7 show depot embodiments having a plurality of alternating therapeutic regions 200 and control regions 300 in accordance with the present technology. The depot 100 may have two or more control regions 300 and/or sub-regions 302 (e.g., 2, 3, 4, 5, 6, 7, 8, 9, 10, 20, etc.), and the depot 100 may have one or more therapeutic regions 200 and/or sub-regions 202 (e.g., 1, 2, 3, 4, 5, 6, 7, 10, 15, 20, etc.) surrounded by at least one control region 300 and/or sub-region 302. In some embodiments, each of the therapeutic regions 200 may comprise a single layer and/or each of the control regions 300 may comprise a single layer. In some embodiments, one, some, or all of the therapeutic regions 200 may comprise multiple layers and/or one, some, or all of the control regions 300 may comprise multiple layers. In some embodiments, for example as shown in FIGS. 5 and 6, two or more sub-regions 302*a-b* (FIG. 5) and 302*a-b* and 302*c-d* (FIG. 6) may be adjacent to each other between sub-regions 202 of the therapeutic region 200. Moreover, one or more of the individual control regions 300 and/or one or more of the therapeutic regions 200 may have the same or different amounts and/or types of releasing agent, and one or more of the therapeutic regions may have the same or different amounts and/or types of therapeutic agent.

The embodiments shown in FIGS. 5-7 may be beneficial where the therapeutic region comprises a large payload of the therapeutic agent (e.g., equivalent to many days, weeks or months of dosage). These embodiments may be beneficial because, with such a large payload, should the therapeutic region 200 be exposed to the body abruptly, the entire payload may be released prematurely, subjecting the patient to an abnormally and undesirably high dose of the therapeutic agent. For example, if the integrity of the control region 300 were compromised, the patient may be exposed in vivo to the therapeutic agent at a higher rate than intended, potentially resulting in a clinical complication. Particularly with respect to the administration of local anesthetics (e.g., bupivacaine, ropivacaine, etc.), manufacturing guidelines recommend no more than 400 mg should be administered within a 24-hour period. However, multiple studies have demonstrated that doses higher than 400 mg from extended release products are safe due to their slower release over an extended period of time. Regardless, in the event that a control region 300 is compromised, it is desirable for the patient to be subjected only to a fraction of the total payload, whereby the fraction to which the patient is exposed if prematurely released would be within safety margins for the particular therapeutic agent. The structural integrity of the control regions 300, as well as that of the therapeutic region(s) 200, is an important property for depots with large masses of therapeutic agents that are to be delivered over a long period of time.

To address this concern, in some embodiments of the present technology, the depot 100 may comprise multiple therapeutic regions 200 separated by one or more control regions 300 (for example, as shown in FIGS. 5-7). Such a configuration allows the therapeutic agent in each therapeutic region 200 (which carries a fraction of the total payload), to be individually sequestered. In the event a particular control region is compromised, only the fractional payload corresponding to the therapeutic region associated with the compromised control region would prematurely release. For example, in some of the foregoing embodiments, the total payload of the depot 100 may be at least 100 mg, at least 150 mg, at least 200 mg, at least 300 mg, at least 400 mg, at least 500 mg, at least 600 mg, at least 700 mg, at least 800 mg, at least 900 mg, or at least 1000 mg of therapeutic agent, such as an analgesic (e.g., bupivacaine, ropivacaine, etc.). Likewise, in some embodiments the fractional payload of each therapeutic region or sub-region may be up to 1%, up to 5%, up to 10%, up to 15%, up to 20%, up to 25%, up to 30%, up to 40%, up to 50%, up to 60%, up to 70%, up to 80%, up to 90%, or up to 100% of the total payload contained within the depot 100. As a result, if any single sub-region 202 of the therapeutic region 200 is compromised, it can release only a proportionate fraction of the total payload of the depot.

In some embodiments, each of the therapeutic regions and each of the control regions is a micro-thin layer, i.e., having a layer thickness that is less than 1 mm. In some embodiments, the depot comprises from about 2 to about 100 therapeutic regions, or from about 2 to about 50 therapeutic regions, or from about 2 to about 10 therapeutic regions.

FIGS. 8-11 show some aspects of the present technology in which the depots 100 may have one or more therapeutic regions 200 completely enclosed or surrounded by one or more control regions 300. In contrast to the previously described embodiments, at least one therapeutic region of such fully-enclosed embodiments does not have any exposed surface area. For example, as shown in FIGS. 8 and 9, in some embodiments the depot 100 may comprise a therapeutic region 200 surrounded or fully-enclosed by a control region 300 such that no portion of the therapeutic region 200 is exposed through the control region 300. As a result, the control region 300 substantially prevents contact between the therapeutic agent and physiologic fluids, thereby preventing an uncontrolled, burst release of the therapeutic agent when implanted. Over time, the releasing agent imbedded in the polymer of the control region 300 contacts physiologic fluids and dissolves, thereby forming diffusion openings in the control region. The combination of the restriction imposed by the control region and the diffusion openings formed by dissolution of the releasing agent enables a controlled release of the therapeutic agent from the depot over the course of several days, weeks, or months. Although the depot 100 is shown as a rectangular, thin film in FIGS. 8 and 9, in other embodiments the depot 100 may have other shapes, sizes, or forms.

FIG. 10 illustrates a depot 100 having a therapeutic region 200 fully-enclosed by a control region 300 having a first control region 300*a* and a second control region 300*b*. As depicted in FIG. 10, in some embodiments the therapeutic region 200 may be sandwiched between the first control region 300*a* and the second control region 300*b*, and the first and second control regions 300*a-b* may be bonded via heat compression around the therapeutic region 200 to enclose the therapeutic region 200 therebetween. In certain embodiments, a bioresorbable polymer may be wrapped around the entire depot and sealed on the top or bottom surface creating a control region structure similar to that depicted in FIG. 9A. The outer portion of the first and second control regions 300*a-b* may be incorporated as the final wrapped layer to seal the edges. Additionally, the first and second control regions 300*a-b* can be integrally formed with each other using dip coating and/or spray coating techniques, such as dipping the therapeutic region 200 in a solution of the control region material or spraying a solution of control region material onto the surfaces of the therapeutic region 200.

In FIG. 10, the first control region 300*a* can have first and second sub-regions 302*a-b*, and the second control region 300*b* can have first and second sub-regions 302*c-d*. The first control region 300*a* can define a top control region member, and the first and second sub-regions 302*a-b* can comprise a first top control layer and a second top control layer, respectively. The second control region 300*b* can define a bottom control region member, and the first and second sub-regions 302*c-d* can comprise a first bottom control layer and a second bottom control layer, respectively. The first and second top/bottom control layers can be any variation of the first and second control sub-regions discussed above with reference to FIG. 5. In addition, the first top control layer of the top control region member may have the same or different properties (e.g., thickness, polymer, releasing agent, concentration of releasing agent, total amount of releasing agent, polymer to releasing agent ratio, etc.) as the first bottom control layer of the bottom control region member. Similarly, the second top control layer of the top control region member may have the same or different properties as the second bottom control layer of the bottom control region member. Variations in the loading and construction of the layers may be designed into the depot 100 to achieve a release profile or kinetics that suits the objectives of the intended therapy. In other embodiments, the first control region 300*a* and/or the second control region 300*b* has a single layer.

Figure 11:
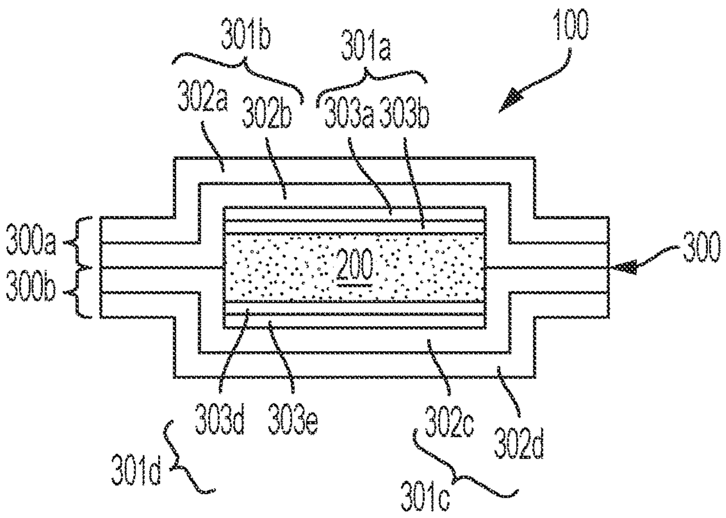
FIG. 11 is a cross-sectional view of a depot in accordance with some embodiments of the present technology.

FIG. 11 shows some embodiments in which the depot 100 may have a therapeutic region 200 fully-enclosed by a control region 300 having different sub-region configurations. The depot 100 of FIG. 11 includes a first control region 300*a* and a second control region 300*b* that together fully enclose the therapeutic region 200. In contrast to the depot 100 shown in FIG. 10, the first control region 300*a* has an outer top control region 301*a* with first and second top sub-control regions 302*a* and 302*b*, respectively, and an inner top control region 301*b* with first and second top layers 303*a* and 303*b*. The first and second top layers 303*a-b* are over only the top surface of the therapeutic region 200, while the first and second top sub-control regions 302*a-b* cover a portion of the lateral surfaces of the therapeutic region 200 and the inner top control region 301*b*. The second control region 300*b* has an outer bottom control region 301*c* with first and second bottom sub-control regions 302*c* and 302*d*, respectively, and an inner bottom control region 301*d* with first and second bottom layers 303*d* and 303*e*, respectively. As such, when the depot 100 is positioned at the treatment site in vivo, the outer top and bottom control regions 301*a* and 301*c* are between: (a) the therapeutic region 200 and the inner top and bottom control regions 301*b* and 301*d*, respectively, and (b) physiologic fluids at the treatment site. In certain embodiments, such as that shown in FIG. 11, one or more of the outer top/bottom control regions 301*a*/301*c* may comprise one or more control sub-regions, and one or more inner top/bottom control regions 301*b*/301*d* may include one or more control sub-regions.

Figure 12:
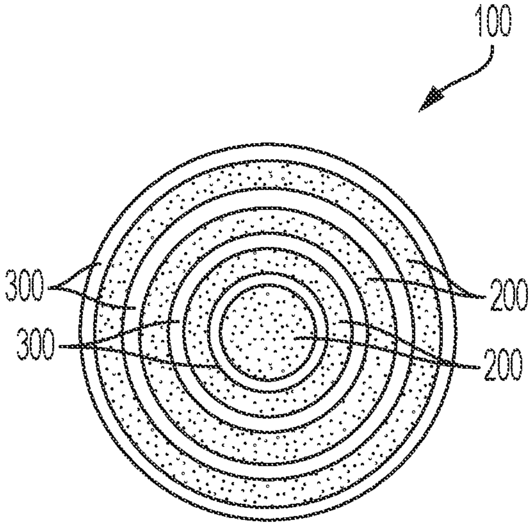
FIG. 12 is a cross-sectional view of a depot in accordance with some embodiments of the present technology.

FIG. 12 shows a cross-section of a spherical depot 100 in accordance with several embodiments of the present technology having a plurality of alternating therapeutic regions 200 and control regions 300 in accordance with the present technology. The depot 100 may have two or more control regions 300 (e.g., 2, 3, 4, 5, 6, 7, 8, 9, 10, 20, etc.), and the depot may have one or more therapeutic regions 200 (e.g., 1, 2, 3, 4, 5, 6, 7, 10, 15, 20, etc.) surrounded by at least one control region 300. In some embodiments, each of the therapeutic regions 200 may comprise a single layer and/or each of the control regions 300 may comprise a single layer. In some embodiments, one, some, or all of the therapeutic regions 200 may comprise multiple layers and/or one, some, or all of the control regions 300 may comprise multiple layers. Moreover, one or more of the individual control regions 200 and/or one or more of the therapeutic regions 300 may have the same or different amounts and/or types of releasing agent, and one or more of the therapeutic regions 200 may have the same or different amounts and/or types of therapeutic agent.

Figure 13:
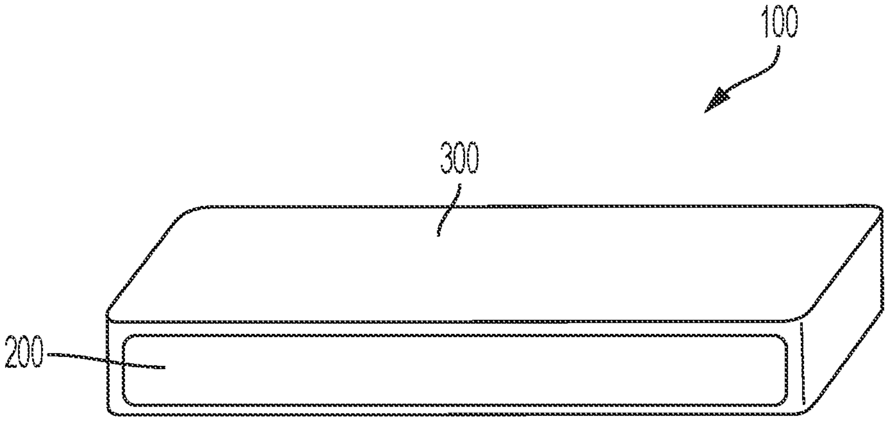
FIG. 13 is an isometric view of a depot in accordance with some embodiments of the present technology.

FIG. 13 shows a depot 100 in accordance with several embodiments of the present technology having a therapeutic region 200 enclosed on the top and bottom surfaces as well as two of the four lateral surfaces by a control region 300. This configuration is expected to release the therapeutic agent more slowly, at least initially, compared to a depot with the same dimensions and fully exposed lateral surfaces (see, e.g., the depot 100 shown in FIG. 3).

The release kinetics of the depots of the present technology may also be tuned for a particular application by varying the shape and size of the depot 100. Depending on the therapeutic dosage needs, anatomical targets, etc., the depot 100 can be different sizes, shapes, and forms for implantation and/or injection in the body by a clinical practitioner. The shape, size, and form of the depot 100 should be selected to allow for ease in positioning the depot at the target tissue site, and to reduce the likelihood of, or altogether prevent, the depot from moving after implantation or injection. This may be especially true for depots being positioned within a joint (such as a knee joint), wherein the depot is a flexible solid that is structurally capable of being handled by a clinician during the normal course of a surgery without breaking into multiple pieces and/or losing its general shape. Additionally, the depot may be configured to be placed in the knee of a patient and release the analgesic in vivo for up to 7 days without breaking into multiple pieces.

Some of the form factors producible from the depot 100 or to be used adjunctive to the depot for implantation and fixation into the body include: strips, ribbons, hooks, rods, tubes, patches, corkscrew-formed ribbons, partial or full rings, nails, screws, tacks, rivets, threads, tapes, woven forms, t-shaped anchors, staples, discs, pillows, balloons, braids, tapered forms, wedge forms, chisel forms, castellated forms, stent structures, suture buttresses, coil springs, sponges, capsules, coatings, matrices, wafers, sheets, strips, ribbons, pills, and pellets.

The depot 100 may also be processed into a component of the form factors mentioned in the previous paragraph. For example, the depot could be rolled and incorporated into tubes, screws, tacks, or the like. In the case of woven embodiments, the depot may be incorporated into a multilayer woven film/braid/mesh wherein some of the filaments used are not the inventive device. In one example, the depot is interwoven with Dacron, polyethylene or the like. For the sake of clarity, any form factor corresponding to the depot of the present technology, including those where only a portion or fragment of the form factor incorporates the depot, may be referred to herein as a "depot."

Figure 14A:
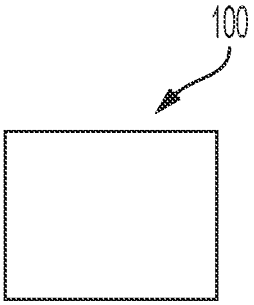
FIGS. 14A-H are depots having different cross-sectional areas and shapes in accordance with the present technology.
Figure 14B:
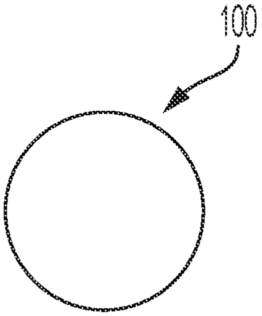
Figure 14C:
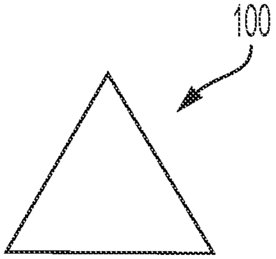
Figure 14D:
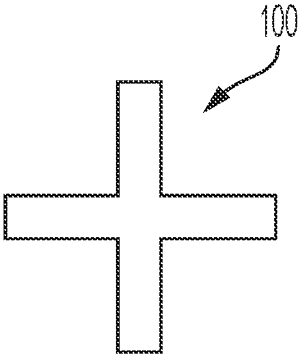
Figure 14E:
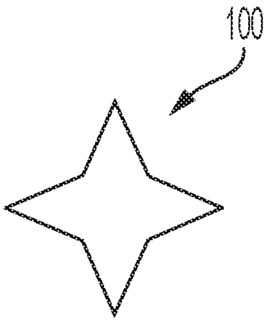
Figure 14F:
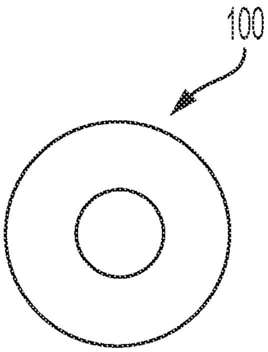
Figure 14G:
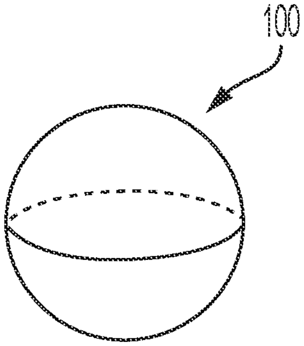
Figure 14H:
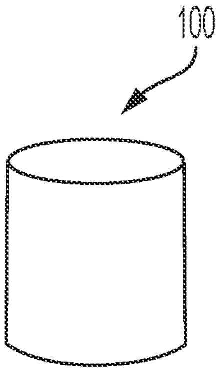

As shown in the cross-sectional views of FIGS. 14A-14H, in various embodiments, the depot 100 can be shaped like a sphere, a cylinder such as a rod or fiber, a flat surface such as a disc, film, ribbon, strip or sheet, a paste, a slab, microparticles, nanoparticles, pellets, mesh or the like. FIG. 14A shows a rectilinear depot 100. FIG. 14B shows a circular depot 100. FIG. shows a triangular depot 100. FIG. 14D show cross-like depot 100, FIG. 14E shows a star-like depot 100, and FIG. 14F shows a toroidal depot 100. FIG. 14G shows a spheroid depot 100, and FIG. 14H shows a cylindrical depot 100. The shape of the depot 100 can be selected according to the anatomy to fit within a given space and provide the desired fixation and flexibility properties. This is because the fit, fixation and flexibility of the depot may enhance the ease of implanting the depot, ensure delivery of the therapeutic agent to the target site, and prolong the durability of the implant in dynamic implant sites.

In various embodiments, the depot can be different sizes, for example, the depot may be a length of from about 0.4 mm to 100 mm and have a diameter or thickness of from about 0.01 to about 5 mm. In various embodiments, the depot may have a layer thickness of from about 0.005 to 5.0 mm, such as, for example, from 0.05 to 2.0 mm. In some embodiments, the shape may be a rectangular or square sheet having a ratio of width to thickness in the range of 20 or greater, 25 or greater, 30 or greater, 35 or greater, 40 or greater, 45 or greater, or 50 or greater.

In some embodiments, a thickness of the control region (a single sub-control region or all sub-control regions combined) is less than or equal to 1/10, 1/12.5, 1/15, 1/17.5, 1/20, 1/22.5, 1/25, 1/27.5, 1/30, 1/32.5, 1/35, 1/37.5, 1/40, 1/42.5, 1/45, 1/47.5, 1/50, 1/55, 1/60, 1/65, 1/70, 1/75, 1/80, 1/85, 1/90, 1/95, or 1/100 of a thickness of the therapeutic region. In those embodiments with multiple sub-control regions, one or more of the sub-control regions may individually be less than or equal to 1/10, 1/12.5, 1/15, 1/17.5, 1/20, 1/22.5, 1/25, 1/27.5, 1/30, 1/32.5, 1/35, 1/37.5, 1/40, 1/42.5, 1/45, 1/47.5, 1/50, 1/55, 1/60, 1/65, 1/70, 1/75, 1/80, 1/85, 1/90, 1/95, or 1/100 of a thickness of the therapeutic region. In those embodiments where the control region comprises a single control region, the control region may have a thickness that is less than or equal to 1/10, 1/12.5, 1/15, 1/17.5, 1/20, 1/22.5, 1/25, 1/27.5, 1/30, 1/32.5, 1/35, 1/37.5, 1/40, 1/42.5, 1/45, 1/47.5, 1/50, 1/55, 1/60, 1/65, 1/70, 1/75, 1/80, 1/85, 1/90, 1/95, or 1/100 of a thickness of the therapeutic region. In those embodiments with multiple sub-control regions, one or more of the sub-control regions may individually be less than or equal to 1/10, 1/12.5, 1/15, 1/17.5, 1/20, 1/22.5, 1/25, 1/27.5, 1/30, 1/32.5, 1/35, 1/37.5, 1/40, 1/42.5, 1/45, 1/47.5, 1/50, 1/55, 1/60, 1/65, 1/70, 1/75, 1/80, 1/85, 1/90, 1/95, or 1/100 of a thickness of the depot. In those embodiments where the control region comprises a single control region, the control region may have a thickness that is less than or equal to 1/10, 1/12.5, 1/15, 1/17.5, 1/20, 1/22.5, 1/25, 1/27.5, 1/30, 1/32.5, 1/35, 1/37.5, 1/40, 1/42.5, 1/45, 1/47.5, 1/50, 1/55, 1/60, 1/65, 1/70, 1/75, 1/80, 1/85, 1/90, 1/95, or 1/100 of a thickness of the depot.

In some embodiments, the depot 100 has a width and a thickness, and a ratio of the width to the thickness is 21 or greater. In some embodiments, the ratio is 22 or greater, 23 or greater, 24 or greater, 25 or greater, 26 or greater, 27 or greater, 28 or greater, 29 or greater, 30 or greater, 35 or greater, 40 or greater, 45 or greater, or 50 or greater.

In some embodiments, the depot 100 has a surface area and a volume, and a ratio of the surface area to volume is at least 1, at least 1.5, at least 2, at least 2.5, or at least 3.

In any of the foregoing embodiments shown and described above with respect to FIGS. 2-14H, dissolution of the releasing agent(s) and elution of the therapeutic agent(s) can change functional mechanical aspects of the depot 100 over time. Such mechanical aspects include structural integrity, flexural strength, tensile strength, or other mechanical characteristics of the depot 100. In some instances, undesirable degradation of the depot 100, such as premature degradation, can cause mechanical failure of the depot 100 and a corresponding undesirable burst release of therapeutic agent into the body. Accordingly, it can be beneficial for the depot 100 to maintain sufficient flexural strength and/or mechanical integrity in vivo for at least a predetermined period of time or until a predetermined proportion of therapeutic agent has been released from the depot 100. The depot 100 can be considered to maintain its structural integrity if the depot 100 remains largely intact with only partial or gradual reduction due to elution of therapeutic agent or dissolution of the control layers or releasing agent. The depot 100 can be considered to lose its structural integrity if it separates (e.g., fractures) into multiple component pieces, for example, with two or more of the resulting pieces being at least 5% of the previous size of the depot 100. Alternatively, or additionally, the depot 100 can be considered to lose its structural integrity if the release rate of the therapeutic agent increases by more than a factor of three as compared to the release rate of therapeutic agent in a control depot submerged in a buffered solution.

In some embodiments, the depot 100 is configured to maintain its structural integrity in vivo for at least a predetermined length of time. For example, the depot 100 can be configured to maintain its structural integrity in vivo for at least I day, at least 2 days, at least 3 days, at least 4 days, at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, at least 20 days, at least 21 days, at least 22 days, at least 23 days, at least 24 days, at least 25 days, at least 26 days, at least 27 days, at least 28 days, at least 29 days, or at least 30 days, at least 40 days, at least 50 days, at least 60 days, at least 70 days, at least 90 days, at least 100 days, at least 200 days, at least 300 days, or at least 365 days.

In some embodiments, the depot 100 is configured to maintain its structural integrity in vivo until at least a predetermined proportion of therapeutic agent payload has been released from the depot. For example, the depot 100 can be configured to maintain its structural integrity in vivo until at least 5% by weight of the original payload has been released, at least 10% by weight of the original payload has been released, at least 15% by weight of the original payload has been released, at least 20% by weight of the original payload has been released, at least 25% by weight of the original payload has been released, at least 30% by weight of the original payload has been released, at least 35% by weight of the original payload has been released, at least 40% by weight of the original payload has been released, at least 45% by weight of the original payload has been released, at least 50% by weight of the original payload has been released, at least 55% by weight of the original payload has been released, at least 60% by weight of the original payload has been released, at least 65% by weight of the original payload has been released, at least 70% by weight of the original payload has been released, at least 75% by weight of the original payload has been released, at least 80% by weight of the original payload has been released, at least 85% by weight of the original payload has been released, at least 90% by weight of the original payload has been released, or until at least 95% by weight of the original payload has been released.

One aspect of the structural integrity of the depot 100 when it is in vivo can be quantified using a bend test, such as a three-point bend test that measures flexural properties including the flexural strength and/or maximum flexural stress sustained by a specimen before breaking. Such a bend test may represent (e.g., simulate) the forces that the depot 100 will encounter in vivo in an anatomical joint (e.g., a knee joint). In one example, a depot can be subjected to a three-point bend test based on ASTM-D790-17, "Standard Test Methods for Flexural Properties of Unreinforced and Reinforced Plastics and Electrical Insulating Materials." The text of this standard is hereby incorporated by reference in its entirety. The depot 100 may be suspended in a medium configured to simulate in vivo conditions, for example a phosphate buffered saline (PBS) at approximately 37° C. The bend test may be performed after different time periods of submersion in the medium to evaluate changes in the flexural strength of the depot 100 over time in simulated in vivo conditions.

Figure 15:
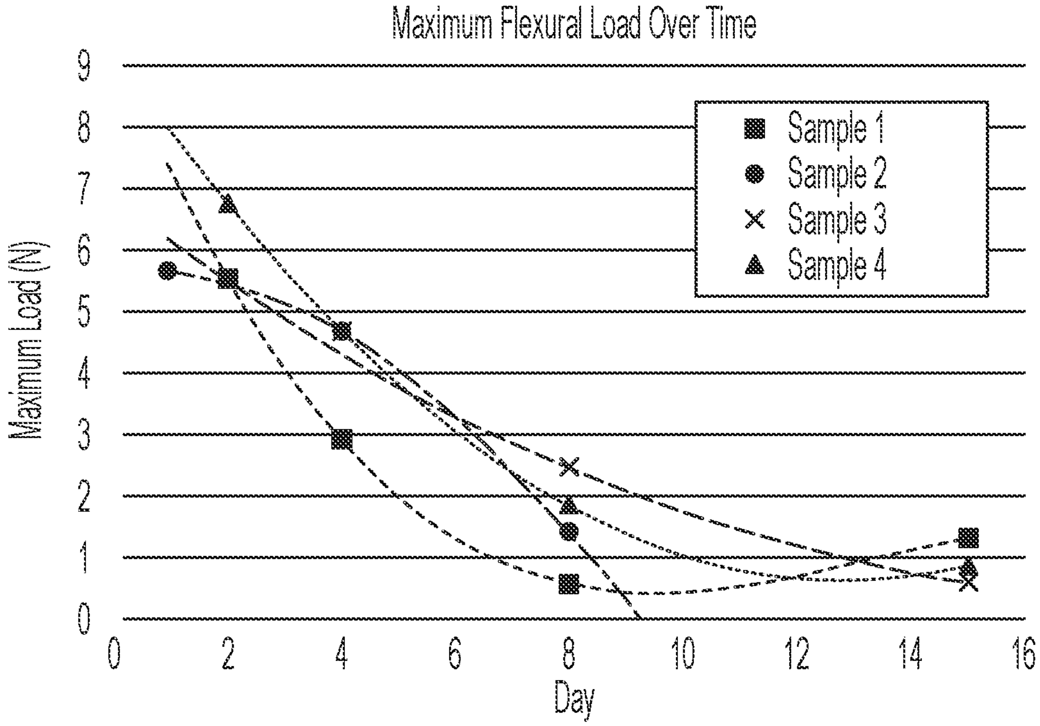
FIG. 15 depicts the maximum flexural load of an implant over time from testing performed on implant samples submerged in buffered solution.

Table 1 shows the maximum flexural load sustained by four different samples of the depot 100 at different time periods following submersion in the medium as measured using a three-point bend test with maximum deflection set at 2.13 mm. The values in Table 1 reflect measurements made from two instances of each of the listed samples. FIG. 15 is a graph illustrating these values plotted graphically and fitted with trendlines. In each of these four samples, the depot 100 includes a therapeutic region 200 surrounded by upper and lower control regions 300*a-b* as shown and described above with reference to FIG. 4 or 5. The therapeutic region 200 has exposed lateral surfaces 202 between the first and second control regions 300*a-b*. The depots 100 each have lateral dimensions of approximately 2.5 cm by 1.5 cm, with a thickness of approximately 1 mm.

Sample 1 is a depot having a therapeutic region with a ratio by weight of releasing agent to polymer to therapeutic agent of 0.5:10:20. The polymer in this sample is P(DL)GACL with a PDLLA:PGA:PCL ratio of 6:3:1, the releasing agent is Tween 20, and the therapeutic agent is bupivacaine hydrochloride. In this sample, the depot includes a first control region 300*a* comprising a single control layer over the upper surface of the therapeutic region 200 and a second control region 300*b* comprising single control layer over the lower surface of the therapeutic region 200, as shown and described above with reference to FIG. 3. Each control region 300*a-b* individually has a ratio of releasing agent to polymer of 5:10.

Sample 2 is a depot having a therapeutic region 200 with a ratio by weight of releasing agent to polymer to therapeutic agent of 1:10:20. The polymer in this sample is PLGA with control layer over the lower surface of the therapeutic region 200, as shown and described above with reference to FIG. 3. Each control region 300*a-b* individually has a ratio of releasing agent to polymer of 5:10.

Sample 3 is a depot having therapeutic region 200 with a ratio by weight of releasing agent to polymer to therapeutic agent of 5:10:20. The polymer in this sample is P(DL)GACL with a PDLLA:PGA:PCL ratio of 6:3:1, the releasing agent is Tween 20, and the therapeutic agent is bupivacaine hydrochloride. In this sample, the depot includes a control region 300 comprising a first control region 300*a* with two sub-control regions 302*a-b* over the upper surface of the therapeutic region 200, and a second control region 300*b* with two sub-control regions 302*c-d*, as shown and described above with reference to FIG. 5. Each of the inner sub-control regions 302*b* and 302*c* contacts the surface of the therapeutic region 200 and has a ratio of releasing agent to polymer of 5:10, and each of the outer sub-control regions 302*a* and 302*d* has a ratio of releasing agent to polymer of 1:10. The depot of Sample 3, therefore, includes a total of four sub-control regions.

Sample 4 is a depot having a therapeutic region 200 with a ratio by weight of releasing agent to polymer to therapeutic agent of 5:10:20. The polymer in this sample is PLGA with a PLA:PGA ratio of 1:1, the releasing agent is Tween 20, and the therapeutic agent is bupivacaine hydrochloride. As with Sample 3, the depot of Sample 4 includes a control region 300 having first and second control region 300*a-b* that each have two sub-control regions 302*a-b* and 302*c-d*, respectively, as shown and described with respect to FIG. 5. The depot of Sample 4 according also has a total of four sub-control regions 302*a-d*, two over the upper surface of the therapeutic region 200 and two over the lower surface of the therapeutic region 200. The inner of the sub-control regions 302*b* and 302*c* has a ratio of releasing agent to polymer of 5:10, and the outer of the sub-control regions 302*a* and 302*d* has a ratio of releasing agent to polymer of 1:10.

TABLE 1

| Depot Sample | Day 0 | Day 1 | Day 3 | Day 7 | Day 14 | Day 28 |
|---|---|---|---|---|---|---|
| Sample 1: P(DL)GACL 6:3:1 2 control layers | No break | 5.553 N 1.25 lbf | 2.903 N 0.0653 lbf | 0.569 N 0.134 lbf | 1.263 N 0.284 lbf | Not tested |
| Sample 2: PLGA 1:1 2 control layers | 5.623 N 1.264 lbf | 5.447 N 1.22 lbf | 4.623 N 1.04 lbf | 1.386 N 0.312 lbf | Not tested | Not tested |
| Sample 3: P(DL)GACL 6:3:1 4 control layers | No break | 5.474 N 1.23 lbf | Not tested | 2.430 N 0.546 lbf | 0.605 N 0.136 lbf | Sample degraded |
| Sample 4: PLGA 1:1 4 control layers | No break | 6.763 N 1.52 lbf | Not tested | 1.816 N 0.408 lbf | 0.869 N 0.195 lbf | Sample degraded |

a PLA:PGA ratio of 1:1, the releasing agent is Tween 20, and the therapeutic agent is bupivacaine hydrochloride. Similar to Sample 1, the depot of Sample 2 includes a control region 300 comprising a first control region 300*a* with a single control layer over the upper surface of the therapeutic region 200 and a second control region 300*b* comprising a single As shown in Table 1, all samples were intact and maintained sufficient structural integrity after 14 days of being suspended in the medium to withstand a bending force before fracturing. Although the maximum load tolerated by each sample decreased over time, the flexural strength of these samples at 14 days was sufficient to maintain the structural integrity desired for implantation in an active joint, such as the knee or shoulder. As shown above, for two of the samples tested at 28 days, the samples had degraded such that the test could not be performed because the sample was no longer structurally intact. In such instances, it may be desirable to configure the depots such that all or substantially all the therapeutic agent payload has been released from the depot prior to its degradation and loss of structural integrity.

In this series of experiments summarized in Table 1, the sample depots are generally flexible at Day 0 before submersion in PBS. Following submersion, the flexural strength of the depots decreased such that the depots became more brittle with time. Yet, at 7-14 days, the depots were still sufficiently functionally intact. Without being bound by theory, it is believed that after the therapeutic agent has eluted, the depots gradually become an empty polymer matrix. For example, after 14-28 days in the solution, the depots may weigh only approximately 30% of their starting weight before submersion in the PBS. At this lower weight and in the porous state, the depots may be more brittle, with lower flexural strength and less resistance to bending loads.

As noted above, it can be advantageous for the depots 100 to maintain their structural integrity and flexural strength even while they gradually degrade as the therapeutic agent payload releases into the body. In some embodiments, the depot 100 can be configured such that, in in vitro testing utilizing a three-point bend test, the flexural strength of the depot 100 decreases by no more than 95%, no more than 90%, no more than 85%, no more than 80%, no more than 75%, no more than 70%, no more than 65%, no more than 60%, no more than 55%, no more than 50%, no more than 45%, no more than 40%, no more than 35%, no more than 30%, no more than 25%, no more than 20%, no more than 15%, no more than 10%, or no more than 5% after being submerged in PBS for a predetermined period of time. In various embodiments, the predetermined period of time that the depot 100 is submerged in PBS before being subjected to the three-point bend test is 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, after 21 days, after 22 days, 23 days, 24 days, 25 days, 26 days, 27 days, 28 days, or more. In at least some embodiments, the change in flexural strength of the depot 100 can be measured between day 0 (e.g., before submersion in the PBS) and a subsequent time after some period of submersion in PBS. In other embodiments, the change in flexural strength of the depot 100 can be measured between day 1 (e.g., after 24 hours of submersion in PBS) and a subsequent time following longer submersion in PBS.

In some embodiments, the depot 100 can be configured such that, in in vitro testing utilizing a three-point bend test, the flexural strength of the depot 100 decreases by no more than 95%, no more than 90%, no more than 85%, no more than 80%, no more than 75%, no more than 70%, no more than 65%, no more than 60%, no more than 55%, no more than 50%, no more than 45%, no more than 40%, no more than 35%, no more than 30%, no more than 25%, no more than 20%, no more than 15%, no more than 10%, or no more than 5% over the time period in which a predetermined percentage of the initial therapeutic agent payload is released while the depot 100 is submerged in PBS. In various embodiments, the predetermined percentage of payload released when the depot 100 is submerged in PBS before being subjected to the three-point bend test is about 5%, about 10%, about 15%, about 20%, about 25%, about 30%, about 35%, about 40%, about 45%, about 50%, about 55%, about 60%, about 65%, about 70%, about 75%, about 80%, about t 85%, about 90%, or about 95%. As noted above, in at least some embodiments, the change in flexural strength of the depot 100 can be measured between day 0 (prior to submersion in PBS) or day 1 (after 24 hours of submersion in PBS) and a subsequent following longer submersion in PBS.

In some embodiments, the depot 100 has (a) lateral dimensions of about 1.0-3.0 cm, (b) a thickness of about 0.5-2.5 mm, and (c) a payload of therapeutic agent sufficient to release about 100 mg to about 500 mg of therapeutic agent per day for up to 7, 8, 9, 10, 11, 12, 13, 14, 15, 16, 17, 18, 19, or 20 days, and the depot 100 is configured to remain sufficiently mechanically intact to provide sustained, controlled release of therapeutic agent for at least 7 days. Such embodiments of the depot 100 can comprise the therapeutic region 200 with a therapeutic agent and the control region 300. The control region 300 can have first and second control regions 300*a-b*, such as those shown and described above with reference to FIGS. 4-13, and the control region 300 comprises a bioresorbable polymer and a releasing agent mixed with the bioresorbable polymer. The releasing agent is configured to dissolve when the depot 100 is placed in vivo to form diffusion openings in the control region 300. The depot 100 is further configured such that, following submersion of the depot 100 in a buffer solution for seven days, the flexural strength of the depot 100 decreases by no more than 75%, or by no more than 70%, or by no more than 65%, or by no more than 60%, or by no more than 55%, or by no more than 50%, or by no more than 45%

In some embodiments, the depot 100 has (a) lateral dimensions of about 1.0-3.0 cm, (b) a thickness of about 0.5-2.5 mm, and (c) a payload of therapeutic agent sufficient to release about 100 mg to about 500 mg of therapeutic agent per day for up to 7, 8, 9, 10, 11, 12, 13, 14, 15, 16, 17, 18, 19, or 20 days, and the depot 100 is configured to remain sufficiently mechanically intact to provide sustained, controlled release of therapeutic agent for at least 7 days. Such embodiments of the depot 100 can comprise the therapeutic region 200 with a therapeutic agent and the control region 300. The control region 300 can have first and second control regions 300*a-b*, such as those shown and described above with reference to FIGS. 4-13, and the control region 300 comprises a bioresorbable polymer and a releasing agent mixed with the bioresorbable polymer. The releasing agent is configured to dissolve when the depot 100 is placed in vivo to form diffusion openings in the control region 300. The depot is further configured such that, following submersion of the depot in buffer solution until approximately 75% of the therapeutic agent by weight has been released, the flexural strength of the depot decreases by no more than 75%, or by no more than 70%, or by no more than 65%, or by no more than 60%, or by no more than 55%, or by no more than 50%, or by no more than 45%.

A. Therapeutic Region

The total payload and release kinetics of the depots 100 of the present technology may be tuned for a particular application by varying the composition of the therapeutic region 200. In many embodiments, the therapeutic region 200 may include a high therapeutic payload of a therapeutic agent, especially as compared to other known polymer devices of equal thickness or polymer weight percentage. For example, the depots 100 of the present technology may comprise at least 15% by weight of the therapeutic agent, at least 20% by weight of the therapeutic agent, at least at least 25% by weight of the therapeutic agent, at least 30% by weight of the therapeutic agent, at least 35% by weight of the therapeutic agent, at least 40% by weight of the therapeutic agent, at least 45% by weight of the therapeutic agent, at least 50% by weight of the therapeutic agent, at least 55% by weight of the therapeutic agent, at least 60% by weight of the therapeutic agent, at least 65% by weight of the therapeutic agent, at least 70% by weight of the therapeutic agent, at least 75% by weight of the therapeutic agent, at least 80% by weight of the therapeutic agent, at least 85% by weight of the therapeutic agent, at least 90% by weight of the therapeutic agent, at least 95% by weight of the therapeutic agent, or 100% by weight of the therapeutic agent.

The therapeutic agent may be any of the therapeutic agents disclosed herein, for example in Section C ("Therapeutic Agents") below.

In various embodiments of the depots 100 disclosed herein, the therapeutic region 200 may take several different forms. In some embodiments (for example, FIG. 3), the therapeutic region 200 may comprise a single layer comprised of a therapeutic agent, a therapeutic agent mixed with a bioresorbable polymer, or a therapeutic agent mixed with a bioresorbable polymer and a releasing agent. In some embodiments, the therapeutic region 200 itself may comprise a structure having multiple layers or sub-regions of therapeutic agent (and/or bioresorbable polymer and/or releasing agent). Some or all layers or sub-regions of such a multiple layer therapeutic region 200 may be directly adjacent (i.e., in contact with) one another (laterally or axially), and/or some or all layers or sub-regions may be spaced apart with one or more other regions therebetween (such as control region(s) 300 and/or barrier region(s))). In some embodiments, 2, 3, 4, 5, 6, 7, 8, 9, 10 or more therapeutic sub-regions or layers may be grouped together and spaced apart from another therapeutic region or group of therapeutic sub-regions or layers (having the same or different numbers of layers as the other group) with one or more other regions therebetween (such as control region(s) 300 and/or barrier region(s))) (see, for example, FIG. 5, FIG. 6, etc.).

In any of the depot embodiments disclosed herein, the ratio of the mass of the therapeutic agent in the depot to the mass of polymer in the depot is at least 3:1, 3.5:1, 4:1, 4.5:1, 5:1, 5.5:1, 6:1, 6.5:1, 7:1, 8:1, 9:1, 10:1, 11:1, 12:1, 13:1, 14:1, 15:1, or 16:1.

In any of the depot embodiments disclosed herein, the ratio of the mass of the polymer in the therapeutic region 200 to the mass of therapeutic agent in the therapeutic region 200 is at least 1:1, 1:1.5, 1:2, 1:2.5, 1:3, 1:3.5, 1:4, 1:4.5, 1:5, 1:5.5, 1:6, 1:6.5, 1:7, 1:7.5, 1:8, 1:8.5, 1:9, 1:9.5, or 1:10.

In any of the embodiments disclosed herein, the weight ratio of releasing agent to polymer in the therapeutic region 200 may be 1:1, 1:1.5, 1:2, 1:3, 1:4, 1:5, 1:6, 1:7, 1:8, 1:9, 1:10, 1:11, 1:12, 1:13, 1:14, 1:15, or 1:16.

In some embodiments, the ratio of releasing agent to polymer to therapeutic agent in the therapeutic region 200 is of from about 0.1:10:20 to about 2:10:20, about 0.1:10:20 to about 1:10:20, about 0.1:10:20 to about 0.5:10:20, about 0.5:10:20 to about 0.1:10:20, or about 0.5:10:20 to about 1:10:20.

In any of the embodiments disclosed herein having a single therapeutic region 200, the therapeutic region 200 may have a thickness of from about 5 μm to 100 μm, 5 μm to 50 μm, 5 μm to 25 μm, 5 μm to 10 μm, 5 μm to 7 μm, 7 μm to 9 μm, 10 μm to 80 μm, 10 μm to 70 μm, 10 μm to 60 μm, 20 μm to 60 μm, 15 μm to 50 μm, about 15 μm, about 20 μm, about 25 μm, about 30 μm, about 35 μm, about 40 μm, about 45 m, about 50 μm, about 55 μm, about 60 μm, about 65 μm, about 70 μm, about 75 μm, about 80 μm, about 85 μm, about 90 μm, about 95 μm, about 100 μm, 100 μm to 2 mm, 100 μm to 1.5 mm, 100 μm to 1 mm, 100 μm to 200 μm, 200 μm to 300 μm, 300 μm to 400 μm, 400 μm to 500 μm, 500 μm to 600 μm, 600 μm to 700 μm, 700 μm to 800 μm, 800 μm to 900 μm, 900 μm to 1 mm, 1 mm to 1.5 mm, 200 μm to 600 μm, 400 μm to 1 mm, 500 μm to 1.1 mm, 800 μm to 1.1 mm, about 200 μm, about 300 μm, about 400 μm, about 500 μm, about 600 μm, about 700 μm, about 800 μm, about 900 μm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, or about 2 mm.

In those embodiments having multiple therapeutic regions and/or sub-regions, the individual sub-regions or combinations of some or all sub-regions may have a thickness of from about 5 μm to 100 μm, 5 μm to 50 μm, 5 μm to 25 μm, 5 μm to 10 μm, 5 μm to 7 μm, 7 μm to 9 μm, 10 μm to 80 μm, 10 μm to 70 μm, 10 μm to 60 μm, 20 μm to 60 μm, 15 μm to 50 μm, about 15 μm, about 20 μm, about 25 μm, about 30 μm, about 35 μm, about 40 μm, about 45 μm, about 50 μm, about 55 μm, about 60 μm, about 65 μm, about 70 μm, about 75 μm, about 80 μm, about 85 μm, about 90 μm, about 95 μm, about 100 μm, 100 μm to 2 mm, 100 μm to 1.5 mm, 100 μm to 1 mm, 100 μm to 200 μm, 200 μm to 300 μm, 300 μm to 400 μm, 400 μm to 500 μm, 500 μm to 600 μm, 600 μm to 700 μm, 700 μm to 800 μm, 800 μm to 900 μm, 900 μm to 1 mm, 1 mm to 1.5 mm, 200 μm to 600 μm, 400 μm to 1 mm, 500 μm to 1.1 mm, 800 μm to 1.1 mm, about 200 μm, about 300 μm, about 400 μm, about 500 μm, about 600 μm, about 700 μm, about 800 μm, about 900 μm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, or about 2 mm.

The therapeutic regions 200 of the present technology may comprise at least 15% by weight of the therapeutic agent, at least 20% by weight of the therapeutic agent, at least at least 25% by weight of the therapeutic agent, at least 30% by weight of the therapeutic agent, at least 35% by weight of the therapeutic agent, at least 40% by weight of the therapeutic agent, at least 45% by weight of the therapeutic agent, at least 50% by weight of the therapeutic agent, at least 55% by weight of the therapeutic agent, at least 60% by weight of the therapeutic agent, at least 65% by weight of the therapeutic agent, at least 70% by weight of the therapeutic agent, at least 75% by weight of the therapeutic agent, at least 80% by weight of the therapeutic agent, at least 85% by weight of the therapeutic agent, at least 90% by weight of the therapeutic agent, at least 95% by weight of the therapeutic agent, or 100% by weight of the therapeutic agent.

In any of the embodiments disclosed herein, the therapeutic region 200 may include of from about 0.1%-10% by weight of the releasing agent, about 0.1%-6% by weight of the releasing agent, 0.2%-10% by weight of the releasing agent, about 0.3%-6% by weight of the releasing agent, about 0.1%-1% by weight of the releasing agent, about 0.1%-0.5% by weight of the releasing agent, 1%-2% by weight of the releasing agent, about 1%-3% by weight of the releasing agent, or about 2%-6% by weight of the releasing agent. In those embodiments having multiple therapeutic regions or sub-regions, one or more of the therapeutic regions or sub-therapeutic regions may individually include of from about 0.1%-10% by weight of the releasing agent, about 0.1%-6% by weight of the releasing agent, 0.2%-10% by weight of the releasing agent, about 0.3%-6% by weight of the releasing agent, about 0.1%-1% by weight of the releasing agent, about 0.1%-0.5% by weight of the releasing agent, 1%-2% by weight of the releasing agent, about 1%-3% by weight of the releasing agent, or about 2%-6% by weight of the releasing agent. The therapeutic region 200 may not include any releasing agent. In those embodiments having multiple therapeutic regions and/or sub-regions, one, some, or all of the individual therapeutic regions and/or sub-regions may not include any releasing agent.

In any of the embodiments disclosed herein, the therapeutic region 200 may include no more than 5% by weight of the polymer, no more than 10% by weight of the polymer, no more than 15% by weight of the polymer, no more than 20% by weight of the polymer, no more than 25% by weight of the polymer, no more than 30% by weight of the polymer, no more than 35% by weight of the polymer, no more than 40% by weight of the polymer, no more than 45% by weight of the polymer, or no more than 50% by weight of the polymer. In those embodiments having multiple therapeutic regions or sub-regions, one or more of the therapeutic regions or sub-therapeutic regions may individually include no more than 5% by weight of the polymer, no more than 10% by weight of the polymer, no more than 15% by weight of the polymer, no more than 20% by weight of the polymer, no more than 25% by weight of the polymer, no more than 30% by weight of the polymer, no more than 35% by weight of the polymer, no more than 40% by weight of the polymer, no more than 45% by weight of the polymer, or no more than 50% by weight of the polymer. In some embodiments, the therapeutic region 200 may not include any polymer.

In those embodiments disclosed herein where the therapeutic region 200 includes multiple therapeutic regions or sub-regions, some or all of the therapeutic regions or sub-therapeutic regions may have the same or different amounts of releasing agent, the same or different concentrations of releasing agent, the same or different releasing agents, the same or different amounts of polymer, the same or different polymers, the same or different polymer to releasing agent ratios, the same or different amounts of therapeutic agents, the same or different types of therapeutic agents, and/or the same or different thicknesses. Moreover, a single therapeutic region or sub-region may comprise a single type of polymer or multiple types of polymers, a single type of releasing agent or multiple types of releasing agents, and/or a single type of therapeutic agent or multiple types of therapeutic agents. In those embodiments having multiple therapeutic regions and/or sub-regions, one, some, or all of the individual therapeutic regions and/or sub-regions may not include any polymer.

In some embodiments the therapeutic region 200 (or one or more therapeutic sub-regions) comprises the therapeutic agent as an essentially pure compound or formulated with a pharmaceutically acceptable carrier such as diluents, adjuvants, excipients or vehicles known to one skilled in the art B. Control Region The composition of the control region 300 may also be varied. For example, in many embodiments, the control region 300 does not include any therapeutic agent at least prior to implantation of the depot at the treatment site. In some embodiments, the control region 300 may include a therapeutic agent which may be the same as or different than the therapeutic agent in the therapeutic region 200.

Within the control region 300, the amount of releasing agent may be varied to achieve a faster or slower release of the therapeutic agent. In those embodiments where both the therapeutic region 200 and control region 300 include a releasing agent, the type of releasing agent within the therapeutic region 200 may be the same or different as the releasing agent in the control region 300. In some embodiments, a concentration of a first releasing agent within the control region is the greater than a concentration of a second releasing agent (the same or different as the first releasing agent) within the therapeutic region. In some embodiments, a concentration of the releasing agent within the control region is less than a concentration of the releasing agent within the therapeutic region. In some embodiments, a concentration of the releasing agent within the control region 300 is the same as a concentration of the releasing agent within the therapeutic region 200.

In various embodiments of the depots disclosed herein, the control region 300 may take several different forms. In some embodiments (for example, FIG. 3), the control region 300 may comprise a single layer on either side of the therapeutic region 200 comprised of a bioresorbable polymer mixed with a releasing agent. In some embodiments, the control region 300 itself may comprise a structure having multiple layers or sub-regions of bioresorbable polymer and releasing agent. Some or all layers or sub-regions of such a multiple layer control region 300 may be directly adjacent (i.e., in contact with) one another (laterally or axially), and/or some or all layers or sub-regions may be spaced apart with one or more other regions therebetween (such as therapeutic region(s) 200 and/or barrier region(s))). In some embodiments, 2, 3, 4, 5, 6, 7, 8, 9, 10 or more control sub-regions or layers may be grouped together and spaced apart from another control region or group of control sub-regions or layers (having the same or different numbers of layers as the other group) with one or more other regions therebetween (such as therapeutic region(s) 200 and/or barrier region(s))) (see, for example, FIG. 4, FIG. 5, etc.).

Without being bound by theory, it is believed that such a multilayer configuration improves the control region's ability to control the release of the therapeutic agent as compared to a single layer control region, even if the multilayer configuration has the same or lower thickness as the single layer control region. The channels left by dissolution of the releasing agent in both microlayers and/or sub-regions of the control region create a path for a released therapeutic agent to travel that is longer and, potentially, more cumbersome to traverse as compared to the more direct path created by the channels in the single layer control region. The control region(s) and/or sub-regions thereby regulate the therapeutic agent release rate by allowing a releasing agent to form independent non-contiguous channels through one or more control regions and/or sub-regions. In those embodiments having multiple control layers or sub-regions, some or all of the control layers or sub-regions may be heat compressed together. The one or more control regions, heat-compressed first or not, may be heat compressed together with the therapeutic region 200. Having a control region 300 with multiple layers may provide a more linear, controlled release of the therapeutic agent over time (beyond the first day of implantation). In addition, layering of the control region 300 may also contribute to a more flexible, structurally competent depot (as compared to a depot having a therapeutic region comprised of pure therapeutic agent). Such durability is beneficial for the clinician when handling/manipulating the depot 100 before and while positioning the depot 100 at a treatment site.

In any of the embodiments disclosed herein having a single control region 300, the thickness of the control region 300 may be of from about 5 μm to 100 μm, 5 μm to 50 μm, 5 μm to 25 μm, 5 μm to 10 μm, 5 μm to 7 μm, 7 μm to 9 μm, 10 μm to 80 μm, 10 μm to 70 μm, 10 μm to 60 μm, 20 μm to 60 μm, 15 μm to 50 μm, about 15 μm, about 20 μm, about 25 μm, about 30 μm, about 35 μm, about 40 μm, about 45 μm, about 50 μm, about 55 μm, about 60 μm, about 65 μm, about 70 μm, about 75 μm, about 80 μm, about 85 μm, about 90 μm, about 95 μm, or about 100 μm. In those embodiments having multiple control regions and/or sub-regions, the individual sub-regions or combinations of some or all sub-regions may have a thickness of from about 5 μm to 100 μm, 5 μm to 50 μm, 5 μm to 25 μm, 5 μm to 10 μm, 5 μm to 7 μm, 7 μm to 9 μm, 10 μm to 80 μm, 10 μm to 70 μm, 10 μm to 60 μm, 20 μm to 60 μm, 15 μm to 50 μm, about 15 μm, about 20 μm, about 25 μm, about 30 μm, about 35 μm, about 40 μm, about 45 μm, about 50 μm, about 55 μm, about 60 μm, about 65 μm, about 70 μm, about 75 μm, about 80 μm, about 85 μm, about 90 μm, about 95 μm, or about 100 μm.

In any of the embodiments disclosed herein, the weight ratio of releasing agent to polymer in the control region 300 may be 2:1, 1.5:1, 1:1, 1:1.5, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, or 1:25.

In any of the embodiments disclosed herein, the control region 300 may include at least 5% by weight of the releasing agent, at least 10% by weight of the releasing agent, at least 15% by weight of the releasing agent, at least 20% by weight of the releasing agent, at least 25% by weight of the releasing agent, at least 30% by weight of the releasing agent, at least 35% by weight of the releasing agent, at least 40% by weight of the releasing agent, at least 45% by weight of the releasing agent, or at least 50% by weight of the releasing agent. In those embodiments having multiple control regions or sub-regions, one or more of the control regions or sub-control regions may individually include at least 5% by weight of the releasing agent, at least 10% by weight of the releasing agent, at least 15% by weight of the releasing agent, at least 20% by weight of the releasing agent, at least 25% by weight of the releasing agent, at least 30% by weight of the releasing agent, at least 35% by weight of the releasing agent, at least 40% by weight of the releasing agent, at least 45% by weight of the releasing agent, or at least 50% by weight of the releasing agent.

In any of the embodiments disclosed herein, the control region 300 may include at least 5% by weight of the polymer, at least 10% by weight of the polymer, at least 15% by weight of the polymer, at least 20% by weight of the polymer, at least 25% by weight of the polymer, at least 30% by weight of the polymer, at least 35% by weight of the polymer, at least 40% by weight of the polymer, at least 45% by weight of the polymer, at least 50% by weight of the polymer, at least 55% by weight of the polymer, at least 60% by weight of the polymer, at least 65% by weight of the polymer, at least 70% by weight of the polymer, at least 75% by weight of the polymer, at least 80% by weight of the polymer, at least 85% by weight of the polymer, at least 90% by weight of the polymer, at least 95% by weight of the polymer, or 100% by weight of the polymer. In those embodiments having multiple control regions or sub-regions, one or more of the control regions or sub-control regions may individually include at least 5% by weight of the polymer, at least 10% by weight of the polymer, at least 15% by weight of the polymer, at least 20% by weight of the polymer, at least 25% by weight of the polymer, at least 30% by weight of the polymer, at least 35% by weight of the polymer, at least 40% by weight of the polymer, at least 45% by weight of the polymer, at least 50% by weight of the polymer, at least 55% by weight of the polymer, at least 60% by weight of the polymer, at least 65% by weight of the polymer, at least 70% by weight of the polymer, at least 75% by weight of the polymer, at least 80% by weight of the polymer, at least 85% by weight of the polymer, at least 90% by weight of the polymer, at least 95% by weight of the polymer, or 100% by weight of the polymer.

In those embodiments disclosed herein where the control region 300 includes multiple control regions or sub-regions, some or all of the control regions or sub-control regions may have the same or different amounts of releasing agent, the same or different concentrations of releasing agent, the same or different releasing agents, the same or different amounts of polymer, the same or different polymers, the same or different polymer to releasing agent ratios, and/or the same or different thicknesses. A single control region or sub-region may comprise a single type of polymer or multiple types of polymers and/or a single type of releasing agent or multiple types of releasing agents.

C. Therapeutic Agents

The therapeutic agent carried by the depots 100 of the present technology may be any biologically active substance (or combination of substances) that provides a therapeutic effect in a patient in need thereof. As used herein, "a therapeutic agent," "the therapeutic agent," "a drug," or "the drug" may refer to a single therapeutic agent, or may refer to a combination of therapeutic agents for simultaneous or sequential release. For example, "a therapeutic agent" may refer to a single chemotherapeutic agent, a single anti-inflammatory agent, a single anesthetic agent, etc., or may refer to a combination of chemotherapeutic agents, a single chemotherapeutic agent and a single anti-inflammatory agent, multiple chemotherapeutic agents in combination with a single anti-inflammatory agent and a single anti-microbial agent, multiple chemotherapeutic agents and multiple immunotherapeutic agents, etc.

As mentioned above, the therapeutic agent may include one or more chemotherapeutic agents. A "chemotherapeutic agent," as used herein, may refer to a drug used in the treatment of cancer or a pharmaceutically acceptable salt thereof. As used herein, "a chemotherapeutic agent," "the chemotherapeutic therapeutic agent," or "a drug," or "the drug" may refer to a single chemotherapeutic agent, or may refer to a combination of chemotherapeutic agents for simultaneous or sequential release. In some embodiments, the therapeutic agent may include only a single chemotherapeutic agent (such as, for example, those listed elsewhere herein). In some embodiments, the therapeutic agent may include two or more chemotherapeutic agents for simultaneous or sequential release (such as, for example, those listed in this section or elsewhere herein).

Chemotherapeutic agents for use with the depots 100 of the present technology include antibodies, alkylating agents, angiogenesis inhibitors, antimetabolites, DNA cleavers, DNA crosslinkers, DNA intercalators, DNA minor groove binders, enediynes, heat shock protein 90 inhibitors, histone deacetylase inhibitors, immunomodulators, microtubule stabilizers, nucleoside (purine or pyrimidine) analogs, nuclear export inhibitors, proteasome inhibitors, topoisomerase (I or II) inhibitors, tyrosine kinase inhibitors, and serine/threonine kinase inhibitors. Specific therapeutic agents include, but are not limited to, adalimumab, ansamitocin P3, auristatin, bendamustine, bevacizumab, bicalutamide, bleomycin, bortezomib, busulfan, callistatin A, camptothecin, capecitabine, carboplatin, carmustine, cetuximab, cisplatin, cladribin, cytarabin, cryptophycins, dacarbazine, dasatinib, daunorubicin, docetaxel, doxorubicin, duocarmycin, dynemycin A, epothilones, etoposide, floxuridine, fludarabine, 5-fluorouracil, gefitinib, gemcitabine, ipilimumab, hydroxyurea, imatinib, infliximab, interferons, interleukins, beta-lapachone, lenalidomide, irinotecan, maytansine, mechlorethamine, melphalan, 6-mercaptopurine, methotrexate, mitomycin C, nilotinib, oxaliplatin, paclitaxel, procarbazine, suberoylanilide hydroxamic acid (SAHA), 6-thioguanidine, thiotepa, teniposide, topotecan, trastuzumab, trichostatin A, vinblastine, vincristine, vindesine, and tamoxifen.

Exemplary combinations of chemotherapeutic agents include any combination of the single chemotherapeutic agents listed in the first column of 0, the combinations of chemotherapeutic agents listed in the second column below, and/or any combinations discussed elsewhere herein.

| Examples of Single Chemotherapeutic Agents | Examples of Combinations of Chemotherapeutic Agents |
|---|---|
| Ramucirumab | 5-FU leucovorin calcium (together referred to as "5-FU-LIV") |
| docetaxel | 5-FU, leucovorin, and capecitabine |
| trastuzumab | capecitabine and irinotecan hydrochloride (together referred to as "XELIRI") |
| fluorouracil or 5-FU | carboplatin and paclitaxel (Taxol ®) |
| paclitaxel | cisplatin and 5-FU |
| Oxaliplatin | epirubicin, cisplatin, and 5-FU (together referred to as "ECF") |
| Epirubicin | epirubicin, oxaliplatin, and 5-FU |
| Capecitabine | epirubicin, cisplatin, and capecitabine |
| oxaliplatin | irinotecan and 5-FU |
| Irinotecan | irinotecan, 5-FU, and leucovorin |
| Floxuridine | docetaxel, cisplatin, and 5-FU (together referred to as "DCF") |
| Porfimer | docetaxel, oxaliplatin, cisplatin, and 5-FU |
| aminolevulinic acid ("ALA") | docetaxel, oxaliplatin, cisplatin, and 5-FU |
| methyl aminolevulinate ("MAL") | docetaxel, cisplatin, 5-FU, and leucovorin |
| carboplatin | docetaxel, oxaliplatin, and 5-FU |
| Cisplatin | docetaxel, carboplatin, and 5-FU |
| | cisplatin and capecitabine |
| | oxaliplatin and 5-FU |
| | oxaliplatin, 5-FU, and leucovorin |
| | oxaliplatin and capecitabine |
| | epirubicin, cisplatin, and capecitabine |
| | epirubicin (Ellence ®), oxaliplatin, and capecitabine |
| | platinum plus fluoropyrimidine doublet (e.g., FOLFOX, CAPOX, S-1 plus oxaliplatin, cisplatin/FU, or S-1 plus cisplatin) |
| | a fluoropyrimidine, oxaliplatin, docetaxel |
| | capecitabine and irinotecan HCL |
| | irinotecan and cisplatin |
| | paclitaxel and capecitabine |
| | cisplatin and capecitabine |
| | paclitaxel and cisplatin |
| | docetaxel and cisplatin |
| | paclitaxel and 5-FU |
| | 5-FU and leucovorin |
| | 5-FU, cisplatin, and leucovorin |
| | docetaxel and irinotecan |
| | paclitaxel and docetaxel |
| | ramucirumab and paclitaxel |

Instead of or in addition to any of the therapeutic agents listed herein, the therapeutic agent may include one or more photosensitizing agents The photosensitizing agents may include one or more porphyrin-based compounds, chlorins, and dyes) in combination with one or more chemoprotectants (e.g., leucovorin). Unless otherwise specified, "chemotherapeutic agent" as used herein includes photosensitizing agents. In some embodiments, the therapeutic agent may include one or more vasoconstrictors (e.g., epinephrine, clonidine, etc.).

Instead of or in addition to any of the therapeutic agents listed herein, the therapeutic agent may include an analgesic agent. For example, the therapeutic region 200 may include a local analgesic to limit any pain caused by the placement of the depot 100 or the action of the chemotherapeutic agents. As used herein, the term "analgesic agent" or "analgesic" includes one or more local or systemic anesthetic agents that are administered to reduce, prevent, alleviate or remove pain entirely. The analgesic agent may comprise a systemic and/or local anesthetic, narcotics, and/or anti-inflammatory agents. The analgesic agent may comprise the pharmacologically active drug or a pharmaceutically acceptable salt thereof. Suitable local anesthetics include, but are not limited to, bupivacaine, ropivacaine, mepivacaine, etidocaine, levobupivacaine, trimecaine, carticaine, articaine, lidocaine, prilocaine, benzocaine, procaine, tetracaine, chloroprocaine, and combinations thereof. Preferred local anesthetics include bupivacaine, lidocaine and ropivacaine. Typically, local anesthetics produce anesthesia by inhibiting excitation of nerve endings or by blocking conduction in peripheral nerves. Such inhibition is achieved by anesthetics reversibly binding to and inactivating sodium channels. Sodium influx through these channels is necessary for the depolarization of nerve cell membranes and subsequent propagation of impulses along the course of the nerve. When a nerve loses depolarization and capacity to propagate an impulse, the individual loses sensation in the area supplied by the nerve. Any chemical compound possessing such anesthetic properties is suitable for use in the present technology.

Instead of or in addition to any of the therapeutic agents listed herein, the therapeutic agent may include one or more anti-inflammatory agents. Examples of appropriate anti-inflammatory agents include steroids, such as prednisone, betamethasone, cortisone, dexamethasone, hydrocortisone and methylprednisolone. Other appropriate anti-inflammatory agents include non-steroidal anti-inflammatory drugs (NSAIDs), such as aspirin, Ibuprofen, naproxen sodium, diclofenac, diclofenac-misoprostol, celecoxib, piroxicam, indomethacin, meloxicam, ketoprofen, sulindac, diflunisal, nabumetone, oxaprozin, tolmetin, salsalate, etodolac, fenoprofen, flurbiprofen, ketorolac, meclofenamate, mefenamic acid, and other COX-2 inhibitors, and combinations thereof.

Instead of or in addition to any of the therapeutic agents listed herein, the therapeutic agent may include an antibiotic, an antimicrobial or antifungal agent or combinations thereof. For example, suitable antibiotics and antimicrobials include, but arc not limited to, amoxicillin, amoxicillin/clavulanate, cephalexin, ciprofloxacin, clindamycin, metronidazole, azithromycin, levofloxacin, sulfamethoxazole/trimethoprim, tetracycline(s), minocycline, tigecycline, doxycycline, rifampin, triclosan, chlorhexidine, penicillin(s), aminoglycides, quinolones, fluoroquinolones, vancomycin, gentamycin, cephalosporin(s), carbapenems, imipenem, ertapenem, antimicrobial peptides, cecropin-mellitin, magainin, dermaseptin, cathelicidin, a-defensins, and α-protegrins. Antifungal agents include, but are not limited to, ketoconazole, clortrimazole, miconazole, econazole, intraconazole, fluconazole, bifoconazole, terconazole, butaconazole, tioconazole, oxiconazole, sulconazole, saperconazole, voriconazole, terbinafine, amorolfine, naftifine, griseofulvin, haloprogin, butenafine, tolnaftate, nystatin, cyclohexamide, ciclopirox, flucytosine, terbinafine, and amphotericin B.

Instead of or in addition to any of the therapeutic agents listed herein, the therapeutic agent may include one or more of an adrenocorticostatic, a β-adrenolytic, an androgen or antiandrogen, an antianemic, a antiparasitic, an anabolic, an anesthetic or analgesic, an analeptic, an antiallergic, an antiarrhythmic, an anti-arteriosclerotic, an antibiotic, an antidiabetic, an antifibrinolytic, an anticonvulsive, an angiogenesis inhibitor, an anticholinergic, an enzyme, a coenzyme or a corresponding inhibitor, an antihistaminic, an antihypertensive, an antihypotensive, an anticoagulant, an antimycotic, an antiseptic, an anti-infective, an antihemorrhagic, a β-receptor antagonist, a calcium channel antagonist, an antimyasthenic, an antiphlogistic, an antipyretic, an antirheumatic, a cardiotonic, a chemotherapeutic, a coronary dilator, a cytostatic, a glucocorticoid, a hemostatic, an immunoglobulin or its fragment, a chemokine, a cytokine, a mitogen, a cell differentiation factor, a cytotoxic agent, a hormone, an immunosuppressant, an immunostimulant, a morphine antagonist, an muscle relaxant, a narcotic, a vector, a peptide, a (para)sympathicomimetic, a (para)sympatholytic, a protein, a cell, a selective estrogen receptor modulator (SERM), a sedating agent, an antispasmodic, a substance that inhibits the resorption of bone, a vasoconstrictor or vasodilator, a virustatic or a wound-healing agent.

In some embodiments, the therapeutic agent comprises a botulinum toxin (or neurotoxin) drug used in the treatment of various neuromuscular and/or neuroglandular disorders and neuropathies associated with pain. The botulinum toxin (or neurotoxin) may comprise the pharmacologically active drug or a pharmaceutically acceptable salt thereof. The botulinum toxin (or neurotoxin) as described and used herein may be selected from a variety of strains of *Clostridium botulinum* and may comprise the pharmacologically active drug or a pharmaceutically acceptable salt thereof. In one embodiment, the botulinum toxin is selected from the group consisting of botulinum toxin types A, B, C, D, E, F and G. In a preferred embodiment, the botulinum toxin is botulinum toxin type A. Commercially available botulinum toxin, BOTOX® (Allergan, Inc., Irvine, CA), consists of a freeze-dried, purified botulinum toxin type A complex, albumin and sodium chloride packaged in sterile, vacuum-dried form.

The paralytic effect of botulinum toxin is the most common benefit of commercial therapeutics, where muscles are relaxed in order to treat muscle dystonias, wrinkles and the like. However, it has been shown that in addition to its anti-cholinergic effects on muscle and smooth muscle, the neurotoxin can have therapeutic effects on other non-muscular cell types, and on inflammation itself. For example, it has been shown that cholinergic goblet cells, which produce mucus throughout the airway system, react to and can be shut down by introduction of botulinum toxin. Research also shows that botulinum toxin has direct ant-inflammatory capabilities. All of these therapeutic effects, muscle, smooth muscle, goblet cell and anti-inflammatory affects, may be derived from delivery of the toxin from the inventive devices.

A pharmaceutically acceptable salt refers to those salts that retain the biological effectiveness and properties of neutral therapeutic agents and that are not otherwise unacceptable for pharmaceutical use. Pharmaceutically acceptable salts include salts of acidic or basic groups, which groups may be present in the therapeutic agents. The therapeutic agents used in the present technology that are basic in nature are capable of forming a wide variety of salts with various inorganic and organic acids. Pharmaceutically acceptable acid addition salts of basic therapeutic agents used in the present technology are those that form non-toxic acid addition salts, i.e., salts comprising pharmacologically acceptable anions, such as the hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)]salts. The therapeutic agents of the present technology that include an amino moiety may form pharmaceutically acceptable salts with various amino acids, in addition to the acids mentioned above. Suitable base salts are formed from bases which form non-toxic salts and examples are the aluminum, calcium, lithium, magnesium, potassium, sodium, zinc and diethanolamine salts.

A pharmaceutically acceptable salt may involve the inclusion of another molecule such as water or another biologically compatible solvent (a solvate), an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterion.

The therapeutic agent or pharmaceutically acceptable salt thereof may be an essentially pure compound or be formulated with a pharmaceutically acceptable carrier such as diluents, adjuvants, excipients or vehicles known to one skilled in the art. The carrier(s) must be "acceptable" in the sense of being compatible with the other ingredients of the formulations and not deleterious to the recipient thereof. For example, diluents include lactose, dextrose, sucrose, mannitol, sorbitol, cellulose, glycine and the like. For examples of other pharmaceutically acceptable carriers, see Remington: THE SCIENCE AND PRACTICE OF PHARMACY (21st Edition, University of the Sciences in Philadelphia, 2005).

The therapeutic agent or pharmaceutically acceptable salt form may be jet milled or otherwise passed through a sieve to form consistent particle sizes further enabling the regulated and controlled release of the therapeutic agent. This process may be particularly helpful for highly insoluble therapeutic agents.

In one embodiment, the biodegradable, bioresorbable polymer used in various layers of the depot may manifest as a layer of electrospun microfibers or nanofibers. Biocompatible electrospun microfibers/nanofibers are known in the art and may be used, for example, to manufacture implantable supports for the formation of replacement organs in vivo (U.S. Patent Publication No. 2014/0272225; Johnson; Nanofiber Solutions, LLC), for musculoskeletal and skin tissue engineering (R. Vasita and D. S. Katti, Int. J. Nanomedicine, 2006, 1:1, 15-30), for dermal or oral applications (PCT Publication No. 2015/189212; Hansen; Dermtreat APS) or for management of postoperative pain (U.S. Patent Publication No. 2013/0071463; Palasis et al.). As a manufacturing technique, electrospinning offers the opportunity for control over the thickness and the composition of the nano- or micro-fibers along with control of the porosity of the fiber meshes (Vasita and Katti, 2006). These electrospun scaffolds are three-dimensional and thus provide ideal supports for the culture of cells in vivo for tissue formation. Typically, these scaffolds have a porosity of 70-90% (U.S. Pat. No. 9,737,632; Johnson; Nanofiber Solutions, LLC). Suitable biodegradable polymers and copolymers for the manufacture of electrospun microfibers include, but are not limited to, natural materials such as collagen, gelatin, elastin, chitosan, silk fibrion, and hyaluronic acid, as well as synthetic materials such as poly(ε-caprolactone) (PCL), poly(glycolic acid) (PGA), poly(lactic-co-glycolic acid) (PLGA), poly(l-lactide-co-ε-caprolactone), and poly(lactic acid) (PLA).

Electrospun microfibers that are made from a bioresorbable polymer or copolymer and have been used in conjunction with a therapeutic agent are known in the art. For example, Johnson et al. have disclosed the treatment of joint inflammation and other conditions with an injection of biocompatible polymeric electrospun fiber fragments along with a carrier medium containing chitosan (U.S. Published Application No. 2016/0325015; Nanofiber Solutions, LLC). Weldon et al. reported the use of electrospun bupivacaine-eluting sutures manufactured from poly(lactic-co-glycolic acid) in a rat skin wound model, wherein the sutures provided local anesthesia at an incision site (J. Control Release, 2012, 161:3, 903-909). Similarly, Palasis et al. disclosed the treatment of postoperative pain by implanting electrospun fibers loaded with an opioid, anesthetic or a non-opioid analgesic within a surgical site (U.S. Patent Publication No. 2013/0071463; Palasis et al.). Electrospun microfibers suitable for use in the present technology may be obtained by the methods disclosed in the above cited references, which are herein incorporated in their entirety.

An important criterion for determining the amount of therapeutic agent needed for the treatment of a particular medical condition is the release rate of the drug from the depot of the present technology. The release rate is controlled by a variety of factors, including, but not limited to, the rate that the releasing agent dissolves in vivo into the surrounding fluid, the in vivo degradation rate of the bioresorbable polymer or copolymer utilized. For example, the rate of release may be controlled by the use of multiple control regions between the therapeutic region and the physiological fluid. See, for example, FIGS. 6-8.

Suitable dosage ranges utilizing the depot of the present technology are dependent on the potency of the particular therapeutic agent, but are generally about 0.001 mg to about 500 mg of drug per kilogram body weight, for example from about 0.1 mg to about 200 mg of drug per kilogram body weight, and about 1 to about 100 mg/kg-body wt. per day. Dosage ranges may be readily determined by methods known to one skilled in the art.

In some embodiments, the therapeutic region 200 includes at least 15% by weight of the therapeutic agent, at least 20% by weight of the therapeutic agent, at least 30% by weight of the therapeutic agent, at least 40% by weight of the therapeutic agent, at least 50% by weight of the therapeutic agent, at least 60% by weight of the therapeutic agent, at least 70% by weight of the therapeutic agent, at least 80% by weight of the therapeutic agent, at least 90% by weight of the therapeutic agent, or 100% by weight of the therapeutic agent.

In some embodiments, the depot includes at least 15% by weight of the therapeutic agent, at least 20% by weight of the therapeutic agent, at least 30% by weight of the therapeutic agent, at least 40% by weight of the therapeutic agent, at least 50% by weight of the therapeutic agent, at least 60% by weight of the therapeutic agent, at least 70% by weight of the therapeutic agent, at least 80% by weight of the therapeutic agent, at least 90% by weight of the therapeutic agent, or 100% by weight of the therapeutic agent. In many embodiments, the depot 100 includes at least 50% by weight of the therapeutic agent.

In some aspects of the technology, the therapeutic region 200 may include multiple layers. In such embodiments, the multiple layers may improve efficient loading of therapeutic agents. For example, multilayering may be a direct and effective way of loading substantial amounts of therapeutic agent. It can often be challenging to load a large amount of therapeutic agent in a single film layer, even by increasing the drug to polymer ratio or increasing the thickness of the layer. Even when the thickness of the therapeutic region can be theoretically increased to load more drug, consistent fabrication of a thick therapeutic region via casting could prove to be a challenge. In contrast, the stacking and bonding of thin films or sheets, each with a predetermined load of therapeutic agent, may present as a more reliable casting alternative. Data from an example of loading an analgesic (i.e., ropivacaine) is provided in Table 2.

TABLE 2

| | Drug load (ug) | Thickness (mm) |
|---|---|---|
| Single layer | 212.66 | 0.019 |
| Five layers | 1120.83 | 0.046 |
| Multiple | 5.27 | 2.42 |

As but one example, a single layer loaded with ropivacaine and having a thickness of 0.019 mm was produced. A 5-layer film sample, where each layer was loaded with ropivacaine, having a thickness of 0.046 mm was also produced. Even though the thickness of the 5-layer film sample was only 2.42 times the thickness of the single layer, the load of therapeutic agent in the 5-layer sample was 5.27 times that of the single layer sample. Accordingly, the multilayering approach enabled a substantially higher density of therapeutic agent.

As described above, heat compression bonding of multiple layers enables an effective reduction in film thickness and an increased density of therapeutic agent loading. In the example illustrated in Table 2, the multilayer structure enabled a 124% increase in the density of the therapeutic agent. In other embodiments, the increase in density of the therapeutic agent enabled by a multilayer structure of the therapeutic region may be approximately 50%, 75%, 100%, 125%, 150% or 200The therapeutic agent carried by the depots 100 of the present technology may be any biologically active substance (or combination of substances) that provides a therapeutic effect in a patient in need thereof. As used herein, "therapeutic agent" or "drug" may refer to a single therapeutic agent, or may refer to a combination of therapeutic agents. In some embodiments, the therapeutic agent may include only a single therapeutic agent, and in some embodiments, the therapeutic agent may include two or more therapeutic agents for simultaneous or sequential release.

In several embodiments, the therapeutic agent includes an analgesic agent. The term "analgesic agent" or "analgesic" includes one or more local or systemic anesthetic agents that are administered to reduce, prevent, alleviate or remove pain entirely. The analgesic agent may comprise a systemic and/or local anesthetic, narcotics, and/or anti-inflammatory agents. The analgesic agent may comprise the pharmacologically active drug or a pharmaceutically acceptable salt thereof. Suitable local anesthetics include, but are not limited to, bupivacaine, ropivacaine, mepivacaine, etidocaine, levobupivacaine, trimecaine, carticaine, articaine, lidocaine, prilocaine, benzocaine, procaine, tetracaine, chloroprocaine, and combinations thereof. Preferred local anesthetics include bupivacaine, lidocaine, and ropivacaine. Typically, local anesthetics produce anesthesia by inhibiting excitation of nerve endings or by blocking conduction in peripheral nerves. Such inhibition is achieved by anesthetics reversibly binding to and inactivating sodium channels. Sodium influx through these channels is necessary for the depolarization of nerve cell membranes and subsequent propagation of impulses along the course of the nerve. When a nerve loses depolarization and capacity to propagate an impulse, the individual loses sensation in the area supplied by the nerve. Any chemical compound possessing such anesthetic properties is suitable for use in the present technology.

In some embodiments, the analgesic may comprise dexamethasone. In some embodiments, the therapeutic agent may comprise a first analgesic and a second analgesic. In some of such embodiments, one of the first or second analgesic is dexamethasone. Dexamethasone may also act as an anti-inflammatory agent.

In some embodiments, the analgesic may comprise tetrodotoxin. In some embodiments, the therapeutic agent may comprise a first analgesic and a second analgesic. In some of such embodiments, one of the first or second analgesic is tetrodotoxin.

In some embodiments, the analgesic may comprise saxitoxin. In some embodiments, the therapeutic agent may comprise a first analgesic and a second analgesic. In some of such embodiments, one of the first or second analgesic is saxitoxin.

In some embodiments, the therapeutic agent includes narcotics, for example, cocaine, and anti-inflammatory agents. Examples of appropriate anti-inflammatory agents include steroids, such as prednisone, betamethasone, cortisone, dexamethasone, hydrocortisone, and methylprednisolone. Other appropriate anti-inflammatory agents include non-steroidal anti-inflammatory drugs (NSAIDs), such as aspirin, Ibuprofen, naproxen sodium, diclofenac, diclofenac-misoprostol, celecoxib, piroxicam, indomethacin, meloxicam, ketoprofen, sulindac, diflunisal, nabumetone, oxaprozin, tolmetin, salsalate, etodolac, fenoprofen, flurbiprofen, ketorolac, meclofenamate, mefenamic acid, and other COX-2 inhibitors, and combinations thereof.

In some embodiments, the therapeutic agent comprises an antibiotic, an antimicrobial or antifungal agent or combinations thereof. For example, suitable antibiotics and antimicrobials include, but are not limited to, amoxicillin, amoxicillin/clavulanate, cephalexin, ciprofloxacin, clindamycin, metronidazole, azithromycin, levofloxacin, sulfamethoxazole/trimethoprim, tetracycline(s), minocycline, tigecycline, doxycycline, rifampin, triclosan, chlorhexidine, penicillin(s), aminoglycides, quinolones, fluoroquinolones, vancomycin, gentamycin, cephalosporin(s), carbapenems, imipenem, ertapenem, antimicrobial peptides, cecropin-mellitin, magainin, dermaseptin, cathelicidin, α-defensins, and α-protegrins. Antifungal agents include, but are not limited to, ketoconazole, clortrimazole, miconazole, econazole, intraconazole, fluconazole, bifoconazole, terconazole, butaconazole, tioconazole, oxiconazole, sulconazole, saperconazole, voriconazole, terbinafine, amorolfine, naftifine, griseofulvin, haloprogin, butenafine, tolnaftate, nystatin, cyclohexamide, ciclopirox, flucytosine, terbinafine, and amphotericin B.

The depot of any one of the preceding clauses, wherein the analgesic is a local anesthetic, and wherein the release of the analgesic to the treatment site over the five days inhibits the growth of bacteria and fungi.

In some embodiments, the therapeutic agent is a local anesthetic and release of the anesthetic to the treatment site over the duration of delivery inhibits the growth of bacteria and fungi. In some embodiments, the depot is configured to inhibit the growth of bacteria and fungi such that a number of bacteria on the depot is 10×, 20×, 30×, 40×, or 50× less than a number of bacteria present on a comparable depot containing no analgesic.

In several embodiments, the therapeutic agent may be an adrenocorticostatic, a β-adrenolytic, an androgen or antiandrogen, an antianemic, a antiparasitic, an anabolic, an anesthetic or analgesic, an analeptic, an antiallergic, an antiarrhythmic, an anti-arteriosclerotic, an antibiotic, an antidiabetic, an antifibrinolytic, an anticonvulsive, an angiogenesis inhibitor, an anticholinergic, an enzyme, a coenzyme or a corresponding inhibitor, an antihistaminic, an antihypertensive, an antihypotensive, an anticoagulant, an antimycotic, an antiseptic, an anti-infective, an antihemorrhagic, a β-receptor antagonist, a calcium channel antagonist, an antimyasthenic, an antiphlogistic, an antipyretic, an antirheumatic, a cardiotonic, a chemotherapeutic, a coronary dilator, a cytostatic, a glucocorticoid, a hemostatic, an immunoglobulin or its fragment, a chemokine, a cytokine, a mitogen, a cell differentiation factor, a cytotoxic agent, a hormone, an immunosuppressant, an immunostimulant, a morphine antagonist, an muscle relaxant, a narcotic, a vector, a peptide, a (para)sympathicomimetic, a (para)sympatholytic, a protein, a cell, a selective estrogen receptor modulator (SERM), a sedating agent, an antispasmodic, a substance that inhibits the resorption of bone, a vasoconstrictor or vasodilator, a virustatic or a wound-healing agent.

In various embodiments, the therapeutic agent comprises a drug used in the treatment of cancer or a pharmaceutically acceptable salt thereof. Such chemotherapeutic agents include antibodies, alkylating agents, angiogenesis inhibitors, antimetabolites, DNA cleavers, DNA crosslinkers, DNA intercalators, DNA minor groove binders, enediynes, heat shock protein 90 inhibitors, histone deacetylase inhibitors, immunomodulators, microtubule stabilizers, nucleoside (purine or pyrimidine) analogs, nuclear export inhibitors, proteasome inhibitors, topoisomerase (I or II) inhibitors, tyrosine kinase inhibitors, and serine/threonine kinase inhibitors. Specific therapeutic agents include, but are not limited to, adalimumab, ansamitocin P3, auristatin, bendamustine, bevacizumab, bicalutamide, bleomycin, bortezomib, busulfan, callistatin A, camptothecin, capecitabine, carboplatin, carmustine, cetuximab, cisplatin, cladribin, cytarabin, cryptophycins, dacarbazine, dasatinib, daunorubicin, docetaxel, doxorubicin, duocarmycin, dynemycin A, epothilones, etoposide, floxuridine, fludarabine, 5-fluorouracil, gefitinib, gemcitabine, ipilimumab, hydroxyurea, imatinib, infliximab, interferons, interleukins, beta-lapachone, lenalidomide, irinotecan, maytansine, mechlorethamine, melphalan, 6-mercaptopurine, methotrexate, mitomycin C, nilotinib, oxaliplatin, paclitaxel, procarbazine, suberoylanilide hydroxamic acid (SAHA), 6-thioguanidine, thiotepa, teniposide, topotecan, trastuzumab, trichostatin A, vinblastine, vincristine, vindesine, and tamoxifen.

In some embodiments, the therapeutic agent comprises a botulinum toxin (or neurotoxin) drug used in the treatment of various neuromuscular and/or neuroglandular disorders and neuropathies associated with pain. The botulinum toxin (or neurotoxin) may comprise the pharmacologically active drug or a pharmaceutically acceptable salt thereof. The botulinum toxin (or neurotoxin) as described and used herein may be selected from a variety of strains of *Clostridium botulinum* and may comprise the pharmacologically active drug or a pharmaceutically acceptable salt thereof. In one embodiment, the botulinum toxin is selected from the group consisting of botulinum toxin types A, B, C, D, E, F and G. In a preferred embodiment, the botulinum toxin is botulinum toxin type A. Commercially available botulinum toxin, BOTOX® (Allergan, Inc., Irvine, CA), consists of a freeze-dried, purified botulinum toxin type A complex, albumin and sodium chloride packaged in sterile, vacuum-dried form.

The paralytic effect of botulinum toxin is the most common benefit of commercial therapeutics, where muscles are relaxed in order to treat muscle dystonias, wrinkles and the like. However, it has been shown that in addition to its anti-cholinergic effects on muscle and smooth muscle, the neurotoxin can have therapeutic effects on other non-muscular cell types, and on inflammation itself. For example, it has been shown that cholinergic goblet cells, which produce mucus throughout the airway system, react to and can be shut down by introduction of botulinum toxin. Research also shows that botulinum toxin has direct ant-inflammatory capabilities. All of these therapeutic effects, muscle, smooth muscle, goblet cell and anti-inflammatory affects, may be derived from delivery of the toxin from the inventive devices.

A pharmaceutically acceptable salt refers to those salts that retain the biological effectiveness and properties of neutral therapeutic agents and that are not otherwise unacceptable for pharmaceutical use. Pharmaceutically acceptable salts include salts of acidic or basic groups, which groups may be present in the therapeutic agents. The therapeutic agents used in the present technology that are basic in nature are capable of forming a wide variety of salts with various inorganic and organic acids. Pharmaceutically acceptable acid addition salts of basic therapeutic agents used in the present technology are those that form non-toxic acid addition salts, i.e., salts comprising pharmacologically acceptable anions, such as the hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)]salts. The therapeutic agents of the present technology that include an amino moiety may form pharmaceutically acceptable salts with various amino acids, in addition to the acids mentioned above. Suitable base salts are formed from bases which form non-toxic salts and examples are the aluminum, calcium, lithium, magnesium, potassium, sodium, zinc and diethanolamine salts.

A pharmaceutically acceptable salt may involve the inclusion of another molecule such as water or another biologically compatible solvent (a solvate), an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterion.

The therapeutic agent or pharmaceutically acceptable salt thereof may be an essentially pure compound or be formulated with a pharmaceutically acceptable carrier such as diluents, adjuvants, excipients or vehicles known to one skilled in the art. The carrier(s) must be "acceptable" in the sense of being compatible with the other ingredients of the formulations and not deleterious to the recipient thereof. For example, diluents include lactose, dextrose, sucrose, mannitol, sorbitol, cellulose, glycine and the like. For examples of other pharmaceutically acceptable carriers, see Remington: THE SCIENCE AND PRACTICE OF PHARMACY (21st Edition, University of the Sciences in Philadelphia, 2005).

The therapeutic agent or pharmaceutically acceptable salt form may be jet milled or otherwise passed through a sieve to form consistent particle sizes further enabling the regulated and controlled release of the therapeutic agent. This process may be particularly helpful for highly insoluble therapeutic agents.

An important criterion for determining the amount of therapeutic agent needed for the treatment of a particular medical condition is the release rate of the drug from the depot of the present technology. The release rate is controlled by a variety of factors, including, but not limited to, the rate that the releasing agent dissolves in vivo into the surrounding fluid, the in vivo degradation rate of the bioresorbable polymer or copolymer utilized. For example, the rate of release may be controlled by the use of multiple control regions between the therapeutic region and the physiological fluid. See, for example, FIGS. 6-8.

Suitable dosage ranges utilizing the depot of the present technology are dependent on the potency of the particular therapeutic agent, but are generally about 0.001 mg to about 500 mg of drug per kilogram body weight, for example, from about 0.1 mg to about 200 mg of drug per kilogram body weight, and about 1 to about 100 mg/kg-body wt. per day. Dosage ranges may be readily determined by methods known to one skilled in the art. Dosage unit forms will generally contain between about 1 mg to about 500 mg of active ingredient. For example, commercially available bupivacaine hydrochloride, marketed under the brand name Marcaine™ (Pfizer; New York, NY), is generally administered as a peripheral nerve block using a dosage range of 37.5-75 mg in a 0.25% concentration and 25 mg up to the daily maximum level (up to 400 mg) in a 0.5% concentration (Marcaine®™ package insert; FDA Reference ID: 3079122). In addition, commercially available ropivacaine hydrochloride, marketed under the brand name Naropin® (Fresenius Kabi USA, LLC; Lake Zurich, IL), is administered in doses of 5-300 mg for minor and major nerve blocks (Naropin® package insert; Reference ID: 451112G). Suitable dosage ranges for the depot of the present technology are equivalent to the commercially available agents customarily administered by injection.

In some aspects of the technology, the therapeutic region 200 may include multiple layers. In such embodiments, the multiple layers may improve efficient loading of therapeutic agents. For example, multilayering may be a direct and effective way of loading substantial amounts of therapeutic agent. It can often be challenging to load a large amount of therapeutic agent in a single film layer, even by increasing the drug to polymer ratio or increasing the thickness of the layer. Even when the thickness of the therapeutic region can be theoretically increased to load more drug, consistent fabrication of a thick therapeutic region via casting could prove to be a challenge. In contrast, the stacking and bonding of thin films or sheets, each with a predetermined load of therapeutic agent, may present as a more reliable casting alternative. Data from an example of loading an analgesic (i.e., ropivacaine) is provided in Table 3.

TABLE 3

| | Drug load (ug) | Thickness (mm) |
|---|---|---|
| Single layer | 212.66 | 0.019 |
| Five layers | 1120.83 | 0.046 |
| Multiple | 5.27 | 2.42 |

As but one example, a single layer loaded with ropivacaine and having a thickness of 0.019 mm was produced. A 5-layer film sample, where each layer was loaded with ropivacaine, having a thickness of 0.046 mm was also produced. Even though the thickness of the 5-layer film sample was only 2.42 times the thickness of the single layer, the load of therapeutic agent in the 5-layer sample was 5.27 times that of the single layer sample. Accordingly, the multilayering approach enabled a substantially higher density of therapeutic agent.

As described above, heat compression bonding of multiple layers enables an effective reduction in film thickness and an increased density of therapeutic agent loading. In the example illustrated in Table 3, the multilayer structure enabled a 124% increase in the density of the therapeutic agent. In other embodiments, the increase in density of the therapeutic agent enabled by a multilayer structure of the therapeutic region may be approximately 50%, 75%, 100%, 125%, 150% or 200%.

D. Polymers

The depots 100 of the present technology are comprised of bioresorbable polymers. In some embodiments, both the therapeutic region 200 and the control region 300 comprise a polymer (or mix of polymers), which can be the same or different polymer (or mix of polymers) in the same or different amount, concentration, and/or weight percentage. In some embodiments, the control region 300 comprises a polymer and the therapeutic region 200 does not include a polymer. In some embodiments, the therapeutic region 200 comprises a polymer and the control region 300 does not include a polymer. At least as used in this section, "the polymer" applies to a polymer that may be used in the therapeutic region 200 and/or in the control region 300.

The bioresorbable polymers used in the present technology preferably have a predetermined degradation rate. The terms "bioresorbable," or "bioabsorbable," mean that a polymer will be absorbed within the patient's body, for example, by a cell or tissue. These polymers are "biodegradable" in that all or parts the polymeric film will degrade over time by the action of enzymes, by hydrolytic action and/or by other similar mechanisms in the patient's body. In various embodiments, the bioresorbable polymer film can break down or degrade within the body to non-toxic components while a therapeutic agent is being released. Polymers used as base components of the depots of the present technology may break down or degrade after the therapeutic agent is fully released. The bioresorbable polymers are also "bioerodible," in that they will erode or degrade over time due, at least in part, to contact with substances found in the surrounding tissue, fluids or by cellular action.

Criteria for the selection of the bioresorbable polymer suitable for use in the present technology include: 1) in vivo safety and biocompatibility; 2) therapeutic agent loading capacity; 3) therapeutic agent releasing capability; 4) degradation profile; 5) potential for inflammatory response; and 6) mechanical properties, which may relate to form factor and manufacturability. As such, selection of the bioresorbable polymer may depend on the clinical objectives of a particular therapy and may involve trading off between competing objectives. For example, PGA (polyglycolide) is known to have a relatively fast degradation rate, but it is also fairly brittle. Conversely, polycaprolactone (PCL) has a relatively slow degradation rate and is quite elastic. Copolymerization provides some versatility if it is clinically desirable to have a mix of properties from multiple polymers. For biomedical applications, particularly as a bioresorbable depot for drug release, a polymer or copolymer using at least one of poly(L-lactic acid) (PLA), PCL, and PGA are generally preferred. The physical properties for some of these polymers are provided in Table 4 below.

TABLE 4

| Materials | Tg (° C.) | Tm (° C.) | Elastic Modulus (GPa) | Tensile Strength (MPa) | Tensile Elongation (%) | Degradation Time (months) |
|---|---|---|---|---|---|---|
| PLA | 45-60 | 150-162 | 0.35-3.5 | 21-60 | 2.5-6 | 12-16 |
| PLLA | 55-65 | 170-200 | 2.7-4.14 | 15.5-150 | 3-10 | >24 |

TABLE 4-continued

| Materials | Tg (° C.) | Tm (° C.) | Elastic Modulus (GPa) | Tensile Strength (MPa) | Tensile Elongation (%) | Degradation Time (months) |
|---|---|---|---|---|---|---|
| PDLA | 50-60 | — | 1.0-3.45 | 27.6-50 | 2-10 | 6-12 |
| PLA/PGA (50:50) | 40-50 | — | 1.0-4.34 | 41.4-55.2 | 2-10 | 3 |
| PGA | 35-45 | 220-233 | 6.0-7.0 | 60-99.7 | 1.5-20 | 6-12 |
| PCL | −60-−65 | 58-65 | 0.21-0.44 | 20.7-42 | 300-1000 | >24 |

In many embodiments, the polymer may include polyglycolide (PGA). PGA is one of the simplest linear aliphatic polyesters. It is prepared by ring opening polymerization of a cyclic lactone, glycolide. It is highly crystalline, with a crystallinity of 45-55%, and thus is not soluble in most organic solvents. It has a high melting point (220-225° C.), and a glass transition temperature of 35-40° C. (Vroman, L., et al., Materials, 2009, 2:307-44). Rapid in vivo degradation of PGA leads to loss of mechanical strength and a substantial local production of glycolic acid, which in substantial amounts may provoke an inflammatory response.

In many embodiments, the polymer may include polylactide (PLA). PLA is a hydrophobic polymer because of the presence of methyl (—CH3) side groups off the polymer backbone. It is more resistant to hydrolysis than PGA because of the steric shielding effect of the methyl side groups. The typical glass transition temperature for representative commercial PLA is 63.8° C., the elongation at break is 30.7%, and the tensile strength is 32.22 MPa (Vroman, 2009). Regulation of the physical properties and biodegradability of PLA can be achieved by employing a hydroxy acids co-monomer component or by racemization of D- and L-isomers (Vroman, 2009). PLA exists in four forms: poly(L-lactic acid) (PLLA), poly(D-lactic acid) (PDLA), meso-poly(lactic acid) and poly(D,L-lactic acid) (PDLLA), which is a racemic mixture of PLLA and PDLA. PLLA and PDLLA have been the most studied for biomedical applications.

Copolymerization of PLA (both L- and D,L-lactide forms) and PGA yields poly(lactide-co-glycolide) (PLGA), which is one of the most commonly used degradable polymers for biomedical applications. In many embodiments, the polymer may include PLGA. Since PLA and PGA have significantly different properties, careful choice of PLGA composition can enable optimization of performance in intended clinical applications. Physical property modulation is even more significant for PLGA copolymers. When a composition is comprised of 25-75% lactide, PLGA forms amorphous polymers which are very hydrolytically unstable compared to the more stable homopolymers. This is demonstrated in the degradation times of 50:50 PLGA, 75:25 PLGA, and 85:15 PLGA, which are 1-2 months, 4-5 months and 5-6 months, respectively. In some embodiments, the polymer may be an ester-terminated poly (DL-lactide-co-glycolide) in a molar ratio of 50:50 (DURECT Corporation).

In some embodiments, the polymer may include polycaprolactone (PCL). PCL is a semi-crystalline polyester with high organic solvent solubility, a melting temperature of 55-60° C., and glass transition temperature of −54° C. (Vroman, 2009). PCL has a low in vivo degradation rate and high drug permeability, thereby making it more suitable as a depot for longer term drug delivery. For example, Capronor® is a commercial contraceptive PCL product that is able to deliver levonorgestrel in vivo for over a year. PCL is often blended or copolymerized with other polymers like PLLA, PDLLA, or PLGA. Blending or copolymerization with polyethers expedites overall polymer erosion. Additionally, PCL has a relatively low tensile strength (~23 MPa), but very high elongation at breakage (4700%), making it a very good elastic biomaterial. PCL also is highly processable, which enables many potential form factors and production efficiencies.

Suitable bioresorbable polymers and copolymers for use in the present technology include, but are not limited to, poly(alpha-hydroxy acids), poly(lactide-co-glycolide) (PLGA or DLG), poly(DL-lactide-co-caprolactone) (DL-PLCL), polycaprolactone (PCL), poly(L-lactic acid) (PLA), poly(trimethylene carbonate) (PTMC), polydioxanone (PDO), poly(4-hydroxy butyrate) (PHB), polyhydroxyalkanoates (PHA), poly(phosphazene), polyphosphate ester), poly(amino acid), polydepsipeptides, poly(butylene succinate) (PBS), polyethylene oxide, polypropylene fumarate, polyiminocarbonates, poly(lactide-co-caprolactone) (PLCL), poly(glycolide-co-caprolactone) (PGCL) copolymer, poly(D,L-lactic acid), polyglycolic acid, poly(L-lactide-co-D,L-lactide), poly(L-lactide-co-glycolide), poly(D,L-lactide-co-glycolide), poly(gycolide-trimethylene carbonate), poly(glycolide-co-carolactone) (PGCL), poly (ethyl glutamate-co-glutamic acid), poly(tert-butyloxy-carbonylmethyl glutamate), poly(glycerol sebacate), tyrosine-derived polycarbonate, poly 1,3-bis-(p-carboxyphenoxy) hexane-co-sebacic acid, polyphosphazene, ethyl glycinate polyphosphazene, polycaprolactone co-butylacrylate, a copolymer of polyhydroxybutyrate, a copolymer of maleic anhydride, a copolymer of poly(trimethylene carbonate), polyethylene glycol (PEG), hydroxypropylmethylcellulose and cellulose derivatives, polysaccharides (such as hyaluronic acid, chitosan and starch), proteins (such as gelatin and collagen) or PEG derivatives and copolymers thereof. Other suitable polymers or copolymers include polyaspirins, polyphosphagenes, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, D-lactide, D,L-lactide, L-lactide, D,L-lactide-caprolactone (DL-CL), D,L-lactide-glycolide-caprolactone (DL-G-CL), dextrans, vinylpyrrolidone, polyvinyl alcohol (PVA), PVA-g-PLGA, PEGT-PBT copolymer (polyactive), methacrylates, poly(N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate)hydroxypropyl cellulose, hydroxypropyl methylcellulose, hydroxyethyl methylcellulose, carboxymethylcellulose or salts thereof, Carbopol®, poly(hydroxyethylmethacrylate), poly (methoxyethylmethacrylate), poly(methoxyethoxy-ethylmethacrylate), polymethylmethacrylate (PMMA), methylmethacrylate (MMA), gelatin, polyvinyl alcohols, propylene glycol, or combinations thereof.

In various embodiments, the molecular weight of the polymer can be a wide range of values. The average molecular weight of the polymer can be from about 1000 to about 10,000,000; or about 1,000 to about 1,000,000; or about 5,000 to about 500,000; or about 10,000 to about 100,000; or about 20,000 to 50,000.

As described above, it may be desirable in certain clinical applications using depots for controlled delivery of therapeutic agents to use copolymers comprising at least two of PGA, PLA, PCL, PDO, and PVA. These include, for example, poly(lactide-co-caprolactone) (PLCL) (e.g. having a PLA to PCL ratio of from 90:10 to 60:40) or its derivatives and copolymers thereof, poly(DL-lactide-co-caprolactone) (DL-PLCL) (e.g. having a DL-PLA to PCL ratio of from 90:10 to 50:50) or its derivatives and copolymers thereof, poly(glycolide-co-caprolactone) (PGCL) (e.g. having a PGA to PCL ratio of from 90:10 to 10:90) or its derivatives and copolymers thereof, or a blend of PCL and PLA (e.g. a ratio blend of PCL and PLA having a wt:wt ratio of 1:9 to 9:1). In one preferred embodiment, the bioresorbable polymer comprises a copolymer of polycaprolactone (PCL), poly(L-lactic acid) (PLA) and polyglycolide (PGA). In such a preferred embodiment, the ratio of PGA to PLA to PCL of the copolymer may be 5-60% PGA, 5-40% PLA and 10-90% PCL. In additional embodiments, the PGA:PLA:PCL ratio may be 40:40:20, 30:30:50, 20:20:60, 15:15:70, 10:10:80, 50:20:30, 50:25:25, 60:20:20, or 60:10:30. In some embodiments, the polymer is an ester-terminated poly (DL-lactide-co-glycolide-co-caprolactone) in a molar ratio of 60:30:10 (DURECT Corporation).

In some embodiments, a terpolymer may be beneficial for increasing the degradation rate and ease of manufacturing, etc.

To minimize the size of a bioresorbable depot, it is generally preferred to maximize the loading of therapeutic agent in the polymer to achieve the highest possible density of therapeutic agent. However, polymer carriers having high densities of therapeutic agent are more susceptible to burst release kinetics and, consequently, poor control over time release. As described above, one significant benefit of the depot structure described herein, and particularly the control region feature of the depot, is the ability to control and attenuate the therapeutic agent release kinetics even with therapeutic agent densities that would cause instability in other carriers. In certain embodiments, the therapeutic agent loading capacity includes ratios (wt:wt) of the therapeutic agent to bioresorbable polymer of approximately 1:3, 1:2, 1:1, 3:2, 2:1, 3:1, 4:1, 5:1, 6:1, 7:1, 8:1, 9:1, 10:1, 12:1, 14:1, or 16:1. In some embodiments, it may be desirable to increase the therapeutic effect or potency of the therapeutic agent released from the depot described herein while still maintaining the same or similar polymer to therapeutic agent ratio. This can be accomplished by using an essentially pure form of the therapeutic agent as opposed to a salt derivative. Additionally or alternatively, the therapeutic agent can be mixed with clonidine or epinephrine, which are known to increase the therapeutic effect of certain drugs.

In some embodiments, the bioresorbable polymer used in various layers of the depot may manifest as a layer of electrospun microfibers or nanofibers. Biocompatible electrospun microfibers/nanofibers are known in the art and may be used, for example, to manufacture implantable supports for the formation of replacement organs in vivo (U.S. Patent Publication No. 2014/0272225; Johnson; Nanofiber Solutions, LLC), for musculoskeletal and skin tissue engineering (R. Vasita and D. S. Katti, Int. J. Nanomedicine, 2006, 1:1, 15-30), for dermal or oral applications (PCT Publication No. 2015/189212; Hansen; Dermtreat APS) or for management of postoperative pain (U.S. Patent Publication No. 2013/0071463; Palasis et al.). As a manufacturing technique, electrospinning offers the opportunity for control over the thickness and the composition of the nano- or micro-fibers along with control of the porosity of the fiber meshes (Vasita and Katti, 2006). These electrospun scaffolds are three-dimensional and thus provide ideal supports for the culture of cells in vivo for tissue formation. Typically, these scaffolds have a porosity of 70-90% (U.S. Pat. No. 9,737,632; Johnson; Nanofiber Solutions, LLC). Suitable bioresorbable polymers and copolymers for the manufacture of electrospun microfibers include, but are not limited to, natural materials such as collagen, gelatin, elastin, chitosan, silk fibrion, and hyaluronic acid, as well as synthetic materials such as poly(ε-caprolactone) (PCL), poly(glycolic acid) (PGA), poly(lactic-co-glycolic acid) (PLGA), poly(1-lactide-co-ε-caprolactone), and poly(lactic acid) (PLA).

Electrospun microfibers that are made from a bioresorbable polymer or copolymer and have been used in conjunction with a therapeutic agent are known in the art. For example, Johnson et al. have disclosed the treatment of joint inflammation and other conditions with an injection of biocompatible polymeric electrospun fiber fragments along with a carrier medium containing chitosan (U.S. Published Application No. 2016/0325015; Nanofiber Solutions, LLC). Weldon et al. reported the use of electrospun bupivacaine-eluting sutures manufactured from poly(lactic-co-glycolic acid) in a rat skin wound model, wherein the sutures provided local anesthesia at an incision site (J. Control Release, 2012, 161:3, 903-909). Similarly, Palasis et al. disclosed the treatment of postoperative pain by implanting electrospun fibers loaded with an opioid, anesthetic or a non-opioid analgesic within a surgical site (U.S. Patent Publication No. 2013/0071463; Palasis et al.). Electrospun microfibers suitable for use in the present technology may be obtained by the methods disclosed in the above cited references, which are herein incorporated in their entirety.

When implanted in a patient's joint (for example, a knee joint), the bioresorbable depot described above may be positioned in the joint such that it will be articulating throughout the duration of release. So as to avoid premature release of the analgesic, it is desirable for the depot to have a threshold level of mechanical integrity and stability until most of the analgesic has been released. While it may be desirable to maximize the loading of therapeutic agent in the bioresorbable depot, as described above, such maximization can typically be at the expense of mechanical integrity and stability of the depot. Given the high dosage of anesthetic necessary to provide analgesia through both the acute and subacute postoperative pain periods and limited space in the knee, it is desirable for the depot described herein to have a high density loading of anesthetic while still maintaining sufficient mechanical integrity and stability in the knee. The layered structure and, particularly, the presence of the control region provide some safeguard against the premature release of anesthetic. Moreover, the use of heat compression in the manufacturing process enables substantial loading of anesthetic into the therapeutic region while creating a thermal bond between the therapeutic region and control region, thereby preventing delamination, and a consequent uncontrolled release of drug, when the depot is subjected to mechanical stress in the knee.

It is generally desirable that the implanted polymer fully degrade following complete delivery of the therapeutic agent. Full degradation is preferred because, unless the implanted polymer provides some structural function or support, the clinical practitioner would have to reconcile leaving in a foreign body with no functional purpose, which could be a source of inflammation or infection, or perform another surgery simply to remove the remaining polymer. As an alternative to full degradation, it would be desirable for any remaining polymer to be fully encapsulated by the body.

The degradation of an implanted polymer consists essentially of two sequential processes: diffusion of an aqueous solution (e.g., physiological fluids) followed by hydrolytic degradation. Degradation usually takes one of two forms: (1) surface erosion; and (2) bulk degradation. Surface erosion of a polymer occurs when the polymer erodes from the surface inward, where hydrolytic erosion at the surface is faster than the ingress of water into the polymer. Conversely, bulk degradation occurs throughout the entire polymer, where water penetrates and degrades the interior of the material faster than the surface can erode. Polymers such as PLA, PGA, PLGA and PCL all resorb into the body via bulk degradation.

The time necessary for complete degradation can vary greatly based on the material selected and the clinical performance requirements of the depot. For example, in the case of treating and managing postoperative pain, it may be desirable for the polymer depot to release therapeutic agent (i.e., an analgesic) for anywhere from 5 to 30 days. In the case of treating or preventing infection of a prosthetic joint (e.g., knee or hip implant), it may be desirable for the polymer depot to release an anti-infective agent for anywhere from 2 to 4 months. Alternatively, even if the entire amount of therapeutic agent loaded into the polymer has been released, it may be desirable for the polymer to degrade over a longer period than the duration of drug release. For example, rapid degradation can often make the polymer brittle and fragile, thereby compromising mechanical performance, or provoking an inflammatory response from the body. In particular, it may be desirable, in certain clinical applications, to have an embodiment wherein degradation of the polymer commenced only after release of substantially all of the therapeutic agent.

In certain embodiments of the present technology, it may be desirable for the polymer to fully resorb into the body after substantially all therapeutic agent loaded therein is released. In certain embodiments, this degradation can be as short as 1 month. Alternatively, in other embodiments, full degradation could take as long as 2 months, 3 months, 4 months, 6 months, 9 months or 12 months. In some embodiments, the bioresorbable polymer substantially degrades in vivo within about one month, about two months, about three months, about four months, about five months or about six months. In some embodiments, it may be desirable for full degradation to be 6 months such that the mechanical properties of the implanted polymer are preserved for the first 2 months following implantation.

Core Acidification

Figure 17:
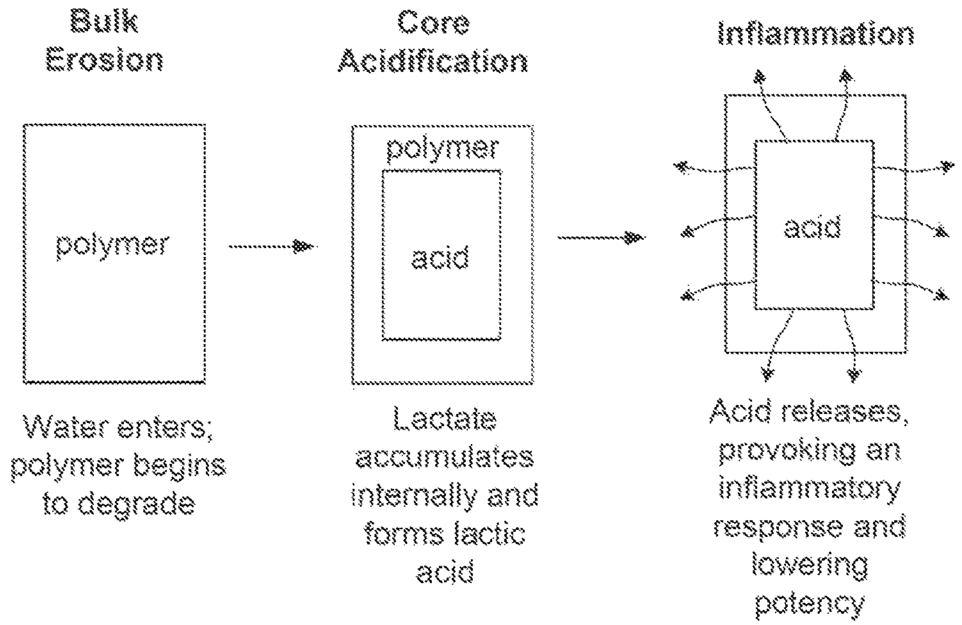
FIG. 17 (Prior Art)
FIG. 17 is a schematic representation of core acidification of the prior art.
Figure 18:
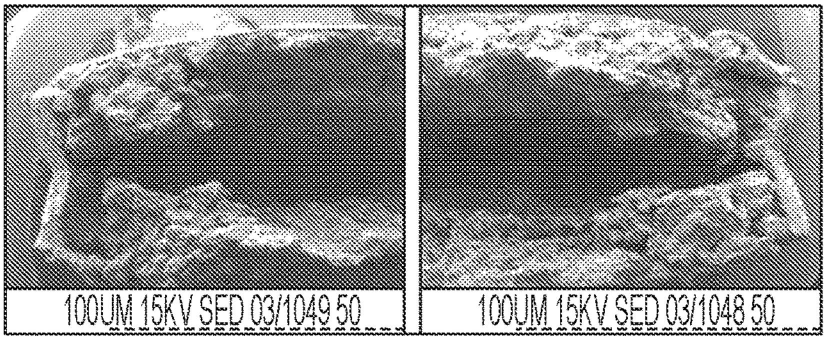
FIG. 18 (Prior Art)
FIG. 18 is a scanning electron microscope image of a polymer tablet of the prior art after 20 days of degradation.

Traditional bioresorbable implants often lead to tissue inflammation due to a phenomenon known as "core acidification." For example, as shown schematically in FIG. 17, polymer implants having a thickness greater than 1 mm degrade by bulk erosion (i.e., degradation occurs throughout the whole material equally; both the surface and the inside of the material degrade at substantially the same time). As the polymer degrades, lactate accumulates at an internal region of the implant. Eventually, because of the high pH in the internal region of the implant, the lactate becomes lactic acid. The accumulated lactic acid will invariably release into the body, thereby provoking an inflammatory response. FIG. 18, for example, is a scanning electron microscope ("SEM") image of a polymer tablet of the prior art after 20 days of degradation. Inflammation in and around a prosthetic joint may be particularly concerning because of the risk of inflammation-induced osteolysis, which may cause a loosening of the newly implanted joint. Moreover, core acidification causes extracellular pH to drop, which then causes the amount of free base bupivacaine to drop. Only free base bupivacaine can cross the lipid bilayer forming the cell membrane into the neuron. Once bupivacaine crosses into the neuron the percent of bupivacaine HCl increases. It is the bupivacaine HCl form that is active by blocking sodium from entering the neuron thus inducing analgesia. Thus, any reduction in extracellular pH (for example, via core acidification) slows transfer of the analgesic into the neuron, thereby reducing or altogether eliminating the therapeutic effects of the analgesic.

The degree of core acidification is determined in large part by the geometry and dimensions of the polymer implant. (See, e.g., Grizzi et al., Hydrolytic degradation of devices based on poly(dl-lactic acid) size-dependence, Biomaterials, 1995, Vol. 16 No. 4, pp. 305-11; Fukuzaki et al., in vivo characteristics of high molecular weight copoly(1-lactide/glycolide) with S-type degradation pattern for application in drug delivery systems, Biomaterials 1991, Vol. 12 May, pp. 433-37; Li et al., Structure-property relationships in the case of degradation of massive alipathic poly-(a-hydroxy acids) in aqueous media, Journal of Materials Science: Materials in Medicine I (1990), pp. 123-130.) For example, degradation in more massive monolithic devices (mm-size scales and greater) proceeds much more rapidly in their interior than on their surface, leading to an outer layer of slowly degrading polymer entrapping more advanced internal degradation products from interior zone autocatalysis (so-called "S-type" non-linear kinetic degradation profile.). In contrast to a thicker film, a thin film of less than 1 mm thickness will typically degrade via surface erosion, wherein the lactate resulting from degradation will not accumulate in the interior of the film. Thin films, because of their high surface area to volume ratios, are known to degrade uniformly and do not lead to core acidification. (See Grizzi et al.)

Figure 19A:
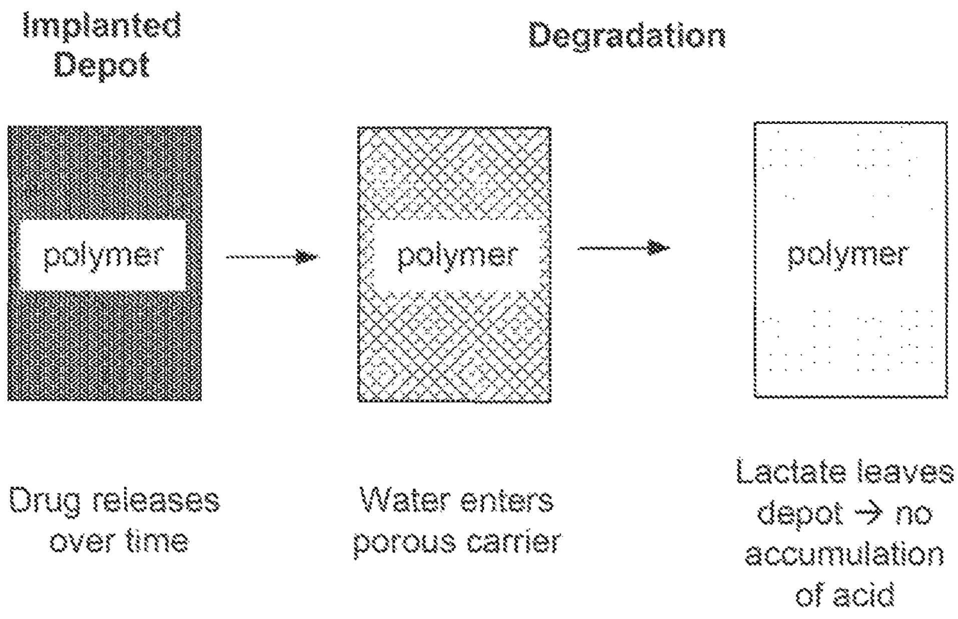
FIG. 19A is a schematic representation of the degradation of the depots of the present technology.
Figure 19B:
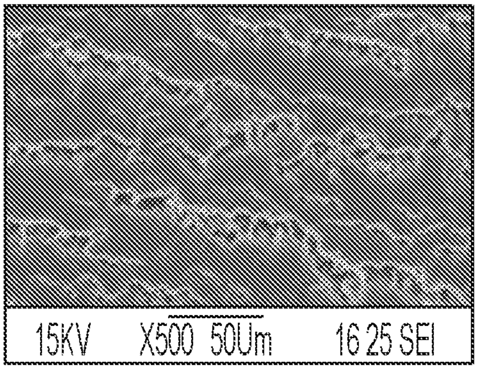
FIGS. 19B and 19C are scanning electron microscope ("SEM") images of cross-sections of depots of the present technology at different timepoints during degradation.
Figure 19C:
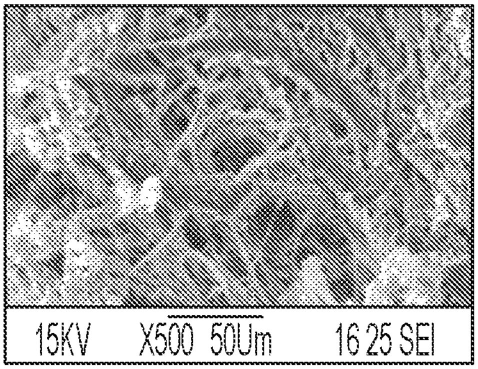

As shown schematically in FIG. 19A, the depots of the present technology may shed up to 50%, 60%, 70% or 80% of their individual mass (anesthetic and releasing agent) over the course of releasing the anesthetic (e.g., 5 days, 7 days, 10 days, 14 days, 20 days, 30 days, etc.), resulting in a highly porous, mesh-like system that—at least for the purpose of degradation—behaves like a thin-film because of its high surface area to volume ratio. Body fluids will invade the highly porous polymer carrier to degrade the remaining polymer via surface erosion, thereby avoiding core acidification and the resulting inflammatory response. Without being bound by theory, it is believed that the drug core matrix of the therapeutic region becomes highly porous as degradation continues. For example, FIGS. 19B and 19C are scanning electron microscope ("SEM") images showing the therapeutic region before and after elution, respectively. However, even after the release of therapeutic agent, there is still a clear porous structure left through which water and acid can diffuse effectively. Thus, depots 100 of the present technology having a thickness greater than about 1 mm degrade like a thin film, and surprisingly do not exhibit core acidification.

E. Releasing Agent

In many implantable drug eluting technologies, the depot provides an initial, uncontrolled burst release of drug followed by a residual release. These drug release kinetics may be desirable in certain clinical applications, but may be unavoidable even when undesirable. Hydrophilic drugs loaded in a polymer carrier will typically provide a burst release when exposed to physiologic fluids. This dynamic may present challenges, particularly when it is desirable to load a large volume of drug for controlled, sustained in vivo administration. For example, although it may be desirable to implant several days or weeks' worth of dosage to achieve a sustained, durable, in vivo pharmacological treatment, it is imperative that the therapeutic agent is released as prescribed, otherwise release of the entire payload could result in severe complications to the patient.

To achieve finer control over the release of the therapeutic agent when exposed to fluids, the depots 100 of the present technology may include a releasing agent. In some embodiments, both the therapeutic region 200 and the control region 300 include a releasing agent (or mix of releasing agents), which can be the same or different releasing agent (or mix of releasing agents) in the same or different amount, concentration, and/or weight percentage. In some embodiments, the control region 300 includes a releasing agent and the therapeutic region 200 does not include a releasing agent. In some embodiments, the therapeutic region 200 includes a releasing agent and the control region 300 does not include a releasing agent. At least as used in this section, "the releasing agent" applies to a releasing agent that may be used in the therapeutic region 200 and/or in the control region 300.

The type and/or amount of releasing agent within the therapeutic region 200 and/or control region 300 may be varied according to the desired release rate of the therapeutic agent into the surrounding biological fluids. For example, choosing releasing agents with different dissolution times will affect the rate of release. Also, the weight percentage of releasing agent in a region of polymer will influence the number and the size of the diffusion openings subsequently formed in the polymer, thereby affecting the rate of therapeutic agent release from the depot 100 (e.g., the greater the weight percentage of releasing agent, the faster the release). The presence of releasing agent in select regions also influences the release rate of therapeutic agent. For example, a depot with releasing agent in the control region 300 and/or therapeutic region 200 will generally release therapeutic agent at a higher rate compared to a depot with no releasing agent. Similarly, releasing agent in both the control region 300 and the therapeutic region 200 will generally release therapeutic agent at a higher rate than when releasing agent is in the control region alone.

In certain embodiments of the present technology, the layer-by-layer ratio of releasing agent to bioresorbable polymer can be adjusted to control the rate of therapeutic agent released from the depot 100. For example, in many embodiments of the present technology, the depot 100 includes a therapeutic region 200 having a weight percentage of releasing agent that is different than the weight percentage of the releasing agent in the control region 200. For example, the therapeutic region 200 may have a greater or lesser weight percentage of releasing agent than the control region 300. In some embodiments, the control region 300 may have a weight percentage of releasing agent that is at least 2 times greater than the weight percentage of the releasing agent in the therapeutic region 200. In some embodiments, the control region 300 may have a weight percentage of releasing agent that is at least 3-20 times greater, at least 4 times greater, at least 5 times greater, at least 6 times greater, at least 7 times greater, at least 8 times greater, at least 9 times greater, at least 10 times greater, at least 11 times greater, at least 12 times greater, at least 13 times greater, at least 14 times greater, at least 16 times greater, at least 17 times greater, at least 18 times greater, at least 19 times greater, at least 20 times greater, at least 25 times greater, at least 30 times greater, about 5 to 10 times greater, about 10 to 15 times greater, about 5 to 15 times greater, or about 15 to 25 times greater than the weight percentage of the releasing agent in the therapeutic region 200.

In many embodiments of the present technology, the releasing agent is a surfactant. Unlike the use as a releasing agent as described herein, surfactants are usually used to control the dispersions, flocculation and wetting properties of a drug or polymer. Fundamentally, surfactants operate on the interface between the polymer and drug or the interface between the drug and biological membrane. Depending on the type of formulation, surfactants typically play a role in several aspects of drug delivery: (1) solubilization or stabilization of hydrophobic drugs by lowering the entropic cost of solvating hydrophobic drug through complexation with drug molecules in solution (C. Bell and K. A. Woodrow, ANTIMICROB. AGENTS CHEMOTHER., 2014, 58:8, 4855-65); (2) improvement of the wetting of tablet or polymer for fast disintegration (M. Irfan, et al., SAUDI PHARM. J., 2016, 24, 537-46); (3) formation of colloidal drug delivery systems, such as reverse micelles, vesicles, liquid crystal dispersions, nanoemulsions and nanoparticles (M. Fanun, Colloids in Drug Delivery, 2010, p. 357); and (4) improvement the bioperformance of drugs by altering the permeability of biological membrane and consequently drug penetration/permeation profile (S. Jain, et al., Lipid Based Vesicular Drug Delivery Systems, 2014, Vol. 2014, Article ID 574673).

In order to illustrate the unique aspects of using a releasing agent in the polymeric control region to form diffusion openings and/or microchannels in the present technology, it is helpful to explain the more common approach of using hydrophilic molecules to enhance drug release. Conventionally, drug release is enhanced by creating a larger surface area in order to increase contact between the drug and the bodily fluid, thereby accelerating drug release. The most common mechanism for forming pores prior to implantation is to use non-surfactant hydrophilic molecules as pore-forming agents in polymer layers, either as a coating layer or a free-standing film (Kanagale, P., et al., AAPS PHARM. SCITECH., 2007; 8(3), E1-7). Usually, pores are pre-formed by blending hydrophilic molecules with polymer, then removing the hydrophilic molecules by contact with water. However, when hydrophilic molecules are blended with hydrophobic polymer, the molecules tend to form hydrophilic domains and hydrophobic domains, which are energetically favorable due to the increase in entropy. When the film contacts water, hydrophilic domains are removed and replaced with large pores. The rate of drug release in this case is solely controlled by the porosity of the film and the resulting increased total surface area. The typical drug release curve in this case has a high, uncontrolled initial burst followed with a very slow release of residual drug afterwards.

Previously, when non-surfactant hydrophilic molecules are mixed into the polymer and then removed, a film with a porous structure is created. This porous layer reduces mechanical strength and elasticity, making it less suitable for certain applications. Additionally, this structure does not withstand heat compression bonding of the film because the pores would collapse. The loss of porous structure during heat compression negates the original intent of using the hydrophilic molecule, thus resulting in a densely packed film without any enhanced therapeutic agent release capability.

Further, if the hydrophilic molecule remains in the polymer layer during heat compression, the dissolution of the hydrophilic molecule in vivo causes the formation of very large pores, approximately 3-10 μm in diameter. Such large pores provide a large surface area, thereby causing a burst release of drug. In contrast to the use of hydrophilic molecules, the use of a surfactant as a releasing agent in the present technology enables the formation of microchannels approximately 5-20 nanometers in diameter, which is two orders of magnitude smaller than the pores resulting from the use of hydrophilic molecules. This allows tight control of the drug release by diffusion and, if desirable, without an uncontrolled burst release upon implantation. Additionally, use of a surfactant as a releasing agent allows the agent to remain present in the polymer prior to use and no pre-formed pores are created. This approach is particularly advantageous because the polymer's mechanical properties are preserved, thereby allowing the polymer to be easily processed and worked into different configurations.

In the present technology, the releasing agent is pre-mixed into the bioresorbable polymer such that each layer of polymer is contiguous and dense. The depot 100 is then formed when these layers are bonded together via heat compression without any adverse impact to the functional capabilities of the film. When the densely packed film is ultimately implanted, the releasing agent dissolves to enable efficient, controlled release of the therapeutic agent.

In some embodiments, the releasing agent comprises a polysorbate. Polysorbate is commonly used in the pharmaceutical industry as an excipient and solubilizing agent. Polysorbate is a non-ionic surfactant formed by the ethoxylation of sorbitan followed by esterification by lauric acid. Polysorbate 20 [IUPAC name: polyoxyethylene(20)sorbitan monolaurate]contains a mixture of ethoxylated sorbitan with 20 repeat units of polyethylene glycol distributed among four different sites in the sorbitan molecule. Common commercial names include Tween™ and Tween 20™ (Croda International Plc, Goole, East Yorkshire, UK) and Alkest® TW 20 (Oxiteno, Houston, TX).

Polysorbate is often utilized to improve oral bioavailability of a poorly water-soluble/hydrophobic drug. For example, polysorbate was used to improve bioavailability of active molecules that possess low solubility and/or intestinal epithelial permeability and it was observed that the bioavailability of this poorly water-soluble drug was greatly enhanced in a formulation with polysorbate or similar surfactants. (WO2008/030425; Breslin; Merck.) Akbari, et al., observed that using the hydrophilic carrier polyethylene glycol (PEG) along with polysorbate leads to faster an oral enhanced drug release rate because the polysorbate brings the drug in close contact with the PEG. (Akbari, J., et al., ADV. PHARM. BULL., 2015, 5(3): 435-41.)

Polysorbate also functions as a water-soluble emulsifier that promotes the formation of oil/water emulsions. For example, the drug famotidine is known to have high solubility in water but low in vivo permeability. Polysorbate was used in an oral microemulsion formulation for enhancing the bioavailability of famotidine. (Sajal Kumar Jha, et al., IJDDR, 2011, 3(4): 336-43.) Polysorbate is also used as a wetting agent to achieve rapid drug delivery. For example, Ball et al., achieved rapid delivery of maraviroc via a combination of a polyvinylpyrrolidone (PVP) electrospun nanofiber and 2.5 wt % Tween 20, which allowed for the complete release of 28 wt % maraviroc in just six minutes. It was believed that use of Tween 20 as a wetting agent allowed water to penetrate the PVP nanofiber matrix more quickly, thereby increasing the rate of drug release. (Ball, C., et al., ANTIMICROB. AGENTS CHEMOTHERAPY, 2014, 58:8, 4855-65.)

As described above, in order to improve drug release in certain polymer carriers, hydrophilic polymers, such as polysorbate, have been added to these carriers to accelerate or to enhance drug release from biocompatible polymers such as polyethylene glycol (PEG) in oral formulations (Akbari, J., et al., ADV. PHARM. BULL., 2015, 5(3): 435-441). However, these formulations are intended to provide an immediate release of a hydrophobic drug into a hydrophilic environment (the in vivo physiologic fluid), not a variable or sustained controlled release as part of a control region.

In some embodiments, the releasing agent is polysorbate 20, commercially known as Tween 20™. Other releasing agents suitable for use in the present technology include polysorbates, such as Polysorbate 80, Polysorbate 60, Polysorbate 40, and Polysorbate 20; sorbitan fatty acid esters, such as sorbitan monostearate (Span 60), sorbitan tristearate (Span 65), sorbitane trioleate (Span 85), sorbitan monooleate (Span 80), sorbitan monopalmitate, sorbitan monostearate, sorbitan monolaurate, sorbitan monopalmitate, sorbitan trioleate, and sorbitan tribehenate; sucrose esters, such as sucrose monodecanoate, sucrose monolaurate, sucrose distearate, and sucrose stearate; castor oils such as polyethoxylated castor oil, polyoxyl hydrogenated castor oil, polyoxyl 35 castor oil, Polyoxyl 40 Hydrogenated castor oil, Polyoxyl 40 castor oil, Cremophor® RH60, and Cremophor® RH40; polyethylene glycol ester glycerides, such as Labrasol®, Labrifil® 1944; poloxamer; polyoxyethylene polyoxypropylene 1800; polyoxyethylene fatty acid esters, such as Polyoxyl 20 Stearyl Ether, diethylene glycol octadecyl ether, glyceryl monostearate, triglycerol monostearate, Polyoxyl 20 stearate, Polyoxyl 40 stearate, polyoxyethylene sorbitan monoisostearate, polyethylene glycol 40 sorbitan diisostearate; oleic acid; sodium desoxycholate; sodium lauryl sulfate; myristic acid; stearic acid; vitamin E-TPGS (vitamin E d-alpha-tocopherol polyethylene glycol succinate); saturated polyglycolized glycerides, such as Gelucire® 44/14 and Gelucire® 50/13; and polypropoxylated stearyl alcohols such as Acconon® MC-8 and Acconon® CC-6.

Diffusion Openings

The channels or voids formed within the therapeutic region 200 and/or control region 300 by dissolution of the releasing agent may be in the form of a plurality of interconnected openings or pores and/or a plurality of interconnected pathways, referred to herein as "diffusion openings." In some embodiments, one or more of the channels may be in the form of discrete pathways, channels, or openings within the respective therapeutic and/or control region. Depending on the chemical and material composition of the therapeutic and control regions, one or more of the formed channels may extend: (a) from a first end within the therapeutic region to a second end also within the therapeutic region; (b) from a first end within the therapeutic region to a second end at the interface of the therapeutic region and the control region; (c) from a first end within the therapeutic region to a second end within the control region; (d) from a first end within the therapeutic region through the control region to a second end at an outer surface of the control region; (e) from a first end at the interface between the therapeutic region and the control region through the control region to a second end within the control region; (f) from a first end at the interface between the therapeutic region and the control region to a second end at an outer surface of the control region; (g) from a first end within the control region to a second end also within the control region; and (h) from a first end within the control region to a second end at an outer surface of the control region. Moreover, one or more of the channels may extend between two or more microlayers of the therapeutic region and/or control region.

F. Constituent Ratios

In some embodiments, the ratio of the polymer in the control region 300 to the releasing agent in the control region 300 is at least 1:1. In some embodiments, the ratio may be at least 1.5:1, at least 2:1, at least 2.5:1, or at least 3:1.

In some embodiments, a ratio of the mass of the therapeutic agent in the depot 100 to the polymer mass of the depot is at least 1:1, at least 2:1, at least 3:1, at least 4:1, at least 5:1, at least 6:1, at least 7:1, at least 8:1, at least 9:1, at least 10:1, at least 11:1, at least 12:1, at least 13:1, at least 14:1, at least 15:1, or at least 16:1.

In some embodiments, the ratio of releasing agent to polymer to therapeutic agent in the therapeutic region 200 is of from about 0.1:10:20 to about 2:10:20, and in some embodiments of from about 0.1:10:20 to about 1:10:20, and in some embodiments of from about 0.1:10:20 to about 0.5:10:20.

In some embodiments, the ratio of releasing agent to polymer in the control region 300 is of from about 1:2 to about 1:10. In some embodiments, one or more of the control regions may have a ratio of releasing agent to polymer of 1:2, and one or more of the other control regions may have a ratio of releasing agent to polymer of 1:10

G. Selected Depot Embodiments Including a Barrier Region

In some embodiments, the depot 100 may be configured to release the therapeutic agent in an omnidirectional manner. In other embodiments, the depot may include one or more barrier regions 400 covering one or more portions of the therapeutic region 200 and/or control region 300, such that release of the therapeutic agent is limited to certain directions. The barrier region 400 may provide structural support for the depot. The barrier region 400 may comprise a low porosity, high density of bioresorbable polymer configured to provide a directional release capability to the depot. In this configuration, the substantial impermeability of this low porosity, high density polymer structure in the barrier region 400 blocks or impedes the passage of agents released from the therapeutic region 200. Accordingly, the agents released from the therapeutic region 200 take a path of less resistance through the control region 300 opposite from the barrier region 400, particularly following the creation of diffusion openings in the control region 300.

Figure 16A:
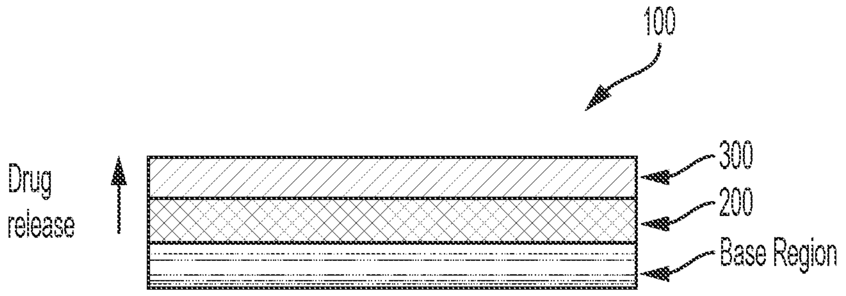
FIGS. 16A-16E depict various depot embodiments including a barrier region in accordance with the technology.

An example a depot 100 of the present technology having a barrier region 400 is shown in FIG. 16A. The barrier region 400 may comprise a low porosity, high density of bioresorbable polymer configured to provide a directional release capability to the multi-region depot. In this configuration, the low porosity, high density polymer structure in the barrier region 400 blocks or impedes passage of agents release from the therapeutic region 200. Accordingly, the agents released from the therapeutic region 200 take a path of lesser resistance through the control region opposite from the barrier region 400, particularly following the creation of channels in the control region. In an additional embodiment, the porosity of other regions of the multi-region depot can be varied to facilitate the release of therapeutic agent. For example, in this embodiment, the barrier region 400, the therapeutic region 200, and the control region 300 of the multi-region depot depicted in FIG. 16A may have different porosities ranging from low porosity in the barrier region 400 to higher porosities in the therapeutic agent and control regions to facilitate the release of therapeutic agent from the multi-region depot. In additional embodiments, the porosities of the edges of the multi-region depot, or within portions of any of the individual regions, can be varied to properly regulate or manipulate the release of therapeutic agent.

Figure 16B:
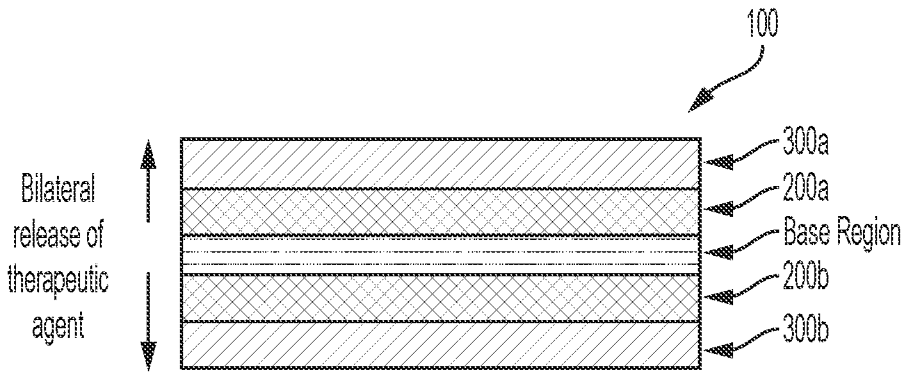

In the embodiment depicted in FIG. 16B, the multi-region depot provides for a bilateral or bidirectional release of therapeutic agent. This bidirectional release capability is accomplished through symmetric regioning about a high-density barrier region 400, wherein, as described above, the therapeutic agent releases along a path of less resistance, thereby releasing away from the high-density barrier region 400. More specifically, disposed on one side of the barrier region 400 is a control region 300*a* and a therapeutic region 200*a* and, disposed on the other side of the barrier region 400, is a control region 300*b* and a therapeutic region 200*b* that are substantially similar to the pair on the other side. These pairs on either side of the barrier region 400 are configured to produce substantially equivalent, bidirectional release of therapeutic agent. In an alternate embodiment, a bidirectional release that is not equivalent (i.e., the therapeutic agent and/or rate of release in each direction is not the same) may be accomplished by asymmetric regioning, whereby the control region and therapeutic region pairs on either side of the barrier region 400 are substantially different.

Figure 16C:
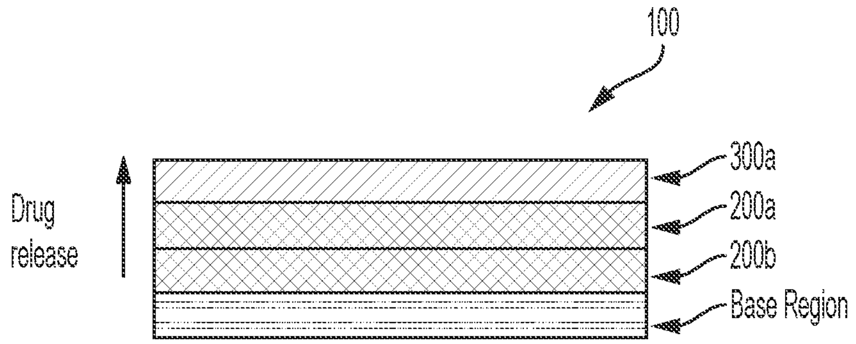

In additional embodiments, it may be desirable for the multi-region depot to release multiple therapeutic agents. This capability can be particularly useful when multimodal pharmacological therapy is indicated. In the embodiment shown in FIG. 16C, the multi-region depot comprises a topmost or outermost control region 300*a*, a first therapeutic region 200*a* adjacent to the control region, a second therapeutic region 200*b* adjacent to the first therapeutic region 200*a*, and a barrier region 400 adjacent to the second therapeutic region 200*b*. In this embodiment, the first therapeutic region 200*a* and the second therapeutic region 200*b* comprise a first therapeutic agent and a second therapeutic agent, respectively. In certain embodiments, the first and second therapeutic agents are different. In one embodiment, the multi-region depot is configured to release the first and second therapeutic agents in sequence, simultaneously, or in an overlapping fashion to yield a complementary or synergistic benefit. In this configuration, the presence and function of the control region 300*a* may also ensure consistent and, if desired, substantially even release of multiple therapeutic agents residing beneath. Since many conventional drug delivery devices can fail to provide an even release of multiple drugs with different molecular weights, solubility, etc., the role of the control region in achieving a substantially even release of different therapeutic agents can be a significant advantage.

In some embodiments, the first therapeutic agent and second therapeutic agent are the same therapeutic agent but are present in the first and second therapeutic regions, respectively, in different relative concentrations to represent different dosages to be administered. In some embodiments, the first and second therapeutic agents of the first and second therapeutic regions, respectively, may have no clinical association or relationship whatsoever. For example, in an embodiment for use as part of a total joint replacement (e.g., total knee arthroplasty, total hip arthroplasty) or other surgical procedure, it may be clinically desirable to administer in the vicinity of the surgical site both an analgesic (e.g., local anesthetic) to treat and better manage postoperative pain for several days or weeks following the surgery and an antibiotic to treat or prevent surgical site infection associated with the surgery or implanted prosthesis (if any) for several weeks or months following the surgery. In this embodiment, the first therapeutic region 200*a* may comprise a therapeutically effective dose of local anesthetic to substantially provide pain relief for no less than 3 days and up to 15 days following the surgery and the second therapeutic region 200*b* may comprise a therapeutically effective dose of antibiotics to substantially provide a minimally effective concentration of antibiotic in the vicinity of the surgical site for up to three months following the surgery.

Figure 16D:
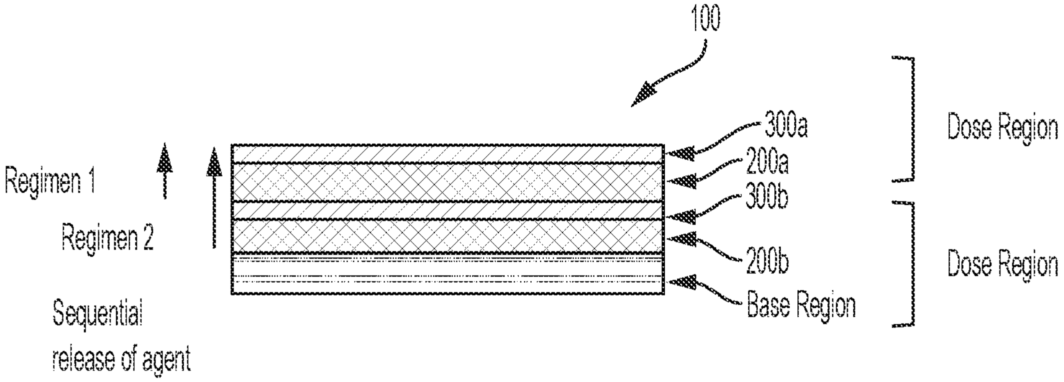

In some embodiments, as shown in FIG. 16D, the depot 100 comprises a first dosage region and a second dosage region, wherein the first and second dosage regions correspond to first and second dosage regimens. More specifically, each dosage region comprises a control region and therapeutic region pair, wherein each pair is configured for controlled release of a therapeutic agent from the therapeutic region 200*a*, 200*b* in accordance with a predetermined dosage regimen. For example, in treating and/or managing postoperative pain, it may be desirable for the multi-region depot to consistently release 50-400 mg/day of local anesthetic (e.g., bupivacaine, ropivacaine and the like) for at least 2-3 days following surgery (i.e., first dosage regimen) and then release a local anesthetic at a slower rate (e.g., 25-200 mg/day) for the next 5 to 10 days (i.e., second dosage regimen). In this exemplary embodiment, the first dosage region, and the control region and therapeutic region pair therein, would be sized, dimensioned, and configured such that the multi-region depot releases the first therapeutic agent in a manner that is consistent with the prescribed first dosage regimen. Similarly, the second dosage region, and the control region and therapeutic region pair therein, would be sized, dimensioned and configured such that the multi-region depot releases the second therapeutic agent in a manner that is consistent with the prescribed second dosage regimen. In another embodiment, the first and second dosage regions may correspond to dosage regimens utilizing different therapeutic agents. In one embodiment, the multi-region depot 100 is configured to administer the first and second dosage regimens in sequence, simultaneously, or in an overlapping fashion to yield a complementary or synergistic benefit. In an alternate embodiment of this scenario, the first and second dosage regimens, respectively, may have no clinical association or relationship whatsoever. For example, as described above with respect to the embodiment depicted in FIG. 16C, the first dosage regimen administered via the first dosage region may be treating or managing postoperative pain management and the second dosage regimen administered via the second dosage region may be treating or preventing infection of the surgical site or implanted prosthesis (if any).

Figure 16E:
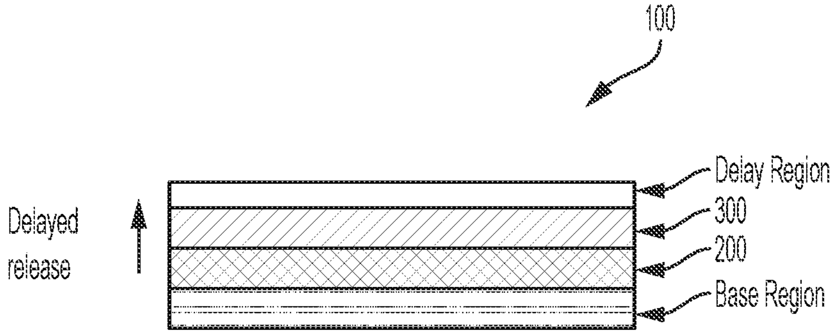

Certain embodiments of the present invention utilize delayed release agents. As illustrated in FIG. 16E, the depot 100 may include a barrier region 400 as the outermost (i.e., topmost) region to the multi-region depot and adjacent to a control region 300 comprising a releasing agent. The barrier region 400 presents a barrier to physiologic fluids from reaching and dissolving the releasing agent within the control region. In one embodiment, the barrier region 400 may comprise a delayed release agent mixed with a bioresorbable polymer, but without a releasing agent. Delayed release agents are different from the releasing agents used in the multi-region depot of the invention. Delayed release agents dissolve in physiological fluids more slowly than do releasing agents and thus provide the possibility for release of a therapeutic agent a defined amount of time following implantation of the multi-region depot. In embodiments where a delayed release agent is not present in the barrier region 400, it may take more time for the physiological fluids to traverse the barrier region 400 and contact the releasing agent. Only when the physiological fluids make contact with the control region will the releasing agent begin to dissolve, thus allowing the controlled release of the therapeutic agent. Delayed release agents may be advantageously used in the therapeutic methods of the invention wherein the therapeutic agent is not immediately required. For example, a nerve blocking agent may be injected prior to a surgical procedure, numbing the entire area around a surgical site. The controlled release of a local anesthetic is not required in such a surgery until the nerve block wears off.

Suitable delayed release agents for use in the present invention are pharmaceutically acceptable hydrophobic molecules such as fatty acid esters. Such esters include, but are not limited to, esters of myristoleic acid, sapienic acid, vaccenic acid, stearic acid, arachidic acid, palmitic acid, erucic acid, oleic acid, arachidonic acid, linoleic acid, linoelaidic acid, eicosapentaenoic acid, docosahexaenoic acid. Preferred esters include stearic acid methyl ester, oleic acid ethyl ester, and oleic acid methyl ester. Other suitable delayed release agents include tocopherol and esters of tocopherol, such as tocopheryl nicotinate and tocopheryl linolate.

H. Additional Depot Configurations

Figure 20:
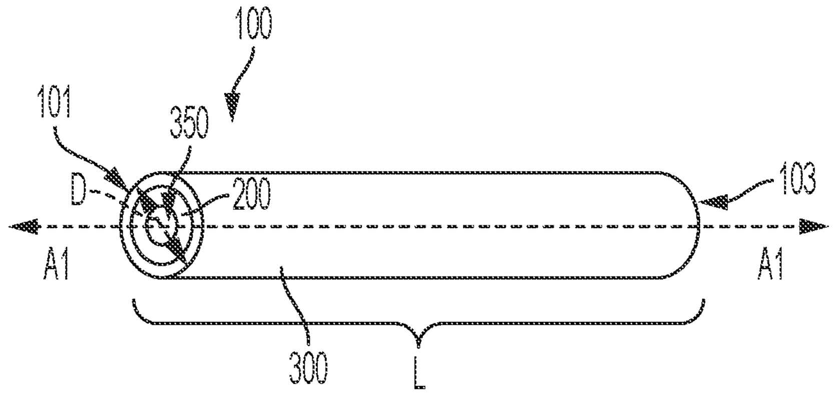
FIG. 20 is a perspective view of a depot in accordance with some embodiments of the present technology.

FIGS. 20-36 illustrate various examples of depots 100 having an elongated form. As depicted in FIG. 20, an "elongated depot" or an "elongated form" as used herein refers to a depot configuration in which the depot 100 has a length L between its ends along a first axis A1 (e.g., a longitudinal axis) that is at least 1.1, 1.2, 1.3, 1.4, 1.5, 1.6, 1.7, 1.8, 1.9, 2, 3, 4, 5, 6, 7, 8, 9, 10, 20, or 30 times greater than a maximum dimension D of a cross-sectional slice of the depot 100 within a plane orthogonal to the first axis A1. The elongated depots 100 described herein may include a therapeutic region 200 containing a therapeutic agent (such as any of the therapeutic agents described herein) and a control region 300 at least partially surrounding the therapeutic region 200 to control release of the therapeutic agent from the depot 100. The therapeutic region 200 may optionally include a bioresorbable polymer (such as any of the polymers described herein) and/or a releasing agent (such as any of the releasing agents described herein). The control region 300 may include a bioresorbable polymer (such as any of the polymers described herein) mixed with a releasing agent (such as any of the releasing agents described herein), but does not include any therapeutic agent at least prior to implantation. In some embodiments, the control region 300 may include some therapeutic agent prior to implantation, for example having a lower concentration of therapeutic agent than the therapeutic region 200. As discussed in greater detail below, the thickness of the control region 300, the concentration of releasing agent in the control region 300, the amount of exposed (uncovered) surface area of the therapeutic region 200, the shape and size of the depot 100, and other suitable parameters may be varied to achieve a desired release profile for the sustained, controlled release of the therapeutic agent from the depot 100.

In the embodiments shown in FIGS. 20-36, the elongated depot 100 has a cylindrical, columnar, and/or rod-like shape such that the cross-sectional shape is a circle and the cross-sectional dimension D is the diameter of the circle. In some embodiments, however, the elongated depot 100 may have another elongated configuration and/or cross-sectional shape along all or a portion of its length L. For example, the depot 100 may be in the form of a ribbon-like strip and thus have a square or rectangular cross-sectional shape. In other embodiments, the elongated depot 100 may have a circular, triangular, rhomboid, or other polygonal or non-polygonal cross-sectional shape based on the desired application. The elongated depot 100 may be a solid or semi-solid formulation with sufficient column strength to be pushed or pulled from a delivery device and sufficient durability and/or structural integrity to maintain its shape while the therapeutic agent is released into the surrounding anatomy for the desired duration of release.

A length L of the elongated depot 100 can be about 2 mm to about 300 mm, about 10 mm to about 200 mm, or about 10 mm to about 100 mm. In some embodiments, the maximum cross-sectional dimension D of the depot 100 can be between about 0.01 mm to about 5 mm, between about 0.1 mm to about 3 mm, or between about 0.5 mm to about 2 mm. The elongated form may be particularly well suited for injection or insertion to a subcutaneous, intramuscular, or other location through a needle or other suitable delivery device. Additionally or alternatively, the elongated depots 100 may be implanted using other techniques, for example surgical implantation through an open incision, a minimally invasive procedure (e.g. laparoscopic surgery), or any other suitable technique based on the application.

FIG. 20 illustrates an example of an elongated, generally cylindrical depot 100 comprising tubular, concentric therapeutic and control regions 200 and 300. The therapeutic region 200 comprises a tubular sidewall having an outer surface covered by the control region 300 and an exposed inner surface defining a lumen 350 that extends through the length L of the depot 100. The lumen 350 can be devoid of any material such that when the depot 100 is exposed to physiological fluid in vivo, the inner surface of the therapeutic region 200 is in direct contact with the fluid, thereby enhancing release of the therapeutic agent (relative to an elongated depot without a lumen through the therapeutic region). As shown in FIG. 20, the end surfaces of the therapeutic region 200 at the longitudinal ends 101, 103 of the depot 100 may also remain exposed/uncovered by the control region 300 (only one end surface is visible in FIG. 20). In some embodiments, the elongated depot 100 may include multiple, layered control regions 300 having the same composition or different compositions and/or the same thickness or different thicknesses. In these and other embodiments, the control region 300 may extend over one or both end surfaces of the therapeutic region 200. In particular embodiments, the lumen 350 extends through only a portion of the length L of the depot 100 and/or the tubular therapeutic region 200 is not concentric with the control region 300.

Figure 21:
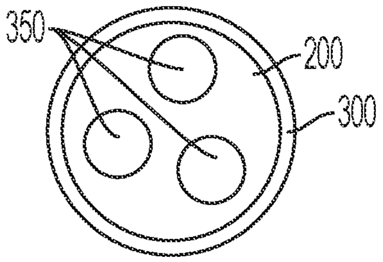
FIG. 21 is cross-sectional view of a depot in accordance with some embodiments of the present technology.

In some embodiments, the elongated depot 100 may include multiple lumens (e.g., two, three, four, five, six, etc.) extending through all or a portion of the length of the depot 100 and/or the length of the therapeutic region 200. For example, FIG. 21 is an end view of an elongated depot 100 having an inner therapeutic region 200 and an outer core region 300 covering an outer surface of the therapeutic region 200 along its length. In this particular example, the depot 100 includes three lumens 350 extending through the length of the therapeutic region 200. In the illustrated embodiment, each of the lumens 350 has a substantially circular cross-section and similar dimensions. In other embodiments, the lumens 350 may have other cross-sectional shapes, and/or the dimensions of each lumen 350 may vary from one another. In some embodiments, the elongated depot 100 may include multiple, layered control regions 300 having the same composition or different compositions and/or the same thickness or different thicknesses. In these and other embodiments, the control region 300 may extend over one or both end surfaces of the therapeutic region 200.

Figure 22:
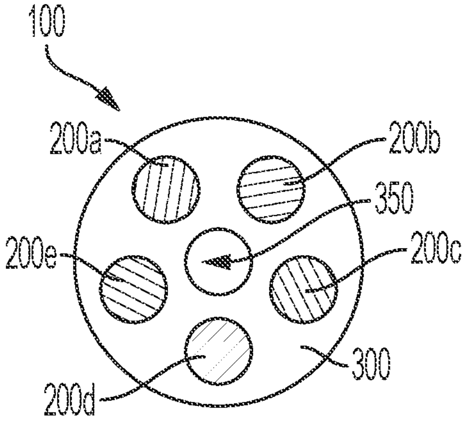
FIG. 22 is cross-sectional view of a depot in accordance with some embodiments of the present technology.

As shown in the end view of FIG. 22, the depot 100 can include a plurality of separate therapeutic regions 200 (labeled 200*a*-200*e*) extending longitudinally along the length of the depot 100. Although the depot 100 is shown having five therapeutic regions 200, in other embodiments the depot 100 may have more or fewer therapeutic regions 200 (e.g., two, three, four, six, seven, eight, etc.). The therapeutic regions 200 may be separated from one another by the control region 300. In the illustrated example, a central lumen 350 extends through the length of the control region 300, and the therapeutic regions 200 are distributed around the central lumen 350. In other embodiments, the elongated depot 100 may not include a lumen extending through any of its regions and may be solid across its cross-sectional dimension.

The therapeutic regions 200*a*-200*e* may have the same or different compositions, shapes, and/or dimensions. For example, the therapeutic regions 200*a*-200*e* may contain the same or different therapeutic agents, the same or different amount of therapeutic agent, the same or different polymers, and/or the same or different concentrations of releasing agents, depending on the desired release profile of each of the therapeutic regions 200*a*-200*e*. In the illustrated embodiment, each of the elongated therapeutic regions 200 has a substantially circular cross-section and similar dimensions. In other embodiments, the elongated therapeutic regions 200 may have other cross-sectional shapes and/or dimensions. In some embodiments, the elongated depot 100 may include one or more additional control regions 300 layered on top of the inner control region 300 surrounding the therapeutic regions 200*a*-200*e*. having the same composition or different compositions and/or the same thickness or different thicknesses. In these and other embodiments, the control region 300 may extend over one or both end surfaces of the therapeutic region 200.

Figure 23:
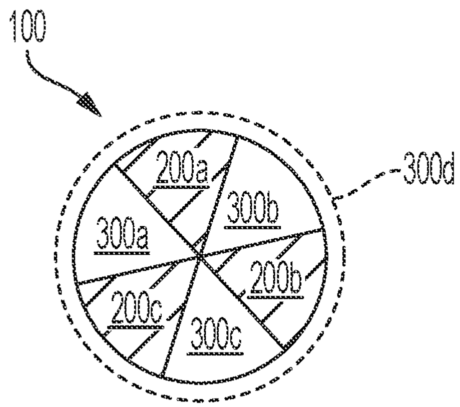
FIG. 23 is cross-sectional view of a depot in accordance with some embodiments of the present technology.

FIG. 23 illustrates another embodiment of an elongated depot 100 in which the cross-sectional area is composed of three elongated therapeutic regions 200*a*-200*c* separated radially from one another by three elongated control regions 300. In the illustrated embodiment, each of the separate regions intersects at a center in a pie-shaped configuration, however the constituent control regions 300*a*-300*c* and therapeutic regions 200*a*-200*c* can take any shape and form in different embodiments. Optionally, the depot 100 may include an additional control region 300*d* covering an outer surface of the more inner therapeutic regions 300*a*-300*c* and control regions 300*a*-300*c* to provide another layer of controlled release. In some embodiments, the elongated depot 100 may include multiple, layered control regions 300 having the same composition or different compositions and/or the same thickness or different thicknesses. In these and other embodiments, the control region 300 may extend over one or both end surfaces of the therapeutic region 200.

Figure 24A:
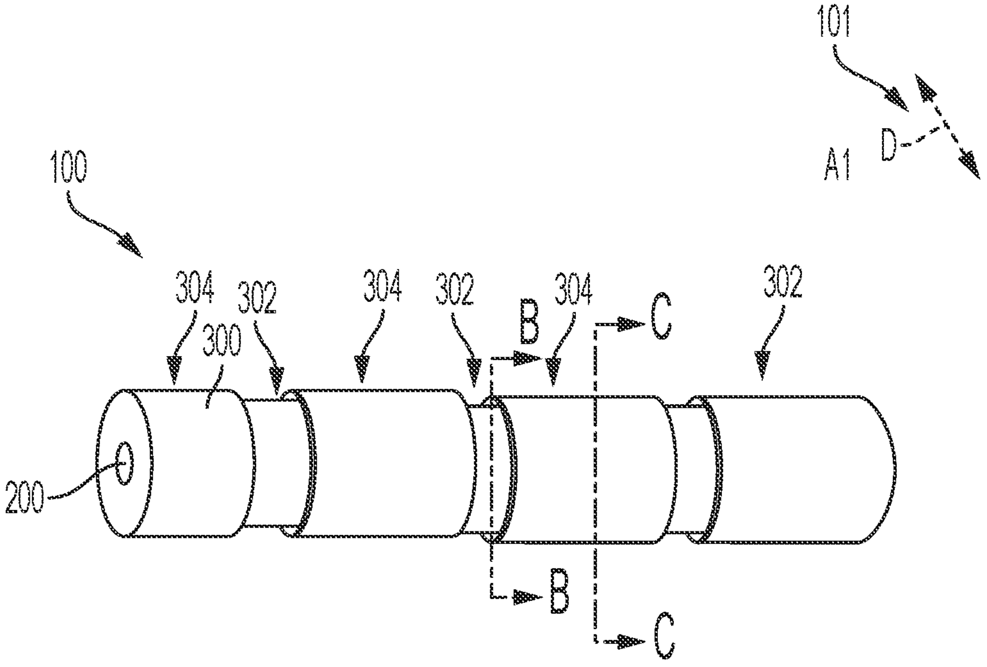
FIG. 24A is a perspective view of a depot in accordance with some embodiments of the present technology.
Figure 24B:
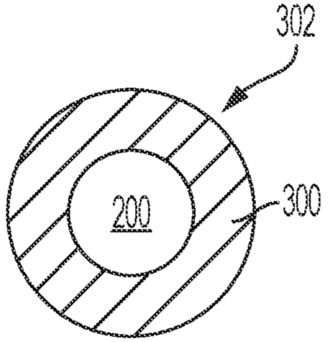
FIG. 24B is cross-sectional view of the depot shown in FIG. 24A taken along line B-B.
Figure 24C:
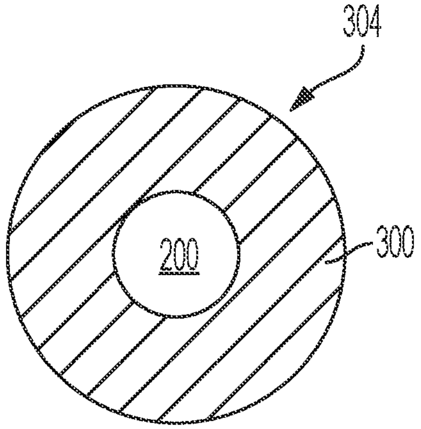
FIG. 24C is cross-sectional view of the depot shown in FIG. 24A taken along line C-C.

In certain instances, it may be beneficial to provide an elongated depot 100 having an inner therapeutic region 200 and an outer control region 300 of variable thickness and/or non-uniform coverage. Several examples of such depots 100 are shown FIGS. 24A-28. As depicted in FIGS. 24A-24C, the depot 100 can include an elongated therapeutic region 200 having a substantially uniform cross-sectional profile. The outer control region 300 radially surrounds the therapeutic region 200 along the length of the depot 100 and has a thickness that varies along the length of the depot 100. As shown in FIG. 24A, the control region 300 may have alternating first and second portions 305, 307 along its length. The first portions 302 can have a first thickness and the second portions 304 can have a second thickness greater than the first thickness. As such, the first portions 302 form annular grooves within the control region 300 at the outer surface of the depot 100. When implanted, the thinner first portions 302 may release the therapeutic agent more quickly than the thicker second portions 304, as the therapeutic agent has less control region to travel through before leaving the depot 100. By separately providing for faster-releasing portions and slower-releasing portions of the depot 100, the overall release rate of therapeutic agent from the therapeutic region 200 to a treatment site can be precisely tailored to a desired application. In addition to controlling the overall release rate, the release of therapeutic agent(s) can be spatially controlled, for example by directing a first therapeutic agent towards a first portion of the treatment site and a second therapeutic agent towards a second portion of the treatment site.

Figure 24D:
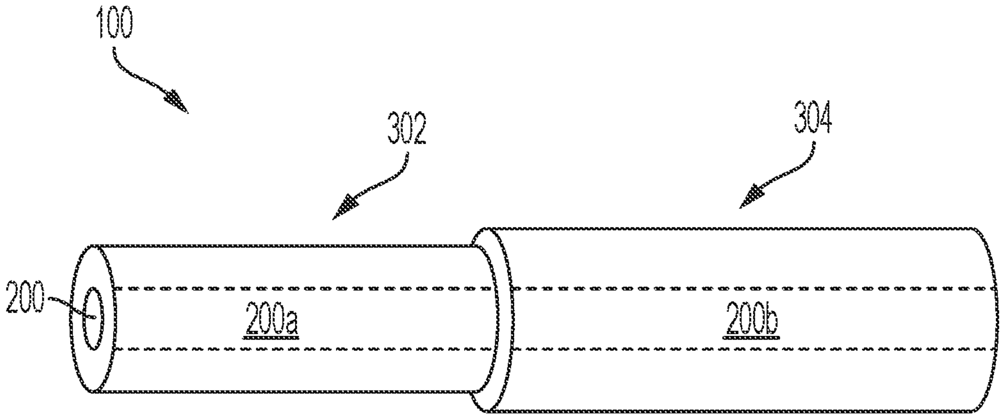
FIG. 24D is a perspective view of a depot in accordance with some embodiments of the present technology.

As shown in FIG. 24D, in some embodiments the elongated therapeutic region 200 may have different therapeutic agents disposed at different sections 200*a*, 200*b* along the length of the therapeutic region 200, where each section having a different therapeutic agent is axially aligned with a corresponding section of the control region 300 that has a thickness that is specific to the desired release profile of the underlying therapeutic agent. For example, in some applications it may be beneficial to release a first therapeutic agent at a faster rate and shorter duration and a second therapeutic agent at a slower rate for a longer duration. In such instances, the elongated therapeutic region 200 may have a first section 200*a* containing the first therapeutic agent (and optionally a polymer and/or releasing agent) and a second section 200*b* adjacent the first section 200*a* along the length of the therapeutic region 200 that has a second therapeutic agent (and optionally a polymer and/or releasing agent). The first section 302 of the control region 300 surrounding the first section 200*a* may have a thickness that is less than a thickness of the second section 304 of the control region 300 surrounding the second section 200*b*. As such, the first therapeutic agent contained in the first section 200*a* may release at a faster rate than the second therapeutic agent contained in the second section 200*b*. In some embodiments, a depot 100 can be configured to deliver two, three, four, five, or more different therapeutic agents, any or all of which can have different rates and times of release from the depot 100.

Figure 25:
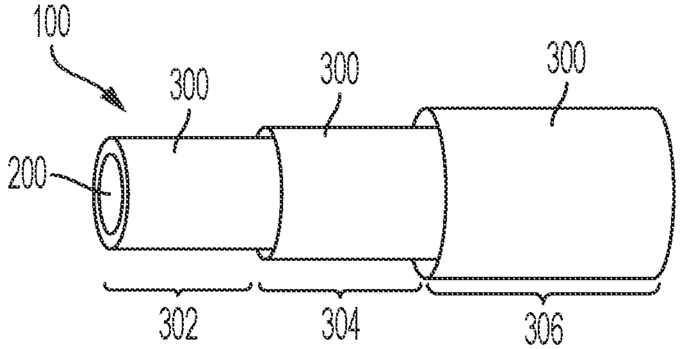
FIG. 25 is a perspective view of a depot in accordance with some embodiments of the present technology.

FIG. 25 illustrates another embodiment of an elongated depot 100 comprising an inner therapeutic region 200 radially surrounded by an outer control region 300. In the illustrated embodiment, the control region 300 includes three discrete sections 302, 304, 306 having increasing thickness. Although these increases in thickness are shown as step-changes between discrete sections, in other embodiments there may be a gradual taper or change in thickness of the control region 300 over the length of the depot 100. In some embodiments, the number of discrete sections may be varied as desired (e.g., two, four, five, six, seven, eight, nine, ten, or more discrete sections), and each discrete section may have an increased or decreased thickness and/or length relative to adjacent discrete sections. Each discrete section may be positioned around a corresponding section of the therapeutic region 200, and each section of the therapeutic region may include the same therapeutic agent, or may include different therapeutic agents as described with respect to FIG. 24D.

Figure 26:
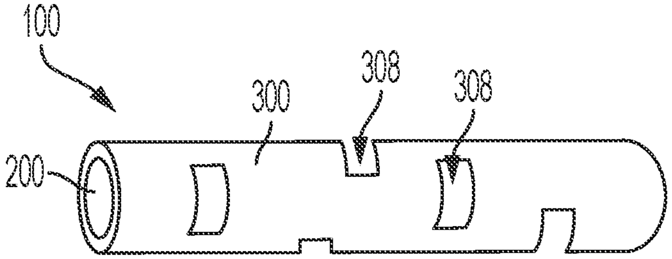
FIG. 26 is a perspective view of a depot in accordance with some embodiments of the present technology.
Figure 27:
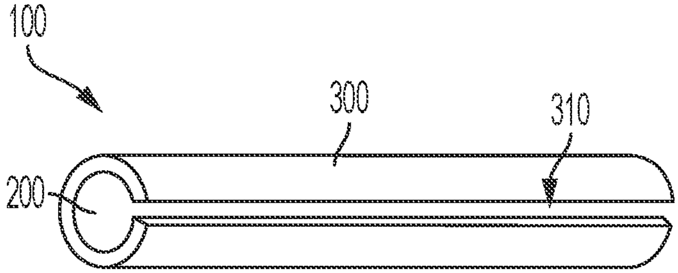
FIG. 27 is a perspective view of a depot in accordance with some embodiments of the present technology.
Figure 28:
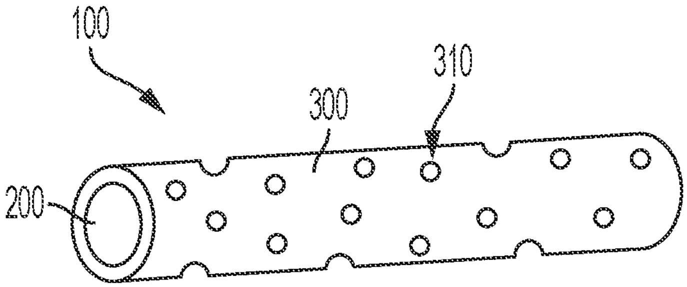
FIG. 28 is a perspective view of a depot in accordance with some embodiments of the present technology.

FIGS. 26-28 depict examples of elongated depots 100 comprising an inner therapeutic region 200 radially surrounded by an outer control region 300, where the outer control region 300 has one or more windows or openings extending through the entire thickness of the control region 300 to expose the underlying therapeutic region 200 through the opening(s). The openings can be notched into or laser cut from the control region 300, or the therapeutic region 200 can be masked while the control region 300 is applied (e.g., via spray- or dip-coating) to achieve the desired openings. The opening(s) provide a more rapid release route for the therapeutic agent to operate in concert with the more gradual release of therapeutic agent through the covered portions of the therapeutic region. The geometry of the opening(s) may be varied as desired, and can include squares, rectangles, circles, ellipses, slits, polygonal shapes, linear shapes, non-linear shapes, or combinations thereof.

As shown in FIG. 26, in some embodiments the openings may comprise a plurality of windows 308, some or all of which may extend around all or a portion of the circumference of the depot 100 and may be spaced apart along the length of the depot 100. FIG. 27 illustrates another embodiment of an elongated depot 100 in which the control region 300 is provided with a single elongated slit or opening 310. The opening 310 extends along the entire length of the control region 300 and/or depot 100 such that the control region 300 has a C-shape in cross-section. In the illustrated embodiment, the opening 310 extends substantially straight along a path parallel to the long axis of the depot 100, however in other embodiments the opening 310 may be curved, wind helically around the depot 100, or take any other suitable shape. The depot 100 shown in FIG. 28 is similar to that of FIGS. 26 and 27 except that the openings 350 are a plurality of circular holes or apertures extending through the thickness of the control region 300.

Figure 29A:
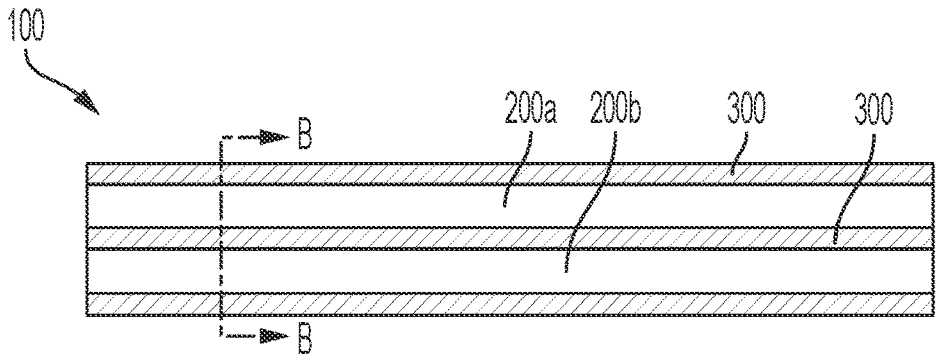
FIG. 29A is a side cross-sectional view of a depot in accordance with some embodiments of the present technology.
Figure 29B:
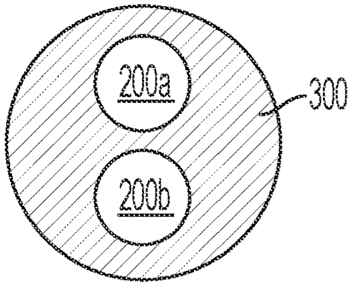
FIG. 29B is a cross-sectional view of the depot shown in FIG. 29A taken along line B-B.

FIGS. 29A and 29B are side and end cross-sectional views, respectively, of an elongated depot 100 comprising first and second elongated therapeutic regions 200*a* and 200*b* extending longitudinally within a surrounding control region 300. In the depicted embodiment, the central longitudinal axes of first and second therapeutic regions 200*a* and 200*b* are offset from each other and from the central longitudinal axis of the control region 300. In some embodiments, the first therapeutic region 200*a* can be configured to release the therapeutic agent more quickly than the second therapeutic region 200*b*, for example by varying the releasing agent concentration (if present), the therapeutic agent concentration, the polymer composition (if present), or other properties of the respective therapeutic regions 200*a* and 200*b*. The first and second therapeutic regions 200*a* and 200*b* can contain the same or different therapeutic agents.

Figure 30:
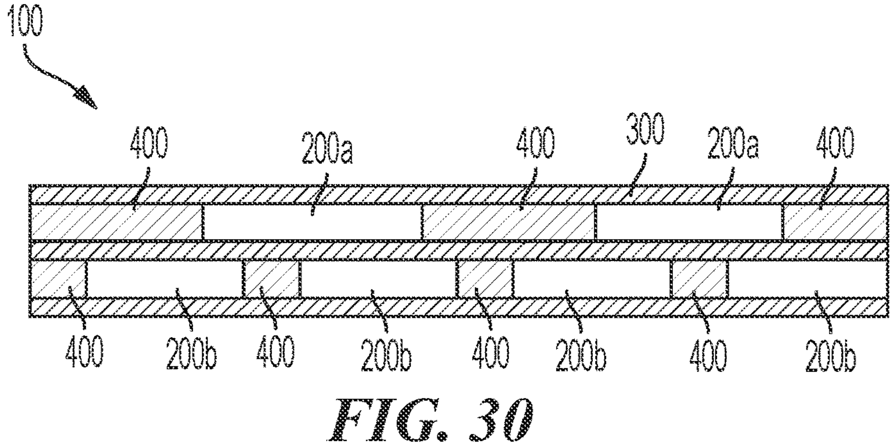
FIG. 30 is a side cross-sectional view of a depot in accordance with some embodiments of the present technology.

The depot 100 shown in FIG. 30 is similar to that of FIG. 29A except that each therapeutic region 200*a* is interspersed along its length by barrier regions 400. As noted previously, certain embodiments of the depots 100 described herein employ barrier regions that present a barrier to physiologic fluids. In one embodiment, one or more of the barrier regions 400 may comprise a bioresorbable polymer without any releasing agent. In another embodiment, one or more of the barrier regions 400 can include a delayed release agent mixed with a bioresorbable polymer, but without a releasing agent.

As depicted in FIG. 30, the first therapeutic region 400*a* is interspersed with three barrier regions 400 of a first length, while the second therapeutic region 200*b* is interspersed with four delayed release regions 400 having a shorter length. The relative lengths, number, composition, and spacing of the barrier regions 400 can be selected to achieve the desired release profiles. In operation, an exposed portion of the first or second therapeutic regions 200*a* or 200*b* may release therapeutic agent relatively quickly. However, once the therapeutic region 200*a* or 200*b* has been eroded and the exposed face of the depot 100 is a barrier region 400, the release of therapeutic agent from that particular therapeutic region may drop significantly. Accordingly, the use of such barrier regions 400 can allow for highly controlled release, with multiple periods of relatively steady release of therapeutic agent punctuated by periods in which little or no therapeutic agent is released due to the presence of the barrier regions 400.

Figure 31:
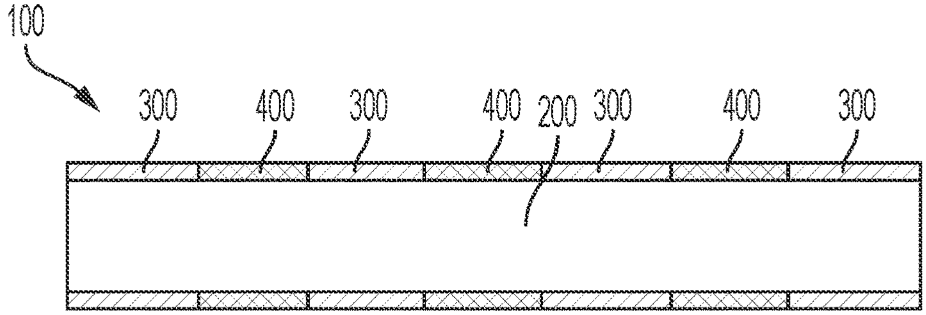
FIG. 31 is a side cross-sectional view of a depot in accordance with some embodiments of the present technology.

FIG. 31 illustrates a depot 100 in which the inner therapeutic region 200 is continuous along the length of the depot 100, while the control region 300 is punctuated by barrier regions 400. The incorporation of these barrier regions 400 reduces the exposed surface area of the control region 300 and thereby decreases the rate of release of therapeutic agent from the depot 100.

Figure 32:
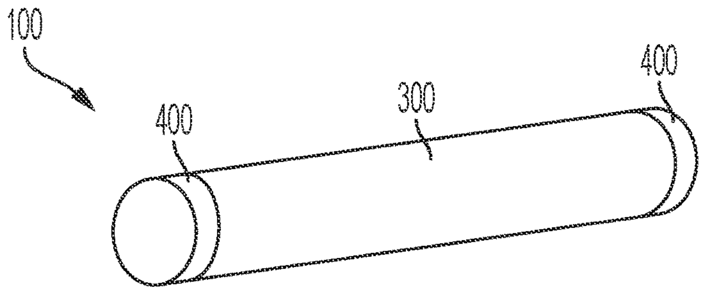
FIG. 32 is a perspective view of a depot in accordance with some embodiments of the present technology.
Figure 33:
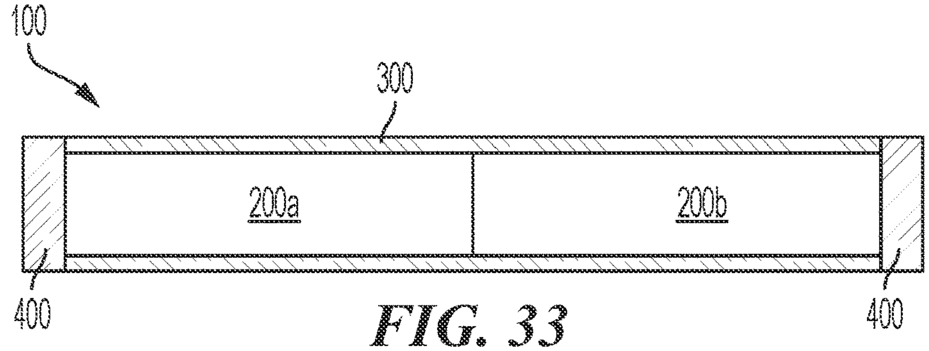
FIG. 33 is a side cross-sectional view of a depot in accordance with some embodiments of the present technology.

In the embodiments shown in FIG. 32-35, the elongated, columnar depot 100 includes first and second end caps formed of barrier regions 400. This configuration can eliminate the exposed surface at the ends of the columnar structure, thereby reducing the rate of release of therapeutic agent from the therapeutic region 200. As seen in FIGS. 32 and 33, the end caps formed of barrier regions 400 can have a diameter or cross-sectional transverse dimension substantially similar to that of the control region 300, such that the outer surface of the control region 300 is coplanar with a radially outermost surface of the barrier regions 400 forming the end caps.

Figure 34:
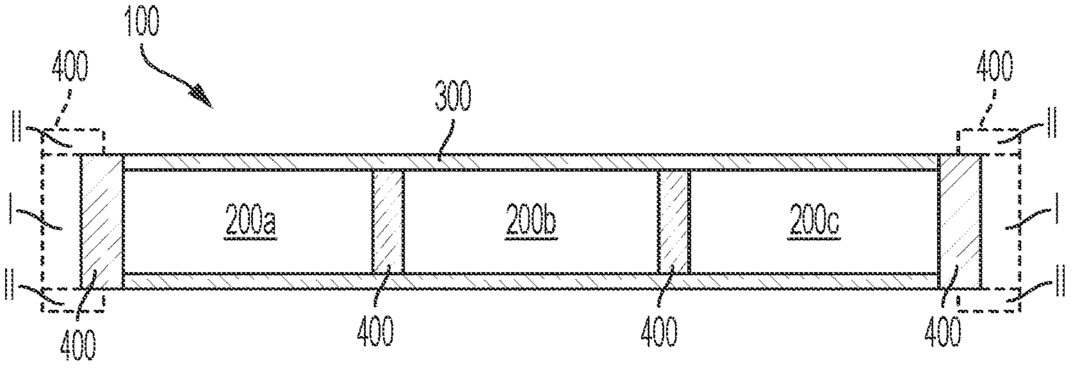
FIG. 34 is a side cross-sectional view of a depot in accordance with some embodiments of the present technology.
Figure 35:
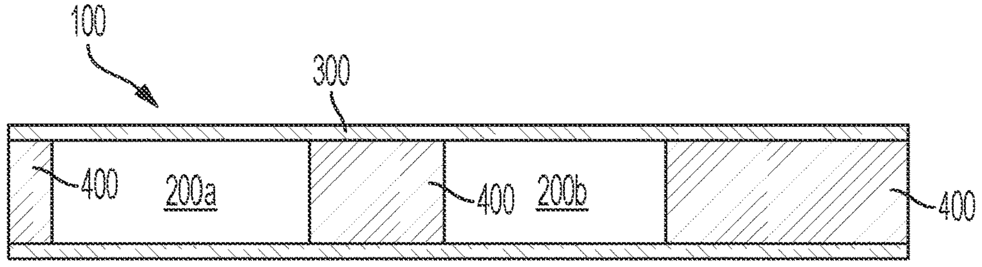
FIG. 35 is a side cross-sectional view of a depot in accordance with some embodiments of the present technology.

In the embodiment shown in FIG. 33, the depot 100 includes first and second therapeutic regions 200*a* and 200*b* that are coaxially aligned and directly adjacent to one another (e.g., arranged in an end-to-end fashion along their longitudinal axes), while in FIGS. 34 and 35 the adjacent therapeutic regions 200*a*-200*c* are separated from one another by intervening barrier regions 400. FIG. 34 additionally shows optional end caps 400 that extend further radially, for example as shown in section I, the end caps formed by barrier regions 400 can have the same diameter or transverse dimension as the control region 300, or alternatively as shown in section II, the barrier regions 400 forming the end caps can project radially beyond the control region 300. In some embodiments, as best seen in FIG. 35, the thickness of the barrier regions 400 can vary across the depot 100 in order to achieve the desired release profile.

FIGS. 36A-39B illustrate various configurations of a depot 100 containing one or more therapeutic regions 200 that are at least partially surrounded by one or more control regions 300 and/or one or more barrier regions 400, with a form factor configured to provide the desired release profile. As noted previously, different therapeutic regions 200 can vary from one another in the composition of therapeutic agent(s) contained therein, the concentration of therapeutic agent(s) contained therein, polymer composition, or any other parameter that can vary the release profile. Similarly, in some embodiments the depot 100 may include multiple, layered control regions 300 and/or barrier regions 400 having the same composition or different compositions and/or the same thickness or different thicknesses. These depots 100 that include a plurality of different therapeutic regions 200, a plurality of different control regions 300, and/or a plurality of different barrier regions 400 can allow for controlled release of a single therapeutic agent or multiple different therapeutic agents according to a desired release profile. For example, in some applications it may be beneficial to release a first therapeutic agent at a faster rate and shorter duration and a second therapeutic agent at a slower rate for a longer duration. As described in more detail below, by varying the configuration and composition of the depots 100, the release profile of therapeutic agent(s) can be sequential (in the case of multiple therapeutic agents), delayed, zero-order, or otherwise.

In some embodiments, a plurality of depots can be provided together (for example as a kit, an assembly, pre-loaded into a delivery device such as a syringe, etc.). In some embodiments, the depots can have a variety of different release profiles. For example, a system can include a plurality of depots selected from at least two of the following groups: (1) depots configured to provide for a substantially immediate burst release of therapeutic agent, (2) depots configured to provide for a substantially first-order release of therapeutic agent, (3) depots configured to provide for a substantially zero-order release of therapeutic agent, and (4) depots configured to exhibit delayed release of therapeutic agents (as discussed below with respect to FIGS. 39A-39B).

Figure 36B:
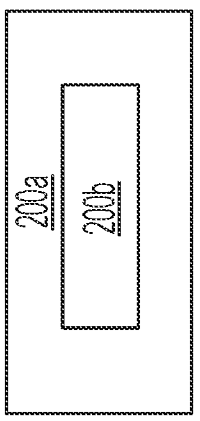
FIG. 36B is a cross-sectional view of the depot shown in FIG. 36A taken along line B-B.
Figure 36D:
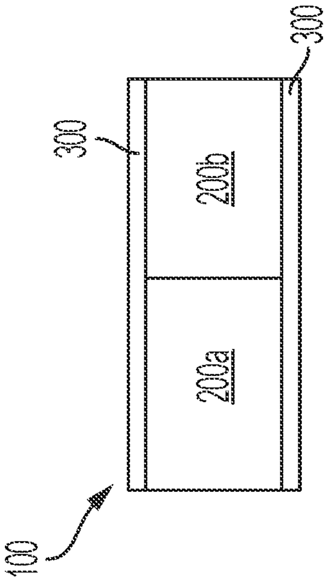
FIG. 36D is a side cross-sectional view of a depot in accordance with some embodiments of the present technology.
Figure 36A:
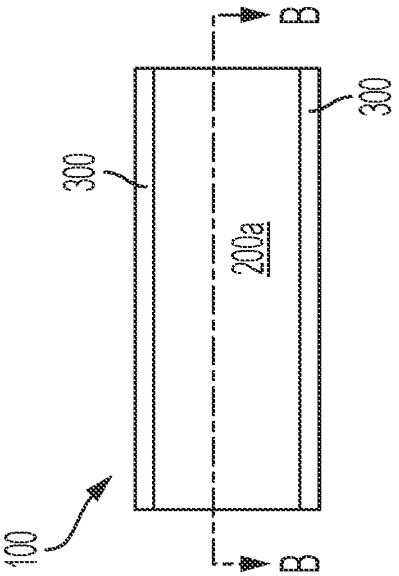
FIG. 36A is a side cross-sectional view of a depot in accordance with some embodiments of the present technology.

FIG. 36A shows a side view of a depot 100, and FIG. 36B shows a cross-sectional view taken along line B-B in FIG. 36A. As seen in FIGS. 36A-36B, in some embodiments the first therapeutic region 200*a* can envelop or at least partially or completely surround the second therapeutic region 200*b*. As a result, the first therapeutic region 200*a* will release its therapeutic agent(s) first, and release of therapeutic agent(s) from the second therapeutic region 200*b* will be relatively delayed. In some embodiments, the first therapeutic region 200*a* completely encapsulates the second therapeutic region 200*b*, such that no surfaces of the second therapeutic region 200*b* are directly exposed to physiologic fluids upon implantation in a patient's body. In other embodiments, the second therapeutic region 200*b* can be exposed along at least one face, thereby allowing more immediate release of therapeutic agent from the second therapeutic region 200*b*. In the illustrated embodiment, the first and second therapeutic regions 200*a* and 200*b* are arranged concentrically around the long axis of the depot 100, however in other embodiments the second therapeutic region 200*b* may be off-center, such that the first therapeutic region 200*a* is thicker along one side of the second therapeutic region 200*b* than along another side.

Figure 36C:
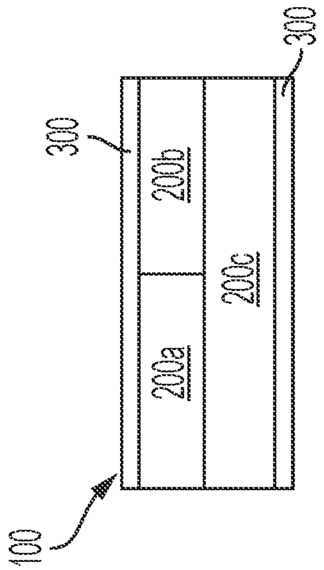
FIG. 36C is a side cross-sectional view of a depot in accordance with some embodiments of the present technology.

In the embodiment shown in FIG. 36C, first and second therapeutic regions 200*a* and 200*b* are arranged in an end-to-end fashion (e.g., in direct contact with one another), while a parallel third therapeutic region 200*c* extends along the length of the depot 100 and contacts both the first and second therapeutic regions 200*a* and 200*b*. FIG. 36D illustrates another embodiment in which first and second therapeutic regions 200*a* and 200*b* are arranged end-to-end and aligned along the length of the depot 100. These embodiments may be used to achieve directional release of therapeutic agents, e.g., the therapeutic agent of the first therapeutic region 200*a* is primarily released from a first end of the depot 100, and the therapeutic agent of the second therapeutic region 200*b* is primarily released from a second, opposite end of the depot 100, while the therapeutic agent of the third therapeutic region 200*c* releases from both ends of the depot 100.

Figure 37A:
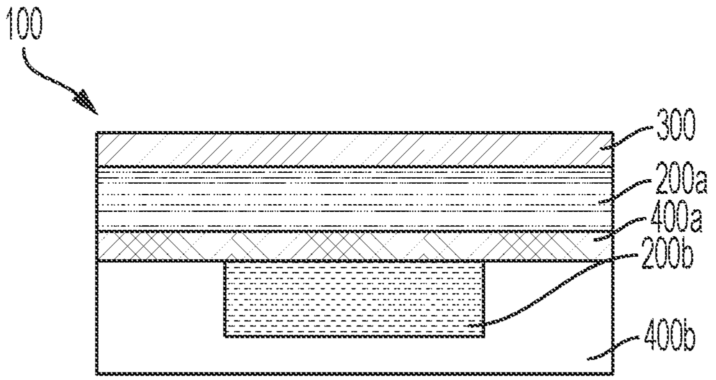
FIG. 37A is a side cross-sectional view of a depot in accordance with some embodiments of the present technology.

FIG. 37A illustrates a depot 100 configured to release therapeutic agent(s) from first and second therapeutic regions 200*a* and 200*b* in a sequential manner. As seen in FIG. 37A, the first therapeutic region 200*a* is partially covered by an overlying control region 300. The first therapeutic region 200*a* in turn overlies a first barrier region 400*a*. In the illustrated embodiment, the first therapeutic region 200*a*, the control region 300, and the first barrier region 400*a* each extend the entire length of the depot 100 and are each exposed along the side surfaces of the depot 100, however in other embodiments side surfaces may be covered completely or partially by a control region 300 and/or a barrier region 400. Beneath the first barrier region 400*a* is the second therapeutic region 200*b*, which may contain the same or different polymer composition and/or therapeutic agent as the first therapeutic region 200*a*. The second therapeutic region 200*b* is surrounded laterally by a second barrier region 400*b*, which also extends beneath the second therapeutic region 200*b*. As a result, the second therapeutic region 200*b* has at least one surface in contact with the first barrier region 400*a* and one or more remaining surfaces in contact with the second barrier region 400*b*, such that the second therapeutic region 200*b* is completely encapsulated by the first and second barrier regions 400*a*, 400*b*. In some embodiments, one or both of the barrier regions 400*a* and 400*b* can be substituted for control regions having a lower concentration of release agent than the control region 300.

As noted previously, barrier regions may present a barrier to physiologic fluids, for example by comprising a bioresorbable polymer without any releasing agent, or a delayed release agent mixed with a bioresorbable polymer, but without a releasing agent. The first barrier region 400*a* and the second barrier region 400*b* may differ from one another in composition, thickness, or any other parameters affecting dissolution of the barrier regions 400*a* and 400*b*. In some embodiments, the second barrier region 400*b* can be configured to dissolve more slowly than the first barrier region 400*a*, such that, after the first barrier region 400*a* has partially or completely dissolved, the second barrier region 400*b* remains intact and continues to block or delay passage of physiologic fluids therethrough.

In operation, the first barrier region 400*a* dissolves more slowly than either the control region 300 or the first and second therapeutic regions 200*a* and 200*b*, and therefore presents a barrier to physiological fluids passing through the first barrier region 400*a*. As a result, when the depot 100 is first placed into contact with physiologic fluids, the release agent of the control region 300 may begin to dissolve, thereby creating diffusion openings for the therapeutic agent(s) in the first therapeutic region 200*a* to escape therethrough. The therapeutic agent(s) in the first therapeutic region 200*a* may also escape directly through the exposed surfaces of the first therapeutic region 200*a*. However, at least in the initial period following implantation, the first barrier region 400*a* may stop or slow the passage of physiologic fluids through the barrier region 400*a* and to the underlying second therapeutic region 200*b*, such that the therapeutic agent(s) within the second therapeutic region 200*b* exhibits minimal or no release in the initial period. After a first period of time, the control region 300, first therapeutic region 200*a* and/or the first barrier region 400*a* may be partially or completely dissolved, thereby allowing at least some physiologic fluid to pass therethrough and come into contact with the second therapeutic region 200*b*. At this point, therapeutic agent(s) contained within the second therapeutic region 200*b* may begin to be released from the depot 100, for example by passing through openings formed in the first or second barrier regions 400*a* and 400*b*. Accordingly, the depot 100 can be configured such that all or substantially all (e.g., more than 80%, more than 90%) of the therapeutic agent(s) from the first therapeutic region 200*a* are released from the depot 100 before the therapeutic agent(s) from the second therapeutic region 200*b* are released in any substantial quantity (e.g., more than 1%, more than 5%, more than 10% of the therapeutic agent(s) contained within the second therapeutic region 200*b*). In some embodiments, the therapeutic agent(s) from the second therapeutic region 200*b* are not released in any substantial quantity until at least 12 hours, at least 18 hours, at least 24 hours, at least 36 hours, at least 48 hours, at least 3 days, at least 4 days, at least 5 days, at least 6 days, at least 7 days, at least 8 days, at least 9 days, at least 10 days, at least 11 days, at least 12 days, at least 13 days, at least 2 weeks, at least 3 weeks, at least 4 weeks, at least 5 weeks, at least 6 weeks, at least 7 weeks, at least 8 weeks, at least 9 weeks, at least 10 weeks, at least 11 weeks, or at least 12 weeks after implantation of the depot 100 and/or after release of substantially all of the therapeutic agent(s) from the first therapeutic region 200*a*.

In one example, the control region 300 is a PLGA film with a releasing agent, the first therapeutic region 200*a* is a PLGA film loaded with a first therapeutic agent (e.g., bupivacaine), the first barrier region 400*a* is a PLGA film with no releasing agent, the second therapeutic region 200*b* is a PLCL film loaded with a second therapeutic agent (e.g., 5-fluorouracil), and the second barrier region 400*b* is a PLCL film with no releasing agent. As will be understood, the particular polymers, therapeutic agents, releasing agents, concentrations thereof, and dimensions can be selected to achieve the desired release profiles of the first and second therapeutic agents and to achieve the desired total erosion of the depot 100 after a predetermined period of time.

Figure 37B:
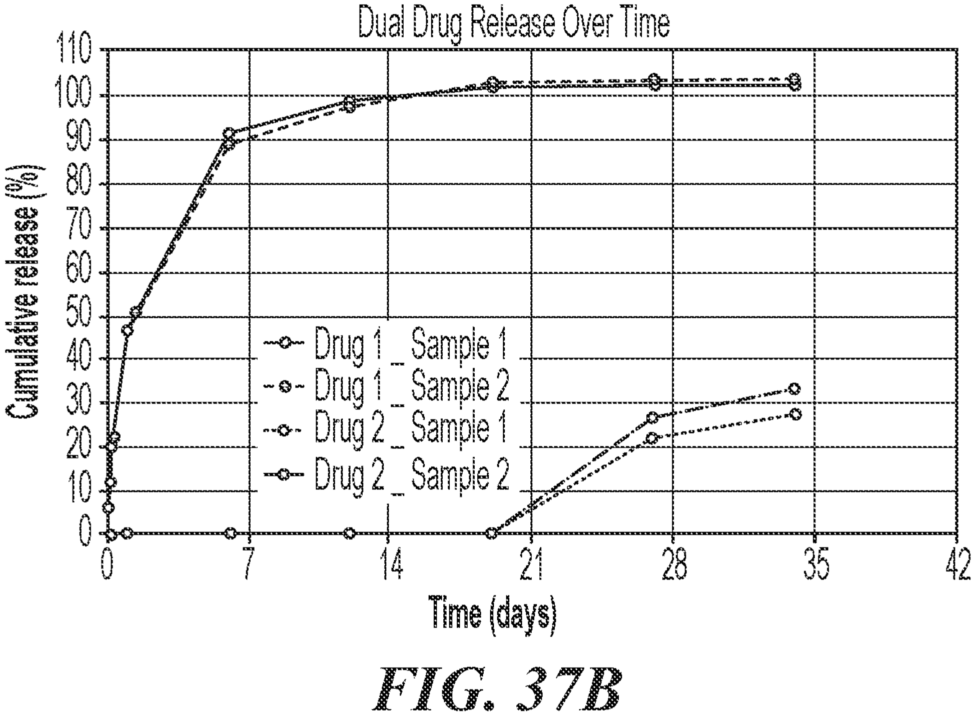
FIG. 37B depicts example release profiles over time of the depot shown in FIG. 37A.

Examples of the release profile from the depot 100 of FIG. 37A are illustrated in FIG. 37B. In this example, Samples 1 and 2 were each prepared with a configuration as shown in FIG. 37A with a thickness of approximately 1.8 mm and a length and width of approximately 20 mm. The control region 300 includes PLGA with polysorbate 20, commercially known as Tween 20™ as a releasing agent, with the ratio of Tween to polymer of 5:10. The first therapeutic region 200*a* includes a PLGA polymer with Tween 20 and bupivacaine HCl, with the ratio of tween to polymer to bupivacaine of 1:10:20. The first barrier region 400*a* includes a PLGA film with no releasing agent or therapeutic agent, and the second barrier region 400*b* includes a PLCL film with no releasing agent or therapeutic agent. The second therapeutic region 200*b* includes a PLCL polymer with 5-FU and no releasing agent, with a polymer to 5-FU ratio of 1:1.

Referring to FIG. 37B, the "Drug 1" lines illustrate release of a first therapeutic agent from the first therapeutic region 200*a*. The "Drug 2" lines illustrate release of a second therapeutic agent from the second therapeutic region 200*b*, which is not released in any substantial amount until a first period has passed (approximately 19 days in the embodiment of FIG. 37B), after which the second therapeutic agent begins to release from the depot 100. The result is a sequential release in which the first therapeutic agent is substantially completely released (e.g., more than 80%, more than 90%, more than 95%, more than 99% of the first therapeutic agent is released from the depot 100) before the second therapeutic agent begins to be released in any significant amount (e.g., more than 1%, more than 5%, or more than 10% of the second therapeutic agent is released from the depot 100).

Figure 38A:
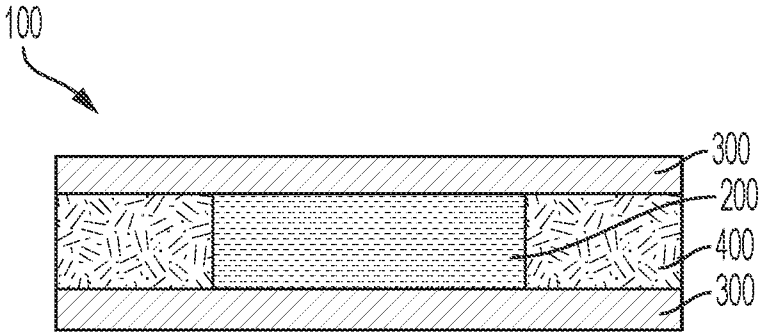
FIG. 38A is a side cross-sectional view of a depot in accordance with some embodiments of the present technology.

FIG. 38A illustrates a depot 100 configured to release a therapeutic agent from a therapeutic region 200 in accordance with a substantially zero-order release profile. In the illustrated embodiment, the depot 100 includes a therapeutic region 200 that is laterally surrounded by one or more barrier regions 400. In some embodiments, the therapeutic region 200 and the barrier region 400 can have a substantially similar thickness such that upper and lower surfaces of the therapeutic region and the barrier region 400 are substantially coplanar. First and second control regions 300 can be disposed over upper and lower surfaces of both the therapeutic region 200 and the barrier region 400, such that the therapeutic region 200 is completely encapsulated by the first and second control regions 300 and the barrier region 400.

When the depot 100 is placed in contact with physiological fluids (e.g., when implanted at a treatment site in vivo), the release agent in the control regions 300 will begin to dissolve to form diffusion openings therein, after which therapeutic agent(s) contained within the therapeutic region 200 may begin to pass through to be released from the depot 100. By virtue of the laterally disposed barrier regions 400, little or no therapeutic agent may pass from the therapeutic region 200 through the barrier regions 400 for at least a period of time (e.g., at least 1 day, at least 2 days, at least 3 days, at least 4 days, at least 5 days, at least 6 days, at least 7 days, at least 8 days, at least 9 days, at least 10 days, at least 11 days, at least 12 days, at least 13 days, at least 2 weeks, at least 3 weeks, at least 4 weeks, at least 5 weeks, at least 6 weeks, at least 7 weeks, at least 8 weeks, at least 9 weeks, at least 10 weeks, at least 11 weeks, or at least 12 weeks). As a result, substantially linear release of therapeutic agent can be achieved by controlling the dimensions and composition of the control regions 300 and the therapeutic region 200. As used herein, "substantially linear" includes a release profile in which the rate of release over the specified time period does not vary by more than 5%, or more than 10% from the average release rate over the time period. The substantially linear release profile can be maintained over a desired period of time, e.g., over at least 1 day, at least 2 days, at least 3 days, at least 4 days, at least 5 days, at least 6 days, at least 7 days, at least 8 days, at least 9 days, at least 10 days, at least 11 days, at least 12 days, at least 13 days, at least 2 weeks, at least 3 weeks, at least 4 weeks, at least 5 weeks, at least 6 weeks, at least 7 weeks, at least 8 weeks, at least 9 weeks, at least 10 weeks, at least 11 weeks, or at least 12 weeks.

In one example, the control region 300 can be a PLCL or PLGA film containing a releasing agent, the therapeutic region can be a PLCL film loaded with a therapeutic agent (e.g., bupivacaine; 5-fluorouracil, etc.), and the barrier region 400 can be a PLCL film with no releasing agent. As will be understood, the particular polymers, therapeutic agents, releasing agents, concentrations thereof, and dimensions can be selected to achieve the desired release profiles of the therapeutic agent(s) and to achieve the desired total erosion of the depot 100 after a predetermined period of time (e.g., approximately 40 days).

Figure 38B:
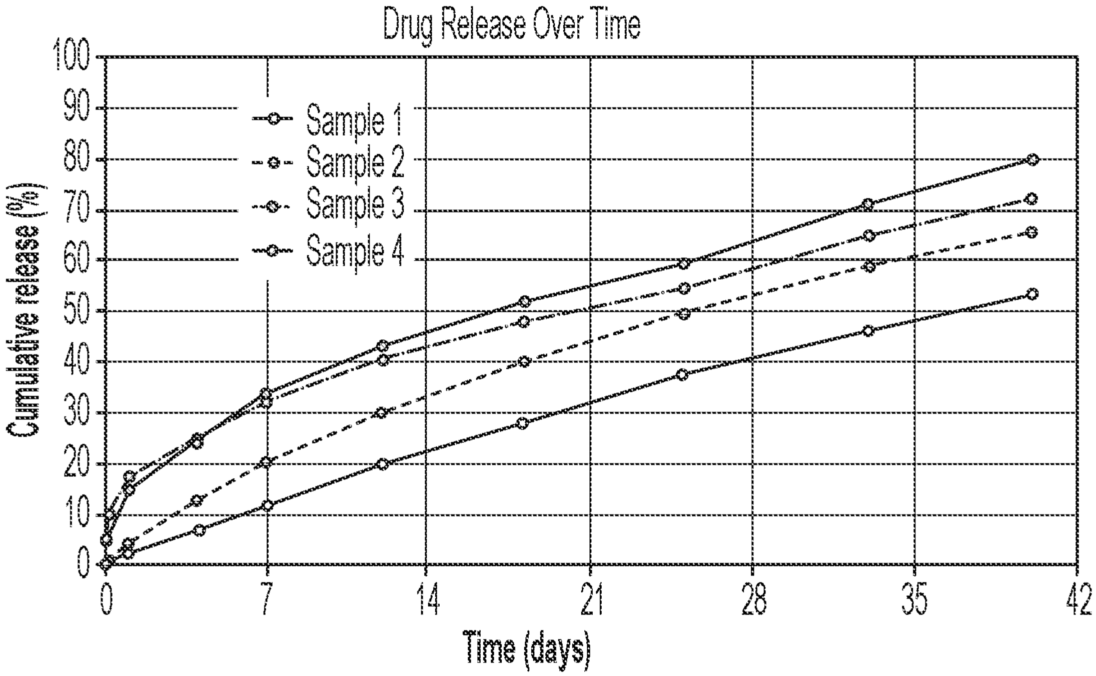
FIG. 38B depicts example release profiles over time of the depot shown in FIG. 38A.

Examples of the release profile from the depot 100 of FIG. 38A are illustrated in FIG. 38B, with four samples with varying polymer configurations illustrated. In this example, Samples 1-4 were each prepared with a configuration as shown in FIG. 38A with a thickness of approximately 0.8 mm and a length and width of approximately 20 mm. Samples 1 and 2 were prepared using the same configuration, in which the control region 300 includes a PLCL polymer and Tween as a releasing agent with a Tween to polymer ratio of 1:2. The therapeutic region 200 includes a PLCL polymer with 5-FU and no releasing agent, with a polymer to 5-FU ratio of 1:1, and the barrier region 400 includes a PLCL polymer with no releasing agent. Samples 3 and 4 were prepared using the same configuration, in which the control region 300 includes a PLGA polymer and Tween as a releasing agent with a Tween to polymer ratio of 1:2. The therapeutic region 200 includes a PLCL polymer with 5-FU and no releasing agent, with a polymer to 5-FU ratio of 1:1, and the barrier region 400 includes a PLGA polymer with no releasing agent.

As seen in FIG. 38B, by varying the polymer configurations (e.g., composition, release agent, thickness, etc.), the zero-order release profile can be tuned to release at different rates. In some embodiments, there is an initially higher rate of release for a first short period (e.g., approximately 1 day in the illustrated examples), followed by a substantially linear release for the remaining period of time.

Figure 39A:
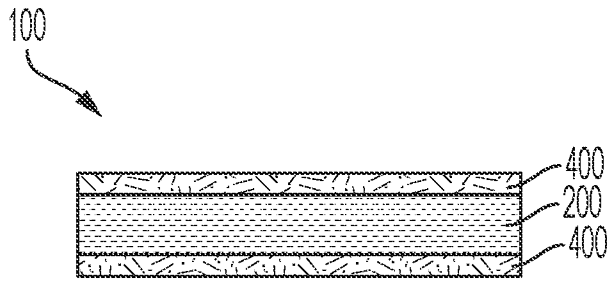
FIG. 39A is a side cross-sectional view of a depot in accordance with some embodiments of the present technology.

FIG. 39A illustrates a depot 100 configured to release a therapeutic agent from a therapeutic region 200 in accordance with a delayed release profile, in which little or none of the therapeutic agent(s) are released in a first period (e.g., less than 10%, less than 20% of the therapeutic agent(s) are released), followed by a rapid increase in release rate during a second period in which the therapeutic agent is released from the depot 100. In the illustrated embodiment, the depot 100 includes a therapeutic region 200 that is at least partially surrounded on opposing sides (e.g., over top and bottom surfaces) by barrier regions 400. In some embodiments, the therapeutic region 200 and the barrier region 400 can have a substantially similar length and width such that the therapeutic region 200 is exposed at one or more side surfaces of the depot 100.

When the depot 100 is placed in contact with physiological fluids (e.g., when implanted at a treatment site in vivo), the therapeutic agent(s) contained within the therapeutic region 200 will pass from the therapeutic region 200 into the surrounding environment through the exposed side surface(s) of the therapeutic region 200. In some embodiments, little or none of the therapeutic agent passes through the barrier regions 400 during an initial period. During this period, a relatively small portion of the therapeutic agent may be released through the exposed side surfaces (e.g., less than 20%, less than 15%, less than 10%, or less than 5% of the therapeutic agent may be released). After the first time period, the barrier regions 400 may begin to degrade, after which the therapeutic agent begins to be released through openings formed in the barrier regions 400. As a result, the depot 100 achieves a delayed release in which little or none of the therapeutic agent is released over a first time period (e.g., more than 1 week, more than 2 weeks, more than 3 weeks, more than 4 weeks, more than 5 weeks, more than 6 weeks, more than 7 weeks, more than 8 weeks, more than 9 weeks, more than 10 weeks), after which the therapeutic agent is released from the depot 100 at an increased rate. In some embodiments, the exposed side surfaces of the therapeutic region 200 can be partially or completely covered by one or more control regions 300 and/or by one or more barrier regions 400, which can further delay release of the therapeutic agent from the therapeutic region 200.

In one example, the therapeutic region 200 can be a PLCL film loaded with a therapeutic agent (e.g., bupivacaine; 5-fluorouracil, etc.), and the barrier regions 400 can be PLGA film with no release agent or PLCL film with no release agent. As will be understood, the particular polymers, therapeutic agents, concentrations thereof, and dimensions can be selected to achieve the desired release profiles of the therapeutic agent and to achieve the desired total erosion of the depot 100 after a predetermined period of time.

Figure 39B:
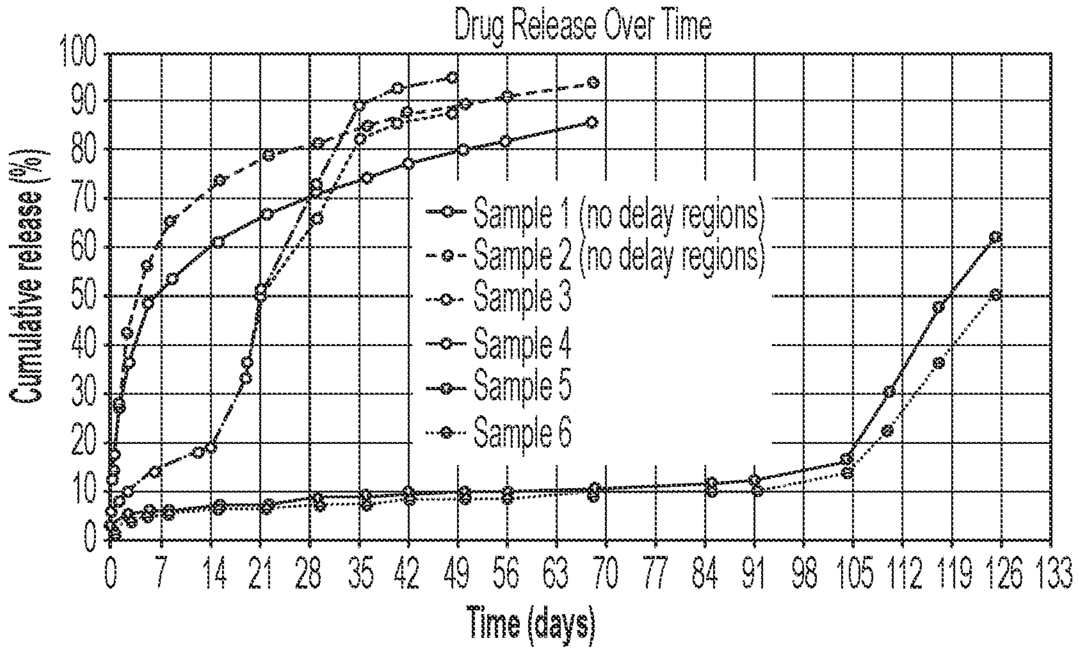
FIG. 39B depicts example release profiles over time of the depot shown in FIG. 39A.

Examples of the release profile from the depot 100 of FIG. 39A are illustrated in FIG. 39B. Samples 1 and 2 illustrate a release profile for a bare therapeutic region with no surrounding barrier regions. In samples 1 and 2, release of the therapeutic agent commences immediately after exposure to fluid. Samples 3-6 were each prepared with a configuration as shown in FIG. 39A. Samples 3 and 4 were prepared using the same configuration, in which the control region 300 includes a PLCL polymer and Tween as a releasing agent with a Tween to polymer ratio of 1:2. The therapeutic region 200 includes a PLCL polymer with 5-FU and no releasing agent, with a polymer to 5-FU ratio of 1:1, and the barrier region 400 includes a PLCL polymer with no releasing agent.

Samples 3-6 illustrate different examples of release profiles for the depot 100 of FIG. 39B with varying polymer configurations illustrated. In samples 3 and 4, the barrier regions 400 are made of a PLGA polymer, while in samples 5 and 6, the barrier regions 400 are made of a PLCL polymer. In samples 3 and 4, release of the therapeutic agent is delayed for approximately 2 weeks (e.g., less than 20%, less than 15%, less than 10%, or less than 5% of the therapeutic agent is released from the depot 100), after which the therapeutic agent is released from the depot 100 at an increased rate (e.g., at least 2 times, at least 3 times, at least 4 times, at least 5 times, or at least 10 times of the initial release rate). In samples 5 and 6, release of the therapeutic agent delayed for approximately 15 weeks (e.g., less than 20%, less than 15%, less than 10%, or less than 5% of the therapeutic agent is released from the depot 100), after which the therapeutic agent is released at an increased rate (e.g., at least 2 times, at least 3 times, at least 4 times, at least 5 times, or at least 10 times of the initial release rate). The barrier regions 400 in samples 3 and 4 are configured to degrade more quickly than the barrier regions 400 in samples 5 and 6, because PLGA degrades more quickly than PLCL. As a result, the delay period in samples 3 and 4 is shorter than the delay period in samples 5 and 6. In various embodiments, the degradation rate of the barrier regions 400 can be tuned by varying dimensions, selecting different polymers, or making any other suitable modifications to the barrier regions 400. By varying the polymer configurations (e.g., composition, thickness, etc.), the delayed release profile can be tuned to have different delay periods (e.g., an initial period during which little or none of the therapeutic agent is released) and to release the therapeutic agent at different rates following the delay period.

In some embodiments, it can be beneficial to provide a plurality of pre-formed openings or apertures extending through the depot 100, either in a regular or irregular pattern. Such openings can provide additional pathways for a therapeutic agent to pass from the therapeutic region to the treatment site, and as such can be controlled to vary the desired release profile. For example, in some embodiments the openings or apertures permit at least some of the therapeutic agent to be released directly from the therapeutic region 200 to the surrounding area, without passing through any overlying control region 300. These pre-formed openings or apertures may differ from diffusion openings formed by dissolution of releasing agent in that the openings or apertures are formed in the depot 100 prior to implantation in the patient's body. The openings or apertures may be used in combination with diffusion openings formed by dissolution of releasing agent to modulate the release profile of therapeutic agent. For example, a depot 100 having openings or apertures may release therapeutic agent at a higher rate than a depot 100 without openings or apertures.

Figure 40A:
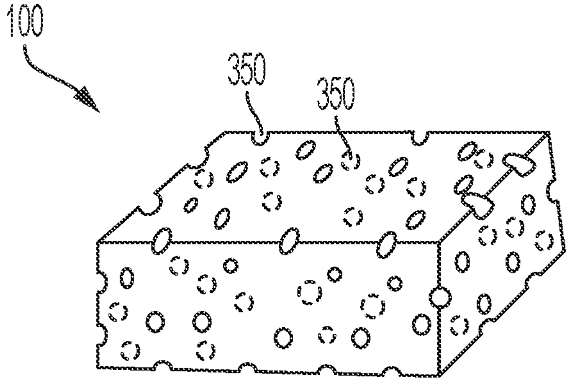
FIG. 40A is a perspective view of a depot in accordance with some embodiments of the present technology.

FIG. 40A illustrates a depot 100 with a sponge-like configuration in which a plurality of irregular openings 350 are formed through the depot 100. In some embodiments, such a depot 100 may be formed by introducing air or otherwise agitating the polymer composition during formation of the depot 100 and while encouraging the solvent to evaporate, resulting in a porous depot 100 with a plurality of openings therein. Such a depot 100 can be substantially uniform in its composition or can include an outer control region and an inner therapeutic region, one or both of which are permeated by some or all of the openings formed in the depot 100.

Figure 40B:
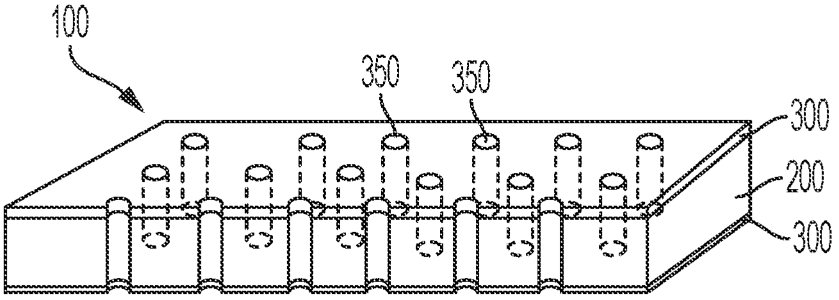
FIG. 40B is a perspective view of a depot in accordance with some embodiments of the present technology.

FIG. 40B illustrates a depot 100 in which a plurality of openings 350 extend through a thickness of the depot 100. In the illustrated embodiment, the openings 350 are substantially cylindrical and pass through upper and lower control regions 300 as well as an inner therapeutic region 200 along substantially parallel trajectories. In other embodiments, the openings 350 can assume other cross-sectional shapes, extend along other axes, and/or vary among one another in orientation, size, shape, etc.

Figure 41A:
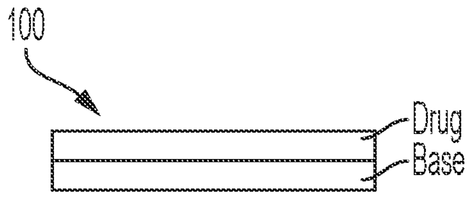
FIG. 41A is a side view of a depot in a straightened state in accordance with some embodiments of the present technology.
Figure 41B:
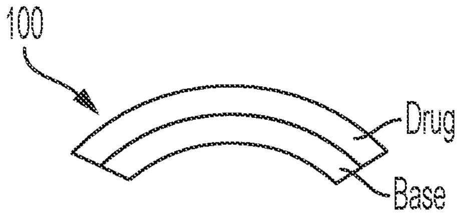
FIG. 41B is a side view of the depot shown in FIG. 41A in a curved state.

In some instances, it can be useful to provide a depot that has a curved, bent, or rounded configuration. For example, such curved depots can beneficially provide adequate contact with a curved surface area of a treatment site, such as the interior of a bladder, an abdominal wall, a surface of a tumor, or any other suitable treatment site. In some embodiments, the depot can have a substantially straight configuration prior to being deployed in vivo and the curved configuration can be achieved after the depot 100 is deployed in vivo in the presence of physiological fluids, while in other embodiments the depot 100 can have maintain the curved configuration both prior to and after being deployed in vivo. FIGS. 41A-44 illustrate various examples of depots 100 having curved configurations. With reference to FIGS. 41A-41B, the depot 100 can have an actuating region 320 that is less elastic than a therapeutic region 200. For example, the actuating region 320 can have a different composition, different dimensions, and/or can be manufactured according to different processes than the therapeutic region 200. By stretching the depot 100 beyond the elastic hysteresis point of the less elastic actuating region 320, the depot 100 can transition from the substantially straightened configuration (shown in FIG. 41A) to the curved configuration (shown in FIG. 41B), in which the less elastic actuating region 320 pulls the depot 100 into the curved shape. In some embodiments, this stretching can occur after implantation, while in other instances the stretching is performed during manufacturing or by a surgeon before implantation. In some embodiments, this transition involves plastic deformation of the depot 100, such that the depot 100 maintains the curved shape even after the stretching force has been removed.

Figure 42A:
FIG. 42A is a side view of a depot in a straightened state in accordance with some embodiments of the present technology.
Figure 42B:
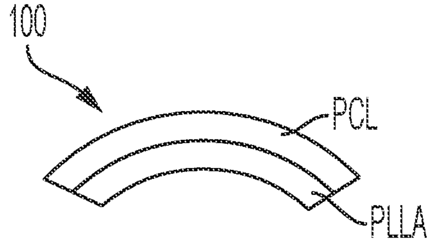
FIG. 42B is a side view of the depot shown in FIG. 42A in a curved state.

A similar result can be achieved by varying the polymer compositions of different layers or regions as in FIGS. 42A and 42B. For example a first region 322 may have a polymer composition that is more hydrophilic than a second region 324, and accordingly the first region 322 may absorb more water or other fluids when implanted in vivo than the second region 324. In various embodiments, either or both of the first and second regions 322, 324 can carry a therapeutic agent. In the embodiment illustrated in FIGS. 42A and 42B, the second region 324 is made of poly(L-lactic acid) (PLLA) and the first region 322 is made of polycaprolactone (PCL). In the presence of water, the PCL will experience a higher water uptake than the PLLA when placed in the presence of fluids. As a result, the PCL expands to a greater degree than the PLLA, resulting in a transition from the straightened state (shown in FIG. 42A) to the curved state (shown in FIG. 42B). In this embodiment, the depot 100 may advantageously retain the straightened state until it is deployed in vivo at the treatment site, at which point the depot 100 will begin to absorb water, resulting in a transition to the curved state.

Figure 43A:
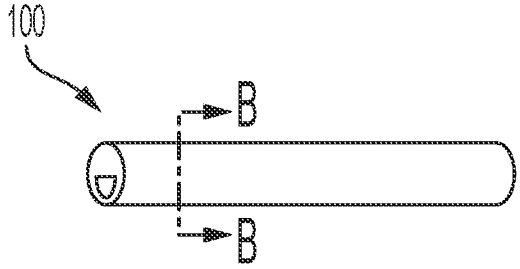
FIG. 43A is a perspective view of a depot in a straightened state in accordance with some embodiments of the present technology.
Figure 43B:
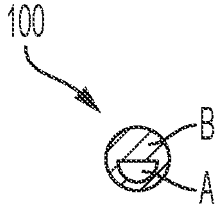
FIG. 43B is cross-sectional view of the depot shown in FIG. 43A taken along line B-B.
Figure 43C:
FIG. 43C is a side view of the depot shown in FIG. 43A in a curved state.

FIGS. 43A-43C illustrate another mechanism for achieving a curved depot. As shown in FIGS. 43A and 43B, the depot 100 may include an outer region B and an axially offset inner region A. The inner region A can have a different composition (e.g., different polymer, the presence of therapeutic agent, etc.) compared to the outer region B. Because the inner region A if offset from the axial centerline of the depot 100, a difference in elasticity or expansion between the inner region A and the outer region B can result in curvature of the depot 100. In one example, the inner region A may include PLLA and the outer region B may include PCL, such that when exposed to water, outer region B expands more than the inner region A, resulting in a curved state.

Figure 44:
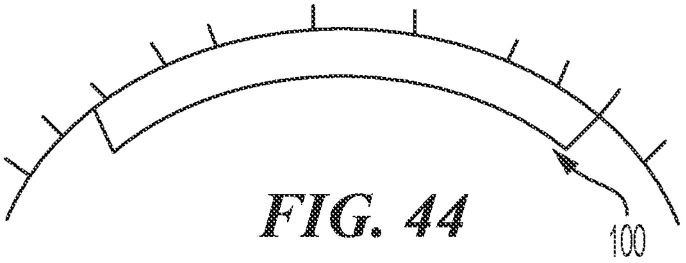
FIG. 44 is a side view of a depot deployed at a target site in a body in accordance with some embodiments of the present technology.
Figure 45:
FIG. 45 is a side view of a depot deployed at a target site in a body in accordance with some embodiments of the present technology.

As noted previously, a curved depot 100 may advantageously be deployed against a curved treatment site, for example in apposition with a concavely curved tissue surface (e.g., the interior of the bladder) as shown in FIG. 44, or in apposition with a convexly curved tissue surface (e.g., over a surface of a protruding tumor) as shown in FIG. 45. In other embodiments, the depot 100 may be configured to have a more complex curvature, for example at least one concave region and at least one convex region, or having different regions with different degrees of curvature. Such complex curvature can be tailored to achieve tissue apposition at a desired treatment site, and can improve delivery of therapeutic agent to the treatment site.

Figure 46:
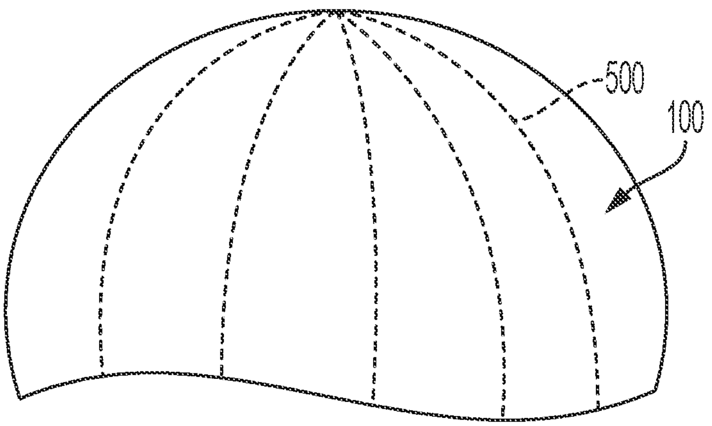
FIG. 46 is a side view of a depot in accordance with some embodiments of the present technology.
Figure 47:
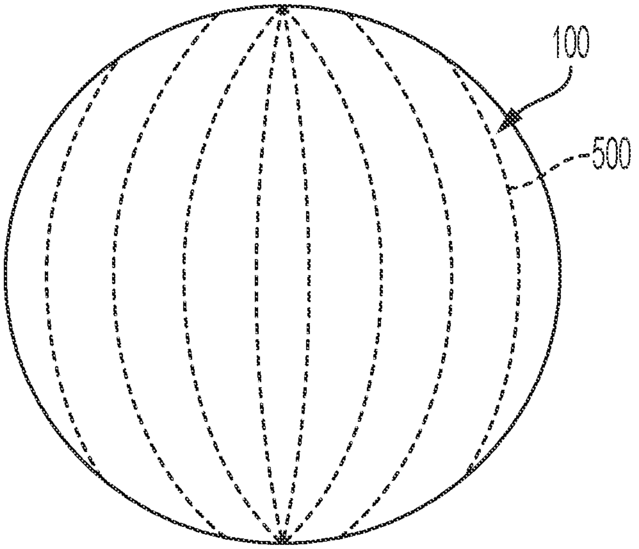
FIG. 47 is a side view of a depot in accordance with some embodiments of the present technology.

As shown in FIGS. 46 and 47, in some embodiments a treatment device can include an anchoring member 500 and a depot 100 carried on a surface of the anchoring member 500. The anchoring member 500 may be a generally hemispherical (as in FIG. 46), spherical (as in FIG. 47), or other suitable structure configured to expand from a low-profile state to a deployed state in apposition with a treatment site. The anchoring member 500 is configured to provide structural support to the treatment device, engage the adjacent anatomy (e.g., a bladder, etc.) to secure the treatment device to a selected treatment site.

In some embodiments, the depot 100 is bonded or otherwise adhered to the surface of the anchoring member 500. In other embodiments, the treatment device may include a depot 100 without an anchoring member 500. The depot 100 may comprise a biocompatible carrier loaded with one or more therapeutic agents and configured for a controlled, sustained release of the therapeutic agent(s) following in vivo placement of the depot. In some embodiments, the depot may be a thin, multilayer film loaded with a therapeutic agent, wherein, as described herein, the depot 100 is configured to release the therapeutic agent(s) at the treatment site.

In some embodiments the structure forming the anchoring member 500 may be a mesh structure. As used herein, "mesh" or "mesh structure" refers to any material (or combination of materials) having one or more openings extending therethrough. For example, in some embodiments, the anchoring member 500 comprises a plurality of filaments (e.g., wires, threads, sutures, fibers, etc.) that have been braided or woven into a tubular shape and heat set. In some embodiments, the mesh structure may be a stent formed of a laser-cut tube or laser-cut sheet, or the mesh structure may be a stent formed via thin film deposition. The anchoring member 500 may be in the form of a flat wire coil attached to a single longitudinal strut, a slotted tube, a helical band that extends circumferentially and longitudinally along the length of the anchoring member, a modular ring, a coil, a basket, a plurality of rings attached by one or more longitudinal struts, a braided tube surrounding a stent, a stent surrounding a braided tube, and/or any suitable configuration or embodiment disclosed herein.

In some embodiments, the anchoring member 500 may be formed of a superelastic material (e.g., nickel-titanium alloys, etc.) or other resilient materials such as stainless steel, cobalt-chromium alloys, etc. configured to self-expand when released from a delivery catheter. For example, the anchoring member may self-expand when pushed through the distal opening of the catheter, or by the delivery catheter being pulled proximally of the anchoring member. In some embodiments the anchoring member 500 may self-expand upon release from other constraining mechanisms (e.g., removable filaments, etc.). In some embodiments, the anchoring member 500 may be expanded manually (e.g., via balloon expansion, a push wire, a pull wire, etc.).

In some embodiments, the anchoring member 500 includes gold, magnesium, iridium, chromium, stainless steel, zinc, titanium, tantalum, and/or alloys of any of the foregoing metals or including any combination of the foregoing metals. In some embodiments, the anchoring member 500 may include collagen or other suitable bioresorbable materials such as PLA, PLG, PLGA etc. In certain embodiments, the metal comprising the mesh structure may be highly polished and/or surface treated to further improve its hemocompatibility. The anchoring member 500 may be constructed solely from metallic materials without the inclusion of any polymer materials, or may include a combination of polymer and metallic materials. For example, in some embodiments the anchoring member 500 may include silicone, polyurethane, polyethylene, polyesters, polyorthoesters, polyanhydrides, and other suitable polymers. This polymer may form a complete sphere or hemisphere to block passage of tumor or drug though the anchoring member 500, or it may have microscopic pores to allow passage of drug but not tumor cells, or it may have small or large openings. In addition, all or a portion of the anchoring member may include a radiopaque coating to improve visualization of the device during delivery, and/or the anchoring member 500 may include one or more radiopaque markers.

In some embodiments, the anchoring member 500 may have other suitable shapes, sizes, and configurations. To improve fixation, in some embodiments the anchoring member 500 may have one or more protrusions extending radially outwardly from the mesh structure along all or a portion of its length, the one or more protrusions being configured to engage with tissue at the treatment site. For example, the anchoring member 500 may include one or more barbs, hooks, ribs, tines, and/or other suitable traumatic or atraumatic fixation members.

As previously mentioned, the depot 100 may be bonded or otherwise adhered to an outer surface of the anchoring member 500. For example, the depot 100 may be bonded to the anchoring member 500 by adhesive bonding, such as cyanoacrylate or UV curing medical grade adhesive, chemical or solvent bonding, and/or thermal bonding, and other suitable means. The depot 100 may also be sewn or riveted to the anchoring member 500. In some embodiments, the depot 100 may be woven into the anchoring member 500 at one or more sections of the anchoring member 500. In some embodiments, the anchoring member 500 may be dip coated in a solution comprising the material elements of the depot 100, and/or the anchoring member 500 may be spray coated with the depot 100. Sections of the anchoring member 500 may be selectively masked such that only certain portions of the anchoring member 500 may be coated with the depot 100. In some embodiments, the anchoring member 500 may be originally in the form of a sheet, and the sheet may be embedded into the depot 100 (for example, with the depot 100 as a multilayer film construction.) The resulting sheet structure (i.e., the anchoring member 500 embedded within the depot 100) may be rolled into a tubular structure (with or without the adjacent ends attached) for delivery into the body. In some embodiments, the depot may be coated with a bioresorbable adhesive derived from polyethylene glycol (PEG or PEO), for example, or from other hydrogels. The PEG or hydrogel may also be integral to the depot 100 via mixing in solution with the depot materials and not a separate coating.

The depot 100 may be disposed along all or a portion of the surface of the anchoring member 500, all or a portion of the circumference of the mesh structure, and/or cover or span all or some of the openings in the mesh structure depending on the local anatomy of the treatment site. For example, the volume, shape, and coverage of the tumor may vary patient-to-patient. In some cases, it may be desirable to use a treatment device having a depot 100 extending around the entire outer surface and/or inner surface of the anchoring member 500. In other cases, it may be desirable to use a treatment device having a depot 100 extending around less than the entire outer surface and/or inner surface of the anchoring member 500 to reduce exposure of potentially healthy tissue to the chemotherapeutic agents.

In some cases, the depot 100 may be elastically expandable, such that the depot 100 expands with the anchoring member 500 as it is deployed. The depot 100 may also be less elastic but can be folded for delivery in a compact form. Alternatively, the depot 100 could be configured to change shape as it is expanded. For example, a tubular depot could have a pattern of overlapping longitudinal slots, so that it expands into a diamond-shaped pattern as it is expanded. The expanded pattern of the depot 100 may align with the pattern of the anchoring member 500, or it may be totally independent of the anchoring member 500. This approach may enable the highest volume of therapeutic agent to be delivered in the most compact delivery format, while still enabling expansion on delivery and flexion, compression and expansion while positioned at the treatment site.

Figure 48A:
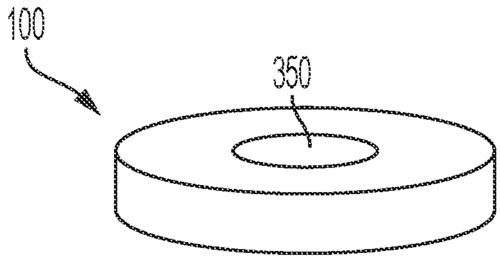
FIGS. 48A and 48B are perspective views of depots in accordance with some embodiments of the present technology.
Figure 48B:
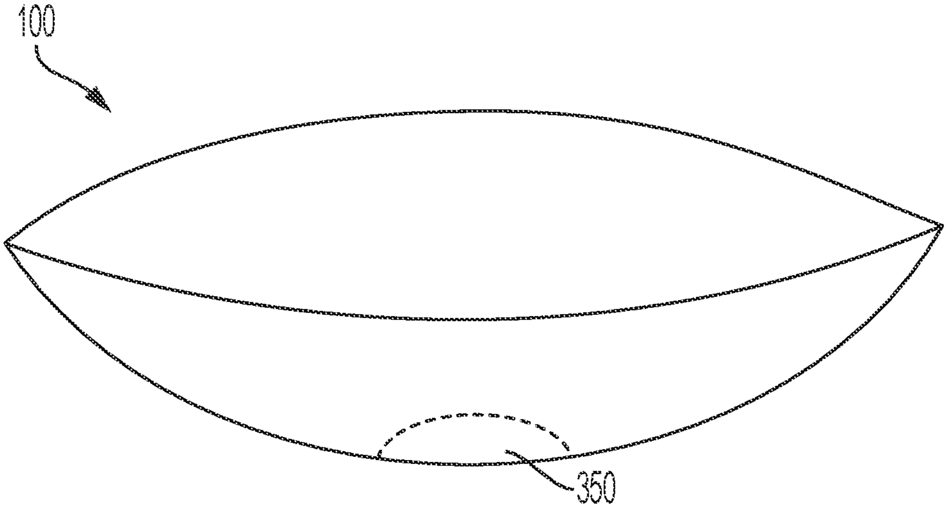

In certain cases, it can be useful to provide a depot 100 with a larger opening or lumen 350 therethrough. For example, a depot 100 deployed in a bladder may benefit from a relatively large opening that allows urine to pass therethrough. Such an opening can reduce the risk of the depot 100 interfering with normal physiological function. FIGS. 48A and 48B illustrate two different embodiments of such depots 100. As seen in FIG. 48A, the depot 100 can be substantially annular or ring-like structure with a central opening 350. For example, the central opening 350 can have a greatest transverse dimension that is more than 10%, more than 20%, more than 30%, more than 40%, or more than 50% of the length of a maximum transverse dimension and the annular depot 100. In the embodiment shown in FIG. 48B, the depot 100 can be a curved (e.g., semi-spherical or semi-ellipsoid) structure with a central opening 350 configured to allow fluid to pass therethrough. Although single openings 350 are illustrated in these embodiments, in other embodiments there may be two or more openings 350 configured to facilitate normal physiological function when the depot 100 is implanted at a treatment site.

Figure 49A:
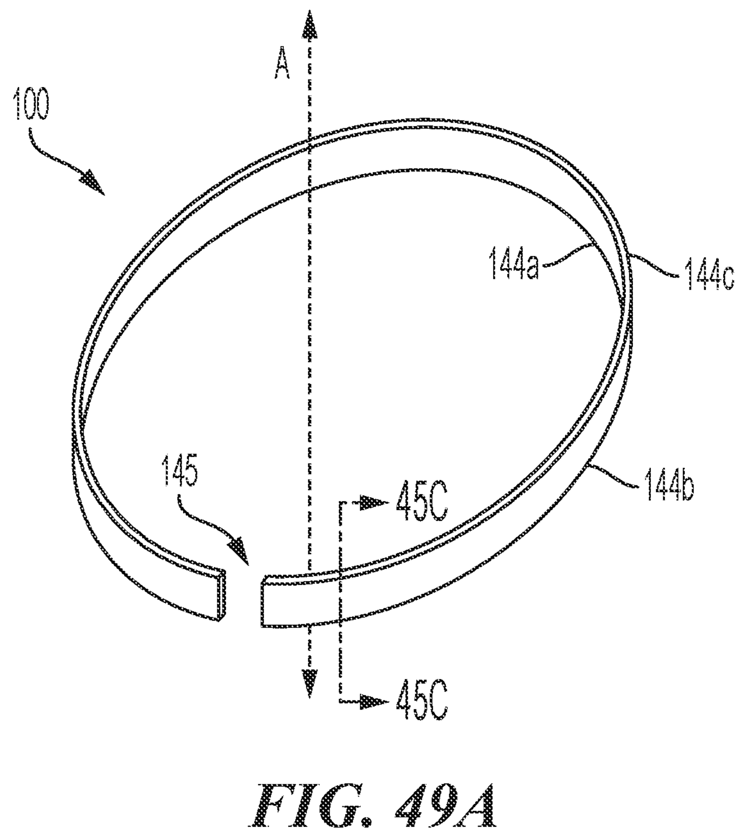
FIG. 49A-C are perspective, top, and side views, respectively, of a depot in accordance with some embodiments of the present technology.
Figure 49B:
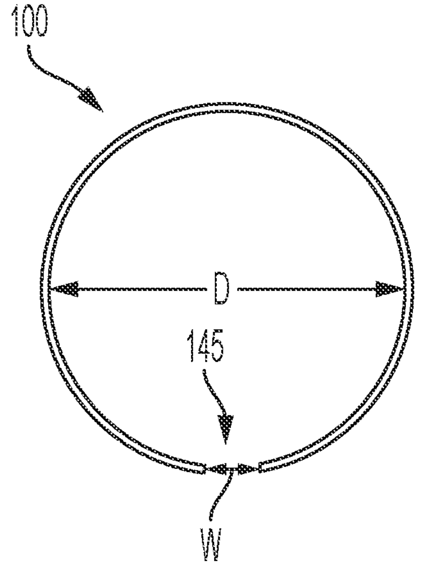
Figure 49C:
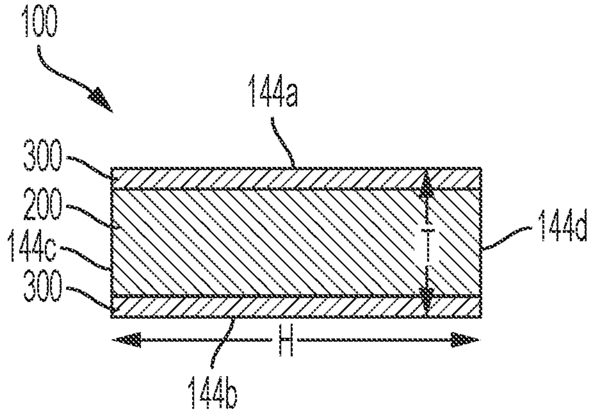

FIGS. 49A-C illustrate perspective, top, and cross-sectional views, respectively, of a depot 100 having an annular semi-annular shape. As illustrated, the depot 100 is an elongated strip, ribbon, or band that curls about an axis A. The depot 100 in the form of an elongated strip has an inwardly facing lateral surface 144*a* and an outwardly facing lateral surface 144*b* each having a width W. First and side second surfaces 144*c* and 144*d* can extend between the lateral surfaces 144*a* and 144*b*, defining a thickness T, such that the depot has a substantially rectangular cross-section as seen in FIG. 49C. In some embodiments, the band can have a thickness T of between about 0.1 mm and about 10 mm, or between about 0.5 mm and about 5 mm, or about 2 mm. In some embodiments, the depot 100 can have a height H of between about 0.1 mm and about 10 mm, or between about 0.5 mm and about 5 mm, or about 1 mm. The depot 100 can be curled about the axis A such that first and seconds ends are adjacent to one another, while leaving a gap 145 therebetween. In this curled configuration, the depot 100 is characterized by an inner diameter D. In some embodiments, for example for use in a bladder, the diameter D can be between about 2 cm and about 20 cm, for example between about 2 cm and about 10 cm, or between about 4 cm and about 8 cm, or approximately 6 cm. In some embodiments, the depot 100 can have a length of between about 20 cm and about 100 cm, for example between about 30 cm and about 50 cm, or approximately 38 cm.

In some embodiments, the ends can be joined together, creating a closed annular shape. As seen in FIG. 49C, in some embodiments the depot 100 includes a control region 300 disposed on the inwardly facing lateral surface 144*a* and another control region 300*b* disposed on the outwardly facing lateral surface 144*b*. In some embodiments, a therapeutic region 200 disposed between the two control regions 200 can be partially or completely exposed along the side surface 144*c*. Optionally, the therapeutic region 200 can also be partially or completely exposed along an opposing side surface 144*d* disposed opposite the first side surface 144*c*.

In some embodiments, the depot 100 of FIGS. 49A-49C can be delivered to the treatment site in a compressed configuration, either straightened longitudinally, or curled tightly about a central axis, or other compressed state. When delivered, the depot 100 can expand into the annular or semi-annular configuration as shown in FIG. 49A. In some embodiments, the depot 100 can be positioned such that the outwardly facing lateral surface 144*b* is in apposition with tissue along at least a portion of its length.

Figure 50A:
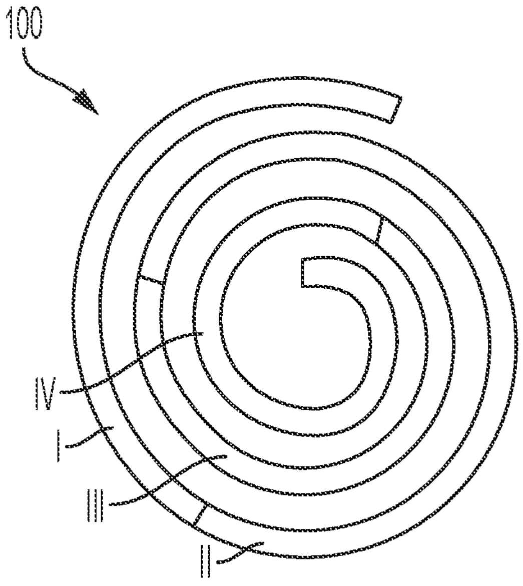
FIG. 50A is an end view of a depot in a curled state in accordance with some embodiments of the present technology.
Figure 50B:
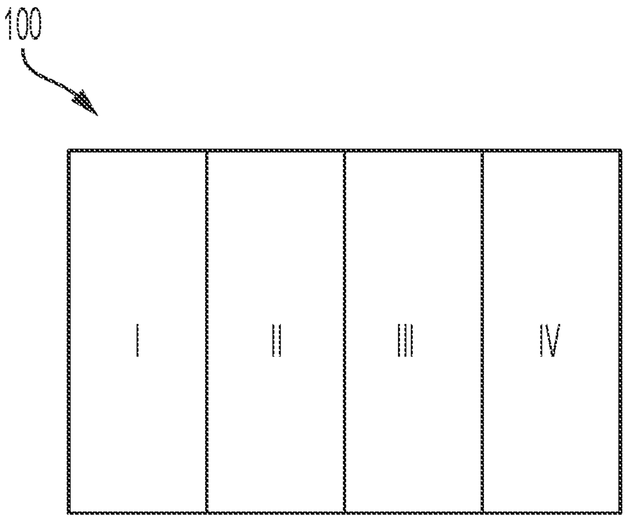
FIG. 50B is a side view of the depot shown in FIG. 50A in an uncurled state.

FIG. 50A shows an end view of a depot 100 in a spirally curled state and FIG. 50B shows a side view of the depot 100 in an uncurled state. The depot 100 includes a plurality of segments I-IV having different structural and mechanical properties that cause the depot 100 to assume the spirally curled configuration shown in FIG. 50A when placed in the presence of physiological fluids in vivo at a treatment site. For example, the different segments I-IV can vary in polymer composition, therapeutic agent, concentration of therapeutic agent, concentration of release agent, or any other parameter that affects the mechanical and structural properties of the depot 100, resulting in a spirally wound depot 100 as seen in FIG. 50A. In some embodiments, the spiral winding can facilitate placement of the depot 100 at a treatment site, and/or improve attachment to anatomical tissue at the treatment site.

Figure 51:
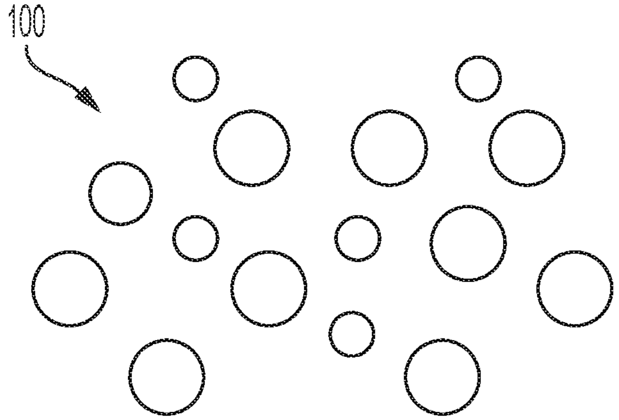
FIG. 51 illustrates a plurality of depots in accordance with some embodiments of the present technology.

FIG. 51 illustrates a plurality of depots 100 in the form of microbeads, microspheres or particles. In various embodiments, each microbead can include a therapeutic region at its core and one or more control regions partially, substantially, or completely surrounding the therapeutic region. In some embodiments, the microbead may include multiple, layered control regions and/or therapeutic regions having the same composition or different compositions and/or the same thickness or different thicknesses. The release profile of any particular microbead is determined by its size, composition, and the thickness of the control region and therapeutic region. In some embodiments, a plurality of microbeads are provided having varying dimensions, varying shapes (e.g. spherical, ellipsoid, etc.), varying polymer compositions, varying concentration of therapeutic agent in the therapeutic region, varying concentration of releasing agent in the control region, or variation of any other parameters that affect the release profile. As a result, the composite release profile of the plurality of microbeads can be finely tuned to achieve the desired cumulative release of therapeutic agent to the treatment site. In various embodiments, some or all of the microbeads can have a diameter or largest cross-sectional dimension of between about 0.01 to about 5 mm, or between about 0.1 mm to about 1.0 mm. In some embodiments, some or all of the microbeads can have a diameter or largest cross-sectional dimension that is less than about 5 mm, less than about 2 mm, less than about 1.0 mm, less than about 0.9 mm, less than about 0.8 mm, less than about 0.7 mm, less than about 0.6 mm, less than about 0.5 mm, less than about 0.4 mm, less than about 0.3 mm, less than about 0.2 mm, or less than about 0.1 mm.

Figure 52A:
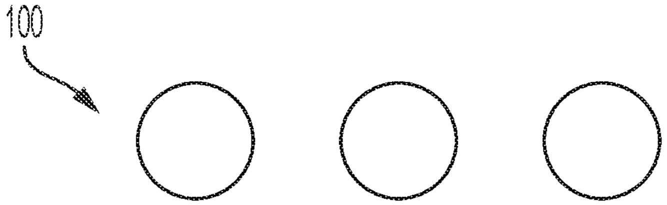
FIG. 52A is an end view of a plurality of depots in accordance with some embodiments of the present technology.
Figure 52B:
FIG. 52B is a side view of the depots shown in FIG. 52A.

FIGS. 52A and 52B illustrate end and side views, respectively, of a plurality of depots 100 in the form of pellets. In the illustrated embodiment, the pellets are substantially cylindrical, however the particular shape and dimensions of the pellets may vary to achieve the desired release kinetics and form factor. For example, the pellets can have rounded ends (e.g., ellipsoid), and/or can have a cross-sectional shape that is circular, elliptical, square, rectangular, regular polygonal, irregular polygonal, or any other suitable shape. In some embodiments, each pellet can include an inner therapeutic region at least partially surrounded by an outer control region. In some embodiments, the pellet may include multiple, layered control regions and/or therapeutic regions having the same composition or different compositions and/or the same thickness or different thicknesses. As with the microbeads shown in FIG. 51, individual pellets of the plurality can vary from one another in one or more of shape, polymer composition, concentration of therapeutic agent in the therapeutic region, concentration of the releasing agent in the control region, thickness of the control region, thickness of the therapeutic region, and any other parameter that affect the release profile. As a result, the composite release profile of the plurality of pellets can be finely tuned to achieve the desired cumulative release of therapeutic agent to the treatment site.

In various embodiments, the depot can be different sizes, for example, the depot may be a length of from about 0.4 mm to 100 mm and have a diameter or thickness of from about 0.01 to about 5 mm. In various embodiments, the depot may have a layer thickness of from about 0.005 to 5.0 mm, such as, for example, from 0.05 to 2.0 mm. In some embodiments, the shape may be a rectangular or square sheet having a ratio of width to thickness in the range of 20 or greater, 25 or greater, 30 or greater, 35 or greater, 40 or greater, 45 or greater, or 50 or greater.

In some embodiments, a thickness of the control region (a single sub-control region or all sub-control regions combined) is less than or equal to 1/10, 1/15, 1/20, 1/25, 1/30, 1/35, 1/40, 1/45, 1/50, 1/75, or 1/100 of a thickness of the therapeutic region. In some embodiments, the depot 100 has a width and a thickness, and a ratio of the width to the thickness is 21 or greater. In some embodiments, the ratio is 22 or greater, 23 or greater, 24 or greater, 25 or greater, 26 or greater, 27 or greater, 28 or greater, 29 or greater, 30 or greater, 35 or greater, 40 or greater, 45 or greater, or 50 or greater. In some embodiments, the depot 100 has a surface area and a volume, and a ratio of the surface area to volume is at least 1, at least 1.5, at least 2, at least 2.5, or at least 3.

I. Example Methods of Manufacture

The depots of the present technology may be constructed using various combinations of bioresorbable polymer layers, wherein these layers may include therapeutic agents, releasing agents, delayed release agents, etc., in varying combinations and concentrations in order to meet the requirements of the intended clinical application(s). In some embodiments, the polymer regions or layers may be constructed using any number of known techniques to form a multilayer film of a particular construction. For example, a bioresorbable polymer and a therapeutic agent can be solubilized and then applied to the film via spray coating, dip coating, solvent casting, and the like. In an alternative embodiment, a polymer layer for use as a control region and/or a therapeutic region can be constructed from electrospun nanofibers.

The depots 100 described herein may be constructed by placing therapeutic regions (and/or sub-regions) and/or control regions (and/or sub-regions) on top of one another in a desired order and heat compressing the resulting multilayer configuration to bond the layers together. Heat compression may be accomplished using any suitable apparatus known in the art. In one embodiment, the heat compression process consists of utilizing a heat compressor (Kun Shan Rebig Hydraulic Equipment Co. Ltd., China), and heat compressing the stacked assembly of therapeutic 200 and/or control regions 300 at a temperature that is above room temperature (e.g., at least 30° C., 35° C., 40° C., 45° C., 50° C., 55° C., 60° C., 65° C., 70° C., 75° C., 80° C., 85° C., 90° C., 95° C., 100° C., 105° C., 110° C., 115° C., or 120° C., etc.) and a pressure of from about 0.01 MPa to about 1.0 MPa, or about 0.10 MPa to about 0.8 MPa, or about 0.2 MPa to about 0.6 MPa. The inventors have discovered that heating the therapeutic and control regions during compression (separately or after stacking) increases the therapeutic agent density in the depot 100. The inventors have also discovered that heat compression at lower pressures enable higher drug densities.

Depending on the therapeutic dosage needs, anatomical targets, etc., the depot 100 can be processed, shaped and otherwise engineered to produce form factors that can be administered to the patient by implantation in the body by a clinical practitioner. For example, various configurations of the film may be achieved by using a jig with a pre-shaped cutout, hand cutting the desired shape or both. Some of the form factors producible from the multilayer film for implantation into the body include: strips, ribbons, hooks, rods, tubes, patches, corkscrew-formed ribbons, partial or full rings, nails, screws, tacks, rivets, threads, tapes, woven forms, t-shaped anchors, staples, discs, pillows, balloons, braids, tapered forms, wedge forms, chisel forms, castellated forms, stent structures, suture buttresses, coil springs, and sponges. As described below with respect to FIG. 52C, in some embodiments a pellet-like or mini-cylindrical depot 100 can be punched or otherwise cut out of a sheet of a multilayer film. A depot 100 may also be processed into a component of the form factors mentioned above. For example, the depot 100 could be rolled and incorporated into tubes, screws tacks or the like. In the case of woven embodiments, the depot 100 may be incorporated into a multi-layer woven film wherein some of the filaments used are not the inventive device. In one example, the depot 100 is interwoven with Dacron, polyethylene or the like.

In some embodiments, one or more depots 100 can be cut into a desired shape or form factor using precision laser cutting. Various laser modalities may be used, for example infrared lasers, near-infrared lasers, deep ultraviolet lasers, or other suitable lasers for cutting depots 100 to the desired configurations. Such laser cutting can use continuous or pulsed, and the operating parameters (e.g., intensity, frequency, polarization, etc.) may be selected to achieve the desired cut. Using computer-controller laser-cutting can provide for a precise, repeatable manufacturing process that achieves consistent dimensions and release profiles. In some embodiments, the cut surfaces resulting from the laser-cut can be significantly smoother than those achieved using a mechanical stamp, jig, or punch to cut depots from a sheet of a multi-layer film. In some instances, the smoother cut surfaces can provide for improved release profiles, for example with more consistency among depots 100 manufactured according to this process.

In some embodiments, the therapeutic region 200 can be extruded into an elongated form (e.g., a cylindrical rod), after which the control region 300 may be spray- or dip-coated over the extruded therapeutic region 200. Portions of the extruded therapeutic region 200 may be masked to leave gaps in the control region 300, or alternatively portions of the control region 300 may be removed via etching, scraping, or other techniques to achieve any desired openings or thinning of the control region 300 in any desired portions. In some embodiments, an extruded cylinder having a lumen extending therethrough can be selectively filled with a therapeutic region 200 and/or a control region 300 along its length to form an elongated depot 100.

In some embodiments, a therapeutic region 200 in the shape of a cylindrical rod is formed by dissolving the therapeutic region composition (e.g., a mixture of polymer(s) and therapeutic agent) into acetone, and then loading the dissolved therapeutic region composition into a syringe (e.g., a 1 mL syringe) and attaching a needle thereto (e.g., a 19G needle). The therapeutic region solution is then injected into ethanol for polymer solidification. After waiting for the solution to harden (e.g., approximately 90 seconds), the resulting rod can be removed from the ethanol and air-dried. In another embodiment, the therapeutic region composition can be injected into a cross-linking solution to solidify the polymer.

The therapeutic region 200 may be spray- or dip-coated with a surrounding control region 300. Alternatively, in some embodiments, the therapeutic region 200 in elongated cylindrical form can be inserted into an inner lumen of a coaxial needle. The coaxial needle can include an inner needle disposed coaxially within the lumen of an outer needle. In one example, the inner needle can have an inner diameter of approximately 0.84 mm and an outer diameter of approximately 1.24 mm, and the outer needle can have an inner diameter of approximately 1.6 mm and an outer diameter of approximately 2.11 mm, though these dimensions can vary and be tailored to the desired dimensions of the therapeutic region 200 and control region 300. A control region composite (e.g., a mixture of polymer and releasing agent) can be dissolved in acetone, and then loaded into a syringe (e.g., a 1 mL syringe). The control region solution is then injected through the outer needle, surrounding the cylindrical therapeutic region disposed within the inner needle. The resulting depot 100 is a cylindrical form with a control region 300 substantially uniformly surrounding the inner cylindrical therapeutic region 200. In some embodiments, the resulting cylindrical form can be suitable for injecting using a needle, thereby providing for a convenient mechanism to deliver the depot to any number of different treatment sites. In other embodiments, a coaxial needle having three or more coaxial lumens can be used for the formation of multiple therapeutic and/or control regions, for example having a plurality of different therapeutic agents that can be configured to be released sequentially from the depot 100.

In some embodiments, an extruded depot 100 in the form an elongated columnar structure (e.g., a cylindrical rod, strip, etc.) can be pinched down at one or more positions along its length to be subdivided into discrete portions. For example, an elongated depot 100 may be pinched such that the depot is completely severed into discrete sections, or to provide a narrowed, weakened portion that can be susceptible to flexing and/or breaking.

Figure 52C:
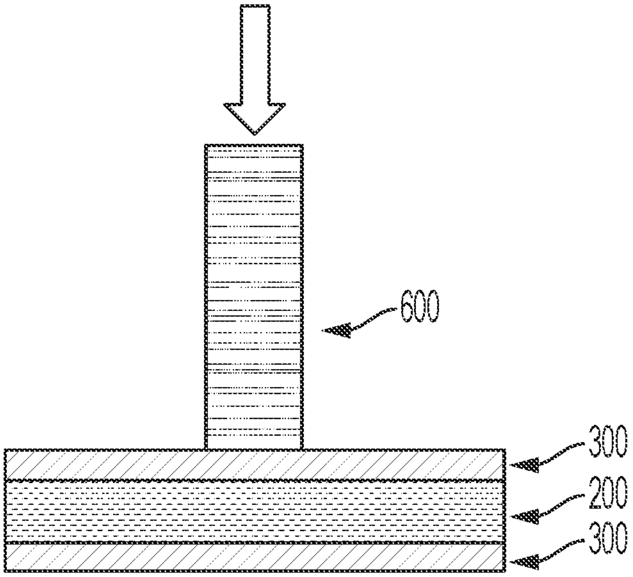
FIG. 52C illustrates a method of manufacturing the depots shown in FIGS. 52A and 52B.
Figure 53:
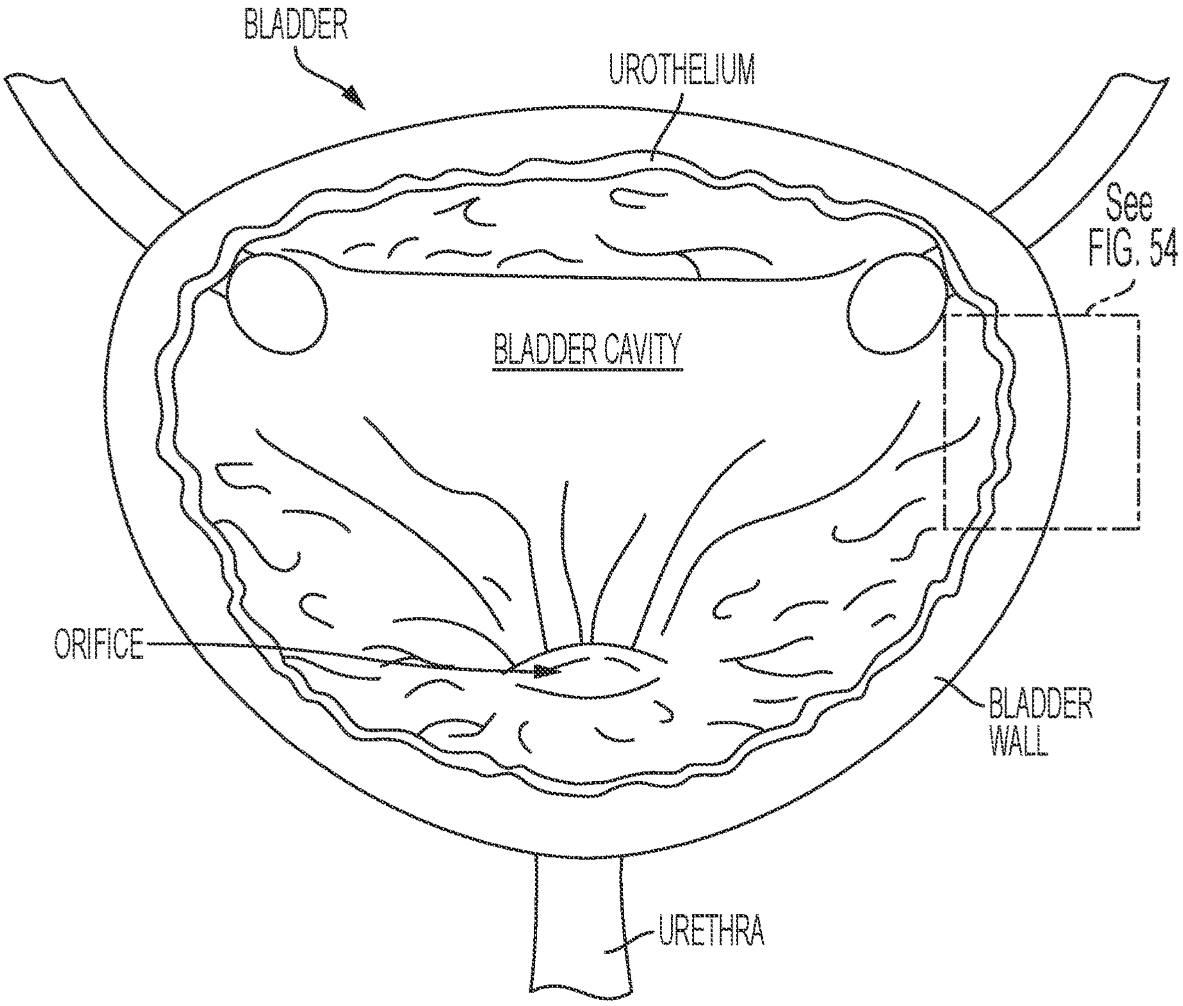
FIG. 53 is a schematic, partial cross-sectional view of a human bladder.
Figure 55:
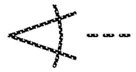
FIG. 55 is a direct-on view of the depot as shown in FIG. 54, positioned proximate a tumor at the bladder wall in accordance with the present technology.
Figure 54:
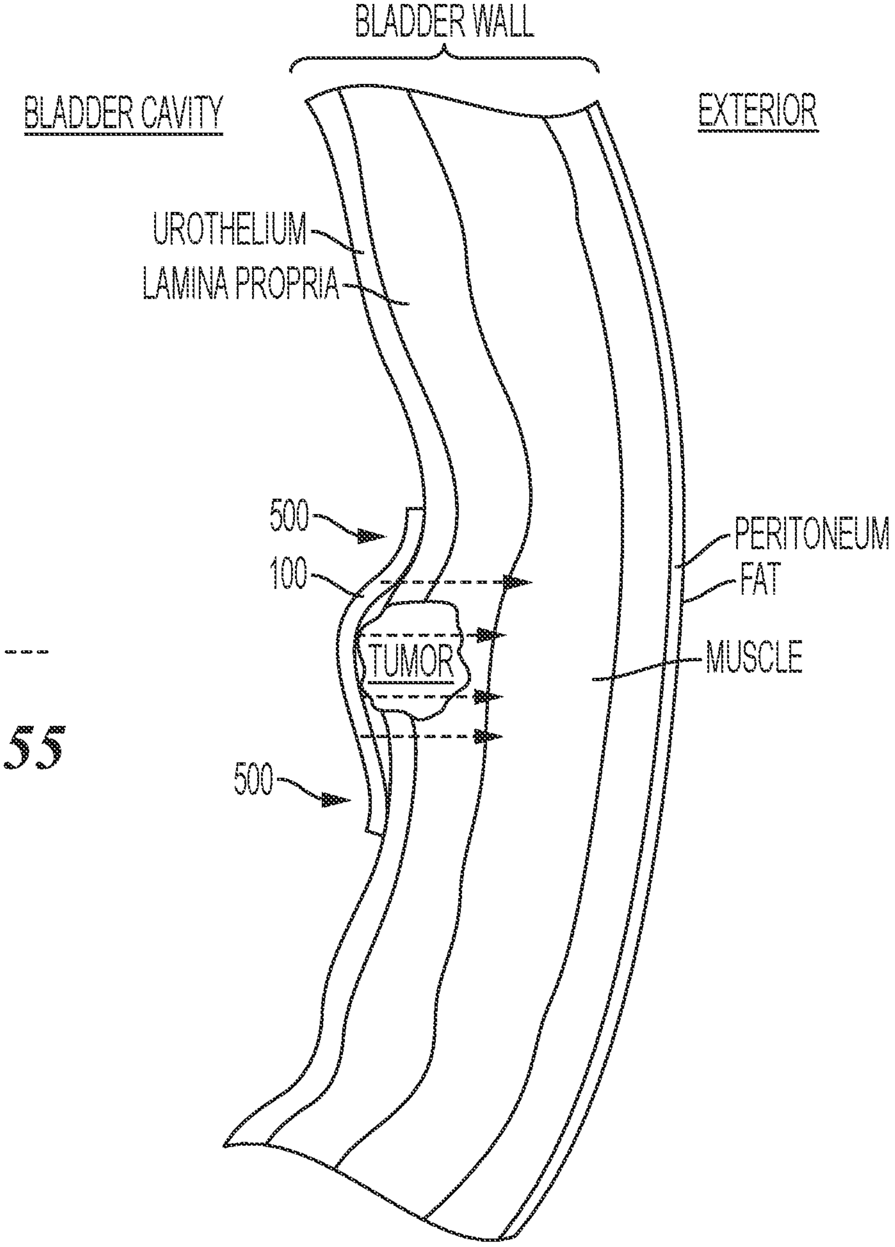
FIG. 54 is an enlarged, cross-sectional side view of the bladder wall shown in FIG. 53.
Figure 55:
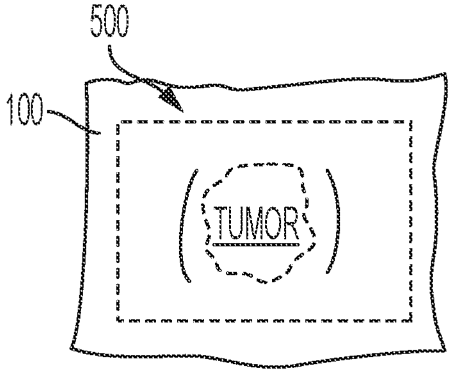
Figure 56:
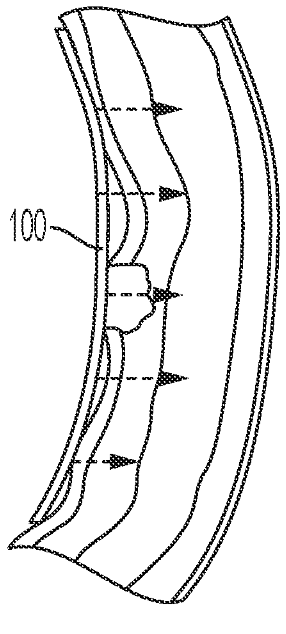
FIG. 56 is an enlarged, cross-sectional side view of a bladder wall showing a depot of the present technology positioned against the bladder wall.
Figure 57:
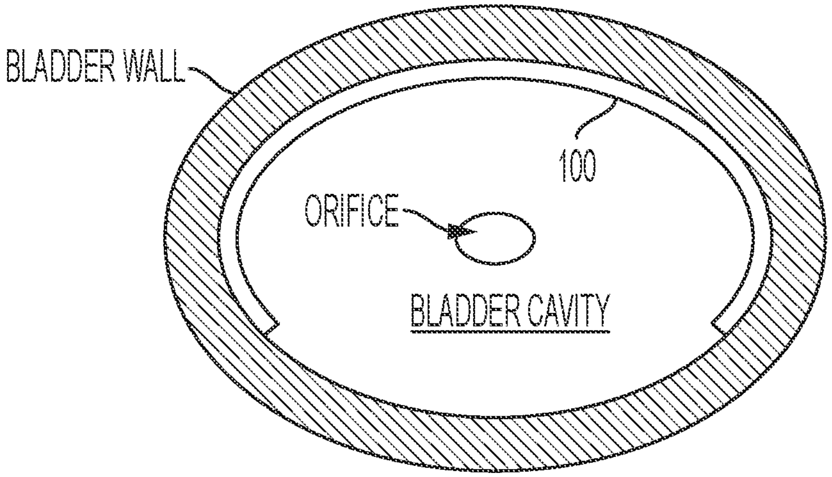
FIG. 57 is a top cross-sectional, schematic view of a depot positioned within a bladder.

FIG. 52C illustrates one method of manufacturing depots in the form of pellets as shown in FIGS. 52A and 52B. A sheet including a plurality of layered regions such as outer control regions 300 at least partially surrounding an inner therapeutic region 200 is provided. A punch 600 with a hollow blade can be used to cut out individual pellets from the sheet, for example by pressing the punch 600 through the sheet along an axis orthogonal to the surface of the sheet. In some embodiments, the resulting pellets each retain the layered regions of the sheet (e.g., a therapeutic region 200 sandwiched between first and second control regions 300). In such embodiments, the resulting pellet can have at least a portion of the therapeutic region 200 exposed through the control region(s) 300, for example with lateral sides of the pellet having exposed portions of the therapeutic region 200. Such exposed portions of the therapeutic region 200 can contribute to a higher initial release rate of the therapeutic agent.

In some embodiments, the punch 600 is heated before cutting the pellets from the sheet, for example by being heated in an oven to approximately 80° C., or to a suitable temperature to at least partially melt or deform the control region 300. The heated punch 600 can at least partially deform the top layer (e.g., partially melting the upper control region 300) causing it to wrap around the lateral edges of the therapeutic region 200. The resulting depot 100 may then take the form of a pellet 100 in which the inner therapeutic region 200 is completely or substantially completely surrounded by the control region(s) 300. In some embodiments, the motion of pressing the punch 600 can be varied to achieve the desired coverage of the control region(s) 300 over the therapeutic region 200. For example, in some embodiments, the punch 600 can be rotated while being pressed through the sheet, and in some embodiments the punch 600 can be moved more slowly or move quickly to allow varying degrees of deformation and flow of the control region(s) 300. In other embodiments, the punch 600 is not heated before being pressed through the sheet.

The dimensions of the depots 100 in the form of pellets or mini-cylinders can be controlled by varying the thickness of the sheet and by selecting the diameter or lumen cross-sectional dimensions of the punch 600. In some embodiments, the sheet can have a thickness of between about 0.5 and 2 mm (e.g., approximately 0.85 mm), and the punch 600 can have a circular lumen with a diameter of between about 0.5 mm and about 3 mm (e.g., approximately 1 mm). In other embodiments, the punch 600 can cut out depots 100 in other shapes, for example, square, rectangular, elliptical, star-shaped, wavy, irregular polygonal, or any other suitable cross-sectional shape. In some embodiments, a wavy or jagged shape can provide a larger surface area for the resulting pellets, thereby increasing a rate of release of therapeutic agent from the pellets. In some embodiments, the resulting depots 100 in the form of pellets or mini-cylinders are insertable through a needle or other suitable delivery shaft. For example, a plurality of approximately pellets having 1 mm diameters may be loaded coaxially into a 17-gauge needle and inserted subcutaneously to a treatment site in a patient. Smaller pellet-like depots 100 could be inserted through even smaller needles, for example 18- to 22-gauge needles. Such pellets or mini-cylinders can achieve a considerably high drug loading, as described elsewhere herein, for example at least 50% by weight of the therapeutic agent or more.

In some embodiments, microbead and/or pellet-like depots (e.g., as in FIGS. 51-52) can be formed by providing an elongated structure (e.g., a cylindrical, columnar, or rod-shaped structure) having a therapeutic region 200 at least partially surrounded by a control region 300, and then cutting or otherwise dividing the structure into a plurality of pellets, particles, or microbeads along its length.

II. Treatment of Cancers Via Localized, Sustained Drug Delivery and Associated Endpoints In various embodiments, depots of the present technology can be used to treat a variety of cancers or other conditions. A number of specific cancers are described below in more detail. However, these are exemplary only, and in various embodiments the present technology can be used for treatment of additional cancers or other conditions not specifically discussed herein. In any particular case, one or more depots as described herein can be used to provide local sustained delivery of one or more therapeutic agents to a treatment site (e.g., a site proximate a tumor). The therapeutic agents can include one or more agents suitable for treating the particular cancer or associated conditions. Examples include chemotherapeutics, hormone therapeutics, immunotherapeutics, targeted therapeutics, supportive therapeutics, or any other suitable therapeutic agent(s) as listed and described in more detail elsewhere herein (e.g., with reference to FIGS. 105-113). In various embodiments, a single depot can be configured to deliver one or more therapeutic agents, whether concurrently, sequentially, or otherwise. In some embodiments, multiple depots can be used in conjunction for delivery of one or more therapeutic agents to the treatment site.

In some instances, one or more depots can be used to provide local sustained delivery of the therapeutic agent(s) to the treatment site, which alone can provide effective treatment. In some embodiments, the local sustained delivery may be used in combination with one or more other treatment approaches. The local sustained delivery may work in concert with the other treatment options to achieve better treatment outcomes, and/or the local sustained delivery may at least partially replace or reduce the severity of the other treatment options. For example, local sustained delivery of a chemotherapeutic agent (e.g., using one or more depots of the present technology) can be combined with systemic delivery of another chemotherapeutic agent. This combined therapy may provide improved patient outcomes as compared to systemic drug delivery alone. Additionally or alternatively, the combined therapy may enable use of a smaller dose of a systemically delivered chemotherapeutic while achieving similar treatment outcomes, thereby increasing patient safety and comfort.

In some embodiments, combined treatment includes local sustained delivery of one or more therapeutic agents (e.g., using depot(s) of the present technology) in combination with surgery. For example, one or more depot(s) can be placed proximate a treatment site to deliver therapeutic agent to the tumor, either before surgery (e.g., as a neoadjuvant with the goal of shrinking the tumor to increase the probability of full resection of the tumor) or with or after surgery (e.g., as an adjuvant to mitigate/minimize risk of recurrence by killing any remaining cancer cells).

In some embodiments, combined treatment includes local sustained delivery of one or more therapeutic agents (e.g., using depot(s) of the present technology) in combination with systemic drug therapy and/or radiation. This combined approach may achieve better patient outcomes than systemic drug therapy and/or radiation alone. Additionally or alternatively, the combined approach may achieve similar or better patient outcomes while permitting a lower dose of systemic drug therapy and/or radiation, thereby potentially reducing undesirable side effects and improving patient comfort and safety.

In some embodiments, local sustained delivery of one or more therapeutic agents (e.g., using depot(s) of the present technology) can be used as an alternative to surgery and/or radiation, either removing the need for surgery or radiation altogether, or reducing a severity, dose, or intensity thereof (e.g., requiring a smaller dose of radiation to achieve similar or better patient outcomes). This can be particularly useful in instances in which a tumor is not surgically accessible or resectable and/or surgical intervention poses considerable risk of collateral damage to non-target tissue. Similarly, this approach can be useful when the risk of radiation exposure to non-target tissue limits use of external beam radiation or local implantation of brachytherapy seeds, such as in the case of cancers of the head and neck.

In some embodiments, the local sustained delivery of one or more therapeutic agents (e.g., using depot(s) of the present technology) can provide support and/or palliative care. For example, in instances in which the cancer or other condition is advanced and the prognosis for survival is low, local delivery of therapeutic agents may still provide therapeutic relief to significantly improve a patient's quality of life. In some embodiments, local delivery of therapeutic agents for palliative or supportive care can include medications for pain/inflammation (anesthetics, steroidal and non-steroidal anti-inflammatories, anti-bodies), infection (antimicrobials, antibiotics), or combinations thereof.

In various embodiments, local sustained delivery of one or more therapeutic agents can involve placement of one or more depots of the present technology using any suitable route of administration. For example, one or more depots can be placed at a treatment site via surgical, endoscopic, endovascular, percutaneous, or other approach depending on the particular condition being treated, the location of the tumor, the patient's anatomy, and other relevant factors. In some embodiments, surgical access includes implantation or direct needle injection or insertion of one or more depots at the treatment site as part of a laparoscopic or open procedure with direct visualization and/or palpation. In some embodiments, percutaneous access can include direct needle injection and/or insertion into or around the tumor. Such percutaneous access can be guided using appropriate imaging techniques (e.g., CT, MRI, etc.). In some embodiments, endovascular or endoscopic approaches can include the use of drug-eluting stents, stent grafts, catheters, or other such medical devices configured in accordance with the present technology. In at least some instances, multiple different routes of administration can be used for the treatment of a single patient.

The particular depot configuration, therapeutic agent(s), and route of administration may be selected to suit the particular cancer or other condition being treated. Additionally, any accompanying treatment that is combined with local sustained delivery via the depot(s) can be selected to suit the particular cancer or other condition being treated.

Whether used alone or in combination with one or more additional treatment modalities (e.g., systemic drug delivery, surgery, radiation, etc.), treatment that includes local sustained delivery of one or more therapeutic agents can be assessed or evaluated using suitable clinical endpoints or response criteria. Such endpoints can be used to assess individual patient responses, and/or may be used across a population of patients, such as in the case of a clinical study. Various example endpoints are disclosed herein throughout. Any particular endpoint or combination of endpoints disclosed herein or as known to one of skill in the art may be used to assess efficacy of a particular treatment involving local sustained delivery of one or more therapeutic agents. In some embodiments, a clinical trial for assessing the efficacy of local sustained delivery as described herein can include a control group receiving standard treatment for a particular cancer (e.g., surgical intervention, radiation therapy, systemic drug delivery, etc.) and a treatment group receiving standard treatment in addition to locally delivered therapeutic agent(s) as described herein. In such a clinical trial, the outcomes for each group can be assessed using any suitable endpoint, including those listed herein, to assess the efficacy of the various interventions.

Any of the following endpoints and/or response criteria may be utilized to assess the effectiveness of treatment utilizing the sustained-release formulations and/or depots of the present technology, whether used alone or in combination with one or more additional treatment approaches such as radiation, surgery, or systemic drug therapy:

Overall survival: as measured in time from treatment (or randomization) to death due to any cause.

Progression free survival: as measured from the date of start of treatment (or randomization) to the date of the first documented progression (PD) or death due to any cause. An indication of progressive disease (PD) can be based on at least a particular percentage increase in tumor size (e.g., 20% increase in the sum of the diameters of the target lesions).

Time to progression: as measured from the date of start of treatment (or randomization) to the date of first documented progression (PD).

Duration of response.

Overall/objective response rate: a patient's response can be categorized as complete response (CR) (e.g., disappearance of all target lesions), partial response (PR) (e.g., at least X % (e.g., 20%, 25%, 30%, 35%, 40%, 45%, 50%, etc.) decrease in tumor size (e.g., sum of diameters of the target lesions), or stable disease (SD) (e.g., neither sufficient shrinkage to quality as a partial response (PR) nor sufficient increase to quality for a progressive disease (PD). Objective response criteria for patients with solid tumors can be assessed using the Response Evaluation Criteria in Solid Tumors (RECIST) protocol (e.g., RECIST 1.0 or RECIST 1.1).

Disease control rate: the number of participants that achieve either a complete response (CR), a partial response (PR), or a stable disease (SD) indication.

Evaluation of best overall response: The best overall response is the best response recorded from the start of the treatment (or randomization) until disease progression/recurrence (taking as reference for PD the smallest measurements recorded since the treatment started). In general, the patient's best response assignment will depend on the achievement of both measurement and confirmation criteria.

Quality of life: as measured by functional health survey (EQ-5D module) or other suitable patient survey or assessment.

Safety and tolerability: as assessed either by a clinician or patient self-reports.

Progression to surgical resection or other intervention (e.g., whether or when the patient required surgical or other treatment interventions following the subject intervention involving local sustained delivery of therapeutic agent(s)).

Tumor marker serum levels: patient samples can be assayed to identify one or more biomarkers related to tumors. Examples include embryonic antigens (e.g., alpha-fetoprotein (AFP and glycoforms AFP-L1, AFP-L2 and AFP-L3)), proteantigens (e.g., heat shock protein (HSP), glypican-3 (GPC3), squamous cell carcinoma antigen (SCCA), golgi protein 73 (GP73), fucosylated GP73 (FC-GP73), tumor-associated glycoprotein 72 (TAG-72), zinc-α2-glycoprotein (ZAG)), enzymes and isozymes (e.g., des-γ-carboxyprothrombin (DCP), γ-glutamyl transferase (GGT), α-I-fucosidase (AFU)), cytokines (e.g., transforming growth factor-β1 (TGF-β1), vascular endothelial growth factor (VEGF)), or genetic biomarkers (e.g., AFP mRNA, MicroRNAs, A-like 1 homolog (DLK-1), hepatoma-associated gene (HTA), villin1 (Vill)). Additional example biomarkers include EpCAM, cancer antigen 125, pteroyl-D-glutamic acid, human epidermal growth factor receptor 2 (HER2), EFGR, inhibit A and B, lactate dehydrogenase, cancer antigen 19-9. The biomarkers listed here are for purposes of illustration only. In various embodiments, any suitable biomarkers, now known or later discovered, can be used to assess the efficacy of a particular treatment.

III. Bladder Cancer

One of most expensive cancers to treat is bladder cancer. When measured as a cumulative lifetime per patient cost, bladder cancer exceeds all other forms of cancer. Bladder cancer affects roughly 2.7 million people worldwide, including nearly 600,000 in the US. NCI estimates that there will be a total of nearly 77,000 new cases and 16,000 deaths due to this disease. Men are about three to four times more likely than women to get bladder cancer, but women are typically diagnosed with more-advanced cancer and have a worse prognosis. Worldwide, bladder cancer is the ninth-most common cancer and the thirteenth deadliest. But in more-developed countries, it poses a bigger threat than many other cancers because fewer new treatment and prevention options have been developed.

Non-muscle-invasive bladder cancer ("NMIBC") represents 70-75% of newly diagnosed cases. NMIBC tumors are confined to the innermost layers of the bladder wall and have not progressed into the deeper muscle layer or beyond. These tumors are currently managed using local resection (transurethral resection of bladder tumors or "TURBT") and local pharmacological intervention. While current treatments often eliminate the existing tumor(s), the disease frequently recurs, requiring lifelong monitoring and repeated intervention. Further, higher-risk tumors that recur or progress despite these therapies often require the patient to undergo radical cystectomy (complete surgical removal of the bladder). Radical cystectomy is a major, life-changing procedure, and many patients are medically unfit and/or unwilling to undergo this surgery.

Unlike many other cancers, there has been no improvement in survival rates for bladder cancer for three decades.

Although TURBT is the gold standard for the initial diagnosis and treatment of NMIBC, intravesical therapy has become an integral component in the management of NMIBC. Intravesical therapy is used to reduce and/or delay the risk for recurrence, prevent progression of disease, and as adjunctive therapy in where diffuse tumor prevent complete tumor resection. Most of the commonly used intravesical therapies for NMIBC can be categorized in 2 groups, immunomodulatory agents and chemotherapeutic agents, primarily based on their mechanism of action. It is used only for these early-stage cancers because medicines given this way mainly affect the cells lining the inside of the bladder, with little to no effect on cells elsewhere. Drugs delivered into the bladder also cannot reach cancer cells in the kidneys, ureters, and urethra, or those that have spread to other organs.

One such immunotherapy drug used to treat bladder cancer is *Bacillus* Calmette-Guerin (BCG), which is a vaccine used to protect against tuberculosis. BCG can both decrease recurrence and retard progression of bladder cancer and is reportedly superior to chemotherapy. Adjuvant therapy must include maintenance therapy for one year in intermediate-risk disease and for up to three years (if tolerable) for high-risk disease to achieve maximal efficacy. Side effects and cost are the major disadvantages of intravesical BCG treatment; consequently, urologists are reluctant to recommend BCG to their patients. It has been reported that only about 50% of patients with intermediate or high-risk NMIBC receive BCG therapy, and adverse effects related to BCG are one of the major obstacles. Therefore, many strategies have been explored to reduce the side effects of BCG, the most studied option being a decrease in dose.

One recent approach is the use of hydrogels as depot formulations on the bladder walls. This enables longer exposure of the urinary tract tissue to existing drugs, as compared to standard intravesical instillation, as they remain attached to the bladder wall even after urine voiding. TCGel® is a novel hydrogel with reverse thermal gelation properties produced by TheraCoat Ltd (Raanana, Israel). When the gel is in contact with urine, it dissolves and gradually releases the drug over a period of 6-8 hours. TCGel® is slowly excreted from the bladder during urination. It is 100% biocompatible and harmless to the body.

The TARIS® system is a controlled release dosage form for use in the bladder. The current design uses a dual-lumen silicone tube, which contains a solid drug core in one lumen and a super elastic wire form in the other to impart shape. The system uses passive delivery principles to continuously release drug in the bladder over weeks to months. However, many patients find the device uncomfortable, and administration of the drug must occur often.

A. Example Depots for Treating Bladder Cancer

According to some embodiments, for example as shown in FIGS. 53-57, the present technology includes depots 100 for treating bladder cancer via sustained, controlled release of a therapeutic agent to a patient. The depot may comprise a therapeutic region comprising a therapeutic agent, and a control region comprising a polymer and a releasing agent mixed with the polymer. the therapeutic agent comprising at least a chemotherapeutic agent. The releasing agent may be configured to dissolve when the depot is placed in vivo to form diffusion openings in the control region. The depot 100 may be configured to be implanted at a treatment site proximate a bladder of the patient and, while implanted, release the chemotherapeutic agent at the treatment site for a period of time that is no less than 7 days.

In some embodiments, the depot is configured to be positioned adjacent a wall of the bladder. In some embodiments, the depot is configured to be positioned adjacent a wall of the bladder and release the chemotherapeutic agent to treat a tumor at a thickness of the bladder wall corresponding to one or more of the urothelium, lamina propria, muscle, fat, and peritoneum.

The present technology includes a depot for treating bladder cancer via sustained, controlled release of a therapeutic agent to a patient, the depot comprising a therapeutic region comprising a therapeutic agent, the therapeutic agent comprising at least a chemotherapeutic agent, a control region comprising a polymer and a releasing agent mixed with the polymer, wherein the releasing agent is configured to dissolve when the depot is placed in vivo to form diffusion openings in the control region, wherein the depot is configured to be implanted at a treatment site proximate a bladder of the patient and, while implanted, release the chemotherapeutic agent at the treatment site for a period of time that is no less than 7 days.

In some embodiments, the depot is configured to self-expand into apposition with an inner surface of the bladder wall when released from a delivery device.

In some embodiments, the depot is configured to self-expand into apposition with a tumor at an inner surface of the bladder wall when released from a delivery device.

In some embodiments, the depot contains at least one opening extending therethrough such that, if positioned over the opening to the urethra within the bladder, the depot will not substantially block flow from an interior region of the bladder into the urethra.

In some embodiments, the depot has a preset shape such that, when released from a delivery device, the depot assumes the preset shape. preset shape that is curved.

In some embodiments, the depot has a first region and a second region, each extending longitudinally and coextensive with one another over all or a portion of their respective lengths, the first region having a first elasticity and the second region having a second elasticity less than the first elasticity.

In some embodiments, the depot has been stretched beyond the elastic hysteresis point of the second region such that, when released from a delivery device, the depot transitions from a straightened state to a curved state in which the second region pulls the depot into the curved shape.

In some embodiments, the depot has a first region and a second region, each extending longitudinally and coextensive with one another over all or a portion of their respective lengths, the first region being more hydrophilic than the second region.

In some embodiments, when the depot is released from a delivery device, the depot transitions from a straightened state to a curved state in which the second region pulls the depot into the curved shape.

In some embodiments, the depot includes an axial centerline, a first region sharing the axial centerline, and a second region surrounded by the first region and having an axial centerline offset from the axial centerline of the depot, each of the first and second regions extending longitudinally and coextensive with one another over all or a portion of their respective lengths, and wherein the first region is more elastic or more hydrophilic than the second region such that the depot is biased towards a curved shape.

In some embodiments, the depot comprises an impermeable base region surrounding all or a portion of one or both of the control region and the therapeutic region such that, when the depot is positioned at the treatment site, the chemotherapeutic agent is selectively released in a direction away from the base region.

In some embodiments, the depot comprises an elongated polymer strip having a length between its longitudinal ends and a width between lateral edges, the length greater than the width, and wherein the depot has a preset shape in an expanded configuration in which the strip is curled about an axis with the width of the strip facing the axis, thereby forming a ring-like shape.

In some embodiments, the chemotherapeutic agent is at least one of epirubicin, doxorubicin, mitomycin C, gemcitabine, and docetaxel.

In some embodiments, the polymer includes a bioresorbable polymer. In some embodiments, the polymer includes a non-bioresorbable polymer.

In some embodiments, the polymer is a first polymer, and wherein the therapeutic region comprises a second polymer.

In some embodiments, the first and/or second polymer includes a bioresorbable polymer. In some embodiments, the first and/or second polymer includes a non-bioresorbable polymer. In some embodiments, the first and/or second polymer includes thermoplastic polyurethane. In some embodiments, the first and/or second polymer includes ethyl vinyl acetate. In some embodiments, the first polymer is non-bioresorbable and the second polymer is bioresorbable. In some embodiments, the first and second polymers are the same.

In some embodiments, the therapeutic region is configured to release the chemotherapeutic agent continuously at a constant rate for the period of time. In some embodiments, the therapeutic region is configured to release the chemotherapeutic agent continuously at a rate that increases over time.

In some embodiments, the period of time is no less than 2 weeks, no less than 3 weeks, no less than 4 weeks, no less than 5 weeks, no less than 6 weeks, no less than 7 weeks, no less than 8 weeks, no less than 2 months, no less than 3 months, no less than 4 months, no less than 6 months, no less than 7 months, no less than 8 months, no less than 9 months, no less than 10 months, no less than 12 months, no less than 1 year.

In some embodiments, the chemotherapeutic agent includes mitomycin C, and the depot is configured to release mitomycin at a continuous rate for at least 3 weeks, for at least 4 weeks, for at least 5 weeks, for at least 6 weeks, for at least 7 weeks, or for at least 8 weeks.

In some embodiments, the chemotherapeutic agent includes mitomycin, and the therapeutic region contains no less than 120 mg, 150 mg, 180 mg, 210 mg, 240 mg, 270 mg, 300 mg, 330 mg, 360 mg, 390 mg, 420 mg, 450 mg, 480 mg, or 510 mg of mitomycin.

In some embodiments, the chemotherapeutic agent includes gemcitabine, and the depot is configured to release gemcitabine at a continuous rate for at least 3 weeks, for at least 4 weeks, for at least 5 weeks, for at least 6 weeks, for at least 7 weeks, or for at least 8 weeks.

In some embodiments, the chemotherapeutic agent includes gemcitabine, and the therapeutic region contains no less than 200 mg, 300 mg, 400 mg, 500 mg, 600 mg, 700 mg, 800 mg, 900 mg, 1000 mg, 1100 mg, 1200 mg, 1300 mg, 1400 mg, 1500 mg, 1600 mg, 1700 mg, 1800 mg, 1900 mg, 2000 mg, 2100 mg, 2200 mg, 2300 mg, 2400 mg, 2500 mg, 2600 mg, 2700 mg, 2800 mg, 2900 mg, or 3000 mg of gemcitabine.

In some embodiments, the period of time is a first period of time, and wherein the therapeutic agent further comprises an immunotherapeutic agent and the depot is configured to release the immunotherapeutic agent for a second period of time.

In some embodiments, the first period of time is longer than the second period of time. In some embodiments, the second period of time is shorter than the first period of time. In some embodiments, the first and second periods of time are different. In some embodiments, the first and second periods of time are the same.

In some embodiments, the depot is configured to begin releasing a therapeutic dosage of the chemotherapeutic agent and a therapeutic dosage of the immunotherapeutic agent at substantially the same time.

In some embodiments, the depot is configured to begin releasing a therapeutic dosage of the chemotherapeutic agent at a first time after implantation, and wherein the depot is configured to begin releasing a therapeutic dosage of the immunotherapeutic agent at a second time after implantation, the second time different than the first time. In some embodiments, the second time is 1 day, 2, days, 3 days, 4 days, 5 days, 6 days, one week, two weeks, three weeks, four weeks, five weeks, six weeks, seven weeks, or eight weeks before the first time. In some embodiments, the second time is 1 day, 2, days, 3 days, 4 days, 5 days, 6 days, one week, two weeks, three weeks, four weeks, five weeks, six weeks, seven weeks, or eight weeks after the first time.

In some embodiments, the immunotherapeutic agent includes *bacillus* Calmette-Guerin ("BCG").

In some embodiments, the therapeutic region includes a first portion and a second portion, wherein the first portion comprises the chemotherapeutic agent and the second portion comprises the immunotherapeutic agent.

In some embodiments, the first portion is closer to an exterior surface of the depot than the second portion.

In some embodiments, the first portion is farther from an exterior surface of the depot than the second portion.

In some embodiments, the depot is configured to release the immunotherapeutic agent continuously over the period of time.

In some embodiments, the therapeutic region is configured to release the immunotherapeutic agent intermittently over the period of time.

In some embodiments, the depot is configured to release the chemotherapeutic agent at a first rate and the immunotherapeutic agent at a second rate. In some embodiments, the first rate is the same as the second rate. In some embodiments, the first rate is different than the second rate. In some embodiments, the first rate is greater than the second rate. In some embodiments, the first rate is less than the second rate.

In some embodiments, the depot includes a securing portion configured to adhere to an inner surface of the bladder wall.

In some embodiments, a surface of the depot comprises a positively-charged polymer configured to secure the depot to the bladder wall.

In some embodiments, the depot comprises a thermosensitive gel and/or a hydrogel with reverse thermal gelation.

In some embodiments, the depot includes a fixation portion configured to penetrate at least a portion of the thickness of the bladder wall, thereby securing the depot at the bladder wall.

In some embodiments, the depot includes an anchor member coupled to the therapeutic region, control region, and/or base region, and wherein the anchor member is configured to self-expand into apposition with at least a portion of the inner surface of the bladder wall, thereby securing the depot at or within the bladder.

B. Routes of Administration and Clinical Endpoints

Any of the depot embodiments and delivery approaches described can be used for local sustained delivery of therapeutic agents for treatment of bladder cancer. In various embodiments, treatment of bladder cancers can involve local delivery of one or more therapeutic agents (e.g., via one or more depot(s) of the present technology) administrated using any suitable route. In some embodiments, one or more depots can be delivered into the bladder, for example through trans-urethral access. Optionally, such access can include using a cystoscope.

Any suitable therapeutic agents, whether delivered locally (e.g., via one or more depots as described herein), systemically (e.g., via intravenous delivery or otherwise), or both, can be used for treatment of bladder cancers. Example therapeutic agents include chemotherapeutics such as mitomycin-C, gemcitabine, thiotepa, cisplatin, doxorubicin, valrubicin, carboplatin, methotrexate, vinblastine, or any combination thereof. In some embodiments, one or more locally delivered therapeutic agents can be used in combination with one or more systemically delivered therapeutic agents and/or in combination with other treatments (e.g., surgery, radiation, etc.). In some embodiments, the systemically delivered therapeutic agents can include any one of the chemotherapeutic agents listed above, as well as targeted agents (e.g., erdafitinib, enfortumab vedotin-ejfv), or immunotherapeutics (e.g., local immunotherapeutics such as BCG or interferon or systemic immunotherapeutics such as immune checkpoint inhibitors (e.g., atezolizumab, nivolumab, avelumab, durvalumab, pembrolizumab)).

Treatment of bladder cancers as disclosed herein can be utilized to achieve one or more endpoints. In various embodiments, such endpoints can involve clinical measures for a particular patient or a population of patients (e.g., a population undergoing a clinical trial). Examples of such endpoints include: (1) overall survival (e.g., as measured in time from treatment (or randomization) to death due to any cause); (2) progression free survival (e.g., as measured measure from the date of start of treatment to the date of the first documented progression (PD) or death due to any cause, in which progressive disease (PD) is defined as at least a 20% increase in the sum of the diameters of target lesions); (3) overall/objective response rate (e.g., providing a score of complete response (CR): disappearance of all target lesions; partial response (PR): at least X % (20%, 25%, 30%, 35%, 40%, 45%, 50%) decrease in the sum of the diameters of target lesions; or stable disease (SD): neither sufficient shrinkage to qualify for PR nor sufficient increase to qualify for PD); (4) disease control rate: the number of participants that achieve either a CR, PR or SD; (5) quality of Life (QoL) as measured by functional health survey (EQ-5D module); (6): safety and tolerability; (7) tumor tissue biomarkers (e.g., PD-L1, CD8 expression), or (8) non-urinary tract recurrence free survival (NURFS), which can measure a time from randomization to time of first occurrence of a NURFS event evaluated via radiographic analysis. Any one or any combination of these endpoints can be utilized to assess and/or establish efficacy of treatment of bladder cancer via depots of the present technology, whether used alone or in combination with one or more other treatments.

IV. Malignant Pleural Effusion (MPE)

MPE is the infiltration of cancer cells into the pleural tissue surrounding the lung. It occurs in 15% of lung cancer patients but is secondary to other cancers, including breast, ovarian, prostate and lymphoma. MPE is an indicator of advanced stage cancer with average mortality 4-7 months from diagnosis. Quality of life is severely impaired due to dyspnea caused by fluid buildup in the pleural cavity. Given the advanced stage of the cancer, treatment is palliative and consists of frequent draining of the pleural cavity via thoracentesis (or other tube/catheter means) and/or pleurodesis, which is the sealing of the pleural space. Treating the underlying malignancy through surgery, radiation, and/or systemic drug therapy may also help resolve the MPE. The pleural cavity represents a sequestered local environment, where there are challenges in achieving local effect from systemic administration of drug.

Figure 58:
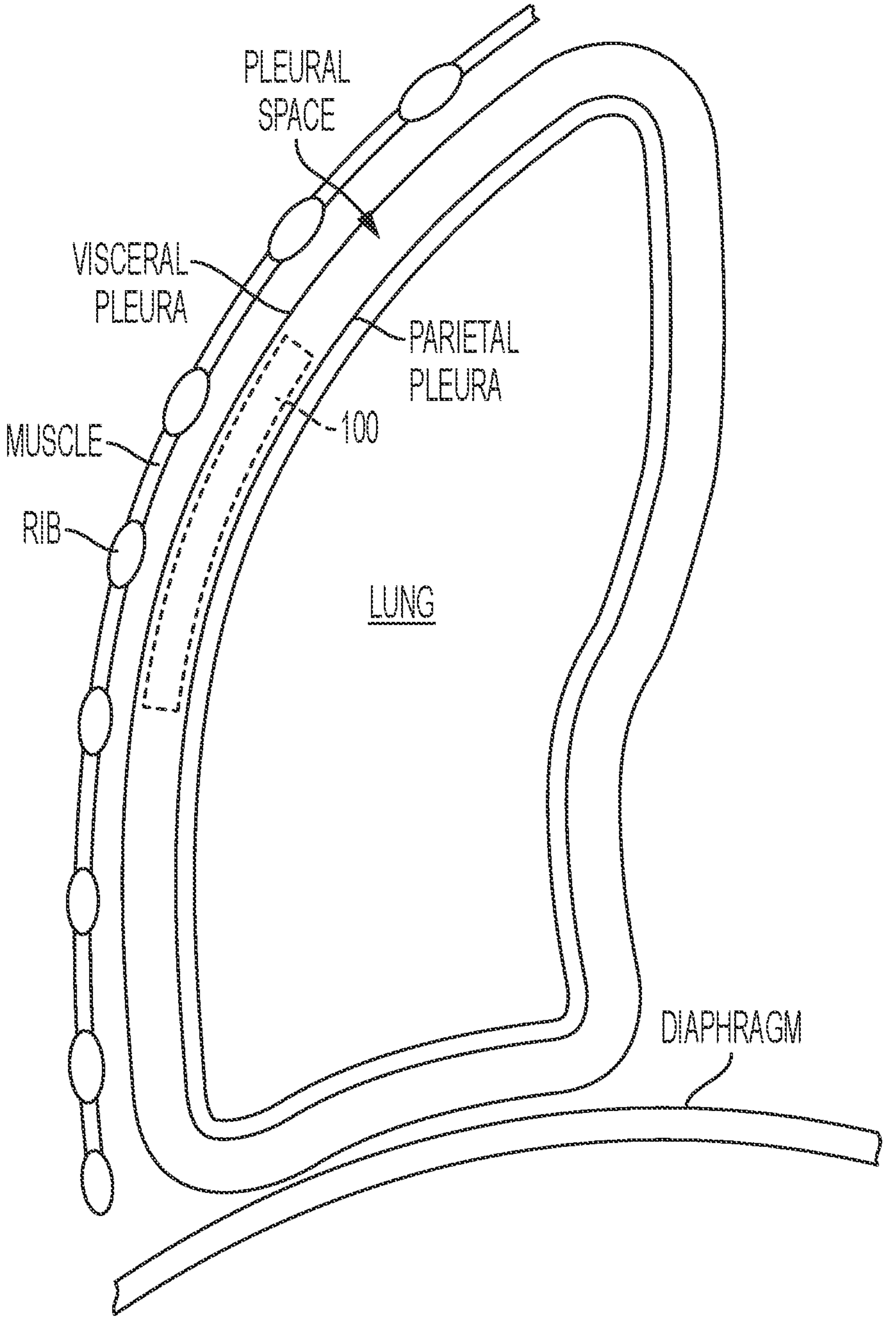
FIGS. 58 and 59 are schematic side cross-sectional views showing one or more depots of the present technology positioned at or near a pleural space of a mammalian patient.
Figure 59:
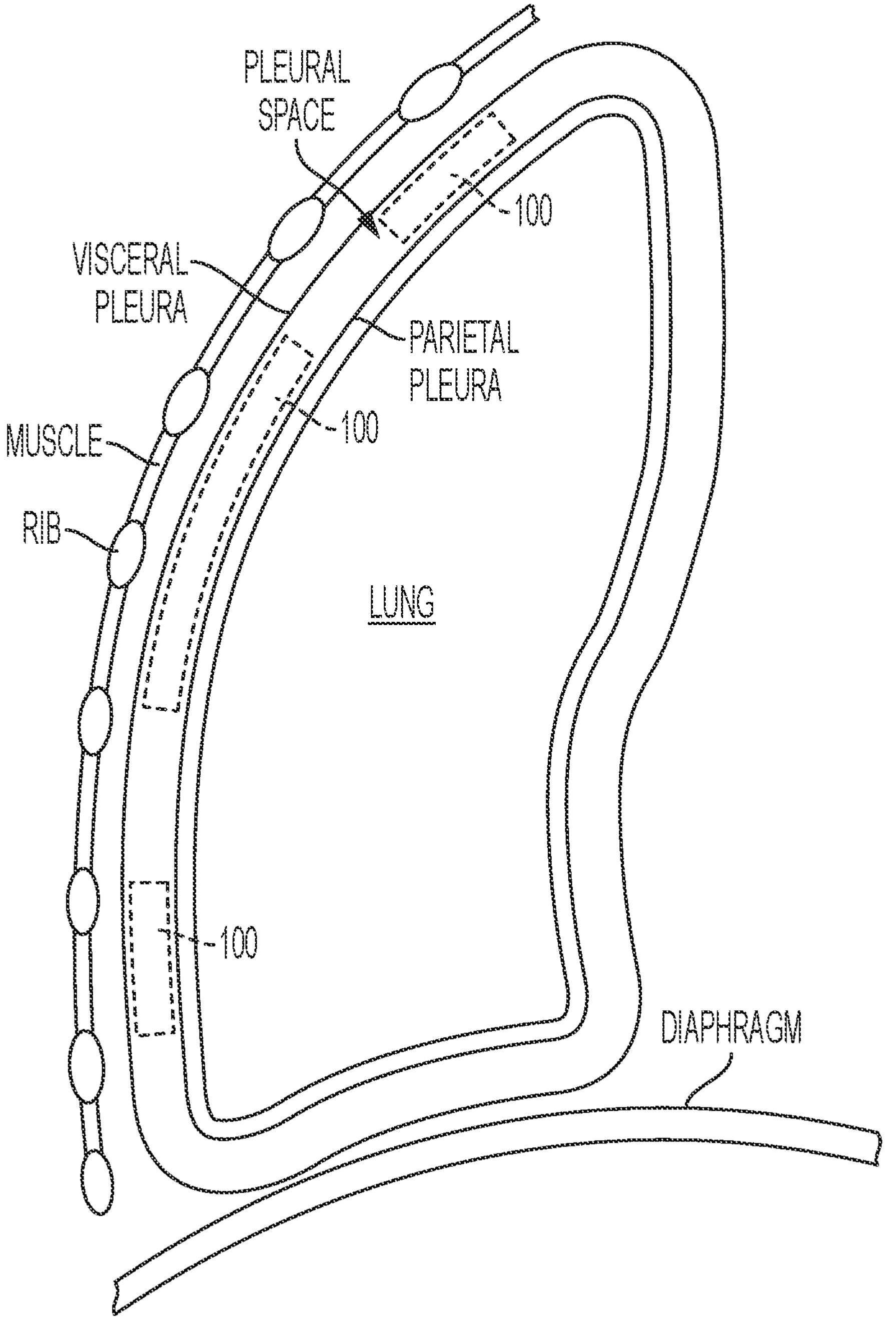
Figure 60:
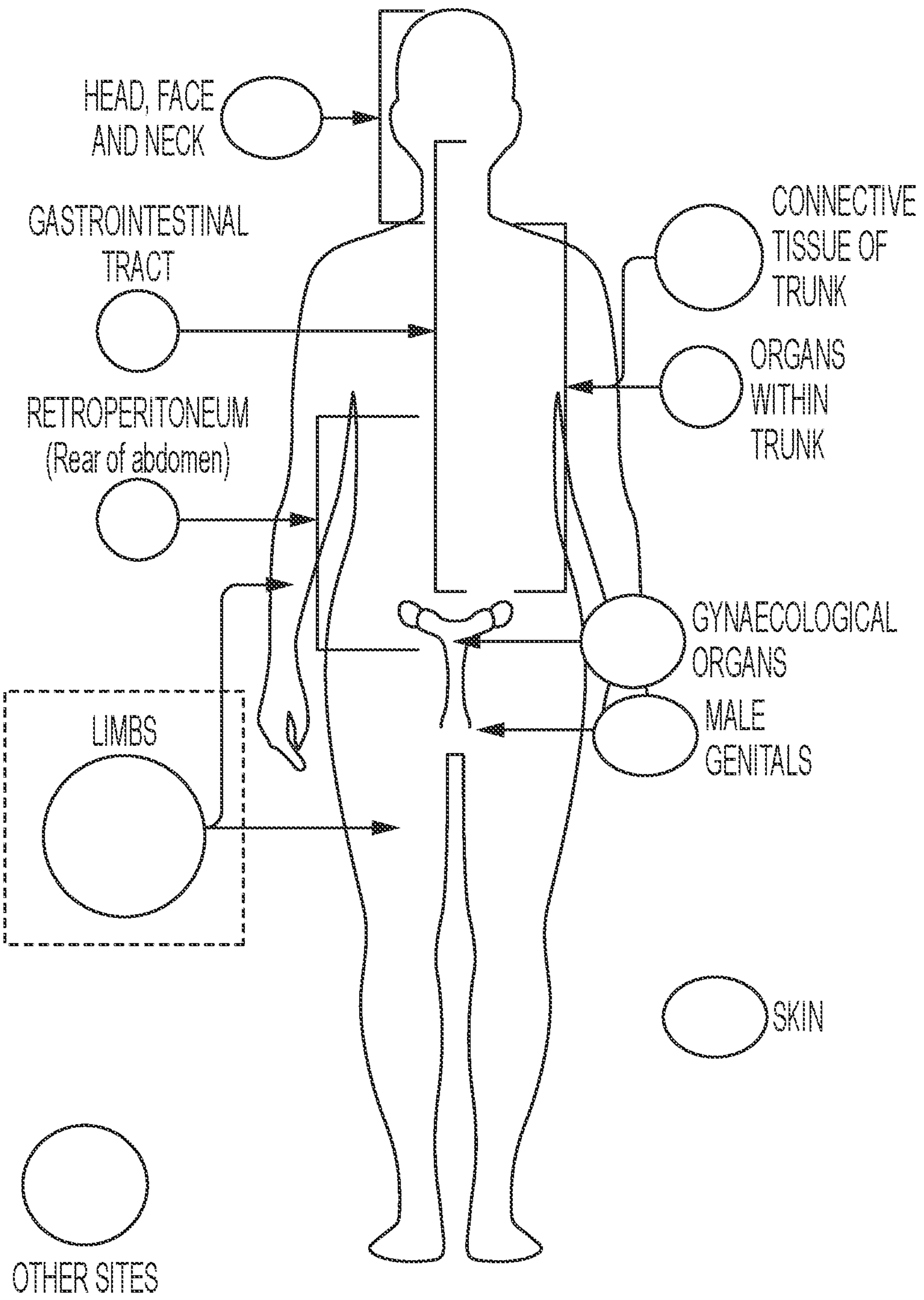
FIG. 60 is a schematic illustration of a human patient showing common anatomical sites for soft tissue sarcoma.

According to some embodiments, for example as shown in FIGS. 58 and 59, the present technology comprises depots for treating MPE via sustained, controlled release of a therapeutic agent to a patient. The depot may comprise a therapeutic region comprising a therapeutic agent, and a control region comprising a polymer and a releasing agent mixed with the polymer. The releasing agent is configured to dissolve when the depot is placed in vivo to form diffusion openings in the control region. The therapeutic agent may comprise at least a chemotherapeutic agent. The depot may be configured to be implanted at a treatment site proximate a pleural membrane of the patient and, while implanted, release the chemotherapeutic agent at the treatment site for a period of time that is no less than 7 days.

In some embodiments, the depot has a low-profile state for delivery through a delivery device to the treatment site and a deployed state for positioning proximate the pleural membrane.

In some embodiments, the depot is a flexible, thin film.

In some embodiments, the depot is rolled upon itself in the low-profile state and unrolls when released from a delivery device at the treatment site.

In some embodiments, the depot has a preset shape that is curved.

In some embodiments, the chemotherapeutic agent is at least one of cisplatin, pemetrexed sodium, carboplatin, irinotecan, and/or liposomal irinotecan.

In some embodiments, the therapeutic region is configured to release the chemotherapeutic agent intermittently over the period of time.

In some embodiments, the therapeutic region is configured to release the chemotherapeutic agent continuously over the period of time.

In some embodiments, the period of time is at least 4 weeks, and wherein the therapeutic region is configured to release a dose of the chemotherapeutic agent once a week or once every 2 weeks over the period of time.

In some embodiments, the period of time is at least 8 weeks, and wherein the therapeutic region is configured to release a dose of the chemotherapeutic agent once every week or once every 2 weeks over the period of time.

In some embodiments, the period of time is at least 12 weeks, and wherein the therapeutic region is configured to release a dose of the chemotherapeutic agent once every week, every 2 weeks, or every 3 weeks over the period of time.

In some embodiments, the period of time is at least 16 weeks, and wherein the therapeutic region is configured to release a dose of the chemotherapeutic agent once every week, every 2 weeks, or every 4 weeks over the period of time.

In some embodiments, the chemotherapeutic agent includes cisplatin, and wherein each dose of cisplatin is less than or equal to 100 μg/ml.

In some embodiments, the chemotherapeutic agent includes pemetrexed sodium, and wherein each dose of the pemetrexed sodium is less than or equal to 500 mg/m2.

In some embodiments, the chemotherapeutic agent includes irinotecan or liposomal irinotecan, and wherein each dose of the irinotecan or liposomal irinotecan is less than or equal to 200 mg/m2.

In some embodiments, the chemotherapeutic agent includes irinotecan or liposomal irinotecan, and wherein each dose of the irinotecan or liposomal irinotecan is less than or equal to 120 mg/m2.

In some embodiments, the period of time is no less than 2 weeks, no less than 3 weeks, no less than 4 weeks, no less than 5 weeks, no less than 6 weeks, no less than 7 weeks, no less than 8 weeks, no less than 2 months, no less than 3 months, no less than 4 months, no less than 6 months, no less than 7 months, no less than 8 months, no less than 9 months, no less than 10 months, no less than 12 months, no less than 1 year.

In some embodiments, the depot has a preset shape such that, when released from a delivery device, the depot assumes the preset shape.

In some embodiments, the therapeutic agent further comprises a sclerosant.

In some embodiments, the sclerosant comprises at least one of talc and/or doxycycline.

In some embodiments, at least prior to implantation, the portion of the therapeutic region containing the sclerosant is closer to an exterior surface of the depot than the portion of the therapeutic region containing the chemotherapeutic agent.

In some embodiments, the depot is configured to release all of the sclerosant within less than a day.

In some embodiments, the depot is configured to release all of the sclerosant within less than 1 hour, 2 hours, 3 hours, 4 hours, 5 hours, 6 hours, 12 hours, 16 hours, or 18 hours.

In some embodiments, the sclerosant is talc or a talc slurry, and wherein the therapeutic region contains 3-10 g, 4-8 g, about 2 g, 2-3 g, 3-4 g, 4-5 g, 5-6 g, 6-7 g, 7-8 g, 8-9 g, 9-10 g, about 3 g, about 4 g, about 5 g, about 6 g, about 7 g, about 8 g, about 9 g, or about 10 g of talc or a talc slurry.

In some embodiments, the sclerosant is doxycycline, and wherein the therapeutic region contains at 200-800 mg, 300-700 mg, 400-600 mg, about 300 mg, about 400 mg, about 500 mg, about 600 mg, about 700 mg, or about 800 mg of doxycycline.

In some embodiments, the therapeutic agent further comprises an analgesic.

In some embodiments, at least prior to implantation, the portion of the therapeutic region containing the analgesic is closer to an exterior surface of the depot than the portion of the therapeutic region containing the chemotherapeutic agent.

In some embodiments, at least prior to implantation, the portion of the therapeutic region containing the sclerosant is closer to an exterior surface of the depot than the portion of the therapeutic region containing the chemotherapeutic agent and the portion containing the analgesic, and wherein the portion containing the analgesic is closer to the exterior surface of the portion of the therapeutic region containing the chemotherapeutic agent.

In some embodiments, the therapeutic agent further comprises an immunotherapeutic agent.

In some embodiments, the therapeutic agent further comprises a targeted therapy.

In some embodiments, the therapeutic region includes a first portion and a second portion, wherein the first portion comprises the chemotherapeutic agent and the second portion comprises the sclerosant.

In some embodiments, the first portion is closer to an exterior surface of the depot than the second portion.

In some embodiments, the first portion is farther from an exterior surface of the depot than the second portion.

In some embodiments, the depot is configured to release the chemotherapeutic agent at a first rate and the sclerosant at a second rate.

In some embodiments, the first rate is the same as the second rate.

In some embodiments, the first rate is different than the second rate.

In some embodiments, the first rate is greater than the second rate.

In some embodiments, the first rate is less than the second rate.

In some embodiments, the depot is configured to be positioned adjacent a chest wall of the patient.

In some embodiments, the depot is configured to be positioned between a chest wall and a pleural membrane.

In some embodiments, the depot is configured to be positioned between a visceral pleura and a parietal pleura.

In some embodiments, the depot is configured to be positioned between at least partially within the pleural space.

In some embodiments, the depot is configured to be delivered through a tube having an external diameter of from about 3 mm to about 7 mm or of from about 4 mm to about 6 mm.

In some embodiments, the depot comprises a tubular member having an external diameter of from about 6 Fr to about 40 Fr.

Any of the depot embodiments and delivery approaches described can be used for local sustained delivery of therapeutic agents for treatment of MPE. In various embodiments, treatment of MPE can involve local delivery of one or more therapeutic agents (e.g., via one or more depot(s) of the present technology) administrated using any suitable route. For example, treatment of MPE can include intrapleural placement of depots for localized, sustained release of therapeutic agents into the pleural cavity. This could be as a standalone local treatment, adjuvant to surgical debulking of primary tumor(s) or combined with non-local treatment (e.g., radiation, systemic drug therapy). The implanted depot may also have the added function of occupying space in the pleural cavity to prevent the buildup of fluid. In various embodiments, the therapeutic indication may be for MPE or may be for primary malignancies such as lung cancer, breast cancer, ovarian cancer, prostate cancer, or lymphoma.

For treatment, one or more depots can be delivered into the pleural cavity via thoracoscopic access, percutaneous access, or surgical access. Thoracoscopic access can include needle injection or implantation as part of a video-assisted thoracic surgery (VATS) or thoracentesis. Percutaneous access can include direct injection or insertion via a needle or trocar catheter into the cavity and/or surrounding tissue using image guidance (e.g., CT, MR, ultrasound). Surgical access can include open surgical implantation or needle injection as part of a cytoreductive procedure (e.g., lobectomy, wedge resection, etc.)

Any suitable therapeutic agents, whether delivered locally (e.g., via one or more depots as described herein), systemically (e.g., via intravenous delivery or otherwise), or both, can be used for treatment of MPE. Example therapeutic agents include chemotherapeutic agents (e.g., mitomycin-C, cisplatin, docetaxel, paclitaxel, or tetracycline), immunotherapeutics (e.g., interferon (α2b, IL-2), tumor infiltrating lymphocytes (TIL), monoclonal antibodies (tocilizumab), trifunctional antibodies (e.g., catumaxomab, ertumaxomab)), or any combinations thereof.

In some embodiments, one or more locally delivered therapeutic agents can be used in combination with one or more systemically delivered therapeutic agents and/or in combination with other treatments (e.g., surgery, radiation, etc.). In some embodiments, the systemically delivered therapeutic agents can include any one of the chemotherapeutic or immunotherapeutic agents listed above.

Treatment of MPE as disclosed herein can be utilized to achieve one or more endpoints. In various embodiments, such endpoints can involve clinical measures for a particular patient or a population of patients (e.g., a population undergoing a clinical trial). Examples of such endpoints include: (1) puncture-free survival (e.g., time to next therapeutic puncture (thoracentesis) or death; (2) time to next therapeutic puncture; (3) overall survival (e.g., as measured in time from treatment (or randomization) to death due to any cause); (2) overall/objective response rate (e.g., providing a score of complete response (CR) (relief of symptoms related to the effusion with absence of fluid reaccumulation on chest radiographs); or partial response (PR) (diminution of dyspnea related to the effusion, with partial reaccumulation of fluid (<50% of the initial radiographic evidence of fluid)). Additional endpoint examples include patient-related outcome measures such as reduction in time spent in hospital, palliation of symptoms including dyspnea, improvement in quality of life (e.g., as measured by survey or other patient input, e.g. FACIT-TA, FACIT-PAL).

Any one or any combination of these endpoints can be utilized to assess and/or establish efficacy of treatment of MPE via depots of the present technology, whether used alone or in combination with one or more other treatments.

V. Soft Tissue Sarcoma

Sarcomas are rare cancers of the bone and connective tissue, such as bone, fat, muscle, nerves, fibrous tissue, tendons, ligaments, blood vessels, and deep skin tissue. Soft tissue sarcoma is responsible for 15,000 new cases/year in the United States, 6,500 deaths, and 500,000 new cases/year worldwide. At least 25% of sarcomas, regardless of their source, occur in the legs. The current treatment is Isolated Limb Infusion (ILI), which is a regional technique which involves temporarily isolating the blood supply to an extremity to concentrate chemotherapy treatment at that location. While this method can help shrink tumors, it is unclear whether it prolongs life relative to standard chemotherapy treatment. Accordingly, improved methods for treating soft tissue sarcomas are needed.

A. Example Depots for Treating Soft Tissue Sarcoma (STS)

The depots of the present technology may be used as an adjunctive therapy to systemic administration of chemotherapeutic agents to improve survival and decrease local recurrence. In some cases, the depot may comprise a non-directional wafers configured to be applied at time of surgical resection. For example, the depot may be configured to be laid in the wound cavity.

Several embodiments of the present technology include a depot for treating STS via sustained, controlled release of a therapeutic agent to a patient, the depot comprising a therapeutic region comprising a chemotherapeutic agent; a control region comprising a bioresorbable polymer and a releasing agent mixed with the polymer, wherein the releasing agent is configured to dissolve when the depot is placed in vivo to form diffusion openings in the control region; and wherein the depot is configured to be implanted at a treatment site proximate an STS of the patient and, while implanted, release the chemotherapeutic agent at the treatment site at a first time and a second time, the second time being a period of time after the first time of no less than 7 days.

In some embodiments, the depot is a flexible, thin film.

In some embodiments, the chemotherapeutic agent comprises a first chemotherapeutic agent and a second chemotherapeutic agent, wherein the depot is configured to release the first chemotherapeutic agent at the first time and the second chemotherapeutic agent at the second time. In some embodiments, the depot is configured to release the first chemotherapeutic agent at a consistent, continuous rate that extends from the first time to after the second time.

In some embodiments, the chemotherapeutic agent is at least one of doxorubicin, imatinib, sirolimus, sunitinib, sorafenib, rapamycin, trabectedin, eribulin, gemcitabine, cediranib, rapamycin, olaratumab, ifosfamide, paclitaxel, regoraferib, and/or pazopanib.

In some embodiments, the chemotherapeutic agent includes pazopanib, and wherein the depot is configured to release the pazopanib continuously over the period of time. In some embodiments, the chemotherapeutic agent includes doxorubicin, and wherein the depot is configured to release the doxorubicin continuously over the period of time. In some embodiments, the chemotherapeutic agent includes trabectedin, and wherein the depot is configured to release the trabectedin intermittently over the period of time. In some embodiments, the chemotherapeutic agent includes eribulin, and wherein the depot is configured to release the eribulin intermittently over the period of time. In some embodiments, the chemotherapeutic agent includes doxorubicin and olaratumab.

In some embodiments, the period of time is 2, 3, 4, 5, 6, 7, or 8 weeks, and wherein the chemotherapeutic agent is delivered once a week throughout the period of time.

In some embodiments, the period of time is 2, 3, 4, 5, 6, 7, or 8 weeks and the chemotherapeutic agent is paclitaxel and/or liposomal doxorubicin, and wherein the depot is configured to deliver the chemotherapeutic agent once a week throughout the period of time.

In some embodiments, the treatment site is a gastrointestinal stromal sarcoma of the patient and the period of time is 2, 3, 4, 5, 6, 7, or 8 weeks and the chemotherapeutic agent is imatinib and/or sunitinib, and wherein the depot is configured to deliver the chemotherapeutic agent once a week throughout the period of time.

In some embodiments, the treatment site is a dermatofibrosarcoma of the patient and the period of time is 2, 3, 4, 5, 6, 7, or 8 weeks and the chemotherapeutic agent is imatinib, and wherein the depot is configured to deliver the chemotherapeutic agent to the treatment site once a week throughout the period of time.

In some embodiments, the treatment site is a perivascular epithelioid cell tumor of the patient and the period of time is 2, 3, 4, 5, 6, 7, or 8 weeks and the chemotherapeutic agent is rapamycin, and wherein depot is configured to deliver the chemotherapeutic agent to the treatment site once a week throughout the period of time.

In some embodiments, the treatment site is an alveolar soft part sarcoma of the patient and the period of time is 2, 3, 4, 5, 6, 7, or 8 weeks and the chemotherapeutic agent is sunitinib, and wherein the depot is configured to deliver the chemotherapeutic agent to the treatment site once a week throughout the period of time.

In some embodiments, the treatment site is a leiomyosarcoma of the patient and the period of time is 2, 3, 4, 5, 6, 7, or 8 weeks and the chemotherapeutic agent is rapamycin, and wherein the depot is configured to deliver the chemotherapeutic agent to the treatment site once a week throughout the period of time.

In some embodiments, the treatment site is a leiomyosarcoma or a liposarcoma of the patient and the period of time is 2, 3, 4, 5, 6, 7, or 8 weeks, and the chemotherapeutic agent is trabectedin, and wherein the depot is configured to deliver the chemotherapeutic agent to the treatment site once a week throughout the period of time.

In some embodiments, the therapeutic region is configured to release the chemotherapeutic agent continuously or intermittently over the period of time.

In some embodiments, the period of time is at least 4 weeks, and wherein the therapeutic region is configured to release a dose of the chemotherapeutic agent once a week or once every 2 weeks over the period of time.

In some embodiments, the period of time is at least 8 weeks, and wherein the therapeutic region is configured to release a dose of the chemotherapeutic agent once every week or once every 2 weeks over the period of time.

In some embodiments, the period of time is at least 12 weeks, and wherein the therapeutic region is configured to release a dose of the chemotherapeutic agent once every week, every 2 weeks, or every 3 weeks over the period of time.

In some embodiments, the period of time is at least 16 weeks, and wherein the therapeutic region is configured to release a dose of the chemotherapeutic agent once every week, every 2 weeks, or every 4 weeks over the period of time.

In some embodiments, the period of time is no less than 2 weeks, no less than 3 weeks, no less than 4 weeks, no less than 5 weeks, no less than 6 weeks, no less than 7 weeks, no less than 8 weeks, no less than 2 months, no less than 3 months, no less than 4 months, no less than 6 months, no less than 7 months, no less than 8 months, no less than 9 months, no less than 10 months, no less than 12 months, no less than 1 year.

In some embodiments, the chemotherapeutic agent comprises a first chemotherapeutic agent and a second chemotherapeutic agent different than the first chemotherapeutic agent. In some embodiments, the first chemotherapeutic agent comprises doxorubicin and the second chemotherapeutic agent includes at least one of trabectedin, pazopanib, and/or eribulin. In some embodiments, the depot is configured to release the first chemotherapeutic agent continuously and the second chemotherapeutic agent intermittently over the period of time. In some embodiments, the depot is configured to release the first chemotherapeutic agent at a first rate and the second chemotherapeutic agent at a second rate. In some embodiments, the first rate is the same as the second rate, the first rate is different than the second rate, the first rate is greater than the second rate, or the first rate is less than the second rate.

In some embodiments, the treatment site is at a head, neck, and/or face of the patient, at a gastrointestinal tract of the patient, at a retroperitoneum of the patient, at a limb of the patient, at an arm of the patient, at a leg of the patient at the skin of the patient at a gynaecological organ of the patient, at a genital region of the patient at an organ within a trunk region of the patient, and at connective tissue within a trunk region of the patient.

In some embodiments, the depot is configured to be positioned in direct contact with connective tissue of the patient to deliver the chemotherapeutic agent to the connective tissue.

In some embodiments, the depot is configured to be positioned in direct contact with soft tissue of the patient to deliver the chemotherapeutic agent to the soft tissue.

In some embodiments, the depot is configured to be positioned in direct contact with fat of the patient to deliver the chemotherapeutic agent to the fat.

In some embodiments, the depot is configured to be positioned in direct contact with muscle of the patient to deliver the chemotherapeutic agent to the muscle.

In some embodiments, the depot is configured to be positioned in direct contact with deep skin tissue of the patient to deliver the chemotherapeutic agent to the deep skin tissue.

In some embodiments, the depot is configured to be positioned in direct contact with a blood vessel of the patient to deliver the chemotherapeutic agent to the blood vessel.

In some embodiments, the depot is configured to be positioned in direct contact with a cartilage of the patient at the treatment site to deliver the chemotherapeutic agent to the cartilage.

In some embodiments, the depot is configured to be positioned in direct contact with a tendon of the patient to deliver the chemotherapeutic agent to the tendon.

In some embodiments, the depot is configured to be positioned in direct contact with a ligament of the patient to deliver the chemotherapeutic agent to the ligament.

In some embodiments, the chemotherapeutic agent is configured to treat an angiosarcoma at the treatment site, an osteosarcoma at the treatment site. an Ewing's sarcoma at the treatment site, a chondrosarcoma at the treatment site, a gastrointestinal stromal tumor at the treatment site, a liposarcoma at the treatment site, a fibrosarcoma at the treatment site, and a hemangioendothelioma at the treatment site.

VI. Head and Neck Cancers

Figure 61:
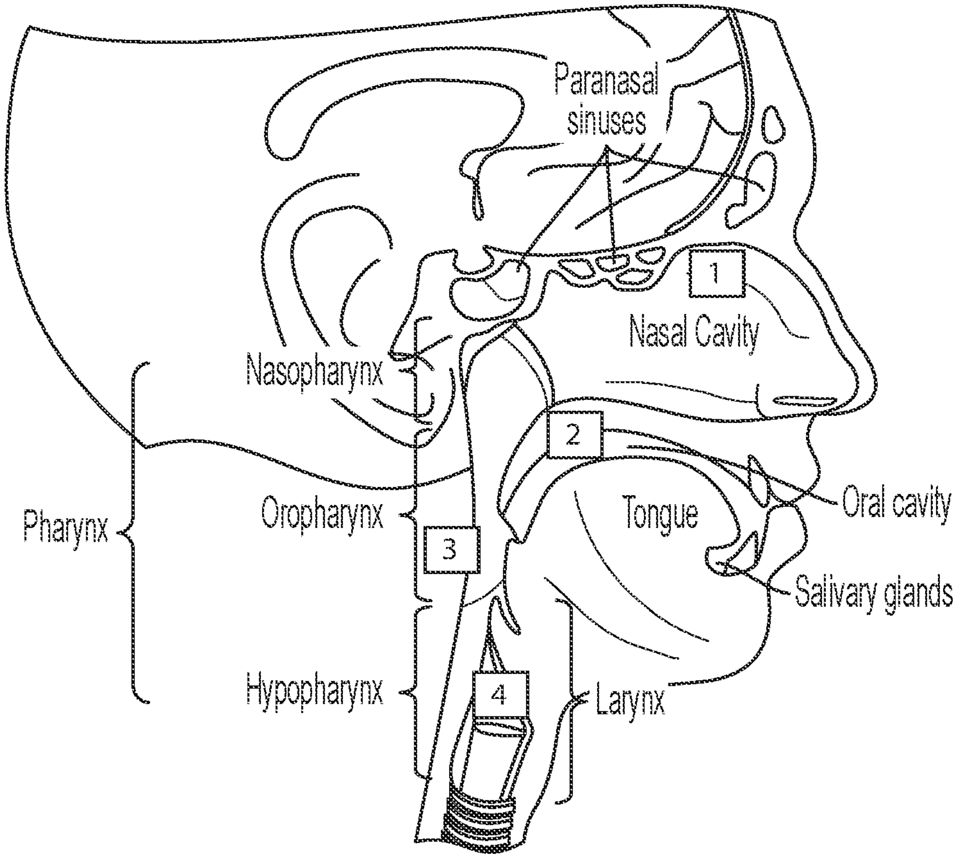
FIG. 61 is a schematic illustration of a head and neck region of a human patient.

Head and neck cancers account for approximately 4% of all cancers in the United States, and are more than twice as common among men as they are among women. Tobacco users are at particularly high risk of developing head and neck cancers. Such cancers typically begin in the squamous cells lining the mucosal surfaces in the upper aerodigestive tract, but may also begin in the salivary glands or other tissue in the head and neck. Head and neck cancers are categorized by the area in which they begin. With reference to FIG. 61, head and neck cancers can begin in the oral cavity (including the lips, jaw, palate, and tongue), pharynx (including the nasopharynx, oropharynx, and hypopharynx), the larynx, the paranasal sinuses and nasal cavity, and the salivary glands on the floor of the mouth near the jawbone.

Current treatments for head and neck cancers include surgery, systemic chemotherapy (e.g., intravenous delivery of chemotherapeutic agents), external radiation therapy (e.g., delivering x-rays to the treatment site using from an externally positioned machine), internal radiation (e.g., insertion of beads, catheters, wires, needles, or other structures that contain a radioactive substance at the treatment site), or any combination of these treatments.

Patients receiving radiation to the head and neck (whether external or internal) may experience a range of undesirable side effects, including redness, irritation, sores in the mouth, dry mouth (xerostomia) or thickened saliva, difficulty swallowing, or nausea. Xerostomia (a dry mouth due to reduce or absent saliva flow) and oral mucositis (OM) are two particularly common and unpleasant conditions associated with radiation therapy of the head and neck.

Xerostomia can result from radiation injury of the salivary gland, and is a common side effect of radiation of the head and neck, especially with concurrent chemotherapy. Current treatments for xerostomia include saliva substitutes (e.g., water or glycerin-based substances), saliva stimulants (e.g., sour sweets, chewing gum), and pilocarpine. Although pilocarpine has been found to be more effective than artificial saliva, its efficacy may not be established until 12 weeks of therapy.

Oral mucositis (OM) can occur when radiation and/or chemotherapy break down the epithelial cells lining the upper aerodigestive tract, leaving the exposed mucosal tissue open to ulceration and infection. This condition affects essentially all head and neck cancer patients receiving concomitant chemoradiotherapy. Symptoms include swollen mouth and gums, sores, bleeding, difficulty swallowing, dryness or burning when eating, white patches or pus on the mouth or tongue, and increased mucus in the mouth. OM can be one of the most debilitating complications of cancer treatments, causing significant pain, nutritional problems due to inability to eat, and an increased risk of infection due to open sores in the patient's mucosa. Treatment of head and neck cancers can be reduced, suspended, or stopped altogether as a result of OM. There are no currently defined strategies for preventing mucosal injury or lessening its severity. Currently available treatments for OM include topical anesthetics (e.g., viscous lidocaine), mucoadhesive coating agents that are applied via oral rinses, and dietary interventions (e.g., bland diet, avoidance of alcohol and coffee). Clinical trials are also evaluating the use of anti-inflammatory compounds for treatment of OM.

Xerostomia, OM, and any undesirable side effects of radiation therapy for head and neck cancer patients can present dose-limiting barriers to effective treatment. In certain cases, radiation and/or chemotherapeutic doses may need to be reduced to lessen the severity of these undesirable side effects. In many cases, patients must suffer these debilitating symptoms throughout the course of treatment, leading to a significant impairment in quality of life.

A. Selected Depot Embodiments and Associated Devices, Systems, and Methods for Treating or Reducing the Effects of Head and Neck Cancer The present technology relates to implants and insertables configured to be disposed at a treatment site proximate a patient's upper aerodigestive tract for controlled release of a therapeutic agent over a period of time to treat, reduce the effects of, and/or reduce the recurrence of head and neck cancer. For example, one or more depots may be disposed at one or more of locations (1), (2), (3), and (4) denoted in FIG. 61. As described in more detail below, in some embodiments the depots 100 described herein can be implanted on or proximate a user's mouth or throat, and release one or more therapeutic agents (e.g., chemotherapeutic agents, analgesics, anti-inflammatory agents, immunotherapy agents, and/or combinations thereof) configured to eliminate the cancerous tissue or limit the likelihood of recurrence at the head and neck. The depot 100 of the present technology may be tuned to meet the particular conditions of head and neck cancer patients, e.g., by altering various factors (e.g., shape and/or configuration) of the depot 100 such that the depot 100 has a particular release profile, duration of release, and/or desired effect on the tumor or cancerous tissue.

Embodiments of the present technology enable short and long-term treatment of head and neck cancer in that therapeutic agents released from the depot 100 can immediately act on any cancerous tissue present, as well as limit the recurrence of head and neck cancer due to the continuous release from the depot 100 over an extended duration of release. In doing so, patients avoid post-surgical radiotherapy and/or chemotherapy and the side effects therefrom. Accordingly, embodiments of the present technology enable a comprehensive treatment of head and neck cancer compared to conventional or treatments.

The deleterious consequences of xerostomia, oral mucositis, and/or other side effects associated with radiation therapy of the head and neck may be alleviated by using one or more depots 100 of the present technology to provide controlled, sustained, localized delivery of one or more therapeutic agents to a treatment site in the head and neck. For example, local, controlled, sustained delivery of chemotherapeutic agents may allow for improved local response to treatment, thereby reducing the need for concurrent radiation therapy (e.g. either reducing the required dosage of radiation therapy or eliminating the need for radiation therapy altogether). Lowering the dose of radiation and/or systemic chemotherapy can significantly alleviate a patient's xerostomia, OM, and/or other side effects.

In some embodiments, in addition or (or instead of) delivery of chemotherapeutic agents, one or more therapeutic agents can be delivered that treat undesirable side effects directly. For example, pilocarpine or another suitable therapeutic agent can be delivered to the treatment site using one or more depots as described herein to alleviate xerostomia. Similarly, benzydamine hydrochloride, a mucoadhesive (e.g., MuGard), an anti-inflammatory agent, or any other suitable therapeutic agent can be delivered to the treatment site to alleviate oral mucositis. In some embodiments, pain associated with OM can be treated via the use of analgesic therapeutic agents delivered via one or more depots. In some instances, a combination of chemotherapeutic agents and agents that treat the side effects of radiation therapy (e.g., agents that treat xerostomia, oral mucositis, or any other undesirable side effect of conventional therapy) can be delivered together via one or more depots. (e.g., simultaneous concurrent delivery, or sequential delivery).

The therapeutic agent carried by the depots 100 of the present technology may be any biologically active substance (or combination of substances) that provide a therapeutic effect in a patient in need thereof. Suitable chemotherapeutic agents include, but are not limited to, cisplatin, palifermin, bleomycin, cetuximab, docetaxel, erbitux, hydroxyurea, methotrexate, nivolumab, pembrolizumab, and combinations thereof.

In some embodiments, the therapeutic agent includes an agent that treats one or more side effects such as xerostomia or OM directly. Such therapeutic agents can include, but are not limited to, keratinocyte growth factor 1 (KGF-1), amifostine, or glutamine, oral immunomodulatory solutions, anti-IL-6Ab, *Lactobacillus brevis* CD2, *Lactococcus lactis* secreting trefoil factor 1. In some embodiments, the therapeutic agents can include or be combined with one or more adjunctive agents, including anesthetics, anti-inflammatory agents, antibiotics and/or antimicrobial agents, and/or antifungal agents. The anesthetics include, but are not limited to, bupivacaine, ropivacaine, mepivacaine, etidocaine, levobupivacaine, trimecaine, carticaine, articaine, lidocaine, prilocaine, benzocaine, procaine, tetracaine, chloroprocaine, and/or combinations thereog. The anti-inflammatory agents include, but are not limited to, prednisone, betamethasone, cortisone, dexamethasone, hydrocortisone, methylprednisolone, aspirin, Ibuprofen, naproxen sodium, diclofenac, diclofenac-misoprostol, celecoxib, piroxicam, indomethacin, meloxicam, ketoprofen, sulindac, diflunisal, nabumetone, oxaprozin, tolmetin, salsalate, etodolac, fenoprofen, flurbiprofen, ketorolac, meclofenamate, mefenamic acid, COX-2 inhibitors, and/or combinations thereof. The antibiotics and/or antimicrobial agents include, but are not limited to, amoxicillin, amoxicillin/clavulanate, cephalexin, ciprofloxacin, clindamycin, metronidazole, azithromycin, levofloxacin, sulfamethoxazole/trimethoprim, tetracycline(s), minocycline, tigecycline, doxycycline, rifampin, triclosan, chlorhexidine, penicillin(s), aminoglycides, quinolones, fluoroquinolones, vancomycin, gentamycin, cephalosporin(s), carbapenems, imipenem, ertapenem, antimicrobial peptides, cecropin-mellitin, magainin, dermaseptin, cathelicidin, α-defensins, α-protegrins, and/or combinations thereog. The antifungal agents include, but are not limited to, ketoconazole, clortrimazole, miconazole, econazole, intraconazole, fluconazole, bifoconazole, terconazole, butaconazole, tioconazole, oxiconazole, sulconazole, saperconazole, voriconazole, terbinafine, amorolfine, naftifine, griseofulvin, haloprogin, butenafine, tolnaftate, nystatin, cyclohexamide, ciclopirox, flucytosine, terbinafine, amphotericin, and/or combinations thereof.

In some embodiments, the total payload (e.g., the total amount of a particular therapeutic agent or the total amount of all therapeutic agents) of the depot 100 may be at least 20 mg, at least 50 mg, at least 100 mg, at least 150 mg, at least 200 mg, at least 300 mg, at least 400 mg, at least 500 mg, at least 600 mg, at least 700 mg, at least 800 mg, at least 900 mg, at least 1000 mg.

In some embodiments, the depot 100 is configured to release the therapeutic agent through the duration of release at a rate of from about 0.1 mg/day to about 200 mg/day, about 0.1 mg/day to about 150 mg/day, about 0.1 mg/day to about 100 mg/day, about 0.1 mg/day to about 90 mg/day, about 0.1 mg/day to about 80 mg/day, about 0.1 mg/day to about 70 mg/day, about 0.1 mg/day to about 60 mg/day, about 0.1 mg/day to about 50 mg/day, about 0.1 mg/day to about 40 mg/day, about 0.1 mg/day to about 30 mg/day, about 1 mg/day to about 30 mg/day, about 1 mg/day to about 20 mg/day, about 5 mg/day to about 20 mg/day, about 10 mg/day to about 20 mg/day, or about 15 mg/day to about 20 mg/day, or any other incremental ranges therebetween.

In some embodiments, the depot may be configured to release the therapeutic agent through the duration of release at a rate no more than 100 mg/day, no more than 90 mg/day, no more than 80 mg/day, no more than 70 mg/day, no more than 60 mg/day, no more than 50 mg/day, no more than 40 mg/day, no more than 30 mg/day, no more than 20 mg/day, no more than 15 mg/day, no more than 10 mg/day, no more than 5 mg/day, no more than 1 mg/day, no more than 0.5 mg/day, no more than 0.1 mg/day, no more than 75 pg/day, no more than 50 pg/day, no more than 25 pg/day, or no more than 10 pg/day.

As previously described, in some embodiments the depot 100 is configured to release the therapeutic agent over a varying period of time. For those embodiments associated with treating head and neck cancer, the depot 100 can be configured to release the therapeutic agent and/or adjunctive agents at the treatment site in vivo for no less than 1 day, no less than 2 days, no less than 3 days, no less than 4 days, no less than 5 days, no less than 6 days, no less than 7 days, no less than 8 days, no less than 9 days, no less than 10 days, no less than 11 days, no less than 12 days, no less than 13 days, no less than 14 days, no less than 15 days, no less than 16 days, no less than 17 days, no less than 18 days, no less than 19 days, no less than 20 days, no less than 21 days, no less than 22 days, no less than 23 days, no less than 24 days, no less than 25 days, no less than 26 days, no less than 27 days, no less than 28 days, no less than 29 days, no less than 30 days, no less than 40 days, no less than 50 days, no less than 60 days, no less than 70 days, no less than 90 days, no less than 100 days, no less than 150 days, no less than 200 days, no less than 300 days, or no less than 365 days.

As previously described, the depot 100 of the present technology can achieve a release profile or kinetics that suits the objectives of the intended therapy. For those embodiments, directed to treating head and neck cancer, including the recurrence thereof, the release profile may be (a) zero-order such that release of the payload of therapeutic agent is at substantially the same rate over the duration of release, (b) first-order such that release of the payload of the therapeutic agent increases in a linear manner over the duration of release, or (c) a second-order such that release of the payload of the therapeutic agent at a high, substantially linear rate for a first period of time and then at a lower, substantially linear rate for a second period of time over the duration of release. Each release profile can be advantageous for head and neck cancer patients. For example, a zero-order release profile may be desired where cancerous tissue is concentrated in a single mass that has been removed and the therapeutic agent is used predominantly to prevent recurrence. In such cases, release of the therapeutic agent in a substantially consistent manner over a duration of release can maximize the amount of time drug is released from the depot, thereby maximizing the amount of time that recurrence is actively limited by the therapeutic agent. As another example, a second-order release profile may be desired when cancerous tissue is not concentrated in a single mass and instead is believed to also be present at proximate portions of the head and neck. In such cases, release of therapeutic agent during a first period of time is used to first target the cancerous tissue believed to present, and a subsequent release of therapeutic agent during a second period of time is used to prevent recurrence. Embodiments of the present technology enable the depot to be tuned according to the optimal treatment needed for each patient.

In some embodiments, the depot 100 can include multiple therapeutic agents, each with configured to the same or different release profiles. For example, sequential release of therapeutic agents can be achieved using a configuration as described above with respect to FIGS. 33A-33B. In such embodiments, a first therapeutic agent can be released over a first period of time and a second therapeutic agent can be released over a second period of time that is after the first period of time, or at least extends beyond the first period of time. In some embodiments, the depot 100 can be configured to provide a delayed release of therapeutic agents, for example using a configuration as described above with respect to FIGS. 35A-35B. In such embodiments, the therapeutic agent may not be released in significant amount until after a first period of time following delivery of the depot 100 to the treatment site in vivo. After the first period of time, the depot 100 may begin to release therapeutic agent to surrounding tissue along a zero-order, first-order, or second-order release profile as desired.

B. Selected Methods of Use

As noted previously, one or more depots 100 as described above can be disposed at or adjacent to a treatment site to treat head and neck cancer. In various embodiments, the treatment site can be any suitable location within the upper aerodigestive tract of the patient. In some embodiments, the treatment site can be a site proximate to a tumor in the patient's mouth or throat. One or more depots 100 of the present technology may be delivered to a treatment site in the patient's head and neck, including, for example, any site at or adjacent to the patient's lips, jaws palate, tongue, pharynx, nasopharynx, oropharynx, hypopharynx, larynx, paranasal sinus, nasal cavity, or salivary glands. In some embodiments, one or more depots 100 in the form of a rolled sheet, an elongated rod or shaft (as in FIGS. 16-31), microbeads (as in FIG. 47), or pellets (as in FIGS. 48A-48B) can be delivered to a treatment site in the head and neck, for example using a cannula, needle, or other suitable delivery device.

Figure 62:
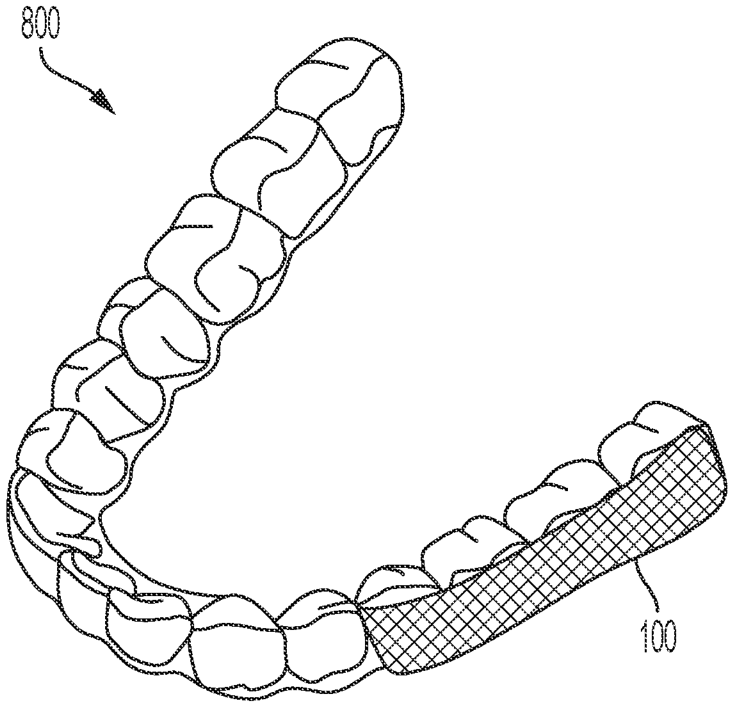
FIGS. 62 and 63 depict oral devices configured for use with the depots of the present technology.

In some embodiments, one or more depots 100 can be configured to be coupled to a dental appliance or prosthesis for delivery of therapeutic agents to surrounding tissue. For example, as shown in FIG. 62, a depot 100 can be coupled to a dental appliance 800. The appliance 800 can be removable, for example being temporarily positioned over a patient's teeth, similar to a retainer, mouthguard, or bleaching tray. The depot 100 can be any one of the multilayer films as described above that is disposed over at least a portion of a surface of the appliance 800. In some embodiments, the depot 100 is coupled to an exterior surface of the appliance 800 and configured to dispense therapeutic agent into surrounding tissue (e.g., adjacent to a patient's cheek, lips, or tongue) when in the presence of saliva. In some embodiments the depot 100 is coupled to an interior surface of the appliance 800 and configured to dispense therapeutic agent into adjacent structures (e.g., towards the patient's teeth and gums). In some embodiments, the depot 100 can be additionally configured to provide ancillary patient benefits. For example, the depot 100 can release adjuvant agents such as flavorants to help control oral malodor, desensitizing agents (e.g., potassium nitrate, strontium acetate and chloride, calcium sodium phosphosilicate) to treat tooth sensitivity, or any other suitable agents. Additionally, the depot 100 and/or the appliance 800 can include biocompatible dyes or colorants that are released over time when exposed to salivary fluids.

In operation, the dental appliance 800 can be placed at an appropriate position within a patient's mouth, for example by being removably fitted over the patient's teeth. Once in place, the depot 100 coupled to the dental appliance 800 will come into contact with salivary fluids and begin to release therapeutic agent(s) (e.g., chemotherapeutic agents, agents to treat the symptoms of oral mucositis, or other suitable agents) to surrounding tissue at a controlled rate for a sustained period of time. The appliance 800 may be left in place for an extended period of time (e.g., hours, days, weeks), or may be left in place within the patient's mouth only for intermittent periods of time, for example with the patient removing the appliance 800 for meals.

Figure 63:
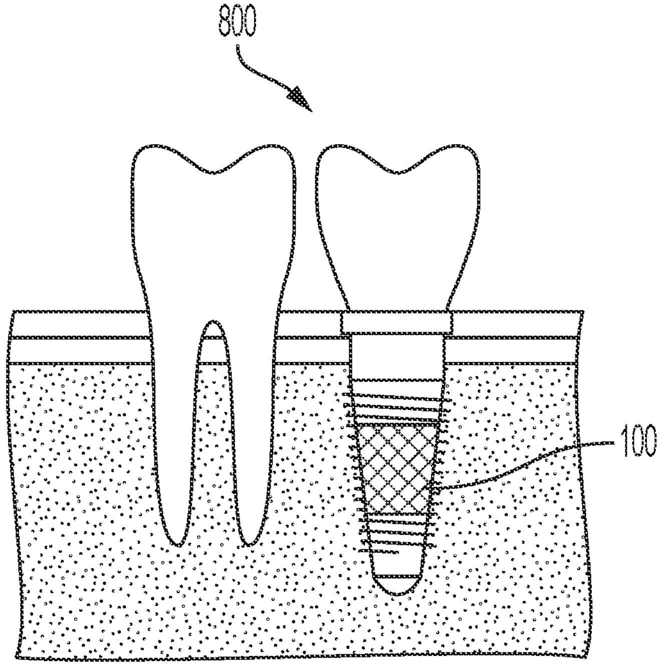

In some embodiments, as shown in FIG. 63, a depot 100 can be coupled to a dental implant 802. The dental implant 802 may be a prosthetic tooth, post, dental bridge, or any other device configured to be permanently or substantially permanently implanted within a patient's mouth. The implant 802 include an upper crown portion configured to be exposed above the patient's gumline, and a lower anchor portion configured to be implanted at least partially within the patient's jaw bone. The upper crown portion can include a hard exterior surface configured to provide a chewing surface and to visibly resemble a tooth. The lower anchor portion can be a threaded screw, shaft, spike, or other structure configured to be implanted within the jaw bone. In the illustrated embodiment, a depot 100 is coupled to the anchor portion of the implant 800, for example being disposed along at least a portion of an exterior surface of the anchor portion. In other embodiments, the depot 100 can be disposed within a reservoir within the anchor portion or crown portion, with apertures provided to allow salivary fluids to enter the reservoir and contact the depot(s) 100 disposed therein. Once in contact with the salivary fluids, the depot 100 may begin to release therapeutic agents, which can be released to the surrounding area through apertures in the anchor portion and/or crown portion of the implant 802.

In operation, the dental appliance 802 can be placed at an appropriate position within a patient's mouth, for example by being implanted within the patient's jawbone. Once in place, the depot 100 coupled to the dental implant 802 will come into contact with salivary fluids or other physiologic fluids and begin to release therapeutic agent(s) (e.g., chemotherapeutic agents, agents to treat the symptoms of oral mucositis, or other suitable agents) to surrounding tissue at a controlled rate for a sustained period of time. The appliance 802 may be left in place permanently, or may be removed after some or all of the therapeutic agent(s) of the depot 100 have been released.

Radiotherapy is the standard of care when treating patients having malignant tumors. A patient will be subjected to numerous sessions of radiotherapy with the goal of subjecting the tumors to a substantial dose of radiation. Unfortunately, there are many non-targeted tissues that also receive a radiation dose alongside the tumors. In certain parts of the body, this radiation exposure can impact critical, highly sensitive tissues and cause debilitating side effects. The patient's ability to tolerate these side effects can often influence the frequency and dosage of the radiotherapy itself. For example, in head and neck tumors, mucositis in the oral cavity and throat is a very common complication associated with radiation therapy. Treatment can be reduced, suspended or stopped altogether as a result of mucositis. Similarly, radiation to treat (1) head and neck tumors may cause xerostomia in the salivary glands, (2) lung cancer may cause pneumonitis in the lungs or respiratory system, (3)

esophageal cancer may cause esophagitis in the esophagus and (4) prostate cancer may cause proctitis in the prostate and rectum.

Localized, sustained administration of chemotherapeutic agents to these tumors may allow for improved local response to treatment or, at a minimum, a comparable response to radiation therapy without such complications of the radiation (e.g., mucositis). Depots embodying the technology described herein may be placed proximate to the target tumor(s) to locally administer therapeutic agents (e.g., chemotherapeutic agents) to the target tumor(s). The combination of local, sustained chemotherapeutic agent and radiotherapy can both optimize the anti-cancer therapy as well as minimize the radiation dose to the patient and, accordingly, the side effect profile to the patient.

C. Routes of Administration and Clinical Endpoints

Any of the depot embodiments and delivery approaches described can be used for local sustained delivery of therapeutic agents for treatment of head and neck cancer. In various embodiments, treatment of head and neck cancer can involve local delivery of one or more therapeutic agents (e.g., via one or more depot(s) of the present technology) administrated using any suitable route. For example, one or more depots can be delivered to a treatment site using direct needle injection or insertion into and/or around the tumor via transoral access using direction visualization from an endoscopic camera. As another example, one or more depots can be inserted via needle injection into and/or around the tumor via percutaneous access using imaging (e.g., ultrasound, CT, MRI) and/or palpation. As yet another example, one or more depots can be placed during surgery to address potential residual disease. In some instances, maxillofacial implants used in reconstructive surgery can be configured to receive one or more depots to provide adjuvant therapy.

Any suitable therapeutic agents, whether delivered locally (e.g., via one or more depots as described herein), systemically (e.g., via intravenous delivery or otherwise), or both, can be used for treatment of head and neck cancers. Example therapeutic agents include chemotherapeutic agents (e.g., cisplatin, carboplatin, paclitaxel, methotrexate, docetaxel, cetuximab, or any combination thereof). In some embodiments, one or more locally delivered therapeutic agents can be used in combination with one or more systemically delivered therapeutic agents and/or in combination with other treatments (e.g., surgery, radiation, etc.). In some embodiments, the systemically delivered therapeutic agents can include any one of the chemotherapeutic agents listed above, as well as targeted agents (e.g., EGFR inhibitors such as cetuximab, simertinib, erlotinib, afatinib, dacomitinib, or gefitinib, or tumor-agnostic therapeutics such as larotrectinib) and immunotherapeutics (e.g., PD-1/PD-L1 antibodies such as pembrolizumab, atezolizumab, durvalumab, or nivolumab).

Treatment of head and neck cancers as disclosed herein can be utilized to achieve one or more endpoints. In various embodiments, such endpoints can involve clinical measures for a particular patient or a population of patients (e.g., a population undergoing a clinical trial). In some embodiments, a clinical trial for assessing the efficacy of local sustained delivery as described herein can include a control group receiving standard treatment (e.g., surgical intervention, radiation therapy, etc.) and a treatment group receiving standard treatment in addition to locally delivered therapeutic agent(s) as described herein. Examples of suitable endpoints include: (1) overall survival (time from treatment (or randomization) to death due to any cause); (2) time to next standard treatment; (3) reduction of extent of standard treatment requirements; (4) reduction of frequency of standard treatment required; (5) increase in duration between standard treatments; and (6) patient-reported quality of life measures (e.g., using FACT-H&N, FACT-N&P, EORTC QLQ-H&N35, UWQOL, etc.).

Any one or any combination of these endpoints can be utilized to assess and/or establish efficacy of treatment of head and neck cancer via depots of the present technology, whether used alone or in combination with one or more other treatments.

VII. Breast Cancer

Figure 64:
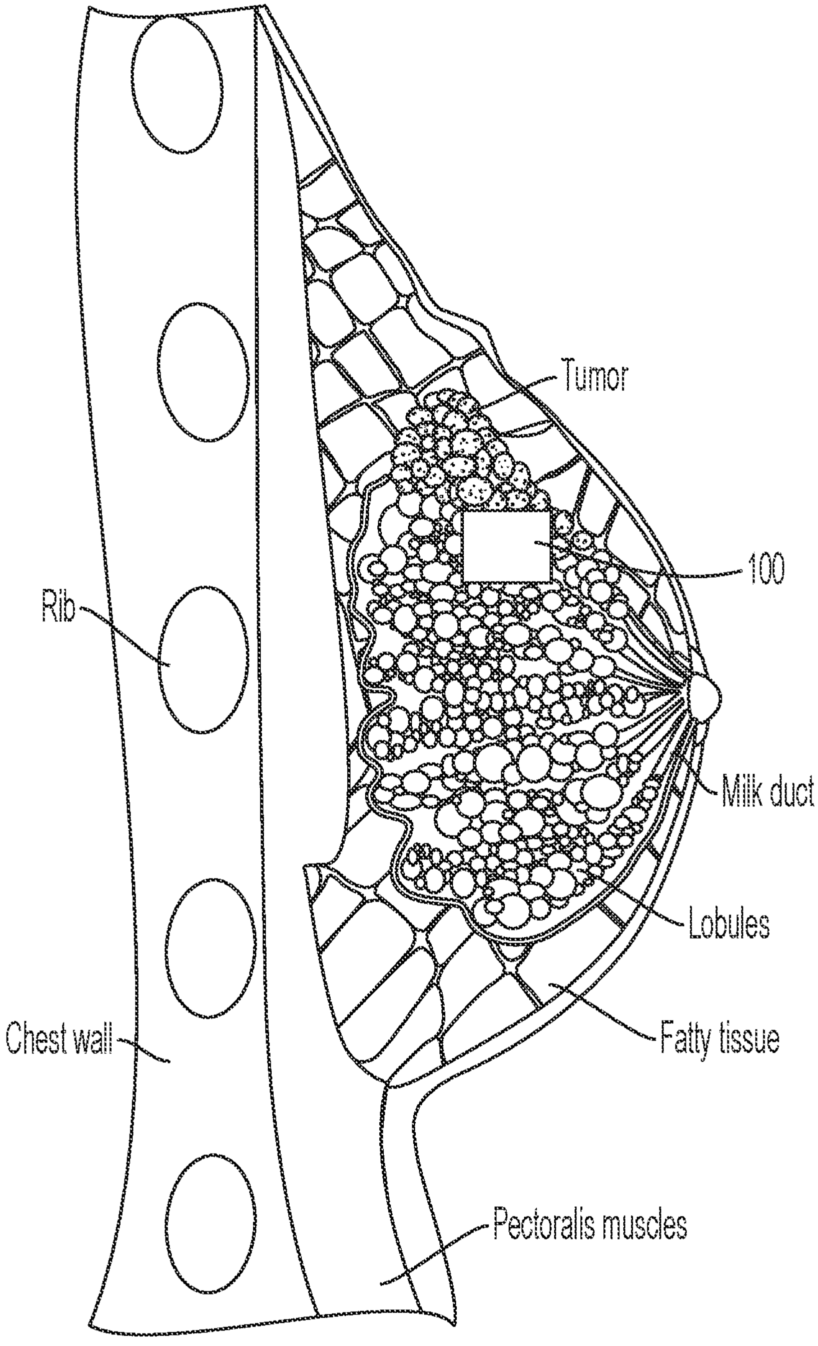
FIG. 64 is a schematic illustration of a breast region of a human patient.

Breast cancer is the most common cancer among women worldwide. It is estimated that 1 in 8 women who live to the age of 70 will develop breast cancer in her lifetime. As shown in FIG. 64, cancer of the breast may form in the lymph nodes, lobules, or ducts. Conventional treatments for breast cancer include surgery (e.g., lumpectomy, partial or total mastectomy), systemic chemotherapy (e.g., intravenous delivery of chemotherapeutic agents), external radiation therapy (e.g., delivery of X-rays from an externally positioned machine), or internal radiation (e.g., insertion of beads, catheters, wires, needles, or other structures that contain a radioactive substance to a treatment site in the breast), and hormonal therapy.

Radiation therapy for breast cancer is associated with a litany of undesirable side effects, including depression, fatigue, dermatitis, cardiovascular disease, and pneumonitis. Similarly, patients undergoing systemic chemotherapy may suffer fatigue, hair less, bruising and bleeding, infection, anemia, nausea and vomiting, and constipation, among other diminutions in quality of life. The undesirable side effects associated with systemic chemotherapy and radiation therapy can be alleviated by using controlled, sustained, localized delivery of one or more therapeutic agents to a treatment site in the breast. For example, local delivery of chemotherapeutic agents may allow for improved local response to treatment, and can reduce the need for concurrent radiation therapy (e.g. either reducing the required dosage of radiation therapy or eliminating the need for radiation therapy altogether).

There are a number of currently available sustained-release chemotherapeutic agents intended for use in treating breast cancer. These include protein-based formulations such as nab-paclitaxel, liposomal formulations such as Doxil® (doxorubicin liposomal), and liposome-encapsulated agents such as liposome-encapsulated doxorubicin citrate (Myocet®). Each of these suffers from significant drawbacks. For example, nab-paclitaxel has shown limited efficacy against solid tumors. Doxil® has been shown to preferentially concentrate in the skin, thereby reducing its efficacy in delivering the chemotherapeutic agent to the tumor site. Additionally, Doxil® is susceptible to drug leakage, resulting in hand-foot syndrome, in which a patient suffers redness, swelling, and pain on the palms of the hands and/or sores of the feet. Myocet® has been also shown to have low stability, which can lead to an undesirable burst of drug release in vivo. As a result, the currently available means for delivering medication typically provide a burst of drug upon contact with surrounding physiologic fluids, but lack an ability to then release the drug in a consistent manner over an extended period of time. Accordingly, there remains a need for implantable systems capable of providing a local, controlled, sustained release of chemotherapeutic agents and/or other therapeutic agents to treat breast cancer.

A. Example Depots for Treating Breast Cancer

The present technology relates to implants and insertables configured to be disposed at a treatment site proximate a patient's chest tissue for controlled release of a therapeutic agent over a period of time to treat, reduce the effects of, and/or reduce the recurrence of breast cancer. As described in more detail below, in some embodiments the depots 100 described herein can be implanted on or proximate a treatment site in the breast, and release one or more therapeutic agents (e.g., chemotherapeutic agents, analgesics, anti-inflammatory agents, immunotherapy agents, and/or combinations thereof) configured to eliminate the cancerous tissue or limit the likelihood of recurrence at the breast. The depot(s) 100, for example, may be positioned at, on, or adjacent a tumor, as shown in FIG. 64. The depot 100 of the present technology may be tuned to meet the particular conditions of breast cancer patients, e.g., by altering various factors (e.g., shape and/or configuration) of the depot 100 such that the depot 100 has a particular release profile, duration of release, and/or desired effect on the tumor or cancerous tissue.

In various embodiments, the depot 100 can be provided in any of the forms described above, including a multilayer thin film, flat sheet, rolled sheet, an elongated rod or shaft (as in FIGS. 16-31), microbeads (as in FIG. 47), pellets (as in FIGS. 48A-48B), or any other suitable configuration for delivery of the therapeutic agent to the treatment site. In some embodiments, the depot 100 can include at least one radiopaque element such that the depot 100 may function as a breast tissue marker to facilitate visualization and evaluation of the tumor size and position over time. The radiopaque elements may be clips, beads, or other structures formed of platinum, titanium, or other biocompatible radiopaque material. In some embodiments, the depot 100 may have an elongated or ribbon-like shape that is helically wound, which may facilitate tissue in-growth and aid in visualization of the depot 100 following implantation in the breast.

Embodiments of the present technology enable short and long-term treatment of breast cancer in that therapeutic agents released from the depot 100 can immediately act on any cancerous tissue present, as well as limit the recurrence of breast cancer due to the continuous release from the depot 100 over an extended duration of release. In doing so, patients avoid post-surgical radiotherapy and/or chemotherapy and the side effects therefrom. Additionally, the local, controlled, sustained release of chemotherapeutic or other therapeutic agents to the treatment site can provide improvements in efficacy and patient comfort over radiation, systemic chemotherapy, or other therapeutic approaches. Accordingly, embodiments of the present technology enable a comprehensive treatment of breast cancer compared to conventional or treatments.

The therapeutic agent carried by the depots 100 of the present technology may be any biologically active substance (or combination of substances) that provide a therapeutic effect in a patient in need thereof. Suitable chemotherapeutic agents include, but are not limited to, doxorubicin, paclitaxel, raloxifene, tamoxifen, abemaciclib, ado-trastuzumab emtansine, anastrozole, capecitabine, cyclophosphamide, docetaxel, epirubicin, eribulin mesylate, everolimus, exemestane, 5-FU, fulvestrant, gemcitabine hydrochloride, goserelin acetate, ixabepilone, letrozole, megestrol acetate, methotrexate, nab-paclitaxel, neratinib maleate, olaparib, paclitaxel albumin, palbociclib, pamidronate disodium, pertuzumab, ribociclib, talazoparib tosylate, tamoxifen citrate, thiotepa, toremifene, trastuzumab, trastuzumab and hyaluronidase-oysk, vinblastine sulfate, any other suitable chemotherapeutic agent, and/or any combination thereof.

In some embodiments, the therapeutic agent includes an immunotherapy agent that targets immune cells associated with a body's immune response. The immunotherapy agents may comprise the pharmacologically active drug or a pharmaceutically acceptable salt thereof. Suitable local immunotherapeutic agents include, but are not limited to, nivolumab, pembrolizumab, cyramza, and combinations thereof. These and other immunotherapy agents may reduce the growth and/or spread of cancerous tissue by targeting the programmed death-ligand 1 and/or programmed cell death protein 1. Any chemical compound possessing such targeting properties is suitable for use in the present technology.

In some embodiments, the therapeutic agents can include or be combined with one or more adjunctive agents, including anesthetics, anti-inflammatory agents, antibiotics and/or antimicrobial agents, and/or antifungal agents. The anesthetics include, but are not limited to, bupivacaine, ropivacaine, mepivacaine, etidocaine, levobupivacaine, trimecaine, carticaine, articaine, lidocaine, prilocaine, benzocaine, procaine, tetracaine, chloroprocaine, and/or combinations thereog. The anti-inflammatory agents include, but are not limited to, prednisone, betamethasone, cortisone, dexamethasone, hydrocortisone, methylprednisolone, aspirin, Ibuprofen, naproxen sodium, diclofenac, diclofenac-misoprostol, celecoxib, piroxicam, indomethacin, meloxicam, ketoprofen, sulindac, diflunisal, nabumetone, oxaprozin, tolmetin, salsalate, etodolac, fenoprofen, flurbiprofen, ketorolac, meclofenamate, mefenamic acid, COX-2 inhibitors, and/or combinations thereof. The antibiotics and/or antimicrobial agents include, but are not limited to, amoxicillin, amoxicillin/clavulanate, cephalexin, ciprofloxacin, clindamycin, metronidazole, azithromycin, levofloxacin, sulfamethoxazole/trimethoprim, tetracycline(s), minocycline, tigecycline, doxycycline, rifampin, triclosan, chlorhexidine, penicillin(s), aminoglycides, quinolones, fluoroquinolones, vancomycin, gentamycin, cephalosporin(s), carbapenems, imipenem, ertapenem, antimicrobial peptides, cecropin-mellitin, magainin, dermaseptin, cathelicidin, α-defensins, α-protegrins, and/or combinations thereog. The antifungal agents include, but are not limited to, ketoconazole, clortrimazole, miconazole, econazole, intraconazole, fluconazole, bifoconazole, terconazole, butaconazole, tioconazole, oxiconazole, sulconazole, saperconazole, voriconazole, terbinafine, amorolfine, naftifine, griseofulvin, haloprogin, butenafine, tolnaftate, nystatin, cyclohexamide, ciclopirox, flucytosine, terbinafine, amphotericin, and/or combinations thereof.

In some embodiments, the total payload (e.g., the total amount of a particular therapeutic agent or the total amount of all therapeutic agents) of the depot 100 may be at least 20 mg, at least 50 mg, at least 100 mg, at least 150 mg, at least 200 mg, at least 300 mg, at least 400 mg, at least 500 mg, at least 600 mg, at least 700 mg, at least 800 mg, at least 900 mg, at least 1000 mg.

In some embodiments, the depot 100 is configured to release the therapeutic agent through the duration of release at a rate of from about 0.1 mg/day to about 200 mg/day, about 0.1 mg/day to about 150 mg/day, about 0.1 mg/day to about 100 mg/day, about 0.1 mg/day to about 90 mg/day, about 0.1 mg/day to about 80 mg/day, about 0.1 mg/day to about 70 mg/day, about 0.1 mg/day to about 60 mg/day, about 0.1 mg/day to about 50 mg/day, about 0.1 mg/day to about 40 mg/day, about 0.1 mg/day to about 30 mg/day, about 1 mg/day to about 30 mg/day, about 1 mg/day to about 20 mg/day, about 5 mg/day to about 20 mg/day, about 10 mg/day to about 20 mg/day, or about 15 mg/day to about 20 mg/day, or any other incremental ranges therebetween.

In some embodiments, the depot may be configured to release the therapeutic agent through the duration of release at a rate no more than 100 mg/day, no more than 90 mg/day, no more than 80 mg/day, no more than 70 mg/day, no more than 60 mg/day, no more than 50 mg/day, no more than 40 mg/day, no more than 30 mg/day, no more than 20 mg/day, no more than 15 mg/day, no more than 10 mg/day, no more than 5 mg/day, no more than 1 mg/day, no more than 0.5 mg/day, no more than 0.1 mg/day, no more than 75 pg/day, no more than 50 pg/day, no more than 25 pg/day, or no more than 10 pg/day.

As previously described, in some embodiments the depot 100 is configured to release the therapeutic agent over a varying period of time. For those embodiments associated with treating breast cancer, the depot 100 can be configured to release the therapeutic agent and/or adjunctive agents at the lung in vivo for no less than 1 day, no less than 2 days, no less than 3 days, no less than 4 days, no less than 5 days, no less than 6 days, no less than 7 days, no less than 8 days, no less than 9 days, no less than 10 days, no less than 11 days, no less than 12 days, no less than 13 days, no less than 14 days, no less than 15 days, no less than 16 days, no less than 17 days, no less than 18 days, no less than 19 days, no less than 20 days, no less than 21 days, no less than 22 days, no less than 23 days, no less than 24 days, no less than 25 days, no less than 26 days, no less than 27 days, no less than 28 days, no less than 29 days, no less than 30 days, no less than 40 days, no less than 50 days, no less than 60 days, no less than 70 days, no less than 90 days, no less than 100 days, no less than 150 days, no less than 200 days, no less than 300 days, or no less than 365 days.

As previously described, the depot 100 of the present technology can achieve a release profile or kinetics that suits the objectives of the intended therapy. For those embodiments, directed to treating breast cancer, including the recurrence thereof, the release profile may be (a) zero-order such that release of the payload of therapeutic agent is at substantially the same rate over the duration of release, (b) first-order such that release of the payload of the therapeutic agent increases in a linear manner over the duration of release, or (c) a second-order such that release of the payload of the therapeutic agent at a high, substantially linear rate for a first period of time and then at a lower, substantially linear rate for a second period of time over the duration of release. Each release profile can be advantageous for breast cancer patients. For example, a zero-order release profile may be desired where cancerous tissue is concentrated in a single mass that has been removed and the therapeutic agent is used predominantly to prevent recurrence. In such cases, release of the therapeutic agent in a substantially consistent manner over a duration of release can maximize the amount of time drug is released from the depot, thereby maximizing the amount of time that recurrence is actively limited by the therapeutic agent. As another example, a second-order release profile may be desired when cancerous tissue is not concentrated in a single mass and instead is believed to also be present at proximate portions of the breast. In such cases, release of therapeutic agent during a first period of time is used to first target the cancerous tissue believed to present, and a subsequent release of therapeutic agent during a second period of time is used to prevent recurrence. Embodiments of the present technology enable the depot to be tuned according to the optimal treatment needed for each patient.

In some embodiments, the depot 100 can include multiple therapeutic agents, each with configured to the same or different release profiles. For example, sequential release of therapeutic agents can be achieved using a configuration as described above with respect to FIGS. 33A-33B. In such embodiments, a first therapeutic agent can be released over a first period of time and a second therapeutic agent can be released over a second period of time that is after the first period of time, or at least extends beyond the first period of time. In some embodiments, the depot 100 can be configured to provide a delayed release of therapeutic agents, for example using a configuration as described above with respect to FIGS. 35A-35B. In such embodiments, the therapeutic agent may not be released in significant amount until after a first period of time following delivery of the depot 100 to the treatment site in vivo. After the first period of time, the depot 100 may begin to release therapeutic agent to surrounding tissue along a zero-order, first-order, or second-order release profile as desired.

B. Example Systems and Methods

A depot as described herein may be used to treat a tumor formed in any portion of the breast. In some embodiments, one or more depots 100 in the form of a rolled sheet, an elongated rod or shaft (as in FIGS. 16-31), microbeads (as in FIG. 47), pellets (as in FIGS. 48A-48B), or any other suitable form can be inserted, implanted, or injected into or adjacent to the tumor using a needle, cannula, or other delivery device. In some embodiments, the tumor can be removed and then one or more depots 100 can be implanted at or adjacent to the tumor bed. In some embodiments, the depot 100 disposed at or adjacent to the treatment site includes one or more fixation features configured to resist migration of the depot after implantation, for example tabs, ridges, hooks, barbs, protrusions, notches, or other structural features.

In some embodiments, one or more depots can be implanted at the treatment site during the same procedure in which a breast tissue marker is positioned (e.g., during a biopsy or a lumpectomy). As noted previously, in some embodiments, the depot 100 can include at least one radiopaque element. In such embodiments, the depot 100 may function as a breast tissue marker to facilitate visualization and evaluation of the tumor size and position over time. In some embodiments, the depot 100 may have a helically wound elongated shape, which can facilitate tissue in-growth and aid in visualization of the depot 100 following implantation. C. Routes of Administration and Clinical Endpoints Any of the depot embodiments and delivery approaches described can be used for local sustained delivery of therapeutic agents for treatment of breast cancer. In various embodiments, treatment of breast cancer can involve local delivery of one or more therapeutic agents (e.g., via one or more depot(s) of the present technology) administrated using any suitable route. For example, one or more depots can be delivered to a treatment site using direct needle injection or insertion into and/or around the tumor via percutaneous access using imaging such as ultrasound, CT, MRI, and/or palpation. As another example, one or more depots can be placed during surgery (e.g., lumpectomy/mastectomy) to address potential residual disease. In some embodiments, one or more depots can be configured to be coupled to a breast implant or incorporated into a breast implant.

Any suitable therapeutic agents, whether delivered locally (e.g., via one or more depots as described herein), systemically (e.g., via intravenous delivery or otherwise), or both, can be used for treatment of breast cancers. Example therapeutic agents include chemotherapeutic agents, such as cisplatin, carboplatin, doxorubicin, epirubicin, gemcitabine, capecitabine, cyclophosphamide, eribulin, fluorouracil (5-FU), paclitaxel, nab-paclitaxel, docetaxel, ixabepilone, methotrexate, vinorelbine, or any combination thereof.

In some embodiments, one or more locally delivered therapeutic agents can be used in combination with one or more systemically delivered therapeutic agents and/or in combination with other treatments (e.g., surgery, radiation, etc.). In some embodiments, the systemically delivered therapeutic agents can include any one of the chemotherapeutic agents listed above, as well as hormone therapy agents (e.g. tamoxifen, aromatase inhibitors (e.g., anastrozole, letrozole, exemestane), or ovarian suppressors (e.g., gonadotropin or luteinizing releasing hormone agonist drugs such as goserelin or leuprolide)), targeted agents (e.g., human epidermal growth factor receptor 2 (HER2) (e.g., trastuzumab, pertuzumab, hyluronidase-zzxf, neratinib, ado-trastuzumab emtansine), bone modifying drugs (e.g., isphosphonates, denosumab), alpelisib, CDK4/6 protein targeting, lapatinib, tucatinib, Sacituzumab govitecan-hzly, Larotrectinib, Olaparib, talazoparib), immunotherapeutics (e.g., PD-1/PD-L1 antibodies such as pembrolizumab, atezolizumab) or any combination thereof.

Treatment of breast cancers as disclosed herein can be utilized to achieve one or more endpoints. In various embodiments, such endpoints can involve clinical measures for a particular patient or a population of patients (e.g., a population undergoing a clinical trial). In some embodiments, a clinical trial for assessing the efficacy of local sustained delivery as described herein can include a control group receiving standard treatment (e.g., surgical intervention, radiation therapy, etc.) and a treatment group receiving standard treatment in addition to locally delivered therapeutic agent(s) as described herein. Examples of suitable endpoints include: (1) overall survival (time from treatment (or randomization) to death due to any cause); (2) time to progression; (3) progression-free survival; (4) disease-free survival and event-free survival; (5) time to treatment failure; (6) duration of response; (7) overall/objective response rate (e.g., assigning a score of complete response (CR), partial response (PR), or stable disease (SD)); (8) disease control rate (e.g., number of participants that achieve either a CR, PR, or SD score); (9) quality of life measures (e.g., based on patient survey or other input); and (10) assessment of relevant biomarkers such as estrogen receptor, progesterone receptor, human epidermal growth factor receptor 2, and/or Mib1/Ki-67 proliferation index.

Any one or any combination of these endpoints can be utilized to assess and/or establish efficacy of treatment of breast cancer via depots of the present technology, whether used alone or in combination with one or more other treatments.

VIII. Pancreatic Cancer

Pancreatic cancer is the third leading cause of cancer deaths in the United States and is expected to be the second leading cause of cancer-related deaths by 2020. In Europe, death rates for pancreatic cancer are expected to soon overtake that of breast cancer. This mortality rate is in part because pancreatic cancer is difficult to detect, as approximately 90% of patients are diagnosed after the pancreatic cancer has already begun to spread. Moreover, the likelihood of death once a patient is diagnosed is one of the highest of all cancers, with over 70% of diagnosed patients dying within the first year of diagnosis and over 90% dying within the fifth year.

Figure 65:
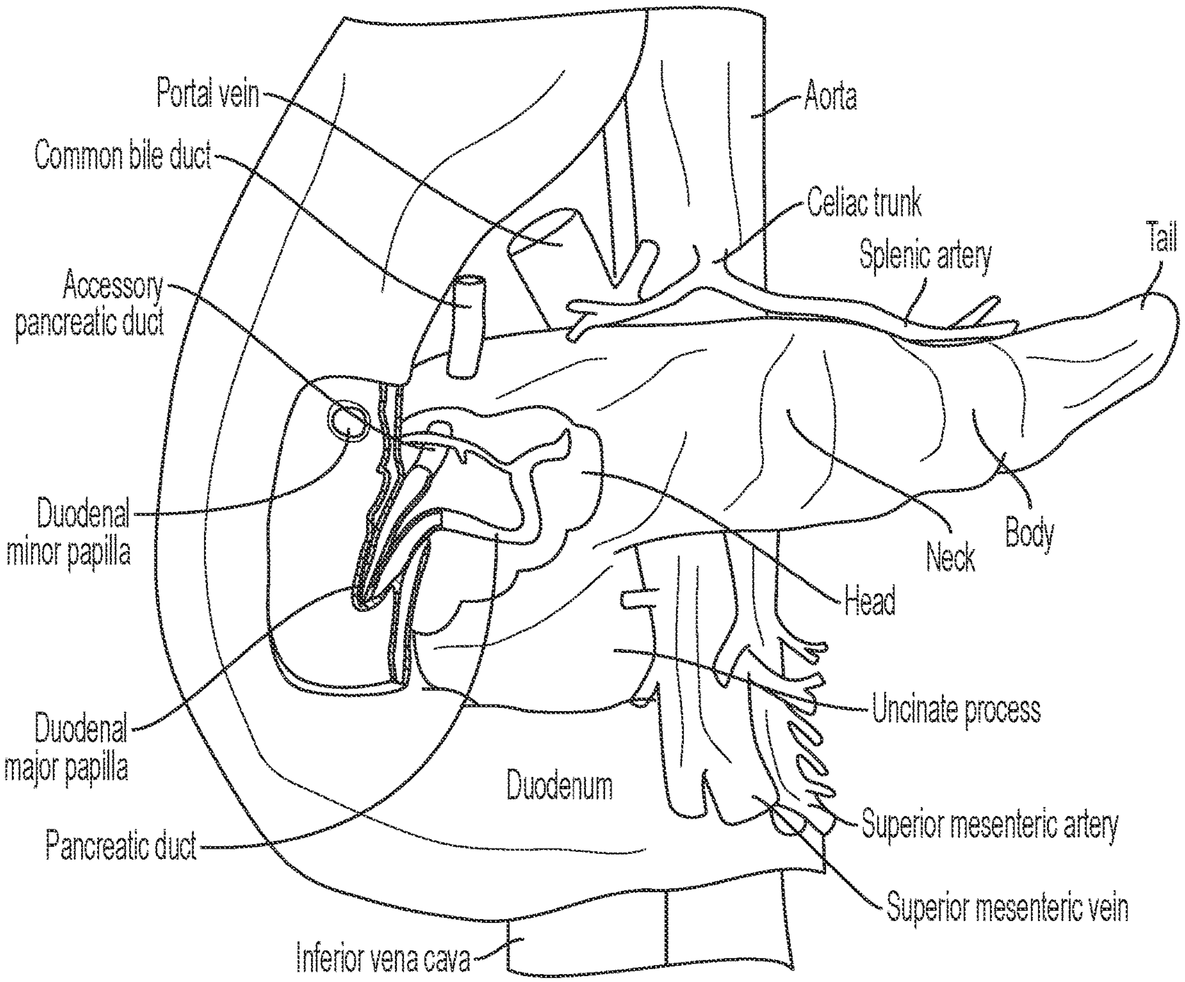
FIG. 65 is a schematic illustration of a pancreas of a human patient.

FIG. 65 is an anatomical illustration of the pancreas for ease of reference. As shown, the pancreas is an elongated, tapered organ positioned along the back of the abdomen, behind the stomach. The head of the pancreas lies in the curve of the duodenum, and the body of the pancreas extends slightly upward and ends near the spleen, referred to as the tail of the pancreas. The pancreatic duct connects the pancreas head to the duodenum.

The standard of care for treating pancreatic cancer depends on the stage of the cancer and how far it has spread, but generally includes a combination of surgery, chemotherapy, radiotherapy, and targeted therapy. Stage 0 pancreatic cancer has no spread, Stage I pancreatic cancer has local growth but is limited to the pancreas, Stage II of pancreatic cancer has spread locally (i.e., possibly to local lymph nodes but not distant sites) and is over 4 cm, Stage III pancreatic cancer has a wider spread to nearby major blood vessels or nerves, but has not metastasized, and Stage IV pancreatic cancer has spread to distant organs. Generally speaking, Stages III and IV pancreatic cancer cannot be treated via resection because the cancerous cells have spread outside the local region. Moreover, local delivery of chemotherapeutic agents by themselves are often ineffective in treating Stage II and IV pancreatic cancer. This is due to a number of reasons, including that implants fail to deliver sufficient concentrations of the chemotherapeutic agent to the cancerous tissue for an extended period of time.

For treating Stages 0, I, and II pancreatic cancer, surgical options include a (a) Whipple procedure (i.e., a pancreaticoduodenectomy), in which the head of the pancreas, the gallbladder and parts of the stomach, small intestine and/or bile duct are removed, (b) a distal pancreatectomy, in which the body and tail of the pancreas are removed, and (c) a total pancreatectomy, in which the entire pancreas and parts of the small intestine, common bile duct, gallbladder, spleen and adjacent lymph nodes are removed.

Despite the aggressive removal/resection of the pancreatic tissue performed by these surgeries, local cancer recurrence rates after resection have been shown to be over 35%. As such, patients often need to undergo radiotherapy to remove any remaining and/or recurring cancerous tissue after the above-mentioned resection surgeries. It is well known that radiotherapy has significant side effects, including diarrhea and bleeding, tissue inflammation (e.g., esophagitis, pneumonitis), a decrease in white blood cells, and additional cancers (e.g., soft tissue sarcoma), amongst others. Accordingly, radiotherapy is a non-optimal treatment option for patients, especially after having already undergone surgery and/or previous radiotherapy.

To avoid radiotherapy while still addressing the recurrence concern associated with resection, radioactive implants (e.g., brachytherapy seeds) are often inserted into the tissue after resection of the pancreas. Example radioactive agents commonly used to treat pancreatic cancers can include paclitaxel (Taxol®), irinotecan (Camptosar®), cisplatin (Platinol®), and gemcitabine (Gemzar®). The radioactive agents provide localized treatment to the treated region of the pancreas and limit the likelihood of recurrence.

The radioactive agents may be delivered via implants to extend the duration of release of the radioactive agent in vivo.

Despite the benefits provided by current therapies, however, there are multiple drawbacks standing in the way of effectively treating pancreatic cancer and/or limiting recurrence. For example, the lifetime of the radioactive agents even when disposed in implants is limited, and thus the ability for brachytherapy or related treatments to prevent or inhibit recurrence is also limited. Specifically, the physiological environment in which the radioactive agents are implanted can cause them to degrade in a relatively short timeframe. As such, the ability for these radioactive agents to actively treat cancerous tissue does not occur over a sufficient period of time. Moreover, the implants, injectables, extended release systems, and other means currently available to prolong the release duration of the radioactive agents still lack a true controlled release mechanism. For example, the currently available means for delivering medication typically provide a burst of drug upon contact with surrounding physiologic fluids, but lack an ability to then release the drug in a consistent manner over an extended period of time.

Thus, a need exists for implantable systems capable of providing a controlled release of medication to treat pancreatic cancer and/or the recurrence thereof.

A. Example Depots for Treating Pancreatic Cancer

One of more depots 100 of the present technology may be positioned at a surgical or interventional treatment site proximate a patient's pancreas for controlled release of a therapeutic agent over a period of time to treat, reduce the effects of, and/or reduce the extent and/or incidence of local recurrence of pancreatic cancer. As described in more detail below, in some embodiments the depots 100 described herein can be implanted on or proximate cancerous tissue of the pancreas and release one or more therapeutic agents (e.g., chemotherapeutic agents, targeted agents, immunotherapy agents, and/or combinations thereof) configured to eliminate the cancerous tissue or limit the likelihood of recurrence at the pancreas or adjacent organs, lymph nodes, nerves, etc. The depot 100 of the present technology may be tuned to meet the particular conditions of pancreatic cancer patients, e.g., by altering various factors (e.g., shape and/or configuration) of the depot 100 such that the depot 100 has a particular release profile, duration of release, and/or desired effect on the tumor or cancerous tissue.

Embodiments of the present technology enable short and long-term treatment of pancreatic cancer in that therapeutic agents released from the depot 100 can immediately act on any cancerous pancreatic tissue present, as well as limit the recurrence of pancreatic cancer due to the continuous release from the depot 100 over an extended duration. In doing so, patients can avoid post-surgical radiotherapy and/or chemotherapy and the side effects therefrom. Accordingly, embodiments of the present technology enable a comprehensive treatment of pancreatic cancer compared to conventional treatments.

1. Therapeutic Agents

The therapeutic agent carried by the depots 100 of the present technology may be any biologically active substance (or combination of substances) that provide a therapeutic effect in a patient in need thereof. In some embodiments, the therapeutic agent includes a chemotherapeutic agent. The chemotherapeutic agent may comprise the pharmacologically active drug or a pharmaceutically acceptable salt thereof. Suitable local chemotherapeutic agents include, but are not limited to, paclitaxel, irinotecan, nab-paclitaxel, cisplatin, oxaliplatin, capecitabine, albumin-bound paclitaxel, 5-fluorouracil, gemcitabine, vinorelbine, pemetrexed, and combinations thereof.

In some embodiments, the therapeutic agent includes a targeting agent that targets specific receptors or growth factors to reduce the growth and/or spread of cancerous tissue and/or masses. The targeting agents may comprise the pharmacologically active drug or a pharmaceutically acceptable salt thereof. Suitable local targeting agents include, but are not limited to, palbociclib, abemaciclib, tipifarnib, tanomastat, marimastat erlotinib, algenpanticel-L, ibilimumab, and combinations thereof. These and other targeting agents may reduce the growth and/or spread of cancerous tissue by targeting certain chemical compounds such as cyclin-dependent kinases (CDKs), farnesyltransferases, matrix metalloproteinases or the like. Any chemical compound possessing such targeting properties is suitable for use in the present technology.

In some embodiments, the therapeutic agent includes an immunotherapy agent that targets immune cells associated with a body's immune response. The immunotherapy agents may comprise the pharmacologically active drug or a pharmaceutically acceptable salt thereof. Suitable local immunotherapeutic agents include, but are not limited to, nivolumab, pembrolizumab, cyramza, and combinations thereof. These and other immunotherapy agents may reduce the growth and/or spread of cancerous tissue by targeting the programmed death-ligand 1 and/or programmed cell death protein 1. Any chemical compound possessing such targeting properties is suitable for use in the present technology.

In some embodiments, the therapeutic agents (e.g., chemotherapeutic agents, targeting agents, immunotherapy agents, etc.) previously-described may be combined with one or more adjunctive agents, including anesthetics, anti-inflammatory agents, antibiotics and/or antimicrobial agents, and/or antifungal agents. The anesthetics include, but are not limited to, bupivacaine, ropivacaine, mepivacaine, etidocaine, levobupivacaine, trimecaine, carticaine, articaine, lidocaine, prilocaine, benzocaine, procaine, tetracaine, chloroprocaine, and/or combinations thereof. The anti-inflammatory agents include, but are not limited to, prednisone, betamethasone, cortisone, dexamethasone, hydrocortisone, methylprednisolone, aspirin, Ibuprofen, naproxen sodium, diclofenac, diclofenac-misoprostol, celecoxib, piroxicam, indomethacin, meloxicam, ketoprofen, sulindac, diflunisal, nabumetone, oxaprozin, tolmetin, salsalate, etodolac, fenoprofen, flurbiprofen, ketorolac, meclofenamate, mefenamic acid, COX-2 inhibitors, and/or combinations thereof. The antibiotics and/or antimicrobial agents include, but are not limited to, amoxicillin, amoxicillin/clavulanate, cephalexin, ciprofloxacin, clindamycin, metronidazole, azithromycin, levofloxacin, sulfamethoxazole/trimethoprim, tetracycline(s), minocycline, tigecycline, doxycycline, rifampin, triclosan, chlorhexidine, penicillin(s), aminoglycides, quinolones, fluoroquinolones, vancomycin, gentamycin, cephalosporin(s), carbapenems, imipenem, ertapenem, antimicrobial peptides, cecropin-mellitin, magainin, dermaseptin, cathelicidin, α-defensins, α-protegrins, and/or combinations thereof. The antifungal agents include, but are not limited to, ketoconazole, clortrimazole, miconazole, econazole, intraconazole, fluconazole, bifoconazole, terconazole, butaconazole, tioconazole, oxiconazole, sulconazole, saperconazole, voriconazole, terbinafine, amorolfine, naftifine, griseofulvin, haloprogin, butenafine, tolnaftate, nystatin, cyclohexamide, ciclopirox, flucytosine, terbinafine, amphotericin, and/or combinations thereof.

2. Depot Payload and Release Rates

In some embodiments, the total payload (e.g., the total therapeutic agent or combination of therapeutic agent and adjunctive agent) of the depot 100 may be at least 100 mg, at least 150 mg, at least 200 mg, at least 300 mg, at least 400 mg, at least 500 mg, at least 600 mg, at least 700 mg, at least 800 mg, at least 900 mg, at least 1000 mg.

In some embodiments, the depot 100 is configured to release the therapeutic agent through the duration of release at a rate of from about 0.1 mg/day to about 200 mg/day, about 0.1 mg/day to about 150 mg/day, about 0.1 mg/day to about 100 mg/day, about 0.1 mg/day to about 90 mg/day, about 0.1 mg/day to about 80 mg/day, about 0.1 mg/day to about 70 mg/day, about 0.1 mg/day to about 60 mg/day, about 0.1 mg/day to about 50 mg/day, about 0.1 mg/day to about 40 mg/day, about 0.1 mg/day to about 30 mg/day, about 1 mg/day to about 30 mg/day, about 1 mg/day to about 20 mg/day, about 5 mg/day to about 20 mg/day, about 10 mg/day to about 20 mg/day, or about 15 mg/day to about 20 mg/day, or any other incremental ranges therebetween (e.g., 50 mg/day to 100 mg/day, 150 mg/day to 175 mg/day, etc.).

In some embodiments, the depot 100 may be configured to release the therapeutic agent through the duration of release at a rate no more than 100 mg/day, no more than 90 mg/day, no more than 80 mg/day, no more than 70 mg/day, no more than 60 mg/day, no more than 50 mg/day, no more than 40 mg/day, no more than 30 mg/day, no more than 20 mg/day, no more than 15 mg/day, no more than 10 mg/day, no more than 5 mg/day, no more than 1 mg/day, no more than 0.5 mg/day, no more than 0.1 mg/day, no more than 75 pg/day, no more than 50 pg/day, no more than 25 pg/day, or no more than 10 pg/day.

As previously described, in some embodiments the depot 100 is configured to release the therapeutic agent over a varying period of time (i.e., duration of release). For those embodiments associated with treating pancreatic cancer, the depot 100 can be configured to release the therapeutic agent and/or adjunctive agents at the pancreas for no less than 1 day, no less than 2 days, no less than 3 days, no less than 4 days, no less than 5 days, no less than 6 days, no less than 7 days, no less than 8 days, no less than 9 days, no less than 10 days, no less than 11 days, no less than 12 days, no less than 13 days, no less than 14 days, no less than 15 days, no less than 16 days, no less than 17 days, no less than 18 days, no less than 19 days, no less than 20 days, no less than 21 days, no less than 22 days, no less than 23 days, no less than 24 days, no less than 25 days, no less than 26 days, no less than 27 days, no less than 28 days, no less than 29 days, no less than 30 days, no less than 40 days, no less than 50 days, no less than 60 days, no less than 70 days, no less than 90 days, no less than 100 days, no less than 150 days, no less than 200 days, no less than 300 days, or no less than 365 days.

As previously described, the depot 100 of the present technology can achieve a release profile or kinetics that suits the objectives of the intended therapy. For those embodiments directed to treating pancreatic cancer, including the recurrence thereof, the release profile may be (a) zero-order such that release of the payload of therapeutic agent is at a substantially steady rate over the duration of release, (b) first-order such that release of the payload of the therapeutic agent increases in a substantially linear manner over the duration of release, or (c) a second-order such that release of the payload of the therapeutic agent occurs at a high, substantially linear rate for a first period of time and then at a lower, substantially linear rate for a second period of time over the duration of release.

Each of these release profiles can be advantageous for pancreatic cancer patients depending on their particular condition. For example, a zero-order release profile may be desired when cancerous tissue is concentrated in a single mass that has been removed and the therapeutic agent is used predominantly to prevent recurrence. In such cases, release of the therapeutic agent in a substantially consistent manner over a duration of release can maximize the amount of time drug is released from the depot, thereby maximizing the amount of time that recurrence is actively limited by the therapeutic agent. As another example, a second-order release profile may be desired when cancerous tissue is present is still present in portions of the pancreas. In such cases, release of therapeutic agent during a first period of time at the higher rate is used to first target the cancerous tissue, and a subsequent release of therapeutic agent during a second period of time at the lower rate is used to prevent recurrence. Embodiments of the present technology enable the depot to be tuned according to the optimal treatment needed for each patient.

3. Example Form Factors

The depots 100 of the present technology previously described are generally applicable to treating pancreatic cancer. In some embodiments, certain form factors may be particularly beneficial to achieve more effective treatment. Moreover, the depot 100 can be delivered to the pancreas via multiple methods, including transarterially (e.g., transarterial chemoembolization), endoscopically (e.g., gastrointestinal endoscopic ultrasound delivery), or generally post-surgery. Using these or other delivery methods, depots 100 of the present technology may be positioned at the pancreas, e.g., behind, around, or at an arterial entrance to the pancreas.

In some embodiments, depots 100 that include a configuration resembling a microspherical depot (e.g., microcylinders, pellets, beads, or the like, as previously described) may be particularly beneficial for treating pancreatic cancer. Specifically, a microspherical depot, e.g., having a 1 mm diameter or maximum lateral length, can be placed in or proximate cancerous tissue of the pancreas via multiple delivery methods, including transarterially. Arteries that perfuse the pancreas are sufficiently large, thus enabling intravascular, catheter-based delivery of microspherical depots to cancerous pancreas tissue.

Other depot configurations that may be particularly beneficial for treating cancerous pancreatic tissue include (a) a depot sheet or film that can at least partially surround the pancreas, or (b) a depot having multiple layers, such as those depot embodiments comprising a therapeutic region including a first portion having a therapeutic agent, and a second portion having an adjunctive agent (e.g., an immunotherapeutic agent, anesthetic, anti-inflammatory agent, antibiotic agent and/or antifungal agent). Such embodiments can provide the combined release (e.g., simultaneous or sequential release) of the therapeutic agent and adjunctive agent.

B. Routes of Administration and Clinical Endpoints

Any of the depot embodiments and delivery approaches described can be used for local sustained delivery of therapeutic agents for treatment of pancreatic cancer. In various embodiments, treatment of pancreatic cancer can involve local delivery of one or more therapeutic agents (e.g., via one or more depot(s) of the present technology) administrated using any suitable route. In some embodiments, one or more depots can be delivered to a treatment site using endoscopic access (e.g., needle injection delivery from duct lumen into or adjacent the tumor, a drug-coated stent or stent graft in the duct lumen, a stent made of a bioresorbable depot in the duct lumen, etc.). In some embodiments, one or more depots can be delivered to a treatment site using catheter access into a vessel adjacent to the tumor in the pancreas (e.g., using needle injection delivery from the vessel lumen into the tumor, a drug-coated stent or stent graft in the vessel lumen, or a stent made of a bioresorbable depot in the vessel lumen). In some embodiments, direct needle injection or implantation into or around the tumor can be used to position one or more depots via laparoscopic or open surgical access (e.g., with direct visualization and/or palpation).

Any suitable therapeutic agents, whether delivered locally (e.g., via one or more depots as described herein), systemically (e.g., via intravenous delivery or otherwise), or both, can be used for treatment of pancreatic cancers. Example therapeutic agents include chemotherapeutic agents, such as fluorouracil (5-FU), gemcitabine, capecitabine, paclitaxel, nab-paclitaxel, irinotecan, leucovorin, oxaliplatin, cisplatin, FOLFIRINOX, FOLFOX, FOLFIRI, or any combination thereof. Example therapeutic agents also include supportive care agents, such as anesthetics and/or anti-inflammatory agents to palliate symptoms prior to surgery, following surgery, or as an alternative to surgery.

In some embodiments, one or more locally delivered therapeutic agents can be used in combination with one or more systemically delivered therapeutic agents and/or in combination with other treatments (e.g., surgery, radiation, etc.). In some embodiments, the systemically delivered therapeutic agents can include any one of the chemotherapeutic agents or supportive agents listed above, as well as targeted agents (e.g., EGFR inhibitors (e.g., erlotinib), poly (ADP-ribose) polymerase (PARP) inhibitors (e.g., niraparib, alaparib, rucaparib), BRCA mutation target (e.g., Olaparib (targeting BRCA mutation), or Larotrectinib or entrecetinib (targeting NTRK fusion)), immunotherapeutics (e.g., PD-1/PD-L1 antibodies such as pembrolizumab), or any combination thereof.

Treatment of pancreatic cancers as disclosed herein can be utilized to achieve one or more endpoints. In various embodiments, such endpoints can involve clinical measures for a particular patient or a population of patients (e.g., a population undergoing a clinical trial). In some embodiments, a clinical trial for assessing the efficacy of local sustained delivery as described herein can include a control group receiving standard treatment (e.g., surgical intervention, radiation therapy, etc.) and a treatment group receiving standard treatment in addition to locally delivered therapeutic agent(s) as described herein. Examples of suitable endpoints include: (1) overall survival (time from treatment (or randomization) to death due to any cause); (2) time to progression; (3) progression-free survival; (4) disease-free survival and event-free survival; (5) time to treatment failure; (6) duration of response; (7) overall/objective response rate (e.g., assigning a score of complete response (CR), partial response (PR), or stable disease (SD)); (8) disease control rate (e.g., number of participants that achieve either a CR, PR, or SD score); (9) quality of life measures (e.g., based on patient survey or other input such as EORTC QLC-30); and (10) assessment of relevant biomarkers.

Any one or any combination of these endpoints can be utilized to assess and/or establish efficacy of treatment of pancreatic cancer via depots of the present technology, whether used alone or in combination with one or more other treatments.

IX. Lung Cancer

For more than 30 years, lung cancer has been the leading cancer killer in both men and women worldwide. In 2018, an estimated 1.8 million people died from lung cancer, and 2.1 million people were newly diagnosed as having lung cancer. In the U.S. alone, there are over 500,000 people living today that have been diagnosed with lung cancer at some point in their lives. Moreover, because lung cancer predominantly affects the elderly, it will continue to be one of the leading causes of death as the worldwide population ages.

Figure 66:
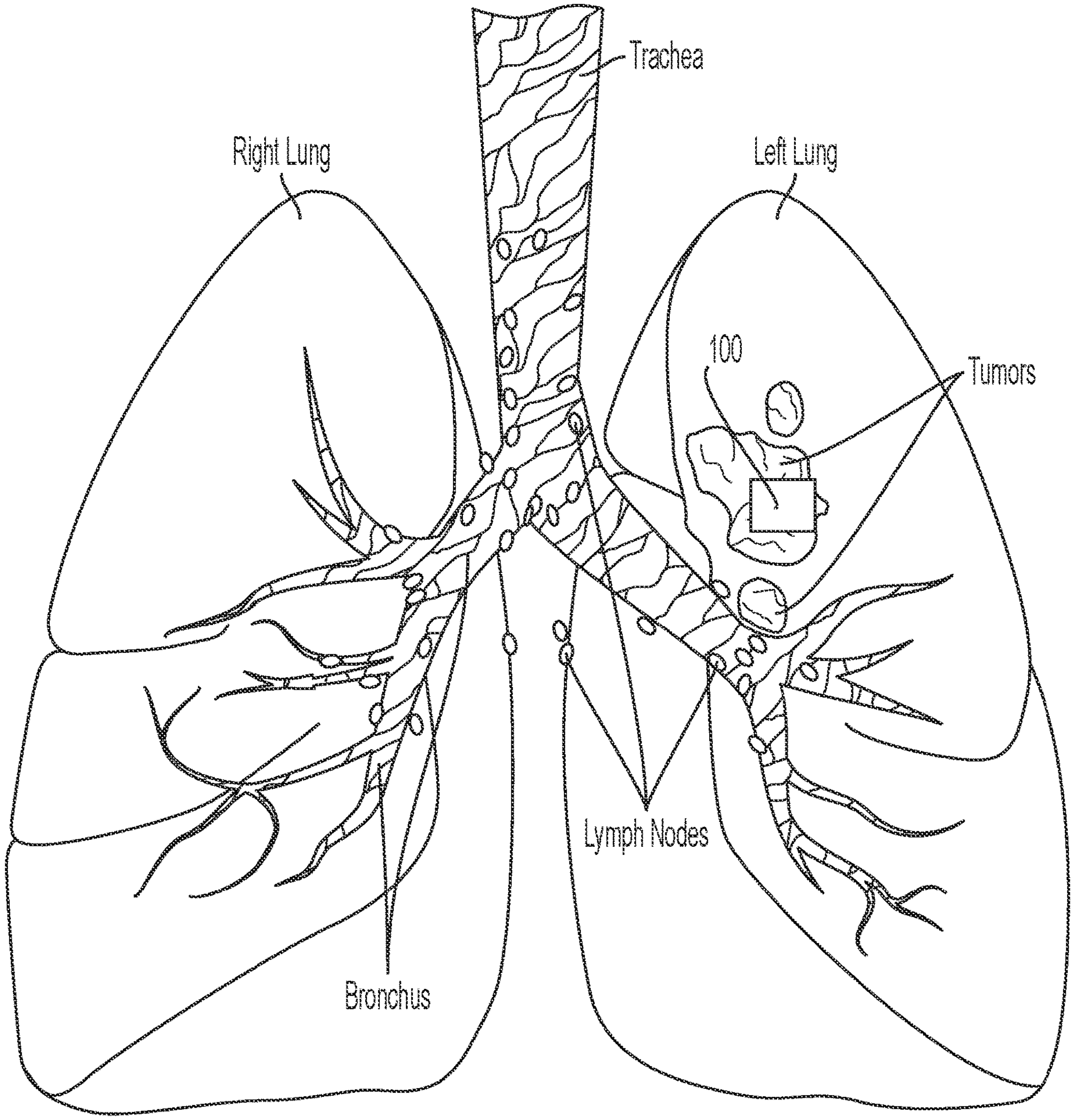
FIG. 66 is a schematic illustration of a lung of a human patient.

FIG. 66 is an anatomical illustration of a right lung and a left lung having multiple cancerous tumors. The standard of care for treating lung cancer includes a combination of thoracic surgery, chemotherapy, radiotherapy and targeted therapy. Thoracic surgery involves removing the portion of the lung with cancerous tissue. Depending on where the cancerous tissue is located, the specific type of thoracic surgery required can include (a) wedge resection, in which the tumor and a section of tissue surrounding the tumor are removed, (b) segmentectomy, in which a section of a lobe of the lung is removed, (c) lobectomy, in which an entire lobe of the lung is removed, and (d) pneumonectomy, in which an entire lung is removed. For wedge resections, segmentectomies, and lobectomies, a stapler and staple buttress are typically used to seal the edges of the lung post removal/resection to prevent leakage of air therefrom. Video-assisted thoracoscopic surgery (VATS) is another commonly-used procedure in which a small camera inserted into the chest is used to conduct the tissue removal procedure.

Despite the aggressive removal/resection of lung tissue performed by these surgeries, local cancer recurrence rates have been shown to approach 30% (Bille, A., et al., ANN. THORAC. SURG., 2016, 102(4): 1067-1073). As such, patients often need to undergo radiotherapy to remove any remaining and/or recurring cancerous tissue even after the above-mentioned thoracic surgeries. It is well known that radiotherapy has significant side effects, including diarrhea and bleeding, tissue inflammation (e.g., esophagitis, pneumonitis), a decrease in white blood cells, and additional cancers (e.g., soft tissue sarcoma), amongst others. Accordingly, radiotherapy is a non-optimal treatment option for patients, especially after having already undergone thoracic surgery and/or previous radiotherapy.

To avoid radiotherapy while still addressing high recurrence rates, radioactive implants such as brachytherapy seeds are often inserted into the tissue after resection of the lung. Example radioactive agents commonly used to treat lung cancers can include paclitaxel (Taxol®), cisplatin (Platinol®), docetaxel (Taxotere®), and gemcitabine (Gemzar®). The radioactive agents provide localized treatment to the treated region of the lung and limit the likelihood of recurrence. The radioactive agents may be delivered via implants to extend the duration of release of the radioactive agent in vivo. One specific example of a radioactive implant is AcuityBio®'s ABC103 staple buttress implant, which includes radioactive agents positioned within the buttress that are administered over time to the surrounding area of the lung.

Despite the benefits provided by current therapies, however, there are multiple drawbacks standing in the way of effectively treating lung cancer and/or limiting its recurrence. For example, the lifetime of the radioactive agents, even when disposed in implants, is limited, and thus the ability for brachytherapy or related treatments to prevent or inhibit recurrence is also limited. Specifically, the physiological environment in which the radioactive agents are implanted can cause them to degrade in a relatively short timeframe. As such, the ability for these radioactive agents to actively treat cancerous tissue often does not occur over a sufficient period of time. Moreover, the implants, injectables, extended release systems, and other means currently available to prolong the release duration of the radioactive agents still lack a true controlled release mechanism. For example, the currently available means for delivering medication typically provide a burst of drug upon contact with surrounding physiologic fluids, but lack an ability to then release the drug in a consistent manner. It follows that current treatment options are generally unable to provide for the consistent release of a drug over an extended period of time.

Thus, a need exists for implantable systems capable of providing a controlled release of medication to treat lung cancer and/or the recurrence thereof

A. Example Depots for Treating Lung Cancer

The present technology relates to implants and insertables configured to be disposed at a surgical or interventional treatment site proximate a patient's lung for controlled release of a therapeutic agent over a period of time to treat, reduce the effects of, and/or reduce the recurrence of lung cancer. FIG. 66, for example, shows a depot 100 of the present technology positioned at a lung tumor. As described in more detail below, in some embodiments the depots 100 described herein can be implanted on or proximate cancerous tissue of the lung, and release one or more therapeutic agents (e.g., chemotherapeutic agents, targeted agents, immunotherapy agents, and/or combinations thereof) configured to eliminate the cancerous tissue or limit the likelihood of recurrence at the lung. The depot 100 of the present technology may be tuned to meet the particular conditions of lung cancer patients, e.g., by altering various factors (e.g., shape and/or configuration) of the depot 100 such that the depot 100 has a particular release profile, duration of release, and/or desired effect on the tumor or cancerous tissue.

Embodiments of the present technology enable short and long-term treatment of lung cancer in that therapeutic agents released from the depot 100 can immediately act on any cancerous lung tissue present, as well as limit the recurrence of lung cancer due to the continuous release from the depot 100 over an extended duration of release. In doing so, patients can avoid post-surgical radiotherapy and/or chemotherapy and the side effects therefrom. Accordingly, embodiments of the present technology enable a comprehensive treatment of lung cancer compared to conventional treatments.

1. Therapeutic Agents

The therapeutic agent carried by the depots 100 of the present technology may be any biologically active substance (or combination of substances) that provide a therapeutic effect in a patient in need thereof. In some embodiments, the therapeutic agent includes a chemotherapeutic agent. The chemotherapeutic agent may comprise the pharmacologically active drug or a pharmaceutically acceptable salt thereof. Suitable local chemotherapeutic agents include, but are not limited to, paclitaxel, cisplatin, carboplatin, albumin-bound paclitaxel, docetaxel, gemcitabine, vinorelbine, pemetrexed, and combinations thereof.

In some embodiments, the therapeutic agent includes a targeting agent that targets specific receptors or growth factors to reduce the growth and/or spread of cancerous tissue and/or masses. The targeting agents may comprise the pharmacologically active drug or a pharmaceutically acceptable salt thereof. Suitable local targeting agents include, but are not limited to, bevacizumab, erlotinib, afatinib, gefitinib, crizotinib, ceritinib, and combinations thereof. These and other targeting agents may reduce the growth and/or spread of cancerous tissue by targeting the vascular endothelial growth factor and/or the epidermal growth factor receptor. Any chemical compound possessing such targeting properties is suitable for use in the present technology.

In some embodiments, the therapeutic agent includes an immunotherapy agent that targets immune cells associated with a body's immune response. The immunotherapy agents may comprise the pharmacologically active drug or a pharmaceutically acceptable salt thereof. Suitable local immunotherapeutic agents include, but are not limited to, nivolumab, pembrolizumab, cyramza, and combinations thereof. These and other immunotherapy agents may reduce the growth and/or spread of cancerous tissue by targeting the programmed death-ligand I and/or programmed cell death protein 1. Any chemical compound possessing such targeting properties is suitable for use in the present technology.

In some embodiments, the therapeutic agents (e.g., chemotherapeutic agents, targeting agents, immunotherapy agents, etc.) previously-described may be combined with one or more adjunctive agents, including anesthetics, anti-inflammatory agents, antibiotics and/or antimicrobial agents, and/or antifungal agents. The anesthetics include, but are not limited to, bupivacaine, ropivacaine, mepivacaine, etidocaine, levobupivacaine, trimecaine, carticaine, articaine, lidocaine, prilocaine, benzocaine, procaine, tetracaine, chloroprocaine, and/or combinations thereof. The anti-inflammatory agents include, but are not limited to, prednisone, betamethasone, cortisone, dexamethasone, hydrocortisone, methylprednisolone, aspirin, Ibuprofen, naproxen sodium, diclofenac, diclofenac-misoprostol, celecoxib, piroxicam, indomethacin, meloxicam, ketoprofen, sulindac, diflunisal, nabumetone, oxaprozin, tolmetin, salsalate, etodolac, fenoprofen, flurbiprofen, ketorolac, meclofenamate, mefenamic acid, COX-2 inhibitors, and/or combinations thereof. The antibiotics and/or antimicrobial agents include, but are not limited to, amoxicillin, amoxicillin/clavulanate, cephalexin, ciprofloxacin, clindamycin, metronidazole, azithromycin, levofloxacin, sulfamethoxazole/trimethoprim, tetracycline(s), minocycline, tigecycline, doxycycline, rifampin, triclosan, chlorhexidine, penicillin(s), aminoglycides, quinolones, fluoroquinolones, vancomycin, gentamycin, cephalosporin(s), carbapenems, imipenem, ertapenem, antimicrobial peptides, cecropin-mellitin, magainin, dermaseptin, cathelicidin, α-defensins, α-protegrins, and/or combinations thereof. The antifungal agents include, but are not limited to, ketoconazole, clortrimazole, miconazole, econazole, intraconazole, fluconazole, bifoconazole, terconazole, butaconazole, tioconazole, oxiconazole, sulconazole, saperconazole, voriconazole, terbinafine, amorolfine, naftifine, griseofulvin, haloprogin, butenafine, tolnaftate, nystatin, cyclohexamide, ciclopirox, flucytosine, terbinafine, amphotericin, and/or combinations thereof.

2. Depot Payload and Release Rates

In some embodiments, the total payload (e.g., the total therapeutic agent or combination of therapeutic agent and adjunctive agent) of the depot 100 may be at least 100 mg, at least 150 mg, at least 200 mg, at least 300 mg, at least 400 mg, at least 500 mg, at least 600 mg, at least 700 mg, at least 800 mg, at least 900 mg, at least 1000 mg.

In some embodiments, the depot 100 is configured to release the therapeutic agent through the duration of release at a rate of from about 0.1 mg/day to about 200 mg/day, about 0.1 mg/day to about 150 mg/day, about 0.1 mg/day to about 100 mg/day, about 0.1 mg/day to about 90 mg/day, about 0.1 mg/day to about 80 mg/day, about 0.1 mg/day to about 70 mg/day, about 0.1 mg/day to about 60 mg/day, about 0.1 mg/day to about 50 mg/day, about 0.1 mg/day to about 40 mg/day, about 0.1 mg/day to about 30 mg/day, about 1 mg/day to about 30 mg/day, about 1 mg/day to about 20 mg/day, about 5 mg/day to about 20 mg/day, about 10 mg/day to about 20 mg/day, or about 15 mg/day to about 20 mg/day, or any other incremental ranges therebetween (e.g., 50 mg/day to 100 mg/day, 150 mg/day to 175 mg/day, etc.).

In some embodiments, the depot 100 may be configured to release the therapeutic agent through the duration of release at a rate no more than 100 mg/day, no more than 90 mg/day, no more than 80 mg/day, no more than 70 mg/day, no more than 60 mg/day, no more than 50 mg/day, no more than 40 mg/day, no more than 30 mg/day, no more than 20 mg/day, no more than 15 mg/day, no more than 10 mg/day, no more than 5 mg/day, no more than 1 mg/day, no more than 0.5 mg/day, no more than 0.1 mg/day, no more than 75 μg/day, no more than 50 μg/day, no more than 25 μg/day, or no more than 10 μg/day.

As previously described, in some embodiments the depot 100 is configured to release the therapeutic agent over a varying period of time (i.e., duration of release). For those embodiments associated with treating lung cancer, the depot 100 can be configured to release the therapeutic agent and/or adjunctive agents at the lung for no less than 1 day, no less than 2 days, no less than 3 days, no less than 4 days, no less than 5 days, no less than 6 days, no less than 7 days, no less than 8 days, no less than 9 days, no less than 10 days, no less than 11 days, no less than 12 days, no less than 13 days, no less than 14 days, no less than 15 days, no less than 16 days, no less than 17 days, no less than 18 days, no less than 19 days, no less than 20 days, no less than 21 days, no less than 22 days, no less than 23 days, no less than 24 days, no less than 25 days, no less than 26 days, no less than 27 days, no less than 28 days, no less than 29 days, no less than 30 days, no less than 40 days, no less than 50 days, no less than 60 days, no less than 70 days, no less than 90 days, no less than 100 days, no less than 150 days, no less than 200 days, no less than 300 days, or no less than 365 days.

As previously described, the depot 100 of the present technology can achieve a release profile or kinetics that suits the objectives of the intended therapy. For those embodiments directed to treating lung cancer, including the recurrence thereof, the release profile may be (a) zero-order such that release of the payload of therapeutic agent is at a substantially steady rate over the duration of release, (b) first-order such that release of the payload of the therapeutic agent increases in a substantially linear manner over the duration of release, or (c) a second-order such that release of the payload of the therapeutic agent occurs at a high, substantially linear rate for a first period of time and then at a lower, substantially linear rate for a second period of time over the duration of release.

Each of these release profiles can be advantageous for lung cancer patients depending on their particular condition. For example, a zero-order release profile may be desired when cancerous tissue is concentrated in a single mass that has been removed and the therapeutic agent is used predominantly to prevent recurrence. In such cases, release of the therapeutic agent in a substantially consistent manner over a duration of release can maximize the amount of time drug is released from the depot, thereby maximizing the amount of time that recurrence is actively limited by the therapeutic agent. As another example, a second-order release profile may be desired when cancerous tissue is present is still present in portions of the lung. In such cases, release of therapeutic agent during a first period of time at the higher rate is used to first target the cancerous tissue, and a subsequent release of therapeutic agent during a second period of time at the lower rate is used to prevent recurrence. Embodiments of the present technology enable the depot to be tuned according to the optimal treatment needed for each patient.

A. Specific Design Embodiments

The depots 100 of the present technology previously described are generally applicable to treating lung cancer. In some embodiments, certain form factors may be particularly beneficial to achieve more effective treatment. For example, depots 100 that include a configuration resembling a microspherical depot (e.g., microcylinders, pellets, beads, or the like, as previously described) may be particularly beneficial for treating lung cancer. Specifically, a microspherical depot, e.g., having a 1 mm diameter or maximum lateral length, can be placed in or proximate cancerous tissue of the lung via multiple delivery methods, including transbronchially and transarterially. For transbronchial delivery, cancerous lung tissue can be located and biopsied, e.g., using endobronchial ultrasound or electromagnetic navigation bronchoscopy, and then treated thereafter via deposition of the microspherical depot. For transarterial delivery, arteries that perfuse the lung are sufficiently large, thus enabling intravascular, catheter-based delivery of microspherical depots to cancerous lung tissue.

Other depot configurations that may be particularly beneficial for treating cancerous lung tissue include a layered design, such as those depot embodiments comprising a therapeutic region including a first portion having a therapeutic agent, and a second portion having an adjunctive agent (e.g., an immunotherapeutic agent, anesthetic, anti-inflammatory agent, antibiotic agent and/or antifungal agent). Such embodiments can provide the combined release (e.g., simultaneous or sequential release) of the therapeutic agent and adjunctive agent.

Figure 67:
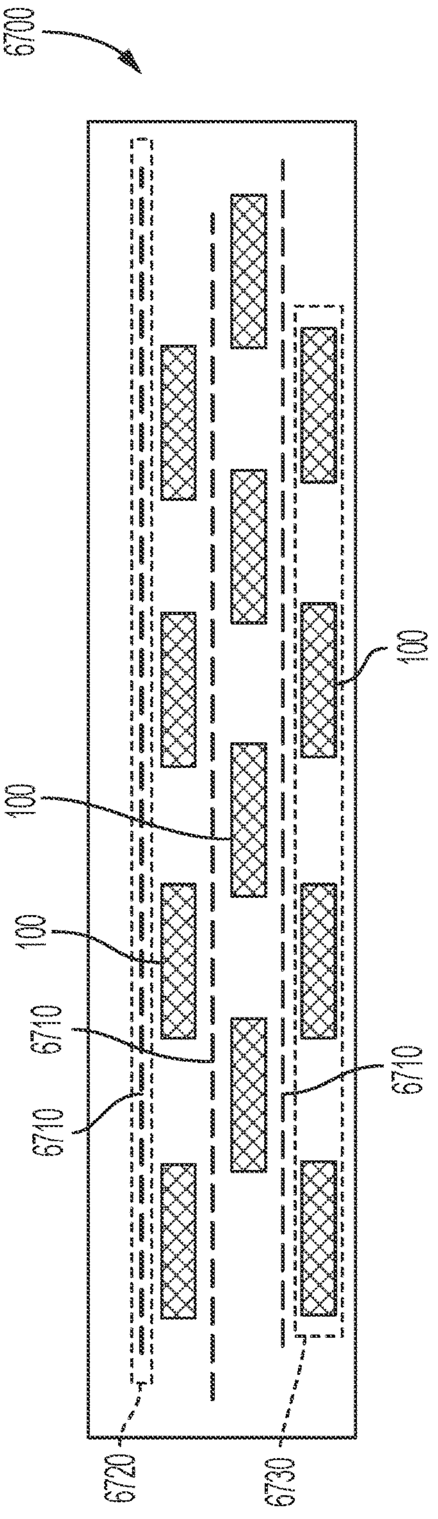
FIG. 67 is a staple buttress configured for use with the depots of the present technology.

Other depot configurations that may be particularly beneficial for treating cancerous lung tissue can include depots configured to be disposed in a staple buttress. As previously described, when a portion of the lung is removed/resected, a stapler (e.g., Medtronic's Endo GIA™ Reinforced Reload stapler) is typically used to seal the edges of the lung to prevent leakage of air. A staple buttress can come preloaded on the stapler and be used to create a more robust seal against the tissue. FIG. 67 illustrates a top view of a staple buttress 6700 including a plurality of depots 100 in accordance with the present technology. As shown in the illustrated embodiment, the buttress 6700 includes a fixation region 6720 comprising staples 6710, and a drug-releasing region 6730 comprising the depots 100. The drug-releasing region 6730 can include any area of the buttress 6700 other than the fixation region 6720, such that the fixation region 6720 does not inhibit or impede the depot's 100 ability to release therapeutic agent to the surrounding area. The staples 6710 are configured to penetrate tissue and the buttress 6700 to create a seal at edge portions of a resected organ. The depots 100 are coupled to the buttress 6700, e.g., via one or more fixation structures or means (e.g., barbs, hooks, protrusions, sutures, etc.). As a specific example, the depots 100 can be coupled to the buttress 6700 via a suture extending through a fixation member of the depot 100. The buttress 6700 can be made in part or in whole of PGA and/or TMC (e.g., a PGA or TMC mesh). In some embodiments, the buttress 6700 can be coated, e.g., with PLGA and/or PEG.

As shown in the illustrated embodiment, the depots 100 can be dispersed throughout the buttress to provide a relatively uniform release of therapeutic agent to the surrounding area. In other embodiments, however, the depots 100 may be concentrated in an area (e.g., the upper area, lower area, right side, left side, upper right area, lower left area, etc.) of the buttress 6700, e.g., to deliver a more concentrated dosage of therapeutic agent to a particular region of the lung, such as where a mass of cancerous tissue is known to exist.

As shown in the illustrated embodiment, the depots 100 are disposed over (e.g., on an upper surface) the buttress 6700 such that the buttress 6700 is between the depots 100 and the tissue. In other embodiments, the depots 100 can be disposed beneath the buttress 6700 such that the depots 100 are between the tissue and portions of the buttress 6700. In such embodiments, the cover provided by the buttress 6700 can slow the degradation of the depot 100, thereby extending the duration of release of the depot 100.

Figure 70:
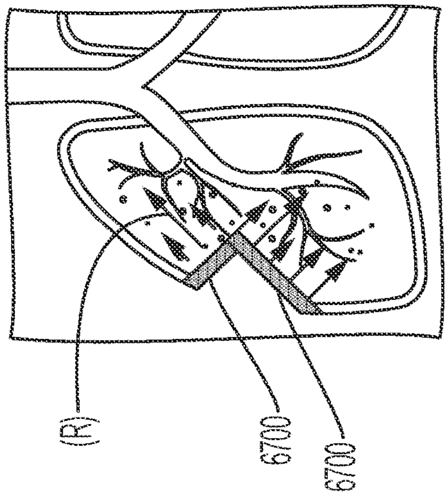
FIGS. 68-70 are partially-schematic illustrations of the staple buttress in FIG. 67 being implanted following a resection procedure in accordance with the present technology.
Figure 69:
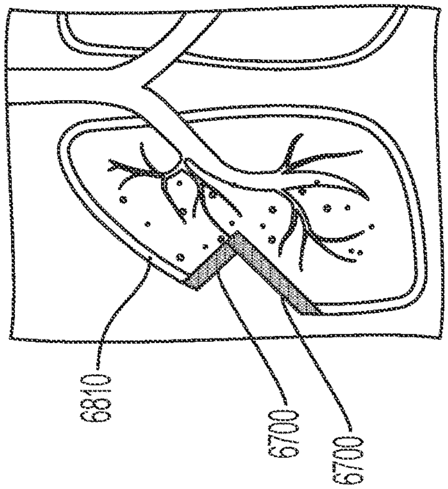
Figure 68:
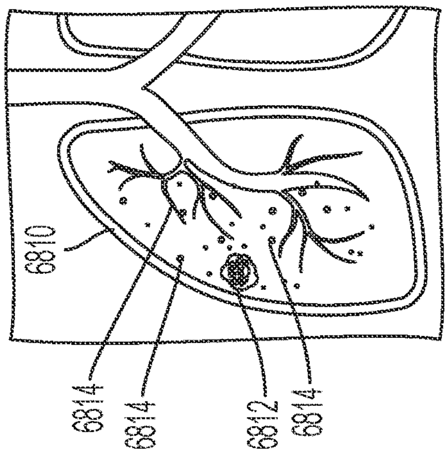

FIGS. 68-70 are partially-schematic illustrations of the staple buttress 6700 in FIG. 67 being implanted following a resection procedure. Specifically, FIG. 68 illustrates a lung 6810 having a tumor 6812 and other adjacent cancerous tissue 6814, FIG. 68 illustrates the lung 6810 after the tumor 6812 has been removed via wedge resection and buttresses 6700 have been implanted, and FIG. 69 illustrates the release (R) of therapeutic agents from the buttresses 6700. As shown in FIG. 69, the release (R) of therapeutic agent extends varying distances from the buttresses 6700. This variability may be caused by the placement (e.g., the concentration) of depots 100 on the buttresses 6700, wherein more depots 100 enables therapeutic agent to be delivered to more peripheral areas of the lung 6810 relative to the buttresses 6700 and less depots 100 enables therapeutic agent to be deliver to areas more proximate to the buttresses 6700.

B. Routes of Administration and Clinical Endpoints

Any of the depot embodiments and delivery approaches described can be used for local sustained delivery of therapeutic agents for treatment of lung cancer. In various embodiments, treatment of lung cancer can involve local delivery of one or more therapeutic agents (e.g., via one or more depot(s) of the present technology) administrated using any suitable route. In some embodiments, one or more depots can be delivered to a treatment site using a percutaneous approach such as direct needle injection into and/or around the tumor using imaging such as CT, MRI, or ultrasound. In some embodiments, one or more depots can be delivered via thoracoscopic or open surgical access via direction surgical visualization and/or palpation using direct needle (or trocar, etc.) injection into or around the tumor. As another example, one or more depots can be delivered endoscopically using electromagnetic navigation bronchoscopy or endobronchial ultrasound. Endoscopic delivery can utilize needle injection from an airway lumen into the tumor, a drug-coated stent or stent graft within an airway lumen, and/or a stent made of a bioresorbable depot within an airway lumen.

Any suitable therapeutic agents, whether delivered locally (e.g., via one or more depots as described herein), systemically (e.g., via intravenous delivery or otherwise), or both, can be used for treatment of lung cancers. Example therapeutic agents include chemotherapeutic agents, such as cisplatin, carboplatin, gemcitabine, capecitabine, paclitaxel, nab-paclitaxel, docetaxel, pemetrexed, vinorelbine, or any combination thereof.

In some embodiments, one or more locally delivered therapeutic agents can be used in combination with one or more systemically delivered therapeutic agents and/or in combination with other treatments (e.g., surgery, radiation, etc.). In some embodiments, the systemically delivered therapeutic agents can include any one of the chemotherapeutic agents listed above, as well as targeted agents (e.g., EGFR inhibitors (e.g., osimertinib, erlotinib, afatinib, dacomitinib, gefitinib), anaplastic lymphoma kinase (ALK) inhibitors (e.g., alectinib, brigatinib, cretinib, crizotinib, lorlatinib), crizotinib or etrecetinib (targeting ROSI gene), Larotrectinib (targeting NTRK fusion), dabrafenib or trametinib (targeting BRAF V600E), capmatinib (targeting MET Exon 14 skipping), selpercatinib (targeting RET fusion), etc.), immunotherapeutics (e.g., PD-1/PD-L1 antibodies such as Pembrolizumab, atezolizumab, durvalumab, nivolumab; CTLA-4 antibodies such as ipilimumab), or any combination thereof.

Treatment of lung cancers as disclosed herein can be utilized to achieve one or more endpoints. In various embodiments, such endpoints can involve clinical measures for a particular patient or a population of patients (e.g., a population undergoing a clinical trial). In some embodiments, a clinical trial for assessing the efficacy of local sustained delivery as described herein can include a control group receiving standard treatment (e.g., surgical intervention, radiation therapy, etc.) and a treatment group receiving standard treatment in addition to locally delivered therapeutic agent(s) as described herein. Examples of suitable endpoints include: (1) overall survival (time from treatment (or randomization) to death due to any cause); (2) time to progression; (3) progression-free survival; (4) disease-free survival and event-free survival; (5) recurrent free survival; (6) duration of response; (7) overall/objective response rate (e.g., assigning a score of complete response (CR), partial response (PR), or stable disease (SD)); (8) quality of life measures (e.g., based on patient survey or other input such as EORTC QLC-30+LC13, the lung cancer symptom scale (LCSS), or FACT-G+FACT-L); and (9) assessment of relevant biomarkers (e.g., EFGR).

Any one or any combination of these endpoints can be utilized to assess and/or establish efficacy of treatment of lung cancer via depots of the present technology, whether used alone or in combination with one or more other treatments.

X. Prostate Cancer

Figure 72A:
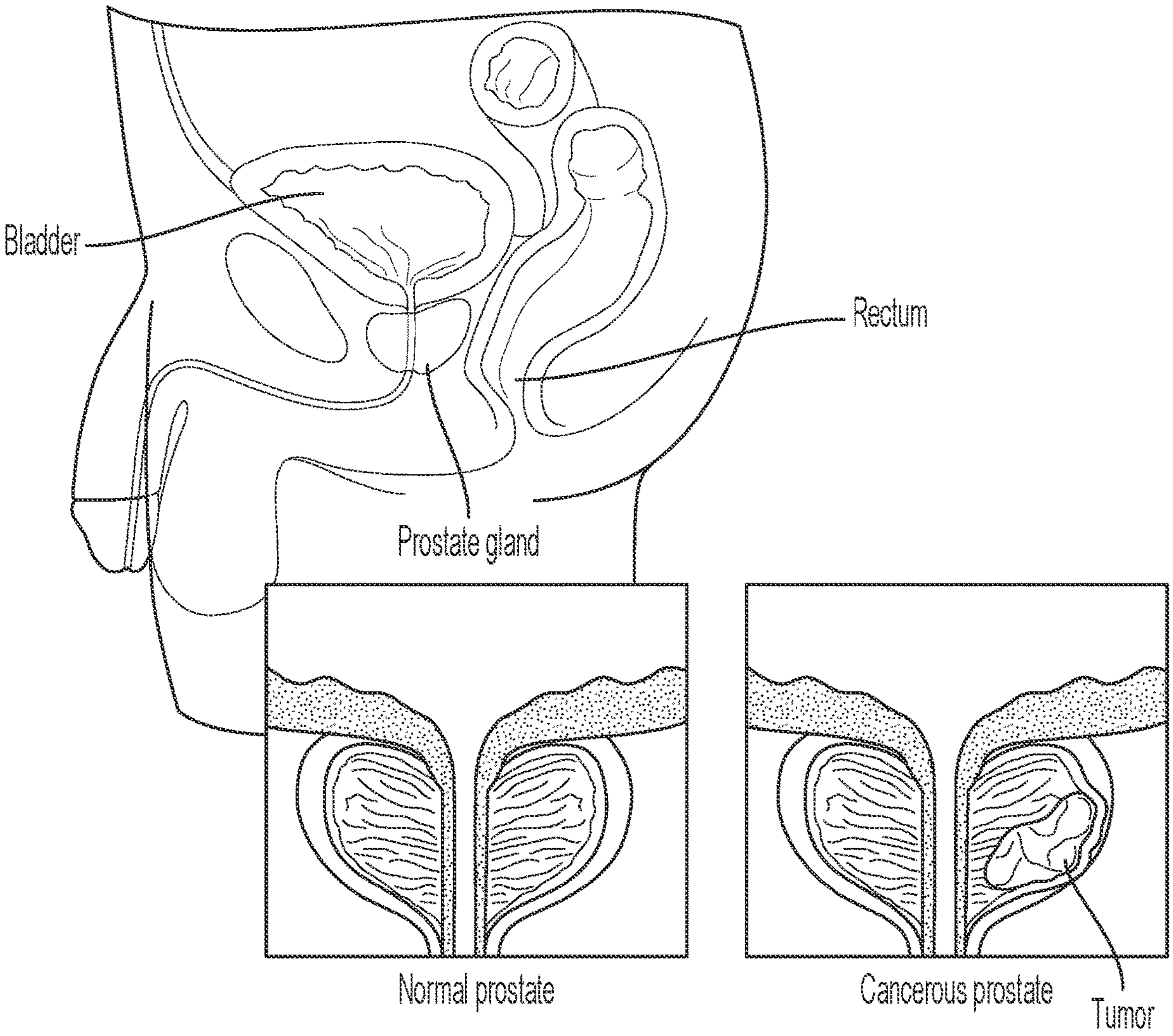
FIG. 72A depicts a normal human prostate gland and a cancerous human prostate gland.

FIG. 72A depicts a normal human prostate gland and a cancerous human prostate gland. The prostate is commonly described as being the size of a walnut. Roughly two-thirds of the prostate is glandular in structure and the remaining third is fibromuscular. The gland itself is surrounded by a thin fibrous capsule, similar to the adventitia in large blood vessels. The prostate is positioned inferior to the neck of the bladder, superior to the external urethral sphincter (see FIG. 72C), and anterior of the rectum.

Prostate cancer is the second leading cause of cancer death in men in the United States. About 1 in 9 men will be diagnosed with prostate cancer during their lifetime, and about 1 in 41 men will die of prostate cancer. Most prostate cancers (90%) are detected early when the disease is still local or regional (i.e., confined to the prostate and nearby organs) and have a 5-year survival rate of nearly 100%. For men diagnosed with prostate cancer that has metastasized, however, the 5-year survival rate is 30%.

The recommended approach for treating localized prostate cancer depends on the likelihood of the cancer spreading. "High-risk" tumors have a high risk of progression, and thus the recommended treatment approach is surgical removal of the prostate ("radical prostatectomy") or radiation therapy. In contrast, "low-risk" tumors have a low risk of progression and typically do not require surgery or radiation therapy. Instead, the tumor is monitored regularly ("active surveillance") and only treated with radiotherapy or surgery if the tumor grows or becomes more aggressive.

Nevertheless, anxiety about disease progression often leads to low-risk prostate cancer patients opting for the more radical treatment approach-such as prostate removal surgery or radiation therapy-despite being eligible for active surveillance. High-risk prostate cancer accounts for 24% of all localized prostate cancer diagnoses, yet 84% of localized prostate cancer patients undergo prostate removal or radiation therapy. While the more radical treatment therapies may come with greater peace of mind, these therapies are also accompanied by significant side effects. For example, prostate removal surgery causes erectile dysfunction in more than 50% of patients and urinary incontinence in 5-30% of patients. External beam radiation causes erectile dysfunction in more than 50% of patients, urinary issues in 30-40% of patients, and bowel issues in 33% of patients. Brachytherapy causes urinary issues in more than 70% of patients, erectile dysfunction in 25-50% of patients, and bowel issues in 17% of patients. In addition, radiation therapy patients cannot have any future prostate surgery, should the need arise, because of the damage caused to the patient's peri-prostatic tissue during radiation treatment.

Figure 72B:
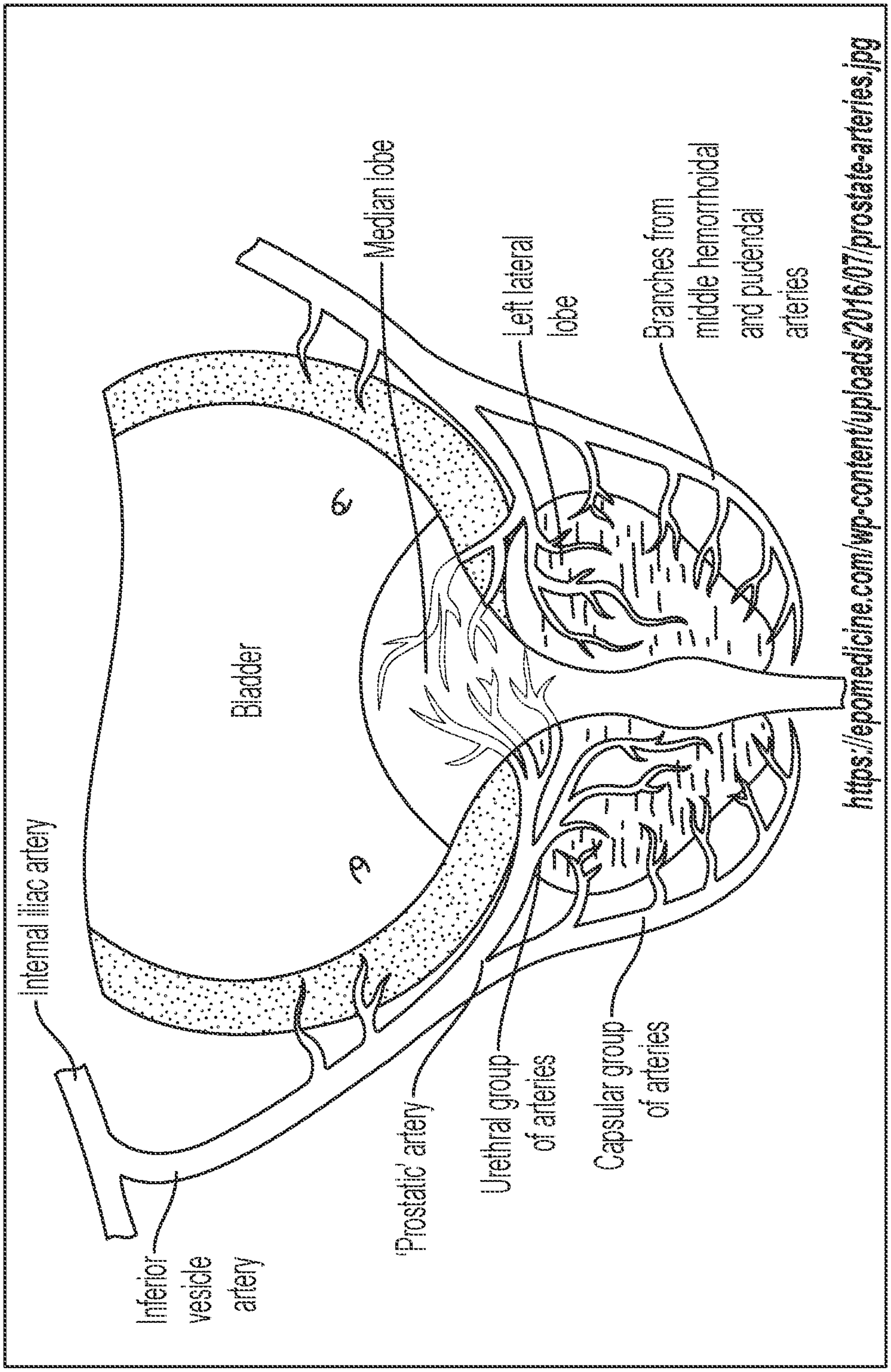
FIGS. 72B-72D are different views of a human prostate gland and selective portions of the local anatomy.
Figure 72C:
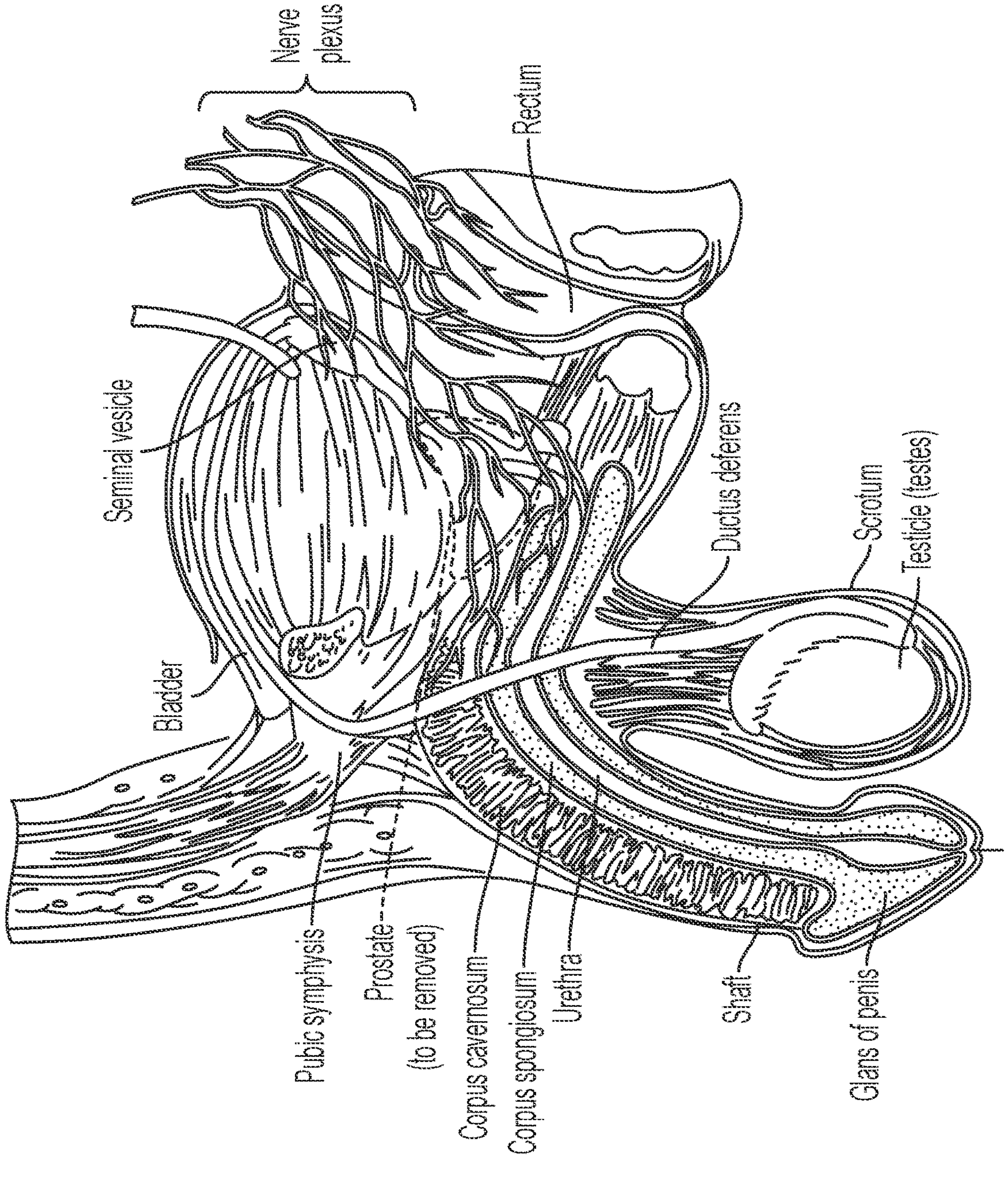
Figure 72D:
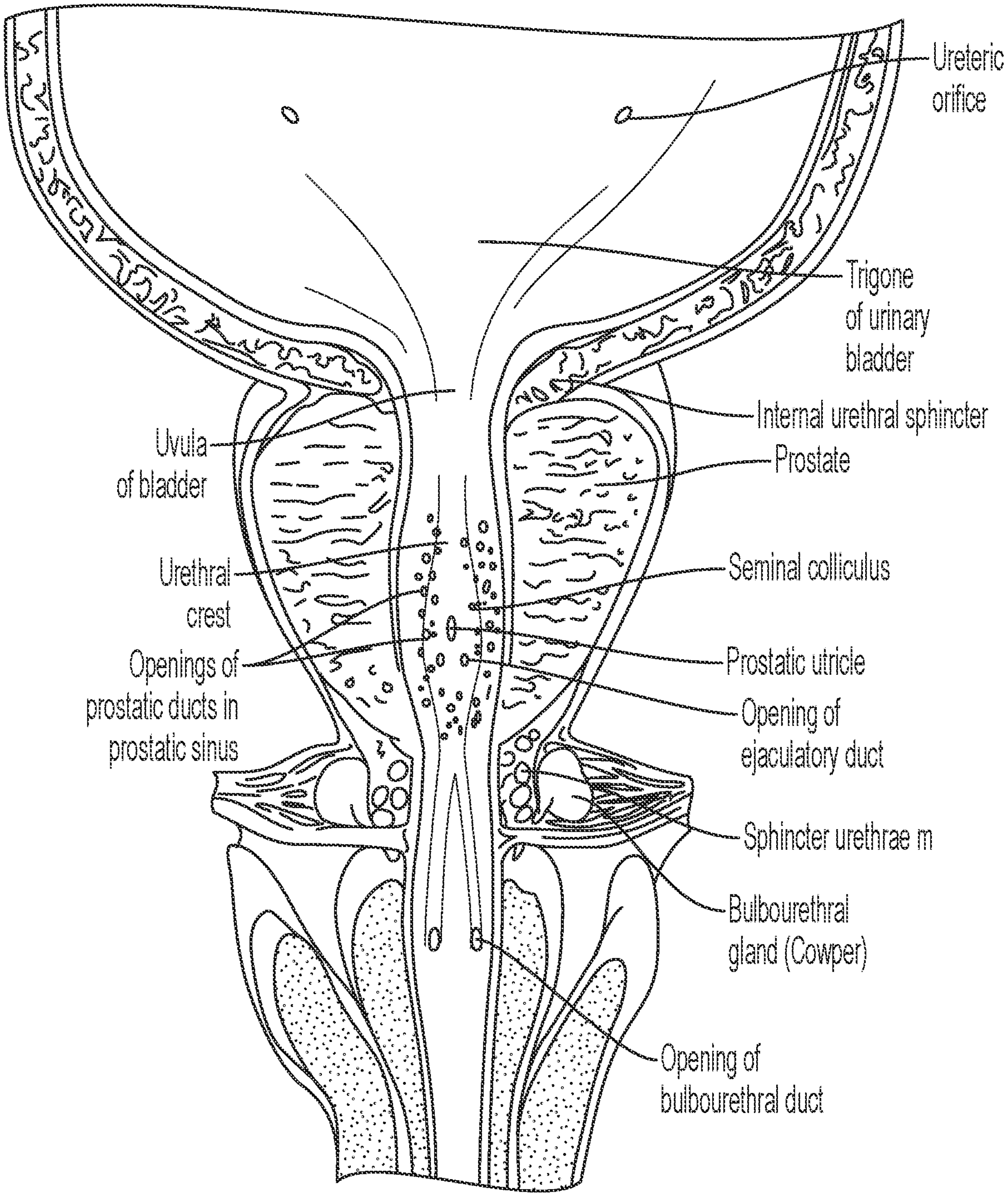

To better appreciate the foregoing side effects, FIGS. 72B-72D show different views of the prostate gland and selective portions of the local anatomy that are commonly disrupted/injured during conventional prostate therapies. Post-therapy erectile dysfunction, for example, is typically the result of damage to the arteries and nerves along prostate capsule. FIG. 72B shows the arterial supply to the prostate, and FIG. 72C shows the nerves proximate the prostate. As shown in FIG. 72B, the arterial supply to the prostate comes from the prostatic arteries, which are mainly derived from the internal iliac arteries. Some branches may also arise from the internal pudendal and middle rectal arteries. Venous drainage of the prostate is via the prostatic venous plexus, draining into the internal iliac veins. However, the prostatic venous plexus also connects posteriorly by networks of veins, including the Batson venous plexus, to the internal vertebral venous plexus.

As shown in FIG. 72C, the prostate receives sympathetic, parasympathetic and sensory innervation from the inferior hypogastric plexus. The smooth muscle of the prostate gland is innervated by sympathetic fibers, which activate during ejaculation. The prostate is flanked by the two neurovascular bundles that travel through the pelvic floor towards the penis, supplying it with nerve fibers and blood vessels for the corpora cavernosa. The integrity of these bundles is critical for normal erection. During surgery for prostate cancer (radical prostatectomy), damage is often inevitable to one or both of these bundles, resulting in impairment of erectile function.

As previously mentioned, urethral sphincter incompetence is one of the most important contributing factors for post-radical prostatectomy urinary incontinence. Post-therapy incontinence is typically caused by injury to all or a portion of the urethral sphincter. As shown in FIG. 72D, the urethral sphincter is a muscular structure comprising the external and internal urethral sphincters that together regulate the outflow of urine from the bladder into the urethra. The internal sphincter is located where the bladder neck (just superior to the prostate), and the external sphincter sits below the prostate near the pelvic floor and is continuous with the isthmus of the prostate.

The implantable depots of the present technology address the shortcomings of conventional treatments by providing a localized, sustained, controlled release of one or more therapeutic agents directly to cancerous prostate tissue to treat prostate cancer and to prostate tissue that may have pre-cancerous tissue such as PIN, or tissue undergoing hyperplasia (such as tissue associated with BPH). In several aspects of the technology, the depots are configured to provide a controlled, whole gland therapy to reduce the risk of disease progression while inducing less side effects than existing approaches and preserving the patient's options to perform future radical therapies. In some cases, the localized, sustained delivery of therapeutic agents may weaken the tumor such that the tumor is more susceptible to a lower dose of radiation.

A. Example Depots for Treating Prostate Cancer

Figure 73A:
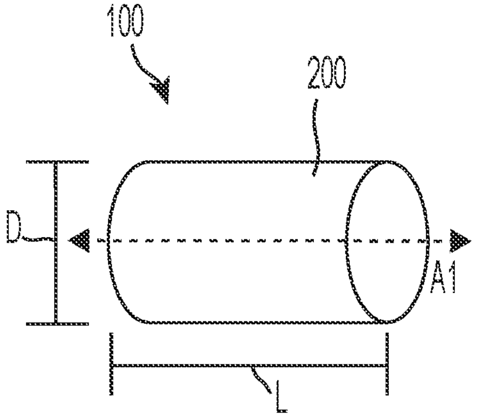
FIGS. 73A and 73B illustrate examples of depots of the present technology configured to treat prostate cancer.

FIG. 73A shows an example depot 100 configured to be implanted at or within a prostate gland of a human patient to treat prostate cancer in accordance with the present technology. As shown in FIG. 73A, in some embodiments the depot 100 may have a generally elongated form. As previously noted, "elongated depot" or an "elongated form" as used herein refers to a depot configuration in which the depot 100 has a length L between its ends along a first axis A1 (e.g., a longitudinal axis) that is at least 1.1, 1.2, 1.3, 1.4, 1.5, 1.6, 1.7, 1.8, 1.9, 2, 3, 4, 5, 6, 7, 8, 9, 10, 20, or 30 times greater than a maximum dimension D of a cross-sectional slice of the depot 100 within a plane orthogonal to the first axis A1. The elongated form may be particularly well suited for injection or insertion to a location within the prostate gland through a needle or other suitable delivery device. Additionally or alternatively, the elongated depots 100 may be implanted using other techniques, for example surgical implantation through an open incision, a minimally invasive procedure (e.g. laparoscopic surgery), or any other suitable technique based on the application.

As shown in FIG. 73A, the elongated depot 100 may comprise a substantially cylindrical member formed of a polymer mixed with a locally acting therapeutic agent. The therapeutic agent may be any drug or combination of drugs (such as any of the therapeutic agents disclosed herein, including those described elsewhere herein) configured to treat prostate cancer via sustained, local exposure to cancerous (or pre-cancerous) tissue. The depot 100 may include a therapeutic region 200 representing the portion of the depot 100 containing the therapeutic agent. For example, in some embodiments the depot 100 may include polymer-only portions, and in some embodiments the therapeutic agent may be dispersed throughout the entire depot (in which case the entire depot is a therapeutic region). The therapeutic region 200 may comprise all or a portion of the depot 100, as detailed herein. The therapeutic region 200 may optionally include a releasing agent, such as any of the releasing agents described herein.

Figure 73B:
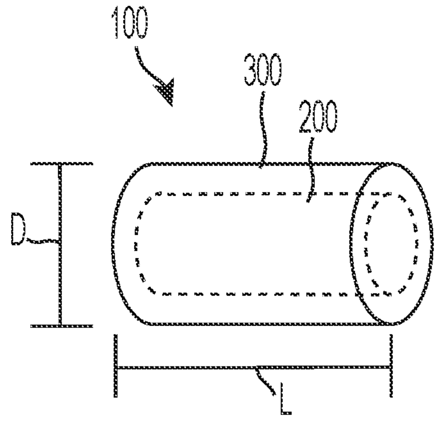

According to some embodiments, for example as shown in FIG. 73B, the depot 100 may include a control region 300 in addition to the therapeutic region 200. For example, as shown in FIG. 73B, the depot 100 may comprise a therapeutic region 200 containing a therapeutic agent configured to treat prostate cancer and a control region 300 at least partially surrounding the therapeutic region 200 to control release of the therapeutic agent from the depot 100. The therapeutic region 200 may optionally include a bioresorbable polymer (such as any of the polymers described herein) and/or a releasing agent (such as any of the releasing agents described herein). The control region 300 may include a bioresorbable polymer (such as any of the polymers described herein) mixed with a releasing agent (such as any of the releasing agents described herein), but does not include any therapeutic agent at least prior to implantation. In some embodiments, the control region 300 may include some therapeutic agent prior to implantation, for example having a lower concentration of therapeutic agent than the therapeutic region 200.

As shown in FIGS. 73A and 73B, the elongated depot 100 may have a substantially cylindrical, columnar, and/or rod-like shape such that the cross-sectional shape of the depot 100 is generally circular and the cross-sectional dimension D is the diameter of the circle. A cylindrically-shaped depot (such as those disclosed herein) may be especially beneficial for needle delivery as the cylindrical shape provides the maximum volume per unit length ratio for a depot delivered through a needle. Maximizing the volume per unit length of the depot may be advantageous for delivering a large payload of the therapeutic agent. In some instances, however, a generally cylindrical depot may release the therapeutic agent too slowly for the desired prostate application. In order to increase the release rate while using the same total depot volume, the generally cylindrical depot may be in the form of a plurality of depot(s) that, when put together, form a generally cylindrical depot. The resulting depot assembly comprised of the plurality of depots will have a greater surface area than the generally cylindrical depot formed of a unitary member. In some embodiments, for example, the depot(s) 100 may comprise a plurality of discs, a plurality of half-cylinders, a plurality of elongated pie-slices, etc. In these and other embodiments, the individual depots 100 may comprise a plurality of fibers or microspheres that are organized together to have a generally cylindrical form.

It will be appreciated that the depots of the present technology configured to treat prostate cancer may comprise any of the depots discussed within the present section and/or any of the depots disclosed herein, including the elongated depot configurations disclosed with respect to FIGS. 20-35. Moreover, the elongated depot 100 may have other elongated shapes along all or a portion of its length L. For example, the depot 100 may be in the form of a ribbon-like strip and thus have a square or rectangular cross-sectional shape. In other embodiments, the elongated depot 100 may have a circular, triangular, rhomboid, or other polygonal or non-polygonal cross-sectional shape based on the desired application. The elongated depot 100 may be a solid or semi-solid formulation with sufficient column strength to be pushed or pulled from a delivery device and sufficient durability and/or structural integrity to maintain its shape while the therapeutic agent is released into the surrounding anatomy for the desired duration of release.

The elongated depot 100 may have an average diameter D along its length L of about 0.5 mm to about 3 mm, about 0.5 mm to about 2 mm, about 0.5 mm to about 1.5 mm, no greater than 1.5 mm, or no greater than 1.0 mm. The depot 100, for example, may have a diameter D that is configured to be slidably received within a lumen of a 16-, 17-, or 18-gauge needle. The depot 100 may have a length L of about 50 mm to about 4 cm, of about 50 mm to about 3 cm, of about 500 mm to about 2.5 cm, of about 1 cm to about 3 cm, of about 1 cm to 2 cm, about 1 cm or less, about 1.1 cm or less, about 1.2 cm or less, about 1.3 cm or less, about 1.4 cm or less, about 1.5 cm or less, about 1.6 cm or less, about 1.7 cm or less, about 1.8 cm or less, about 1.9 cm or less, or about 2 cm or less. Moreover, the ratio of the length L of the depot 100 to an average cross-sectional dimension of the depot 100 may be at least 10/1, at least 12.5/1, at least 15/1, at least 17.5/1, at least 20/1, at least 22.5/1, at least 25/1, at least 27.5/1, at least 30/1, at least 32.5/1, at least 35/1, at least 37.5/1, or at least 40/1. In some embodiments, the depot 100 has a volume of no more than 10 $mm^3$, 20 $mm^3$, 40 $mm^3$, 50 $mm^3$, 60 $mm^3$, 70 $mm^3$, 80 $mm^3$, 90 $mm^3$, 100 $mm^3$, 110 $mm^3$, 120 $mm^3$, 130 $mm^3$, 140 $mm^3$, 150 $mm^3$, 160 $mm^3$, 170 $mm^3$, 180 $mm^3$, 190 $mm^3$, 200 $mm^3$, 210 $mm^3$, or 220 $mm^3$.

Figure 74:
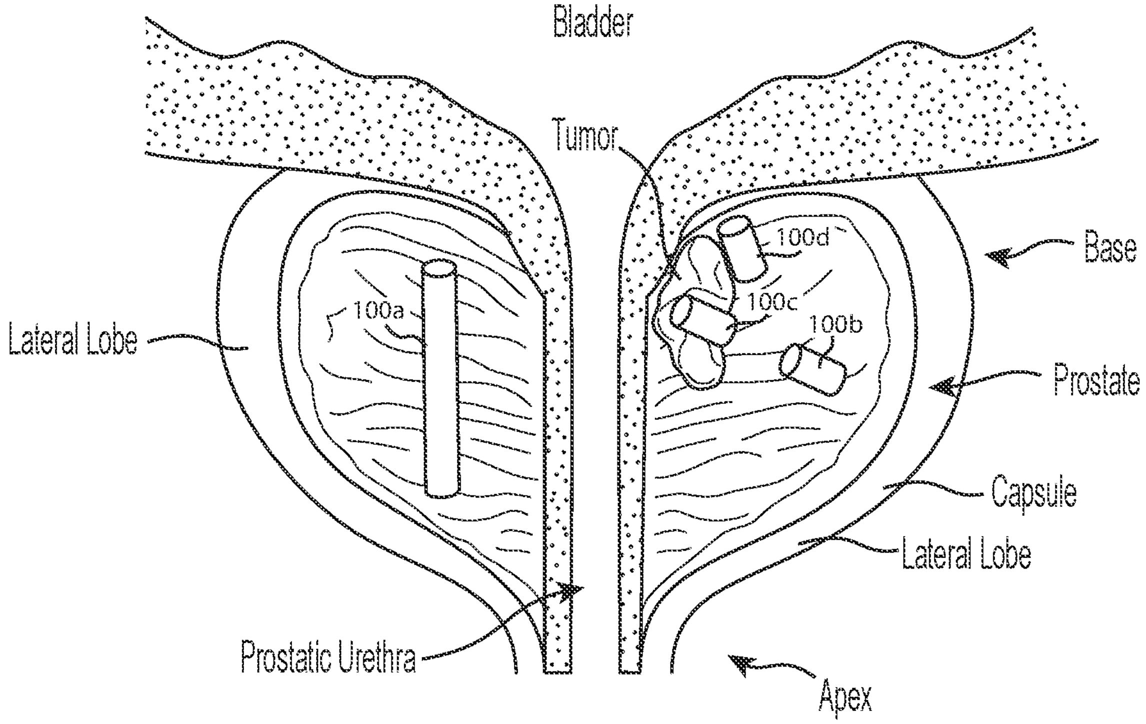
FIG. 74 shows a plurality of depots of the present technology implanted within a cancerous prostate gland.

FIG. 74 is a cross-sectional view of a prostate gland having multiple depots 100*a*-100*d* implanted therein. Although four depots are shown in FIG. 74, depot systems of the present technology may include more or fewer depots and/or may be configured to treat prostate cancer with more or fewer depots. For example, some aspects of the present technology include a single depot configured to be implanted within the prostate gland to treat prostate cancer. Other aspects of the present technology include depot systems comprising a plurality of depots configured to be positioned within the prostate gland at the same time. In such embodiments, the therapeutic payload may be spread out amongst the plurality of depots such that, when implanted, the plurality of depots combine to release the therapeutic payload. Within a given depot system, the individual depots may have the same or different sizes, shapes, amount of therapeutic agent, releasing agent concentrations, type of therapeutic agent, type of polymer, etc. For ease of description, portions of the following discussion are with reference to a single depot. However, it will be appreciated that the same description applies to one, some, or all depots within a depot system of the present technology.

As shown in FIG. 74, the depot 100 may be configured to be positioned within the prostate gland such that the depot 100 is adjacent and/or in direct contact with the tumor (for example, see depots 100*d* and 100*c*). Depending on the shape and size of the tumor as well as the location of the tumor within the prostate, the depot 100 may be placed at a superior, lateral, posterior, medial, or inferior aspect of the tumor. In some embodiments, the depot 100 may be positioned partially or completely within the tumor (see depot 100*c*), or the depot 100 may be spaced apart from the tumor (for example, see depot 100*b*).

In some cases it may be beneficial to position at least one depot within a lobe of the prostate that does not include a detectable tumor. For example, some prostate cancers are invisible to magnetic resonance imaging (MRI) and go undetected. Pre-cancerous tissue, such as PIN, is also likely to go undetected. Prostate cancer is often multi-focal, and a patient with a visible (detectable) tumor at one prostate lobe and an MRI-invisible tumor or pre-cancerous tissue at a different lobe may only be treated at the site of the visible tumor, thereby leaving the invisible tumor or undetected pre-cancerous tissue untreated. Existing focal therapies such as MRI-guided laser ablation, cryotherapy, and high-intensity focused ultrasound (HIFU), for example, target only the parts of the prostate gland where the cancer is detected. In contrast, the depot systems of the present technology are configured to either provide focal therapy or provide whole gland therapy that treats both visible/detected and invisible/undetected tumors. While conventional radical treatments such as prostate removal and radiation therapy also achieve whole gland therapy, the tissue damage caused by these treatment methods is not contained to prostate tissue and causes permanent, significant side effects, such as erectile dysfunction and urinary incontinence. The novel depots 100 and depot systems of the present technology are configured to provide whole gland therapy via sustained release of high drug concentrations in a controlled, minimally-invasive manner such that the treatment is contained within the prostate and does not induce the side effects associated with radical therapies. Moreover, the sustained exposure to high concentrations of the therapeutic agent may weaken the tumor such that the tumor is more susceptible to radiation therapy or the agent may act as a radiosensitizer to the cancerous tissue. As such, the patient may receive therapeutic radiation therapy at a lower dose than would be required to achieve a similar therapeutic effect without the localized, sustained release of the therapeutic agent. The depots of the present technology thus provide the additional advantage of reducing a radiation side effect profile, both because the local drug delivery weakens the tumor and also because the depot may make the cancerous tissue more sensitive to radiation. Additionally, depots may be placed outside of the prostate to potentially shield critical non-target tissues from radiation. For example, one or more depots may be positioned between the prostate and the rectum to create space between the two and direct the drug towards the prostate. In other instances it may be beneficial to position one or more depots such that they create an effective treatment zone throughout the entire prostate.

In certain instances there may be certain areas where the concentration of therapeutic agent is high enough to cause necrosis of healthy prostate tissue in addition to the cancerous or prostate intraepithelial neoplastic tissue. This may be an acceptable side-effect of the treatment which kills the cancerous or neoplastic tissue.

Figure 75:
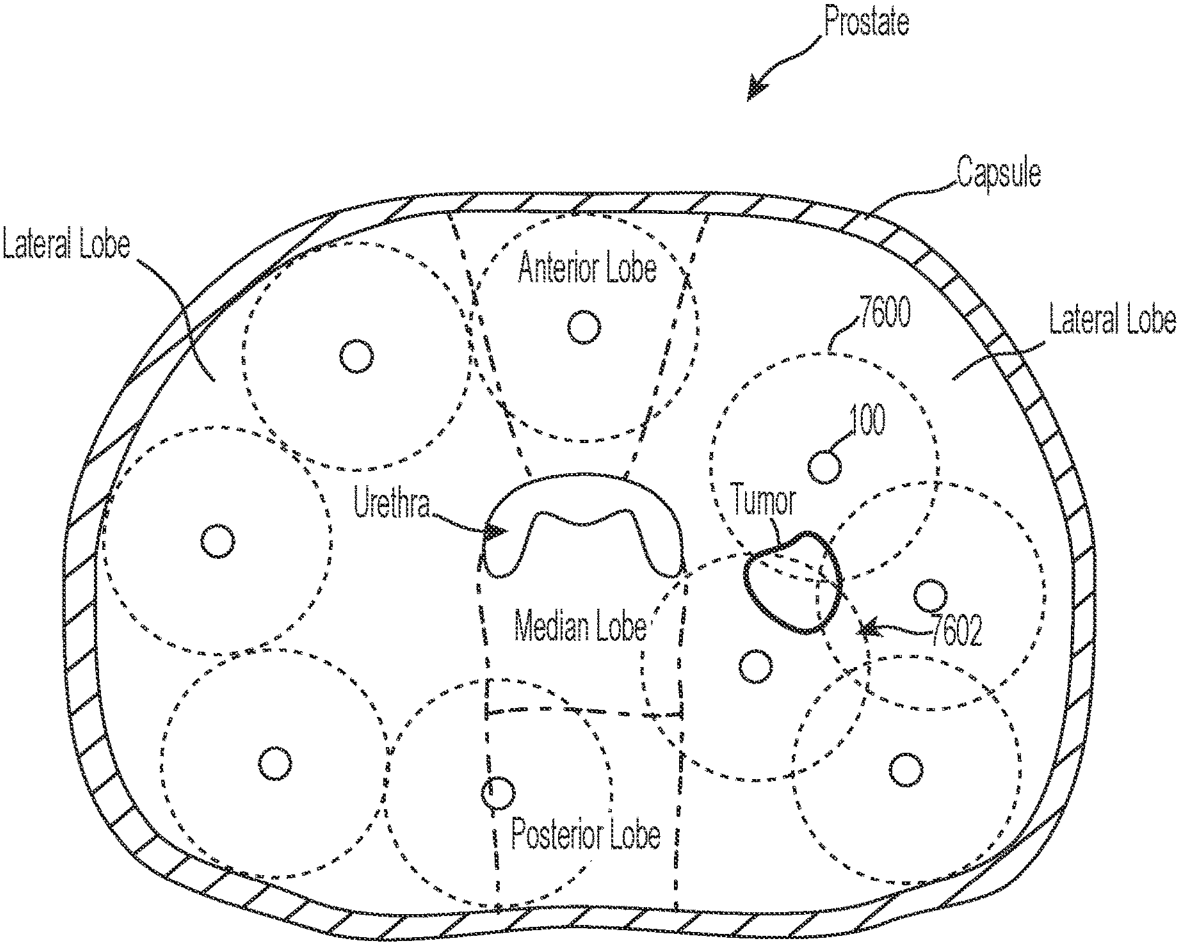
FIG. 75 depicts an example of therapeutic agent coverage for a plurality of depots of the present technology implanted within a prostate gland of a human patient.

FIG. 75 is a transverse view of a prostate gland with a plurality of depots 100 (only one labeled) implanted therein. As shown, each of the depots 100 may have a corresponding treatment zone 7600 (only one labeled), which represents an area surrounding the depot 100 in which the therapeutic agent released from the depot 100 provides a therapeutic effect. The depots 100 may be positioned within the prostate spaced apart from one another such that the respective treatment zones 7600 abut one another without excessive overlapping or excessive dosing in a specific area. The size, shape, and number of depots for implantation may be selected based on a desired coverage.

In some instances it may be beneficial to position two or more of the depots 100 at a distance from one another such that the treatment zones 7600 of the depots overlap to form a concentrated treatment zone 7602. In the example shown in FIG. 75, several of the depots 100 are clustered together within a lateral lobe near the tumor such that the tumor falls within a concentrated treatment zone 7602. As such, the tumor is exposed to a higher concentration of the therapeutic agent than other portions of the prostate. In other instances it may be beneficial to position one or more depots such that they create an effective treatment zone throughout the entire prostate.

In certain instances there may be certain areas where the concentration of therapeutic agent is high enough to cause necrosis of healthy prostate tissue in addition to the cancerous or prostate intraepithelial neoplastic tissue. This may be an acceptable side-effect of the treatment which kills the cancerous or neoplastic tissue.

As described above, certain critical nerve, arterial and muscular structures that reside on, near or outside of the prostate gland are often disrupted or damaged by more conventional prostate treatments (e.g., radical prostatectomy, radiation, etc.). Even with brachytherapy, where radioactive seeds are implanted within the prostate, these critical structures are subjected to toxic doses of radiation that originate from inside the prostate. It is desirable to achieve an exposure of therapeutic agent within the prostate that is sufficient to yield a therapeutic benefit while avoiding toxic exposure to critical, non-target structures residing outside of the prostate. Intra-prostate, pharmacological therapy described herein provides a localized, sustained release of agent(s) from within the prostate to achieve a high, sustained concentration of agent in the prostate without subjecting these critical, non-target structures to the same exposure. In particular, it is desirable to administer treatment from within the prostate, via the implantation of one or more drug releasing depots inside the prostate, to achieve a high local concentration of agent over time inside the prostate sufficient to cause toxicity of cancerous or neoplastic tissue while avoiding toxic exposure outside of the prostate and, particularly, avoiding toxic exposure to the aforementioned critical, non-target structures. This pharmacokinetic profile may optimize treatment of the cancer while minimizing complication.

The circumstance of a high, sustained concentration of therapeutic agent intra-prostate and a lower concentration of therapeutic agent extra-prostate may be achieved via capsular containment, whereby the capsule of the prostate creates a diffusion barrier preventing toxic doses of therapeutic agent from reaching these critical, non-target structures. Capsular containment is enabled by the dense capsular layer at the outer surface of the prostate, which is composed of an outer layer of epithelial cells and inner layers of fibromuscular and adipose tissue. Stamey et al. observed that systemic and local administration of antibiotics to treat bacterial prostatitis was ineffective because of the low resulting concentration of antibiotics in prostatic fluid resulting from the inability of the antibiotics to diffuse across the epithelial layer. It is anticipated that therapeutics agents released from the previously described depot/implant may be similarly challenged to travel across the capsular layer such that the concentration of agent within the prostate exceeds the concentration of drug outside the prostate. This capsular containment enables implantation of such depots into the prostate with the expectation and objective of achieving toxic exposure of cancerous tissue within the prostate while achieving non-toxic exposure outside of the prostate.

The concept of capsular containment is further exemplified by Wientjes et al. who identified "[s]everal properties of the prostate [that]make it an ideal candidate for regional [drug] therapy . . . enabling the achievement of high local drug concentrations whereas limiting toxicity to the extracapsular tissues." Wientjes et al., *Intraprostatic Chemotherapy: Distribution and Transport Mechanisms*, Clin Cancer Res 2005; 11(11). In particular, the fibromuscular stroma that separates the lobules within the prostate presents a diffusion barrier that allows for high concentrations of drug to be delivered into and maintained within the prostate. However, Wientjes et al. acknowledge that "the few attempts at developing this [prostate]treatment modality have not met with success." This presents a considerable opportunity for the technology disclosed herein to overcome these failed previous attempts. By providing sustained, localized, controlled delivery of therapeutic agents via one or more depots implanted within the prostate, this will create a sustained exposure to the prostate tissue sufficient to achieve a therapeutic effect will avoiding diffusion of drug to non-target tissue. In particular, implantation of a system of drug delivery depots, wherein at least one depot is implanted in at least one lobule, would allow for a high local, sustained exposure of therapeutic agent that is concentrated in areas of the prostate most needy of therapy.

Capsular containment may also be enhanced by the at least partial separation of the vascular beds between the intraprostatic tissue and the surrounding tissue outside the prostate. Administration of vasoconstricting agents may also enhance the capsular containment. For example, coadministration of epinephrine at the time of implantation may cause local vasoconstriction that will minimize diffusion of the therapeutic agent and regional and systemic impact. Additionally or alternatively, the depot may be formulated with a vasoconstricting agent to provide a sustained local presence of therapeutic agent in the prostatic tissue.

In addition, or alternatively, to capsular containment, the treatment described herein can be administered to achieve the desired pharmacokinetic profile through thoughtful implantation of depots in the prostate. As described with respect to FIG. 75 above, each depot provides a zone of treatment based on a radius of diffusion from the site of implantation. The radius of diffusion invariably creates a concentration gradient in which the concentration of agent is highest closest to the depot and lowest farthest from the depot. By placing each depot inside the prostate at a distance from the capsular layer, the concentration at the capsular layer will be lower than at the depot itself, and any diffusion through the capsular layer will be further reduced, while still providing a therapeutic dose to tissue right at the inner surface of the capsular layer. If the distance of the depot from the capsular layer that is equal to or greater than the radius of diffusion of the depot, the zone of treatment will be localized to the prostate itself, thereby ensuring non-toxic exposure outside of the prostate.

1. Therapeutic Agents

The therapeutic agent carried by the depots 100 of the present technology for treating prostate cancer may be any biologically active substance (or combination of substances) that provide a therapeutic effect in a patient in need thereof. Therapeutic agents of the present technology configured to treat prostate cancer include at least one of a chemotherapeutic agent, an antiandrogen, a targeting agent, or an adjunctive agent, each of which is described below.

a. Chemotherapeutic Agents

The therapeutic agent may include a chemotherapeutic agent. The term "chemotherapeutic agent" includes one or more local therapeutic agents that are administered to reduce, remove, or prevent the spread of cancerous tissue and/or masses. The chemotherapeutic agent may comprise the pharmacologically active drug, a pro-drug, or a pharmaceutically acceptable salt thereof. Because the depots disclosed herein administer the chemotherapeutic agent locally, the present technology can deliver greater amounts of chemotherapeutic agent to the tumor locally than would be possible through systemic administration without exposing the patient to toxic levels of the agent systemically. The normal prostate weighs 7 to 16 grams, or approximately 0.01% of the body weight. Locally delivering an acute chemotherapeutic dose at 100 times the typical concentration for systemic chemotherapy would still expose the body to only 1% of the drug used in systemic chemotherapy. In some embodiments, the therapeutic region 200 may be configured to deliver a high, sustained local dose to a prostate tumor over the course of days, weeks, or months, while still exposing the body to a lower overall dose of chemotherapy.

In some embodiments, the therapeutic agent includes one or more chemotherapeutic agents including, for example, at least one of an alkylating agent, an antineoplastic agent, a plant alkaloid, an antitumor antibiotic, a topoisomerase inhibitor, an antineoplastic agent, an antimicrotubule agent, and others. For example, the chemotherapeutic agent may include one or more miscellaneous antineoplastic agents, such as at least one of a mustard gas derivatives (e.g., mechlorethamine, cyclophosphamide, chlorambucil, melphalan, ifosfamide, and others), an ethylenimine (e.g., thiotepa, hexamethylmelamine, and others), an alkylsulfonate (e.g., busulfan and others), a hydrazine and/or triazine (e.g., altretamine, procarbazine, dacarbazine, temozolomide, and others), a nitrosureas (e.g., carmustine, lomustine, streptozocin, and others), and a metal salt (e.g., carboplatin, cisplatin, oxaliplatin, and others). In some embodiments, the chemotherapeutic agent may include one or more plant alkaloids, such as at least one of a *vinca* alkaloid (e.g., vincristine, vinblastine, vinorelbine, and others), a taxane (e.g., paclitaxel, docetaxel, and others), a podophyllotoxin, (e.g., toposide, tenisopide, and others), and a camptothecan analogs, (e.g., irinotecan, topotecan, and others). In some embodiments, the chemotherapeutic agent may include one or more antitumor antibiotics, such as at least one of an anthracyclines (e.g., doxorubicin, daunorubicin, epirubicin, mitoxantrone, idarubicin, and others), a chromomycin (e.g., dactinomycin, plicamycin, and others), a mitomycin, and a bleomycin. In some embodiments, the chemotherapeutic agent may include one or more antimetabolites, such as at least one of a folic acid antagonist (e.g., methotrexate and others), a pyrimidine antagonist (e.g., 5-fluorouracil, foxuridine, cytarabine, capecitabine, gemcitabine, and others), a purine antagonist (e.g., 6-mercaptopurine, 6-thioguanine, and others), and an adenosine deaminase inhibitor (e.g., cladribine, fludarabine, nelarabine, pentostatin, and others). In some embodiments, the chemotherapeutic agent may include one or more topoisomerase inhibitors, such as at least one of a topoisomerase I inhibitor (e.g., ironotecan, topotecan, and others) and a topoisomerase II inhibitor (e.g., amsacrine, etoposide, etoposide phosphate, teniposide, and others). In some embodiments, the chemotherapeutic agent may include one or more miscellaneous antineoplastic agents, such as at least one of a ribonucleotide reductase inhibitor (e.g., hydroxyurea and others), an adrenocortical steroid inhibitor (e.g., mitotane), an enzyme (e.g., asparaginase, pegaspargase, and others), an antimicrotubule agent (e.g., estramustine, docetaxel, paclitaxel, and others), and a retinoid (e.g., bexarotene, isotretinoin, tretinoin (ATRA), and others).

In some embodiments, the therapeutic agent includes a chemotherapeutic agent that may be, for example, an antimicrotubule agent or any drug that blocks cell growth by stopping cell division. Example antimicrotubule agents include paclitaxel, docetaxel, and cabazitaxel. In some embodiments, the therapeutic region 200 and/or the entire depot 100 may only contain the chemotherapeutic agent (and not the antiandrogen).

Docetaxel may be especially effective for local treatment of prostate cancer as it is often used to treat patients with advanced prostate cancer that has become resistant to androgen-deprivation therapy. In those embodiments where the therapeutic agent includes docetaxel, the therapeutic region 200 may contain no less than 1 mg, no less than 2 mg, no less than 3, no less than 4, no less than 5 mg, no less than 6 mg, no less than 7 mg, no less than 8 mg, no less than 9 mg, no less than 10 mg, no less than 11 mg, no less than 12 mg, no less than 13 mg, no less than 14 mg, no less than 15 mg, no less than 16 mg, no less than 17 mg, no less than 18 mg, less than 19 mg, no less than 20 mg, no less than 22 mg, no less than 24 mg, no less than 26 mg, no less than 28 mg, no less than 30 mg, no less than 32 mg, no less than 34 mg, no less than 36 mg, no less than 38 mg, or no less than 40 mg of docetaxel.

In those embodiments where the therapeutic agent includes paclitaxel, the amount of paclitaxel (a) in the therapeutic region 200 of a single depot 100 or (b) within the combined therapeutic regions 200 of a plurality of depots configured to be implanted within the prostate gland at the same time may comprise no less than 3 mg, no less than 4 mg, no less than 5 mg, no less than 6 mg, no less than 7 mg, no less than 8 mg, no less than 9 mg, no less than 10 mg, no less than 11 mg, no less than 12 mg, no less than 13 mg, no less than 14 mg, no less than 15 mg, no less than 16 mg, no less than 17 mg, no less than 18 mg, less than 19 mg, no less than 20 mg, no less than 22 mg, no less than 24 mg, no less than 26 mg, no less than 28 mg, no less than 30 mg, no less than 32 mg, no less than 34 mg, no less than 36 mg, no less than 38 mg, no less than 40 mg, no less than 42 mg, no less than 44 mg, no less than 46 mg, no less than 48 mg, no less than 50 mg, no less than 52 mg, no less than 54 mg, no less than 56 mg, no less than 58 mg, or no less than 60 mg of paclitaxel.

The depots 100 disclosed herein for treating prostate cancer may be configured to release a chemotherapeutic agent continuously or intermittently for at least a week. In some embodiments, the depot 100 can be configured to release the chemotherapeutic agent for no less than 8 days, no less than 9 days, no less than 10 days, no less than 11 days, no less than 12 days, no less than 13 days, no less than 14 days, no less than 15 days, no less than 16 days, no less than 17 days, no less than 18 days, no less than 19 days, no less than 20 days, no less than 21 days, no less than 22 days, no less than 23 days, no less than 24 days, no less than 25 days, no less than 26 days, no less than 27 days, no less than 28 days, no less than 29 days, no less than 30 days, no less than 40 days, no less than 50 days, no less than 60 days, no less than 70 days, no less than 90 days, no less than 100 days, no less than 150 days, no less than 200 days, no less than 300 days, or no less than 365 days.

In some embodiments, the therapeutic agent includes enzalutamide and the depot and/or therapeutic region contains no less than 2 mg of enzalutamide. In some embodiments, the depot contains no less than 3 mg of enzalutamide. In some embodiments, the depot contains no less than 4 mg of enzalutamide. In some embodiments, the depot contains no less than 5 mg of enzalutamide. In several embodiments, the depot contains between about 3 mg and about 4 mg of enzalutamide.

Additionally or alternatively, the therapeutic agent includes bicalutamide and the depot and/or therapeutic region contains no less than 2 mg of bicalutamide. In some embodiments, the depot contains no less than 3 mg of bicalutamide. In some embodiments, the depot contains no less than 4 mg of bicalutamide. In some embodiments, the depot contains no less than 5 mg of bicalutamide. In several embodiments, the depot contains between about 3 mg and about 4 mg of bicalutamide.

According to some embodiments, the therapeutic agent includes bicalutamide and enzalutamide, and the depot and/or therapeutic region contains no less than 3 mg of bicalutamide and no less than 3 mg of enzalutamide. In several embodiments, the depot contains between about 3 mg and about 4 mg of bicalutamide and between about 3 mg and about 4 mg of enzalutamide. According to several embodiments, the depot contains between about 2 mg and about 4 mg of bicalutamide and enzalutamide combined. In some embodiments, the depot contains no more than 4 mg of bicalutamide and enzalutamide combined. In some embodiments, the depot contains at least 2 mg of bicalutamide and enzalutamide combined.

As previously mentioned, in several embodiments chemotherapeutic agent and an antiandrogen. In some of such embodiments, the chemotherapeutic agent comprises at least one of docetaxel and paclitaxel and the antiandrogen comprises at least one of abiraterone acetate, apalutimide, darolutimide enzalutamide, and bicalutamide. According to several embodiments, the chemotherapeutic agent comprises at least one of docetaxel, paclitaxel, and cabazitaxel and the antiandrogen comprises at least one of enzalutamide and bicalutamide. In some embodiments, the chemotherapeutic agent comprises docetaxel and the antiandrogen comprises at least one of enzalutamide and bicalutamide.

b. Hormone Therapy Agents

In some embodiments, the therapeutic agent may include one or more hormone therapy agents, such as one or more androgen receptor blockers (or "antiandrogen") and/or one or more androgen-synthesis inhibitors. The antiandrogen agent blocks the androgen receptor of prostate cancer cells, thereby preventing the testosterone stimulation needed for cell growth. In certain embodiments, the therapeutic region 200 and/or the entire depot 100 may only comprise an antiandrogen and not include any chemotherapeutic agent. In other embodiments, the therapeutic region 200 and/or depot 100 may include both an antiandrogen and a chemotherapeutic agent. The antiandrogen may include at least one of enzalutamide, bicalutamide, flutamide, apalutamide, and nilutamide.

In those embodiments in which the therapeutic agent includes enzalutamide, the therapeutic region 200 may contain at least 0.5 mg, at least 1 mg, at least 2 mg, at least 3 mg, at least 4 mg, at least 5 mg, at least 6 mg, at least 7 mg, at least 8 mg, at least 9 mg, at least 10 mg, at least 11 mg, at least 12 mg, at least 13 mg, at least 14 mg, or at least 15 mg of enzalutamide. In some embodiments, therapeutic region contains no less than 3 grams of enzalutamide, no less than 4 grams of bicalutamide, no less than 5 grams of enzalutamide. In several embodiments, the therapeutic region contains between about 3 grams and about 4 grams of enzalutamide.

In those embodiments in which the therapeutic agent includes bicalutamide, the therapeutic region 200 may contain at least 0.5 mg, at least 1 mg, at least 2 mg, at least 3 mg, at least 4 mg, at least 5 mg, at least 6 mg, at least 7 mg, at least 8 mg, at least 9 mg, at least 10 mg, at least 11 mg, at least 12 mg, at least 13 mg, at least 14 mg, or at least 15 mg of bicalutamide. In some embodiments, the therapeutic region contains no less than 3 grams of bicalutamide, no less than 4 grams of bicalutamide, no less than 5 grams of bicalutamide. In several embodiments, the therapeutic region contains between about 3 grams and about 4 grams of bicalutamide.

According to some embodiments, the therapeutic agent includes bicalutamide and enzalutamide. In several of those embodiments, the therapeutic region contains no less than 3 grams of bicalutamide and no less than 3 grams of enzalutamide. In some embodiments, the therapeutic region contains between about 3 grams and about 4 grams of bicalutamide and between about 3 grams and about 4 grams of enzalutamide.

In some embodiments, the therapeutic agent may include one or more hormone therapy agents, such as one or more androgen-synthesis inhibitors. In certain embodiments, the therapeutic region 200 and/or the entire depot 100 may only comprise an androgen-synthesis inhibitor and not include any chemotherapeutic agent. In other embodiments, the therapeutic region 200 and/or depot 100 may include both an androgen-synthesis inhibitor and a chemotherapeutic agent. The androgen-synthesis inhibitor may include, for example, abiraterone acetate, ketoconazole, and aminoglutethamide. In those embodiments in which the therapeutic agent includes abiraterone acetate, the therapeutic region 200 may contain at least at least 4 mg, at least 6 mg, at least 8 mg, at least 10 mg, at least 20 mg, at least 30 mg, at least 40 mg, at least 50 mg, at least 60 mg, at least 70 mg, or at least 80 mg of abiraterone acetate.

The depots 100 disclosed herein for treating prostate cancer may be configured to release a hormone therapy agent continuously or intermittently for at least a week. In some embodiments, the depot 100 can be configured to release the antiandrogen for no less than 8 days, no less than 9 days, no less than 10 days, no less than 11 days, no less than 12 days, no less than 13 days, no less than 14 days, no less than 15 days, no less than 16 days, no less than 17 days, no less than 18 days, no less than 19 days, no less than 20 days, no less than 21 days, no less than 22 days, no less than 23 days, no less than 24 days, no less than 25 days, no less than 26 days, no less than 27 days, no less than 28 days, no less than 29 days, no less than 30 days, no less than 40 days, no less than 50 days, no less than 60 days, no less than 70 days, no less than 90 days, no less than 100 days, no less than 150 days, no less than 200 days, no less than 300 days, or no less than 365 days.

The depots 100 disclosed herein for treating prostate cancer may be configured to release an antiandrogen agent continuously or intermittently for at least a week. In some embodiments, the depot 100 can be configured to release the antiandrogen for no less than 8 days, no less than 9 days, no less than 10 days, no less than 11 days, no less than 12 days, no less than 13 days, no less than 14 days, no less than 15 days, no less than 16 days, no less than 17 days, no less than 18 days, no less than 19 days, no less than 20 days, no less than 21 days, no less than 22 days, no less than 23 days, no less than 24 days, no less than 25 days, no less than 26 days, no less than 27 days, no less than 28 days, no less than 29 days, no less than 30 days, no less than 40 days, no less than 50 days, no less than 60 days, no less than 70 days, no less than 90 days, no less than 100 days, no less than 150 days, no less than 200 days, no less than 300 days, or no less than 365 days.

The depots 100 disclosed herein for treating prostate cancer may be configured to release an androgen-synthesis inhibitor continuously or intermittently for at least a week. In some embodiments, the depot 100 can be configured to release the antiandrogen for no less than 8 days, no less than 9 days, no less than 10 days, no less than 11 days, no less than 12 days, no less than 13 days, no less than 14 days, no less than 15 days, no less than 16 days, no less than 17 days, no less than 18 days, no less than 19 days, no less than 20 days, no less than 21 days, no less than 22 days, no less than 23 days, no less than 24 days, no less than 25 days, no less than 26 days, no less than 27 days, no less than 28 days, no less than 29 days, no less than 30 days, no less than 40 days, no less than 50 days, no less than 60 days, no less than 70 days, no less than 90 days, no less than 100 days, no less than 150 days, no less than 200 days, no less than 300 days, or no less than 365 days.

c. Additional Agents

The therapeutic agent may optionally include a targeting agent that targets specific receptors or growth factors to reduce the growth and/or spread of cancerous tissue and/or masses. The targeting agents may comprise the pharmacologically active drug, pro-drug, or a pharmaceutically acceptable salt thereof. Suitable local targeting agents include, but are not limited to, palbociclib, abemaciclib, tipifarnib, tanomastat, marimastat erlotinib, algenpanticel-L, ibilimumab, and combinations thereof. These and other targeting agents may reduce the growth and/or spread of cancerous tissue by targeting certain chemical compounds such as cyclin-dependent kinases (CDKs), farnesyltransferases, matrix metalloproteinases or the like. Any chemical compound possessing such targeting properties is suitable for use in the present technology.

In some embodiments, the therapeutic agent may include one or more immunotherapy agents. For example, the therapeutic agent may include at least one of sipuleucel-T, DCVAC/PCa, PROSTVAC-VF, ADXS31-142, ProstAtak, ipilimumab, nivolumab, pembrolizumab, durvalumab, tremelimumab, atezolizumab, and CAR T cells.

In some embodiments, the previously-described therapeutic agents (e.g., chemotherapeutic agents, targeting agents, immunotherapy agents, etc.) may be combined with one or more adjunctive agents, including anesthetics, analgesics, anti-inflammatory agents, antibiotics and/or antimicrobial agents, vasoconstricting agents and/or antifungal agents. The anesthetics include, but are not limited to, bupivacaine, ropivacaine, mepivacaine, etidocaine, levobupivacaine, trimecaine, carticaine, articaine, lidocaine, prilocaine, benzocaine, procaine, tetracaine, chloroprocaine, and/or combinations thereof. The anti-inflammatory agents include, but are not limited to, prednisone, betamethasone, cortisone, dexamethasone, hydrocortisone, methylprednisolone, aspirin, Ibuprofen, naproxen sodium, diclofenac, diclofenac-misoprostol, celecoxib, piroxicam, indomethacin, meloxicam, ketoprofen, sulindac, diflunisal, nabumetone, oxaprozin, tolmetin, salsalate, etodolac, fenoprofen, flurbiprofen, ketorolac, meclofenamate, mefenamic acid, COX-2 inhibitors, and/or combinations thereof. The antibiotics and/or antimicrobial agents include, but are not limited to, amoxicillin, amoxicillin/clavulanate, cephalexin, ciprofloxacin, clindamycin, metronidazole, azithromycin, levofloxacin, sulfamethoxazole/trimethoprim, tetracycline(s), minocycline, tigecycline, doxycycline, rifampin, triclosan, chlorhexidine, penicillin(s), aminoglycides, quinolones, fluoroquinolones, vancomycin, gentamycin, cephalosporin (s), carbapenems, imipenem, ertapenem, antimicrobial peptides, cecropin-mellitin, magainin, dermaseptin, cathelicidin, α-defensins, α-protegrins, and/or combinations thereof. The vasoconstricting agents include, but are not limited to, alpha-adrenoceptor agonists, vasopressin analogs, epinephrine, norepinephrine, phenylephrine, dopamine and dobutamine and/or combinations thereof. The antifungal agents include, but are not limited to, ketoconazole, clortrimazole, miconazole, econazole, intraconazole, fluconazole, bifoconazole, terconazole, butaconazole, tioconazole, oxiconazole, sulconazole, saperconazole, voriconazole, terbinafine, amorolfine, naftifine, griseofulvin, haloprogin, butenafine, tolnaftate, nystatin, cyclohexamide, ciclopirox, flucytosine, terbinafine, amphotericin, and/or combinations thereof.

2. Polymers

The depots 100 of the present technology configured to treat prostate cancer may comprise one or more polymers. For example, the depots may comprise at least one of polyglycolide (PGA), polycaprolactone (PCL), poly(DL-lactic acid) (PLA), poly(alpha-hydroxy acids), poly(lactide-co-glycolide)(PLGA or DLG), poly(DL-lactide-co-caprolactone) (DL-PLCL), poly(trimethylene carbonate) (PTMC), polydioxanone (PDO), poly(4-hydroxy butyrate) (PHB), polyhydroxyalkanoates (PHA), poly(phosphazene), polyphosphate ester), poly(amino acid), polydepsipeptides, poly(butylene succinate) (PBS), polyethylene oxide, polypropylene fumarate, polyiminocarbonates, poly(lactide-co-caprolactone) (PLCL), poly(glycolide-co-caprolactone) (PGCL) copolymer, poly(D,L-lactic acid), polyglycolic acid, poly(L-lactide-co-D,L-lactide), poly(L-lactide-co-glycolide), poly(D,L-lactide-co-glycolide), poly(gycolide-trimethylene carbonate), poly(ethyl glutamate-co-glutamic acid), poly(tert-butyloxy-carbonylmethyl glutamate), poly (glycerol sebacate), tyrosine-derived polycarbonate, poly 1,3-bis-(p-carboxyphenoxy) hexane-co-sebacic acid, polyphosphazene, ethyl glycinate polyphosphazene, polycaprolactone co-butylacrylate, a copolymer of polyhydroxybutyrate, a copolymer of maleic anhydride, a copolymer of poly(trimethylene carbonate), polyethylene glycol (PEG), PEG 400, PEG 500, PEG 600, PEG 700, PEG 800, PEG 900, PEG 10K, hydroxypropylmethylcellulose and cellulose derivatives, polysaccharides (such as hyaluronic acid, chitosan and starch), proteins (such as gelatin and collagen) or PEG derivatives, polyaspirins, polyphosphagenes, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, D-lactide, D,L-lactide, L-lactide, D,L-lactide-caprolactone (DL-CL), D,L-lactide-glycolide-caprolactone (DL-G-CL), dextrans, polyvinylpyrrolidone, polyvinyl alcohol (PVA), PVA-g-PLGA, PEGT-PBT copolymer (polyactive), methacrylates, poly(N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate)hydroxypropyl cellulose, hydroxypropyl methylcellulose, hydroxyethyl methylcellulose, carboxymethylcellulose or salts thereof, Carbopol®, poly(hydroxyethylmethacrylate), poly(methoxyethylmethacrylate), poly (methoxyethoxy-ethylmethacrylate), polymethylmethacrylate (PMMA), methylmethacrylate (MMA), gelatin, propylene glycol, and poly(DL-lactide-co-glycolide-co-caprolactone).

In some embodiments, the polymer comprises one or more polyesters, one or more synthetic polyethers, or a mixture of one or more polyesters and one or more polyethers. In these and other embodiments, the polymer may comprise PEG, such as PEG 200, PEG 400, PEG 500, PEG 600, PEG 700, PEG 800, PEG 900, PEG 10K, and others. In some cases, the polymer may comprise no more than 10% PEG, and in some cases no more than 5% PEG. In these and other embodiments, the polymer may comprise PLGA. For example, the polymer may comprise a PLGA having a lactide to glycolide ratio of 50:50, or a lactide to glycolide ratio of 75:25. According to several embodiments, the polymer comprises PLGA and PEG. In these and other embodiments, the polymer may comprise no more than 5% PEG, or no more than 10% PEG. According to several embodiments, the polymer comprises PLGA and PEG10K. In these and other embodiments, the polymer may comprise no more than 5% PEG10K, or no more than 10% PEG10K.

In some embodiments, the polymer comprises a first polymer and a second polymer, and the therapeutic region comprises a first polymer to second polymer to therapeutic agent ratio of 5:5:40. In some embodiments, for example, the first polymer is PEG (of any molecular weight, such as PEG 400, 800, 10K, etc.), the second polymer is PLGA, and the therapeutic agent is at least one of a chemotherapeutic agent and an antiandrogen.

In some embodiments, the polymer comprises a first polymer and a second polymer, and the therapeutic region comprises a first polymer to second polymer to therapeutic agent ratio of 3:7:40. In some embodiments, for example, the first polymer is PEG (of any molecular weight, such as PEG 400, 800, 10K, etc.), the second polymer is PLGA, and the therapeutic agent is at least one of a chemotherapeutic agent and an antiandrogen.

In some embodiments, the polymer comprises a first polymer and a second polymer, and the therapeutic region comprises a first polymer to second polymer to therapeutic agent ratio of 1:9:40. In some embodiments, for example, the first polymer is PEG (of any molecular weight, such as PEG 400, 800, 10K, etc.), the second polymer is PLGA, and the therapeutic agent is at least one of a chemotherapeutic agent and an antiandrogen.

The bioresorbable polymers used in the present technology preferably have a predetermined degradation rate. The terms "bioresorbable," or "bioabsorbable," mean that a polymer will be absorbed within the patient's body, for example, by a cell or tissue. These polymers are "biodegradable" in that all or parts the polymeric film will degrade over time by the action of enzymes, by hydrolytic action and/or by other similar mechanisms in the patient's body. In various embodiments, the bioresorbable polymer film can break down or degrade within the body to non-toxic components while a therapeutic agent is being released. Polymers used as base components of the depots of the present technology may break down or degrade after the therapeutic agent is fully released. The bioresorbable polymers are also "bioerodible," in that they will erode or degrade over time due, at least in part, to contact with substances found in the surrounding tissue, fluids or by cellular action.

Criteria for the selection of the bioresorbable polymer suitable for use in the present technology include: 1) in vivo safety and biocompatibility; 2) therapeutic agent loading capacity; 3) therapeutic agent releasing capability; 4) degradation profile; 5) potential for inflammatory response; and 6) mechanical properties, which may relate to form factor and manufacturability. As such, selection of the bioresorbable polymer may depend on the clinical objectives of a particular therapy and may involve trading off between competing objectives. For example, PGA (polyglycolide) is known to have a relatively fast degradation rate, but it is also fairly brittle. Conversely, polycaprolactone (PCL) has a relatively slow degradation rate and is quite elastic. Copolymerization provides some versatility if it is clinically desirable to have a mix of properties from multiple polymers. For biomedical applications, particularly as a bioresorbable depot for drug release, a polymer or copolymer using at least one of poly(L-lactic acid) (PLA), PCL, and PGA are generally preferred.

In many embodiments, the polymer may include polyglycolide (PGA). PGA is one of the simplest linear aliphatic polyesters. It is prepared by ring opening polymerization of a cyclic lactone, glycolide. It is highly crystalline, with a crystallinity of 45-55%, and thus is not soluble in most organic solvents. It has a high melting point (220-225° C.), and a glass transition temperature of 35-40° C. (Vroman, L., et al., Materials, 2009, 2:307-44). Rapid in vivo degradation of PGA leads to loss of mechanical strength and a substantial local production of glycolic acid, which in substantial amounts may provoke an inflammatory response.

In many embodiments, the polymer may include polylactide (PLA). PLA is a hydrophobic polymer because of the presence of methyl (—CH3) side groups off the polymer backbone. It is more resistant to hydrolysis than PGA because of the steric shielding effect of the methyl side groups. The typical glass transition temperature for representative commercial PLA is 63.8° C., the elongation at break is 30.7%, and the tensile strength is 32.22 MPa (Vroman, 2009). Regulation of the physical properties and biodegradability of PLA can be achieved by employing a hydroxy acids co-monomer component or by racemization of D- and L-isomers (Vroman, 2009). PLA exists in four forms: poly(L-lactic acid) (PLLA), poly(D-lactic acid) (PDLA), meso-poly(lactic acid) and poly(D,L-lactic acid) (PDLLA), which is a racemic mixture of PLLA and PDLA. PLLA and PDLLA have been the most studied for biomedical applications.

Copolymerization of PLA (both L- and D,L-lactide forms) and PGA yields poly(lactide-co-glycolide) (PLGA), which is one of the most commonly used degradable polymers for biomedical applications. In many embodiments, the polymer may include PLGA. Since PLA and PGA have significantly different properties, careful choice of PLGA composition can enable optimization of performance in intended clinical applications. Physical property modulation is even more significant for PLGA copolymers. When a composition is comprised of 25-75% lactide, PLGA forms amorphous polymers which are very hydrolytically unstable compared to the more stable homopolymers. This is demonstrated in the degradation times of 50:50 PLGA, 75:25 PLGA, and 85:15 PLGA, which are 1-2 months, 4-5 months and 5-6 months, respectively. In some embodiments, the polymer may be an ester-terminated poly (DL-lactide-co-glycolide) in a molar ratio of 50:50 (DURECT Corporation).

In some embodiments, the polymer may include polycaprolactone (PCL). PCL is a semi-crystalline polyester with high organic solvent solubility, a melting temperature of 55-60° C., and glass transition temperature of −54° C. (Vroman, 2009). PCL has a low in vivo degradation rate and high drug permeability, thereby making it more suitable as a depot for longer term drug delivery. For example, Capronor® is a commercial contraceptive PCL product that is able to deliver levonorgestrel in vivo for over a year. PCL is often blended or copolymerized with other polymers like PLLA, PDLLA, or PLGA. Blending or copolymerization with polyethers expedites overall polymer erosion. Additionally, PCL has a relatively low tensile strength (~23 MPa), but very high elongation at breakage (4700%), making it a very good elastic biomaterial. PCL also is highly processable, which enables many potential form factors and production efficiencies.

Suitable bioresorbable polymers and copolymers for use in the present technology include, but are not limited to, poly(alpha-hydroxy acids), poly(lactide-co-glycolide) (PLGA or DLG), poly(DL-lactide-co-caprolactone) (DL-PLCL), polycaprolactone (PCL), poly(L-lactic acid) (PLA), poly(trimethylene carbonate) (PTMC), polydioxanone (PDO), poly(4-hydroxy butyrate) (PHB), polyhydroxyalkanoates (PHA), poly(phosphazene), polyphosphate ester), poly(amino acid), polydepsipeptides, poly(butylene succinate) (PBS), polyethylene oxide, polypropylene fumarate, polyiminocarbonates, poly(lactide-co-caprolactone) (PLCL), poly(glycolide-co-caprolactone) (PGCL) copolymer, poly(D,L-lactic acid), polyglycolic acid, poly(L-lactide-co-D,L-lactide), poly(L-lactide-co-glycolide), poly(D,L-lactide-co-glycolide), poly(gycolide-trimethylene carbonate), poly(glycolide-co-carolactone) (PGCL), poly (ethyl glutamate-co-glutamic acid), poly(tert-butyloxy-carbonylmethyl glutamate), poly(glycerol sebacate), tyrosine-derived polycarbonate, poly 1,3-bis-(p-carboxyphenoxy) hexane-co-sebacic acid, polyphosphazene, ethyl glycinate polyphosphazene, polycaprolactone co-butylacrylate, a copolymer of polyhydroxybutyrate, a copolymer of maleic anhydride, a copolymer of poly(trimethylene carbonate), polyethylene glycol (PEG), hydroxypropylmethylcellulose and cellulose derivatives, polysaccharides (such as hyaluronic acid, chitosan and starch), proteins (such as gelatin and collagen) or PEG derivatives and copolymers thereof. Other suitable polymers or copolymers include polyaspirins, polyphosphagenes, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, D-lactide, D,L-lactide, L-lactide, D,L-lactide-caprolactone (DL-CL), D,L-lactide-glycolide-caprolactone (DL-G-CL), dextrans, vinylpyrrolidone, polyvinyl alcohol (PVA), PVA-g-PLGA, PEGT-PBT copolymer (polyactive), methacrylates, poly(N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate)hydroxypropyl cellulose, hydroxypropyl methylcellulose, hydroxyethyl methylcellulose, carboxymethylcellulose or salts thereof, Carbopol®, poly(hydroxyethylmethacrylate), poly (methoxyethylmethacrylate), poly(methoxyethoxy-ethylmethacrylate), polymethylmethacrylate (PMMA), methylmethacrylate (MMA), gelatin, polyvinyl alcohols, propylene glycol, or combinations thereof.

In various embodiments, the molecular weight of the polymer can be a wide range of values. The average molecular weight of the polymer can be from about 1000 to about 10,000,000; or about 1,000 to about 1,000,000; or about 5,000 to about 500,000; or about 10,000 to about 100,000; or about 20,000 to 50,000.

As described above, it may be desirable in certain clinical applications using depots for controlled delivery of therapeutic agents to use copolymers comprising at least two of PGA, PLA, PCL, PDO, and PVA. These include, for example, poly(lactide-co-caprolactone) (PLCL) (e.g. having a PLA to PCL ratio of from 90:10 to 60:40) or its derivatives and copolymers thereof, poly(DL-lactide-co-caprolactone) (DL-PLCL) (e.g. having a DL-PLA to PCL ratio of from 90:10 to 50:50) or its derivatives and copolymers thereof, poly(glycolide-co-caprolactone) (PGCL) (e.g. having a PGA to PCL ratio of from 90:10 to 10:90) or its derivatives and copolymers thereof, or a blend of PCL and PLA (e.g. a ratio blend of PCL and PLA having a wt:wt ratio of 1:9 to 9:1). In one preferred embodiment, the bioresorbable polymer comprises a copolymer of polycaprolactone (PCL), poly(L-lactic acid) (PLA) and polyglycolide (PGA). In such a preferred embodiment, the ratio of PGA to PLA to PCL of the copolymer may be 5-60% PGA, 5-40% PLA and 10-90% PCL. In additional embodiments, the PGA:PLA:PCL ratio may be 40:40:20, 30:30:50, 20:20:60, 15:15:70, 10:10:80, 50:20:30, 50:25:25, 60:20:20, or 60:10:30. In some embodiments, the polymer is an ester-terminated poly (DL-lactide-co-glycolide-co-caprolactone) in a molar ratio of 60:30:10 (DURECT Corporation).

In some embodiments, a terpolymer may be beneficial for increasing the degradation rate and ease of manufacturing, etc.

To minimize the size of a bioresorbable depot, it is generally preferred to maximize the loading of therapeutic agent in the polymer to achieve the highest possible density of therapeutic agent. However, polymer carriers having high densities of therapeutic agent are more susceptible to burst release kinetics and, consequently, poor control over time release. As described above, one significant benefit of the depot structure described herein is the ability to control and attenuate the therapeutic agent release kinetics even with therapeutic agent densities that would cause instability in other carriers. In certain embodiments, the therapeutic agent loading capacity includes ratios (wt:wt) of the therapeutic agent to bioresorbable polymer of approximately 1:3, 1:2, 1:1, 3:2, 2:1, 3:1, 4:1, 5:1, 6:1, 7:1, 8:1, 9:1, 10:1, 12:1, 14:1, or 16:1. In some embodiments, it may be desirable to increase the therapeutic effect or potency of the therapeutic agent released from the depot described herein while still maintaining the same or similar polymer to therapeutic agent ratio. This can be accomplished by using an essentially pure form of the therapeutic agent as opposed to a salt derivative. Additionally or alternatively, the therapeutic agent can be mixed with clonidine or epinephrine, which are known to increase the therapeutic effect of certain drugs.

In some embodiments, the bioresorbable polymer used in various layers of the depot may manifest as a layer of electrospun microfibers or nanofibers. Biocompatible electrospun microfibers/nanofibers are known in the art and may be used, for example, to manufacture implantable supports for the formation of replacement organs in vivo (U.S. Patent Publication No. 2014/0272225; Johnson; Nanofiber Solutions, LLC), for musculoskeletal and skin tissue engineering (R. Vasita and D. S. Katti, Int. J. Nanomedicine, 2006, 1:1, 15-30), for dermal or oral applications (PCT Publication No. 2015/189212; Hansen; Dermtreat APS) or for management of postoperative pain (U.S. Patent Publication No. 2013/0071463; Palasis et al.). As a manufacturing technique, electrospinning offers the opportunity for control over the thickness and the composition of the nano- or micro-fibers along with control of the porosity of the fiber meshes (Vasita and Katti, 2006). These electrospun scaffolds are three-dimensional and thus provide ideal supports for the culture of cells in vivo for tissue formation. Typically, these scaffolds have a porosity of 70-90% (U.S. Pat. No. 9,737,632; Johnson; Nanofiber Solutions, LLC). Suitable bioresorbable polymers and copolymers for the manufacture of electrospun microfibers include, but are not limited to, natural materials such as collagen, gelatin, elastin, chitosan, silk fibrion, and hyaluronic acid, as well as synthetic materials such as poly(ε-caprolactone) (PCL), poly(glycolic acid) (PGA), poly(lactic-co-glycolic acid) (PLGA), poly(l-lactide-co-ε-caprolactone), and poly(lactic acid) (PLA).

Electrospun microfibers that are made from a bioresorbable polymer or copolymer and have been used in conjunction with a therapeutic agent are known in the art. For example, Johnson et al. have disclosed the treatment of joint inflammation and other conditions with an injection of biocompatible polymeric electrospun fiber fragments along with a carrier medium containing chitosan (U.S. Published Application No. 2016/0325015; Nanofiber Solutions, LLC). Weldon et al. reported the use of electrospun bupivacaine-eluting sutures manufactured from poly(lactic-co-glycolic acid) in a rat skin wound model, wherein the sutures provided local anesthesia at an incision site (J. Control Release, 2012, 161:3, 903-909). Similarly, Palasis et al. disclosed the treatment of postoperative pain by implanting electrospun fibers loaded with an opioid, anesthetic or a non-opioid analgesic within a surgical site (U.S. Patent Publication No. 2013/0071463; Palasis et al.). Electrospun microfibers suitable for use in the present technology may be obtained by the methods disclosed in the above cited references, which are herein incorporated in their entirety

3. Duration and Release Profile

The release kinetics of the depots of the present technology configured to treat prostate cancer may be tuned for a particular diagnosis by varying one or more aspects of the depot's structure and/or composition, such as the exposed surface area of the therapeutic region 200, the porosity of the control region 300 during and after dissolution of the releasing agent, the concentration of the therapeutic agent in the therapeutic region, the post-manufacturing properties of the polymer, the relative thicknesses of the therapeutic region 200 compared to the control region 300, and other properties of the depots.

The depots 100 disclosed herein for treating prostate cancer may have a release profile that is: (a) zero-order such that the amount of therapeutic agent released per unit time is substantially constant over the duration of release, (b) first-order such that the amount of the therapeutic agent release per unit time decreases in a substantially parabolic manner over the duration of release, or (c) a second-order such that the amount of therapeutic agent released per unit time decreases at a substantially exponential rate over the duration of release.

The depot 100 may be configured to release the therapeutic agent to adjacent prostate tissue (and/or cancerous tissue) for a period of time is no less than 2 weeks, no less than 3 weeks, no less than 4 weeks, no less than 5 weeks, no less than 6 weeks, no less than 7 weeks, no less than 8 weeks, no less than 2 months, no less than 3 months, no less than 4 months, no less than 6 months, no less than 7 months, no less than 8 months, no less than 9 months, no less than 10 months, no less than 11 months, no less than 12 months, no less than 13 months, no less than 14 months, no less than 15 months, no less than 16 months, no less than 17 months, or no less than 18 months. The therapeutic region 200 may be configured to release the therapeutic agent continuously at a constant rate for the period of time, continuously at a varying rate over the period of time, or intermittently over the period of time.

In those embodiments including both a chemotherapeutic agent and an antiandrogen, the depot 100 may be configured such that the chemotherapeutic agent is delivered over a first period of time and the antiandrogen is released over a second period of time. The first period of time may be the same as, different than, longer than, or shorter than the second period of time. The depot 100 may be configured to begin releasing a therapeutic dosage of the chemotherapeutic agent and a therapeutic dosage of the antiandrogen at substantially the same time or at different times. In certain embodiments, the depot may be configured to release the chemotherapeutic agent at a first rate and the antiandrogen at a second rate that is the same as, different than, greater than, or less than the second rate.

Figure 76:
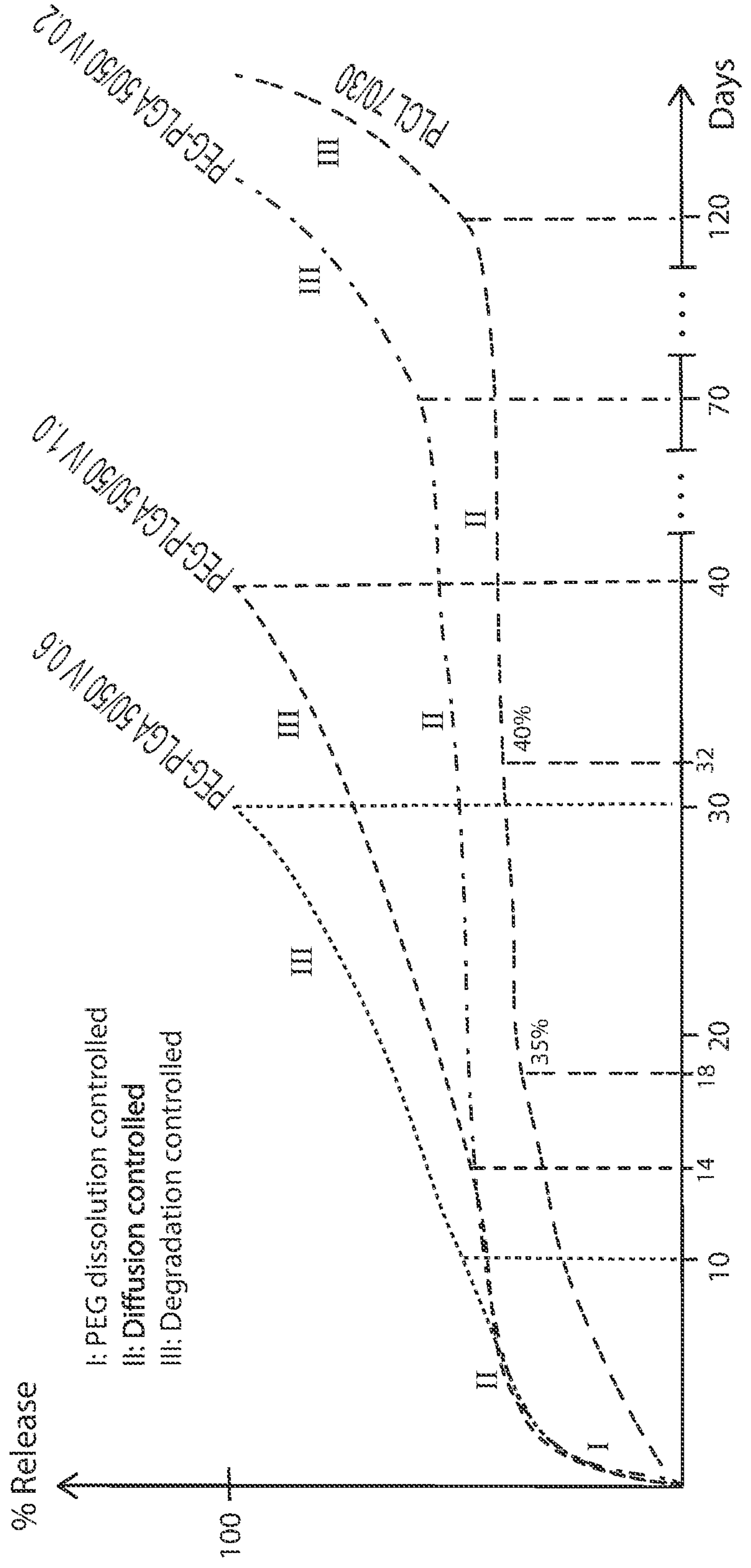
FIG. 76 is a graph showing several release profiles of the depots of the present technology.

FIG. 76 is a graph depicting different release profiles for depots having different formulations. As demonstrated by FIG. 76, the depots 100 of the present technology may have a lactide:glycolide ratio, inherent vicosity (IV), and/or drug to polymer ratio selected to achieve a desired release profile. Lactide:glycolide ratio, for example, is often the primary determinant of polymer matrix degradation time. Polymer inherent vicosity (IV) can fine tune the degradation rate, with selection of lower IV leading to faster degradation. As previously mentioned, drug to polymer ratio is also meaningful lever with higher ratio of hydrophobic drug to polymer leading to slower release.

B. Example Delivery Systems and Methods

Figure 77A:
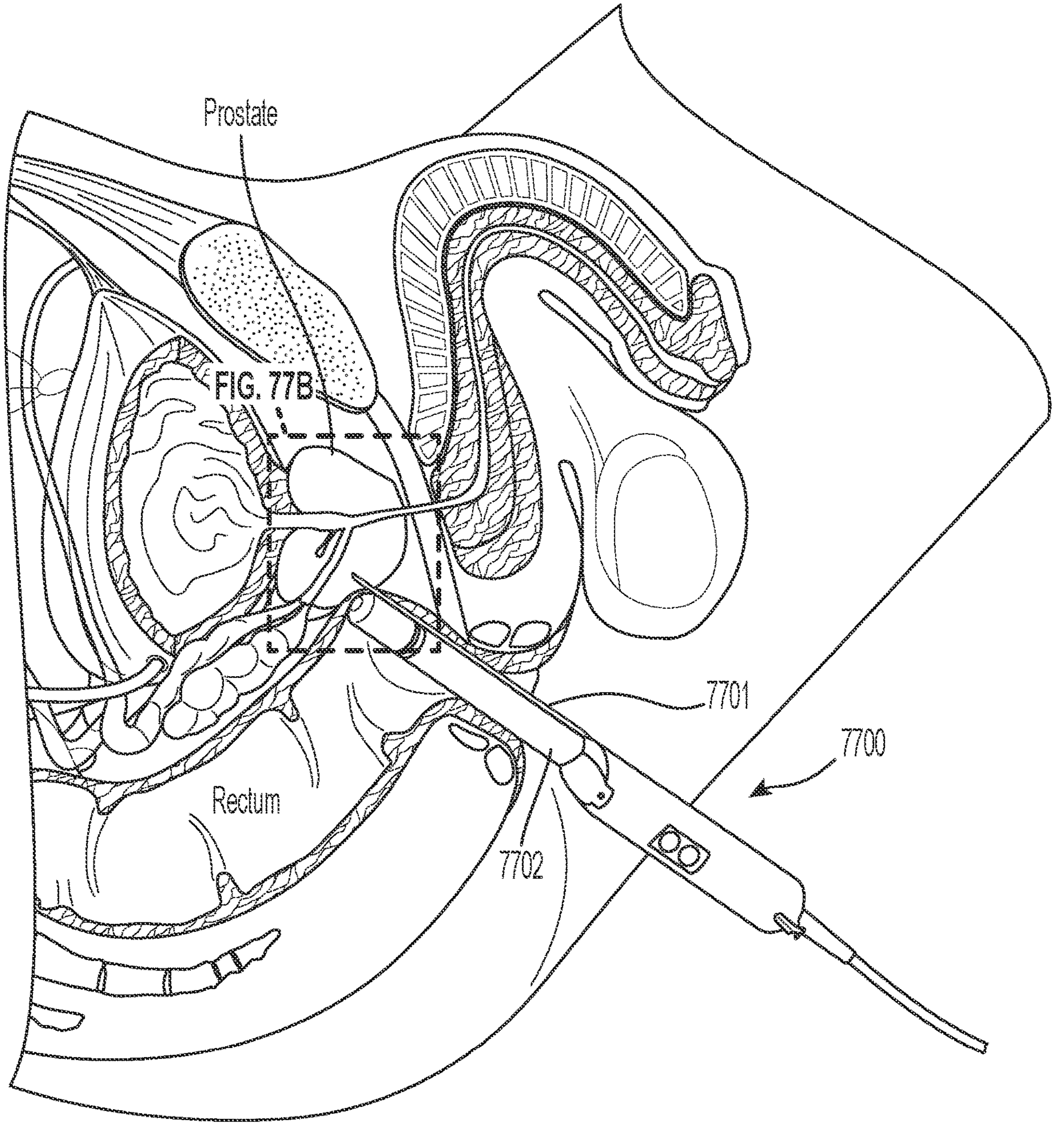
FIG. 77A-77D show an example method for implanting a depot of the present technology at a prostate gland of a human patient via a transrectal approach.

FIGS. 77A-77D, for example, show a delivery system 7700 and method for implanting a depot of the present technology at a prostate gland of a human patient via a transrectal approach. As shown in FIG. 77A, the delivery system may comprise a hollow needle 7701 and an ultrasound probe 7702. The ultrasound probe 7702 may be inserted into the rectum, and the needle 7701 may be advanced through the wall of the rectum and into the prostate under ultrasound guidance. In some embodiments, the needle 7701 is advanced within the probe 7702 through the rectum. In some embodiments, the delivery system 7700 does not include an ultrasound probe.

Figure 77B:
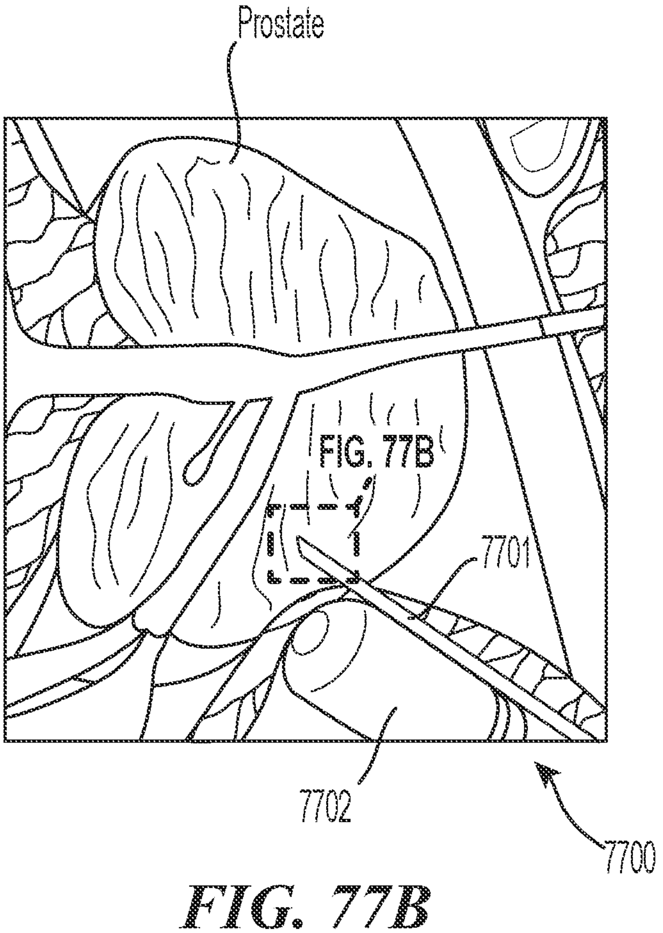
Figure 77C:
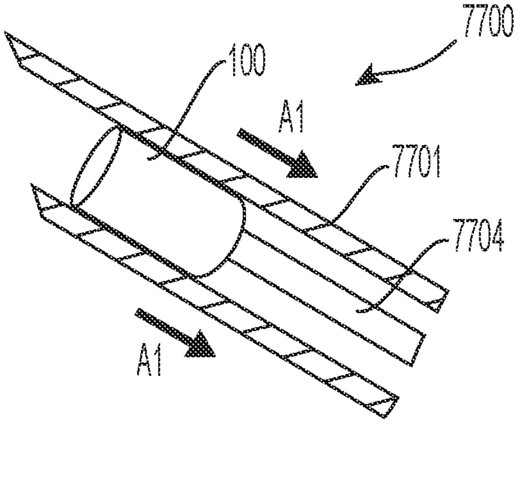
Figure 77D:
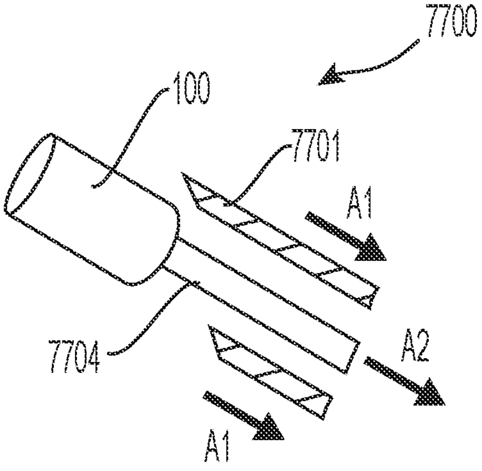

FIG. 77B is an enlarged view of a distal portion of the delivery system positioned at the prostate as shown in FIG. 77A. FIG. 77C is an enlarged, cross-sectional view of a distal portion of the needle 7701. As shown, the delivery system 7700 may further comprise an elongated member 7704 extending along the needle lumen. The elongated depot 100 (or any depot disclosed herein configured to treat prostate cancer) may be positioned within a distal portion of the needle lumen with a proximal end of the depot 100 adjacent a distal end of the elongated member 7704. To implant the depot 100 within the prostate, the physician may retract the needle 7701 (indicated by arrows A1) while holding the elongated member 7704. As shown in FIG. 77D, once the needle 7701 is proximal of the depot 100, both the needle 7701 and the elongated member 7704 may be withdrawn (indicated by arrows A1 and A2), thereby leaving the depot 100 implanted within the prostate. In some embodiments, a physician may push the elongated member 7704 distally to expel the depot 100 from the needle lumen.

For any of the delivery systems and methods disclosed herein, all or a portion of the delivery system may be disposable, such as the needle 7701 and/or the elongated member 7704. In some embodiments, the depot(s) may be pre-loaded in a disposable cartridge having protective features to minimize cytotoxic exposure to the physician or other caregiver, and the cartridge may be configured to be advanced through the needle lumen.

Figure 78:
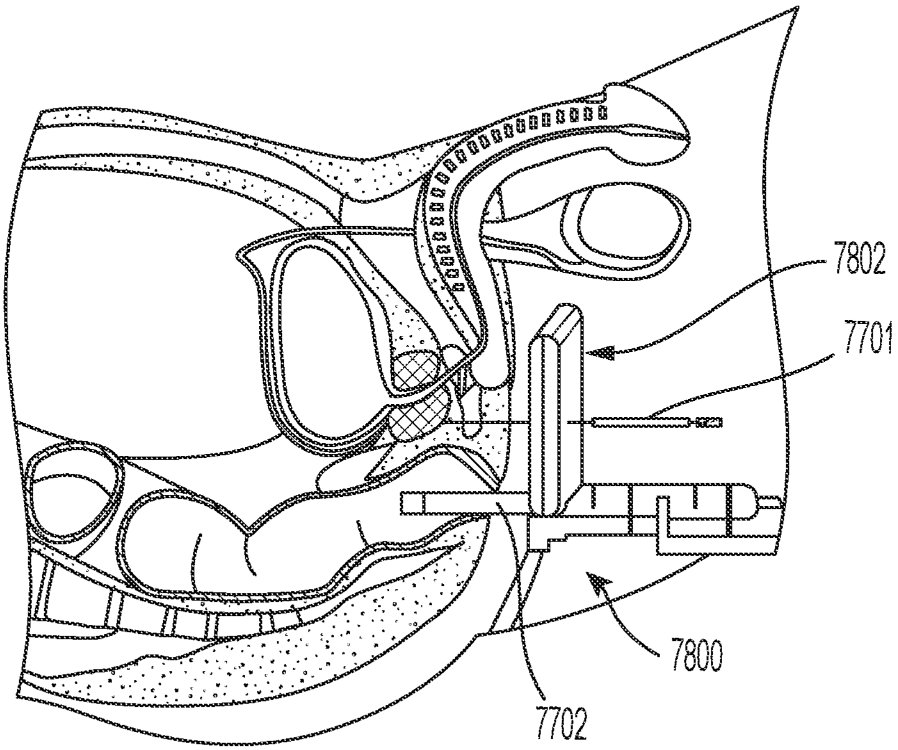
FIG. 78 shows an example method for implanting a depot of the present technology at a prostate gland of a human patient via a transperineal approach.

FIG. 78 shows an example delivery system 7800 method for implanting a depot of the present technology at a prostate gland of a human patient via a transperineal approach. As shown in FIG. 78, the delivery system may comprise a hollow needle 7701, an ultrasound probe 7702, and a guidance grid 7802. The ultrasound probe 7702 may be inserted into the rectum, and the needle 7701 may be advanced through the skin behind the testicles and into the prostate. The guidance grid 7802 may be positioned in front of the skin behind the scrotum and the needle 7701 may be advanced through the grid to aid accurate placement of the needle 7701. Once in the prostate, the depot loaded within the needle 7701 may be implanted as detailed above with respect to FIGS. 77B and 77C.

Figure 79A:
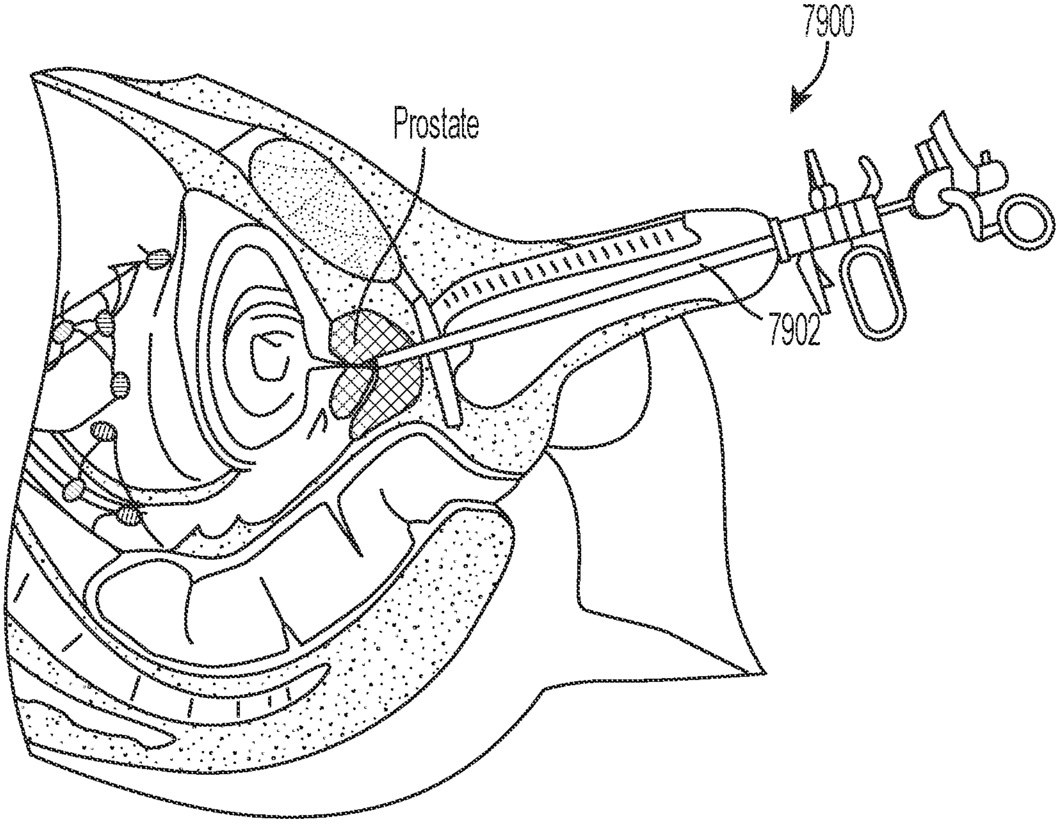
FIGS. 79A-79C show example methods for implanting a depot of the present technology at a prostate gland of a human patient via a transurethral approach.
Figure 79B:
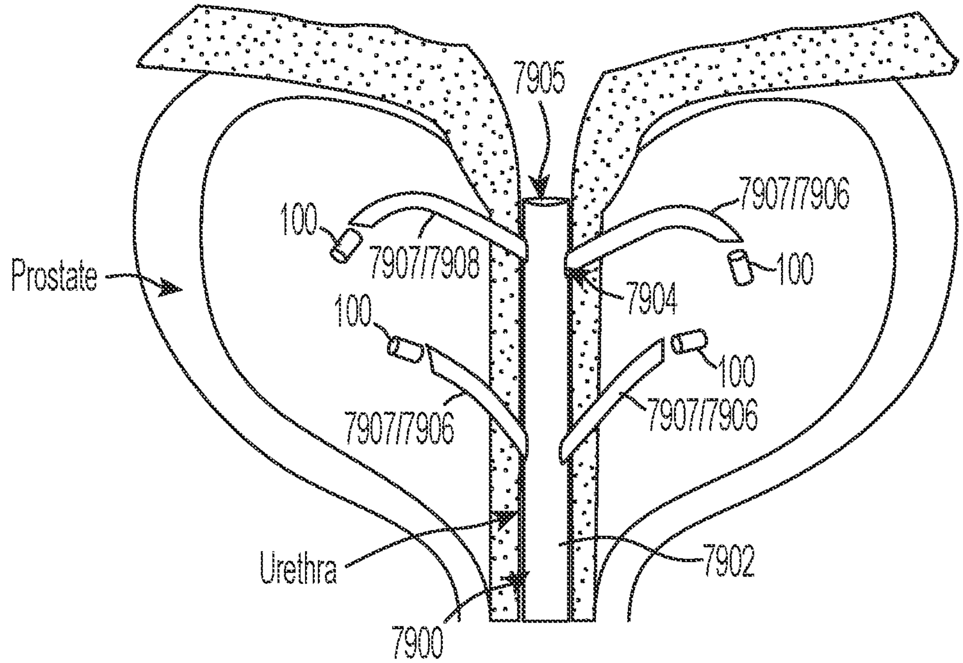
Figure 79C:
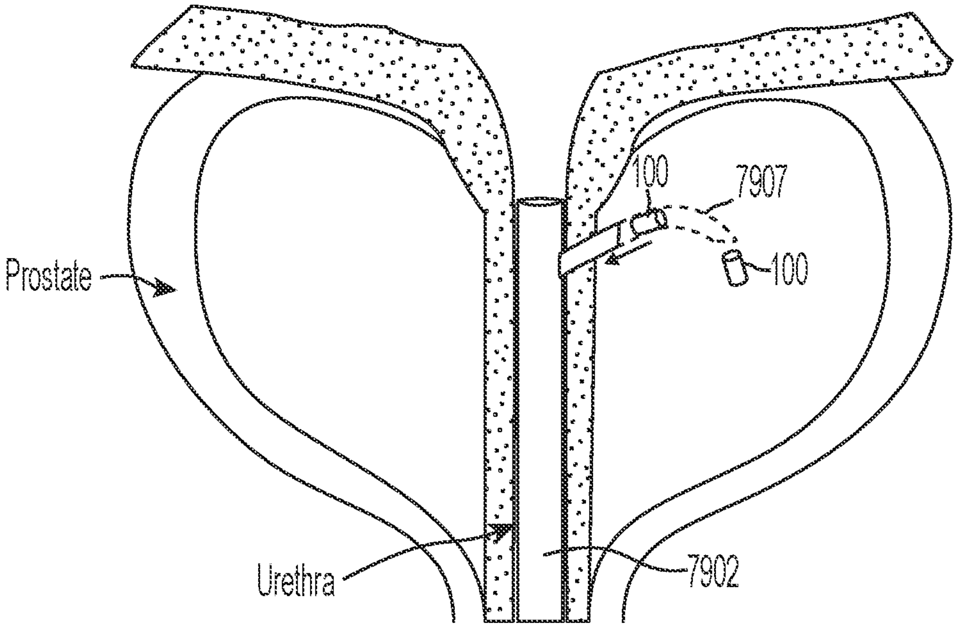

FIGS. 79A-79C show an example delivery system 7900 and method for implanting a depot of the present technology at a prostate gland of a human patient via a transurethral approach. The delivery system 7900 may include a shaft 7902 and one or more hollow needles 7907 (not shown in FIG. 79A) configured to be positioned through one or more lumens of the shaft 7902. In some embodiments, the shaft 7902 may be part of a combined visual and surgical instrument, such as a resectoscope. The shaft 7902 may have one or more discrete lumens extending therethrough and, as best shown in FIG. 79B, each of the lumens may terminate distally at a respective opening 7904 (only one labeled in FIG. 79B) at a distal portion of the shaft 7902 and/or at an opening 7905 at the distal tip of the shaft 7902. The openings 7904 or 7905 may be configured to receive the one or more needles therethrough. The shaft 7902 may include only a single side opening, or a plurality of openings 7904. The openings 7904 may be positioned at different circumferential locations at generally the same axial location along the shaft 7902 (i.e., two or more openings arranged in a band around the shaft 7902), at different circumferential locations at different axial locations along the shaft 7902, or at different axial locations at the same circumferential location about the shaft 7902.

As shown in FIG. 79A, the shaft 7902 may be inserted into the patient's urethra and advanced distally until at least a distal portion of the shaft 7902 is aligned with the portion of the urethra extending through the prostate. The shaft 7902 may be positioned within the urethra such that the openings 7904 at the distal portion of the shaft 7902 are adjacent the prostate gland. As shown in FIG. 79B, one or more of the needles 7907 can be advanced distally through the shaft 7902 until exiting the shaft 7902 through a corresponding opening 7904 to penetrate the urethral wall and prostate. A depot 100 of the present technology may then be delivered to the prostate tissue via the inserted needle(s), for example as described with respect to FIGS. 77A-77C and/or FIGS. 81A-81I.

In some embodiments, one or more of the needles 7907 may be configured to extend laterally away from the shaft 7902 as it penetrates the urethral wall and enters the prostate tissue. For example, one or more of the shaft lumens may have a ramp proximally adjacent the opening 7904 such that a needle being advanced distally through the opening exits the shaft 7902 at an angle relative to the shaft 7902. FIG. 79B depicts two relatively straight needles 7906 extending into the prostate tissue at an angle via a ramp (not visible) adjacent the exit opening 7904. In these and other embodiments, the system may include one or more needles 7908 having a pre-set curve such that, regardless of the presence of a ramp proximal to the opening, the curved needle 7908 will curve away from the shaft 7902 as it exits the corresponding opening 7904.

In any of the foregoing embodiments, the needles 7906 may be withdrawn into the shaft 7902, rotated, and re-deployed to target different radial locations of the prostate. Likewise, in any of the foregoing embodiments, the needles

7906 may be translated proximally or distally relative to the shaft 7902 to release a depot at different distances from the urethra. For example, as shown in FIG. 79C, in some embodiments a single needle 7907 may include multiple depots and may implant each of the depots at different locations as the needle is being withdrawn.

Figure 80:
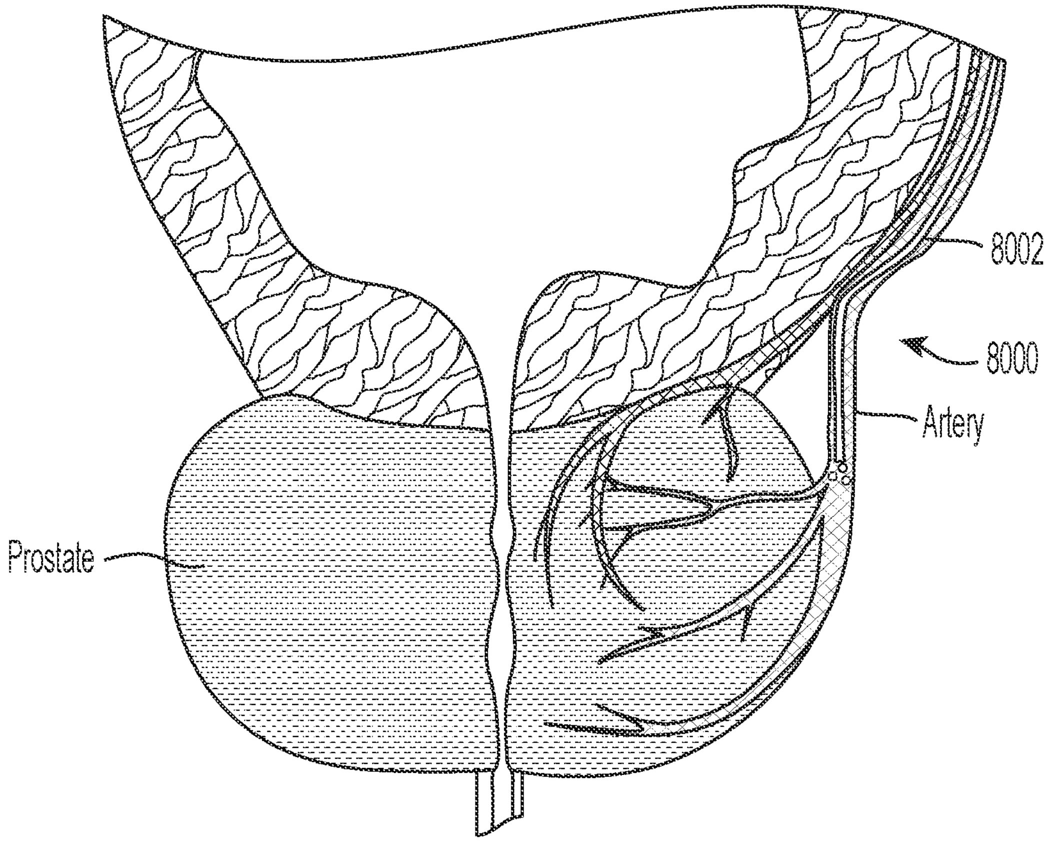
FIG. 80 shows an example method for implanting a depot of the present technology at a prostate gland of a human patient via a transvascular approach.

FIG. 80 shows an example delivery system 8000 and method for local delivery of a therapeutic agent to a prostate gland of a human patient via a vascular approach. The delivery system 8000 may comprise a catheter 8002 having a distal portion configured to be positioned within a blood vessel (such as an artery or vein) proximate the prostate gland. In some embodiments, the catheter 8002 is positioned under fluoroscopic guidance. The catheter 8002 may deliver one or more depots to an intravascular location within the distal branches of the blood vessel, closest to the prostate gland. The depots 100 may at least partially occlude the blood vessels to starve the tumor of blood, and also elute the therapeutic agent into the vessel lumen such that the therapeutic agent is delivered to the prostate.

Figure 81A:
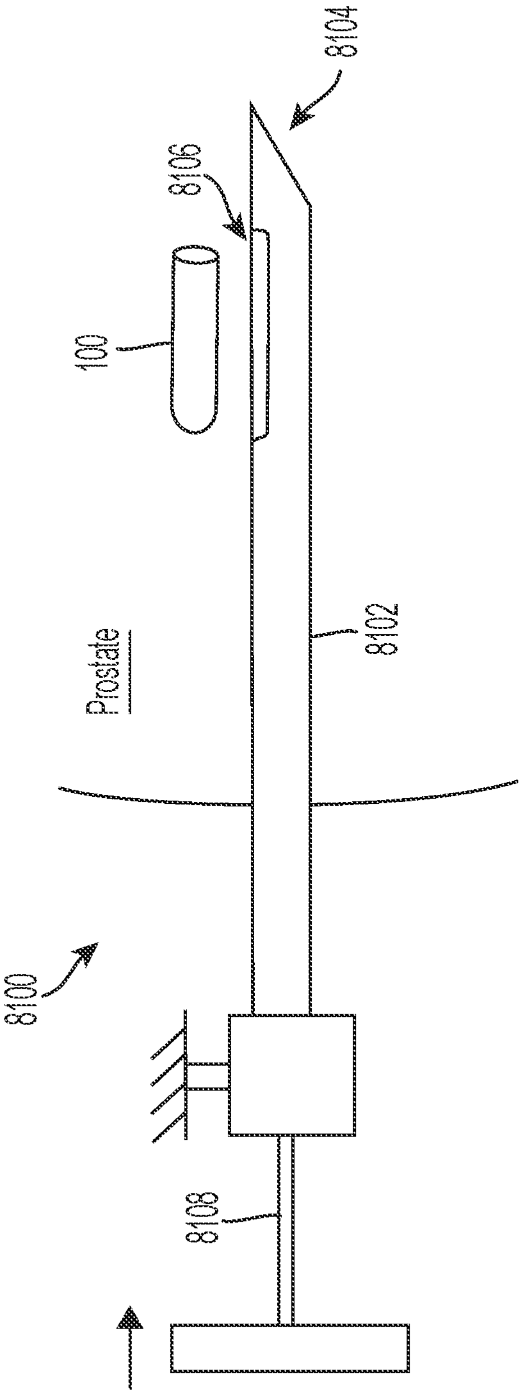
FIGS. 81A-81I show an example method for implanting a depot of the present technology at a prostate gland of a human patient via a delivery member with a side opening.

In some embodiments, it may be beneficial to deliver one or more of the depots 100 through an opening other than the one at the distal end of the needle, or at least to a location in the prostate laterally adjacent the needle during release of the depot 100. FIG. 81A, for example, shows an example delivery system 8100 for implanting one or more depots 100 of the present technology at a prostate gland of a human patient via a delivery shaft with a side opening. As shown, the delivery system 8100 may comprise an elongated shaft 8102 (such as a hollow needle) and an elongated member 8108 slidably received within the shaft lumen. The shaft 8102 may have an opening 8104 at its distal tip, as well as a side opening 8106 extending through its sidewall at the distal portion. In some embodiments, the shaft 8102 may have a closed distal tip (as described elsewhere herein). The side opening 8106, for example, may extend around less than a full circumference of the shaft 8102. It may extend around somewhat less than 180 degrees of the circumference of the shaft, so that the depot is retained within the shaft until it is actively deployed by one of the methods described herein. The side opening 8106 may be sized to receive a depot 100 therethrough.

Figure 81B:
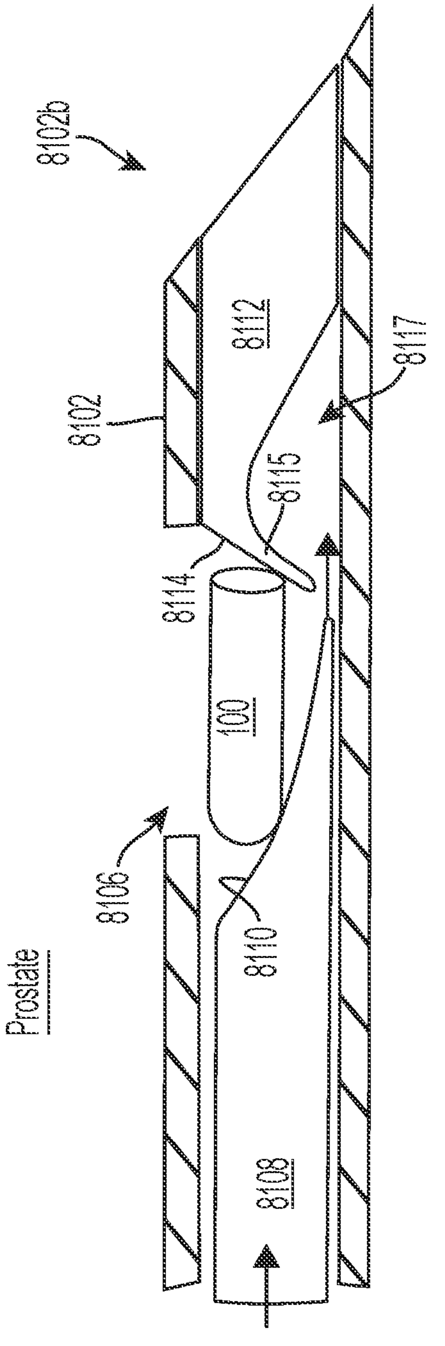
Figure 81C:
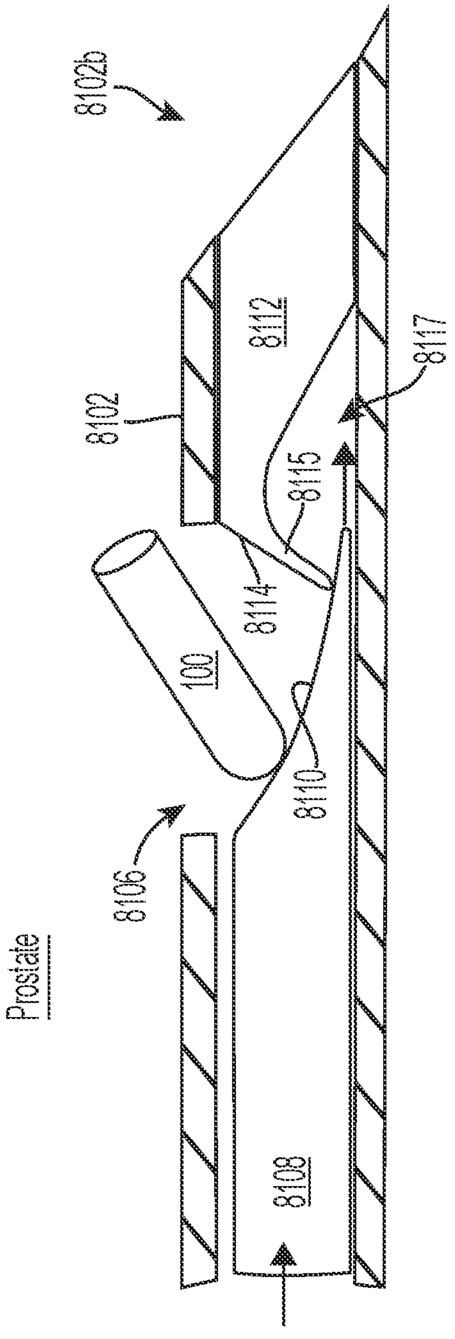

FIGS. 81B and 81C depict an example delivery system and method for implanting a depot 100 through a side opening of a delivery member. As shown in FIG. 81B, the delivery system may comprise an elongated shaft 8102 (such as a hollow needle) and an elongated member 8108 slidably received within the shaft lumen. The shaft 8102 may have a side opening 8106 extending through its sidewall, and a guide element 8112 positioned in the shaft lumen such that all or a portion of the element 8112 is distal of the opening 8106. The side opening 8106 is sized to receive a depot 100 therethrough.

The elongated member 8108 may have an angled or ramped distal surface 8110, and the depot 100 may be positioned on or otherwise in contact with the distal surface 8110 within the shaft lumen. The guide element 8112 may have a ramped proximal surface 8114 configured to guide a distal end of the depot 100 through the opening 8106 as the elongated member 8108 pushes the depot 100 distally. The guide element 8112 may obstruct all or a portion of the cross-sectional area of the shaft lumen. In the embodiment shown in FIGS. 81B and 81C, the guide element 8112 fills the distal portion of the shaft lumen, essentially forming a plug at the distal end.

In some embodiments, such as that shown in FIGS. 81B and 81C, the guide element 8112 comprises a proximal flange 8115 that extends proximally from the body of the guide element 8112 and includes the proximal surface 8114. The guide element 8112 may comprise a recessed portion 8117 just distal of the flange 8115. The proximal flange 8115 may extend across less than the entire diameter of the shaft lumen, thereby leaving room for a leading edge of the elongated member 8108 to move distally beyond (as shown in FIG. 81C). In some embodiments, the flange 8115 may be configured to flex and/or bend to adapt to distal advancement of the elongated member 8108.

In use, the physician may push the elongated member 8108 distally to advance the depot 100 towards the guide element 8112 and ultimately through the opening 8106. As depicted in FIG. 81C, in some embodiments, as the distal end of the depot 100 is urged against the proximal surface 8114 of the flange 8115, the depot 100 may pivot or rotate about its proximal end (which is still in contact with and being pushed distally by the elongated member 8108) and move through the opening 8106. In some embodiments, the depot 100 may pivot or rotate about its distal end as the distal end of the depot 100 is urged against the proximal surface 8114 of the flange 8115 (not shown). In these and other embodiments, the depot 100 may be forced through the opening 8106 without any substantial rotation. It will be appreciated that the orientation of the depot 100 as it is expelled from the shaft 8106 depends on a variety of factors, including the speed at which the elongated member 8108 is advanced, the angle of the distal surface 8110 relative to the longitudinal axis of the shaft 8102, and the angle of the proximal surface 8114 relative to the longitudinal axis, the shape of the depot 100, the formulation of the depot 100, the topography and/or contour of the inner surface of the shaft lumen, and others.

In some embodiments, the depot(s) 100 may have a curved and/or smooth proximal and/or distal surface to improve pushability of the depot 100 through the lumen between the ramped surface 8110, the inner surface of the shaft lumen, and/or the guide element 8112.

Figure 81D:
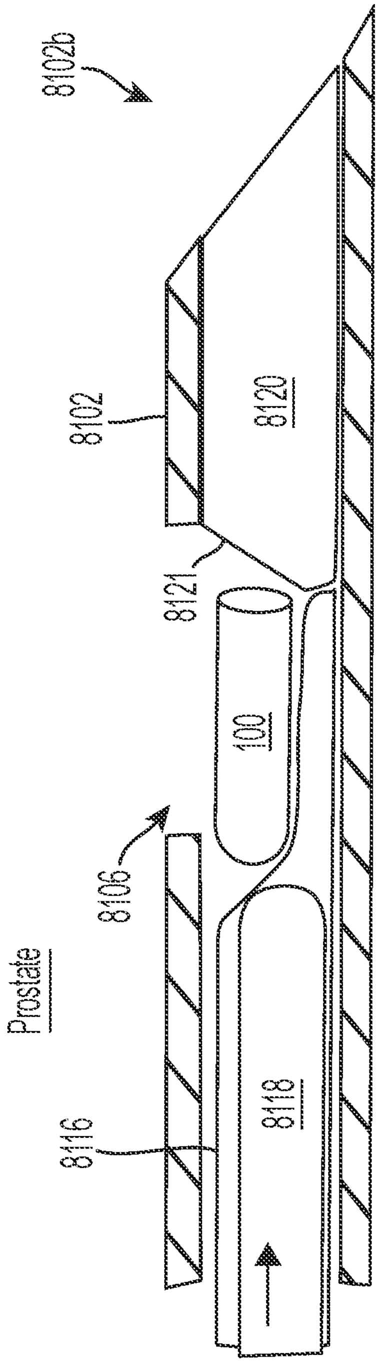
Figure 81E:
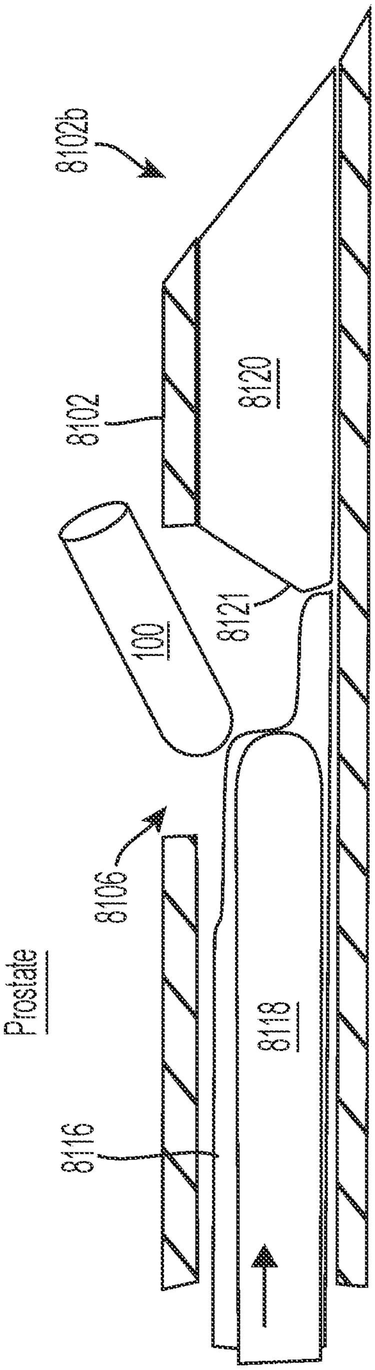

FIGS. 81D and 81E depict another example delivery system and method for implanting a depot 100 through a side opening of a delivery member. The delivery system may comprise an elongated shaft 8102 (such as a hollow needle), a flexible sleeve 8116 positioned within the shaft lumen, and an elongated member 8118 slidably received within the sleeve 8116. The shaft 8102 may have a side opening 8106 extending through its sidewall configured to receive the depot 100 therethrough. The system may further comprise a guide element 8120 positioned in the shaft lumen such that all or a portion of the element 8120 is distal of the opening 8106. As shown, the guide element 8120 may have a ramped proximal surface 8121.

In some embodiments, such as that shown in FIGS. 81D and 81E, the guide element 8120 may extend to the distal end 8102*b* of the shaft. In these and other embodiments, the guide element 8120 may have a beveled distal end surface that is substantially flush with the beveled end of the shaft 8102. In some embodiments, the guide element 8120 may not extend to the distal end of the shaft 8102 and/or may not have a distal surface that is beveled and/or substantially flush with the beveled distal end of the shaft 8102.

The sleeve 8116 may be formed of an elastic material, such as any elastic material used in making conventional medical device balloons. A distal portion of the sleeve 8116 may be fixed to the shaft lumen at or distal of the opening 8106. Less than the full circumference of the sleeve 8116 may be attached to the shaft 8102, thereby leaving a collapsible portion that is free to move relative to the shaft wall.

The depot 100 may be positioned on the collapsible portion (in its collapsed state). To expel the depot 100, a physician may push the elongated member 8118 distally within the sleeve 8116 to force the collapsed portion of the sleeve 8116 to expand, thereby pushing the depot 100 towards and/or through the window 8106. The ramped proximal surface 8121 of the guide element 8120 may guide the depot 100 through the opening 8106 as the elongated member 8118 pushes the depot 100 distally.

In some embodiments, the depot(s) 100 and/or elongated member 8118 may have a curved and/or smooth proximal and/or distal surface to improve pushability of the depot 100 and/or engagement with the depot 100.

Figure 81F:
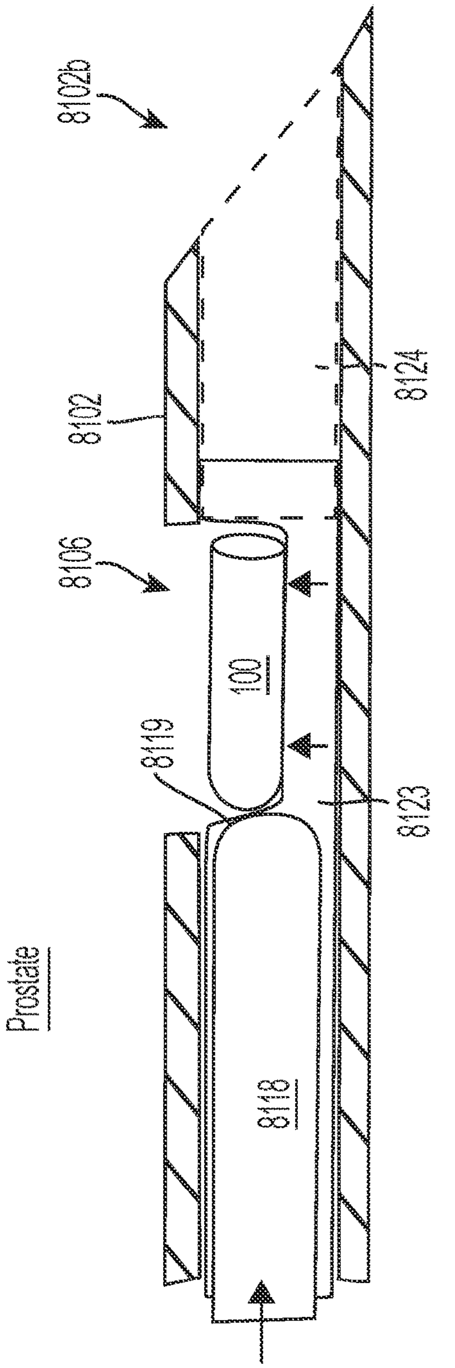
Figure 81G:
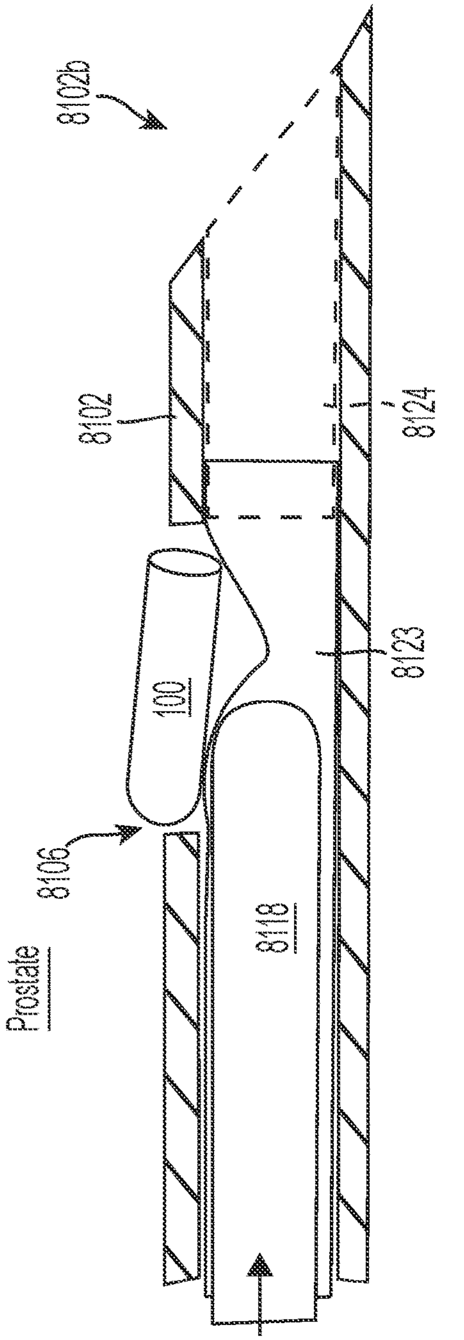

FIGS. 81F and 81G depict another example delivery system and method for implanting a depot 100 through a side opening of a delivery member. The delivery system may comprise an elongated shaft 8102 (such as a hollow needle), a flexible tube 8123 positioned within the shaft lumen, and an elongated member 8118 slidably received within the sleeve 8123. The shaft 8102 may have a side opening 8106 extending through its sidewall configured to receive the depot 100 therethrough. The flexible tube 8123 may extend across the opening 8106. The system may optionally comprise a distal element 8124 positioned in the shaft lumen such that all or a portion of the element 8124 is distal of the opening 8106. In such embodiments, all or a portion of the distal element 8124 may overlap axially with the sleeve 8116. In some embodiments, a distal portion of the tube 8123 is positioned between the distal element 8124 and an inner surface of the shaft 8102. The distal element 8124 may extend to the distal end 8102*b* of the shaft, and in some embodiments (such as that shown in FIGS. 81F and 81G) have a beveled distal end surface that is substantially flush with the beveled end of the shaft 8102. In some embodiments, the distal element 8124 may not extend to the distal end of the shaft 8102 and/or may not have a distal surface that is beveled and/or substantially flush with the beveled distal end of the shaft 8102.

The tube 8123 may be formed of an elastic material, such as any elastic material used in making conventional medical device balloons. The tube 8123 may be attached to the shaft 8102 at a location distal of the opening 8106 and at a location proximal of the opening 8106. The tube 8123 may have a length slightly greater than that of the opening 8106 such that the ends of the tube 8123 are just proximal and distal to the opening 8106. In some embodiments, the tube 8123 extends proximally along the length of the shaft lumen. In any case, the depot 100 may be positioned on a collapsed portion of the tube 8123 that is aligned with the opening 8106. To expel the depot 100, a physician may push the elongated member 8118 distally within the tube 8123 to force the collapsed portion of the tube 8123 to expand, thereby pushing the depot 100 towards and/or through the window 8106.

In some embodiments, the tube 8123 may be replaced with a strip (not shown) that extends across the opening 8106, similar to a hammock. The proximal and distal ends of the strip may be attached to the shaft 8102 at locations proximal and distal of the opening 8106. The strip may have a circumferential width that is less than, greater than, or equal to the circumferential width of the opening 8106. Similar to the mechanism discussed with reference to FIGS. 81F and 81G, the depot 100 may be expelled from the shaft lumen by advancing the elongated member 8118 distally and exerting a force on the depot 100 through the strip.

In some embodiments, the depot(s) 100 and/or elongated member 8118 may have a curved and/or smooth proximal and/or distal surface to improve pushability of the depot 100 and/or engagement with the depot 100.

Figure 81H:
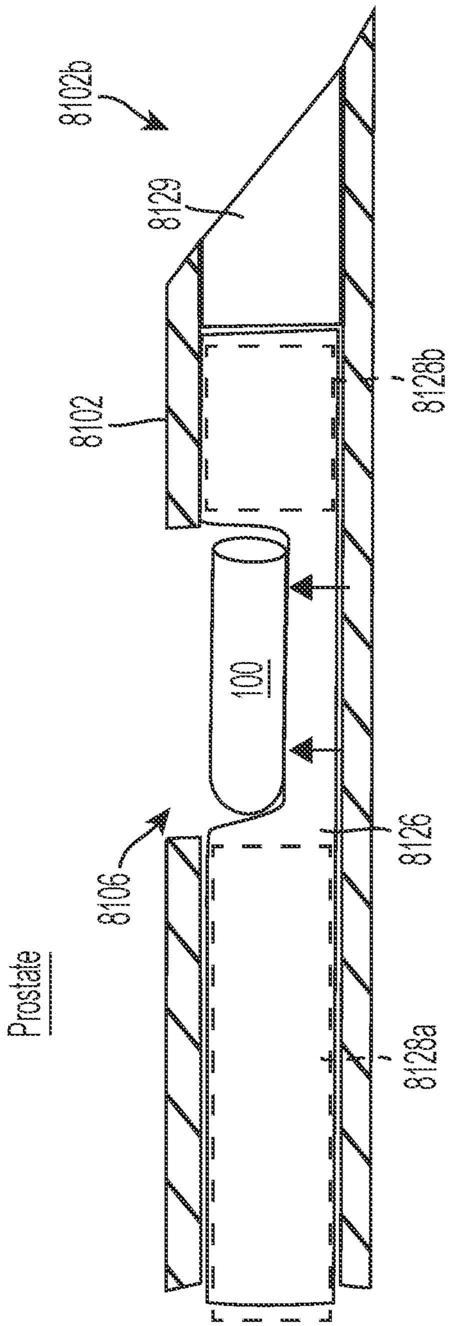
Figure 81I:
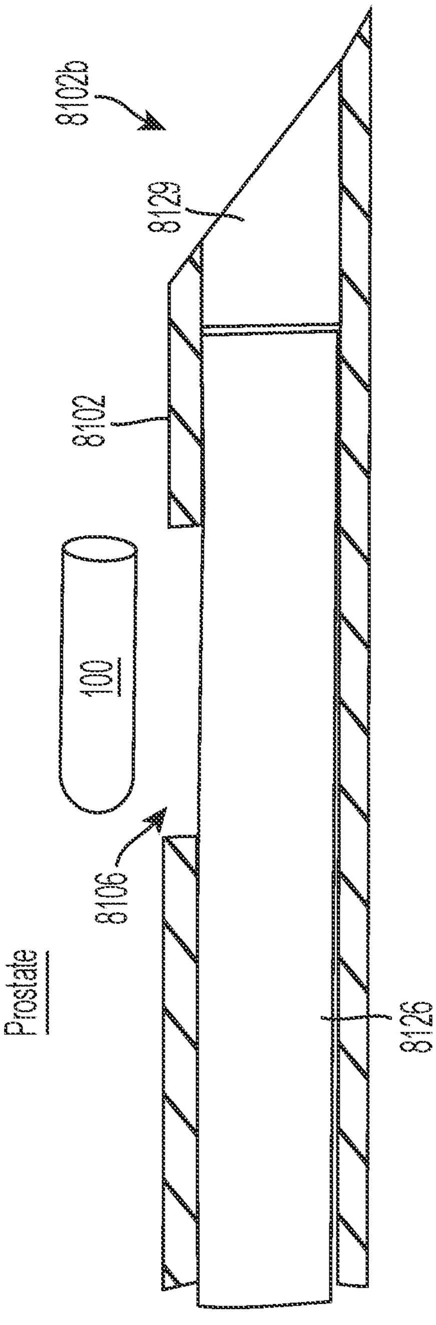

FIGS. 81H and 811 depict another example delivery system and method for implanting a depot 100 through a side opening of a delivery member. The delivery system may comprise an elongated shaft 8102 (such as a hollow needle) and a flexible sleeve 8126 positioned within the shaft lumen. The shaft 8102 may have a side opening 8106 extending through its sidewall configured to receive the depot 100 therethrough. The sleeve 8126 may be formed of an elastic material, such as any elastic material used in making conventional medical device balloons. In operation, a physician may inflate the sleeve 8126 while the depot 100 is positioned on a collapsed portion of the sleeve 8126 that is aligned with the opening 8106 such that the expanding sleeve 8126 pushes the depot 100 towards or through the opening 8106 (as shown in FIG. 811).

The system may optionally include one or both of a proximal member 8128*a* and a distal member 8128*b*. The proximal and distal members 8128*a* and 8128*b* may be positioned in the sleeve 8126 at locations that are proximal and distal of the opening 8106, respectively, when the sleeve 8126 is positioned within the shaft lumen. The proximal and distal members 8128*a* and 8128*b* may be configured to help secure the sleeve 8126 to the shaft and/or limit movement of the depot 100 within the shaft lumen. In some embodiments, the proximal and/or distal members 8128*a* and 8128*b* may be formed of a polymer rod. In other embodiments, the proximal and distal members 8128*a* and 8128*b* may have other suitable shapes, materials, and configurations.

In some embodiments, system may include a distal element 8129 similar to the distal elements 8120 and 8124 discussed elsewhere herein. The distal element 8129, for example, may extend to the distal end 8102*b* of the shaft, and in some embodiments (such as that shown in FIGS. 81F and 81G) have a beveled distal end surface that is substantially flush with the beveled end of the shaft 8102. In some embodiments, the distal element 8129 may not extend to the distal end of the shaft 8102 and/or may not have a distal surface that is beveled and/or substantially flush with the beveled distal end of the shaft 8102.

The sleeve 8128 may have a closed distal end, or the sleeve 8128 may be generally tubular. In those embodiments where the sleeve 8126 is generally tubular, the distal member 8128*b* may be configured to occlude the lumen of the sleeve 8126 so that the sleeve 8126 may be inflated from a proximal end. Likewise, when the system includes the proximal member 8128*a*, the proximal member 8128*a* may only partially occlude the sleeve lumen, thereby allowing the sleeve 8126 to be inflated from its proximal end.

In any of the foregoing embodiments, the depot(s) 100 may be pre-positioned within the shaft lumen in full or partial alignment with the opening 8106. In such embodiments, the delivery system 8100 may include a slidable cover (not shown) prevents the depot from moving through the opening 8106 as the shaft 8102 punctures the body and is inserted into the prostate. As the shaft 8102 is inserted, the slidable cover may slide proximally.

Figure 82A:
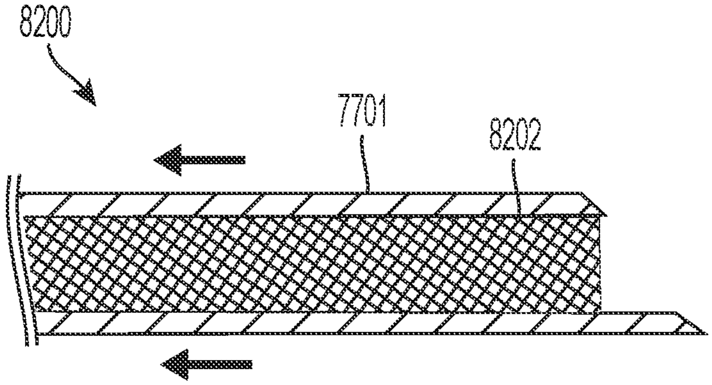
FIGS. 82A-82C depict an example method for implanting a depot of the present technology at a prostate gland of a human patient via a mesh delivery member.
Figure 82B:
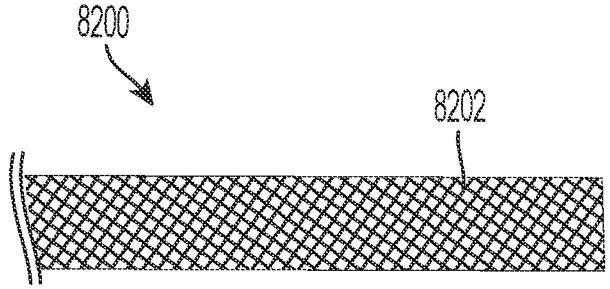
Figure 82C:
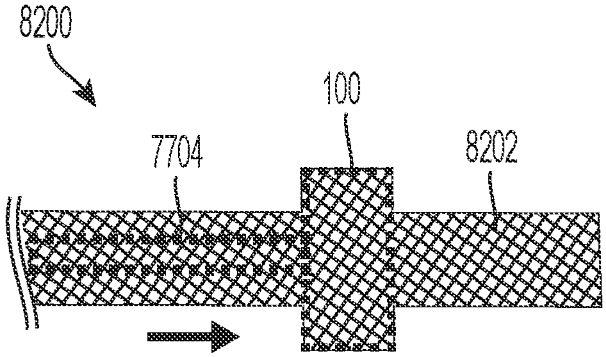

While in many cases it may be advantageous to deliver the depot(s) 100 to the prostate through a hollow needle, for depot(s) 100 above a certain size it may be beneficial to utilize an alternative delivery system. This is because the larger the depot, the larger the size of the needle required for delivery, and the greater the pain and potential complications for the patient (such as bleeding, infection, and nerve injury). FIGS. 82A-82C depict an example delivery system 8200 and method for implanting a depot of the present technology at a prostate gland of a human patient in accordance with the present technology. The delivery system 8200 may include a hollow needle 7701 and an elongated expandable element 8202 configured to be positioned within the needle lumen. In some embodiments, the expandable element 8202 may be configured to be positioned around the exterior of the needle 7701. The expandable element 8202 may be a generally tubular mesh, such as a stent, a braid, a weave, or other suitable lattice-like structure. In use, a distal portion of the needle 7701 containing the mesh 8202 may be inserted into the prostate via any one of the methods described herein, such as those methods described above with reference to FIGS. 76-81B. As indicated by the arrows in FIG. 82A, the needle 7701 may be withdrawn proximally to leave the expandable element 8202 uncovered in the prostate, as shown in FIG. 82B. As depicted in FIG. 82C, the depot 100 may be advanced distally through the expandable element 8202 via an elongated push member 7704. The depot 100 may be slightly larger than the expandable element 8202 such that the depot 100 expands the mesh 8102 as it moves through the unrestrained portion of the expandable element 8202. The depot 100 may be pushed distally by the elongated member 7704 until being expelled from a distal opening of the mesh into prostate tissue.

In the foregoing embodiments in which the expandable element 8202 comprises a mesh, it may be advantageous to encapsulate the expandable element 8202 in an elastomeric coating such that the sidewall of the expandable element 8202 becomes impermeable along its length. This way, when the needle is withdrawn and leaves the expandable element 8202 behind in the tissue, the coating surrounding the expandable element 8202 prevents ingress of bodily fluids to the expandable element 8202 lumen.

Additionally or alternatively, the expandable element 8202 may include a lubricant and/or hydrophobic coating along all or a portion thereof to reduce the friction between the expandable element 8202 and the depot 100 (thereby lowering the forces required to push the depot 100 through the expandable element 8202). For similar reasons, in some embodiments the depot 100 may have a smooth leading edge.

Figure 83A:
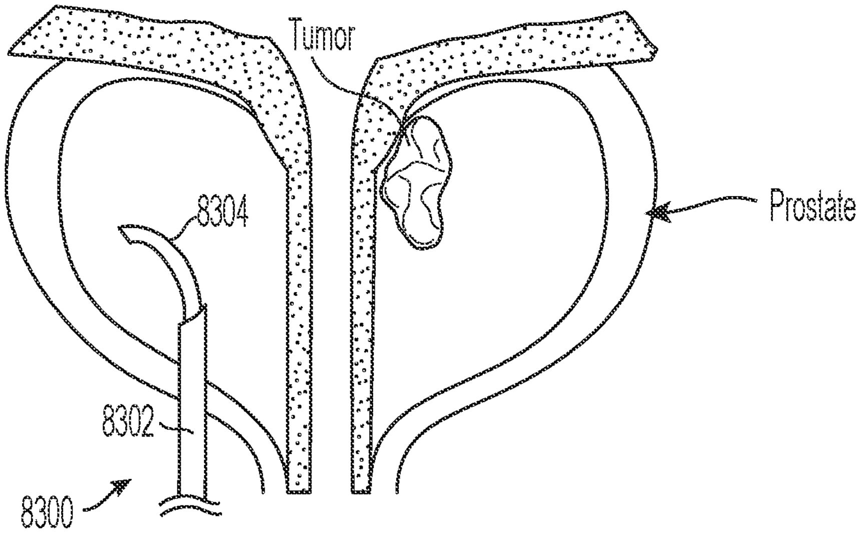
FIGS. 83A-83E depict an example method for implanting a depot of the present technology at a prostate gland of a human patient via a curved delivery member.
Figure 83B:
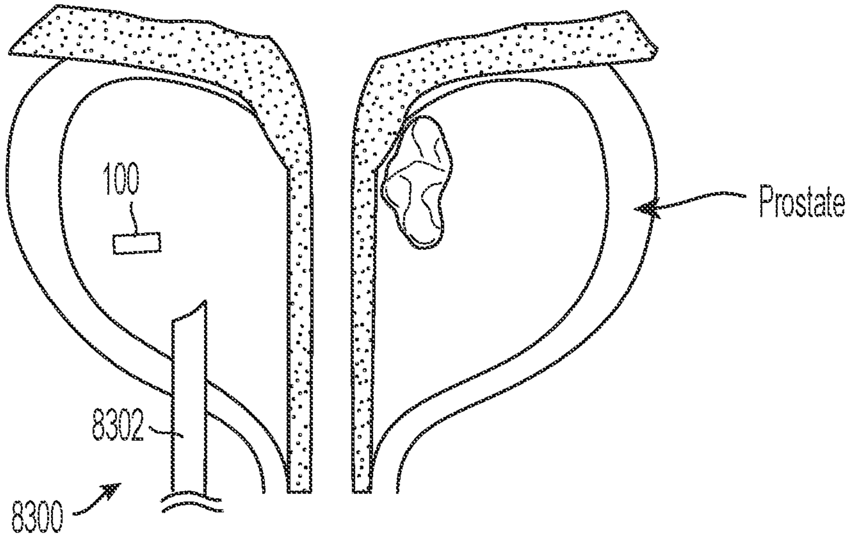
Figure 83C:
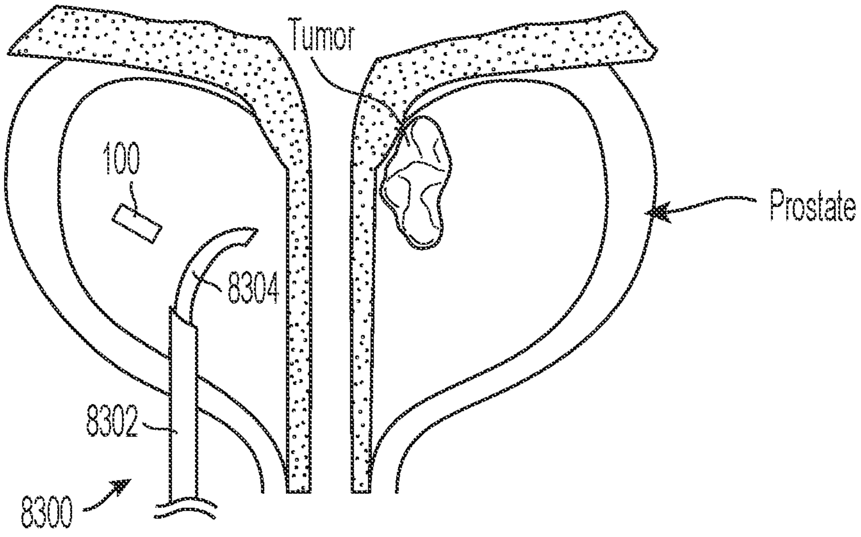
Figure 83D:
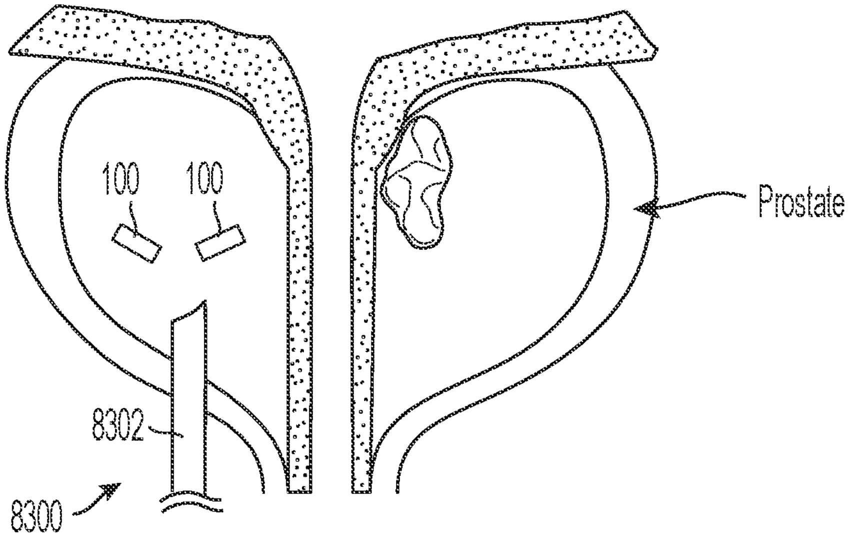
Figure 83E:
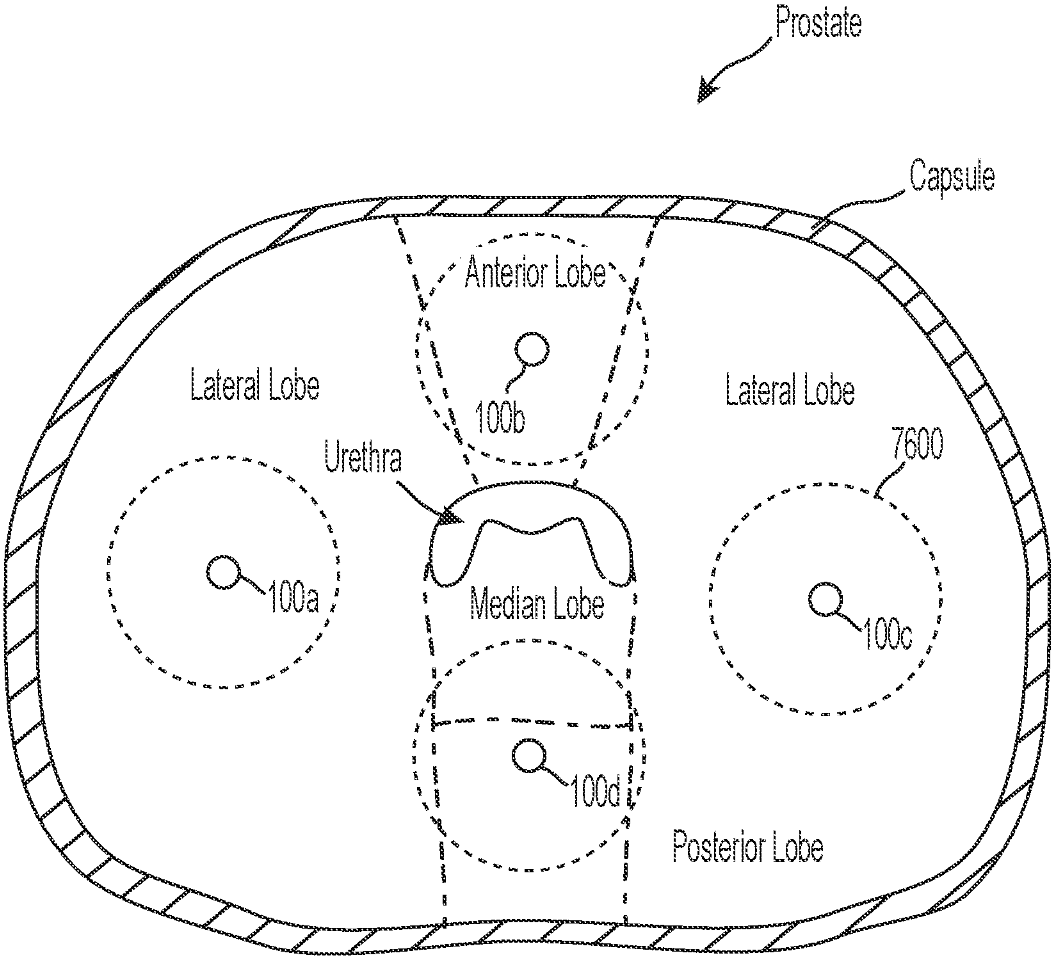

According to various aspects of the technology, multiple depots may be delivered to different locations within the prostate via a single insertion point. FIGS. 83A-83D, for example, depict an example delivery system 8300 and method for implanting a depot of the present technology at a prostate gland of a human patient. The delivery system 8300 may include a guide shaft 8302 (such as a hollow needle), a needle 8304 configured to be slidably and rotatably received through the lumen of the shaft 8302, an elongated member (not visible) configured to be received within the needle lumen, and a plurality of depots (not shown) loaded end-to-end within the distal portion of the needle (for example, as depicted in FIG. 85B). As shown in FIG. 83A, the shaft 8302 may be inserted into the prostate via any one of the methods described herein, such as those methods described above with reference to FIGS. 76-80. The needle 8304 may be advanced through the shaft 8302 and into the prostate. A distal portion of the needle 8304 may have a preset curve such that, when the needle 8304 exits the shaft 8302, the needle 8304 bends away from an axis running along the longitudinal axis of the shaft 8302. As described above with respect to FIGS. 77B and 77C, the needle 8304 may be retracted while the elongated member is held stationary to implant the depot 100 within the prostate. As shown in FIG. 83B, the needle 8304 may be withdrawn into the shaft 8302, and the physician manipulate a distal portion of the delivery system 8300 to rotate the needle 8304. The needle 8304 may then be distally advanced through the distal opening of the shaft 8302 into the prostate, as shown in FIG. 83C. Because of the rotation of the needle 8304, this time the needle 8304 curves away from the shaft 8302 in a direction different than the direction the needle 8304 previously bent towards when advanced from the shaft 8302. As such, the needle 8304 is able to access a different portion or lobe or the prostate than it did during its previous insertion. As described above with respect to FIGS. 77B and 77C, the needle 8304 may then be retracted while the elongated member is held stationary to implant the depot 100 within the prostate, as shown in FIG. 83D. In some embodiments, the delivery system 8300 may be used to position two or more depots in different lobes of the prostate, for example as shown in the transverse view of the prostate in FIG. 83E.

Figure 84:
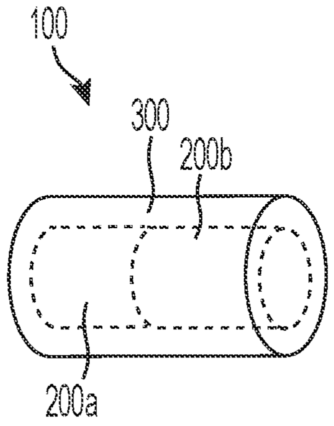
FIG. 84 depicts a depot configured to deliver two or more therapeutic agents in accordance with the present technology.

In some cases it may be desirable for the depot or depot system to release multiple therapeutic agents at the treatment site (or a single therapeutic agent comprising two different therapeutic agents). FIGS. 84-89, for example, depict several embodiments of depots and/or depot systems of the present technology configured to deliver two or more therapeutic agents to a prostate gland. As shown in FIG. 84, the depot 100 may be generally similar to the elongated depot 100 described above with reference to FIG. 73B, except the depot 100 shown in FIG. 84 has a first therapeutic region 200*a* and a second therapeutic region 200*b*, both of which are surrounded by a control region 300. The first therapeutic region 200*a* may include a first therapeutic agent and the second therapeutic region 200*b* may comprise a second therapeutic agent different than the first therapeutic agent. For example, the first therapeutic agent may be a chemotherapeutic agent and the second therapeutic agent may be an antiandrogen. The depot 100 may be configured such that the first and second therapeutic agents are delivered at the same time or at different times, for the same duration or different durations, and/or at the same rate or different rates.

Figure 85A:
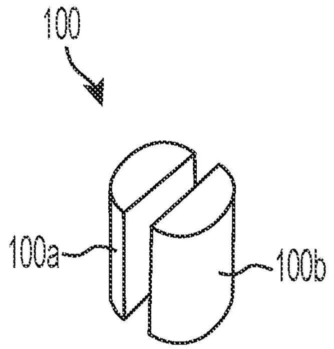
FIG. 85A depicts a depot configured to deliver two or more therapeutic agents in accordance with the present technology.
Figure 85B:
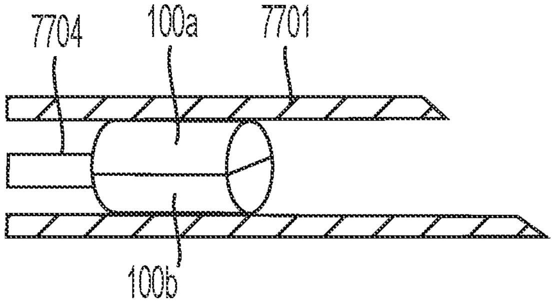
FIG. 85B shows an example delivery system for the depot shown in FIG. 85A.

FIG. 85A depicts a depot 100 or depot system configured to deliver two or more therapeutic agents in accordance with the present technology. FIG. 85B shows an example delivery system for the depot shown in FIG. 85A. As shown, the depot 100 may comprise a first depot portion 100*a* and a second depot portion 100*b*, each containing a different therapeutic agent. For example, the first depot portion 100*a* may include a chemotherapeutic agent and the second depot portion 100*b* may include an antiandrogen. In some embodiments, the first and second depot portions 100*a* and 100*b* have complementary shapes such that the first and second portions 100*a* and 100*b* can be positioned laterally adjacent one another within a delivery shaft and simultaneously delivered from a delivery device. The first depot portion 100*a* may comprise a first half-cylinder and the second depot portion 100*b* may comprise a second half-cylinder. The two half-cylinders may be configured to be positioned within a lumen of a delivery device such that a generally flat side of the first half-cylinder faces a generally flat surface of the second half-cylinder to form a full cylinder.

Figure 86A:
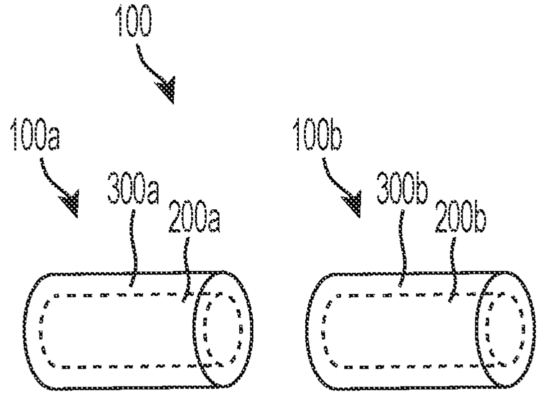
FIG. 86A depicts a depot configured to deliver two or more therapeutic agents in accordance with the present technology.

In some embodiments, the depot and/or depot system may comprise a plurality of discrete depots, at least two of which include different therapeutic agents. FIG. 86A, for example, shows a depot or depot system comprising at least two pellets or microcylinders 100*a*, 100*b*, each comprising respective therapeutic regions 200*a* and 200*b* and control regions 300*a* and 300*b*. The therapeutic regions 200*a*, 200*b* may comprise different therapeutics agents. For example, the first depot portion 100*a* may include a chemotherapeutic agent and the second depot portion 100*b* may include an antiandrogen. In some embodiments, one or both of the depots 100*a*, 100*b* do not include a control region 300 and only comprise a therapeutic region 200. In some embodiments, the discrete depots with different therapeutic agents are attached to one another, and in others the discrete depots are not attached, and are free to separate from one another upon delivery.

Figure 86B:
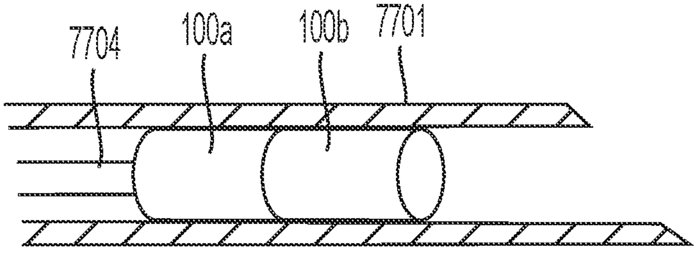
FIG. 86B shows an example delivery system for the depots shown in FIG. 86A.

FIGS. 86B and 87 show example delivery systems for the depot system shown in FIG. 86A. As shown in FIG. 86B, the first and second depots 100*a* and 100*b* may be loaded end-to-end within a hollow needle 7701. The delivery system may include an elongated member 7704 positioned within the needle 7701 and having a distal end adjacent a proximal end of the depots. The depots 100*a* and 100*b* may be released from the needle 7701 at the same time. For example, the needle 7701 may be retracted proximally beyond a proximal end of the most proximal depot while the needle 7701 remains in the same location such that both depots are implanted in substantially the same location. In some embodiments, the depots may be released at different times. For example, the needle 7701 may be retracted enough to release the more distal depot but not enough to release the more proximal depot. The needle 7701 may then be moved before being retracted even further to release the more proximal depot.

When implanting multiple depots in the prostate gland through a single delivery device, it may be beneficial to control the spacing of sequentially delivered depots. As previously mentioned, each of the depots may have a corresponding treatment zone in which the therapeutic agent(s) released from the respective depot provides a therapeutic effect. It may be advantageous to space the depots based on a desired degree of overlap or distance between the treatment zones of the depots. For example, in some cases it may be desirable to space the depots such that their respective treatment zones abut one another without excessive overlapping or excessive dosing in a specific area. In some instances it may be beneficial to space the depots such that their respective treatment zones overlap to form a concentrated treatment zone. The concentrated treatment zone, for example, may coincide with all or a portion of an identified tumor and/or another portion of the prostate gland, including those areas most likely to contain pre-cancerous tissue. In many instances it may be beneficial to position one or more depots such that they create an effective treatment zone throughout the entire prostate.

Figure 87A:
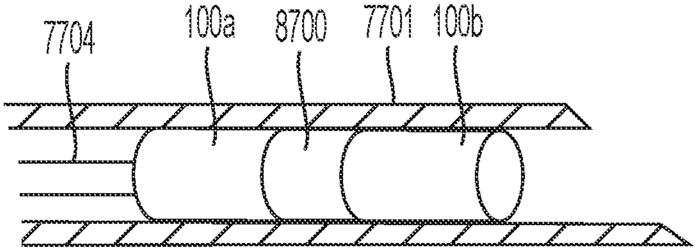
FIGS. 87A-87C depict examples of treatment systems configured to deliver two or more depots with controlled spacing in accordance with the present technology.
Figure 87B:
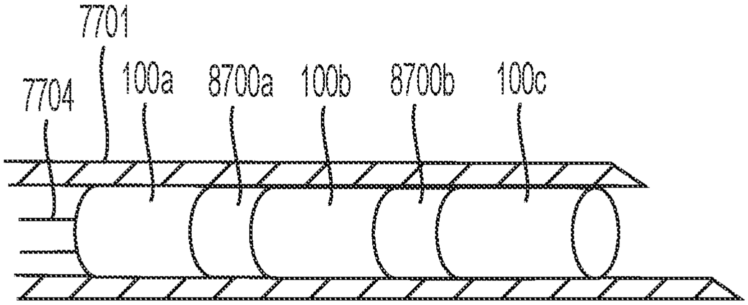
Figure 87C:
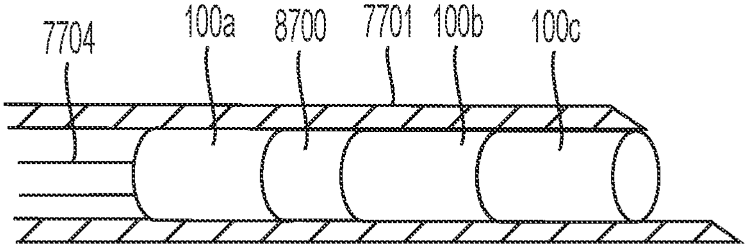

According to some embodiments, for example as shown in FIG. 87A, the delivery system may include a spacer 8700 positioned between adjacent depots within the delivery device. As such, when the depots 100*a* and 100*b* are released from the delivery device (such as a needle 7701), the spacer 8700 ensures that the depots 100*a* and 100*b* are at least a predetermined distance from one another within the prostate. The spacer 8700 may comprise a dissolvable material, such as a sugar, and/or may comprise a biodegradable polymer. As depicted in FIG. 87B, when delivering three or more depots 100, the system may include multiple spacers (labeled 8700*a*, 8700*b*), each preloaded in the delivery device between adjacent depots (labeled 100*a*, 100*b*, 100*c*). Alternatively, as shown in FIG. 87C, some adjacent depots may include a spacer 8700 therebetween (such as depots 100*a* and 100*b*), and some adjacent depots may not include a spacer therebetween (such as depots 100*b* and 100*c*). In any of the foregoing embodiments disclosed herein that employ multiple spacers, the spacers may have the same or different lengths, the same or different shapes, and may comprise the same or different materials.

Figure 88:
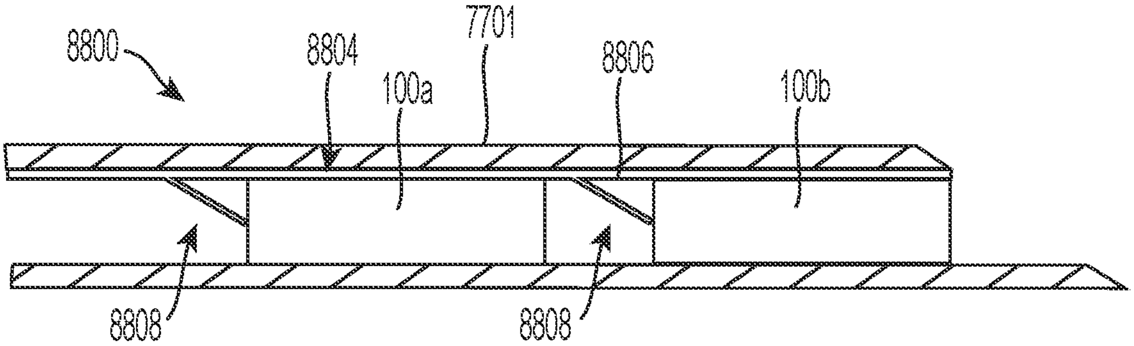
FIG. 88 depicts a delivery system configured to deliver two or more depots with controlled spacing in accordance with the present technology.

FIG. 88 depicts a treatment system 8800 configured to implant multiple depots (labeled 100*a* and 100*b*) at a predetermined spacing. As shown in FIG. 88, in some embodiments the system 8800 may comprise a delivery device (such as a needle 7701) and a spacer 8804 configured to be slidably received within a lumen of the delivery device. The spacer 8804 may comprise an elongated portion 8806 having one or more flexible arms 8808 extending away from the elongated portion 8806 towards the lumen of the device. The depots 100*a*, 100*b* may be loaded within the delivery device such that at least one arm 8808 is positioned between the depots 100*a*, 100*b* to maintain a predetermined distance between the depots 100*a*, 100*b*. The arm(s) 8808 may have a length and/or extension angle configured to achieve a desired spacing between adjacent depots. In those embodiments comprising multiple arms 8808, the arms 8808 may have the same or different length, the same or different extension angle, and/or the same or different orientation relative to the elongated portion 8806. For example, as depicted in FIG. 88, in some embodiments one, some, or all of the arms 8808 extend distally into the lumen of the delivery device. Additionally or alternatively, one, some, or all of the arms 8808 extend proximally into the lumen of the delivery device. In these and other embodiments, one, some, or all of the arms 8808 extend at an angle that is perpendicular or substantially perpendicular to the longitudinal axis of the elongated portion 8806. In some cases it may be preferable to reduce the extension angle as much as possible without compromising the spacing between the depots so that less deflection is needed during retraction.

Figure 89A:
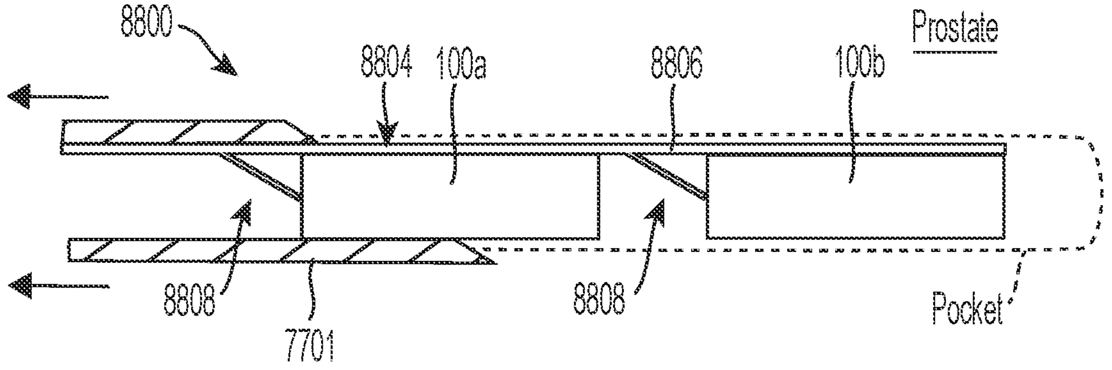
FIGS. 89A-89C show an example system and method for implanting a depot of the present technology at a prostate gland of a human patient with controlled spacing.
Figure 89B:
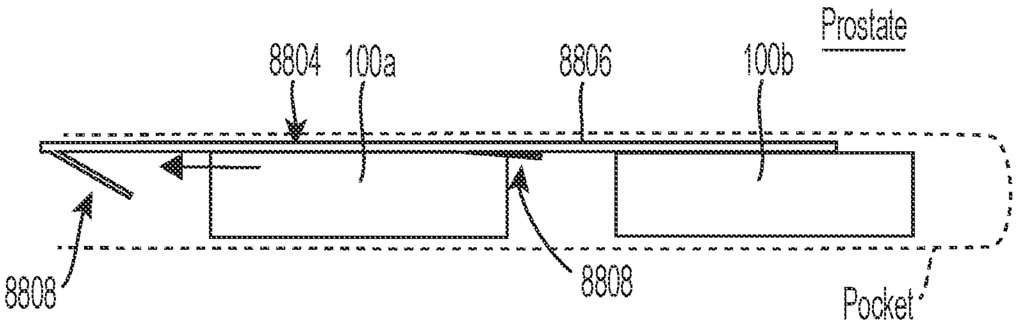
Figure 89C:
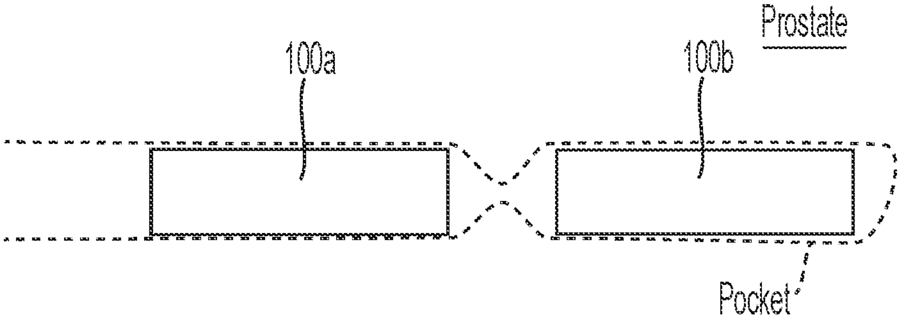

FIGS. 89A-89C show an example method of implanting multiple depots at a predetermined spacing using the system 8800. To begin, a distal portion of the needle 7701 containing depots 100*a*, 100*b* may be inserted into the prostate via any one of the methods described herein, such as any of the methods described above with reference to FIGS. 76-81B. As indicated by the arrows in FIG. 89A, the needle 7701 may be withdrawn proximally while the spacer 8804 is held stationary, thereby leaving the spacer 8804 and the depots 100*a*, 100*b* within a pocket created by the needle 7701. The spacer 8804 may then be withdrawn from the pocket, as shown in FIG. 89B. As the spacer 8804 is withdrawn and a proximal region of the arm 8808 is forced against a distal region of a proximally adjacent depot, the arm 8808 flexes away from the depot and towards the elongated portion 8806, thereby leaving the depots 100*a*, 100*b* in place while allowing the spacer 8804 to be withdrawn. As shown in FIG. 89C, withdrawal of the spacer 8804 leaves the depots 100*a*, 100*b* behind in the prostate tissue at a predetermined spacing. Soon thereafter, the pocket collapses down around the depots 100*a*, 100*b*, thereby preserving the desired spacing.

Figure 90:
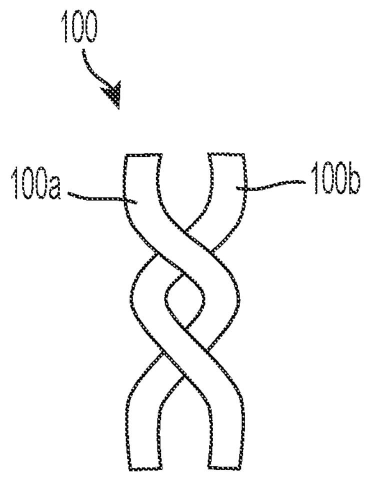
FIG. 90 depicts a depot configured to deliver two or more therapeutic agents in accordance with the present technology.

FIG. 90 depicts a depot or depot system configured to deliver two or more therapeutic agents in accordance with the present technology. As shown, the depot 100 may comprise a first depot portion 100*a* and a second depot portion 100*b*, each containing a different therapeutic agent. For example, the first depot portion 100*a* may include a chemotherapeutic agent and the second depot portion 100*b* may include an antiandrogen. The first and second depot portions 100*a* and 100*b* may be manufactured separately and coupled to one another prior to implantation. For example, each of the first and second depot portions 100*a* and 100*b* may comprise an elongated, cylindrical member, and the first and second depot portions 100*a* and 100*b* may be twisted together prior to implantation.

Figure 91:
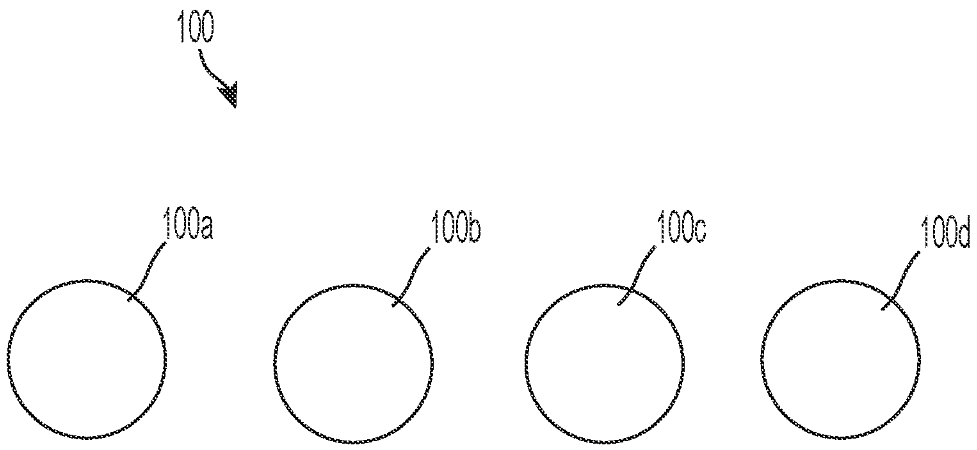
FIG. 91 depicts a depot configured to deliver two or more therapeutic agents in accordance with the present technology.

FIG. 91 depicts a depot 100 or depot system configured to deliver two or more therapeutic agents in accordance with the present technology. In some embodiments, the depot system may comprise a plurality of microspheres or microbeads, at least two of which include different therapeutic agents.

Figure 92:
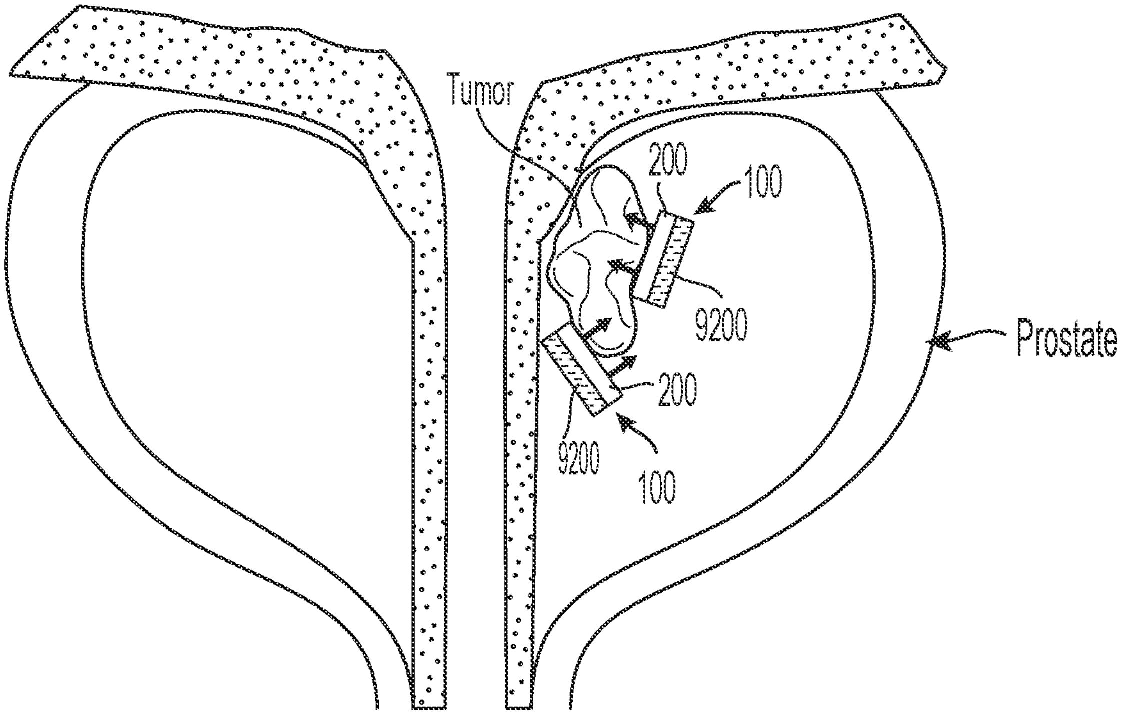
FIG. 92 is a schematic illustration of two depots configured for directional release of a therapeutic agent, shown implanted in a cancerous prostate gland in accordance with the present technology.

FIG. 92 is a schematic illustration of two depots configured for directional release of a therapeutic agent implanted in a cancerous prostate gland in accordance with the present technology. As shown in FIG. 92, the depots of the present technology configured to treat prostate cancer may include a barrier region 9200 for directional release of the therapeutic agent. The depots may be positioned within the prostate, for example, so that the barrier region 9200 is positioned between the therapeutic region 200 and non-tumor tissue. The barrier region 9200 may comprise a low porosity, high density of bioresorbable polymer, which is substantially impermeable, that provides controlled directionality of released therapeutic agent by blocking or impeding passage of the therapeutic agent from the therapeutic region 200. Accordingly, the agents released from the therapeutic region 200 take a path of lesser resistance through the control region 300 or directly into the surrounding tissue. The barrier region 9200 and its position relative to the therapeutic region 200 may be particularly beneficial for concentrating the therapeutic agent towards the targeted tumor and reducing or altogether avoiding the unwanted release of the therapeutic agent towards the prostatic capsule and/or urethra.

In some embodiments, the depot 100 may be configured to release the therapeutic agent in an omnidirectional manner. In other embodiments, the depot may include one or more barrier regions 9200 covering one or more portions of the therapeutic region 200 and/or control region 300, such that release of the therapeutic agent is limited to certain directions. The barrier region 9200 may provide structural support for the depot. The barrier region 9200 may comprise a low porosity, high density of bioresorbable polymer configured to provide a directional release capability to the depot. In this configuration, the substantial impermeability of this low porosity, high density polymer structure in the barrier region 9200 blocks or impedes the passage of agents released from the therapeutic region 200. Accordingly, the agents released from the therapeutic region 200 take a path of less resistance through the control region 300 opposite from the barrier region 9200, particularly following the creation of diffusion openings in the control region 300.

In those depot embodiments including multiple therapeutic agents (such as a chemotherapeutic agent and an antiandrogen), the release of the therapeutic agent(s) can be spatially controlled, for example by utilizing one or more barrier regions 9200 to direct a first therapeutic agent towards a first region of the prostate and/or tumor and a second therapeutic agent towards a second region of the prostate and/or tumor.

In some embodiments, the barrier region 9200 may be configured to provide structural support to the therapeutic region 200 and/or depot 100.

Figure 93:
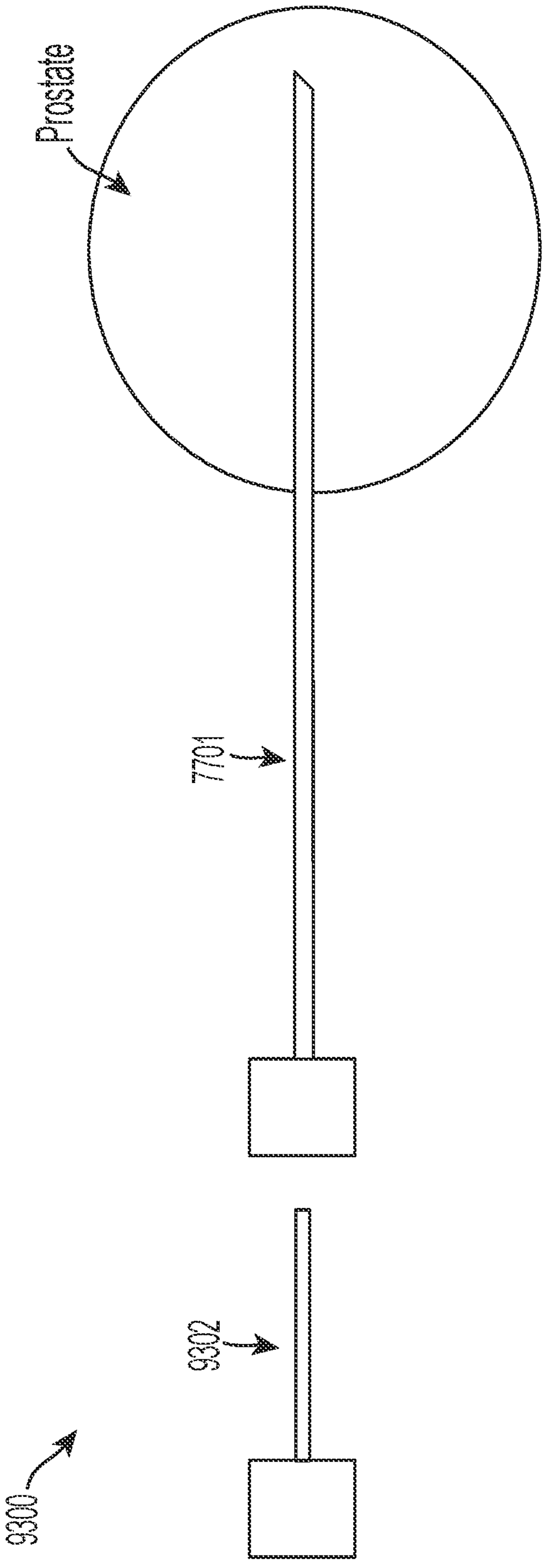
FIG. 93 depicts a delivery system configured to deliver one or more depots in accordance with the present technology.

A challenge in using a needle or similar delivery device for implanting the depot is that the needle has a fixed, relatively short length. This limits the length of the depot that can be implanted, thus affecting the amount of therapeutic agent that can be delivered. To address this challenge and enable delivery of higher payloads, it may be advantageous to maximize an implanted depot length (and thus volume). For example, FIG. 93 is a side view of a treatment system 9300 configured to deliver a depot having a customized length. The ability to deliver a depot having a customized length (and thus volume) may be advantageous, for example, for customizing the dosage for each patient. As shown in FIG. 93, the system 9300 may comprise a delivery device (such as needle 7701), a loading device 9302 configured to be coupled to a proximal portion of the delivery device, and a plurality of depots (not shown) of different lengths. The loading device 9302 may be configured to provide convenient and controlled storage for an entire set of drug depots within a given kit or package. The loading device 9302 may also include an actuator (such as a button, a trigger, etc.) that, when actuated, releases or transfers a desired number and/or type of depots to the delivery device. For example, if a clinician wants to deliver three depots at a particular location, the clinician can actuate the loading device 9302 three times to release three depots into the delivery device, or the clinician may set a dial on the loading device 9302 that releases three depots from the loading device 9302 with a single actuation.

The loading device 9302 may be configured to load a desired total depot length into the delivery device. The total depot length may be achieved with a single depot, or may require a plurality of depots. For example, the depots may comprise one or more short discs (e.g., 1-3 mm), one or more shorter rods (e.g., 3-7 mm), and one or more longer rods (e.g., 7-15 mm) that may be combined as necessary to achieve a desired total depot length. Additionally or alternatively, the system 9300 may include a depot comprising a long, continuous rod that can be cut to a desired length for each deployment location.

Figure 94A:
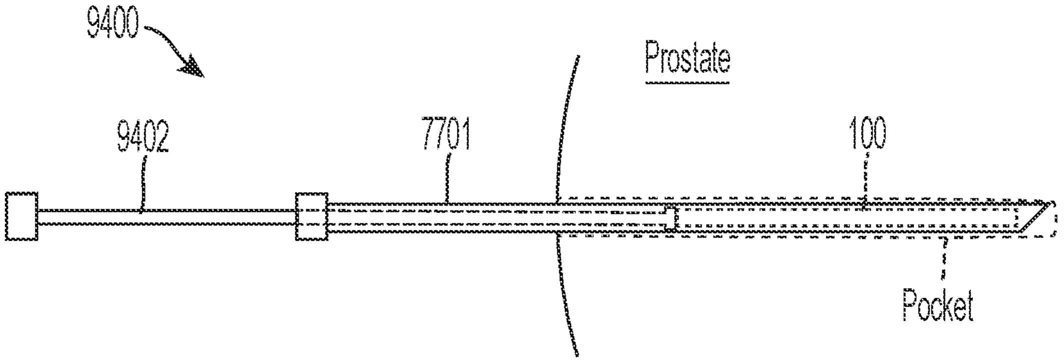
FIGS. 94A-94C depict a system and method for implanting one or more depots in a prostate gland of a human patient in accordance with the present technology.
Figure 94B:
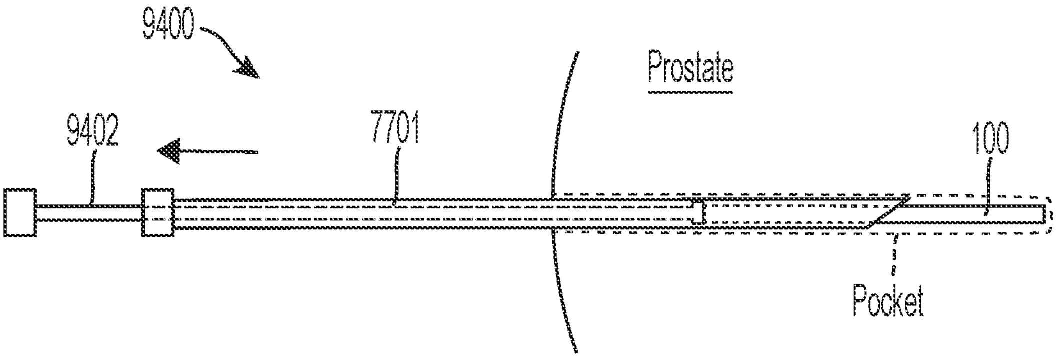
Figure 94C:
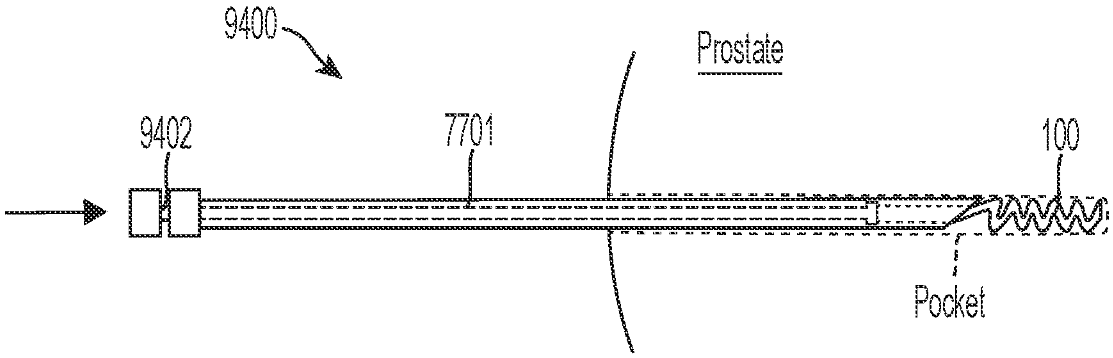

FIGS. 94A-94C show a treatment system 9400 for implanting a depot 100 into a prostate gland configured in accordance with several embodiments of the present technology. As shown in FIG. 94A, the system 9400 may comprise a delivery device (such as needle 7701) and an elongated member 9402 configured to be slidably received through a lumen of the delivery device. An elongated depot 100 may be loaded within a distal region of the delivery device such that a distal end portion of the elongated member 9402 abuts a proximal end portion of the depot 100. To implant the depot 100, the delivery device may be withdrawn proximally while the elongated member 9402 is held substantially stationary, as shown in FIG. 94B, thereby leaving at least a portion of a length of the depot 100 exposed in the pocket created by the device. The elongated member 9402 may then be advanced distally within the delivery device lumen which forces an additional length of the depot 100 into the pocket. As shown in FIG. 94C, the depot 100 may be considerably more flexible and/or compliant relative to the prostate tissue defining the pocket such that as more of the depot is pushed from the device, the depot 100 buckles within the pocket, thereby enabling a greater length of the depot to be implanted in the prostate (as compared to a non-buckling depot).

Figure 95A:
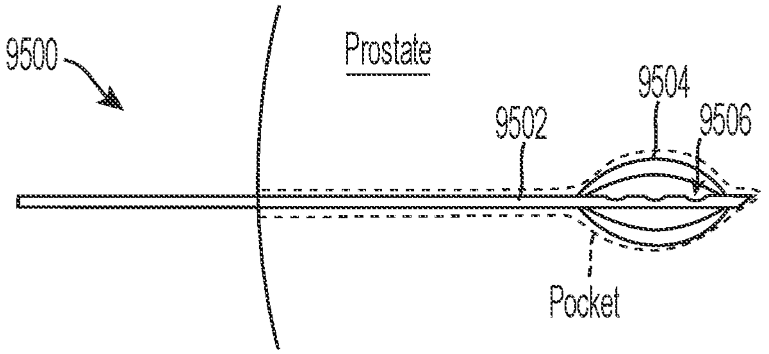
FIGS. 95A-95C depict a system and method for implanting one or more depots in a prostate gland of a human patient in accordance with the present technology.
Figure 95B:
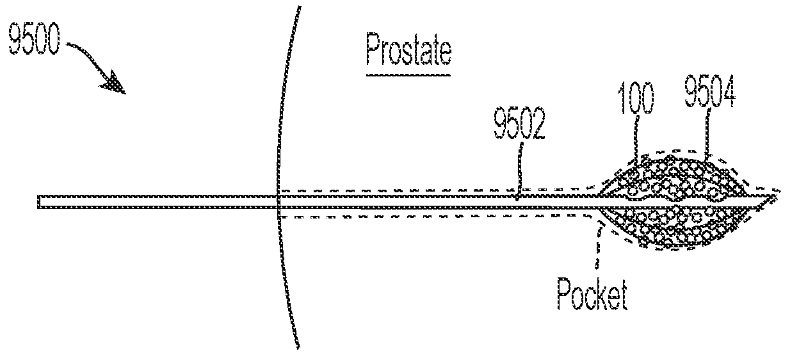
Figure 95C:
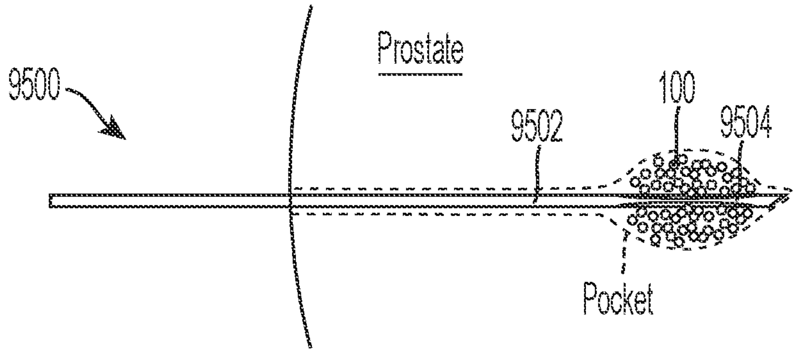

FIGS. 95A-95C show a treatment system 9500 for implanting a depot 100 into a prostate gland configured in accordance with several embodiments of the present technology. As shown in FIG. 95A, the system 9500 may comprise a delivery device 9502 defining a lumen therethrough and a plurality of expandable arms 9504 disposed a distal portion of the device 9502. The arms 9504 may be a portion of the device 9502, or may be part of a separate device configured to be positioned over the device 9502. The device 9502 may further comprise a plurality of openings 9506 at its distal portion that are in fluid communication with the device lumen. To implant the depot(s) 100, at least a distal portion of the delivery device 9502 may be positioned within the prostate with the arms 9504 in a low-profile position. The arms 9504 may then be expanded within the prostate tissue, thereby creating a pocket. As shown in FIG. 95B, a plurality of depots (such as microspheres) may be delivered through the lumen of the device 9502 and through the openings 9506 into the pocket created by the device 9502. When a desired number or volume of depots has been delivered, the arms 9504 may be collapsed to the low-profile configuration and the device 9502 can be withdrawn from the prostate, thereby leaving the depots implanted. The geometric design of the arms relative to the geometric design of the depot may be configured such that, as the arms 9504 are collapsed down to the low-profile configuration, the arms 9504 do not catch any of the depots and pull them towards the delivery device. In some embodiments, for example, one, some, or all of the arms may have substantially circular cross-sectional shapes and the depots may be substantially spherical such that the respective surfaces of the arms and depots are more likely to pass by one another.

The depots 100 of the present technology configured to treat prostate cancer may have a variety of suitable shapes and sizes. For example, in some embodiments the depot 100 may include a plurality of depots 100 in the form of microbeads, microspheres, particles, discs, microcylinders, and/or pellets. One, some, or all of the plurality of depots 100 may be comprised solely of a therapeutic region (and not a control region), and one, some, or all of the plurality of depots 100 may comprise a therapeutic region and a control region.

In those embodiments in which at least some of the plurality of depots comprise microbeads or microspheres, each microbead or microsphere may be comprised solely of the therapeutic region 200, or may comprise a therapeutic region 200 at its core and one or more control regions 300 partially, substantially, or completely surrounding the therapeutic region 200. In some embodiments, the microbead or microsphere may include multiple, layered control regions and/or therapeutic regions having the same composition or different compositions and/or the same thickness or different thicknesses. The release profile of any particular microbead may be determined by its size, composition, concentration of releasing agent, type of polymer, thickness of the control region(s) 300, thickness of the therapeutic region(s) 200, and others. In some embodiments, a plurality of microbeads are provided having varying dimensions, varying shapes (e.g. spherical, ellipsoid, etc.), varying polymer compositions, varying concentrations of therapeutic agent in the therapeutic region, varying concentration of releasing agent in the therapeutic region(s) 200, varying concentration of releasing agent in the control region(s) 300, or variation of any other parameters that affect the release profile. As a result, the composite release profile of the plurality of microbeads can be finely tuned to achieve the desired cumulative release of therapeutic agent to the treatment site. In various embodiments, some or all of the microbeads can have a diameter or largest cross-sectional dimension of between about 0.5 mm to about 5 mm, or between about 0.5 mm to about 1.5 mm. In some embodiments, some or all of the microbeads can have a diameter or largest cross-sectional dimension that is less than about 5 mm, less than about 2 mm, less than about 1.0 mm, less than about 0.9 mm, less than about 0.8 mm, less than about 0.7 mm, less than about 0.6 mm, less than about 0.5 mm, less than about 0.4 mm, or less than about 0.3 mm.

In those embodiments in which at least some of the plurality of depots comprise pellets or microcylinders, each pellet may be comprised solely of the therapeutic region 200, or may comprise a therapeutic region 200 at its core and one or more control regions 300 partially, substantially, or completely surrounding the therapeutic region 200. In some embodiments, the pellet may include multiple, layered control regions and/or therapeutic regions having the same composition or different compositions and/or the same thickness or different thicknesses. The release profile of any particular pellet may be determined by its size, composition, concentration of releasing agent, type of polymer, thickness of the control region(s) 300, thickness of the therapeutic region(s) 200, and others. In some embodiments, a plurality of pellets are provided having varying dimensions, varying polymer compositions, varying concentration of therapeutic agent in the therapeutic region, varying concentration of releasing agent in the control region 300, varying concentration of releasing agent in the therapeutic region 200, or variation of any other parameters that affect the release profile. For example, the particular shape and dimensions of the pellets may vary to achieve the desired release kinetics and form factor. For example, the pellets can have a cross-sectional shape that is circular, elliptical, square, rectangular, regular polygonal, irregular polygonal, or any other suitable shape. In some embodiments, each pellet can include an inner therapeutic region at least partially surrounded by an outer control region. In some embodiments, the pellet may include multiple, layered control regions and/or therapeutic regions having the same composition or different compositions and/or the same thickness or different thicknesses.

In some embodiments the depot may include one or more radiopaque elements configured to improve visualization of the depot in vivo. For example, the therapeutic region 200 and/or the control region 300 may include a contrast media such as barium sulfate, iodine, air and/or carbon dioxide.

In some embodiments, the depot 100 may include or more fixation features configured to resist migration of the depot after implantation. Such fixation features may include one or more ridges, hooks, barbs, protrusions, notches, or other structural features.

In various aspects of the technology, one or more of the depots configured to treat prostate cancer may not include any polymer. For example, the depots may include one or more excipients (such as conventional binders or fillers). In some embodiments, the depots 100 may comprise a permanent implant with a permeable mesh or polymer covering (such as a tubular covering) that allows the therapeutic agent to pass therethrough.

As previously mentioned, different routes of administrations of the sustained-release formulations detailed herein as possible depending on the treatment plan. For example, in some embodiments, the route of administration is direct needle injection into and/or around the tumor via trans-perineal and trans-rectal access using transrectal ultrasound imaging guidance. The route of administration may be direct needle injection into and/or around the tumor via trans-urethral access using transrectal or transurethral ultrasound guidance. In some embodiments, the route of administration is direct needle injection into and/or around the tumor via laparoscopic or open surgical access with direct visualization and/or palpation. The route of administration may be catheter-delivered depot into prostatic arteries for chemo-embolization.

Many of the depot embodiments of the present technology are designed to be implanted inside the prostate, either in the tumor or in prostate tissue, using a needle-based delivery system. The needle-based system can be used with various access means, such as trans-perineal, trans-rectal, and trans-urethral. It can also be done using a laparoscopic technique.

Figure 96:
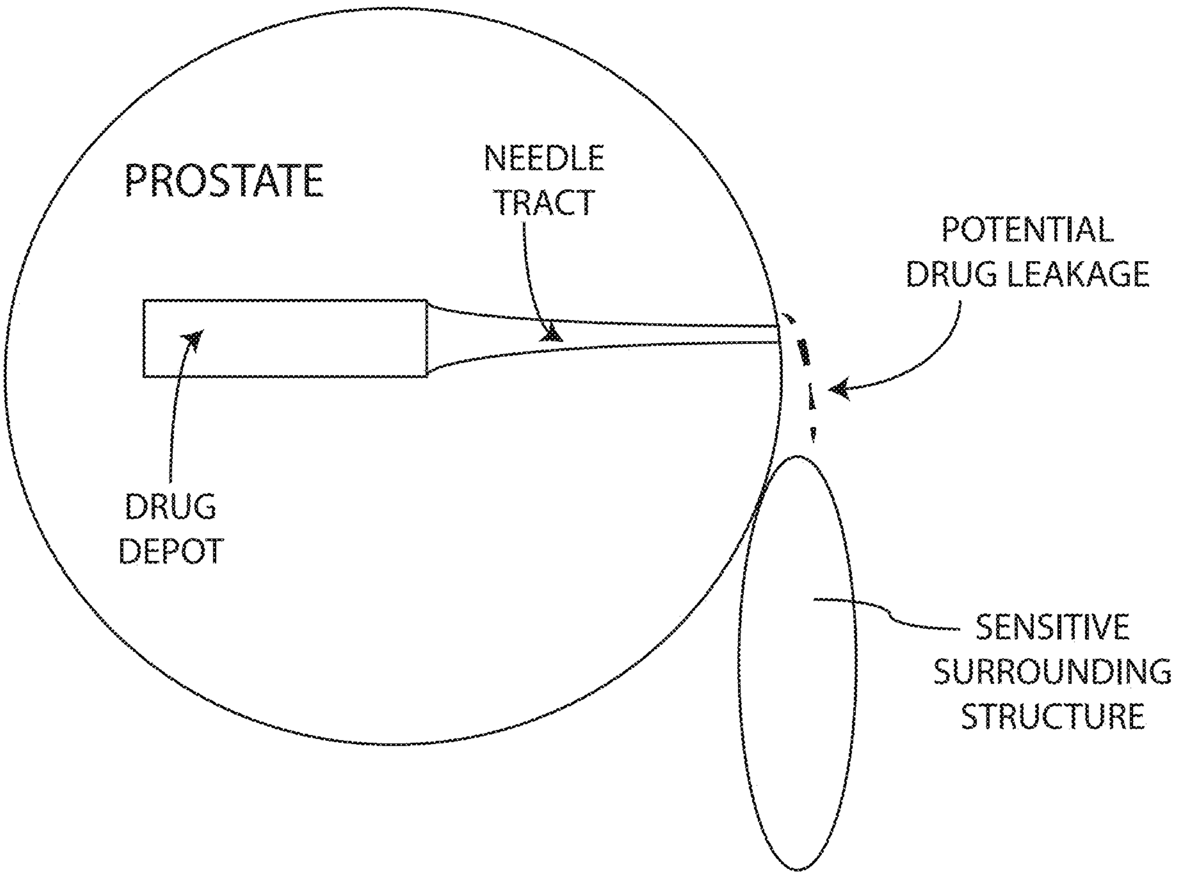
FIG. 96 depicts a depot implanted in a prostate gland in accordance with some embodiments of the present technology.

With any of these access approaches the needle will need to puncture the prostate. As depicted in FIG. 96, other than in the trans-urethral approach, the needle puncture will lead to hole in the prostate, where the exit of the hole is on the outer surface of the prostate.

A hole created by a needle puncture will be small, likely smaller than the size of the needle itself, since most needles cut and dilate the tissue as it's being inserted. When the needle is removed, the tissue that make up the "hole" will collapse down. The natural closure of the "hole" to prevent continued leakage will depend on the size of the "hole" and the fluid pressures (typically blood) inside that "hole". In most needle-based procedures in medicine, these needle-induced "holes" will self-close due to the body's natural coagulative ability.

In the case of several of the depots of the present technology, the "hole" may create a potential leakage path from the implanted depot to the tissues in the abdominal cavity adjacent to the prostate. The leakage contents may include the drug itself as it's eluding from the depot. If a sufficient amount of the drug is leaked out of the prostate onto some sensitive structures near the prostate, it may cause unwanted side-effects due to drug-induced damage to the nearby structures. Additionally, if the drug that is used in the depot has properties such as anti-coagulation, vessel dilation, anti-proliferation, etc. that may enhance leakage or inhibit healing, the "holes" may leak longer than normal.

In order to mitigate the potential of drug leakage out of the prostate with a needle-based delivery of the depot, the following concepts could be employed.

Figure 97:
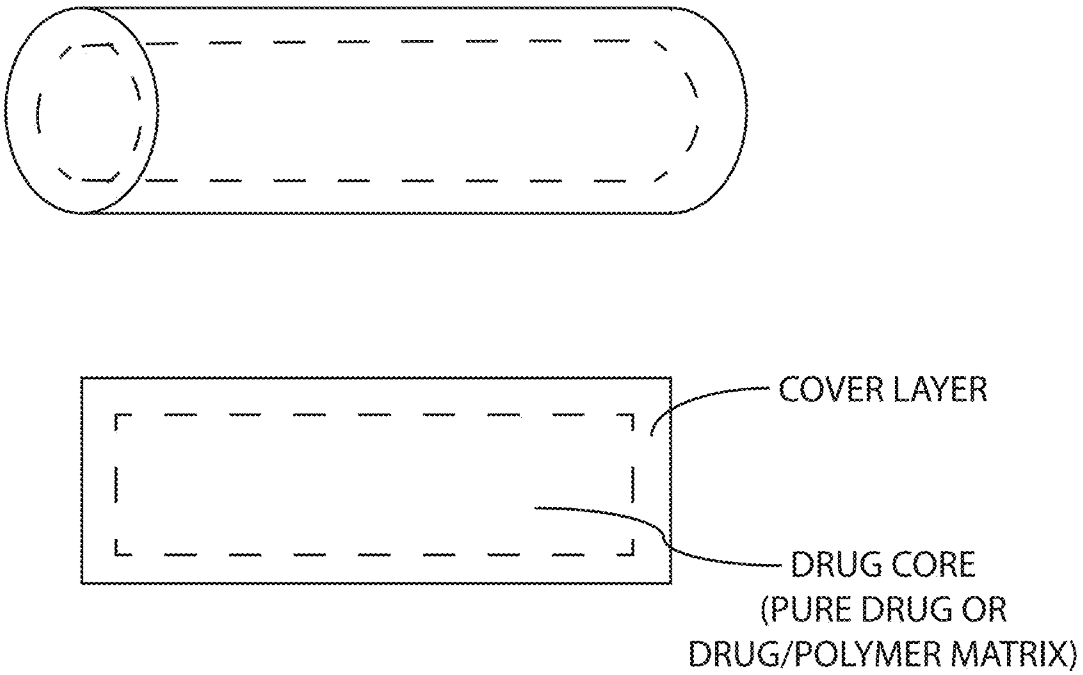
FIG. 97 depicts a depot in accordance with some embodiments of the present technology.
Figure 98:
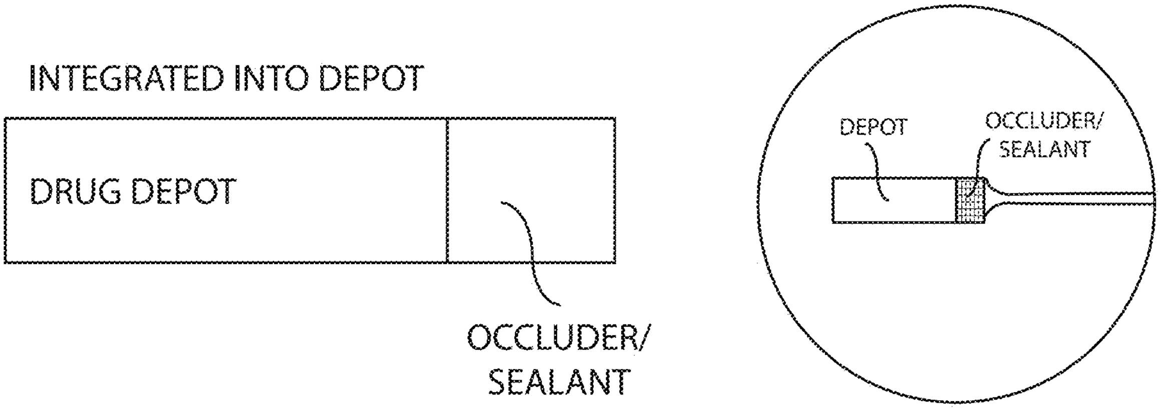
FIG. 98 depicts an occlusion member proximal to a depot in accordance with some embodiments of the present technology.
Figure 99:
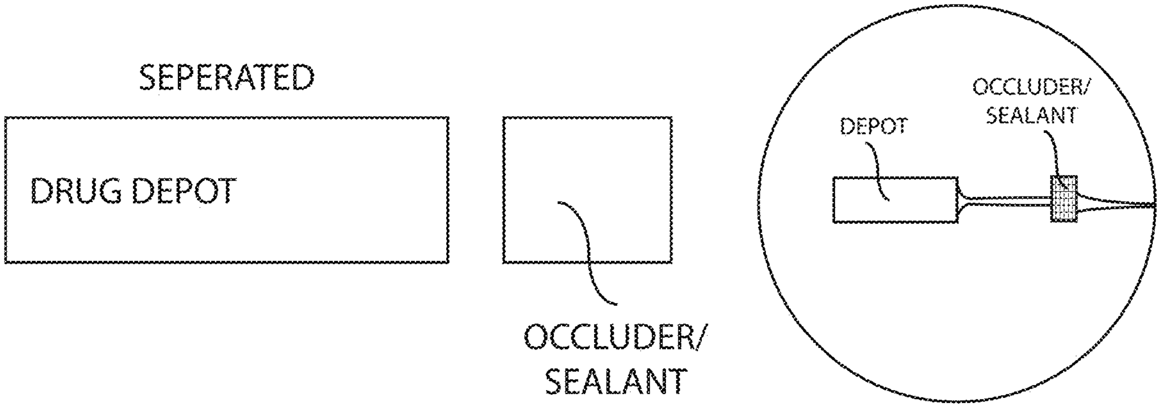
FIG. 99 depicts an occlusion member separate from a depot in accordance with some embodiments of the present technology.
Figure 100:
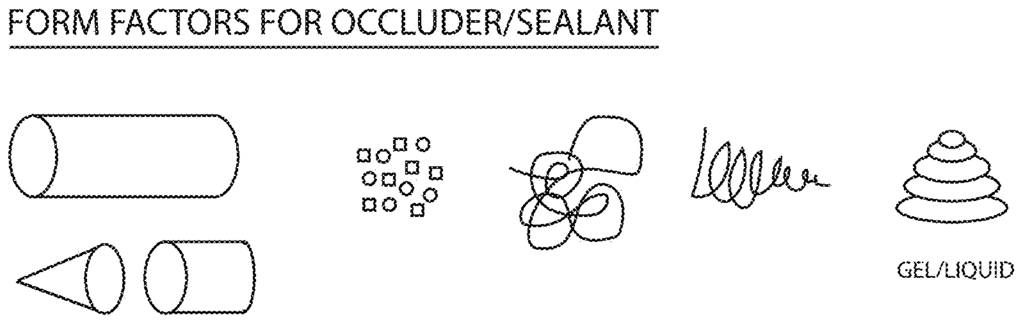
FIG. 100 depicts examples of occlusion members in accordance with some embodiments of the present technology.
Figure 101:
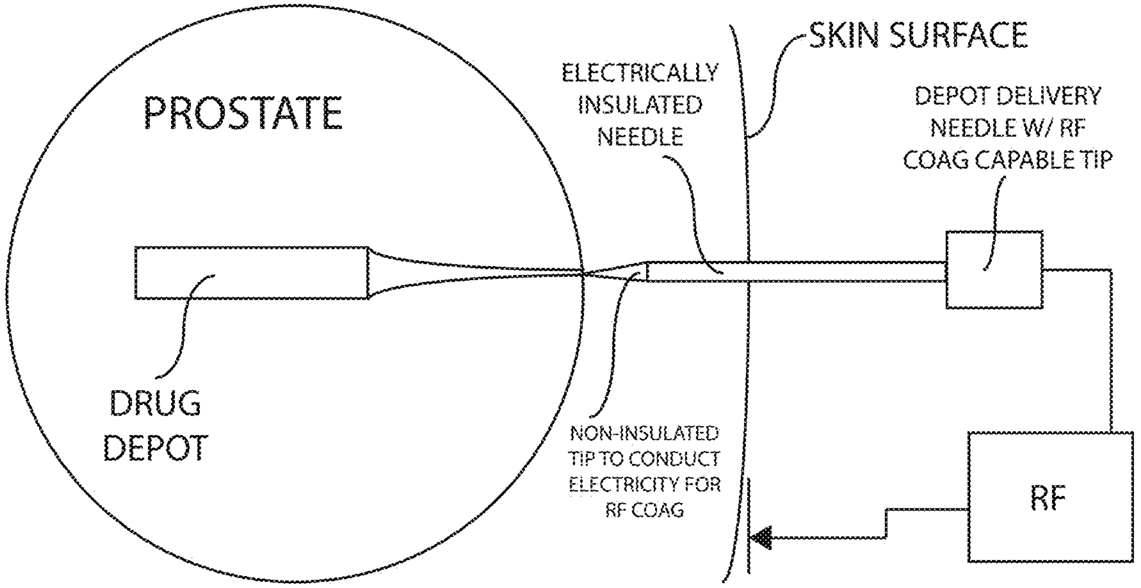
Figure 102:
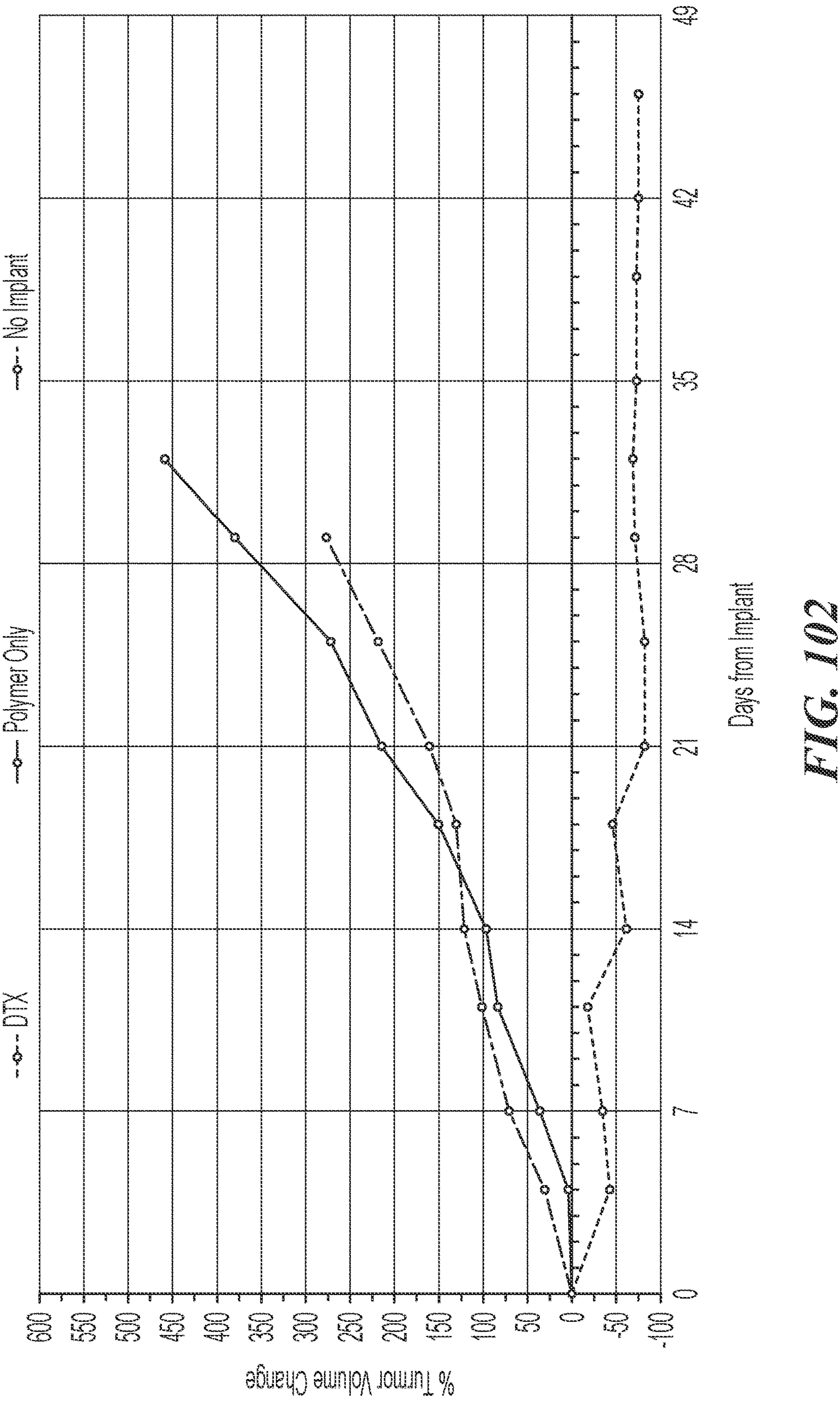

In some embodiments, the depot comprises a delayed drug-release depot. In the case where the drug(s) used in the depot may contribute to the leaking by either creating greater flow or pressure of the fluid inside the "hole" or by inhibiting the proper and expeditious healing of the hole, it may be desirable to delay the release of the drug for an amount of time to allow proper healing and closure of the hole.

le;1.5qAs shown in FIG. 97, the present technology includes a depot core with a fully coated cover layer is designed to be non-porous to not allow the drug from the core to be released until the cover layer has dissolved away. Some of the materials and constructs could be the following: PEG, PLGA, sugars, and other suitable materials.

le;1.5qIn some embodiments the present technology comprises an occlusion member proximal to the depot. For example, the occlusion member may be integrated into the depot (see FIG. 98), or may be a separate structure (see FIG. 99). The occlusion member may be a solid, semi-solid, liquid adhesive, etc. The occlusion member may have a variety of form factors, such as rods, beams, coils, etc. (see FIG. 100). In some embodiments, the occlusion member comprises one or more coagulants, vasoconstrictors, angiogenic agents, etc. Additionally or alternatively, the present technology comprises no-implant sealing, such as the use of RF, microwave, laser, ultrasound heating, etc. to seal the exit (see FIG. 101).

C. Clinical Study Endpoints le;1.5qAny of the following endpoints and/or response criteria may be utilized to assess the effectiveness of treatment utilizing the sustained-release formulations and/or depots of the present technology: Gleason Grade Group upgrading from GG1 to ≥GG2, and GG2 to ≥GG31 Threshold total length Gleason pattern 4 of all cores; Threshold increase in length of Gleason pattern 4; the 2019 National Comprehensive Cancer Network Guidelines: going from favorable to unfavorable intermediate-risk prostate cancer: (a) <50% to ≥50% cores positive on follow up MRI guided biopsy, (b) Going from 1 IRF to 2 or 3 IRFs (Intermediate Risk Factors=T2b–T2c, GG2 or GG3, and PSA 10-20 ng/mL); ≥T3 cancer (tumor extends through the prostate capsule); metastatic disease; prostate cancer-specific death; MRI data: (a) evidence of "definite" or "gross" extracapsular extension, (b) MRI lesion with ≥10 mm capsular contact (with biopsy proof of GG ≥2 cancer), (c) seminal vesical invasion: "probable" or "definite" on digital rectal exam/MRI, (d) Enlarged pelvic lymph nodes: radiographically-suspicious, confirmed by biopsy or functional imaging study (e.g. PSMA PET scan—prostate specific membrane antigen; Fluciclovine PET scan); progression free survival defined as Gleason upgrade, PSA doubling time <3 months, or active treatment; Active treatment including prostatectomy, radiation, systemic androgen deprivation or chemotherapy. Failure-free survival defined as freedom from radical or systemic therapy, metastases, and cancer specific mortality; tumor shrinkage: minimal residual disease (<5 mm tumor); PSA (level/progression, doubling time, density); androgen gene expression and tumor cell proliferation pre and post implant (biomarker assessment and genomic analysis); tissue androgen (dihydrotestosterone) 12 weeks and 24 weeks; validated questionnaires to assess PCa-specific anxiety: (a) MAX-PC (Memorial Anxiety Scale for PCa) score ≥27 and at least 3 points greater than baseline value, patient Reported Outcomes Measures (PROMS, serially measured): (a) Erectile function: IIEF-15; (b) Lower urinary tract symptoms (LUTS): I-PSS; (c) Adverse events: PRO-CTCAE (The NCI Patient Reported Outcomes-Common Terminology Criteria for Adverse Events); (d) Patient anxiety: MAX-PC; (e) Functional Assessment of Cancer Therapy-Prostate (FACT-P Pro Instrument v.4).

D. Examples le;1.5qThe following examples are offered by way of illustration and not by way of limitation.

Example 1 le;1.5qThe inventors of the present technology performed a study to develop a protocol for a mouse xenograft tumor model to evaluate treatment efficacy to assist in selecting drug depot formulations for treating prostate cancer via localized, sustained release of a therapeutic agent. In this study, tumors were successfully grown on the flanks of mice (n=23). Depots of the present technology were prepared according to Table 4 below and implanted in each of the mice using an 18-gauge needle. Some of the mice received a polymer-only depot (i.e., no therapeutic agent), some of the mice received a depot containing docetaxel (DTX), and some of the mice did not receive any implant and were used as a control. The volume of each tumor was then monitored over time. As depicted in the graph shown at FIG. 102, the mice that received the depots containing docetaxel saw a shrinkage in tumor volume for the first three weeks after implantation. These results demonstrate promising efficacy for reducing tumor size via local administration of a chemotherapeutic agent.

TABLE 4

| Therapeutic Agent | Docetaxel-Fast | Docetaxel-Mid | Docetaxel-Baseline | Bicalutamide | Enzalutamide |
|---|---|---|---|---|---|
| PLGA Lactide:Glycolide Ratio | 50:50 | 50:50 | 75:25 | 50:50 | 50:50 |
| PLGA Inherent Viscosity | 0.6 | 1 | 0.2 | 0.6 | 0.6 |
| PEG10K:PLGA:Drug Ratio | 5:5:40 | 3:7:40 | 1:9:40 | 5:5:40 | 5:5:40 |
| PEG10K (g) | 0.22 | 0.132 | 0.044 | 0.44 | 0.44 |
| PLGA (g) | 0.22 | 0.308 | 0.396 | 0.44 | 0.44 |
| Drug (g) | 1.76 | 1.76 | 1.76 | 3.52 | 3.52 |
| Acetone (mL) | 2.8 | 2.8 | 2.8 | 2.5 | 3.5 |
| Acetone (g) | 2.156 | 2.156 | 2.156 | 1.97 | 2.76 |
| Total Drug Content (mg/cm) | 3.37 +/− 0.12 | 3.17 +/− 0.17 | 3.05 +/− 0.04 | 4.92 +/− 0.12 | 4.14 +/− 0.04 |
| Syringe Vol (mL) | 3 | 3 | 3 | 3 | 3 |
| Flow Rate (mL/min) | 0.5 | 0.5 | 0.5 | 0.5 | 0.5 |
| Needle ID (mm) | 0.84 | 0.84 | 0.84 | 0.84 | 0.84 |
| Drying Condition | ambient O/N | ambient O/N | ambient O/N | ambient O/N | ambient O/N |
| Lot Number | D041 | D043 | D044 | B045 | E046 |

Example 2

The inventors of the present technology performed a study to evaluate the efficacy of a novel sustained release drug depot formulation for treating cancer. FIGS. 103-1 to 103-10 detail mouse xenograft tumor studies. The study setup, sustained release formulations, in vitro release kinetics, tumor measurements, and in vivo release kinetics are detailed in FIGS. 103-1 to 103-10. This study showed the sustained release formulation was both successful in providing a sustained, controlled release of the drug to the prostate tissue, and also in reducing tumor size over the course of treatment.

Example 3

The inventors of the present technology performed a study to evaluate the surgical approach, depot implantation, and necropsy procedures in a canine model. In particular, the inventors sought to better understand drug diffusion from an implanted depot in a credible animal prostate model. FIGS. 104-1 to 104-9 detail a canine prostate study. The study setup, sustained release formulations, in vitro release kinetics, tumor measurements, and in vivo release kinetics are detailed in FIGS. 104-1 to 104-9. As best depicted at FIG. 104-8, this canine study showed high local tissue concentrations within the implanted lobe of the prostate that were 1-2 orders of magnitude higher than tissue concentrations outside of the implanted lobe, whether within a different lobe of the prostate or outside of the prostate altogether. Without being bound by theory, the inventors believe the dense fibrous tissue of the interlobular wall and prostate wall provide some barrier to diffusion of the therapeutic agent.

The controlled release of the present technology provides several benefits over existing treatments that lack such control. For example, radiation from brachytherapy seeds often travels beyond the targeted lobe and outside of the prostate. Hoare and Kohane 2018 discuss limitations of hydrogels for drug delivery, including "the low tensile strength of many hydrogels . . . can result in premature dissolution or flow away of hydrogel from a targeted local site." Furthermore, Buwalda 2017 concludes " . . . in situ formation can be regarded as a basic requirement . . . a fast and significant response to environmental/physical gelation triggers are considered essential." However, this is inherently challenging due to local biological variations, as noted by Dimatteo et al 2018 " . . . clinical use of hydrogel depots is hindered by a reliance on intrinsic biological microenvironments for controlled release, where heterogeneity through the body and between individuals limits the efficacy of treatment approaches based on the location of implantation."

XI. Bile Duct Cancer

Embodiments of the present technology may be used to treat bile duct cancers. The bile duct is a 4- to 5-inch long tube that connects the liver and gall bladder to the small intestine. It originates in the liver and allows bile to go from the liver to the gallbladder and ultimately to the small intestine. There are three types of bile duct cancer (cholangiocarcinoma): (1) extrahepatic—outside the liver (most common); (2) hilar (Klatskin's tumor)—where the right and left hepatic ducts join (relatively common); and (3) intrahepatic—inside liver (relatively rare 5-10%). The incidence of bile duct cancer is low, with an incidence of around 8,000 new cases in the US each year, but the mortality rate is high. The 5-year survival is less than 10%. If diagnosed early, the 5-year survival is 15%, but reduces to 2% once the cancer is metastatic. Surgical removal of the bile duct along with partial removal of liver or pancreas (depending on stage/tumor location) is a common treatment followed by chemotherapy to prevent recurrence. Radiation can also be used with/without systemically delivered drugs (chemotherapy, targeted therapy, immunotherapy). Any suitable composition and/or depot configuration can be utilized depending on the particular therapeutic agent(s), desired release profile(s), and routes of administration.

In various embodiments, treatment of bile duct cancers can involve local delivery of one or more therapeutic agents (e.g., via one or more depot(s) of the present technology) administrated using any suitable route. Example administration routes for include endoscopic, endovascular, or surgical routes. Endoscopic administration can include ultrasound-guided or X-ray guided (with or without contrast agent) needle delivery of drug loaded depots into or around the bile duct tumor. Another endoscopic administration route is a biliary stent or catheter that is coated with or otherwise configured to release therapeutic agent to the treatment site. Endovascular administration can include positioning a drug eluting stent in the hepatic artery that releases therapeutic agent(s) into the blood that perfuses the bile duct. Additionally or alternatively, endovascular administration can include a transcatheter arterial chemoembolization (TACE) alternative—e.g., a catheter can be used to deliver therapeutic-agent-containing microbeads that lodge in vessels that supply the bile duct tumor, thereby cutting off blood supply and delivering therapeutic agent(s) to the tumor. Surgical approaches can include laparoscopic routes (e.g., depots may be implanted and/or injected for neoadjuvant therapy or palliative therapy) or open surgery (e.g., one or more depots may be implanted or injected following or during surgery), such as surgery for resection of bile duct, to provide adjuvant or supportive or palliative therapy.

Any suitable therapeutic agents, whether delivered locally (e.g., via one or more depots as described herein), systemically (e.g., via intravenous delivery or otherwise), or both, can be used for treatment of bile duct cancers. Example therapeutic agents include cisplatin, gemcitabine, capecitabine (e.g., 6 months after surgery), fluorouracil (5-FU), paclitaxel, oxaliplatin, or any combinations thereof. In some embodiments, one or more locally delivered therapeutic agents can be used in combination with one or more systemically delivered therapeutic agents and/or in combination with other treatments (e.g., surgery, radiation, etc.).

Treatment of bile duct cancers as disclosed herein can be utilized to achieve one or more clinical endpoints. In various embodiments, such endpoints can involve clinical measures for a particular patient or a population of patients (e.g., a population undergoing a clinical trial). Examples of such endpoints include: (1) overall survival (e.g., as measured in time from treatment (or randomization) to death due to any cause; (2) progression free survival (e.g., as measured measure from the date of start of treatment to the date of the first documented progression (PD) or death due to any cause, in which progressive disease (PD) is defined as at least a 20% increase in the sum of the diameters of target lesions); (3) overall/objective response rate (e.g., providing a score of complete response (CR): disappearance of all target lesions; partial response (PR): at least X % (20%, 25%, 30%, 35%, 40%, 45%, 50%) decrease in the sum of the diameters of target lesions; or stable disease (SD): neither sufficient shrinkage to qualify for PR nor sufficient increase to qualify for PD); (4) disease control rate: the number of participants that achieve either a CR, PR or SD; (5) quality of Life (QoL) as measured by functional health survey (EQ-5D module); (6): safety and tolerability; or (7) progression to surgical resection or other intervention. Any one or any combination of these endpoints can be utilized to assess and/or establish efficacy of treatment of bile duct cancer via depots of the present technology, whether used alone or in combination with one or more other treatments.

XII. Liver Cancer

Embodiments of the present technology may be used to treat liver cancers. The liver is the largest organ in the body. It plays a key role in the digestion of food. Liver cancer can be a primary cancer or secondary to another malignancy. Hepatocellular carcinoma is the most common type of liver cancer. In the US, about 40,000 new cases of liver cancer and 30,000 deaths attributed to liver cancer each year. China has a much higher incidence and prevalence of liver cancer, with 400,000 cases and 368,000 deaths annually. China has nearly 20% of the world's population but over 50% of the global cases. This has been attributed to a disproportionately high prevalence of chronic hepatitis in China. The general 5-year survival rate is 18%, with local disease (early diagnosis) having a 33% survival and regional and distal disease (late diagnosis) having a 11% and 2% 5-year survival, respectively. Depending on the stage of the cancer and treatment objectives, many types of treatment are available, including surgery (e.g., liver transplant, hepatectomy), laparoscopic or percutaneous ablation (e.g., alcohol/ethanol, radiofrequency, microwave, cryotherapy), externally administered radiation (e.g., external beam, stereotactic radiotherapy), non-local drug therapy (e.g., targeted therapy, immunotherapy, chemotherapy) and local therapy (e.g., arterial drug infusion, chemoembolization and radioembolization)

Any suitable composition and/or depot configuration can be utilized depending on the particular therapeutic agent(s), desired release profile(s), and routes of administration. In various embodiments, treatment of liver cancers can involve local delivery of one or more therapeutic agents using any suitable route. Example administration routes include endovascular, percutaneous, or surgical routes. Endovascular administration can include positioning a drug eluting stent in the hepatic artery that releases therapeutic agent into blood that perfuses the bile duct. Additionally or alternatively, endovascular administration can include a transcatheter arterial chemoembolization (TACE) alternative—e.g., a catheter delivered therapeutic agent containing microbeads that lodge in vessels that supply the liver tumor, thereby cutting off blood supply and delivering therapeutic agent(s) to the tumor. Percutaneous delivery can take the form of a direct needle injection of one or more depots into/or around the tumor using imaging (e.g., CT, MRI). Surgical administration can include, for example, implantation or direct needle injection as part of laparoscopic or open procedure with direct visualization and/or palpation.

Any suitable therapeutic agents, whether local, systemic, or both, can be used for treatment of liver cancers. Example therapeutic agents include chemotherapeutic agents such as Cisplatin, Fluorouracil (5-FU), Doxorubicin, Oxaliplatin, Mitomycin C, or any combinations thereof. In some instances, a therapeutic agent can be delivered locally (e.g., cinobufacini) which enhances efficacy of locally delivered chemotherapeutic agents. In some embodiments, one or more locally delivered therapeutic agents can be used in combination with one or more systemically delivered therapeutic agents (e.g., using intravenous injection or other suitable systemic delivery). Examples of such systemic therapeutic agents for treatment of liver cancers include any of the chemotherapeutic agents listed above, as well as targeted therapeutic agents, such as therapeutic agents for anti-angiogenesis (e.g., sorafenib, ramucirumab, regorafenib, Lenvatinib, bevacizumab), immunotherapy (e.g., monoclonal antibodies: nivolumab, Atezolizumab, ipilimumab), or apoptosis inducers.

Treatment of liver cancers as disclosed herein can be utilized to achieve one or more endpoints. In various embodiments, such endpoints can involve clinical measures for a particular patient or a population of patients (e.g., a population undergoing a clinical trial). Examples of such endpoints include: (1) overall survival; (2) progression-free survival, (3) time to tumor progression (as assessed by CT); or (4) tumor marker serum levels. Tumor marker serum levels can include assessment of one or more different specific markers. Examples include: (1) embryonic antigen: alpha-fetoprotein (AFP and glycoforms AFP-L1, AFP-L2 and AFP-L3); (2) proteantigen: heat shock protein (HSP), glypican-3 (GPC3), squamous cell carcinoma antigen (SCCA), golgi protein 73 (GP73), fucosylated GP73 (FC-GP73), tumor-associated glycoprotein 72 (TAG-72), zinc-α2-glycoprotein (ZAG); (3) enzymes and isozymes: Des-Y-carboxyprothrombin (DCP), γ-glutamyl transferase (GGT), α-I-fucosidase (AFU); (4) cytokines: transforming growth factor-β1 (TGF-β1), vascular endothelial growth factor (VEGF); and (5) genetic biomarkers: AFP mRNA, MicroRNAs, A-like 1 homolog (DLK-1), hepatoma-associated gene (HTA), villin1 (Vill). Any one or any combination of these endpoints can be utilized to assess and/or establish efficacy of treatment of liver cancers via depots of the present technology.

XIII. Colorectal Cancer

Embodiments of the present technology may be used to treat colorectal cancers. The large intestine (large bowel), a key part of the gastrointestinal system, is comprised of the colon and rectum. Polyps form and grow in the inner lining of the colon and rectum and can sometimes change into cancer. Most colorectal cancers are adenocarcinomas. The annual incidence of colorectal cancer is approximately 150,000 cases and 400,000 cases in the US and China respectively. Additionally, colorectal cancer causes approximately 50,000 and 200,000 deaths annually in the US and China, respectively. Prognosis and survival is tied closely to stage at diagnosis. Early diagnosis (i.e. when the cancer is localized) produces a 5-year survival of 90%. Regional spread of the cancer results in a 5-year survival of 71% and distal spread reduces 5-year survival to 14%. Depending on the stage of the cancer and treatment objectives, many types of treatment are available, including surgery (e.g., open or laparoscopic resection), endoscopic or percutaneous ablation (e.g., radiofrequency, microwave, cryotherapy), externally administered radiation (e.g., external beam, stereotactic radiotherapy) and non-local drug therapy (e.g., targeted therapy, immunotherapy, chemotherapy).

Any suitable composition and/or depot configuration can be utilized depending on the particular therapeutic agent(s), desired release profile(s), and routes of administration. In various embodiments, treatment of colorectal cancers can involve local delivery of one or more therapeutic agents using any suitable route. Example administration routes include endoscopic, percutaneous, and surgical approaches. Endoscopic access to the intestine can include, for example, needle injection delivery from GI lumen into tumor, use of a drug-coated stent in the GI lumen, use of a drug-coated stent graft in the GI lumen, and/or use of a stent made of a bioresorbable depot in the GI lumen. Percutaneous access can include direct needle injection into/or around the tumor using imaging (e.g., CT, MRI). And surgical administration can take the form of implantation or direct needle injection as part of laparoscopic or open procedure with direct visualization and/or palpation.

Any suitable therapeutic agents, whether local, systemic, or both, can be used for treatment of colorectal cancers. Example therapeutic agents include chemotherapeutic agents such as irinotecan, capecitabine, fluorouracil (5-FU), oxaliplatin, trifluridine/tipiracil, 5-FU+leucovorin, FOLFOX: 5-FU+leucovorin and oxaliplatin, FOLFIRI: 5-FU+leucovorin and irinotecan, XELIRI: capecitabine+irinotecan, XELOX: capecitabine+oxaliplatin, or any combinations thereof. In some embodiments, one or more locally delivered therapeutic agents can be used in combination with one or more systemically delivered therapeutic agents (e.g., using intravenous injection or other suitable systemic delivery). Examples of such systemic therapeutic agents for treatment of colorectal cancers include any of the chemotherapeutic agents listed above, as well as or instead of targeted therapeutic agents (e.g., anti-angiogenesis agents such as ramucirumab, bevacizumab, or regorafenib; vascular endothelial growth factor (VEGF) inhibitors such as ziv-aflibercept; or epidermal growth factor receptor (EGFR) inhibitors such as cetuximab or panitumumab). Additionally or alternatively, such systematic therapeutic agents can include immunotherapeutic agents (e.g., pembrolizumad, nivolumab, or ipilimumab).

Treatment of colorectal cancers as disclosed herein can be utilized to achieve one or more endpoints. In various embodiments, such endpoints can involve clinical measures for a particular patient or a population of patients (e.g., a population undergoing a clinical trial). Examples of such endpoints include: (1) overall survival (e.g., time from treatment (or randomization) to death due to any cause; (2) progression free survival (e.g., measured from the date of start of treatment to the date of the first documented progression (PD) or death due to any cause; or progressive disease (PD): at least a 20% increase in the sum of the diameters of target lesions); (3) objective/overall response rate (e.g., complete response (CR) (disappearance of all target lesions); partial response (PR) (at least X % (20%, 25%, 30%, 35%, 40%, 45%, 50%) decrease in the sum of the diameters of target lesions); or stable disease (SD) (neither sufficient shrinkage to qualify for PR nor sufficient increase to qualify for PD); (4) disease control rate (e.g., the number of participants that achieve either a CR, PR or SD); or (5) duration of (overall) response (e.g., time from when CR or PR is met to the first date of recurrent disease or PD). Any one or any combination of these endpoints can be utilized to assess and/or establish efficacy of treatment of colorectal cancers via depots of the present technology.

XIV. Thyroid Cancer

Embodiments of the present technology may be used to treat thyroid cancers. The thyroid gland is located in the front of the neck, just below the larynx (voice box), and is part of the endocrine system, which regulates hormones in the body. The thyroid, which produces hormones for regulating metabolism, has two lobes, one on each side of the windpipe. Thyroid tumors grow out of follicular cell or C cells. 90% of thyroid tumors are benign. Papillary thyroid cancer and follicular thyroid cancer, both of which develop from follicular cells, represent 95% of all thyroid cancer. Approximately 50,000 patients in the US are newly diagnosed with thyroid cancer, with 80% of those cases being in woman. With 15% of the global incidence, the impact of thyroid cancer in China is disproportionately high. When caught early, the survival rate is quite high.

Any suitable composition and/or depot configuration can be utilized depending on the particular therapeutic agent(s), desired release profile(s), and routes of administration. In various embodiments, treatment of thyroid cancers can involve local delivery of one or more therapeutic agents using any suitable route. Example administration routes include surgical or percutaneous approaches. Surgical approaches can include open surgery (e.g., implantation or direct needle injection with direct visualization or palpation), endoscopic surgery (e.g., needle injection with endoscopic guidance and delivery), or robotic surgery (e.g., needle delivery from elsewhere in the body, such as the armpit, neck, mouth, chest, etc., with a robotic tool).

Any suitable therapeutic agents, whether local, systemic, or both, can be used for treatment of thyroid cancers. Example therapeutic agents include chemotherapeutic agents such as dacarbazine, vincristine, cyclophosphamide, doxorubicin, fluorouracil (5-FU), streptozocin, paclitaxel, docetaxel, carboplatin, or any combination thereof. In some embodiments, the therapeutic agent(s) can also include hormone replacement therapy agents such as levothyroxine. In some embodiments, one or more locally delivered therapeutic agents can be used in combination with one or more systemically delivered therapeutic agents (e.g., using intravenous injection or other suitable systemic delivery). Examples of such systemic therapeutic agents for treatment of thyroid cancers include any one of the therapeutic agents noted above for local deliver, and or on or more targeted therapeutic agents such as sorafenib, lenvatinib, tyrosine kinase inhibitors (e.g., vandetanib, cabozantinib), BRAF inhibitors (e.g., dabrafenib), or MEK inhibitors (e.g., trametinib).

Treatment of thyroid cancers as disclosed herein can be utilized to achieve one or more endpoints. In various embodiments, such endpoints can involve clinical measures for a particular patient or a population of patients (e.g., a population undergoing a clinical trial). In some embodiments, the clinical endpoints include evaluation of target lesions. For patients with a measurable disease at baseline (i.e., for target lesions), evaluation of target lesions can include objective response as defined by a response evaluation criteria in solid tumors (RECIST) protocol (e.g., RECIST 1.0 or RECIST 1.1). Such evaluation can include assessment in terms of: (1) complete response (CR) (e.g., disappearance of all target lesions; any pathological lymph nodes (whether target or non-target) must have reduction in short axis to <10 mm); (2) partial response (PR) (e.g., at least a 30% tumor regression—RECIST 1.1 defines this as at least a 30% decrease in the sum of diameters of target lesions, taking as reference the baseline sum diameters); (3) stable disease (SD) (e.g., neither sufficient shrinkage to qualify for PR nor sufficient increase to qualify for PD, taking as reference the smallest sum diameters while on study); or (4) progressive disease (PD) (e.g., at least a 20% increase in the sum of the LD of target lesions, taking as reference the smallest sum LD recorded since the treatment started or the appearance of one or more new lesions).

In some embodiments, the endpoints can include evaluation of non-target lesions. Such evaluation can include assessment in terms of: (1) complete response (CR) (e.g., disappearance of all non-target lesions and normalization of tumor marker level); (2) incomplete response or stable disease (SD) (e.g., persistence of one or more non-target lesion(s) or/and maintenance of tumor marker level above the normal limits); or (3) progressive disease (PD) (e.g., appearance of one or more new lesions and/or unequivocal progression of existing non-target lesions).

In some embodiments, the endpoints can include evaluation of best overall response. Additional example endpoints include progression free survival (PFS), overall survival (OS), time to response, response duration, safety, and tolerability, patient reported outcomes (e.g., assessment of quality of life, symptoms, etc.). Additionally or alternatively, the endpoints can include assessment of one or more biomarkers, such as serum thyroglobulin and calcitonin, notch1, leptin, interleukin-1, BRAF, HRAS, NRAS, KRAS, RET, RET/PTC, or any combination thereof. Any one or any combination of these endpoints can be utilized to assess and/or establish efficacy of treatment of thyroid cancers via depots of the present technology.

XV. Stomach Cancer

Embodiments of the present technology may be used to treat stomach or gastric cancers. Most stomach cancers are adenocarcinoma, which originates in the glandular tissue lining the inside of the stomach. Other types of malignant stomach tumors include lymphoma, gastric sarcoma and neuroendocrine tumors. Nearly 30,000 people in the US are diagnosed with stomach cancer annually, with 11,000 annual deaths. This incidence is a very low proportion of the 1.2 million incidence globally. Eastern Asia represents nearly one half of the global incidence, with about 370,000 stomach cancer patients dying annually. Five-year survival is 20-30%, but highly dependent on the stage at first diagnosis. If purely localized, five-year survival is 69%, but only 5% when metastatic. Treatment ranges from total or partial surgical excision of the stomach (gastrectomy) to non-local therapy such as radiation or systemic drug therapy (e.g., chemotherapy, targeted therapy, immunotherapy)

Any suitable composition and/or depot configuration can be utilized depending on the particular therapeutic agent(s), desired release profile(s), and routes of administration. In various embodiments, treatment of stomach cancers can involve local delivery of one or more therapeutic agents using any suitable route. Example administration routes include endoscopic access via the GI tract, percutaneous access, or surgical access. Endoscopic access can include Needle injection delivery from GI lumen into tumor, use of a drug-coated stent in the GI lumen, use of a drug-coated stent graft in GI lumen, or use of a stent made of bioresorbable depot in GI lumen. Percutaneous access can include direct needle injection into/or around the tumor using imaging (e.g., CT, MRI, ultrasound). Surgical approaches can include implantation or direct needle injection as part of laparoscopic or open procedure with direct visualization and/or palpation.

Any suitable therapeutic agents, whether local, systemic, or both, can be used for treatment of stomach cancers. Example therapeutic agents include chemotherapeutic agents such as cisplatin, capecitabine, fluorouracil (5-FU), paclitaxel, docetaxel, epirubicin, irinotecan, oxaliplatin, or any combinations thereof. In some embodiments, one or more locally delivered therapeutic agents can be used in combination with one or more systemically delivered therapeutic agents (e.g., using intravenous injection or other suitable systemic delivery). Examples of such systemic therapeutic agents for treatment of stomach cancers include any one of the chemotherapeutic agents listed above, and/or immunotherapeutic agents (e.g., pembrolizumab), or targeted therapeutic agents, such a anti-angiogenesis agents (e.g., ramucirumab, bevacizumab) or targeted agents for human epidermal growth factor receptor 2 (HER2) such as trastuzumap.

Treatment of stomach cancers as disclosed herein can be utilized to achieve one or more endpoints. In various embodiments, such endpoints can involve clinical measures for a particular patient or a population of patients (e.g., a population undergoing a clinical trial). Examples of such endpoints include evaluation of target lesions, such as by using objective response as defined by a Responsive Evaluation Criteria in Solid Tumors (RECIST) protocol (e.g., RECIST 1.0 or RECIST 1.1)). Such evaluation can include assessment of the patient response into one of four categories: (1) complete response (CR) (e.g., disappearance of all target lesions; any pathological lymph nodes (whether target or non-target) must have reduction in short axis to <10 mm); (2) partial response (PR) (e.g., at least a 30% tumor regression; RECIST 1.1 defines this as at least a 30% decrease in the sum of diameters of target lesions, taking as reference the baseline sum diameters); (3) stable disease (SD) (e.g., neither sufficient shrinkage to qualify for PR nor sufficient increase to qualify for PD, taking as reference the smallest sum diameters while on study), or (4) progressive disease (PD) (at least a 20% increase in the sum of the LD of target lesions, taking as reference the smallest sum LD recorded since the treatment started or the appearance of one or more new lesions).

Suitable endpoints can also include evaluation of non-target lesions, for example by assigning a patient response to one of three categories: (1) complete response (CR) (e.g., disappearance of all non-target lesions and normalization of tumor marker level); (2) incomplete response or stable disease (SD) (e.g., persistence of one or more non-target lesion(s) or/and maintenance of tumor marker level above the normal limits); or (3) progressive disease (PD) (e.g., appearance of one or more new lesions and/or unequivocal progression of existing non-target lesions). Additional example endpoints include evaluation of best response, radiographic assessment, early tumor shrinkage (ETS), depth of response (DoR), graphical methods (e.g., waterfall plod, spider or spaghetti plot, swimmer plot, etc.), patient reported outcomes (e.g., assessment of quality of life, symptoms, etc.).

In certain embodiments, for example in patients with advanced or recurrent gastric cancer, suitable endpoints can include assessment for one or more of: objective response rate (ORR) (e.g., 15%, 20%, or 25% or more), progression free survival (PFS) (e.g., 3, 4, 5, 6 months or more); and/or disease control rate (DCR) (e.g., 50, 60, or 70% or more). Any one or any combination of these endpoints can be utilized to assess and/or establish efficacy of treatment of stomach cancers via depots of the present technology.

XVI. Cervical and Uterine Cancer

Embodiments of the present technology may be used to treat cervical and/or uterine cancers. Uterine cancer is the most common cancer occurring in a woman's reproductive system. 80% of uterine cancer is adenocarcinoma, which develops from cells in the endometrium and is commonly called endometrial cancer. 65,000 women in the US are diagnosed with uterine cancer each year. Five-year survival is 80%, due in large part to early stage diagnosis. Cervical cancer is diagnosed in 14,000 women each year in the US. Over 80% of cervical cancer is squamous cell carcinoma.

Surgical excision of the tumor and surrounding tissue is a common treatment. Different types of hysterectomies, simple (uterus and cervix), radical (additional removal of the upper vagina and nearby tissue) and bilateral salpingo-oophorectomy (additional removal of fallopian tubes and ovaries), may be performed depending on the stage/spread of the cancer. Any hysterectomy will deprive the patient of fertility. Lymph node removal may also be necessary to determine the extent the cancer has spread. Radiation therapy (e.g., external beam, brachytherapy, MRI guided) may also be used as an alternative or in addition to surgery. Systemic drug therapy (e.g., chemotherapy, hormone therapy, targeted therapy, immunotherapy) may also be utilized. Uterine cancer is the most common cancer occurring in a woman's reproductive system. 80% of uterine cancer is adenocarcinoma, which develops from cells in the endometrium and is commonly called endometrial cancer. 65,000 women in the US are diagnosed with uterine cancer each year. Five-year survival is 80%, due in large part to early stage diagnosis.

Surgical excision of the tumor and surrounding tissue is common. Different types of hysterectomies, simple (uterus and cervix), radical (removal of the upper vagina and nearby tissue in addition to removal of uterus and cervix) and bilateral salpingo-oophorectomy (removal of the fallopian tubes and ovaries in addition to removal of the uterus and cervix), may be performed depending on the stage/spread of the cancer. Any hysterectomy will deprive the patient of fertility. Lymph node removal may also be necessary to determine the extent the cancer has spread. Radiation therapy (e.g., external beam, brachytherapy, MRI guided) may also be used as an alternative or in addition to surgery. Systemic drug therapy (e.g., chemotherapy, hormone therapy, targeted therapy, immunotherapy) may also be utilized.

Any suitable composition and/or depot configuration can be utilized depending on the particular therapeutic agent(s), desired release profile(s), and routes of administration. In various embodiments, treatment of uterine and/or cervical cancers can involve local delivery of one or more therapeutic agents using any suitable route. Example administration routes include surgical or percutaneous access. Surgical access includes hysteroscopic surgery (e.g., transvaginal and transcervical endoscopic access for needle injection and/or implantation) and implantation or direct needle injection as part of laparoscopic or open procedure with direct visualization and/or palpation. Percutaneous access can include direct needle injection into/or around the tumor using imaging (e.g., CT, MRI, ultrasound).

Any suitable therapeutic agents, whether local, systemic, or both, can be used for treatment of uterine and/or cervical cancers. Example therapeutic agents include chemotherapeutic agents such as cisplatin, carboplatin, doxorubicin, paclitaxel, docetaxel, or any combinations thereof. In some embodiments, one or more locally delivered therapeutic agents can be used in combination with one or more systemically delivered therapeutic agents (e.g., using intravenous injection or other suitable systemic delivery). Examples of such systemic therapeutic agents for treatment of uterine cancers include any one of the chemotherapeutic agents listed above, as well as hormone therapy agents (e.g., progesterone, aromatase inhibitors (e.g., anastrazole, letrozole, exemestane), immunotherapeutics (e.g., pembrolizumab, Lenvatinib), or targeted therapeutics such anti-angiogenesis (e.g. bevacizumab) or mammalian target of rapamycin (mTOR) inhibitors (e.g., everolimus, ridaforolimus, temsirolimus).

Treatment of uterine cancers as disclosed herein can be utilized to achieve one or more endpoints. In various embodiments, such endpoints can involve clinical measures for a particular patient or a population of patients (e.g., a population undergoing a clinical trial). Examples of such endpoints include evaluation of target lesions, such as by using objective response as defined by a Responsive Evaluation Criteria in Solid Tumors (RECIST) protocol (e.g., RECIST 1.0 or RECIST 1.1)). Such evaluation can include assessment of the patient response into one of four categories: (1) complete response (CR) (e.g., disappearance of all target lesions; any pathological lymph nodes (whether target or non-target) must have reduction in short axis to <10 mm); (2) partial response (PR) (e.g., at least a 30% tumor regression; RECIST 1.1 defines this as at least a 30% decrease in the sum of diameters of target lesions, taking as reference the baseline sum diameters); (3) stable disease (SD) (e.g., neither sufficient shrinkage to qualify for PR nor sufficient increase to qualify for PD, taking as reference the smallest sum diameters while on study), or (4) progressive disease (PD) (at least a 20% increase in the sum of the LD of target lesions, taking as reference the smallest sum LD recorded since the treatment started or the appearance of one or more new lesions).

Suitable endpoints can also include evaluation of non-target lesions, for example by assigning a patient response to one of three categories: (1) complete response (CR) (e.g., disappearance of all non-target lesions and normalization of tumor marker level); (2) incomplete response or stable disease (SD) (e.g., persistence of one or more non-target lesion(s) or/and maintenance of tumor marker level above the normal limits); or (3) progressive disease (PD) (e.g., appearance of one or more new lesions and/or unequivocal progression of existing non-target lesions). Additional example endpoints include evaluation of best overall response, progression free survival (PFS), overall survival (OS), time to response, response duration, safety, and tolerability, or patient reported outcomes (e.g., assessment of quality of life, symptoms, etc.).

In some embodiments, a clinical endpoint can include assessment of one or more biomarkers (e.g., detecting a presence of a biomarker or assessing a relative level of a biomarker within a sample). Example biomarkers that may be relevant for cervical and/or uterine cancers includes cancer antigen 125, carcinoembryonic antigen, alpha-fetoprotein, human chorionic gonadotropic, human epididymis protein 4, inhibin A and B, lactate dehydrogenase, and cancer antigen 19-9.

Any one or any combination of these endpoints can be utilized to assess and/or establish efficacy of treatment of uterine cancers via depots of the present technology.

XVII. Ovarian Cancer

Embodiments of the present technology may be used to treat ovarian cancers. Epithelial carcinoma represents nearly 90% of ovarian, fallopian tube and peritoneal cancer. About 22,000 and 40,000 woman in the US and China, respectively, are diagnosed with ovarian cancer each year. Five-year survival is 48%, which can be improved substantially through early diagnosis. Surgical intervention is fundamental to treatment with the type of surgery dependent on the spread of the cancer. Hysterectomy and salpingo-oophorectomy are often necessary. Even if the cancer has metastasized, cytoreductive/debulking surgery helps manage local symptoms. Neoadjuvant and adjuvant chemotherapy are typically used in support of these surgical treatments. Combinations of systemic drugs are typically used to minimize risk of recurrence.

Any suitable composition and/or depot configuration can be utilized depending on the particular therapeutic agent(s), desired release profile(s), and routes of administration. In various embodiments, treatment of ovarian cancers can involve local delivery of one or more therapeutic agents using any suitable route. Example administration routes include surgical or percutaneous access. Surgical access includes hysteroscopic surgery (e.g., transvaginal and transcervical endoscopic access for needle injection and/or implantation) and implantation or direct needle injection as part of laparoscopic or open procedure with direct visualization and/or palpation. Percutaneous access can include direct needle injection into/or around the tumor using imaging (e.g., CT, MRI, ultrasound).

Any suitable therapeutic agents, whether local, systemic, or both, can be used for treatment of ovarian cancers. Example therapeutic agents include chemotherapeutic agents such as cisplatin, carboplatin, doxorubicin, paclitaxel, docetaxel, or any combinations thereof. In some embodiments, one or more locally delivered therapeutic agents can be used in combination with one or more systemically delivered therapeutic agents (e.g., using intravenous injection or other suitable systemic delivery). Examples of such systemic therapeutic agents for treatment of ovarian cancers include any one of the chemotherapeutic agents listed above, as well immunotherapeutic agents (e.g., pembrolizumab, Lenvatinib), or targeted therapeutics such as for anti-angiogenesis (e.g. bevacizumab), poly (ADP-ribose) polymerase (PARP) inhibits such as niraparib, alaparib, or rucaparib, or VEGF inhibitors such as bevacizumab or aflibercept.

Treatment of ovarian cancers as disclosed herein can be utilized to achieve one or more endpoints. In various embodiments, such endpoints can involve clinical measures for a particular patient or a population of patients (e.g., a population undergoing a clinical trial). Examples of such endpoints include evaluation of target lesions, such as by using objective response as defined by a Responsive Evaluation Criteria in Solid Tumors (RECIST) protocol (e.g., RECIST 1.0 or RECIST 1.1)). Such evaluation can include assessment of the patient response into one of four categories: (1) complete response (CR) (e.g., disappearance of all target lesions; any pathological lymph nodes (whether target or non-target) must have reduction in short axis to <10 mm); (2) partial response (PR) (e.g., at least a 30% tumor regression; RECIST 1.1 defines this as at least a 30% decrease in the sum of diameters of target lesions, taking as reference the baseline sum diameters); (3) stable disease (SD) (e.g., neither sufficient shrinkage to qualify for PR nor sufficient increase to qualify for PD, taking as reference the smallest sum diameters while on study), or (4) progressive disease (PD) (at least a 20% increase in the sum of the LD of target lesions, taking as reference the smallest sum LD recorded since the treatment started or the appearance of one or more new lesions).

Suitable endpoints can also include evaluation of non-target lesions, for example by assigning a patient response to one of three categories: (1) complete response (CR) (e.g., disappearance of all non-target lesions and normalization of tumor marker level); (2) incomplete response or stable disease (SD) (e.g., persistence of one or more non-target lesion(s) or/and maintenance of tumor marker level above the normal limits); or (3) progressive disease (PD) (e.g., appearance of one or more new lesions and/or unequivocal progression of existing non-target lesions). Additional example endpoints include evaluation of best overall response, progression free survival (PFS), overall survival (OS), time to response, response duration, safety, and tolerability, or patient reported outcomes (e.g., assessment of quality of life, symptoms, etc.).

In some embodiments, a clinical endpoint can include assessment of one or more biomarkers (e.g., detecting a presence of a biomarker or assessing a relative level of a biomarker within a sample). Example biomarkers that may be relevant for ovarian cancers includes cancer antigen 125, carcinoembryonic antigen, alpha-fetoprotein, human chorionic gonadotropic, human epididymis protein 4, inhibin A and B, lactate dehydrogenase, and cancer antigen 19-9.

Any one or any combination of these endpoints can be utilized to assess and/or establish efficacy of treatment of uterine cancers via depots of the present technology.

XVIII. Malignant Ascites

Embodiments of the present technology may be used to treat malignancy-related ascites (also referred to as malignant ascites). Malignant ascites is the build-up of fluid in the abdomen secondary to cancer elsewhere in the body. The presence of malignant cells in the peritoneal cavity (peritoneal carcinomatosis) is a grave prognostic sign of advanced cancer, with average survival about 20 weeks from diagnosis. Tumors causing malignant ascites are commonly secondary peritoneal surface malignancies, including ovarian, colorectal, pancreatic, uterine, lung, breast, stomach, esophageal and liver. Typical symptoms of malignant ascites include abdominal pain, dyspnea, nausea, vomiting and anorexia. Palliation of these symptoms via drainage of fluid (paracentesis) requires regular, repeated treatments, leads to frequent hospitalizations (subjecting patients to risk of hospital acquired infections), depletes patients of protein and electrolytes and, overall, severely impairs the patients' quality of life. Indwelling catheters and peritoneal-venous shunts have also been used to provide regular relief while avoiding repeated paracentesis, but such approaches have a host of other challenges and complications. In cases in which the primary tumors are surgically accessible, intra-peritoneal chemotherapy is administered for several days following tumor debulking/resection. This allows for "clean up" of any malignant cells that may reside in the peritoneal cavity that could be the basis for future or ongoing ascites. Intraperitoneal chemotherapy has been attempted in cases where the primary cancer is unresectable, but this practice has been debated given patients' vulnerabilities and life expectancies.

Any suitable composition and/or depot configuration can be utilized depending on the particular therapeutic agent(s), desired release profile(s), and routes of administration. In various embodiments, treatment of malignant ascites can involve local delivery of one or more therapeutic agents using any suitable route. Example administration routes include insert routes of administration intraperitoneal placement of depots for localized, sustained release of therapeutic agents into the peritoneal cavity. This could be as a standalone local treatment, adjuvant to surgical debulking of primary tumor(s) or combined with non-local treatment (e.g., radiation, systemic drug therapy). Treatments as described herein may be used for indications such as malignant ascites, peritoneal carcinomatosis or primary malignancies such as gastric cancer, ovarian cancer, colorectal cancer, pancreatic cancer, lung cancer, breast cancer, bladder cancer, fallopian tube cancer, esophageal cancer, solid tumors, and/or adenocarcinoma.

In operation, one or more depots of the present technology can be delivered to the peritoneal cavity via endoscopic access via the GI tract (e.g., needle injection or insertion from the GI lumen into the peritoneal cavity and/or surrounding tissue), percutaneous access (e.g., direct injection or insertion via needle or trocar catheter into the peritoneal cavity and/or surrounding tissue using imaging), or surgical access (e.g., open surgical implantation or needle injection as part of a cytoreductive procedure, or laparoscopic implantation or needle injection with direct visualization and/or palpation). In some instances, a minimally invasive surgical procedure can allow maintenance of cavity pressure, which facilitates distribution of the depot(s) and the therapeutic agent(s) carried thereby.

Any suitable therapeutic agents, whether local, systemic, or both, can be used for treatment of malignant ascites. Example therapeutic agents include chemotherapeutic agents (e.g., mitomycin C, cisplatin, doxorubicin, loplatin, retetrexil, 5-FU, paclitaxel, gemcitabine), targeted agents (e.g., VEGF inhibitors (e.g., bevacizumab, aflibercept), matrix metalloproteinase inhibitors (e.g., batimastat), etc.), immunotherapeutics (e.g., interferon, tumor necrosis factor, tumor necrosis factor-α (TNF-α), monoclonal antibody, or trifunctional antibody (catumaxomab, ertumaxomab)), or any combinations thereof. In some embodiments, one or more locally delivered therapeutic agents can be used in combination with one or more systemically delivered therapeutic agents (e.g., using intravenous injection or other suitable systemic delivery). In various embodiments, any one of the aforementioned therapeutic agents can be administrated systemically in combination with local delivery of one or more other therapeutic agents.

Treatment of malignant ascites as disclosed herein can be utilized to achieve one or more endpoints. In various embodiments, such endpoints can involve clinical measures for a particular patient or a population of patients (e.g., a population undergoing a clinical trial). In some embodiments, a clinical study evaluating treatment for malignant ascites can involve a control group receiving paracentesis alone, and a treatment group receiving local, sustained delivery of one or more therapeutic agent(s) (e.g., via one or more depots as described herein) in combination with paracentesis. In such a study, suitable endpoints can include one or more of: puncture-free survival (e.g., time to next therapeutic puncture (paracentesis) or death), time to next therapeutic puncture, patient reported outcomes of ascites symptoms (such as anorexia, nausea, vomiting, abdominal pain, abdominal swelling/distension, dyspnea), a reduction in relevant biomarker/cell levels (e.g., VEGF level (relative to total protein level), EpCAM, CA-125, pteroyl-D-glutamic acid, or human epidermal growth factor receptor 2 (HER2). Additional endpoint examples include designation of patient outcome as complete response (CR) or partial response (PR), with a CR indicated by relief of symptoms related to the ascites with absence of fluid reaccumulation (as evidenced by radiographic image) and a PR indicated by diminution of abdominal discomfort related to the ascites, with partial reaccumulation of fluid (e.g., less than 50% of the initial radiographic evidence of fluid). Any one or any combination of these endpoints can be utilized to assess and/or establish efficacy of treatment of malignant ascites via depots of the present technology.

XIX. Combined Treatment with Local, Sustained Delivery

For any of the depots and cancers described herein, the local sustained delivery may be used in combination with one or more other treatment options, and/or may replace or reduce the severity of other treatment options. For example:

With surgery: (a) local, sustained delivery as a neoadjuvant-preoperative localized, sustained administration with the goal of shrinking the tumor to increase the probability of full resection of the tumor. (b) local, sustained delivery as an adjuvant—postoperative localized, sustained administration to mitigate/minimize risk of recurrence by killing any remaining cancer cells. This can be an implant at the end of the surgical procedure or a subsequent, minimally invasive implantation.

Local, sustained delivery as an alternative to surgery and/or radiation: The tumor might not be surgically accessible or resectable and/or surgical intervention poses considerable risk of collateral damage to non-target tissue. Risk of radiation exposure to non-target tissue may also limit use of external beam radiation or local implantation of brachytherapy seeds.

Combined with systemic drug therapy and/or radiation: In cases where non-local therapy (e.g., systemic drug delivery, radiation, etc.) is warranted (i.e., when the cancer has spread and is now regional and/or metastatic), localized, sustained drug delivery may be combined with non-local therapy to improve chances of recovery when compared with the outcomes from nonlocal therapy alone. In cases, where there is high risk of central or end organ toxicity (e.g., patient has comorbidities), localized sustained drug therapy can be utilized to enable systemic drug therapy at lower, safer doses. Similarly, in cases where there is higher risk of collateral damage to non-target tissues at standard radiation doses, localized sustained drug therapy can be utilized to enable radiation therapy at lower doses (i.e., (outcomes (local drug delivery+lower non-local dose))≥(outcomes (standard non-local dose alone))).

Supportive and/or palliative: Where the cancer is advanced and the prognosis for survival is low, local drug delivery may still provide therapeutic relief to significantly improve a patient's quality of life. Given that suffering can also impact a patient's will to live, relief of suffering might also improve survival. Localized, sustained delivery of medications for pain/inflammation (anesthetics, steroidal and non-steroidal anti-inflammatories, anti-bodies) and infection (antimicrobials, antibiotics) or combinations thereof may provide a compelling treatment to patients with advanced cancer.

Transarterial chemoembolization (TACE) is an endovascular procedure whereby a catheter is placed in an artery that perfuses a tumor and/or an artery that perfuses an organ in which a malignant tumor resides to deliver therapy in two steps: (1) chemotherapeutic agent(s) are delivered via the catheter to the tumor and (2) particles of synthetic material (e.g., PVC) are then delivered to lodge in the blood vessel(s) perfusing the tumor to trap the chemotherapeutic agent(s) in the tumor and block blood flow to the tumor. An alternative approach would be to create from the present technology chemo-loaded microbeads that could be delivered endovascularly to the tumor to serve two objectives: (1) the microbeads would lodge in the blood vessel(s) perfusing the tumor, thereby reducing or at least partially blocking blood flow to the tumor (i.e., like an embolic) and (2) release chemotherapeutic(s) into the tumor in a controlled, sustained fashion. The combination of reduced blood flow and prolonged local exposure to chemotherapeutic agents would have a greater local impact on the tumor compared to conventional TACE therapy. This therapy could be administered to any tumors that have significant vascularity (e.g., liver, bile duct, colon, breast, pancreas, sarcoma, etc.) either as a singular primary therapy or in combination with surgery, systemic drug therapy (e.g., chemotherapy, immunotherapy, targeted therapy), radiation and/or ablation.

Systemic drug therapy, such as systemic chemotherapy, is a standard of care for most advanced stage cancers. When the cancer spreads outside of its organ of origin, the prognosis for the patient is typically very poor, as the cancer has spread throughout the body. The disease becomes a systemic disease at that point, so the therapies need to have a systemic effect to make a potential impact on patient survival. When a patient is initially diagnosed with metastatic disease, it is rare to try to treat the tumor(s) in the organ of origin because the local therapies, such as surgery or radiation, carries with them some significant side-effects that can greatly impact quality of life. This is especially important with terminal metastatic cancer patients who have a limited life expectancy. With that said, there is some evidence that treatment of the primary tumor, called cytoreductive therapy, can have impact on patient survival. The review article "Cytoreductive prostatectomy in metastatic prostate cancer: current knowledge and future directions" published in the American Journal of Clinical and Experimental Urology looked at all of the published studies where cytoreductive surgery was performed on metastatic prostate cancer patients. Although the data is mostly limited to registry studies, the suggestion is that by removing the primary tumor, it can not only provide the patient with symptomatic relief but also may provide a survival benefit. Safe, localized controlled delivery of drugs to eradicate the primary tumor may be the ideal way to provide this benefit with minimal side-effects and minimal impact on patient quality of life. Some embodiments of the present technology include a method of treating a patient with cancer (such as any of the cancers described herein) by (a) administering cytoreductive therapy at or around the originating primary tumor via localized, sustained drug delivery (e.g., via one or more of the depots detailed herein) and (b) administering non-localized therapy.

Examples of chemotherapeutic drugs for use the with the depots of the present technology, including for treatment of any of the cancers described herein, are shown in FIG. 105. Examples of hormone therapy drugs for use the with the depots of the present technology, including for treatment of any of the cancers described herein, are shown in FIG. 106. Examples of immunotherapy drugs for use the with the depots of the present technology, including for treatment of any of the cancers described herein, are shown in FIG. 107. Examples of targeted therapy drugs for use the with the depots of the present technology, including for treatment of any of the cancers described herein, are shown in FIG. 108. Examples of supportive therapy drugs for use the with the depots of the present technology, including for treatment of any of the cancers described herein, are shown in FIG. 109.

XX. Chemotherapeutics and Cell Cycle Dependency

Chemotherapeutic drugs can be broadly characterized into two categories: cell-cycle specific drugs consisting of antimetabolites, plant alkaloids, and antitumor antibiotics; and cell-cycle non-specific drugs consisting of alkylating agents. Examples of antimetabolites for use with the depots of the present technology, including for treatment of any of the cancers described herein, are shown in FIG. 110. Examples of plant alkaloids for use with the depots of the present technology, including for treatment of any of the cancers described herein, are shown in FIG. 111. Examples of antitumor antibiotics for use the with the depots of the present technology, including for treatment of any of the cancers described herein, are shown in FIG. 112. Examples of cell cycle non-specific drugs for use with the depots of the present technology, including for treatment of any of the cancers described herein, are shown in FIG. 113.

Chemotherapeutic drugs are typically administered systemically during later stages of cancer when cells have spread outside of the tissue of origin (metastasized) and became a systemic disease. These cancer cells have lost their normal checks and balances that control and limit cell division, and thus are rapidly growing and replicating. Cell-cycle specific drugs may elicit side effects on other rapidly dividing cells, such as hair, skin, mucosal lining, etc. For cell-cycle non-specific drugs, these drugs are inherently more toxic and dangerous to be administered systemically as they are active whether a cell is dividing or not, which has the potential to damage all cells in the body via systemic circulation.

Local delivery offers a significant advantage as it offers a safe use of these highly toxic cell-cycle non-specific drugs. This can be achieved by precisely controlling the tissue drug diffusion patterns. In addition, local delivery of cell-cycle non-specific drugs substantially increases the dose seen by the target tumor, and thus increases its potential to eradicate the tumor even at earlier stages when tumors may be slow growing. These advantages of locally delivered cell-cycle non-specific drugs offer potential clinical benefits that could not be achieved by systemic administration due to toxicity concerns.

XXI. Controlled Release of Hydrophobic Therapeutic Agents

The release kinetics of a drug-polymer formulation may depend on where the drug falls on the hydrophilicity—hydrophobicity spectrum. Hydrophilic drugs tend to release quickly when put in the aqueous environment of the body, which may pose challenges to acutely controlling the release of drug, while, in contrast, hydrophobic drugs may not release fast enough. This section summarizes novel formulations for sustained drug release of hydrophobic drugs such as docetaxel, bicalutamide, and enzalutamide. The disclosed formulations are broadly applicable to other chemotherapeutic or non-chemotherapeutic hydrophobic drugs, including any of those disclosed herein. The features described in these formulations can be used to alter and tune the release characteristics to achieve the desired release profile. Any of the following formulations or aspects thereof may be used to treat any of the cancers described herein. A list of abbreviations used in the following discussion is immediately below.

1. PEG10K=polyethylene glycol mol. wt. 10,000; 2. PLGA5050=poly(lactic-co-glycolic acid) with 50:50 lactide:glycolide ratio, inherent viscosity=0.6 dL/g, ester end group terminated; 3. Doce=docetaxel; 4. Bica=bicalutamide; 5. Enza=enzalutamide; 6. P188=poloxamer 188; 7. PBS=phosphate buffered saline.

As previously mentioned, the sustained-release formulations of the present technology may be configured to increase the rate of hydrophobic drug release. In some embodiments, the sustained release formulations and/or depots increase the rate of hydrophobic drug release by decreasing hydrophobicity. In some embodiments, the sustained release formulations and/or depots increase the rate of hydrophobic drug release by increasing drug molecular dispersion.

Using docetaxel as the example drug, and 10:10:80 PEG10K:PLGA5050:Doce as the baseline formulation for comparison, we show below various novel formulations that can increase in vitro drug elution rates as tested in PBS at 37° C. 10:10:80 PEG10K:PLGA5050:Doce was the formulation that was evaluated in our preclinical studies. Average cumulative drug release % values with linear trend line from the first 14 days were plotted, as shown in FIG. 114.

Baseline=PEG:PLGA:Doce 10:10:80 Rod [5]
Fast=PEG:PLGA:Doce 50:10:40 Rod [4]
Faster=PEG:Doce 60:40 Rod [3]
Raw docetaxel powder, milled or unmilled [2]
Fastest=PEG:Doce 1:1 Particles [1]

The mechanism of how each of these novel formulations can achieve increased in vitro drug release rate compared to the baseline 10:10:80 PEG10K:PLGA5050:Doce formulation is explained below. We have developed multiple formulations with tunable drug release rates that takes advantage of either decreasing hydrophobicity (by increasing PEG content) or introducing predominantly molecularly dispersed drug into the polymer matrix. Ultimately, we can combine both benefits in a rod implantable form factor that provides for increased release rate even when compared to free drug powder, creating a formulation that exhibits in vitro drug release rate between PEG:Doce 1:1 particles and raw docetaxel powder.

A. Formulations in Implantable Rod Form Factor

1. 50:10:40 PEG10K:PLGA5050:Doce (1 cm Rod)

By increasing PEG and decreasing drug content, the hydrophobicity of the formulation is decreased, allowing for faster water uptake. Hydrophilic polyethylene glycol 10,000 (PEG10K) serves to control water uptake which improves wettability (increases effective surface area) for drug dissolution. A solid form of PEG is needed to create large phase-separated PEG-rich domains giving rise to an increased drug release from the extensive dissolution and leaching of PEG upon hydration. Much higher molecular weight PEG would slow down dissolution rate of PEG. Much lower molecular weight PEG exists only in liquid form. Docetaxel total drug content per unit length for 50:10:40 PEG:PLGA5050 IV 0.6:Doce=2.07±0.03 mg/cm.

The in vitro drug release data in FIG. 115 shows ~20% higher release rate than 10:10:80 PEG10K:PLGA5050:Doce formulation. N=2 samples per group.

2. PEG10K:PLGA5050:Bica (1 cm Rod)

The plot of FIG. 116 is an example of how changing PEG content could alter the drug release rate using bicalutamide. The polymers consist of PEG 10 kDa and PLGA 50/50 IV 0.6, ester end group terminated. Release rate can be modulated by changing PEG content (10%, 15%, 40%, 50%), with release rate increasing with higher PEG content. For PEG-PLGA-Bica 50:10:40, the release rate is comparable to that of free bica powder. The drug loading increases from 2.2 mg/cm for PEG:PLGA:Bica 50:10:40 to 4.84 mg/cm for PEG:PLGA:Bica 10:10:80. N=2 samples per group.

3. 60:40 PEG10K:Doce (1 cm Rod)

By eliminating PLGA completely from the formulation, drug release becomes dependent only on PEG water uptake and drug dissolution, and potentially can avoid a late phase burst release due to late phase PLGA degradation. However, PEG has a fairly low tensile strength, therefore it wasn't readily apparent that a PEG rod will maintain its structural integrity for handling and processing. We have found that the mechanical properties were not impacted as solid PEG rod formulations can be fabricated, handled, and processed without compromising its structural integrity. Docetaxel total drug content per unit length for 60:40 PEG10K:Doce=1.92±0.05 mg/cm.

In vitro drug release data (shown at FIG. 117) shows an approximately ~200% higher release rate than 50:10:40 PEG10K:PLGA5050:Doce formulation. N=2 samples per group.

4. 60:40 PEG10K:Enzalutamide (1 cm Rod)

FIG. 118 shows an example of significantly increasing the release rate of enzalutamide by loading the drug into PEG10K without PLGA. PEG10K content is at 60%, which significantly increases the water uptake of the formulation. Enzalutamide total drug content per unit length of rod for 60:40 PEG10k:Enza=1.75±0.04 mg/cm (n=2 samples per group).

5. 60:40 PEG10K:Doce (1 mm Disc)

Increasing the surface area of drug depots by physically altering rod dimensions may also help to increase the drug release rate. By cutting 1 cm long 60:40 PEG10K:Doce rod into shorter 1 mm thick discs, a fragmented PEG10K:Doce rod with increased surface area is obtained. As shown in FIG. 119, fragmented 60:40 PEG10K:Doce rod exhibited ~20% faster in vitro drug release compared to unfragmented 60:40 PEG10K:Doce rod, and up to 3 times faster release than 50:10:40 PEG10K:PLGA5050:Doce rod in PBS. Docetaxel total drug content per unit length for 60:40 PEG10K:Doce=1.92±0.05 mg/cm. N=2 samples per group.

Drugs in the above formulations were processed into rod implantable form factor using a solvent-based extrusion process. This processing method results in a solid dispersion where the drug remains predominantly in crystalline form, limiting the potential for further increase in drug release rate. To further increase the drug release significantly, the drug must be predominantly molecularly dispersed in the polymer matrix. Molecularly dispersed drug can more readily diffuse out of the polymer matrix without the being rate limited by drug dissolution. A different processing method was used to create drug microparticles that contain molecularly dispersed drug in the polymer matrix.

B. Formulation in Microparticle Form Factor 1. 1:1 PEG10K:Doce Microparticles

Co-precipitation using solvent/non-solvent mixing to create 1:1 PEG10K:Doce microparticles traps the drug in amorphous phase within PEG. This minimizes drug recrystallization and maximizes molecular drug dispersion. Here the amorphous PEG acts as a stabilizing agent that adheres to the drug molecules and maintains the molecular dispersion. The schematic shown in FIG. 20 details the structural differences between the rod created via solvent-based extrusion (this is how all rods described above have been made) and microparticle created via co-precipitation using solvent/non-solvent mixing.

As shown in FIG. 121, in vitro drug release data shows faster drug release even compared to the milled or unmilled docetaxel powder. Due to its high hydrophobicity, docetaxel does not significantly increase dissolution rate even after milling. The 1:1 PEG10K:Doce microparticles can increase drug release rate higher than the natural dissolution rate of hydrophobic drug solids. N=2 samples per group.

The raw docetaxel and 1:1 PEG10K:Doce particles have similar particles sizes (SEM images below), but the 1:1 PEG10K:Doce particles have faster drug dissolution rate due to drug being molecularly dispersed in the polymer carrier versus raw crystalline drug.

FIG. 122 is an SEM image of raw docetaxel (raw drug particles exhibit needle-like morphology with long axis 5-20 μm, short axis −2 um). FIG. 123 is an SEM image of 1:1 PEG10K:Doce microparticles (microparticle size is 5-15 μm; shown with microparticle aggregation).

C. Formulations in Microparticle Embedded Rod Form Factor

Formulations in FIG. 124 represent embodiments where microparticles were embedded into an implantable rod form factor. The inventors started with the aim to maximize drug loading in microparticles while achieving an implantable rod form factor but found that the in vitro drug release rate was slower compared to the baseline formulation. Consequently, the inventors decreased hydrophobicity of the formulation by switching PEG10K:PLGA5050 to poloxamer 188 rod polymer matrix. This ultimately resulted in a significantly faster release, surprisingly so for a hydrophobic drug. The schematic below highlights the differences of between microparticles embedded in rod form factor versus the rod made via solvent-based extrusion and the microparticles only made via co-precipitation in solvent/non-solvent mixing.

1. 1:8 PEG10K:Doce Microparticles Embedded in 1:1 PEG10K:PLGA5050 (1 cm Rod)

In order to maximize drug loading and achieve an implantable rod form factor, microparticles consisting of 1:8 PEG10K:Doce were formed and loaded into 1:1 PEG10K:PLGA5050 rods. Similar to PEG10K:Doce 1:1 particles, the PEG10K:Doce 1:8 particles have decreased hydrophobicity compared to free drug particle due to presence of PEG. Encapsulation of docetaxel into PEG via co-precipitation maximizes molecular dispersion of docetaxel in PEG and minimizes drug recrystallization with rapid precipitation of docetaxel and PEG.

In terms of processing, first PEG 10K and docetaxel in 1:8 ratio were dissolved in ethanol, then this mixture was added dropwise to non-solvent n-hexane to precipitate PEG10K:Doce 1:8 particles. Fine powder is formed after centrifuging and vacuum drying. The PEG10K:Doce 1:8 particles are then mixed with 1:1 PEG10K:PLGA5050 solution for rod extrusion. Docetaxel total drug content per unit length for PEG10K:Doce 1:8 particles in 1:1 PEG10K:PLGA5050 rods=4.24±0.04 mg/cm.

As shown in FIG. 125, the docetaxel release rate was slower by -20% as compared to 10:10:80 PEG10K:PLGA5050:Doce formulation (FT2-RD-042). The release rate in PBS was slower likely due to the high drug loading leading to increased hydrophobicity in this formulation. N=2 samples per group.

2. 1:1 PEG10K:Doce Microparticles Embedded in Poloxamer 188 (1 cm Rod)

An alternative method to enhance the release of docetaxel is by embedding 1:1 PEG10K:Doce microparticles into implantable rod matrix composed of Poloxamer 188. Poloxamer 188 acts as a solid surfactant to increase water solubility of the drug and its miscibility with PEG, and acts as a dispersing agent for drug solid dispersion. As a result, loading the 1:1 PEG10K:Doce particles into water-soluble Poloxamer 188 rod allowed for faster water penetration and drug release.

Simply replacing hydrophobic PLGA with Poloxamer 188 to form 30:30:40 P188:PEG10K:Doce formulation only achieved similar in vitro release rate as PEG10K:Doce 60:40 formulation. Therefore, 1:1 PEG10K:Doce microparticles were formed and embedded into Poloxamer 188 matrix to enhance drug release via drug molecular dispersion. As shown in FIG. 126, this 1:1 PEG10K:Doce microparticle embedded Polaxamer 188 rod formulation achieved ~80% faster release compared to 60:40 PEG10K:Doce formulation. Docetaxel total drug content per unit length for 1:1

PEG10K:Doce microparticles embedded in Poloxamer 188 rods=1.26±0.08 mg/cm. N=2 samples per group.

D. Summary

In summary, we have formulated multiple types of hydrophobic drugs (docetaxel, bicalutamide, enzalutamide) to show control of hydrophobic drug release by decreasing hydrophobicity (increasing PEG10K content) and/or by increasing drug molecular dispersion (processing into microparticle embedded rod form factor that stabilizes molecularly dispersed drug). Ultimately, we have created a formulation (PEG10K:Doce 1:1 Particles in P188 Rod) that exhibits an in vitro drug release rate in between that of the microparticles and free docetaxel powder in an implantable rod form factor. The plot in FIG. 127 highlights the average in vitro drug release rates in PBS for the tested formulations.

XXII. Conclusion

Although many of the embodiments are described above with respect to systems, devices, and methods for treating certain cancers, the depots of the present technology may be used to treat other cancers as well. Moreover, other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described above with reference to FIGS. 1-127.

The above detailed descriptions of embodiments of the technology are not intended to be exhaustive or to limit the technology to the precise form disclosed above. Where the context permits, singular or plural terms may also include the plural or singular term, respectively. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

Unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present technology. At the very least, and not as an attempt to limit the application of the doctrine of equivalents to the scope of the claims, each numerical parameter should at least be construed in light of the number of reported significant digits and by applying ordinary rounding techniques. Additionally, all ranges disclosed herein are to be understood to encompass any and all subranges subsumed therein. For example, a range of "1 to 10" includes any and all subranges between (and including) the minimum value of 1 and the maximum value of 10, i.e., any and all subranges having a minimum value of equal to or greater than 1 and a maximum value of equal to or less than 10, e.g., 5.5 to 10.

It is noted that, as used in this specification and the appended claims, the singular forms "a," "an," and "the," include plural referents unless expressly and unequivocally limited to one referent. For example, reference to "a therapeutic agent" includes one, two, three or more therapeutic agents.

The headings above are not meant to limit the disclosure in any way. Embodiments under any one heading may be used in conjunction with embodiments under any other heading.

The invention claimed is:

1. A method of treating malignant ascites, the method comprising:

placing an implantable depot in a patient's peritoneal cavity, wherein the depot comprises a therapeutic region and a control region covering at least a potion of the therapeutic agent, the therapeutic region comprising a therapeutic agent mixed with a polymer, and wherein the therapeutic agent includes a chemotherapeutic agent;

via the depot, providing sustained release of the therapeutic agent to the peritoneal cavity, wherein the sustained release causes a greater exposure in the peritoneal cavity to the therapeutic agent over time as compared to exposure resulting from systemic administration of the therapeutic agent.

2. The method of claim 1, further comprising administering one or more treatments selected from the group consisting of surgery, ablation, radiation, and systemic drug therapy in conjunction with administering the implantable depot.

3. The method of claim 2, wherein the surgery comprises open surgery, laparoscopic surgery, or endoscopic surgery.

4. The method of claim 2, wherein the radiation comprises external beam radiation, brachytherapy seed radiation, or sterotactic radiotherapy.

5. The method of claim 1, wherein the period of time is at least one month.

6. The method of claim 1, wherein the period of time is at least three months.

7. The method of claim 1, wherein the period of time is at least six months.

8. The method of claim 1, wherein the period of time is at least twelve months.

9. A method of treating malignant ascites in a peritoneal cavity of a patient, wherein the patient is experiencing one or more symptoms associated with the malignant ascites, the method comprising:

placing an implantable depot in the patient's peritoneal cavity, the depot comprising a therapeutic region and a control region covering at least a portion of a surface of the therapeutic region, wherein the therapeutic region includes a chemotherapeutic agent;

via the implanted depot, providing a sustained release of the chemotherapeutic agent directly to the peritoneal cavity;

administering one or more treatments to the patient, the one or more treatments comprising surgery, radiation, intraperitoneal chemotherapy, and/or systemic drug therapy; and relieving the one or more symptoms of the patient to a greater extent as compared to a patient who receives the one or more treatments but does not receive the implantable depot, wherein the one or more symptoms comprises anorexia, nausea, vomiting, abdominal pain, abdominal swelling, abdominal distension, and/or dyspnea.

10. The method of claim 9, wherein the chemotherapeutic agent is FDA-approved for systemic administration to treat one or more cancers of the human body.

11. The method of claim 9, wherein the chemotherapeutic agent is an alkylating agent, an antimetabolite, an anthracycline antibiotic, an antitumor antibiotic, a taxane, a plant alkaloid, an antimicrotubule agent, or any combination thereof.

* * * * *